US011944627B2

(12) United States Patent
Burrows et al.

(10) Patent No.: US 11,944,627 B2
(45) Date of Patent: Apr. 2, 2024

(54) METHODS FOR TREATING HEMATOLOGICAL MALIGNANCIES AND EWING'S SARCOMA

(71) Applicant: KURA ONCOLOGY, INC., San Diego, CA (US)

(72) Inventors: Francis Burrows, San Diego, CA (US); Linda V. Kessler, San Diego, CA (US); Liansheng Li, San Diego, CA (US); Pingda Ren, San Diego, CA (US); Yi Wang, San Diego, CA (US); Tao Wu, San Diego, CA (US); Jingchuan Zhang, San Diego, CA (US)

(73) Assignee: KURA ONCOLOGY, INC., San Diego, CA (US)

( * ) Notice: Subject to any disclaimer, the term of this patent is extended or adjusted under 35 U.S.C. 154(b) by 168 days.

(21) Appl. No.: 16/494,556

(22) PCT Filed: Mar. 22, 2018

(86) PCT No.: PCT/US2018/023804
§ 371 (c)(1),
(2) Date: Sep. 16, 2019

(87) PCT Pub. No.: WO2018/175746
PCT Pub. Date: Sep. 27, 2018

(65) Prior Publication Data
US 2023/0026872 A1 Jan. 26, 2023

Related U.S. Application Data

(60) Provisional application No. 62/635,256, filed on Feb. 26, 2018, provisional application No. 62/577,640, filed on Oct. 26, 2017, provisional application No. 62/561,119, filed on Sep. 20, 2017, provisional application No. 62/476,710, filed on Mar. 24, 2017.

(51) Int. Cl.
| A61K 31/519 | (2006.01) |
| A61K 31/44 | (2006.01) |
| A61K 31/445 | (2006.01) |
| A61K 31/4523 | (2006.01) |
| A61K 31/453 | (2006.01) |
| A61K 31/454 | (2006.01) |
| A61K 31/4545 | (2006.01) |
| A61K 31/4725 | (2006.01) |
| A61K 31/505 | (2006.01) |
| A61K 31/5377 | (2006.01) |
| A61P 35/02 | (2006.01) |

(52) U.S. Cl.
CPC .......... A61K 31/519 (2013.01); A61K 31/44 (2013.01); A61K 31/445 (2013.01); A61K 31/4523 (2013.01); A61K 31/453 (2013.01); A61K 31/454 (2013.01); A61K 31/4545 (2013.01); A61K 31/4725 (2013.01); A61K 31/505 (2013.01); A61K 31/5377 (2013.01); A61P 35/02 (2018.01)

(58) Field of Classification Search
CPC .... A61K 31/519; A61K 31/44; A61K 31/445; A61K 31/4523; A61K 31/453; A61K 31/454; A61K 31/4545; A61K 31/4725; A61K 31/505; A61K 31/5377; A61P 35/02
See application file for complete search history.

(56) References Cited

U.S. PATENT DOCUMENTS

| 5,033,252 A | 7/1991 | Carter |
| 5,052,558 A | 10/1991 | Carter |
| 5,323,907 A | 6/1994 | Kalvelage |
| 5,445,764 A | 8/1995 | Poetsch et al. |
| 5,861,510 A | 1/1999 | Piscopio et al. |
| 5,863,949 A | 1/1999 | Robinson et al. |
| 5,866,562 A | 2/1999 | Schohe-Loop et al. |
| 6,075,008 A | 6/2000 | Farrell et al. |
| 6,214,872 B1 | 4/2001 | Robinson |
| 6,511,993 B1 | 1/2003 | Dack et al. |
| 6,849,638 B2 | 2/2005 | Stolle et al. |
| 7,030,240 B2 | 4/2006 | Dhanoa et al. |
| 7,030,242 B2 | 4/2006 | Noe et al. |
| 7,744,968 B2 | 6/2010 | Reiffenrath et al. |
| 8,207,174 B2 | 6/2012 | Tasler et al. |
| 8,507,491 B2 | 8/2013 | Cheng et al. |
| 8,722,877 B2 | 5/2014 | Chesworth et al. |

(Continued)

FOREIGN PATENT DOCUMENTS

| CN | 103833759 A | 6/2014 |
| EP | 0606046 A1 | 7/1994 |

(Continued)

OTHER PUBLICATIONS

Patel et al., Acute Myeloid Leykemia with IDH1 or IDH2 Mutations: Frequency and Clinicopathologic Features, American Journal of Clinical Pathology, vol. 135, Issue 1, Jan. 2011, pp. 35-45 (Year: 2011).*
Thol et al., "Incidence and Prognostic Influence of DNMT3A Mutations in Acute Myeloid Leukemia", Journal of Clinical Oncology 29, No. 21 (Jul. 20, 2011) pp. 2889-2896 (Year: 2011).*
Borkin et al., Pharmacologic inhibition of the menin-MLL interaction blocks progression of MLL leukemia in vivo, Cancer Call. Apr. 13, 2015 (Year: 2015).*
Hollink et al., "NUP98/NSD1 characterizes a novel poor prognostic group in acute myeloid leukemia witha distinct HOX gene expression pattern", Blood, 118 (2011), pp. 3645-3656 (Year: 2011).*

(Continued)

Primary Examiner — John S Kenyon
Assistant Examiner — Gillian A Hutter
(74) Attorney, Agent, or Firm — WILSON SONSINI GOODRICH & ROSATI

(57) ABSTRACT

The present disclosure provides methods for treating hematological malignancies and Ewings sarcoma using menin inhibitors. Compositions for use in these methods are also provided.

20 Claims, 17 Drawing Sheets
Specification includes a Sequence Listing.

(56) References Cited

U.S. PATENT DOCUMENTS

| | | |
|---|---|---|
| 8,993,552 B2 | 3/2015 | Grembecka et al. |
| 9,216,993 B2 | 12/2015 | Grembecka et al. |
| 9,505,781 B2 | 11/2016 | Grembecka et al. |
| 9,505,782 B2 | 11/2016 | Grembecka et al. |
| 10,077,271 B2 | 9/2018 | Grembecka et al. |
| 10,160,769 B2 | 12/2018 | Grembecka et al. |
| 10,174,041 B2 | 1/2019 | Grembecka et al. |
| 10,246,464 B2 | 4/2019 | Grembecka et al. |
| 10,407,732 B2 | 9/2019 | Armstrong |
| 10,526,341 B2 | 1/2020 | Tabar et al. |
| 10,781,218 B2 * | 9/2020 | Wu .................... A61P 35/00 |
| 10,869,868 B2 | 12/2020 | Armstrong |
| 2003/0119829 A1 | 6/2003 | Stolle et al. |
| 2003/0153556 A1 | 8/2003 | Levy et al. |
| 2005/0123906 A1 | 6/2005 | Rana |
| 2005/0222175 A1 | 10/2005 | Dhanoa et al. |
| 2005/0222176 A1 | 10/2005 | Dhanoa et al. |
| 2006/0025406 A1 | 2/2006 | Zembower et al. |
| 2006/0281769 A1 | 12/2006 | Baumann et al. |
| 2006/0281771 A1 | 12/2006 | Baumann et al. |
| 2007/0078133 A1 | 4/2007 | Liu et al. |
| 2008/0249114 A1 | 10/2008 | Tasler et al. |
| 2008/0293699 A1 | 11/2008 | Reed et al. |
| 2009/0163545 A1 | 6/2009 | Goldfarb |
| 2009/0298772 A1 | 12/2009 | Thirman |
| 2010/0063047 A1 | 3/2010 | Borchardt et al. |
| 2011/0065690 A1 | 3/2011 | Grembecka et al. |
| 2012/0058998 A1 | 3/2012 | Sanders et al. |
| 2012/0142625 A1 | 6/2012 | Olhava et al. |
| 2012/0322742 A1 | 12/2012 | Thirman |
| 2013/0035347 A1 | 2/2013 | Vuligonda et al. |
| 2013/0210831 A1 | 8/2013 | Su et al. |
| 2014/0100184 A1 | 4/2014 | Song et al. |
| 2014/0275070 A1 | 9/2014 | Grembecka et al. |
| 2014/0371238 A1 | 12/2014 | Zawistoski et al. |
| 2014/0371239 A1 | 12/2014 | Grembecka et al. |
| 2015/0342979 A1 | 12/2015 | Pollock et al. |
| 2016/0045504 A1 | 2/2016 | Grembecka et al. |
| 2016/0046647 A1 | 2/2016 | Grembecka et al. |
| 2018/0105531 A1 | 4/2018 | Grembecka et al. |
| 2018/0117031 A1 | 5/2018 | Jain |
| 2018/0207168 A1 | 7/2018 | Falini et al. |
| 2018/0243303 A1 | 8/2018 | Grembecka et al. |
| 2019/0092783 A1 | 3/2019 | Wu et al. |
| 2019/0092784 A1 | 3/2019 | Wu et al. |
| 2019/0192517 A1 | 6/2019 | Burrows et al. |
| 2019/0307750 A1 | 10/2019 | Armstrong |
| 2020/0165224 A1 | 5/2020 | Li et al. |
| 2020/0216471 A1 | 7/2020 | Wu et al. |
| 2023/0095934 A1 | 3/2023 | Burrows |

FOREIGN PATENT DOCUMENTS

| | | | |
|---|---|---|---|
| EP | 0780386 A1 | 6/1997 | |
| EP | 0606046 B1 | 10/1997 | |
| EP | 0818442 A2 | 1/1998 | |
| EP | 0931788 A2 | 7/1999 | |
| EP | 0945864 A2 | 9/1999 | |
| EP | 1004578 A2 | 5/2000 | |
| EP | 1181017 A1 | 2/2002 | |
| EP | 0780386 B1 | 10/2002 | |
| EP | 0931788 B1 | 11/2002 | |
| EP | 1382603 A1 | 1/2004 | |
| EP | 1004578 B1 | 2/2004 | |
| JP | H10330377 A | 12/1998 | |
| JP | 2009507004 A | 2/2009 | |
| JP | 2011527295 A | 10/2011 | |
| JP | 2013503906 A | 2/2013 | |
| JP | 2016512514 A | 4/2016 | |
| WO | WO-9005719 A1 | 5/1990 | |
| WO | WO-9627583 A1 | 9/1996 | |
| WO | WO-9633172 A1 | 10/1996 | |
| WO | WO-9803415 A1 | 1/1998 | |
| WO | WO-9803516 A1 | 1/1998 | |
| WO | WO-9807697 A1 | 2/1998 | |
| WO | WO-9830566 A1 | 7/1998 | |
| WO | WO-9833768 A1 | 8/1998 | |
| WO | WO-9834915 A1 | 8/1998 | |
| WO | WO-9834918 A1 | 8/1998 | |
| WO | WO-9907675 A1 | 2/1999 | |
| WO | WO-9929667 A1 | 6/1999 | |
| WO | WO-9933172 A1 | 7/1999 | |
| WO | WO-9943675 A1 | 9/1999 | |
| WO | WO-9952889 A1 | 10/1999 | |
| WO | WO-9952910 A1 | 10/1999 | |
| WO | WO-9965909 A1 | 12/1999 | |
| WO | WO-02088138 A1 | 11/2002 | |
| WO | WO-03022214 A2 | 3/2003 | |
| WO | WO-2004030671 A2 | 4/2004 | |
| WO | WO-2004030672 A1 | 4/2004 | |
| WO | WO-2005020897 A2 | 3/2005 | |
| WO | WO-2006135630 A1 | 12/2006 | |
| WO | WO-2006135636 A2 | 12/2006 | |
| WO | WO-2007026024 A2 | 3/2007 | |
| WO | WO-2007042669 A2 | 4/2007 | |
| WO | WO-2007076034 A2 | 7/2007 | |
| WO | WO-2007115822 A1 | 10/2007 | |
| WO | WO-2008031875 A1 | 3/2008 | |
| WO | WO-2008070303 A2 | 6/2008 | |
| WO | WO-2008090140 A1 | 7/2008 | |
| WO | WO-2008099019 A1 | 8/2008 | |
| WO | WO-2008107320 A1 | 9/2008 | |
| WO | WO-2008114275 A2 | 9/2008 | |
| WO | WO-2008135232 A1 | 11/2008 | |
| WO | WO-2009017838 A2 | 2/2009 | |
| WO | WO-2009064388 A2 | 5/2009 | |
| WO | WO-2009143058 A1 | 11/2009 | |
| WO | WO-2010030757 A2 | 3/2010 | |
| WO | WO-2011003418 A1 | 1/2011 | |
| WO | WO-2011014128 A1 | 2/2011 | |
| WO | WO-2011029054 A1 | 3/2011 | |
| WO | WO-2011071069 A2 | 8/2011 | |
| WO | WO-2012075381 A1 | 6/2012 | |
| WO | WO-2012075492 A2 | 6/2012 | |
| WO | WO-2012075500 A2 | 6/2012 | |
| WO | WO-2012082436 A3 | 9/2012 | |
| WO | WO-2013024291 A2 | 2/2013 | |
| WO | WO-2013072694 A1 | 5/2013 | |
| WO | WO-2014026198 A1 | 2/2014 | |
| WO | WO-2014039839 A1 | 3/2014 | |
| WO | WO-2014053581 A1 | 4/2014 | |
| WO | WO-2014100662 A1 | 6/2014 | |
| WO | WO-2014164543 A1 | 10/2014 | |
| WO | WO-2015017863 A1 | 2/2015 | |
| WO | WO-2015154039 A2 | 10/2015 | |
| WO | WO-2015169906 A1 | 11/2015 | |
| WO | WO-2015154039 A3 | 12/2015 | |
| WO | WO-2015191701 A1 | 12/2015 | |
| WO | WO-2016025635 A2 * | 2/2016 | ........... A61K 31/135 |
| WO | WO-2016025649 A1 | 2/2016 | |
| WO | WO-2016040330 A1 * | 3/2016 | ........... C07D 495/04 |
| WO | WO-2016195776 A1 * | 12/2016 | ........... A61K 31/519 |
| WO | WO-2016197027 A1 | 12/2016 | |
| WO | WO-2017112768 A1 | 6/2017 | |
| WO | WO-2017132398 A1 | 8/2017 | |
| WO | WO-2017161002 A1 * | 9/2017 | ........... A61K 31/445 |
| WO | WO-2017161028 A1 * | 9/2017 | ........... A61K 31/535 |
| WO | WO-2017192543 A1 | 11/2017 | |
| WO | WO-2017207387 A1 | 12/2017 | |
| WO | WO-2017214367 A1 | 12/2017 | |
| WO | WO-2018023197 A1 | 2/2018 | |
| WO | WO-2018024602 A1 | 2/2018 | |
| WO | WO-2018050684 A1 | 3/2018 | |
| WO | WO-2018050686 A1 | 3/2018 | |
| WO | WO-2018053267 A1 | 3/2018 | |
| WO | WO-2018106818 A1 | 6/2018 | |
| WO | WO-2018106820 A1 | 6/2018 | |
| WO | WO-2018136202 A2 | 7/2018 | |
| WO | WO-2018175746 A1 | 9/2018 | |

(56) References Cited

FOREIGN PATENT DOCUMENTS

| WO | WO-2019060365 A1 | 3/2019 |
|---|---|---|
| WO | WO-2020069027 A1 | 4/2020 |

OTHER PUBLICATIONS

Patel et al., "Acute Myeloid Leukemia with IDH1 or IDH2 Mutations: Frequency and Clinicopathologic Features", American Journal of Clinical Pathology, vol. 135, Issue 1, Jan. 2011, pp. 35-45 (Year: 2011).*
Thol et al., "Incidence and Prognostic Influence of DNMT3A Mutations in Acute Myeloid Leukemia", Journal of Clinical Oncology 29, No. 21 (Jul. 20, 2011) (Year: 2011).*
Cermakova et al., Lessons Learned: HIV Points the Way Towards Precision Treatment of Mixed-Lineage Leukemia. Trends in Pharmacological Sciences 37(8): 660-671 (2016).
Chen et al., Pancreas++: automated quantification of pancreatic islet cells in microscopy images. Front Physiol 3:482 (2013).
Co-pending U.S. Appl. No. 16/927,844, filed Jul. 13, 2020.
Higuchi et al. Pro-drugs as Novel Delivery Systems. A.C.S. Symposium Series vol. 14 (1975).
Kilimnik et al., Quantification of islet size and architecture. Islets 4(2): 167-172 (2012).
Liu et al., Meis1 is critical to the maintenance of human acute myeloid leukemia cells independent of MLL rearrangements. Annals of Hematology 96(4): 567-574 (2017).
Noorafshan et al., A simple stereological method for estimating the number and the volume of the pancreatic beta cells. JOP 13(4):427-432 (2012).
AC1MFIB7, Pubchem, [Online], 2005, [searched on Mar. 29, 2016], Internet, < url, < a=""href="https://pubchem.ncbi.nlm.nih.gov/compounds/2894865#section=Top">https://pubchem.ncbi.nlm.nih.gov/compounds/2894865#section=Top < /url, > .
AC1N5DGQ, PubChem, [Online], 2005, [searched on Mar. 29, 2016], Internet, < url, < a=""href="https://pubchem.ncbi.nlm.nih.gov/compound/4143243" > https://pubchem.ncbi.nlm.nih.gov/compound/4143243 < /url, > .
Agarwal, et al. Menin molecular interactions: insights into normal functions and tumorigenesis. Horm Matab Res, 37(6), pp. 369-374 (2005).
Arkin et al. Small-molecule inhibitors of protein-protein interactions: progressing toward the reality. Chem Biol. 21(9):1102-1114 (2014).
Bhaskar, et al. Synthesis, Antimicrobial and Antihyperlipidemic Activities of Some 4-Substituted-5,6, 7,8-tetrhydrol. Asian J Chemistry 2007, 19(7):5187-5194.
Blackburn, et al. Identification and characterization of aminopiperidinequinolones and quinazolinones as MCHr1 antagonists. Bioorg Med Chem Lett. May 15, 2006;16(10):2621-7. Epub Mar. 9, 2006.
Borkin et al. Pharmacologic inhibition of the Menin-MLL interaction blocks progression of MLL leukemia in vivo. Cancer Cell. Apr. 13, 2015;27(4):589-602. doi: 10.1016/j.ccell.2015.02.016. Epub Mar. 26, 2015.
Borkin et al. Property Focused Structure-Based Optimization of Small Molecule Inhibitors of the Protein-Protein Interaction between Menin and Mixed Lineage Leukemia (MLL). J Med Chem. Feb. 11, 2016;59(3):892-913.
Bundgaard et al. Design of Prodrugs pp. 7-9, 21-24 (1985).
Chen, et al. The tumor suppressor menin regulates hematopoiesis and myeloid transformation by influencing Hox gene expression. Proc Natl Acad Sci USA, 103(4), pp. 1018-1023 (2006).
Co-pending U.S. Appl. No. 16/453,802, filed Jun. 26, 2019.
Cox, et al. Chromosomal aberration of the 11q23 locus in acute leukemia and frequency of MLL gene translocation: results in 378 adult patients. Am J Clin Pathol, 122(2), pp. 298-306 (2004).
Eguchi, et al. The role of the MLL gene in infant leukemia. Int J Hematol, 78(5), pp. 390-401 (2003).
Gough et al. NUP98-PHF23 is a chromatin-modifying oncoprotein that causes a wide array of leukemias sensitive to inhibition of PHD histone reader function. Cancer Discov 4(5):564-77 (2014).
Grembecka, et al. Menin-MLL inhibitors reverse oncogenic activity of MLL fusion proteins in leukemia. Nature Chemical Biology. 2012 No. 8. pp. 277-284.
International Search Report and Written Opinion dated Aug. 6, 2018 for PCT/US2018/023804.
Kim, et al. Chemical Biology Investigation of Cell Death Pathways Activated by Endoplasmic Reticulum Stress Cytoprotective Modulators of ASK1. J Biological Chemistry Jan. 2009, 284(3):1593-1603.
Kühn et al. Targeting Chromatin Regulators Inhibits Leukemogenic Gene Expression in NPM1 Mutant Leukemia. Cancer Discov. 6(10):1166-1181 (2016).
Kym, et al. Screening for cardiovascular safety: a structure-activity approach for guiding lead selection of melanin concentrating hormone receptor 1 antagonists. J Med Chem. Apr. 6, 2006;49(7):2339-52.
Marx, Stephen J. Molecular genetics of multiple endocrine neoplasia types 1 and 2. Nat Rev Cancer, 5(5), pp. 367-375 (2005).
Mayer, et al. Group epitope mapping by saturation transfer difference NMR to identify segments of a ligand in direct contact with a protein receptor. J Am Chem Soc, 123(25), pp. 6108-6117 (2001).
Mosmann, Rapid colorimetric assay for cellular growth and survival: application to proliferation and cytotoxicity assays. J Immunol Methods. 65(1-2):55-63 (1983).
Nairn, J.G. Solutions, Emulsions, Suspensions and Extracts. Chapter 83 of Remington's Pharmaceutical Sciences. 18th Ed. Gennaro, Alfonso R. Mack Publishing Company, Pennsylvania. 1990. 35 pages.
National Center for Biotechnology Information. PubChem Substance Database; SID=25433807, https://pubchem.ncbi.nlm.nih.gov/substance/25433807, deposit date Jul. 30, 2007.
Ogilvy et al. Promoter elements of vav drive transgene expression in vivo throughout the hematopoietic compartment. Blood. 94(6):1855-63 (1999).
Pollock et al. Rational Design of Orthogonal Multipolar Interactions with Fluorine in Protein-Ligand Complexes. J Med Chem. Sep. 24, 2015;58(18):7465-74.
Pubchem 1323703 (SMR00018765). http://pubchem.ncbi.nlm.nih.gov/summary/summary.cgi?cid=1323703, 2007, 16 pages.
Pubchem CID 88912571. Create Date: Feb. 13, 2015. Date Accessed: Jul. 10, 2017; p. 4, compound listed.
Pubchem F1174-09147, http://pubchem.ncbi.nlm.nih.govisummary/summary.cgi?cid=711090, 2007, 13 pages.
Pubchem SID 241108205. Available date: Feb. 16, 2015 [retrieved Mar. 5, 2018]. retrieved from the Internet: < url: < a=""href="https://pubchem.ncbi.nlm.nih.gov/substance/241108205">https://pubchem.ncbi.nlm.nih.gov/substance/241108205 < /url: > .
Pubchem. CID 10631635. Oct. 25, 2006, pp. 1-12.
Pubchem. CID10614048. Oct. 25, 2006, pp. 1-9. Retrieved from the Internet < url: < a href="https://pubchem.ncbi.nlm.nih.gov/compound/10614048 >" > https://pubchem.ncbi.nlm.nih.gov/compound/10614048. < /url: < a > .
Sharma, et al. Synthesis of Thienopyrimidines and their Antipsychotic Activity. E Journal of Chemistry. 2010. 7(2):655-664.
Shi, et al. Structural insights into inhibition of the bivalent menin-MLL interaction by small molecules in leukemia. Blood. Nov. 29, 2012;120(23):4461-9.
Slany, Robert K. The molecular biology of mixed lineage leukemia. Haematologica. 94(7), pp. 984-993 (2009).
Slany. When epigenetics kills: MLL fusion proteins in leukemia. Hematol Oncol, 23(1), pp. 1-9 (2005).
Sorensen, et al. Molecular rearrangements of the MLL gene are present in most cases of infant acute myeloid leukemia and are strongly correlated with monocytic or myelomonocytic phenotypes. J Clin Invest, 93(1), pp. 429-437 (1994).
Spencer et al. Epigenomic analysis of the HOX gene loci reveals mechanisms that may control canonical expression patterns in AML and normal hematopoietic cells. Leukemia 29(6):1279-1289 (2015).

(56) References Cited

OTHER PUBLICATIONS

Svoboda et al. Tumorigenicity of Ewing sarcoma is critically dependent on the trithorax proteins MLL1 and menin. Oncotarget 38(1):458-471 (2017).
Tang et al. MLL gene amplification in acute myeloid leukemia and myelodysplastic syndromes is associated with characteristic clinicopathological findings and TP53 gene mutation. Hum Pathol. 46(1):65-73 (2015).
Xu et al. NUP98 Fusion Proteins Interact with the NSL and MLL1 Complexes to Drive Leukemogenesis. Cancer Cell 30:863-878 (2016).
Yokoyama, et al. The menin tumor suppressor protein is an essential oncogenic cofactor for MLL-associated leukemogenesis. Cell, 123(2), pp. 207-218 (2005).
Muntean AG, Hess JL. The pathogenesis of mixed-lineage leukemia. Annu Rev Pathol. 2012;7:283-301. doi: 10.1146/annurev-pathol-011811-132434. Epub Oct. 17, 2011.
PCT/US2019/053015 International Search Report and Written Opinion dated Dec. 17, 2019.
PCT/US2021/055644 International Search Report and Written Opinion dated Jan. 27, 2022.
Schembl Pubchem 12418574 (2015).
Xu et al., Design of the First-in-Class, Highly Potent Irreversible Inhibitor Targeting the Menin-MLL Protein-Protein Interaction. Angew Chem Int Ed Engl. 57(6):1601-1605 (2018).
Chung et al.: Epigenetic alterations in hematopoietic malignancies. Int J Hematol. 96(4):413-427 doi:10.1007/s12185-012-1181-z (2012).
Cierpicki et al.: Challenges and opportunities in targeting the menin-MLL interaction. Future Med Chem. 6(4):447-462. doi:10.4155/fmc.13.214 (2014).
He S. et al. High-affinity small-molecule inhibitors of the menin-mixed lineage leukemia (MLL) interaction closely mimic a natural protein-protein interaction. J Med Chem. Feb. 27, 2014;57(4):1543-56.
Kao et al.: High frequency of additional gene mutations in acute myeloid leukemia with MLL partial tandem duplication: DNMT3A mutation is associated with poor prognosis. Oncotarget. 6(32):33217-33225. doi:10.18632/oncotarget.5202 (2015).
Klaus et al.: DOT1L inhibitor EPZ-5676 displays synergistic antiproliferative activity in combination with standard of care drugs and hypomethylating agents in MLL-rearranged leukemia cells. J Pharmacol Exp Ther. 350(3):646-656. doi:10.1124/jpet.114.214577 (2014).
Rau et al.: Nucleophosmin (NPM1) mutations in adult and childhood acute myeloid leukaemia: towards definition of a new leukaemia entity. Hematol Oncol. 27(4):171-181. doi:10.1002/hon.904 (2009).
Schlenk et al.: Mutations and treatment outcome in cytogenetically normal acute myeloid leukemia. N Engl J Med. 358(18):1909-1918. doi: 10.1056/NEJMoa074306 (2008).
Verhaak et al.: Mutations in nucleophosmin (NPM1) in acute myeloid leukemia (AML): association with other gene abnormalities and previously established gene expression signatures and their favorable prognostic significance. Blood 106(12):3747-3754. doi:10.1182/blood-2005-05-2168 (2005).
Ishikawa et al., Genetic alterations in myeloid malignancies. Nippon Rinsho 74(Suppl. 8) Leukemology 1:290-297 (2016) (English description).
Muto et al., Mechanism for leukemogenesis based on chromosome translocation/gene arrangement. Nippon Rinsho 74(Suppl. 8) Leukemology 1:209-214 (2016) (English description).
Suzuki, Development of histone deacetylase inhibitors. Journal of Clinical and Experimental Medicine 266(11):855-858 (2018) (Machine translation of abstract).
Yoshimoto et al., Cancer treatments based on genetic analyses: acute myeloid leukemia. Journal of Molecular Targeted Therapy for Cancer 14(1):41-48 (2016) (English abstract).

\* cited by examiner

FIG. 1

Amino acid sequence of human menin, isoform 1 (SEQ ID NO: 1):

MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGWSPVGTKLDSSGVAFAVVGACQALGLRDVHL
ALSEDHAWVVFGPNGEQTAEVTWHGKGNEDRRGQTVNAGVAERSWLYLKGSYMRCDRKME
VAFMVCAINPSIDLHTDSLELLQLQQKLLWLLYDLGHLERYPMALGNLADLEELEPTPGR
PDPLTLYHKGIASAKTYYRDEHIYPYMYLAGYHCRNRNVREALQAWADTATVIQDYNYCR
EDEEIYKEFFEVANDVIPNLLKEAASLLEAGEERPGEQSQGTQSQGSALQDPECFAHLLR
FYDGICKWEEGSPTPVLHVGWATFLVQSLGRFEGQVRQKVRIVSREAEAAEAEEPWGEEA
REGRRRGPRRESKPEEPPPPKKPALDKGLGTGQGAVSGPPRKPPGTVAGTARGPEGGSTA
QVPAPTASPPPEGPVLTFQSEKMKGMKELLVATKINSSAIKLQLTAQSQVQMKKQKVSTP
SDYTLSFLKRQRKGL

FIG. 2

Amino acid sequence of human menin, isoform 2 (SEQ ID NO: 2):

MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGTKLDSSGVAFAVVGACQALGLRDVHLALSED
HAWVVFGPNGEQTAEVTWHGKGNEDRRGQTVNAGVAERSWLYLKGSYMRCDRKMEVAFMV
CAINPSIDLHTDSLELLQLQQKLLWLLYDLGHLERYPMALGNLADLEELEPTPGRPDPLT
LYHKGIASAKTYYRDEHIYPYMYLAGYHCRNRNVREALQAWADTATVIQDYNYCREDEEI
YKEFFEVANDVIPNLLKEAASLLEAGEERPGEQSQGTQSQGSALQDPECFAHLLRFYDGI
CKWEEGSPTPVLHVGWATFLVQSLGRFEGQVRQKVRIVSREAEAAEAEEPWGEEAREGRR
RGPRRESKPEEPPPPKKPALDKGLGTGQGAVSGPPRKPPGTVAGTARGPEGGSTAQVPAP
TASPPPEGPVLTFQSEKMKGMKELLVATKINSSAIKLQLTAQSQVQMKKQKVSTPSDYTL
SFLKRQRKGL

FIG. 3

Amino acid sequence of human menin, isoform 3 (SEQ ID NO: 3):

MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGTKLDSSGVAFAVVGACQALGLRDVHLALSED
HAWSWLYLKGSYMRCDRKMEVAFMVCAINPSIDLHTDSLELLQLQQKLLWLLYDLGHLER
YPMALGNLADLEELEPTPGRPDPLTLYHKGIASAKTYYRDEHIYPYMYLAGYHCRNRNVR
EALQAWADTATVIQDYNYCREDEEIYKEFFEVANDVIPNLLKEAASLLEAGEERPGEQSQ
GTQSQGSALQDPECFAHLLRFYDGICKWEEGSPTPVLHVGWATFLVQSLGRFEGQVRQKV
RIVSREAEAAEAEEPWGEEAREGRRRGPRRESKPEEPPPPKKPALDKGLGTGQGAVSGPP
RKPPGTVAGTARGPEGGSTAQVPAPTASPPPEGPVLTFQSEKMKGMKELLVATKINSSAI
KLQLTAQSQVQMKKQKVSTPSDYTLSFLKRQRKGL

SEQUENCE LISTING

```
<160> NUMBER OF SEQ ID NOS: 3

<210> SEQ ID NO 1
<211> LENGTH: 615
<212> TYPE: PRT
<213> ORGANISM: Homo sapiens

<400> SEQUENCE: 1

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
    130                 135                 140

Ser Phe Ile Thr Gly Trp Ser Pro Val Gly Thr Lys Leu Asp Ser Ser
145                 150                 155                 160

Gly Val Ala Phe Ala Val Val Gly Ala Cys Gln Ala Leu Gly Leu Arg
                165                 170                 175
```

-continued

```
Asp Val His Leu Ala Leu Ser Glu Asp His Ala Trp Val Val Phe Gly
            180                 185                 190
Pro Asn Gly Glu Gln Thr Ala Glu Val Thr Trp His Gly Lys Gly Asn
        195                 200                 205
Glu Asp Arg Arg Gly Gln Thr Val Asn Ala Gly Val Ala Glu Arg Ser
    210                 215                 220
Trp Leu Tyr Leu Lys Gly Ser Tyr Met Arg Cys Asp Arg Lys Met Glu
225                 230                 235                 240
Val Ala Phe Met Val Cys Ala Ile Asn Pro Ser Ile Asp Leu His Thr
                245                 250                 255
Asp Ser Leu Glu Leu Leu Gln Leu Gln Gln Lys Leu Leu Trp Leu Leu
            260                 265                 270
Tyr Asp Leu Gly His Leu Glu Arg Tyr Pro Met Ala Leu Gly Asn Leu
        275                 280                 285
Ala Asp Leu Glu Glu Leu Glu Pro Thr Pro Gly Arg Pro Asp Pro Leu
    290                 295                 300
Thr Leu Tyr His Lys Gly Ile Ala Ser Ala Lys Thr Tyr Tyr Arg Asp
305                 310                 315                 320
Glu His Ile Tyr Pro Tyr Met Tyr Leu Ala Gly Tyr His Cys Arg Asn
                325                 330                 335
Arg Asn Val Arg Glu Ala Leu Gln Ala Trp Ala Asp Thr Ala Thr Val
            340                 345                 350
Ile Gln Asp Tyr Asn Tyr Cys Arg Glu Asp Glu Ile Tyr Lys Glu
        355                 360                 365
Phe Phe Glu Val Ala Asn Asp Val Ile Pro Asn Leu Leu Lys Glu Ala
    370                 375                 380
Ala Ser Leu Leu Glu Ala Gly Glu Glu Arg Pro Gly Glu Gln Ser Gln
385                 390                 395                 400
Gly Thr Gln Ser Gln Gly Ser Ala Leu Gln Asp Pro Glu Cys Phe Ala
                405                 410                 415
His Leu Leu Arg Phe Tyr Asp Gly Ile Cys Lys Trp Glu Glu Gly Ser
            420                 425                 430
Pro Thr Pro Val Leu His Val Gly Trp Ala Thr Phe Leu Val Gln Ser
        435                 440                 445
Leu Gly Arg Phe Glu Gly Gln Val Arg Gln Lys Val Arg Ile Val Ser
    450                 455                 460
Arg Glu Ala Glu Ala Glu Ala Glu Glu Pro Trp Gly Glu Glu Ala
465                 470                 475                 480
Arg Glu Gly Arg Arg Gly Pro Arg Glu Ser Lys Pro Glu Glu
                485                 490                 495
Pro Pro Pro Lys Lys Pro Ala Leu Asp Lys Gly Leu Gly Thr Gly
            500                 505                 510
Gln Gly Ala Val Ser Gly Pro Arg Lys Pro Pro Gly Thr Val Ala
        515                 520                 525
Gly Thr Ala Arg Gly Pro Glu Gly Gly Ser Thr Ala Gln Val Pro Ala
    530                 535                 540
Pro Thr Ala Ser Pro Pro Glu Gly Pro Val Leu Thr Phe Gln Ser
545                 550                 555                 560
Glu Lys Met Lys Gly Met Lys Glu Leu Leu Val Ala Thr Lys Ile Asn
                565                 570                 575
Ser Ser Ala Ile Lys Leu Gln Leu Thr Ala Gln Ser Gln Val Gln Met
            580                 585                 590
Lys Lys Gln Lys Val Ser Thr Pro Ser Asp Tyr Thr Leu Ser Phe Leu
```

```
                595                 600                 605

Lys Arg Gln Arg Lys Gly Leu
    610                 615

<210> SEQ ID NO 2
<211> LENGTH: 610
<212> TYPE: PRT
<213> ORGANISM: Homo sapiens

<400> SEQUENCE: 2

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
130                 135                 140

Ser Phe Ile Thr Gly Thr Lys Leu Asp Ser Ser Gly Val Ala Phe Ala
145                 150                 155                 160

Val Val Gly Ala Cys Gln Ala Leu Gly Leu Arg Asp Val His Leu Ala
                165                 170                 175

Leu Ser Glu Asp His Ala Trp Val Val Phe Gly Pro Asn Gly Glu Gln
            180                 185                 190

Thr Ala Glu Val Thr Trp His Gly Lys Gly Asn Glu Asp Arg Arg Gly
        195                 200                 205

Gln Thr Val Asn Ala Gly Val Ala Glu Arg Ser Trp Leu Tyr Leu Lys
210                 215                 220

Gly Ser Tyr Met Arg Cys Asp Arg Lys Met Glu Val Ala Phe Met Val
225                 230                 235                 240

Cys Ala Ile Asn Pro Ser Ile Asp Leu His Thr Asp Ser Leu Glu Leu
                245                 250                 255

Leu Gln Leu Gln Gln Lys Leu Leu Trp Leu Leu Tyr Asp Leu Gly His
            260                 265                 270

Leu Glu Arg Tyr Pro Met Ala Leu Gly Asn Leu Ala Asp Leu Glu Glu
        275                 280                 285

Leu Glu Pro Thr Pro Gly Arg Pro Asp Pro Leu Thr Leu Tyr His Lys
    290                 295                 300

Gly Ile Ala Ser Ala Lys Thr Tyr Tyr Arg Asp Glu His Ile Tyr Pro
305                 310                 315                 320

Tyr Met Tyr Leu Ala Gly Tyr His Cys Arg Asn Arg Asn Val Arg Glu
                325                 330                 335

Ala Leu Gln Ala Trp Ala Asp Thr Ala Thr Val Ile Gln Asp Tyr Asn
            340                 345                 350
```

Tyr Cys Arg Glu Asp Glu Glu Ile Tyr Lys Glu Phe Phe Glu Val Ala
            355                 360                 365

Asn Asp Val Ile Pro Asn Leu Leu Lys Glu Ala Ala Ser Leu Leu Glu
370                 375                 380

Ala Gly Glu Glu Arg Pro Gly Glu Gln Ser Gln Gly Thr Gln Ser Gln
385                 390                 395                 400

Gly Ser Ala Leu Gln Asp Pro Glu Cys Phe Ala His Leu Leu Arg Phe
                405                 410                 415

Tyr Asp Gly Ile Cys Lys Trp Glu Gly Ser Pro Thr Pro Val Leu
            420                 425                 430

His Val Gly Trp Ala Thr Phe Leu Val Gln Ser Leu Gly Arg Phe Glu
            435                 440                 445

Gly Gln Val Arg Gln Lys Val Arg Ile Val Ser Arg Glu Ala Glu Ala
            450                 455                 460

Ala Glu Ala Glu Glu Pro Trp Gly Glu Glu Ala Arg Glu Gly Arg Arg
465                 470                 475                 480

Arg Gly Pro Arg Glu Ser Lys Pro Glu Pro Pro Pro Lys
                485                 490                 495

Lys Pro Ala Leu Asp Lys Gly Leu Gly Thr Gly Gln Gly Ala Val Ser
            500                 505                 510

Gly Pro Pro Arg Lys Pro Pro Gly Thr Val Ala Gly Thr Ala Arg Gly
            515                 520                 525

Pro Glu Gly Gly Ser Thr Ala Gln Val Pro Ala Pro Thr Ala Ser Pro
            530                 535                 540

Pro Pro Glu Gly Pro Val Leu Thr Phe Gln Ser Glu Lys Met Lys Gly
545                 550                 555                 560

Met Lys Glu Leu Leu Val Ala Thr Lys Ile Asn Ser Ser Ala Ile Lys
            565                 570                 575

Leu Gln Leu Thr Ala Gln Ser Gln Val Gln Met Lys Lys Gln Lys Val
            580                 585                 590

Ser Thr Pro Ser Asp Tyr Thr Leu Ser Phe Leu Lys Arg Gln Arg Lys
            595                 600                 605

Gly Leu
    610

<210> SEQ ID NO 3
<211> LENGTH: 575
<212> TYPE: PRT
<213> ORGANISM: Homo sapiens

<400> SEQUENCE: 3

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
            85                  90                  95

Ile Arg Gly Ala Val Asp Leu Ser Leu Tyr Pro Arg Glu Gly Gly Val
            100                 105                 110

```
Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
    130                 135                 140

Ser Phe Ile Thr Gly Thr Lys Leu Asp Ser Ser Gly Val Ala Phe Ala
145                 150                 155                 160

Val Val Gly Ala Cys Gln Ala Leu Gly Leu Arg Asp Val His Leu Ala
                165                 170                 175

Leu Ser Glu Asp His Ala Trp Ser Trp Leu Tyr Leu Lys Gly Ser Tyr
            180                 185                 190

Met Arg Cys Asp Arg Lys Met Glu Val Ala Phe Met Val Cys Ala Ile
        195                 200                 205

Asn Pro Ser Ile Asp Leu His Thr Asp Ser Leu Glu Leu Leu Gln Leu
    210                 215                 220

Gln Gln Lys Leu Leu Trp Leu Leu Tyr Asp Leu Gly His Leu Glu Arg
225                 230                 235                 240

Tyr Pro Met Ala Leu Gly Asn Leu Ala Asp Leu Glu Leu Glu Pro
                245                 250                 255

Thr Pro Gly Arg Pro Asp Pro Leu Thr Leu Tyr His Lys Gly Ile Ala
            260                 265                 270

Ser Ala Lys Thr Tyr Tyr Arg Asp Glu His Ile Tyr Pro Tyr Met Tyr
        275                 280                 285

Leu Ala Gly Tyr His Cys Arg Asn Arg Asn Val Arg Glu Ala Leu Gln
    290                 295                 300

Ala Trp Ala Asp Thr Ala Thr Val Ile Gln Asp Tyr Asn Tyr Cys Arg
305                 310                 315                 320

Glu Asp Glu Glu Ile Tyr Lys Glu Phe Phe Glu Val Ala Asn Asp Val
                325                 330                 335

Ile Pro Asn Leu Leu Lys Glu Ala Ala Ser Leu Leu Glu Ala Gly Glu
            340                 345                 350

Glu Arg Pro Gly Glu Gln Ser Gln Gly Thr Gln Ser Gln Gly Ser Ala
        355                 360                 365

Leu Gln Asp Pro Glu Cys Phe Ala His Leu Leu Arg Phe Tyr Asp Gly
    370                 375                 380

Ile Cys Lys Trp Glu Glu Gly Ser Pro Thr Pro Val Leu His Val Gly
385                 390                 395                 400

Trp Ala Thr Phe Leu Val Gln Ser Leu Gly Arg Phe Glu Gly Gln Val
                405                 410                 415

Arg Gln Lys Val Arg Ile Val Ser Arg Glu Ala Glu Ala Glu Ala
        420                 425                 430

Glu Glu Pro Trp Gly Glu Glu Ala Arg Glu Gly Arg Arg Gly Pro
        435                 440                 445

Arg Arg Glu Ser Lys Pro Glu Glu Pro Pro Pro Lys Lys Pro Ala
    450                 455                 460

Leu Asp Lys Gly Leu Gly Thr Gly Gln Gly Ala Val Ser Gly Pro Pro
465                 470                 475                 480

Arg Lys Pro Pro Gly Thr Val Ala Gly Thr Ala Arg Gly Pro Glu Gly
                485                 490                 495

Gly Ser Thr Ala Gln Val Pro Ala Pro Thr Ala Ser Pro Pro Pro Glu
            500                 505                 510

Gly Pro Val Leu Thr Phe Gln Ser Glu Lys Met Lys Gly Met Lys Glu
        515                 520                 525
```

-continued

```
Leu Leu Val Ala Thr Lys Ile Asn Ser Ser Ala Ile Lys Leu Gln Leu
    530                 535                 540

Thr Ala Gln Ser Gln Val Gln Met Lys Lys Gln Lys Val Ser Thr Pro
545                 550                 555                 560

Ser Asp Tyr Thr Leu Ser Phe Leu Lys Arg Gln Arg Lys Gly Leu
                565                 570                 575
```

METHODS FOR TREATING HEMATOLOGICAL MALIGNANCIES AND EWING'S SARCOMA

CROSS-REFERENCE

This application is a National Stage of International Application No. PCT/US2018/023804, filed Mar. 22, 2018, which claims the benefit of U.S. Provisional Application No. 62/476,710, filed Mar. 24, 2017; U.S. Provisional Application No. 62/561,119, filed Sep. 20, 2017; U.S. Provisional Application No. 62/577,640, filed Oct. 26, 2017; and U.S. Provisional Application No. 62/635,256, filed Feb. 26, 2018, each incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 19, 2018, is named 47535727601 SL.txt and is 15,924 bytes in size.

BACKGROUND OF THE INVENTION

The mixed-lineage leukemia (MLL) protein is a histone methyltransferase critical for the epigenetic regulation of gene transcription. The protein-protein interaction between MLL and menin has been shown to play an important role in the development of many diseases. The menin protein, which is encoded by the Multiple Endocrine Neoplasia (MEN) gene, is a ubiquitously expressed nuclear protein that engages in interactions with DNA processing and repair proteins, chromatin modifying proteins and numerous transcription factors (Agarwal, et al.; Horm Metab Res, 2005, 37 (6): 369-374). Menin binds to the N-terminus of MLL proteins, including MLL1, MLL2, and MLL-fusion proteins.

Aberrant expression of HOX genes has been implicated in many diseases, including hematological malignancies such as acute myeloid leukemia (AML), and Ewing's sarcoma. Certain hematological malignancies are characterized by the presence of a specific genetic abnormality or mutation, including a nucleoporin 98 (NUP98) gene fusion (Xu et al.; Cancer Cell. 2016 Dec. 12; 30 (6):863-878.), mutation in the nucleophosmin (NPM1) gene (Kühn et al.; Cancer Discov. 2016 October; 6 (10):1166-1181.), mutation in the DNA (cytosine-5)-methyltransferase 3A (DNMT3A) gene (Spencer et al.; Leukemia. 2015 June; 29 (6):1279-89.), or mixed lineage leukemia (MLL) gene amplification (Tang et al.; Hum Pathol. 2015 January; 46 (1):65-73.). Ewing's sarcoma shows aberrant overexpression of posterior HOXD genes, in particular the HOXD13 gene. Ewing's sarcoma tumors and cell lines express high levels of menin and MLL1, which are required for tumor maintenance and progression, and HOXD13 is a downstream target of MLL1 (Svoboda et al.; Oncotarget. 2017 Jan. 3; 8 (1):458-471.).

SUMMARY OF THE INVENTION

A novel therapeutic strategy is urgently needed to treat these diseases. Small molecule inhibitors that block the menin-MLL interaction are thus valuable targets for treating hematological malignancies and Ewing's sarcoma.

The present disclosure addresses a need in the art by providing compositions and methods for treating hematological malignancies, such as acute myeloid leukemia, or Ewing's sarcoma using a menin inhibitor. The menin inhibitor can inhibit the protein-protein interaction of menin with an MLL protein (e.g., MLL1, MLL2, or MLL fusion protein). The compositions and methods herein may be useful for treating diseases dependent on the activity of menin, MLL1, and/or MLL2, such as a hematological malignancy or Ewing's sarcoma.

In one aspect, the present disclosure provides a method of treating acute myeloid leukemia in a subject exhibiting a nucleoporin 98 (NUP98) gene fusion, mutation in the DNA (cytosine-5)-methyltransferase 3A (DNMT3A) gene, or mixed lineage leukemia (MLL) gene amplification, the method comprising administering to a subject in need thereof a menin inhibitor. In some embodiments, the subject exhibits a nucleoporin 98 (NUP98) gene fusion. In some embodiments, the nucleoporin 98 (NUP98) gene fusion is a gene fusion of NUP98 and a homeodomain partner gene. In some embodiments, the nucleoporin 98 (NUP98) gene fusion is a gene fusion of NUP98 and a non-homeodomain partner gene. In some embodiments, the nucleoporin 98 (NUP98) gene fusion is a gene fusion of NUP98 and a partner gene selected from HOXA9, HOXA11, HOXA13, HOXC11, HOXC13, HOXD11, HOXD13, PMX1, PMX2, HHEX, PHF23, JARID1A, NSD1, NSD3, MLL, SETBP1, LEDGF, CCDC28, HMGB3, IQCG, RAP1GDS1, ADD3, DDX10, TOP1, TOP2B, LNP1, RARG, ANKRD28, and POU1F1. In some embodiments, the subject exhibits a mutation in the DNA (cytosine-5)-methyltransferase 3A (DNMT3A) gene. In some embodiments, the mutation in the DNA (cytosine-5)-methyltransferase 3A (DNMT3A) gene is a mutation of R882. In some embodiments, the mutation in the DNA (cytosine-5)-methyltransferase 3A (DNMT3A) gene is not a mutation of R882. In some embodiments, the mutation in the DNA (cytosine-5)-methyltransferase 3A (DNMT3A) gene is a frameshift deletion, missense mutation, nonsense mutation, splice-site substitution, splice-site deletion, or whole-gene deletion. In some embodiments, the subject exhibits a mixed lineage leukemia (MLL) gene amplification.

In one aspect, the present disclosure provides a method of treating a subject having acute myeloid leukemia or acute lymphoblastic leukemia, comprising: (a) screening the subject for the presence of an MLL rearrangement, a partial tandem duplication of MLL, or elevated MEIS1 expression levels; and (b) administering a menin inhibitor to the subject if one or more of the MLL rearrangement, partial tandem duplication of MLL, or elevated MEIS1 expression levels are determined to be present.

In some embodiments, the menin inhibitor is a compound of Formula (I-A):

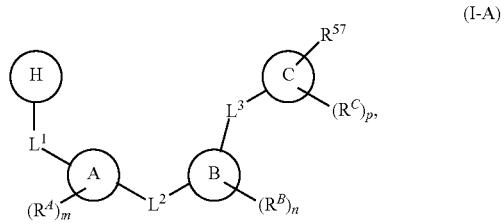

(I-A)

or a pharmaceutically acceptable salt or prodrug thereof, wherein:

H is selected from $C_{5-12}$ carbocycle and 5- to 12-membered heterocycle, each of which is optionally substituted with one or more $R^{50}$;

A is selected from bond, $C_{3-12}$ carbocycle and 3- to 12-membered heterocycle;

B is selected from $C_{3-12}$ carbocycle and 3- to 12-membered heterocycle;

C is 3- to 12-membered heterocycle;

$L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from:
halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from:
hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —C(O)N(R$^{52}$)$_2$, —C(O)NR$^{53}$R$^{54}$, —P(O)(R$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{57}$ is selected from:
halogen, —NO$_2$, —CN, —SR$^{52}$, —NR$^{53}$R$^{54}$, —S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)OR$^{52}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =S, =N(R$^{52}$); and C$_{1-10}$ alkyl, C$_{2-10}$ alkenyl, and C$_{2-10}$ alkynyl, each of which is independently substituted at each occurrence with one or more substituents selected from —NO$_2$, —CN, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$)$_2$, —P(O)(NR$^{52}$)(OR$^{52}$), —P(O)(NR$^{52}$)$_2$, =S, and =N(R$^{52}$); and R$^{58}$ is selected from hydrogen; and C$_{1-20}$ alkyl, C$_{3-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I-A), when C is azetidinylene, piperidinylene or piperazinylene and R$^{57}$ is —S(=O)$_2$R$^{58}$, —S(=O)$_2$N(R$^{52}$)$_2$, or —NR$^{52}$S(=O)$_2$R$^{52}$:

p is an integer from 1 to 6; and/or

L$^3$ is substituted with one or more R$^{50}$, wherein L$^3$ is not —CH$_2$CH(OH)—.

In some embodiments, the menin inhibitor is a compound of Formula (I-B):

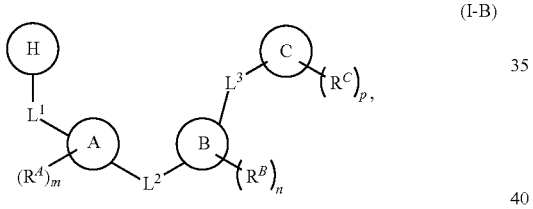

(I-B)

or a pharmaceutically acceptable salt thereof, wherein:

H is selected from C$_{5-12}$ carbocycle and 5- to 12-membered heterocycle, each of which is optionally substituted with one or more R$^{50}$;

A, B and C are each independently selected from C$_{3-12}$ carbocycle and 3- to 12-membered heterocycle;

L$^1$ and L$^2$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

L$^3$ is selected from alkylene, alkenylene, and alkynylene, each of which is substituted with one or more R$^{56}$ and optionally further substituted with one or more R$^{50}$;

R$^A$, R$^B$ and R$^C$ are each independently selected at each occurrence from R$^{50}$, or two R$^A$ groups, two R$^B$ groups or two R$^C$ groups attached to the same atom or different atoms can together optionally form a bridge or ring;

m, n and p are each independently an integer from 0 to 6;

R$^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$)$_2$, —P(O)(NR$^{52}$)(OR$^{52}$), —P(O)(NR$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$)$_2$, —P(O)(NR$^{52}$)(OR$^{52}$), —P(O)(NR$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$)$_2$, —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$)$_2$, —P(O)(NR$^{52}$)(OR$^{52}$), —P(O)(NR$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$ NR$^{53}$R$^{54}$, —C(O)R$^{52}$, —C(O)NR$^{53}$R$^{54}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(C))(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{56}$ is independently selected at each occurrence from:
—NO$_2$, —OR$^{59}$, —SR$^{52}$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-10}$ alkyl, C$_{2-10}$ alkenyl, C$_{2-10}$ alkynyl, C$_{3-12}$ carbocycle and 3- to 12-membered heterocycle, wherein each C$_{1-10}$ alkyl, C$_{2-10}$ alkenyl, and C$_{2-10}$ alkynyl in R$^{56}$ is independently optionally substituted at each occurrence with one or more substituents selected from halogen, —NO$_2$, —CN, —OR$^{59}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$ NR$^{53}$R$^{54}$, —NR$^{52}$S(=O)$_2$R$^{52}$, NR$^{52}$S(=O)$_2$N (R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)OR$^{52}$, NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), P(O)(NR$^{52}$)(OR$^{52}$), —P(O)(NR$^{52}$)$_2$, =O, =S, =N(R$^{52}$), C$_{3-12}$ carbocycle, and 3- to 12-membered heterocycle;

wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N (R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S (=O)$_2$R$^{52}$, —NR$^{52}$S(=O)$_2$N(R$^{52}$)$_2$, —NR$^{52}$S (=O)$_2$ NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and further wherein R$^{56}$ optionally forms a bond to ring C; and R$^{59}$ is independently selected at each occurrence from C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I-B), when R$^{56}$ is —CH$_3$, L$^3$ is not further substituted with —OH, —NH$_2$, or —CN.

In some embodiments, R$^C$ is selected from —C(O)R$^{52}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, =O, C$_{1-3}$ alkyl, and C$_{1-3}$ haloalkyl, or two R$^C$ groups attached to different atoms can together form a C$_{1-3}$ bridge.

In some embodiments, the menin inhibitor is a compound of Formula (II):

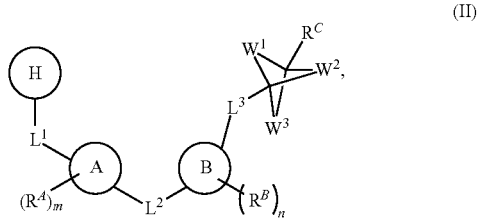

(II)

or a pharmaceutically acceptable salt or prodrug thereof, wherein:

H is selected from C$_{5-12}$ carbocycle and 5- to 12-membered heterocycle, each of which is optionally substituted with one or more R$^{59}$;

A is selected from bond, C$_{3-12}$ carbocycle and 3- to 12-membered heterocycle;

B is selected from C$_{3-12}$ carbocycle and 3- to 12-membered heterocycle;

L$^1$, L$^2$ and L$^3$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N (R$^{51}$)C(O)N(R$^{51}$)—, —N(R$^{51}$)C(O)—, —N(R$^{51}$)C(O) N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N (R$^{51}$)—, —N(R$^{51}$)C(NR$^{51}$)N(R$^{51}$)—, —S(O)$_2$-, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S (O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

R$^A$, R$^B$ and R$^C$ are each independently selected at each occurrence from R$^{50}$, or two R$^A$ groups or two R$^B$ groups attached to the same atom or different atoms can together optionally form a bridge or ring;

m and n are each independently an integer from 0 to 6;

$W^1$ is $C_{1-4}$ alkylene, optionally substituted with one or more $R^{50}$;

$W^2$ is selected from a bond; and $C_{1-4}$ alkylene, optionally substituted with one or more $R^{50}$, $W^3$ is selected from absent; and $C_{1-4}$ alkylene, optionally substituted with one or more $R^{50}$;

$R^{50}$ is independently selected at each occurrence from:
halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —$NO_2$, —CN, —$OR^{52}$, —$SR^{52}$, —N $(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from:
hydrogen, —$C(O)R^{52}$, —$C(O)OR^{52}$, —$C(O)N(R^{52})_2$, —$C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —$NO_2$, —CN, —$OR^{52}$, —$SR^{52}$, —N $(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle; and $R^{53}$ and $R^{54}$ are taken together with the nitrogen atom to which they are attached to form a heterocycle, optionally substituted with one or more $R^{50}$, wherein for a compound or salt of Formula (II), when $W^3$ is absent:
$W^1$ is $C_1$ alkylene, $W^2$ is a bond, and $L^3$ is not a bond;
$W^1$ is $C_{2-4}$ alkylene and $W^2$ is a bond; or
$W^1$ and $W^2$ are each $C_1$ alkylene and $L^3$ is not a bond, wherein each $C_1$ alkylene is independently optionally substituted with one or more $R^{50}$.

In some embodiments, the menin inhibitor is a compound of Formula (III):

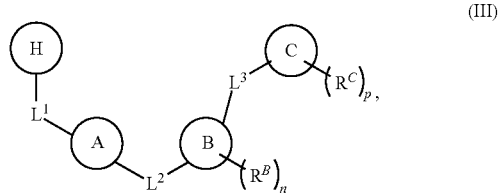

(III)

or a pharmaceutically acceptable salt or prodrug thereof, wherein:

H is selected from $C_{3-12}$ carbocycle and 3- to 12-membered heterocycle, each of which is optionally substituted with one or more $R^{50}$;

A is

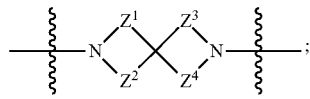

each of $Z^1$, $Z^2$, $Z^3$, and $Z^4$ is independently selected from —$C(R^{A1})(R^{A2})$—, —$C(R^{A1})(R^{A2})$—$C(R^{A1})(R^{A2})$—, —$C(O)$—, and —$C(R^{A1})(R^{A2})$—$C(O)$—, wherein no more than one of $Z^1$, $Z^2$, $Z^3$, and $Z^4$ is —$C(O)$— or —$C(R^{A1})(R^{A2})$—$C(O)$—;

B is selected from bond, $C_{3-12}$ carbocycle and 3- to 12-membered heterocycle;

C is selected from bond, $C_{3-12}$ carbocycle and 3- to 12-membered heterocycle;

L¹, L² and L³ are each independently selected from bond, —O—, —S—, —N(R⁵¹)—, —N(R⁵¹)CH₂—, —C(O)—, —C(O)O—, —OC(O)—, —OC(O)O—, —C(O)N(R⁵¹)—, —C(O)N(R⁵¹)C(O)—, —C(O)N(R⁵¹)C(O)N(R⁵¹)—, —N(R⁵¹)C(O)—, —N(R⁵¹)C(O)N(R⁵¹)—, —N(R⁵¹)C(O)O—, —OC(O)N(R⁵¹)—, —C(NR⁵¹)—, —N(R⁵¹)C(NR⁵¹)—, —C(NR⁵¹)N(R⁵¹)—, —N(R⁵¹)C(NR⁵¹)N(R⁵¹)—, —S(O)₂—, —OS(O)—, —S(O)O—, —S(O)—, —OS(O)₂—, —S(O)₂O—, —N(R⁵¹)S(O)₂—, —S(O)₂N(R⁵¹)—, —N(R⁵¹)S(O)—, —S(O)N(R⁵¹)—, —N(R⁵¹)S(O)₂N(R⁵¹)—, —N(R⁵¹)S(O)N(R⁵¹)—; alkylene, alkenylene, alkynylene, heteroalkylene, heteroalkenylene, and heteroalkynylene, each of which is optionally substituted with one or more R⁵⁰, wherein two R⁵⁰ groups attached to the same atom or different atoms of any one of L¹, L² or L³ can together optionally form a bridge or ring;

R^B is independently selected at each occurrence from R⁵⁰, or two R^B groups attached to the same atom or different atoms can together optionally form a bridge or ring;

R^C is independently selected at each occurrence from hydrogen and R⁵⁰, or two R^C groups attached to the same atom or different atoms can together optionally form a bridge or ring;

R^{A1} and R^{A2} are each independently selected at each occurrence from hydrogen and R⁵⁰;

n is an integer from 0 to 6;

p is an integer from 1 to 6;

R⁵⁰ is independently selected at each occurrence from: halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂R⁵², —NR⁵²S(=O)₂N(R⁵²)₂, —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O)OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, —P(O)(OR⁵²)(R⁵²), —P(O)(NR⁵²)(R⁵²), —NR⁵²P(O)(R⁵²), —P(O)(NR⁵²)(OR⁵²), —P(O)(NR⁵²)₂, =O, =S, =N(R⁵²);

C₁₋₁₀ alkyl, C₂₋₁₀ alkenyl, and C₂₋₁₀ alkynyl, each of which is independently optionally substituted at each occurrence with one or more substituents selected from halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂R⁵², —NR⁵²S(=O)₂N(R⁵²)₂, —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O)OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, —P(O)(OR⁵²)(R⁵²), —P(O)(NR⁵²)(R⁵²), —NR⁵²P(O)(R⁵²), —P(O)(NR⁵²)(OR⁵²), —P(O)(NR⁵²)₂, =O, =S, =N(R⁵²), C₃₋₁₂ carbocycle, and 3- to 12-membered heterocycle; and C₃₋₁₂ carbocycle and 3- to 12-membered heterocycle, wherein each C₃₋₁₂ carbocycle and 3- to 12-membered heterocycle in R⁵⁰ is independently optionally substituted with one or more substituents selected from halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂R⁵², —NR⁵²S(=O)₂N(R⁵²)₂, —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O)OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, —P(O)(OR⁵²)(R⁵²), —P(O)(NR⁵²)(R⁵²), —NR⁵²P(O)(R⁵²), —P(O)(NR⁵²)(OR⁵²), —P(O)(NR⁵²)₂, =O, =S, =N(R⁵²), C₁₋₆ alkyl, C₁₋₆ haloalkyl, C₂₋₆ alkenyl, and C₂₋₆ alkynyl;

R⁵¹ is independently selected at each occurrence from: hydrogen, —C(O)R⁵², —C(O)OR⁵², —C(O)N(R⁵²)₂, —C(O)NR⁵³R⁵⁴;

C₁₋₆ alkyl, C₂₋₆ alkenyl, and C₂₋₆ alkynyl, each of which is independently optionally substituted at each occurrence with one or more substituents selected from halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂R⁵², —NR⁵²S(=O)₂N(R⁵²)₂, —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O)OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, —P(O)(OR⁵²)(R⁵²), —P(O)(NR⁵²)(R⁵²), —NR⁵²P(O)(R⁵²), —P(O)(NR⁵²)(OR⁵²), —P(O)(NR⁵²)₂, =O, =S, =N(R⁵²), C₃₋₁₂ carbocycle and 3- to 12-membered heterocycle; and C₃₋₁₂ carbocycle and 3- to 12-membered heterocycle, wherein each C₃₋₁₂ carbocycle and 3- to 12-membered heterocycle in R⁵¹ is independently optionally substituted with one or more substituents selected from halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂R⁵², —NR⁵²S(=O)₂N(R⁵²)₂, —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O)OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, —P(O)(OR⁵²)(R⁵²), —P(O)(NR⁵²)(R⁵²), —NR⁵²P(O)(R⁵²), —P(O)(NR⁵²)(OR⁵²), —P(O)(NR⁵²)₂, =O, =S, =N(R⁵²), C₁₋₆ alkyl, C₁₋₆ haloalkyl, C₂₋₆ alkenyl, and C₂₋₆ alkynyl;

R⁵² is independently selected at each occurrence from hydrogen; and C₁₋₂₀ alkyl, C₂₋₂₀ alkenyl, C₂₋₂₀ alkynyl, 1- to 6-membered heteroalkyl, C₃₋₁₂ carbocycle, and 3- to 12-membered heterocycle, each of which is optionally substituted by halogen, —CN, —NO₂, —NH₂, —NHCH₃, —NHCH₂CH₃, =O, —OH, —OCH₃, —OCH₂CH₃, C₃₋₁₂ carbocycle, or 3- to 6-membered heterocycle; and R⁵³ and R⁵⁴ are taken together with the nitrogen atom to which they are attached to form a heterocycle, optionally substituted with one or more R⁵⁰.

In some embodiments, the menin inhibitor is a compound of Formula (IV):

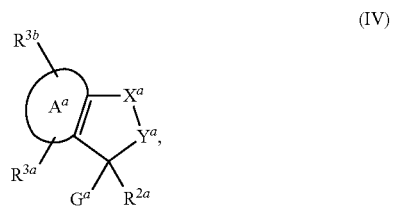

or a pharmaceutically acceptable salt or prodrug thereof, wherein:

is a fused thienyl or fused phenyl group;

$G^a$ is selected from $C_{3-12}$ carbocycle and 3- to 12-membered heterocycle, each of which is substituted with -$E^1$-$R^{4a}$ and optionally further substituted with one or more $R^{50}$;

$R^{2a}$ is selected from hydrogen, alkyl, alkenyl, optionally substituted cycloalkyl, optionally substituted aryl, optionally substituted heterocyclo, optionally substituted heteroaryl, and aralkyl;

$R^{3a}$ and $R^{3b}$ are each independently selected from hydrogen, alkyl, halo, hydroxy, cyano, amino, alkylamino, dialkylamino, haloalkyl, alkoxy, and haloalkoxy;

$X^a$—$Y^a$ is selected from —N($R^{52}$)—C(=O)—, —C(=O)—O—, —C(=O)—N($R^{52}$)—, —CH$_2$N($R^{52}$)—CH$_2$—, —C(=O)N($R^{52}$)—CH$_2$—, —CH$_2$CH$_2$—N($R^{52}$)—, —CH$_2$N($R^{52}$)—C(=O)—, and —CH$_2$O—CH$_2$—; or $X^a$ and $Y^a$ do not form a chemical bond, wherein:
$X^a$ is selected from hydrogen, alkyl, halo, hydroxy, cyano, amino, alkylamino, dialkylamino, haloalkyl, alkoxy, and haloalkoxy; and
$Y^a$ is selected from cyano, hydroxy, and —CH$_2$R$^{50}$;

$E^1$ is selected from absent, —C(=O)—, —C(=O)N($R^{52}$)—, —[C($R^{14a}$)$_2$]$_{1-5}$O—, —[C($R^{14a}$)$_2$]$_{1-5}$NR$^{52}$—, [C($R^{14a}$)$_2$]$_{1-5}$—, —CH$_2$(=O)—, and —S(=O)$_2$—;

$R^{4a}$ is selected from hydrogen, alkyl, optionally substituted alkenyl, optionally substituted alkynyl, optionally substituted cycloalkyl, optionally substituted aryl, optionally substituted heterocyclo, optionally substituted heteroaryl, aralkyl, (heterocyclo)alkyl, and (heteroaryl)alkyl;

$R^{14a}$ is selected from hydrogen and alkyl;

$R^{50}$ is independently selected at each occurrence from:
halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$ NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$ NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle; and $R^{53}$ and $R^{54}$ are taken together with the nitrogen atom to which they are attached to form a heterocycle, optionally substituted with one or more $R^{50}$.

In some embodiments, the menin inhibitor is a compound of Formula (VI):

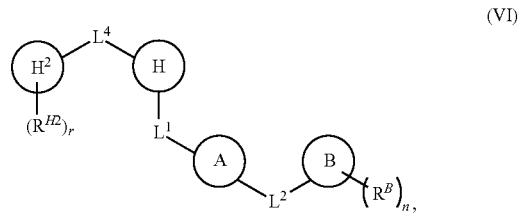

(VI)

or a pharmaceutically acceptable salt or prodrug thereof, wherein:

$H^2$ is selected from $C_{3-12}$ carbocycle and 3- to 12-membered heterocycle;

H is selected from $C_{3-12}$ carbocycle and 3- to 12-membered heterocycle, each of which is optionally substituted with one or more $R^{50}$;

A is

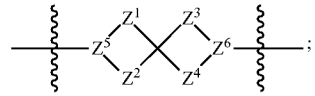

each of $Z^1$, $Z^2$, $Z^3$, and $Z^4$ is independently selected from —C($R^{41}$)($R^{42}$)—, —C($R^{41}$)($R^{42}$)—C($R^{41}$)($R^{42}$)—, —O—, —C($R^{41}$)($R^{42}$)—O—, —C($R^{41}$)($R^{42}$)—N($R^{51}$)—, —C(O)—, —C($R^{41}$)($R^{42}$)—C(O)—, and —N=C(NH$_2$)—, wherein no more than one of $Z^1$, $Z^2$, $Z^3$, and $Z^4$ is —O—, —C($R^{41}$)($R^{42}$)—O—, —C($R^{41}$)

$(R^{A2})-N(R^{51})-$, $-C(O)-$, $-C(R^{A1})(R^{A2})-C(O)-$, or $-N=C(NH_2)-$;

$Z^5$ and $Z^6$ are independently selected from $-C(R^{A3})-$ and $-N-$;

B is selected from bond, $C_{3-12}$ carbocycle and 3- to 12-membered heterocycle;

$L^1$, $L^2$ and $L^4$ are each independently selected from bond, $-O-$, $-S-$, $-N(R^{51})-$, $-N(R^{51})CH_2-$, $-C(O)-$, $-C(O)O-$, $-OC(O)-$, $-OC(O)O-$, $-C(O)N(R^{51})-$, $-C(O)N(R^{51})C(O)-$, $-C(O)N(R^{51})C(O)N(R^{51})-$, $-N(R^{51})C(O)-$, $-N(R^{51})C(O)N(R^{51})-$, $-N(R^{51})C(O)O-$, $-OC(O)N(R^{51})-$, $-C(NR^{51})-$, $-N(R^{51})C(NR^{51})-$, $-C(NR^{51})N(R^{51})-$, $-N(R^{51})C(NR^{51})N(R^{51})-$, $-S(O)_2-$, $-OS(O)-$, $-S(O)O-$, $-S(O)-$, $-OS(O)_2-$, $-S(O)_2O-$, $-N(R^{51})S(O)_2-$, $-S(O)_2N(R^{51})-$, $-N(R^{51})S(O)-$, $-S(O)N(R^{51})-$, $-N(R^{51})S(O)_2N(R^{51})-$, $-N(R^{51})S(O)N(R^{51})-$; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^4$ can together optionally form a bridge or ring;

$R^B$ is independently selected at each occurrence from hydrogen and $R^{50}$, or two $R^B$ groups attached to the same atom or different atoms can together optionally form a bridge or ring;

$R^{H2}$ is independently selected at each occurrence from $R^{50}$, or two $R^{H2}$ groups attached to the same atom or different atoms can together optionally form a bridge or ring;

$R^{A1}$, $R^{A2}$ and $R^{A3}$ are each independently selected at each occurrence from hydrogen and $R^{50}$;

n is an integer from 0 to 6;

r is an integer from 1 to 6;

$R^{50}$ is independently selected at each occurrence from:
halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2 NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $-P(O)(OR^{52})(R^{52})$, $-P(O)(NR^{52})(R^{52})$, $-NR^{52}P(O)(R^{52})$, $P(O)(NR^{52})(OR^{52})$, $-P(O)(NR^{52})_2$, $=O$, $=S$, $=N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $-P(O)(OR^{52})(R^{52})$, $-P(O)(NR^{52})(R^{52})$, $-NR^{52}P(O)(R^{52})$, $-P(O)(NR^{52})(OR^{52})$, $-P(O)(NR^{52})_2$, $=O$, $=S$, $=N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2 NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $-P(O)(OR^{52})(R^{52})$, $-P(O)(NR^{52})(R^{52})$, $-NR^{52}P(O)(R^{52})$, $-P(O)(NR^{52})(OR^{52})$, $-P(O)(NR^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from:
hydrogen, $-C(O)R^{52}$, $-C(O)OR^{52}$, $-C(O)N(R^{52})_2$, $-C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $-P(O)(OR^{52})(R^{52})$, $-P(O)(NR^{52})(R^{52})$, $-NR^{52}P(O)(R^{52})$, $-P(O)(NR^{52})(OR^{52})$, $-P(O)(NR^{52})_2$, $=O$, $=S$, $=N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2 NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $-P(O)(OR^{52})(R^{52})$, $-P(O)(NR^{52})(R^{52})$, $-NR^{52}P(O)(R^{52})$, $-P(O)(NR^{52})(OR^{52})$, $-P(O)(NR^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, $-CN$, $-NO_2$, $-NH_2$, $-NHCH_3$, $-NHCH_2CH_3$, $=O$, $-OH$, $-OCH_3$, $-OCH_2CH_3$, $C_{3-12}$ carbocycle, or 3- to 6-membered heterocycle; and $R^{53}$ and $R^{54}$ are taken together with the nitrogen atom to which they are attached to form a heterocycle, optionally substituted with one or more $R^{50}$.

In one aspect, the present disclosure provides a method of treating acute myeloid leukemia in a subject exhibiting a mutation in the nucleophosmin (NPM1) gene, the method comprising administering to a subject in need thereof a compound of Formula (I-A):

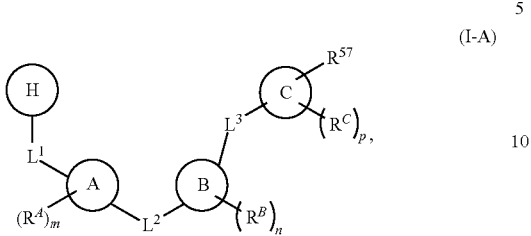

(I-A)

or a pharmaceutically acceptable salt or prodrug thereof, wherein:
H is selected from $C_{5-12}$ carbocycle and 5- to 12-membered heterocycle, each of which is optionally substituted with one or more $R^{50}$;
A is selected from bond, $C_{3-12}$ carbocycle and 3- to 12-membered heterocycle;
B is selected from $C_{3-12}$ carbocycle and 3- to 12-membered heterocycle;
C is 3- to 12-membered heterocycle;
$L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(NR$^{51}$)—, —N($R^{51}$)C(NR$^{51}$)—, —C(NR$^{51}$)N($R^{51}$)—, —N($R^{51}$)C(NR$^{51}$)N($R^{51}$)—, —S(O)$_2$-, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;
$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;
m, n and p are each independently an integer from 0 to 6;
$R^{50}$ is independently selected at each occurrence from:
hydrogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);
$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle, and 3- to 12-membered heterocycle; and
$C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;
$R^{51}$ is independently selected at each occurrence from:
hydrogen, —C(O)R$^{52}$, —C(O)OR$^{52}$, —C(O)N(R$^{52}$)$_2$, —C(O)NR$^{53}$R$^{54}$;
$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle, and 3- to 12-membered heterocycle; and
$C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;
$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{57}$ is selected from:

halogen, —NO$_2$, —CN, —SR$^{52}$, —NR$^{53}$R$^{54}$, —S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)OR$^{52}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =S, =N(R$^{52}$); and C$_{1-10}$ alkyl, C$_{2-10}$ alkenyl, and C$_{2-10}$ alkynyl, each of which is independently substituted at each occurrence with one or more substituents selected from —NO$_2$, —CN, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =S, and =N(R$^{52}$); and R$^{58}$ is selected from hydrogen; and C$_{1-20}$ alkyl, C$_{3-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I-A), when C is azetidinylene, piperidinylene or piperazinylene and R$^{57}$ is —S(=O)$_2$R$^{58}$, —S(=O)$_2$N(R$^{52}$)$_2$, or —NR$^{52}$S(=O)$_2$R$^{52}$:

p is an integer from 1 to 6; and/or

L$^3$ is substituted with one or more R$^{50}$, wherein L$^3$ is not —CH$_2$CH(OH)—.

In one aspect, the present disclosure provides a method of treating a hemtological malignancy in a subject exhibiting a mutation in the nucleophosmin (NPM1) gene, DNA (cytosine-5)-methyltransferase 3A (DNMT3A) gene, FMS-like tyrosine kinase-3 (FLT3) gene, isocitrate dehydrogenase 1 (IDH1) gene, isocitrate dehydrogenase 2 (IDH2) gene, or a combination thereof, the method comprising administering to a subject in need thereof a compound of Formula (I-A).

In one aspect, the present disclosure provides a method of treating acute myeloid leukemia in a subject exhibiting a mutation in the nucleophosmin (NPM1) gene, the method comprising administering to a subject in need thereof a compound of Formula (I-B):

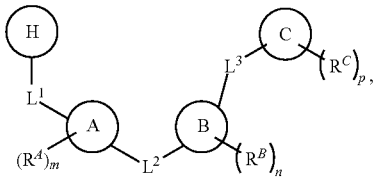

(I-B)

or a pharmaceutically acceptable salt thereof, wherein:

H is selected from C$_{5-12}$ carbocycle and 5- to 12-membered heterocycle, each of which is optionally substituted with one or more R$^{50}$;

A, B and C are each independently selected from C$_{3-12}$ carbocycle and 3- to 12-membered heterocycle;

L$^1$ and L$^2$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$-, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

L$^3$ is selected from alkylene, alkenylene, and alkynylene, each of which is substituted with one or more R$^{56}$ and optionally further substituted with one or more R$^{50}$;

R$^A$, R$^B$ and R$^C$ are each independently selected at each occurrence from R$^{50}$, or two R$^A$ groups, two R$^B$ groups or two R$^C$ groups attached to the same atom or different atoms can together optionally form a bridge or ring;

m, n and p are each independently an integer from 0 to 6;

R$^{50}$ is independently selected at each occurrence from:

halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{56}$ is independently selected at each occurrence from: —NO$_2$, —OR$^{59}$, —SR$^{52}$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$)), —P(O)(NR$^{52}$)$_2$, =O, =S, =N(R$^{52}$), C$_{1-10}$ alkyl, C$_{2-10}$ alkenyl, C$_{2-10}$ alkynyl, C$_{3-12}$ carbocycle and 3- to 12-membered heterocycle, wherein each C$_{1-10}$ alkyl, C$_{2-10}$ alkenyl, and C$_{2-10}$ alkynyl in R$^{56}$ is independently optionally substituted at each occurrence with one or more substituents selected from halogen, —NO$_2$, —CN, —OR$^{59}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle, and 3- to 12-membered heterocycle;

wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and further wherein R$^{56}$ optionally forms a bond to ring C; and R$^{59}$ is independently selected at each occurrence from C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I-B), when R$^{56}$ is —CH$_3$, L$^3$ is not further substituted with —OH, —NH$_2$, or —CN.

In one aspect, the present disclosure provides a method of treating a hematologic malignancy in a subject exhibiting a mutation in the nucleophosmin (NPM1) gene, DNA (cytosine-5)-methyltransferase 3A (DNMT3A) gene, FMS-like tyrosine kinase-3 (FLT3) gene, isocitrate dehydrogenase 1 (IDH1) gene, isocitrate dehydrogenase 2 (IDH2) gene, or a combination thereof, the method comprising administering to a subject in need thereof a compound of Formula (I-B).

In some embodiments, $R^C$ is selected from $-C(O)R^{52}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $=O$, $C_{1-3}$ alkyl, and $C_{1-3}$ haloalkyl, or two $R^C$ groups attached to different atoms can together form a $C_{1-3}$ bridge.

In one aspect, the present disclosure provides a method of treating acute myeloid leukemia in a subject exhibiting a mutation in the nucleophosmin (NPM1) gene, the method comprising administering to a subject in need thereof a compound of Formula (II):

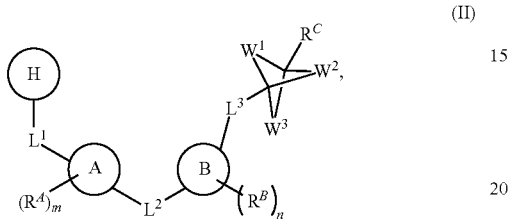

(II)

or a pharmaceutically acceptable salt or prodrug thereof, wherein:

H is selected from $C_{5-12}$ carbocycle and 5- to 12-membered heterocycle, each of which is optionally substituted with one or more $R^{50}$;

A is selected from bond, $C_{3-12}$ carbocycle and 3- to 12-membered heterocycle;

B is selected from $C_{3-12}$ carbocycle and 3- to 12-membered heterocycle;

$L^1$, $L^2$ and $L^3$ are each independently selected from bond, $-O-$, $-S-$, $-N(R^{51})-$, $-N(R^{51})CH_2-$, $-C(O)-$, $-C(O)O-$, $-OC(O)-$, $-OC(O)O-$, $-C(O)N(R^{51})-$, $-C(O)N(R^{51})C(O)-$, $-C(O)N(R^{51})C(O)N(R^{51})-$, $-N(R^{51})C(O)-$, $-N(R^{51})C(O)N(R^{51})-$, $-N(R^{51})C(O)O-$, $-OC(O)N(R^{51})-$, $-C(NR^{51})-$, $-N(R^{51})C(NR^{51})-$, $-C(NR^{51})N(R^{51})-$, $-N(R^{51})C(NR^{51})N(R^{51})-$, $-S(O)_2-$, $-OS(O)-$, $-S(O)O-$, $-S(O)-$, $-OS(O)_2-$, $-S(O)_2O-$, $-N(R^{51})S(O)_2-$, $-S(O)_2N(R^{51})-$, $-N(R^{51})S(O)-$, $-S(O)N(R^{51})-$, $-N(R^{51})S(O)_2N(R^{51})-$, $-N(R^{51})S(O)N(R^{51})-$; alkylene, alkenylene, alkynylene, heteroalkylene, heteroalkenylene, and heteroalkynylene, each of which is optionally substituted with one or more $R^{50}$;

$R^A$, $R^B$ and $R^C$ are each independently selected at each occurrence from $R^{50}$, or two $R^A$ groups or two $R^B$ groups attached to the same atom or different atoms can together optionally form a bridge or ring;

m and n are each independently an integer from 0 to 6;

$W^1$ is $C_{1-4}$ alkylene, optionally substituted with one or more $R^{50}$;

$W^2$ is selected from a bond; and $C_{1-4}$ alkylene, optionally substituted with one or more $R^{50}$;

$W^3$ is selected from absent; and $C_{1-4}$ alkylene, optionally substituted with one or more $R^{50}$, $R^{50}$ is independently selected at each occurrence from: halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, $-C(O)R^{52}$, $-C(O)OR^{52}$, $-C(O)N(R^{52})_2$, $-C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle; and R$^{53}$ and R$^{54}$ are taken together with the nitrogen atom to which they are attached to form a heterocycle, optionally substituted with one or more R$^{50}$, wherein for a compound or salt of Formula (II), when W$^3$ is absent:
W$^1$ is C$_1$ alkylene, W$^2$ is a bond, and L$^3$ is not a bond;
W$^1$ is C$_{2-4}$ alkylene and W$^2$ is a bond; or
W$^1$ and W$^2$ are each C$_1$ alkylene and L$^3$ is not a bond, wherein each C$_1$ alkylene is independently optionally substituted with one or more R$^{50}$.

In one aspect, the present disclosure provides a method of treating a hemtological malignancy in a subject exhibiting a mutation in the nucleophosmin (NPM1) gene, DNA (cytosine-5)-methyltransferase 3A (DNMT3A) gene, FMS-like tyrosine kinase-3 (FLT3) gene, isocitrate dehydrogenase 1 (IDH1) gene, isocitrate dehydrogenase 2 (IDH2) gene, or a combination thereof, the method comprising administering to a subject in need thereof a compound of Formula (II).

In one aspect, the present disclosure provides a method of treating a hematological malignancy in a subject exhibiting a mutation in the nucleophosmin (NPM1) gene, DNA (cytosine-5)-methyltransferase 3A (DNMT3A) gene, FMS-like tyrosine kinase-3 (FLT3) gene, isocitrate dehydrogenase 1 (IDH1) gene, isocitrate dehydrogenase 2 (IDH2) gene, or combination thereof, the method comprising administering to a subject in need thereof a compound of Formula (III):

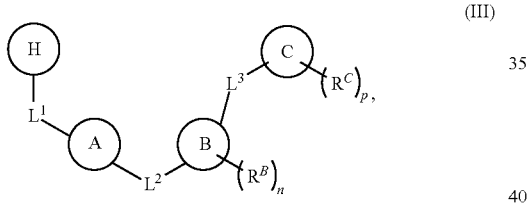

(III)

or a pharmaceutically acceptable salt or prodrug thereof, wherein:

H is selected from C$_{3-12}$ carbocycle and 3- to 12-membered heterocycle, each of which is optionally substituted with one or more R$^{50}$;

A is

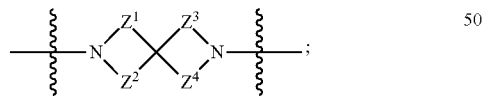

each of Z$^1$, Z$^2$, Z$^3$, and Z$^4$ is independently selected from —C(R$^{A1}$)(R$^{A2}$)—, —C(R$^{A1}$)(R$^{A2}$)—C(R$^{A1}$)(R$^{A2}$)—, —C(O)—, and —C(R$^{A1}$)(R$^{A2}$)—C(O)—, wherein no more than one of Z$^1$, Z$^2$, Z$^3$, and Z$^4$ is —C(O)— or —C(R$^{A1}$)(R$^{A2}$)—C(O)—;

B is selected from bond, C$_{3-12}$ carbocycle and 3- to 12-membered heterocycle;

C is selected from bond, C$_{3-12}$ carbocycle and 3- to 12-membered heterocycle;

L$^1$, L$^2$ and L$^3$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N (R$^{51}$)C(O)N(R$^{51}$)—, —N(R$^{51}$)C(O)—, —N(R$^{51}$)C(O) N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N (R$^{51}$)—, —N(R$^{51}$)C(NR$^{51}$)N(R$^{51}$)—, —S(O)$_{2-}$, —OS (O)—, —S(O)O—, —S(O)—, —OS(O)$_2$—, —S(O)$_2$ O—, —N(R$^{51}$)S(O)$_2$—, —S(O)$_2$N(R$^{51}$)—, —N(R$^{51}$)S (O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$, wherein two R$^{50}$ groups attached to the same atom or different atoms of any one of L$^1$, L$^2$ or L$^3$ can together optionally form a bridge or ring;

R$^B$ is independently selected at each occurrence from R$^{50}$, or two R$^B$ groups attached to the same atom or different atoms can together optionally form a bridge or ring;

R$^C$ is independently selected at each occurrence from hydrogen and R$^{50}$, or two R$^C$ groups attached to the same atom or different atoms can together optionally form a bridge or ring;

R$^{A1}$ and R$^{A2}$ are each independently selected at each occurrence from hydrogen and R$^{50}$;

n is an integer from 0 to 6;

p is an integer from 1 to 6;

R$^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S (=O)$_2$R$^{52}$, —NR$^{52}$S(=O)$_2$N(R$^{52}$)$_2$, —NR$^{52}$S (=O)$_2$ NR$^{53}$R$^{54}$, —C(O)R$^{52}$, —C(O)OR$^{52}$, —OC (O)R$^{52}$, —OC(O)OR$^{52}$, —OC(O)N(R$^{52}$)$_2$, —OC(O) NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$ R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O) OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N (R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S (=O)$_2$R$^{52}$, —NR$^{52}$S(=O)$_2$N(R$^{52}$)$_2$, —NR$^{52}$S (=O)$_2$ NR$^{53}$R$^{54}$, —C(O)R$^{52}$, —C(O)OR$^{52}$, —OC (O)R$^{52}$, —OC(O)OR$^{52}$, —OC(O)N(R$^{52}$)$_2$, —OC(O) NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)

($R^{52}$), —$NR^{52}P(O)(R^{52})$, —$P(O)(NR^{52})(OR^{52})$, —$P(O)(NR^{52})_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from:
hydrogen, —C(O)$R^{52}$, —C(O)O$R^{52}$, —C(O)N($R^{52}$)$_2$, —C(O)N$R^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^{52}$, —$SR^{52}$, —N($R^{52}$)$_2$, —$NR^{53}R^{54}$, —S(=O)$R^{52}$, —S(=O)$_2R^{52}$, —S(=O)$_2$N($R^{52}$)$_2$, —S(=O)$_2NR^{53}R^{54}$, —$NR^{52}$S(=O)$_2R^{52}$, —$NR^{52}$S(=O)$_2$N($R^{52}$)$_2$, —$NR^{52}$S(=O)$_2NR^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, —P(O)(O$R^{52}$)($R^{52}$), —P(O)(N$R^{52}$)($R^{52}$), —$NR^{52}$P(O)($R^{52}$), —P(O)(N$R^{52}$)(O$R^{52}$), —P(O)(N$R^{52}$)$_2$, =O, =S, =N($R^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —$NO_2$, —CN, —$OR^{52}$, —$SR^{52}$, —N($R^{52}$)$_2$, —$NR^{53}R^{54}$, —S(=O)$R^{52}$, —S(=O)$_2R^{52}$, —S(=O)$_2$N($R^{52}$)$_2$, —S(=O)$_2NR^{53}R^{54}$, —$NR^{52}$S(=O)$_2R^{52}$, —$NR^{52}$S(=O)$_2$N($R^{52}$)$_2$, —$NR^{52}$S(=O)$_2$ N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, —P(O)(O$R^{52}$)($R^{52}$), —P(O)(N$R^{52}$)($R^{52}$), —$NR^{52}$P(O)($R^{52}$), —P(O)(N$R^{52}$)(O$R^{52}$), —P(O)(N$R^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle; and $R^{53}$ and $R^{54}$ are taken together with the nitrogen atom to which they are attached to form a heterocycle, optionally substituted with one or more $R^{50}$.

In one aspect, the present disclosure provides a method of treating a hematological malignancy in a subject exhibiting a mutation in the nucleophosmin (NPM1) gene, DNA (cytosine-5)-methyltransferase 3A (DNMT3A) gene, FMS-like tyrosine kinase-3 (FLT3) gene, isocitrate dehydrogenase 1 (IDH1) gene, isocitrate dehydrogenase 2 (IDH2) gene, or combination thereof, the method comprising administering to a subject in need thereof a compound of Formula (IV):

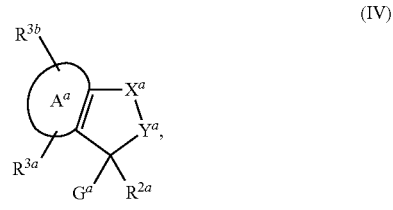

(IV)

or a pharmaceutically acceptable salt or prodrug thereof, wherein:

is a fused thienyl or fused phenyl group;

$G^a$ is selected from $C_{3-12}$ carbocycle and 3- to 12-membered heterocycle, each of which is substituted with -$E^1$-$R^{4a}$ and optionally further substituted with one or more $R^{50}$;

$R^{2a}$ is selected from hydrogen, alkyl, alkenyl, optionally substituted cycloalkyl, optionally substituted aryl, optionally substituted heterocyclo, optionally substituted heteroaryl, and aralkyl;

$R^{3a}$ and $R^{3b}$ are each independently selected from hydrogen, alkyl, halo, hydroxy, cyano, amino, alkylamino, dialkylamino, haloalkyl, alkoxy, and haloalkoxy;

$X^a$—$Y^a$ is selected from —N($R^{52}$)—C(=O)—, —C(=O)—N($R^{52}$)—, —$CH_2$N($R^{52}$)—$CH_2$—, —C(=O)N($R^{52}$)—$CH_2$—, —$CH_2CH_2$—N($R^{52}$)—, —$CH_2$N($R^{52}$)—C(=O)—, and —$CH_2$O—$CH_2$—; or $X^a$ and $Y^a$ do not form a chemical bond, wherein:
$X^a$ is selected from hydrogen, alkyl, halo, hydroxy, cyano, amino, alkylamino, dialkylamino, haloalkyl, alkoxy, and haloalkoxy; and
$Y^a$ is selected from cyano, hydroxy, and —$CH_2R^{50}$;

$E^1$ is selected from absent, —C(=O)—, —C(=O)N($R^{52}$)—, —[C($R^{14a}$)$_2$]$_{1-5}$O—, —[C($R^{14a}$)$_2$]$_{1-5}NR^{52}$—, —[C($R^{14a}$)$_2$]$_{1-5}$—, —$CH_2$(=O)—, and —S(=O)$_2$—;

$R^{4a}$ is selected from hydrogen, alkyl, optionally substituted alkenyl, optionally substituted alkynyl, optionally substituted cycloalkyl, optionally substituted aryl, optionally substituted heterocyclo, optionally substituted heteroaryl, aralkyl, (heterocyclo)alkyl, and (heteroaryl)alkyl;

$R^{14a}$ is selected from hydrogen and alkyl;

$R^{50}$ is independently selected at each occurrence from:
halogen, —$NO_2$, —CN, —$OR^{52}$, —$SR^{52}$, —N($R^{52}$)$_2$, —$NR^{53}R^{54}$, —S(=O)$R^{52}$, —S(=O)$_2R^{52}$, —S(=O)$_2$N($R^{52}$)$_2$, —S(=O)$_2NR^{53}R^{54}$, —$NR^{52}$S(=O)$_2R^{52}$, —$NR^{52}$S(=O)$_2$N($R^{52}$)$_2$, —$NR^{52}$S(=O)$_2$ N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, —P(O)(O$R^{52}$)($R^{52}$), —P(O)(N$R^{52}$)($R^{52}$), —$NR^{52}$P(O)($R^{52}$), —P(O)(N$R^{52}$)(O$R^{52}$), —P(O)(N$R^{52}$)$_2$, =O, =S, =N($R^{52}$);

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{52}$, —$SR^{52}$, —N($R^{52}$)$_2$, —$NR^{53}R^{54}$, —S(=O)$R^{52}$, —S(=O)$_2R^{52}$, —S(=O)$_2$N($R^{52}$)$_2$, —S(=O)$_2NR^{53}R^{54}$, —$NR^{52}$S(=O)$_2R^{52}$, —$NR^{52}$S(=O)$_2$N($R^{52}$)$_2$, —$NR^{52}$S(=O)$_2NR^{53}R^{54}$, —C(O)$R^{52}$, C(O)O$R^{52}$, —OC(O)$R^{52}$, —OC(O)O$R^{52}$, —OC(O)N($R^{52}$)$_2$, —OC(O)N$R^{53}R^{54}$, —$NR^{52}$C(O)$R^{52}$, —$NR^{52}$C(O)O$R^{52}$, —$NR^{52}$C(O)N($R^{52}$)$_2$, —$NR^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, —P(O)(O$R^{52}$)($R^{52}$), —P(O)(N$R^{52}$)($R^{52}$), —$NR^{52}$P(O)($R^{52}$), —P(O)(N$R^{52}$)(O$R^{52}$), —P(O)(NR$^{52}$)$_2$, =O, =S, =N(R$^{52}$), C$_{3-12}$ carbocycle, and 3- to 12-membered heterocycle; and
C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$ NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;
R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle; and
R$^{53}$ and R$^{54}$ are taken together with the nitrogen atom to which they are attached to form a heterocycle, optionally substituted with one or more R$^{50}$.

In one aspect, the present disclosure provides a method of treating a hematological malignancy in a subject exhibiting a mutation in the nucleophosmin (NPM1) gene, DNA (cytosine-5)-methyltransferase 3A (DNMT3A) gene, FMS-like tyrosine kinase-3 (FLT3) gene, isocitrate dehydrogenase 1 (IDH1) gene, isocitrate dehydrogenase 2 (IDH2) gene, or combination thereof, the method comprising administering to a subject in need thereof a compound of Formula (VI):

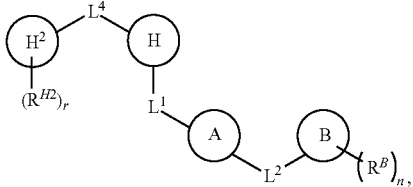

(VI)

or a pharmaceutically acceptable salt or prodrug thereof, wherein:
H$^2$ is selected from C$_{3-12}$ carbocycle and 3- to 12-membered heterocycle;
H is selected from C$_{3-12}$ carbocycle and 3- to 12-membered heterocycle, each of which is optionally substituted with one or more R$^{50}$;
A is

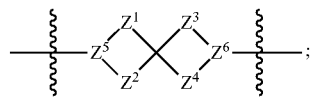

each of Z$^1$, Z$^2$, Z$^3$, and Z$^4$ is independently selected from —C(R$^{A1}$)(R$^{A2}$)—, —C(R$^{A1}$)(R$^{A2}$)—C(R$^{A1}$)(R$^{A2}$)—, —O—, —C(R$^{A1}$)(R$^{A2}$)—O—, —C(R$^{A1}$)(R$^{A2}$)—N(R$^{51}$)—, —C(O)—, —C(R$^{A1}$)(R$^{A2}$)—C(O)—, and —N=C(NH$_2$)—, wherein no more than one of Z$^1$, Z$^2$, Z$^3$, and Z$^4$ is —O—, —C(R$^{A1}$)(R$^{A2}$)—O—, —C(R$^{A1}$)(R$^{A2}$)—N(R$^{51}$)—, —C(O)—, —C(R$^{A1}$)(R$^{A2}$)—C(O)—, or —N=C(NH$_2$)—;
Z$^5$ and Z$^6$ are independently selected from —C(R$^{A3}$)— and —N—;
B is selected from bond, C$_{3-12}$ carbocycle and 3- to 12-membered heterocycle;
L$^1$, L$^2$ and L$^4$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$-, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$, wherein two R$^{50}$ groups attached to the same atom or different atoms of any one of L$^1$, L$^2$ or L$^4$ can together optionally form a bridge or ring;
R$^B$ is independently selected at each occurrence from hydrogen and R$^{50}$, or two R$^B$ groups attached to the same atom or different atoms can together optionally form a bridge or ring;
R$^{H2}$ is independently selected at each occurrence from R$^{50}$, or two R$^{H2}$ groups attached to the same atom or different atoms can together optionally form a bridge or ring;
R$^{A1}$, R$^{A2}$ and R$^{A3}$ are each independently selected at each occurrence from hydrogen and R$^{50}$,
n is an integer from 0 to 6;
r is an integer from 1 to 6;
R$^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$ NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);
C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle, and 3- to 12-membered heterocycle; and
C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle; and R$^{53}$ and R$^{54}$ are taken together with the nitrogen atom to which they are attached to form a heterocycle, optionally substituted with one or more R$^{50}$.

In some embodiments, the hematological malignancy is selected from a malignant lymphoma, a leukemia, a mature B cell neoplasm, a mature T cell and natural killer (NK) cell neoplasm, a precursor lymphoid neoplasm, Hodgkin lymphoma (HL), a plasma cell tumor, a mast cell tumor, a neoplasm of histiocytes and accessory lymphoid cells, an immunoproliferative disease, a myeloid leukemia, and a myelodysplastic syndrome (MDS). In some embodiments, the hematoligical malignancy is selected from acute myeloid leukemia, acute lymphocytic leukemia, chronic myeloid leukemia, non-Hodgkin's lymphoma, multiple myeloma, mixed lineage leukemia and myelodysplastic syndromes. In some embodiments, the hematological malignancy is aceute myeloid leukemia. In some embodiments, a relapse of the hematological malignancy is prevented.

In some embodiments, the mutation in the nucleophosmin (NPM1) gene is a mutation in exon 12 of the NPM1 gene. In some embodiments, the mutation in the nucleophosmin (NPM1) gene is a frameshift mutation. In some embodiments, the mutation in the nucleophosmin (NPM1) gene comprises an insertion of two to nine bases, such as the insertion is of four bases. In some embodiments, the insertion of four bases is selected from TCTG, CATG, CCTG, CGTG, CAGA, CTTG, and TATG. In some embodiments, the insertion is of nine bases. In some embodiments, the insertion of nine bases is selected from CTCTTGCCC and CCCTGGAGA. In some embodiments, the mutation in the nucleophosmin (NPM1) gene comprises a deletion of nucleotides 965 through 969 (GGAGG). In some embodiments, the subject further exhibits a mutation in the FLT3 gene. In some embodiments, the mutation in the FLT3 gene is an internal tandem duplication. In some embodiments, the subject further exhibits a mutation in the DNA (cytosine-5)-methyltransferase 3A (DNMT3A) gene.

In some embodiments, the mutation in the FLT3 gene is in the tyrosine kinase domain. In some embodiments, the mutation is in the nucleophosmin (NPM1) gene and FMS-like tyrosine kinase-3 (FLT3) gene. In some embodiments, the mutation is in the nucleophosmin (NPM1) gene, DNA (cytosine-5)-methyltransferase 3A (DNMT3A) gene, isocitrate dehydrogenase 2 (IDH2) gene, and FMS-like tyrosine kinase-3 (FLT3) gene. In some embodiments, the subject exhibits a mutation in the DNA (cytosine-5)-methyltransferase 3A (DNMT3A) gene.

In one aspect, the present disclosure provides a method of treating Ewing's sarcoma, the method comprising administering to a subject in need thereof a compound of Formula (I-A):

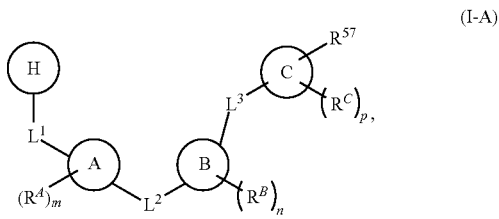

(I-A)

or a pharmaceutically acceptable salt or prodrug thereof, wherein:
H is selected from C$_{5-12}$ carbocycle and 5- to 12-membered heterocycle, each of which is optionally substituted with one or more R$^{50}$;
A is selected from bond, C$_{3-12}$ carbocycle and 3- to 12-membered heterocycle;

B is selected from $C_{3-12}$ carbocycle and 3- to 12-membered heterocycle;

C is 3- to 12-membered heterocycle;

$L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from:
hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{57}$ is selected from:
halogen, —NO$_2$, —CN, —SR$^{52}$, —NR$^{53}$R$^{54}$, —S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)OR$^{52}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =S, =N(R$^{52}$); and $C_{1-10}$ alkyl, $C_{2-10}$ alkenyl, and $C_{2-10}$ alkynyl, each of which is independently substituted at each occurrence with one or more substituents selected from —NO$_2$, —CN, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =S, and =N(R$^{52}$); and R$^{58}$ is selected from hydrogen; and C$_{1-20}$ alkyl, C$_{3-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I-A), when C is azetidinylene, piperidinylene or piperazinylene and R$^{57}$ is —S(=O)$_2$R$^{58}$, —S(=O)$_2$N(R$^{52}$)$_2$, or —NR$^{52}$S(=O)$_2$R$^{52}$:

p is an integer from 1 to 6; and/or

L$^3$ is substituted with one or more R$^{50}$, wherein L$^3$ is not —CH$_2$CH(OH)—.

In one aspect, the present disclosure provides a method of treating Ewing's sarcoma, the method comprising administering to a subject in need thereof a compound of Formula (I-B):

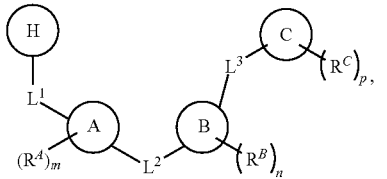

(I-B)

or a pharmaceutically acceptable salt thereof, wherein:

H is selected from C$_{5-12}$ carbocycle and 5- to 12-membered heterocycle, each of which is optionally substituted with one or more R$^{50}$;

A, B and C are each independently selected from C$_{3-12}$ carbocycle and 3- to 12-membered heterocycle;

L$^1$ and L$^2$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$-, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

L$^3$ is selected from alkylene, alkenylene, and alkynylene, each of which is substituted with one or more R$^{56}$ and optionally further substituted with one or more R$^{50}$;

R$^A$, R$^B$ and R$^C$ are each independently selected at each occurrence from R$^{50}$, or two R$^A$ groups, two R$^B$ groups or two R$^C$ groups attached to the same atom or different atoms can together optionally form a bridge or ring;

m, n and p are each independently an integer from 0 to 6;

R$^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from:
hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle and 3- to 12-membered heterocycle; and
C$_{3-12}$ carbocycle and 3- to 12-membered heterocycle,
wherein each C$_{3-12}$ carbocycle and 3- to 12-membered heterocycle in R$^{51}$ is independently optionally substituted with one or more substituents selected from halogen, —NO$_2$, —CN, —OR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$ NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{56}$ is independently selected at each occurrence from:
—NO$_2$, —OR$^{59}$, —NR$^{53}$R$^{54}$, —S(=O)R$^{52}$, —S(=O)$_2$ R$^{52}$, —S(=O)$_2$N(R$^{52}$)$_2$, —S(=O)$_2$ NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-10}$ alkyl, C$_{2-10}$ alkenyl, C$_{2-10}$ alkynyl, C$_{3-12}$ carbocycle and 3- to 12-membered heterocycle,
wherein each C$_{1-10}$ alkyl, C$_{2-10}$ alkenyl, and C$_{2-10}$ alkynyl in R$^{56}$ is independently optionally substituted at each occurrence with one or more substituents selected from halogen, —NO$_2$, —CN, —OR$^{59}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$ NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle, and 3- to 12-membered heterocycle;

wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$ NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and
further wherein R$^{56}$ optionally forms a bond to ring C; and R$^{59}$ is independently selected at each occurrence from C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle,
wherein for a compound or salt of Formula (I-B), when R$^{56}$ is —CH$_3$, L$^3$ is not further substituted with —OH, —NH$_2$, or —CN.

In some embodiments, R$^C$ is selected from —C(O)R$^{52}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, =O, C$_{1-3}$ alkyl, and C$_{1-3}$ haloalkyl, or two R$^C$ groups attached to different atoms can together form a C$_{1-3}$ bridge.

In one aspect, the present disclosure provides a method of treating Ewing's sarcoma, the method comprising administering to a subject in need thereof a compound of Formula (II):

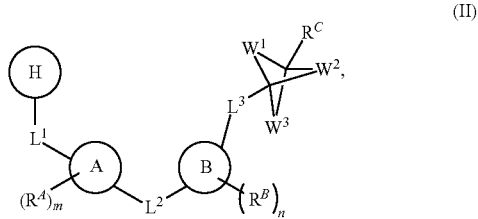

or a pharmaceutically acceptable salt or prodrug thereof, wherein:

H is selected from C$_{5-12}$ carbocycle and 5- to 12-membered heterocycle, each of which is optionally substituted with one or more R$^{50}$;

A is selected from bond, C$_{3-12}$ carbocycle and 3- to 12-membered heterocycle;

B is selected from C$_{3-12}$ carbocycle and 3- to 12-membered heterocycle;

L$^1$, L$^2$ and L$^3$ are each independently selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

$R^A$, $R^B$ and $R^C$ are each independently selected at each occurrence from $R^{50}$, or two $R^A$ groups or two $R^B$ groups attached to the same atom or different atoms can together optionally form a bridge or ring;

m and n are each independently an integer from 0 to 6;

$W^1$ is $C_{1-4}$ alkylene, optionally substituted with one or more $R^{50}$;

$W^2$ is selected from a bond; and $C_{1-4}$ alkylene, optionally substituted with one or more $R^{50}$;

$W^3$ is selected from absent; and $C_{1-4}$ alkylene, optionally substituted with one or more $R^{50}$, $R^{50}$ is independently selected at each occurrence from:
halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2 NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2 NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —$C(O)R^{52}$, —$C(O)OR^{52}$, —$C(O)N(R^{52})_2$, —$C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2 NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle; and $R^{53}$ and $R^{54}$ are taken together with the nitrogen atom to which they are attached to form a heterocycle, optionally substituted with one or more $R^{50}$, wherein for a compound or salt of Formula (II), when $W^3$ is absent:

$W^1$ is $C_1$ alkylene, $W^2$ is a bond, and $L^3$ is not a bond;

$W^1$ is $C_{2-4}$ alkylene and $W^2$ is a bond; or $W^1$ and $W^2$ are each $C_1$ alkylene and $L^3$ is not a bond, wherein each $C_1$ alkylene is independently optionally substituted with one or more $R^{50}$.

In one aspect, the present disclosure provides a method of treating Ewing's sarcoma, the method comprising administering to a subject in need thereof a compound of Formula (III):

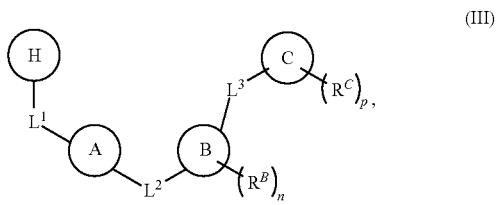

(III)

or a pharmaceutically acceptable salt or prodrug thereof, wherein:

H is selected from $C_{3-12}$ carbocycle and 3- to 12-membered heterocycle, each of which is optionally substituted with one or more $R^{50}$;

A is

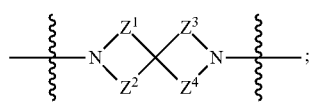

each of $Z^1$, $Z^2$, $Z^3$, and $Z^4$ is independently selected from —$C(R^{41})(R^{42})$—, —$C(R^{41})(R^{42})$—$C(R^{41})(R^{42})$—, —C(O)—, and —C($R^{41}$)($R^{42}$)—C(O)—, wherein no more than one of $Z^1$, $Z^2$, $Z^3$, and $Z^4$ is —C(O)— or —C($R^{41}$)($R^{42}$)—C(O)—;

B is selected from bond, $C_{3-12}$ carbocycle and 3- to 12-membered heterocycle;

C is selected from bond, $C_{3-12}$ carbocycle and 3- to 12-membered heterocycle;

$L^1$, $L^2$ and $L^3$ are each independently selected from bond, —O—, —S—, —N($R^{51}$)—, —N($R^{51}$)$CH_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;

$R^B$ is independently selected at each occurrence from $R^{50}$, or two $R^B$ groups attached to the same atom or different atoms can together optionally form a bridge or ring;

$R^C$ is independently selected at each occurrence from hydrogen and $R^{50}$, or two $R^C$ groups attached to the same atom or different atoms can together optionally form a bridge or ring;

$R^{41}$ and $R^{42}$ are each independently selected at each occurrence from hydrogen and $R^{50}$;

n is an integer from 0 to 6;

p is an integer from 1 to 6;

$R^{50}$ is independently selected at each occurrence from: halogen, —$NO_2$, —CN, —$OR^{52}$, —$SR^{52}$, —N($R^{52}$)$_2$, —$NR^{53}R^{54}$, —S(=O)$R^{52}$, —S(=O)$_2R^{52}$, —S(=O)$_2$N($R^{52}$)$_2$, —S(=O)$_2NR^{53}R^{54}$, —$NR^{52}$S(=O)$_2R^{52}$, —$NR^{52}$S(=O)$_2$N($R^{52}$)$_2$, —$NR^{52}$S(=O)$_2$ $NR^{53}R^{54}$, —C(O)$R^{52}$, —C(O)$OR^{52}$, —OC(O)$R^{52}$, —OC(O)$OR^{52}$, —OC(O)N($R^{52}$)$_2$, —OC(O)$NR^{53}R^{54}$, —$NR^{52}$C(O)$R^{52}$, —$NR^{52}$C(O)$OR^{52}$, —$NR^{52}$C(O)N($R^{52}$)$_2$, —$NR^{52}$C(O)$NR^{53}R^{54}$, —C(O)N($R^{52}$)$_2$, —C(O)$NR^{53}R^{54}$, —P(O)($OR^{52}$)$_2$, —P(O)($R^{52}$)$_2$, —P(O)($OR^{52}$)($R^{52}$), —P(O)($NR^{52}$)($R^{52}$), —$NR^{52}$P(O)($R^{52}$), —P(O)($NR^{52}$)($OR^{52}$), —P(O)($NR^{52}$)$_2$, =O, =S, =N($R^{52}$);

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{52}$, $SR^{52}$, —N($R^{52}$)$_2$, —$NR^{53}R^{54}$, —S(=O)$R^{52}$, —S(=O)$_2$ $R^{52}$, —S(=O)$_2$N($R^{52}$)$_2$, —S(=O)$_2NR^{53}R^{54}$, —$NR^{52}$S(=O)$_2R^{52}$, —$NR^{52}$S(=O)$_2$N($R^{52}$)$_2$, —$NR^{52}$S(=O)$_2NR^{53}R^{54}$, —C(O)$R^{52}$, —C(O)$OR^{52}$, —OC(O)$R^{52}$, —OC(O)$OR^{52}$, —OC(O)N($R^{52}$)$_2$, —OC(O)$NR^{53}R^{54}$, —$NR^{52}$C(O)$R^{52}$, —$NR^{52}$C(O)$OR^{52}$, —$NR^{52}$C(O)N($R^{52}$)$_2$, —$NR^{52}$C(O)$NR^{53}R^{54}$, —C(O)N($R^{52}$)$_2$, —C(O)$NR^{53}R^{54}$, —P(O)($OR^{52}$)$_2$, —P(O)($R^{52}$)$_2$, —P(O)($OR^{52}$)($R^{52}$), —P(O)($NR^{52}$)($R^{52}$), —$NR^{52}$P(O)($R^{52}$), —P(O)($NR^{52}$)($OR^{52}$), —P(O)($NR^{52}$)$_2$, =O, =S, =N($R^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —$NO_2$, —CN, —$OR^{52}$, —$SR^{52}$, —N($R^{52}$)$_2$, —$NR^{53}R^{54}$, —S(=O)$R^{52}$, —S(=O)$_2R^{52}$, —S(=O)$_2$N($R^{52}$)$_2$, —S(=O)$_2NR^{53}R^{54}$, —$NR^{52}$S(=O)$_2R^{52}$, —$NR^{52}$S(=O)$_2$N($R^{52}$)$_2$, —$NR^{52}$S(=O)$_2$ $NR^{53}R^{54}$, —C(O)$R^{52}$, —C(O)$OR^{52}$, —OC(O)$R^{52}$, —OC(O)$OR^{52}$, —OC(O)N($R^{52}$)$_2$, —OC(O)$NR^{53}R^{54}$, —$NR^{52}$C(O)$R^{52}$, —$NR^{52}$C(O)$OR^{52}$, —$NR^{52}$C(O)N($R^{52}$)$_2$, —$NR^{52}$C(O)$NR^{53}R^{54}$, —C(O)N($R^{52}$)$_2$, —C(O)$NR^{53}R^{54}$, —P(O)($OR^{52}$)$_2$, —P(O)($R^{52}$)$_2$, —P(O)($OR^{52}$)($R^{52}$), —P(O)($NR^{52}$)($R^{52}$), —$NR^{52}$P(O)($R^{52}$), —P(O)($NR^{52}$)($OR^{52}$), —P(O)($NR^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)$R^{52}$, —C(O)$OR^{52}$, —C(O)N($R^{52}$)$_2$, —C(O)$NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^{52}$, —$SR^{52}$, —N($R^{52}$)$_2$, —$NR^{53}R^{54}$, —S(=O)$R^{52}$, —S(=O)$_2$ $R^{52}$, —S(=O)$_2$N($R^{52}$)$_2$, —S(=O)$_2NR^{53}R^{54}$, —$NR^{52}$S(=O)$_2R^{52}$, —$NR^{52}$S(=O)$_2$N($R^{52}$)$_2$, —$NR^{52}$S(=O)$_2NR^{53}R^{54}$, —C(O)$R^{52}$, —C(O)$OR^{52}$, —OC(O)$R^{52}$, —OC(O)$OR^{52}$, —OC(O)N($R^{52}$)$_2$, —OC(O)$NR^{53}R^{54}$, —$NR^{52}$C(O)$R^{52}$, —$NR^{52}$C(O) $OR^{52}$, —$NR^{52}$C(O)N($R^{52}$)$_2$, —$NR^{52}$C(O)$NR^{53}R^{54}$, —C(O)N($R^{52}$)$_2$, —C(O)$NR^{53}R^{54}$, —P(O)($OR^{52}$)$_2$, —P(O)($R^{52}$)$_2$, —P(O)($OR^{52}$)($R^{52}$), —P(O)($NR^{52}$)($R^{52}$), —$NR^{52}$P(O)($R^{52}$), —P(O)($NR^{52}$)($OR^{52}$), —P(O)($NR^{52}$)$_2$, =O, =S, =N($R^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —$NO_2$, —CN, —$OR^{52}$, —$SR^{52}$, —N($R^{52}$)$_2$, —$NR^{53}R^{54}$, —S(=O)$R^{52}$, —S(=O)$_2R^{52}$, —S(=O)$_2$N($R^{52}$)$_2$, —S(=O)$_2NR^{53}R^{54}$, —$NR^{52}$S(=O)$_2R^{52}$, —$NR^{52}$S(=O)$_2$N($R^{52}$)$_2$, —$NR^{52}$S(=O)$_2$ $NR^{53}R^{54}$, —C(O)$R^{52}$, —C(O)$OR^{52}$, —OC(O)$R^{52}$, —OC(O)$OR^{52}$, —OC(O)N($R^{52}$)$_2$, —OC(O)$NR^{53}R^{54}$, —$NR^{52}$C(O)$R^{52}$, —$NR^{52}$C(O)$OR^{52}$, —$NR^{52}$C(O)N($R^{52}$)$_2$, —$NR^{52}$C(O)$NR^{53}R^{54}$, —C(O)N($R^{52}$)$_2$, —C(O)$NR^{53}R^{54}$, —P(O)($OR^{52}$)$_2$, —P(O)($R^{52}$)$_2$, —P(O)($OR^{52}$)($R^{52}$), —P(O)($NR^{52}$)($R^{52}$), —$NR^{52}$P(O)($R^{52}$), —P(O)($NR^{52}$)($OR^{52}$), —P(O)($NR^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle; and $R^{53}$ and $R^{54}$ are taken together with the nitrogen atom to which they are attached to form a heterocycle, optionally substituted with one or more $R^{50}$.

In one aspect, the present disclosure provides a method of treating Ewing's sarcoma, the method comprising administering to a subject in need thereof a compound of Formula (IV):

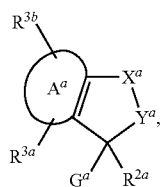
(IV)

or a pharmaceutically acceptable salt or prodrug thereof, wherein:

is a fused thienyl or fused phenyl group;

$G^a$ is selected from $C_{3-12}$ carbocycle and 3- to 12-membered heterocycle, each of which is substituted with -$E^1$-$R^{4a}$ and optionally further substituted with one or more $R^{50}$;

$R^{2a}$ is selected from hydrogen, alkyl, alkenyl, optionally substituted cycloalkyl, optionally substituted aryl, optionally substituted heterocyclo, optionally substituted heteroaryl, and aralkyl;

$R^{3a}$ and $R^{3b}$ are each independently selected from hydrogen, alkyl, halo, hydroxy, cyano, amino, alkylamino, dialkylamino, haloalkyl, alkoxy, and haloalkoxy;

$X^a$—$Y^a$ is selected from —N($R^{52}$)—C(=O)—, —C(=O)—O—, —C(=O)—N($R^{52}$)—, —CH$_2$N($R^{52}$)—CH$_2$—, —C(=O)N($R^{52}$)—CH$_2$—, —CH$_2$CH$_2$—N($R^{52}$)—, —CH$_2$N($R^{52}$)—C(=O)—, and CH$_2$O—CH$_2$—; or $X^a$ and $Y^a$ do not form a chemical bond, wherein:

$X^a$ is selected from hydrogen, alkyl, halo, hydroxy, cyano, amino, alkylamino, dialkylamino, haloalkyl, alkoxy, and haloalkoxy; and $Y^a$ is selected from cyano, hydroxy, and —CH$_2$R$^{50}$;

$E^1$ is selected from absent, —C(=O)—, —C(=O)N($R^{52}$)—, —[C($R^{14a}$)$_2$]$_{1-5}$O—, —[C($R^{14a}$)$_2$]$_{1-5}$NR$^{52}$—, —[C($R^{14a}$)$_2$]$_{1-5}$—, —CH$_2$(=O)—, and —S(=O)$_2$—;

$R^{4a}$ is selected from hydrogen, alkyl, optionally substituted alkenyl, optionally substituted alkynyl, optionally substituted cycloalkyl, optionally substituted aryl, optionally substituted heterocyclo, optionally substituted heteroaryl, aralkyl, (heterocyclo)alkyl, and (heteroaryl)alkyl;

$R^{14a}$ is selected from hydrogen and alkyl;

$R^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle; and $R^{53}$ and $R^{54}$ are taken together with the nitrogen atom to which they are attached to form a heterocycle, optionally substituted with one or more $R^{50}$.

In one aspect, the present disclosure provides a method of treating Ewing's sarcoma, the method comprising administering to a subject in need thereof a compound of Formula (VI):

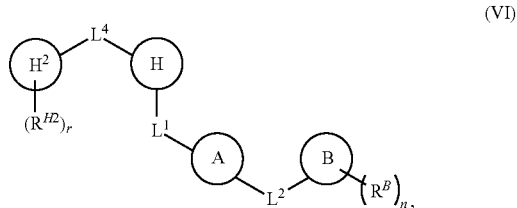
(VI)

or a pharmaceutically acceptable salt or prodrug thereof, wherein:

$H^2$ is selected from $C_{3-12}$ carbocycle and 3- to 12-membered heterocycle;

H is selected from $C_{3-12}$ carbocycle and 3- to 12-membered heterocycle, each of which is optionally substituted with one or more $R^{50}$;

A is

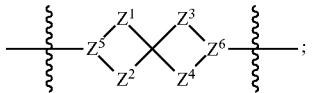

each of $Z^1$, $Z^2$, $Z^3$, and $Z^4$ is independently selected from —C($R^{A1}$)($R^{A2}$)—, —C($R^{A1}$)($R^{A2}$)—C($R^{A1}$)($R^{A2}$)—, —O—, —C($R^{A1}$)($R^{A2}$)—O—, —C($R^{A1}$)($R^{A2}$)—N($R^{51}$)—, —C(O)—, —C($R^{A1}$)($R^{A2}$)—C(O)—, and —N=C(NH$_2$)—, wherein no more than one of $Z^1$, $Z^2$, $Z^3$, and $Z^4$ is —O—, —C($R^{A1}$)($R^{A2}$)—O—, —C($R^{A1}$)($R^{A2}$)—N($R^{51}$)—, —C(O)—, —C($R^{A1}$)($R^{A2}$)—C(O)—, or —N=C(NH$_2$)—;

$Z^5$ and $Z^6$ are independently selected from —C($R^{A3}$)— and —N—;

B is selected from bond, $C_{3-12}$ carbocycle and 3- to 12-membered heterocycle;

$L^1$, $L^2$ and $L^4$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^4$ can together optionally form a bridge or ring;

$R^B$ is independently selected at each occurrence from hydrogen and $R^{50}$, or two $R^B$ groups attached to the same atom or different atoms can together optionally form a bridge or ring;

$R^{H2}$ is independently selected at each occurrence from $R^{50}$, or two $R^{H2}$ groups attached to the same atom or different atoms can together optionally form a bridge or ring;

$R^{A1}$, $R^{A2}$ and $R^{A3}$ are each independently selected at each occurrence from hydrogen and $R^{50}$, n is an integer from 0 to 6;

r is an integer from 1 to 6;

$R^{50}$ is independently selected at each occurrence from: halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, —C(O)N($R^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle; and R$^{53}$ and R$^{54}$ are taken together with the nitrogen atom to which they are attached to form a heterocycle, optionally substituted with one or more R$^{50}$.

In some embodiments, the subject exhibits an EWSR1-FLI1 gene fusion, EWSR1-ERG gene fusion, or EWSR1-FEV gene fusion. In some embodiments, the subject exhibits a FUS-NCATc2 gene fusion, CIC-FOXO4 gene fusion, or ETV6-NTRK3 gene fusion. In some embodiments, the subject exhibits a mutation in a STAG2 gene, mutation in a TP53 gene, or CDKN2A deletion.

In some embodiments, for a compound of Formula (I-A) or Formula (I-B), C is 5- to 12-membered heterocycle, wherein the heterocycle comprises at least one nitrogen atom. In some embodiments, the heterocycle is saturated. In some embodiments, the heterocycle is selected from piperidinyl and piperazinyl. In some embodiments, C is selected from:

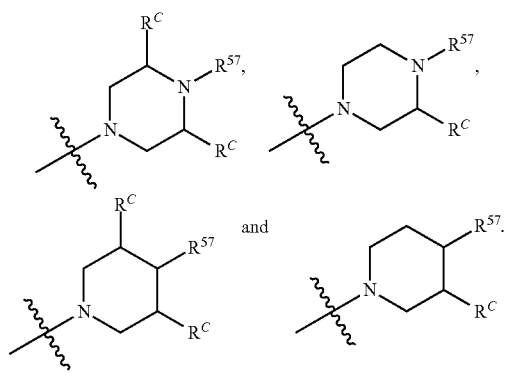

In some embodiments, R$^{57}$ is selected from —S(=O)R$^{52}$, —S(=O)$_2$R$^{58}$, —S(=O)$_2$N(R$^{52}$)$_2$, and —NR$^{52}$S(=O)$_2$R$^{52}$. In some embodiments, C is selected from:

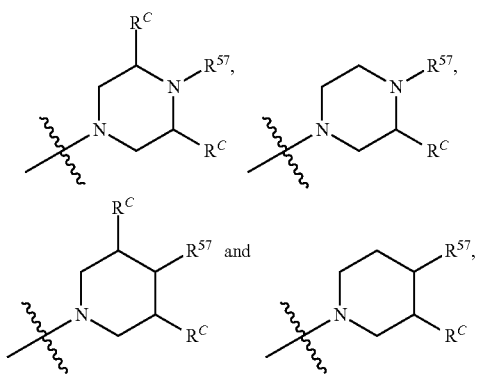

wherein R$^{57}$ is selected from —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$; and C$_{1-10}$ alkyl substituted with one or more substituents selected from —S(=O)R$^{52}$, —S(=O)$_2$R$^{52}$, —S(=O)$_2$N(R$^{52}$)$_2$, —S(=O)$_2$NR$^{53}$R$^{54}$, and —NR$^{52}$S(=O)$_2$R$^{52}$. In some embodiments, for a compound of Formula (I-A) or Formula (I-B), R$^{57}$ is selected from —S(=O)R$^{52}$, —S(=O)$_2$R$^{52}$, —S(=O)$_2$N(R$^{52}$)$_2$, and —NR$^{52}$S(=O)$_2$R$^{52}$. In some embodiments, for a compound of Formula (I-A) or Formula (I-B), R$^{57}$ is selected from —S(=O)CH$_3$, —S(=O)$_2$CH$_3$, —S(=O)$_2$NH$_2$, —NHS(=O)$_2$CH$_3$, and —S(=O)$_2$NHCH$_3$. In some embodiments, for a compound of Formula (I-A) or Formula (I-B), R$^C$ is selected from C$_{1-3}$ alkyl and C$_{1-3}$ haloalkyl.

In some embodiments, for a compound of Formula (I-A), Formula (I-B), Formula (II), or Formula (III), H is 5- to 12-membered heterocycle, optionally substituted with one or more R$^{50}$; A is 3- to 12-membered heterocycle; and B is 3- to 12-membered heterocycle.

In some embodiments, for a compound of Formula (I-A), Formula (I-B), Formula (II) or Formula (III), H is 6- to 12-membered bicyclic heterocycle, optionally substituted with one or more R$^{50}$. In some embodiments, H is thienopyrimidinyl, optionally substituted with one or more R$^{50}$.

In some embodiments, for a compound of Formula (I-A), Formula (I-B), Formula (II), or Formula (III), H is

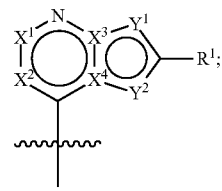

X$^1$ and X$^2$ are each independently selected from CR$^2$ and N; X$^3$ and X$^4$ are each independently selected from C and N; Y$^1$ and Y$^2$ are each independently selected from CR$^3$, N, NR$^4$, O, and S; R$^1$, R$^2$ and R$^3$ are each independently selected at each occurrence from hydrogen and R$^{50}$; and R$^4$ is selected from R$^{51}$. In some embodiments, X$^3$ and X$^4$ are each C. In some embodiments, X$^1$ is CR$^2$, and R$^2$ is selected from hydrogen, halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl. In some embodiments, X$^1$ is CR$^2$, and R$^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-N(R$^{52}$)$_2$, C$_{1-3}$ haloalkyl, C$_{2-3}$ alkenyl, and C$_{2-3}$ alkynyl. In some embodiments, X$^2$ is N. In some embodiments, Y$^2$ is CR$^3$, and R$^3$ is selected from hydrogen, halogen, —OH, —N(R$^{52}$)$_2$, —CN, —C(O)OR$^{52}$, C$_{1-3}$ alkyl, and C$_{1-3}$ haloalkyl. In some embodiments, R$^1$ is C$_{1-3}$ haloalkyl.

In some embodiments, for a compound of Formula (I-A), Formula (I-B), or Formula (II), A is 5- to 8-membered heterocycle. In some embodiments, A is 6-membered monocyclic heterocycle. In some embodiments, the heterocycle comprises at least one nitrogen atom. In some embodiments, A is selected from piperidinylene and piperazinylene. In some embodiments, A is

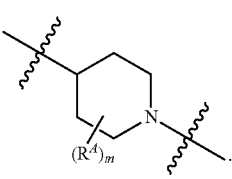

In some embodiments, for a compound of Formula (I-A), Formula (I-B), Formula (II), Formula (III), or Formula (VI), A is 7- to 12-membered spirocyclic heterocycle or $C_{7-12}$ spirocyclic carbocycle. In some embodiments, A is 7- to 12-membered spirocyclic heterocycle, such as 7- to 10-membered spirocyclic heterocycle. In some embodiments, A is

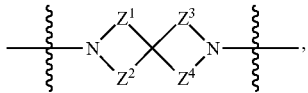

wherein each of $Z^1$, $Z^2$, $Z^3$, and $Z^4$ is independently selected from —C($R^{A1}$)($R^{A2}$)—, —C($R^{A1}$)($R^{A2}$)—C($R^{A1}$)($R^{A2}$)—, —C(O)—, C(O)—, and —C($R^{A1}$)($R^{A2}$)—C(O)—, wherein no more than one of $Z^1$, $Z^2$, $Z^3$, and $Z^4$ is —C(O)— or —C($R^{A1}$)($R^{A2}$)—C(O)—; and $R^{A1}$ and $R^{A2}$ are each independently selected at each occurrence from hydrogen and $R^{50}$. In some embodiments, $R^{A1}$ and $R^{A2}$ are each independently selected at each occurrence from hydrogen, halo, $C_{1-4}$ alkyl, $C_{1-4}$ alkoxy, $C_{1-4}$ haloalkyl, $C_{1-4}$ haloalkoxy, —CN, —NO$_2$, and —OH. In some embodiments, A is selected from:

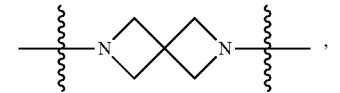

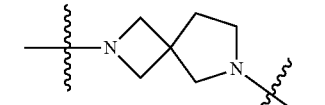

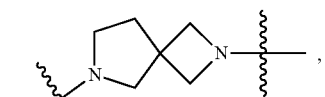

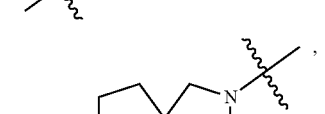

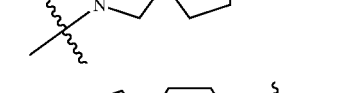

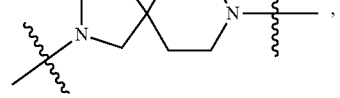

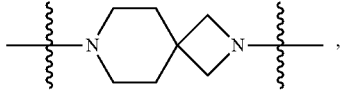

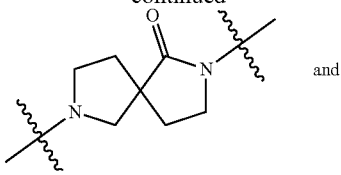 and

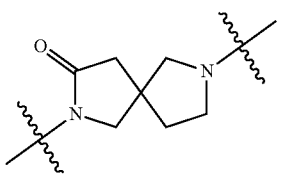.

In some embodiments, for a compound of Formula (I-A), Formula (I-B), Formula (II), Formula (III), or Formula (VI), B is 6- to 12-membered bicyclic heterocycle. In some embodiments, the heterocycle comprises at least one nitrogen atom. In some embodiments, B is indolylene. In some embodiments, B is

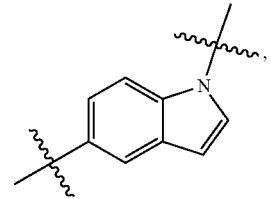 [SMILES: *c1ccc2c(ccn2*)c1]

optionally substituted with one or more $R^B$.

In some embodiments, for a compound of Formula (I-A), Formula (I-B), or Formula (II), H is thienopyrimidinyl substituted with one or more $R^{50}$; A is selected from piperidinylene and piperazinylene; and B is indolylene.

In some embodiments, for a compound of Formula (I-A), Formula (I-B), or Formula (II), H is substituted with —CH$_2$CF$_3$.

In some embodiments, for a compound of Formula (I-A), Formula (I-B), or Formula (II), m is 0. In some embodiments, for a compound of Formula (I-A), Formula (I-B), Formula (II), Formula (III), or Formula (VI), n is an integer from 1 to 3.

In some embodiments, for a compound of Formula (I-A), Formula (I-B), Formula (II), Formula (III), or Formula (VI), $L^1$ comprises less than 10 atoms. In some embodiments, $L^1$ is —N($R^{51}$)—.

In some embodiments, for a compound of Formula (I-A), Formula (I-B), Formula (II), Formula (III), or Formula (VI), $L^2$ comprises less than 10 atoms. In some embodiments, $L^2$ is $C_{1-4}$ alkylene, optionally substituted with one or more $R^{50}$. In some embodiments, $L^2$ is selected from —CH$_2$—, —N($R^{51}$)CH$_2$—, —N($R^{51}$)C(O)—, and —N($R^{51}$)S(O)$_2$—.

In some embodiments, for a compound of Formula (I-A), Formula (I-B), Formula (II), or Formula (III), $L^3$ comprises less than 20 atoms. In some embodiments, $L^3$ is $C_{1-6}$ alkylene, optionally substituted with one or more $R^{50}$. In some embodiments, $L^3$ is $C_{1-4}$ alkylene, optionally substituted with one or more $R^{50}$. In some embodiments, $L^3$ is —CH$_2$—. In some embodiments, $L^3$ is $C_2$ alkylene substituted with at least one $C_{1-3}$ alkyl or $C_{1-3}$ haloalkyl, and optionally further substituted with one or more $R^{50}$. In some embodiments, $L^3$ is substituted with =O, $C_{1-6}$ alkyl, $C_{1-6}$ haloalkyl, $C_{1-3}$ alkyl(cyclopropyl), $C_{1-3}$ alkyl(NR$^{52}$C(O)

$R^{52}$) or —O($C_{1-6}$ alkyl). In some embodiments, $L^3$ is substituted with —$CH_3$. In some embodiments, $L^3$ is selected from

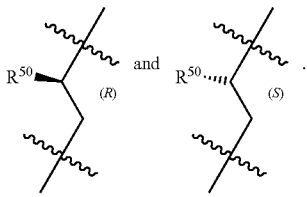

In some embodiments, $R^{50}$ is methyl. In some embodiments, $L^3$ is selected from

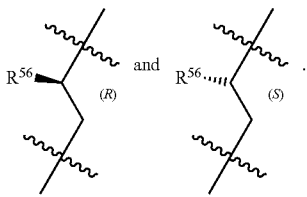

In some embodiments, $R^{56}$ is methyl.

In some embodiments, for a compound of Formula (I-A), Formula (I-B), or Formula (II), H is thienopyrimidinyl, optionally substituted with one or more $R^{50}$; A is 3- to 12-membered heterocycle; B is 6- to 12-membered bicyclic heterocycle; m is an integer from 0 to 3; and n is an integer from 1 to 3.

In some embodiments, for a compound of Formula (I-A),
H is thienopyrimidinyl, optionally substituted with one or more $R^{50}$;
A is selected from piperidinylene and piperazinylene;
B is indolylene;
$L^1$ and $L^2$ are each independently selected from —O—, —S—, —NH—, and —$CH_2$—;
$L^3$ is selected from bond, —O—, —S—, —N($R^{51}$)—, —N($R^{51}$)$CH_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_{2-}$, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of $L^3$ can together optionally form a ring;
$R^A$, $R^B$ and $R^C$ are each independently selected at each occurrence from $R^{50}$, or two $R^A$ groups, two $R^B$ groups or two $R^C$ groups attached to the same atom or different atoms can together optionally form a ring;
m is an integer from 0 to 3;
n is an integer from 1 to 3;
p is an integer from 0 to 6;
$R^{57}$ is selected from:

—S(=O)$R^{52}$, —S(=O)$_2R^{58}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —N$R^{52}$C(O)N($R^{52}$)$_2$, —N$R^{52}$C(O)N$R^{53}R^{54}$, —C(O)NH($C_{1-6}$ alkyl), —C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, —P(O)(O$R^{52}$)($R^{52}$), —P(O)(N$R^{52}$)($R^{52}$), —N$R^{52}$P(O)($R^{52}$), —P(O)(N$R^{52}$)(O$R^{52}$), —P(O)(N$R^{52}$)$_2$; and
$C_{1-10}$ alkyl, $C_{2-10}$ alkenyl, and $C_{2-10}$ alkynyl, each of which is independently substituted at each occurrence with one or more substituents selected from —S(=O)$R^{52}$, —S(=O)$_2R^{58}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —N$R^{52}$C(O)N($R^{52}$)$_2$, —N$R^{52}$C(O)N$R^{53}R^{54}$, —C(O)NH($C_{1-6}$ alkyl), —C(O)N$R^{53}R^{54}$, —P(O)(O$R^{52}$)$_2$, and —P(O)($R^{52}$)$_2$, —P(O)(O$R^{52}$)($R^{52}$), —P(O)(N$R^{52}$)($R^{52}$), —N$R^{52}$P(O)($R^{52}$), —P(O)(N$R^{52}$)(O$R^{52}$), —P(O)(N$R^{52}$)$_2$; and
$R^{58}$ is selected from hydrogen; and $C_{1-20}$ alkyl, $C_{3-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle.

In some embodiments, for a compound of Formula (I-B),
H is thienopyrimidinyl, optionally substituted with one or more $R^{50}$;
A is selected from piperidinylene and piperazinylene;
B is indolylene;
$L^1$ and $L^2$ are each independently selected from —O—, —S—, —NH—, and —$CH_2$—;
$L^3$ is selected from $C_{1-6}$ alkylene, $C_{2-6}$ alkenylene, and $C_{2-6}$ alkynylene, each of which is substituted with one or more $R^{56}$ and optionally further substituted with one or more $R^{50}$;
$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;
m is an integer from 0 to 3;
n is an integer from 1 to 3;
p is an integer from 0 to 6;
$R^{56}$ is independently selected at each occurrence from:
—O$R^{59}$, =O, $C_{1-10}$ alkyl, $C_{2-10}$ alkenyl, and $C_{2-10}$ alkynyl,
wherein each $C_{1-10}$ alkyl, $C_{2-10}$ alkenyl, and $C_{2-10}$ alkynyl in $R^{56}$ is independently optionally substituted at each occurrence with one or more substituents selected from halogen, —NO$_2$, —CN, —O$R^{59}$, —S$R^{52}$, —N($R^{52}$)$_2$, —N$R^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, —N$R^{52}$S(=O)$_2$N($R^{52}$)$_2$, —N$R^{52}$S(=O)$_2$N$R^{53}R^{54}$, —C(O)$R^{52}$, —C(O)O$R^{52}$, —OC(O)$R^{52}$, —OC(O)O$R^{52}$, —OC(O)N($R^{52}$)$_2$, —OC(O)N$R^{53}R^{54}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)N$R^{53}R^{54}$, —P(O)(O$R^{52}$)$_2$, —P(O)($R^{52}$)$_2$, —P(O)(O$R^{52}$)($R^{52}$), —P(O)(N$R^{52}$)($R^{52}$), —N$R^{52}$P(O)($R^{52}$), —P(O)(N$R^{52}$)(O$R^{52}$)), —P(O)(N$R^{52}$)$_2$, =O, =S, =N($R^{52}$), $C_{3-12}$ carbocycle, and 3- to 12-membered heterocycle;
wherein each $C_{3-12}$ carbocycle and 3- to 12-membered heterocycle in $R^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$ NR$^{53}$R$^{54}$, —C(O)R$^{52}$, C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and further wherein R$^{56}$ optionally forms a bond to ring C; and R$^{59}$ is independently selected at each occurrence from C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$carbocycle, or 3- to 6-membered heterocycle.

In some embodiments, for a compound of Formula (I-A), R$^{57}$ is selected from —S(=O)$_2$R$^{58}$, —S(=O)$_2$N(R$^{52}$)$_2$, and —S(=O)$_2$NR$^{53}$R$^{54}$. In some embodiments, R$^{57}$ is selected from —S(=O)$_2$CH$_3$ and —S(=O)$_2$NHCH$_3$.

In some embodiments, for a compound of Formula (I-A), C is substituted with —S(=O)$_2$R$^{58}$, —S(=O)$_2$N(R$^{52}$)$_2$, or —S(=O)$_2$NR$^{53}$R$^{54}$.

In some embodiments, for a compound of Formula (I-A), Formula (I-B), Formula (II), or Formula (III), H is

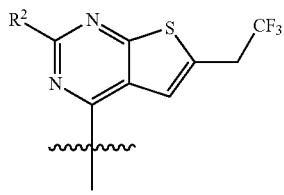

and R$^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-OR$^{52}$, C$_{1-3}$ alkyl-N(R$^{52}$)$_2$, C$_{1-3}$ haloalkyl, C$_{2-3}$ alkenyl, and C$_{2-3}$ alkynyl. In some embodiments, R$^2$ is selected from —NH$_2$, —CH$_3$, and —NHCH$_3$.

In some embodiments, for a compound of Formula (I-A), Formula (I-B), Formula (II), or Formula (III), L$^3$ is selected from

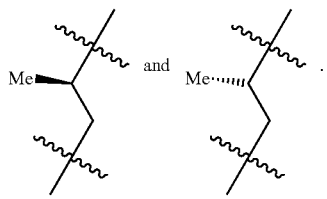

In some embodiments, for a compound of Formula (I-A), Formula (I-B), Formula (II), Formula (III), Formula (IV), or Formula (VI), the compound is provided as a substantially pure stereoisomer. In some embodiments, the stereoisomer is provided in at least 90% enantiomeric excess. In some embodiments, for a compound of Formula (I-A), Formula (I-B), Formula (II), Formula (III), Formula (IV), or Formula (VI), the compound is isotopically enriched. In some embodiments, for a compound of Formula (I-A) or Formula (I-B), the compound is selected from Table 1. In some embodiments, for a compound of Formula (II), the compound is selected from Table 2. In some embodiments, for a compound of Formula (III), the compound is selected from Table 3, Table 5 or Table 7. In some embodiments, for a compound of Formula (IV), the compound is selected from Table 4. In some embodiments, for a compound of Formula (VI), the compound is selected from Table 6.

In some embodiments, for a compound of Formula (II), W$^1$, W$^2$ and W$^3$ are each independently selected from C$_{1-4}$ alkylene, wherein each C$_{1-4}$ alkylene is optionally substituted with one or more R$^{50}$. In some embodiments, W$^1$, W$^2$ and W$^3$ are each C$_1$ alkylene. In some embodiments, W$^1$ and W$^2$ are each C$_1$ alkylene and W$^3$ is absent.

In some embodiments, for a compound of Formula (II), R$^C$ is selected from —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, and —C(O)NR$^{53}$R$^{54}$.

In some embodiments, a method described herein further comprises reducing an expression of a target gene. In some embodiments, the target gene is selected from Hoxa5, Hoxa7, Hoxa9, Hoxa10, Hoxb2, Hoxb3, Hoxb4, Hoxb5, Hoxb8, Hoxd10, Hoxd11, Hoxd13, DLX2, PBX3, Meis1, Mir196b, Flt3, and Bahcc1. In some embodiments, the target gene is Hoxa9, DLX2, PBX3, or Meis1. In some embodiments, a method described herein further comprises administering a second therapeutic agent. In some embodiments, the second therapeutic agent is a DOT1L inhibitor. In some embodiments, the second therapeutic agent is a FLT3 inhibitor. In some embodiments, the FLT3 inhibitor is quizartinib. In some embodiments, the FLT3 inhibitor is midostaurin. In some embodiments, the subject is human. In some embodiments, a method described herein further comprises obtaining a nucleic acid sample from the subject. In some embodiments, the nucleic acid sample comprises a nucleic acid selected from genomic DNA, cDNA, circulating tumor DNA, cell-free DNA, RNA, and mRNA. In some embodiments, a method described herein further comprises obtaining a biological sample from the subject. In some embodiments, the biological sample is a tissue sample. In some embodiments, the tissue sample is fixed, paraffin-embedded, fresh, or frozen. In some embodiments, the tissue sample is derived from fine needle, core, or other types of biopsy. In some embodiments, the biological sample is whole blood or plasma. In some embodiments, a method described herein further comprises conducting a nucleic acid analysis on the nucleic acid sample. In some embodiments, the nucleic acid analysis comprises PCR, sequencing, hybridization, microarray, SNP, cell-free nucleic acid analysis, or whole genome sequencing. In some embodiments, the subject has been tested for the presence of a nucleoporin 98 (NUP98) gene fusion, mutation in the nucleophosmin (NPM1) gene, mutation in the DNA (cytosine-5)-methyltransferase 3A (DNMT3A) gene, or mixed lineage leukemia (MLL) gene amplification. In some embodiments, a method described herein further comprises testing the subject for the presence of a nucleoporin 98 (NUP98) gene fusion, mutation in the nucleophosmin (NPM1) gene, mutation in the DNA (cytosine-5)-methyltransferase 3A (DNMT3A) gene, or mixed lineage leukemia (MLL) gene amplification.

In some embodiments, the subject has been tested for the presence of a nucleoporin 98 (NUP98) gene fusion, mutation in the nucleophosmin (NPM1) gene, mutation in the DNA (cytosine-5)-methyltransferase 3A (DNMT3A) gene, mutation in the FMS-like tyrosine kinase-3 (FLT3) gene, mutation in the isocitrate dehydrogenase 1 (IDH1) gene, mutation in the isocitrate dehydrogenase 2 (IDH2) gene, or mixed lineage leukemia (MLL) gene amplification. In some embodiments, a method described herein further comprises testing the subject for the presence of a nucleoporin 98 (NUP98) gene fusion, mutation in the nucleophosmin (NPM1) gene, mutation in the DNA (cytosine-5)-methyltransferase 3A (DNMT3A) gene, mutation in the FMS-like tyrosine kinase-3 (FLT3) gene, mutation in the isocitrate dehydrogenase 1 (IDH1) gene, mutation in the isocitrate dehydrogenase 2 (IDH2) gene, or mixed lineage leukemia (MLL) gene amplification. In some embodiments, the subject has been tested for the presence of an MLL rearrangement, a partial tandem duplication of MLL, or elevated MEIS1 expression levels. In some embodiments, a method described herein further comprises testing the subject for the presence of an MLL rearrangement, a partial tandem duplication of MLL, or elevated MEIS1 expression levels.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is an amino acid sequence of human menin, isoform 1 (SEQ ID NO: 1).

FIG. 2 is an amino acid sequence of human menin, isoform 2 (SEQ ID NO: 2).

FIG. 3 is an amino acid sequence of human menin, isoform 3 (SEQ ID NO: 3).

DETAILED DESCRIPTION OF THE INVENTION

Figure 4:
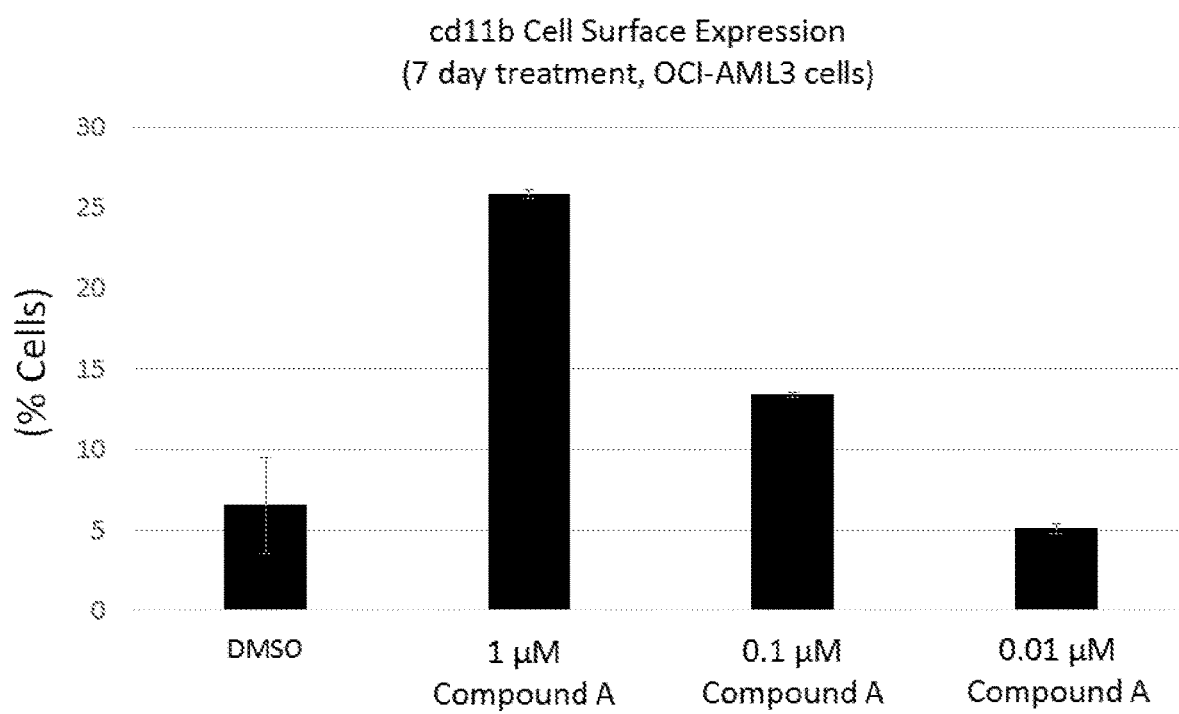
FIG. 4 depicts cd11b cell surface expression in compound treated OCI-AML3 cells.

The present invention provides compositions and methods useful for treating hematological malignancies and Ewing's sarcoma. In one aspect, the present invention provides a method of treating a hematological malignancy, such as acute myeloid leukemia, in a subject exhibiting a nucleoporin 98 (NUP98) gene fusion, mutation in the nucleophosmin (NPM1) gene, mutation in the DNA (cytosine-5)-methyltransferase 3A (DNMT3A) gene, mutation in the FMS-like tyrosine kinase-3 (FLT3) gene, mutation in the isocitrate dehydrogenase 1 (IDH1) gene, mutation in the isocitrate dehydrogenase 2 (IDH2) gene, or mixed lineage leukemia (MLL) gene amplification. In one aspect, the present invention provides a method of treating a hematological malignancy, such as acute myeloid leukemia or acute lymphoblastic leukemia, in a subject exhibiting an MLL rearrangement, optionally wherein the subject further exhibits elevated MEIS1 expression levels. In some embodiments, the subject exhibits a partial tandem duplication of MLL (MLL-PTD). A subject method typically involves administering to a subject in need thereof a menin inhibitor. In some embodiments, the menin inhibitor administered for treating the hematological malignancy is a compound of Formula (I-A) or a compound of Formula (I-B). In some embodiments, the menin inhibitor administered for treating the hematological malignancy is a compound of Formula (II). In some embodiments, the menin inhibitor administered for treating the hematological malignancy is a compound of Formula (III). In some embodiments, the menin inhibitor administered for treating the hematological malignancy is a compound of Formula (IV). In some embodiments, the menin inhibitor administered for treating the hematological malignancy is a compound of Formula (VI).

In a separate aspect, the present invention provides a method of treating Ewing's sarcoma, by administering to a subject in need thereof a menin inhibitor. In some embodiments, the menin inhibitor administered for treating Ewing's sarcoma is a compound of Formula (I-A) or a compound of Formula (I-B). In some embodiments, the menin inhibitor administered for treating Ewing's sarcoma is a compound of Formula (II). In some embodiments, the menin inhibitor administered for treating Ewing's sarcoma is a compound of Formula (III). In some embodiments, the menin inhibitor administered for treating Ewing's sarcoma is a compound of Formula (IV). In some embodiments, the menin inhibitor administered for treating Ewing's sarcoma is a compound of Formula (VI).

In some embodiments, the subject being treated has been tested for the presence of a genetic abnormality or mutation. In some cases, the subject has been tested for the presence of a nucleoporin 98 (NUP98) gene fusion, mutation in the nucleophosmin (NPM1) gene, mutation in the DNA (cytosine-5)-methyltransferase 3A (DNMT3A) gene, mutation in the FMS-like tyrosine kinase-3 (FLT3) gene, mutation in the isocitrate dehydrogenase 1 (IDH1) gene, mutation in the isocitrate dehydrogenase 2 (IDH2) gene, or mixed lineage leukemia (MLL) gene amplification. In some cases, the subject has been tested for elevated MEIS1 expression, MLL rearrangement, or partial tandem duplication of MLL. A wide variety of nucleic acid samples and analyses are available for such testing. A nucleic acid sample may be obtained from the subject. In some cases, the nucleic acid sample comprises a nucleic acid selected from genomic DNA, cDNA, circulating tumor DNA, cell-free DNA, RNA, and mRNA. A biological sample may be obtained from the subject. In some cases, the biological sample is a tissue sample (e.g., fixed, paraffin-embedded, fresh, or frozen tissue sample). The tissue sample may be derived from fine needle, core, or other types of biopsy. In some cases, the biological sample is whole blood or plasma.

In some embodiments, a nucleic acid analysis may be conducted on the biological sample containing nucleic acid. Non-limiting examples of a nucleic acid analysis include PCR, sequencing, hybridization, microarray, SNP, cell-free nucleic acid analysis, and whole genome sequencing.

The subject may exhibit a nucleoporin 98 (NUP98) gene fusion. In some cases, the nucleoporin 98 (NUP98) gene fusion is a gene fusion of NUP98 and a homeodomain partner gene. In some cases, the nucleoporin 98 (NUP98) gene fusion is a gene fusion of NUP98 and a non-homeodomain partner gene. In some cases, the nucleoporin 98 (NUP98) gene fusion is a gene fusion of NUP98 and a partner gene selected from HOXA9, HOXA11, HOXA13, HOXC11, HOXC13, HOXD11, HOXD13, PMX1, PMX2, HHEX, PHF23, JARID1A, NSD1, NSD3, MLL, SETBP1, LEDGF, CCDC28, HMGB3, IQCG, RAP1GDS1, ADD3, DDX10, TOP1, TOP2B, LNP1, RARG, ANKRD28, and POU1F1.

The subject may exhibit a mutation in the nucleophosmin (NPM1) gene. In some cases, the mutation in the nucleophosmin (NPM1) gene is a mutation in exon 12 of the NPM1 gene. In some cases, the mutation in the nucleophosmin (NPM1) gene is a frameshift mutation. In some cases, the mutation in the nucleophosmin (NPM1) gene comprises an insertion of two to nine bases, such as the insertion is of four bases (e.g., TCTG, CATG, CCTG, CGTG, CAGA, CTTG, and TATG). In some cases, the insertion is of nine bases (e.g., CTCTTGCCC and CCCTGGAGA). In some cases, the mutation in the nucleophosmin (NPM1) gene comprises a deletion of nucleotides 965 through 969 (GGAGG).

The subject may exhibit a mutation in the FLT3 gene. In some cases, the mutation in the FLT3 gene is an internal tandem duplication (FLT3-ITD). In some cases, the mutation in the FLT3 gene is an in-frame, internal tandem duplication mutation of a nucleotide sequence within exon 14. The size of the FLT3-ITD mutation may range from 3 to over 400 bp. In some cases, the FLT3-ITD mutation is near residues 590-600 of the FLT3 amino acid sequence. The FLT3-ITD mutation may be located in exon 14, exon 15 and/or in the intron between exons 14 and 15. The subject may comprise both partial tandem duplication of the MLL gene and a FLT3-ITD mutation. The subject may exhibit a FLT3 activating mutation. In some cases, the mutation in the FLT3 gene is a point mutation involving the tyrosine kinase domain. In some cases, the mutation of the FLT3 gene is a point mutation at aspartate 835 or isoleucine 836.

The subject may exhibit a mutation in the DNA (cytosine-5)-methyltransferase 3A (DNMT3A) gene. In some cases, the mutation in the DNMT3A gene is a mutation of R882. In some cases, the mutation in the DNMT3A gene is not a mutation of R882. In some cases, the mutation in the DNMT3A gene is a frameshift deletion, missense mutation, nonsense mutation, splice-site substitution, splice-site deletion, or whole-gene deletion.

The subject may exhibit a mutation in the isocitrate dehydrogenase 1 (IDH1) gene or isocitrate dehydrogenase 2 (IDH2) gene. In some cases, the mutation in the isocitrate dehydrogenase 1 (IDH1) gene is a heterozygous somatic point mutation in codon 132. In some cases, the mutation in the isocitrate dehydrogenase 2 (IDH2) gene is a heterozygous somatic point mutation in codons 172 or 140. In some embodiments, the mutation in the isocitrate dehydrogenase 2 (IDH2) gene is R140Q.

The subject may exhibit one or more of an NPM1 mutation, FLT3 mutation, IDH1 mutation, IDH2 mutation, and DNMT3A mutation. In some cases, the subject exhibits an NPM1 mutation, a FLT3 mutation, an IDH2 mutation and a DNMT3A mutation. In some cases, the subject exhibits an NPM1 mutation, an IDH1 mutation, a FLT3 mutation and a DNMT3A mutation. In some cases, the subject exhibits an NPM1 mutation, a FLT3 mutation and a DNMT3A mutation. In some cases, the subject exhibits an NPM1 mutation, a FLT3 mutation and an IDH1 mutation. In some cases, the subject exhibits an NPM1 mutation, a FLT3 mutation and an IDH2 mutation. In some cases, the subject exhibits an NPM1 mutation, a DNMT3A mutation and an IDH1 mutation. In some cases, the subject exhibits an NPM1 mutation, a DNMT3A mutation and an IDH2 mutation. In some cases, the subject exhibits an NPM1 mutation and a FLT3 mutation.

The subject may exhibit a mixed lineage leukemia (MLL) gene amplification. The subject may exhibit a mixed lineage leukemia (MLL) gene rearrangement. The subject may exhibit an 11q23 rearragement. The subject may exhibit MLL partial tandem duplications.

The subject may exhibit an EWSR1-FLI1 gene fusion, EWSR1-ERG gene fusion, or EWSR1-FEV gene fusion. The subject may exhibit a FUS-NCATc2 gene fusion, CIC-FOXO4 gene fusion, or ETV6-NTRK3 gene fusion. The subject may exhibit a mutation in a STAG2 gene, mutation in a TP53 gene, or CDKN2A deletion.

The subject may exhibit elevated myeloid ecotropic viral integration site 1 homolog (MEIS1) expression levels ($MEIS1^{high}$). As used herein, "expression" refers to the process by which a polynucleotide is transcribed into mRNA and/or the process by which the transcribed mRNA (also referred to as a "transcript") is subsequently translated into peptides, polypeptides, or proteins. The transcripts and the encoded polypeptides are collectedly referred to as "gene product." If the polynucleotide is derived from genomic DNA, expression may include splicing of the mRNA in a eukaryotic cell. The level of expression (or alternatively, the "expression level") of a MEIS1 gene can be determined, for example, by determining the level of MEIS1 polynucleotides, polypeptides, and/or gene products. "Differentially expressed" or "differential expression" as applied to a nucleotide sequence (e.g., a gene) or polypeptide sequence in a subject, refers to the differential production of the mRNA transcribed and/or translated from the nucleotide sequence or the protein product encoded by the nucleotide sequence. A differentially expressed sequence may be over-expressed or underexpressed as compared to the expression level of a reference sample (i.e., a reference level). As used herein, elevated expression levels refer to an increase in expression, generally at least 1.25 fold, or alternatively, at least 1.5 fold, or alternatively, at least 2 fold, or alternatively, at least 3 fold, or alternatively, at least 4 fold, or alternatively, at least 10 fold expression over that detected in a reference sample. As used herein, underexpression is a reduction in expression and generally is at least 1.25 fold, or alternatively, at least 1.5 fold, or alternatively, at least 2 fold, or alternatively, at least 3 fold, or alternatively, at least 4 fold, or alternatively, at least 10 fold expression under that detected in a reference sample. Underexpression also encompasses absence of expression of a particular sequence as evidenced by the absence of detectable expression in a test subject when compared to a reference sample.

The present disclosure provides compounds for modulating the interaction of menin with proteins such as MLL1 and MLL2 and MLL-fusion oncoproteins. In certain embodiments, the disclosure provides compounds and methods for inhibiting the interaction of menin with its upstream or downstream signaling molecules including but not limited to MLL1, MLL2 and MLL-fusion oncoproteins. Compounds of the disclosure may be used in methods for the treatment of a wide variety of cancers and other diseases associated with one or more of MLL1, MLL2, MLL fusion proteins, and menin, such as hematological malignancies and Ewing's sarcoma. In some cases, the hematological maligancy comprises a nucleoporin 98 (NUP98) gene fusion, mutation in the nucleophosmin (NPM1) gene, mutation in the DNA (cytosine-5)-methyltransferase 3A (DNMT3A) gene, mutation in the FMS-like tyrosine kinase-3 (FLT3) gene, mutation in the isocitrate dehydrogenase 1 (IDH1) gene, mutation in the isocitrate dehydrogenase 2 (IDH2) gene, and/or mixed lineage leukemia (MLL) gene amplification. In certain embodiments, a compound of the disclosure interacts non-covalently with menin and inhibits the interaction of menin with MLL. In certain embodiments, a compound of the disclosure covalently binds menin and inhibits the interaction of menin with MLL.

In some aspects, the present disclosure provides a compound or salt thereof that selectively binds to the menin protein and/or modulates the interaction of menin with an MLL protein (e.g., MLL1, MLL2, or an MLL fusion protein). In certain embodiments, the compound modulates the menin protein by binding to or interacting with one or more amino acids and/or one or more metal ions. Certain compounds may occupy the F9 and/or P13 pocket of menin. The binding of a compound disclosed herein may disrupt menin or MLL (e.g., MLL1, MLL2, or an MLL fusion protein) downstream signaling.

Unless defined otherwise, all technical and scientific terms used herein have the same meaning as is commonly understood by one of skill in the art to which this invention belongs.

"Nucleoporin 98 (NUP98) gene fusion" refers to a gene which encodes a protein with an N-terminal fragment of NUP98 fused with a partner protein. "Nucleoporin 98 (NUP98) fusion protein" refers to a protein with an N-terminal fragment of NUP98 fused with a partner protein. Non-limiting examples of a partner protein include HOXA9, HOXA11, HOXA13, HOXC11, HOXC13, HOXD11, HOXD13, PMX1, PMX2, HHEX, PHF23, JARID1A, NSD1, NSD3, MLL, SETBP1, LEDGF, CCDC28, HMGB3, IQCG, RAP1GDS1, ADD3, DDX10, TOP1, TOP2B, LNP1, RARG, ANKRD28, and POU1F1. NUP98 fusion proteins may be created through the joining of a gene that codes for NUP98 and a gene that codes for a partner protein creating a fusion gene. Translation of this fusion gene may result in a single or multiple polypeptides with functional properties derived from each of the original proteins.

"MLL fusion protein" refers to a protein with an N-terminal fragment of MLL fused with a partner protein. Non-limiting examples of a partner protein include 11q23, 11q23.3, 11q24, 1p13.1, 1p32 (EPS15), 21q22, 9p13.3, 9p22 (MLLT3/AF9), ABI1, ABI2, ACACA, ACTN4, AFF1/AF4, AFF3/LAF4, AFF4/AF5, AKAP13, AP2A2, ARHGEF12, ARHGEF17, BCL9L, BTBD18, BUD13, C2CD3, CASC5, CASP8AP2, CBL, CEP164, CEP170B, CREBBP, DCP1A, DCPS, EEFSEC/SELB, ELL, EPS15, FLNA, FNBP1, FOXO3, GAS7, GMPS, KIAA1524, LAMC3, LOC100131626, MAML2, ME2, MLLT1/ENL, MLLT10/AF10, MLLT11/AF1Q, MLLT3/AF9, MLLT4/AF6, MLLT6/AF17, MYH11, MYO1F, NA, NEBL, NRIP3, PDS5A, PICALM, PRPF19, PTD, RUNDC3B, SEPT11, SEPT2, SEPT5, SEPT6, SEPT9, SMAP1, TET1, TNRC18, TOP3A, VAV1, and Xq26.3 (CT45A2). MLL fusion proteins may be created through the joining of a gene that codes for an MLL protein and a gene that codes for a partner protein creating a fusion gene. Translation of this fusion gene may result in a single or multiple polypeptides with functional properties derived from each of the original proteins.

The term "$C_{x\text{-}y}$" or "$C_x$—$C_y$" when used in conjunction with a chemical moiety, such as alkyl, alkenyl, or alkynyl is meant to include groups that contain from x to y carbons in the chain. For example, the term "$C_{x\text{-}y}$ alkyl" refers to substituted or unsubstituted saturated hydrocarbon groups, including straight-chain alkyl and branched-chain alkyl groups that contain from x to y carbons in the chain. The terms "$C_{x\text{-}y}$ alkenyl" and "$C_{x\text{-}y}$ alkynyl" refer to substituted or unsubstituted straight-chain or branched-chain unsaturated hydrocarbon groups that contain at least one double or triple bond respectively. Unless stated otherwise specifically in the specification, a $C_{x\text{-}y}$ alkyl, $C_{x\text{-}y}$ alkenyl, or C, alkynyl is optionally substituted by one or more substituents such as those substituents described herein.

"Carbocycle" refers to a saturated, unsaturated or aromatic ring in which each atom of the ring is a carbon atom. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene.

"Heteroaryl" refers to a 3- to 12-membered aromatic ring that comprises at least one heteroatom wherein each heteroatom may be independently selected from N, O, and S.

As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryls as defined above which are optionally substituted by one or more substituents such as those substituents described herein.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$), —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function (e.g., activity, expression, binding, protein-protein interaction) of a target protein (e.g., menin, MLL1, MLL2, and/or an MLL fusion protein). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a subject by various methods, including intravenous, oral, intramuscular, intraperitoneal, intravesical, subcutaneous, transdermal, buccal, or inhalation or in the form of a suppository.

"Subject" refers to an animal, such as a mammal, for example a human. The methods described herein can be useful in both human therapeutics and veterinary applications. In some embodiments, the subject is a mammal, and in some embodiments, the subject is human. "Mammal" includes humans and both domestic animals such as laboratory animals and household pets (e.g., cats, dogs, swine, cattle, sheep, goats, horses, rabbits), and non-domestic animals such as wildlife and the like.

"Prodrug" is meant to indicate a compound that may be converted under physiological conditions or by solvolysis to a biologically active compound described herein (e.g., compound of Formula (I-A), Formula (I-B), Formula (II), Formula (III), Formula (IV), or Formula (VI)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The present disclosure provides compounds for modulating the interaction of menin with proteins such as MLL1, MLL2 and MLL-fusion oncoproteins. In certain embodiments, the disclosure provides compounds and methods for inhibiting the interaction of menin with its upstream or downstream signaling molecules including, but not limited to, MLL1, MLL2 and MLL-fusion oncoproteins. Compounds of the disclosure may be used in methods for the treatment of a wide variety of cancers and other diseases associated with one or more of MLL1, MLL2, MLL fusion proteins, and menin, such as hematological maligancies or Ewing's sarcoma. In certain embodiments, a compound of the disclosure covalently binds menin and inhibits the interaction of menin with MLL. In certain embodiments, a compound of the disclosure interacts non-covalently with menin and inhibits the interaction of menin with MLL.

In some aspects, the present disclosure provides a compound or salt that selectively binds to the menin protein and/or modulates the interaction of menin with an MLL protein (e.g., MLL1, MLL2, or an MLL fusion protein). In certain embodiments, the compound modulates the menin protein by binding to or interacting with one or more amino acids and/or one or more metal ions. Certain compounds may occupy the F9 and/or P13 pocket of menin. The binding of a compound disclosed herein may disrupt menin or MLL (e.g., MLL1, MLL2, or an MLL fusion protein) downstream signaling.

In certain aspects, the present disclosure provides a compound of Formula (I-A):

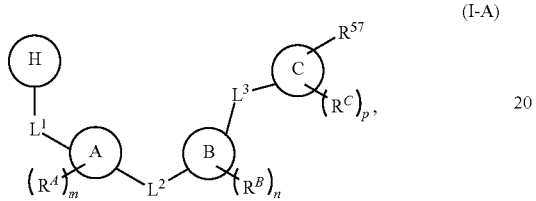

(I-A)

or a pharmaceutically acceptable salt or prodrug thereof, wherein:

H is selected from $C_{5-12}$ carbocycle and 5- to 12-membered heterocycle, each of which is optionally substituted with one or more $R^{50}$;

A is selected from bond, $C_{3-12}$ carbocycle and 3- to 12-membered heterocycle;

B is selected from $C_{3-12}$ carbocycle and 3- to 12-membered heterocycle;

C is 3- to 12-membered heterocycle;

$L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;

$R^A$, $R^B$ and $R^C$ are each independently selected at each occurrence from $R^{50}$, or two $R^A$ groups, two $R^B$ groups or two $R^C$ groups attached to the same atom or different atoms can together optionally form a bridge or ring;

m, n and p are each independently an integer from 0 to 6;

$R^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{57}$ is selected from:

halogen, —NO$_2$, —CN, —SR$^{52}$, —NR$^{53}$R$^{54}$, —S(=O)R$^{52}$, —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)OR$^{52}$, —NR$^{52}$C(O)N(R$^{52}$)$_2$, —NR$^{52}$C(O)NR$^{53}$R$^{54}$, —C(O)NH(C$_{1-6}$ alkyl), —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =S, and =N(R$^{52}$); and C$_{1-10}$ alkyl, C$_{2-10}$ alkenyl, and C$_{2-10}$ alkynyl, each of which is independently substituted at each occurrence with one or more substituents selected from —NO$_2$, —CN, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =S, and =N(R$^{52}$); and R$^{58}$ is selected from hydrogen; and C$_{1-20}$ alkyl, C$_{3-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I-A), when C is azetidinylene, piperidinylene or piperazinylene and R$^{57}$ is —S(=O)$_2$R$^{58}$, —S(=O)$_2$N(R$^{52}$)$_2$, or —NR$^{52}$S(=O)$_2$R$^{52}$:

p is an integer from 1 to 6; and/or

L$^3$ is substituted with one or more R$^{50}$, wherein L$^3$ is not —CH$_2$CH(OH)—.

In certain aspects, a compound of Formula (I-A) may be represented by:

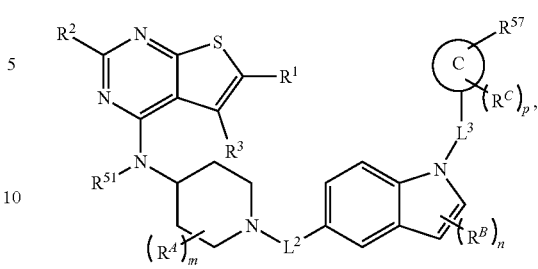

(I-A-1)

such as

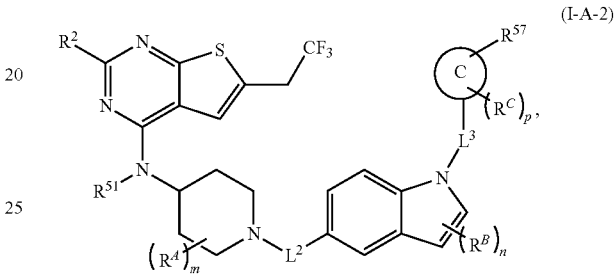

(I-A-2)

wherein R$^1$, R$^2$ and R$^3$ are each independently selected at each occurrence from hydrogen and R$^{50}$. In some embodiments, R$^1$ is selected from R$^{50}$. In some embodiments, R$^1$ is C$_{1-3}$ haloalkyl, such as —CH$_2$CF$_3$. In some embodiments, R$^2$ is selected from R$^{50}$. In some embodiments, R$^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-OR$^{52}$, C$_{1-3}$ alkyl-N(R$^{52}$)$_2$, C$_{1-3}$ haloalkyl, C$_{2-3}$ alkenyl, and C$_{2-3}$ alkynyl. In some embodiments, R$^2$ is selected from halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl, such as R$^2$ is selected from —OH, —OR$^{52}$, —NH$_2$, —N(R$^{52}$)$_2$, —CN, and C$_{1-2}$ alkyl. Optionally, R$^2$ is selected from —NH$_2$, —CH$_3$, —OCH$_3$, —CH$_2$OH, and —NHCH$_3$. In some embodiments, R$^3$ is selected from hydrogen, halogen, —OH, —N(R$^{52}$)$_2$, —CN, —C(O)OR$^{52}$, C$_{1-3}$ alkyl, and C$_{1-3}$ haloalkyl. In some embodiments, R$^{51}$ is selected from selected from hydrogen and alkyl, such as R$^{51}$ is hydrogen. In some embodiments, R$^A$ is selected from halogen, —CN, —OR$^{52}$, —N(R$^{52}$)$_2$, —NR$^{53}$R$^{54}$, —C(O)N(R$^{52}$)$_2$, —C(O)NR$^{53}$R$^{54}$, —C(O)R$^{52}$, C(O)OR$^{52}$, —OC(O)R$^{52}$, —NR$^{52}$C(O)R$^{52}$, C(O)N(R$^{52}$)$_2$, —C(O)NR$^{53}$R$^{54}$, =O, C$_{1-10}$ alkyl, C$_{2-10}$ alkenyl, C$_{2-10}$ alkynyl, optionally substituted C$_{1-10}$ alkyl, optionally substituted C$_{2-10}$ alkenyl, and optionally substituted C$_{2-10}$ alkynyl. In some embodiments, m is 0. In some embodiments, L$^2$ is selected from —O—, —N(R$^{51}$)—, —N(R$^{51}$)CH$_2$—, —C(O)N(R$^{51}$)—, —N(R$^{51}$)C(O)—, —N(R$^{51}$)S(O)$_2$—, —S(O)$_2$N(R$^{51}$)—, C$_{1-4}$ alkylene and C$_{1-4}$ heteroalkylene. In some embodiments, L$^2$ is C$_{1-4}$ alkylene, optionally substituted with one or more R$^{50}$. In some embodiments, L$^2$ is C$_{1-2}$ alkylene, optionally substituted with one or more R$^{50}$. In some embodiments, L$^2$ is selected from —CH$_2$—, —N(R$^{51}$)—, —N(R$^{51}$)CH$_2$—, —N(R$^{51}$)C(O)—, and —N(R$^{51}$)S(O)$_2$—. In some embodiments, L$^2$ is —CH$_2$—. In some embodiments, R$^B$ is present at one or more positions of the indole, such as at position 2, 3, 4, or 6 of the indole. In some embodiments, R$^B$ is selected from halogen, —CN, —OR$^{52}$, —N(R$^{52}$)$_2$, —NR$^{53}$R$^{54}$, —C(O)R$^{52}$, —C(O)OR$^{52}$, —OC(O)R$^{52}$, —NR$^{52}$C(O)R$^{52}$, —C(O)N(R$^{52}$)$_2$, —C(O)NR$^{53}$R$^{54}$, =O, C$_{1-10}$ alkyl, C$_{2-10}$ alkenyl, C$_{2-10}$ alkynyl, optionally substituted C$_{1-10}$ alkyl, optionally substituted C$_{2-10}$ alkenyl, and optionally substituted C$_{2-10}$ alkynyl. In some embodiments, R$^B$ is selected from halogen, —CN, —OR$^{52}$, —N(R$^{52}$)$_2$, —NR$^{53}$R$^{54}$, C$_{1-3}$ alkyl, and optionally substituted C$_{1-3}$ alkyl, such as R$^B$ is selected from halogen, —CN, —OR$^{52}$, —N(R$^{52}$)$_2$, —NR$^{53}$R$^{54}$, and C$_{1-2}$ alkyl. In some embodiments, n is an integer from 1 to 4, such as an integer from 2 to 3. In some embodiments, n is 2. In some embodiments, L$^3$ is selected from C$_{1-6}$ alkylene, C$_{2-6}$ alkenylene, and C$_{2-6}$ alkynylene, each of which is substituted with one or more R$^{50}$. In some embodiments, L$^3$ is C$_{1-6}$ alkylene, optionally substituted with one or more R$^{50}$. In some embodiments, L$^3$ is C2 alkylene substituted with at least one C$_{1-3}$ alkyl or C$_{1-3}$ haloalkyl, and optionally further substituted with one or more R$^{50}$. In some embodiments, L$^3$ is substituted with =O, C$_{1-6}$ alkyl, C$_{1-6}$ haloalkyl, C$_{1-3}$ alkyl(cyclopropyl), C$_{1-3}$ alkyl (NR$^{52}$C(O)R$^{52}$) or —O(C$_{1-6}$ alkyl). In some embodiments, L$^3$ is substituted with —CH$_3$. In some embodiments, L$^3$ is selected from

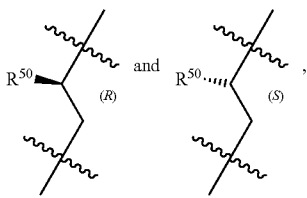

where R$^{50}$ is optionally methyl. In some embodiments, C is 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

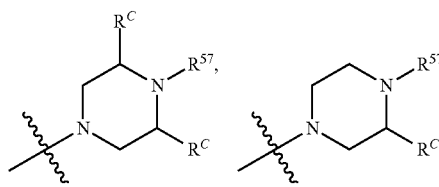

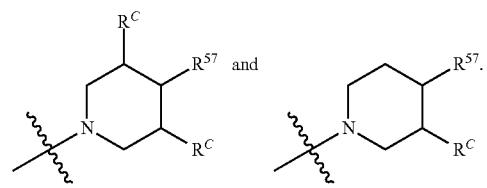

In some embodiments, C is selected from

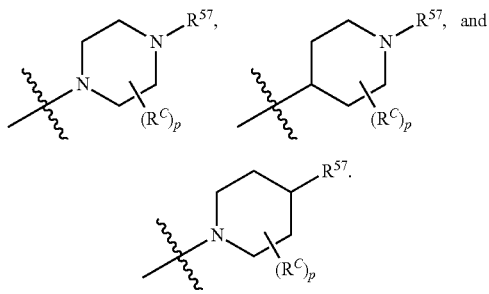

In some embodiments, C is selected from

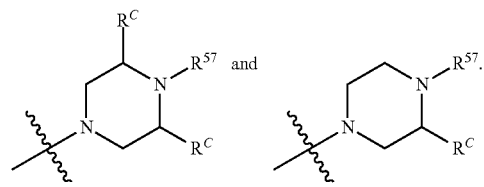

In some embodiments, C is selected from

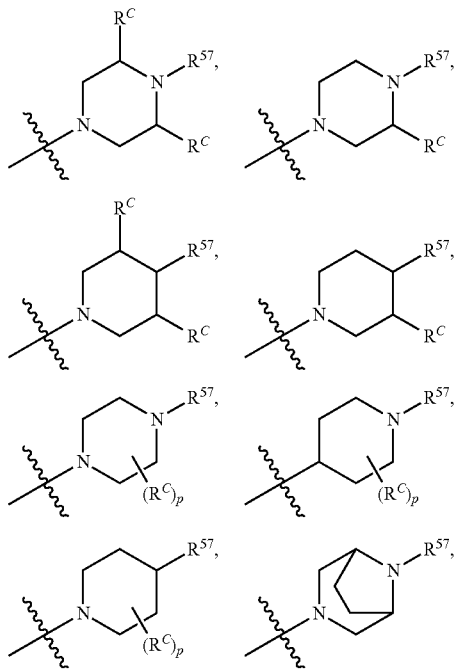

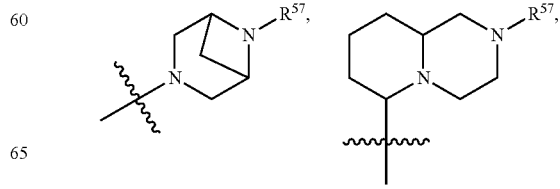

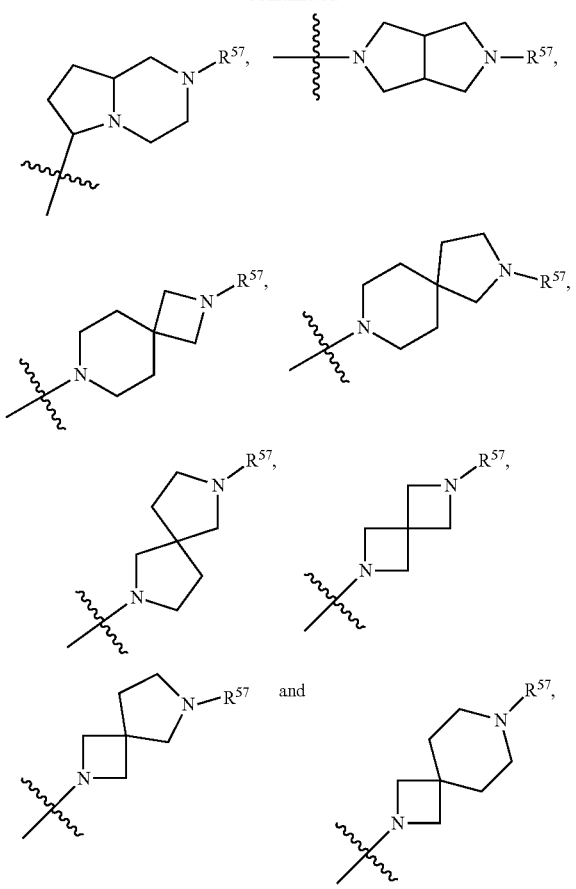

optionally substituted with one or more $R^C$. In some embodiments, C is selected from

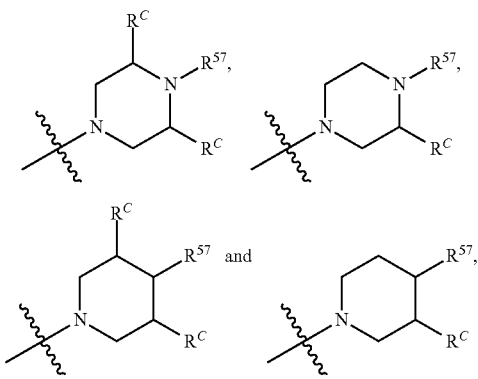

wherein $R^{57}$ is selected from —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2$ $R^{52}$; and $C_{1-10}$ alkyl substituted with one or more substituents selected from —S(=O)$R^{52}$, —S(=O)$_2R^{52}$, —S(=O)$_2$N($R^{52}$)$_2$, —S(=O)$_2$N$R^{53}R^{54}$, and —N$R^{52}$S(=O)$_2R^{52}$. In some embodiments, $R^{57}$ is selected from —S(=O)$R^{52}$, —S(=O)$_2R^{58}$, —S(=O)$_2$N($R^{52}$)$_2$, and —N$R^{52}$S(=O)$_2$ $R^{52}$, such as $R^{57}$ is selected from —S(=O)CH$_3$, —S(=O)$_2$ CH$_3$, —S(=O)$_2$NH$_2$, —NHS(=O)$_2$CH$_3$, and —S(=O)$_2$ NHCH$_3$. In some embodiments, C is selected from In some embodiments, $R^C$ is selected from —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, and —C(O) N$R^{53}R^{54}$. In some embodiments, $R^C$ is selected from —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N ($R^{52}$)$_2$, —C(O)N$R^{53}R^{54}$, $C_{1-6}$ alkyl, and $C_{1-6}$ alkyl substituted with —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O) O$R^{52}$, —N$R^{52}$C(O)N($R^{52}$)$_2$, —N$R^{52}$C(O)N$R^{53}R^{54}$, —C(O) N($R^{52}$)$_2$, or —C(O)N$R^{53}R^{54}$. In some embodiments, C is selected from

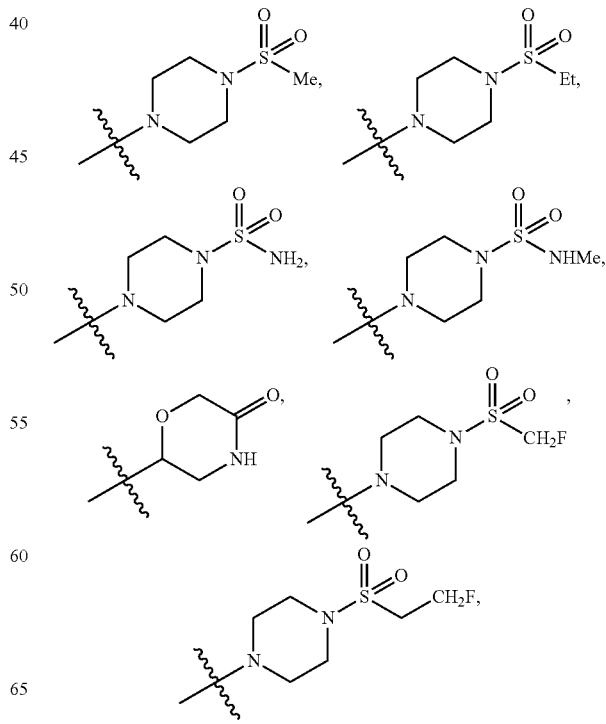

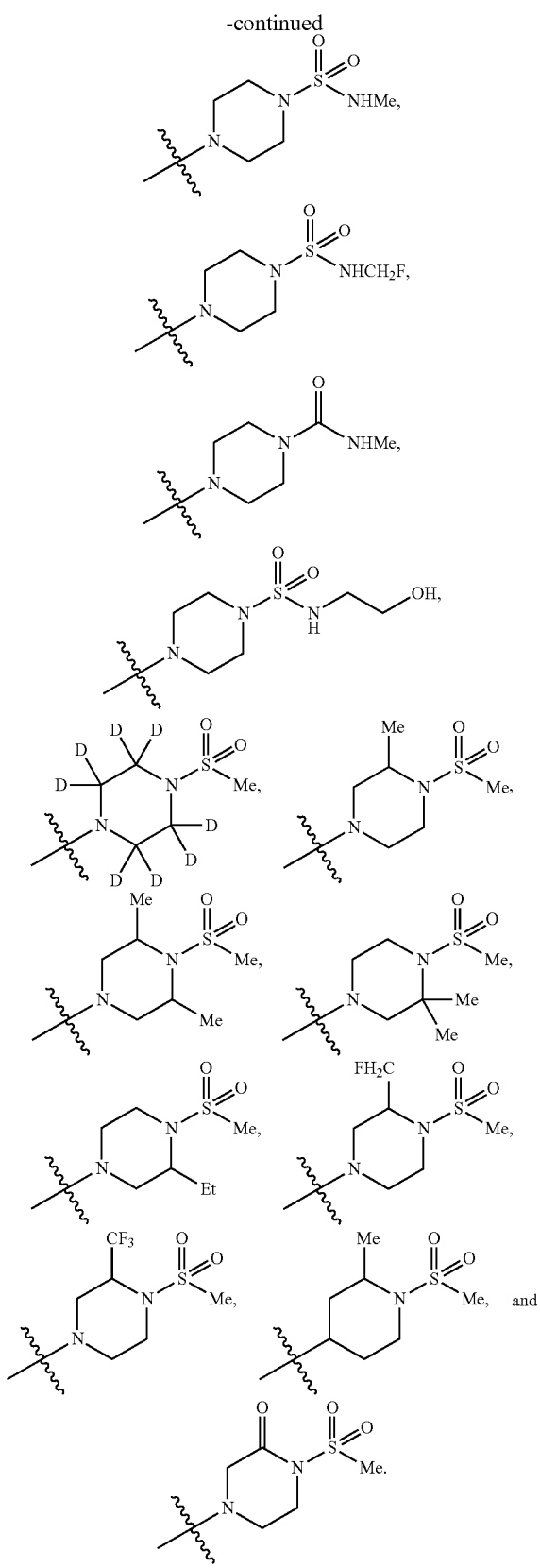

In some embodiments, $R^C$ is selected from —C(O)R$^{52}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, =O, C$_{1-3}$ alkyl, and C$_{1-3}$ haloalkyl, or two R$^C$ groups attached to different atoms can together form a C$_{1-3}$ bridge. In some embodiments, R$^C$ is selected from C$_{1-3}$ alkyl and C$_{1-3}$ haloalkyl, such as —CH$_3$. In some embodiments, p is selected from an integer 0 to 4, such as p is selected from an integer 0 to 2. In some embodiments, p is 0. In some embodiments, R$^{57}$ is selected from —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)NH(C$_{1-6}$ alkyl), —C(O)NR$^{53}$R$^{54}$; and C$_{1-6}$ alkyl and C$_{2-6}$ alkenyl, each of which is independently substituted at each occurrence with one or more substituents selected from —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)NH(C$_{1-6}$ alkyl), —C(O)NR$^{53}$R$^{54}$. In some embodiments, R$^{57}$ is selected from —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$ and C$_{1-6}$ alkyl substituted with one or more substituents selected from —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, and —NR$^{52}$S(=O)$_2$NR$^{53}$R$^{54}$. In some embodiments, R$^{57}$ is selected from —S(=O)R$^{52}$, —S(=O)$_2$R$^{58}$, —S(=O)$_2$N(R$^{52}$)$_2$, and —NR$^{52}$S(=O)$_2$R$^{52}$. In some embodiments, R$^{57}$ is selected from —S(=O)CH$_3$, —S(=O)$_2$CH$_3$, —S(=O)$_2$NH$_2$, —NHS(=O)$_2$CH$_3$, and —S(=O)$_2$NHCH$_3$.

In certain aspects, a compound of Formula (I-A) may be represented by:

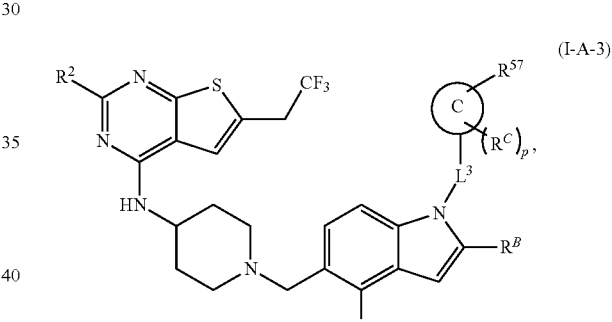

(I-A-3)

such as

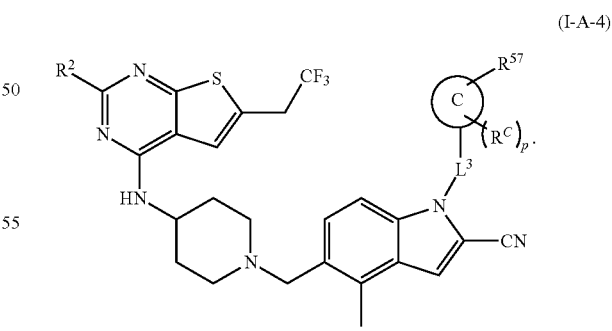

(I-A-4)

In some embodiments, R$^2$ is selected from R$^{50}$. In some embodiments, R$^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-OR$^{52}$, C$_{1-3}$ alkyl-N(R$^{52}$)$_2$, C$_{1-3}$ haloalkyl, C$_{2-3}$ alkenyl, and C$_{2-3}$ alkynyl. In some embodiments, R$^2$ is selected from halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from —OH, —$OR^{52}$, —$NH_2$, —$N(R^{52})_2$, —CN, and $C_{1-2}$ alkyl. Optionally, $R^2$ is selected from —$NH_2$, —$CH_3$, —$OCH_3$, —$CH_2OH$, and —$NHCH_3$. In some embodiments, $R^B$ is selected from halogen, —CN, —$OR^{52}$, —$N(R^{52})_2$, —$NR^{53}R^{54}$, —$C(O)R^{52}$, —$C(O)OR^{52}$, —$OC(O)R^{52}$, —$NR^{52}C(O)R^{52}$, —$C(O)N(R^{52})_2$, —$C(O)NR^{53}R^{54}$, =O, $C_{1-10}$ alkyl, $C_{2-10}$ alkenyl, $C_{2-10}$ alkynyl, optionally substituted $C_{1-10}$ alkyl, optionally substituted $C_{2-10}$ alkenyl, and optionally substituted $C_{2-10}$ alkynyl. In some embodiments, $R^B$ is selected from halogen, —CN, —$OR^{52}$, —$N(R^{52})_2$, —$NR^{53}R^{54}$, $C_{1-3}$ alkyl, and optionally substituted $C_{1-3}$ alkyl, such as $R^B$ is selected from halogen, —CN, —$OR^{52}$, —$N(R^{52})_2$, —$NR^{53}R^{54}$, and $C_{1-2}$ alkyl. In some embodiments, $L^3$ is selected from $C_{1-6}$ alkylene, $C_{2-6}$ alkenylene, and $C_{2-6}$ alkynylene, each of which is substituted with one or more $R^{50}$. In some embodiments, $L^3$ is $C_{1-6}$ alkylene, optionally substituted with one or more $R^{50}$. In some embodiments, $L^3$ is C2 alkylene substituted with at least one $C_{1-3}$ alkyl or $C_{1-3}$ haloalkyl, and optionally further substituted with one or more $R^{50}$. In some embodiments, $L^3$ is substituted with =O, $C_{1-6}$ alkyl, $C_{1-6}$ haloalkyl, $C_{1-3}$ alkyl(cyclopropyl), $C_{1-3}$ alkyl($NR^{52}C(O)R^{52}$) or —$O(C_{1-6}$ alkyl). In some embodiments, $L^3$ is substituted with —$CH_3$. In some embodiments, $L^3$ is selected from

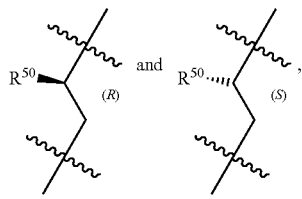

where $R^{50}$ is optionally methyl. In some embodiments, C is 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

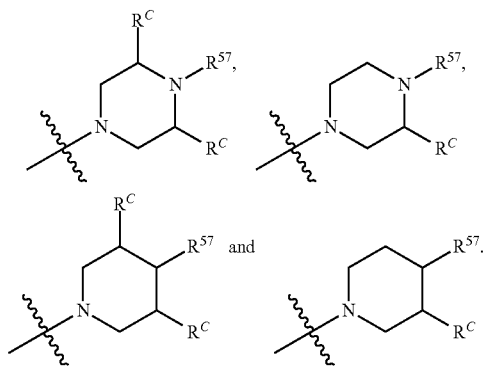

In some embodiments, C is selected from

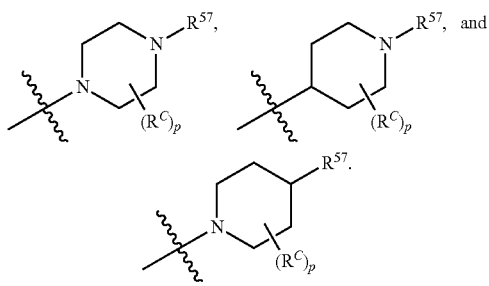

In some embodiments, C is selected from

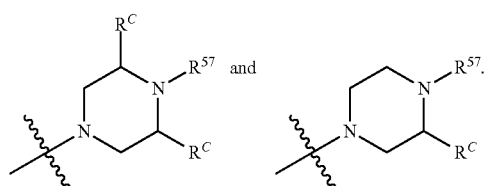

In some embodiments, C is selected from

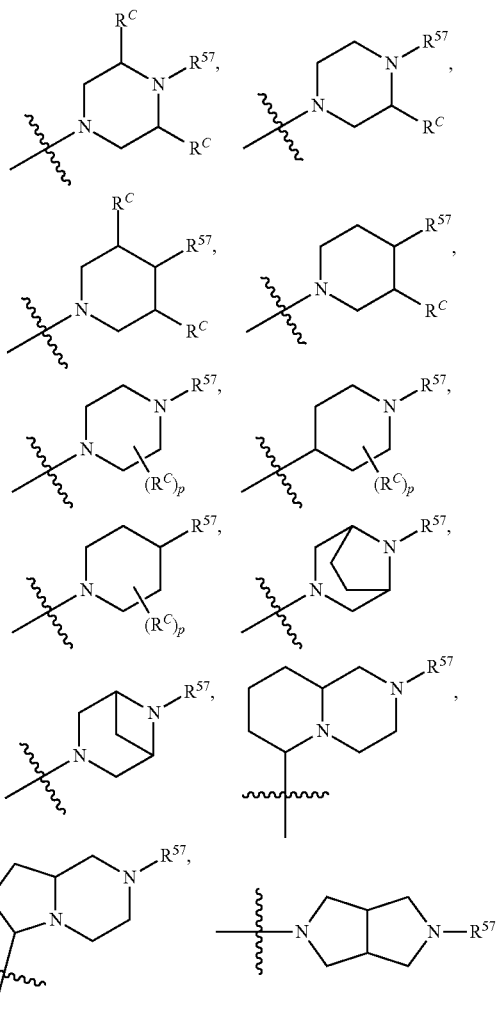

-continued

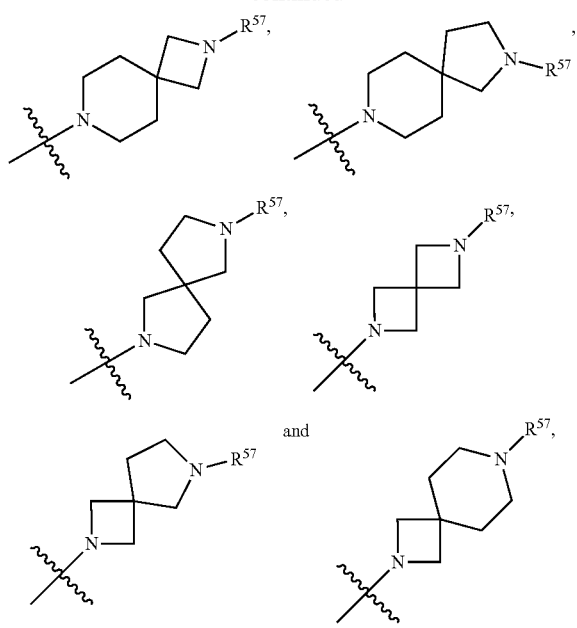

optionally substituted with one or more $R^C$. In some embodiments, C is selected from

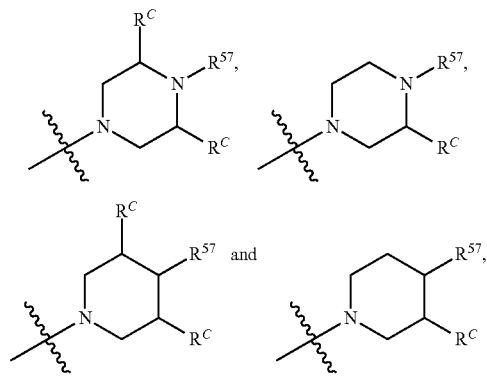

wherein $R^{57}$ is selected from —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2$ $R^{52}$; and $C_{1-10}$ alkyl substituted with one or more substituents selected from —S(=O)$R^{52}$, —S(=O)$_2R^{52}$, —S(=O)$_2$ N($R^{52}$)$_2$, —S(=O)$_2$N$R^{53}R^{54}$, and —N$R^{52}$S(=O)$_2R^{52}$. In some embodiments, $R^{57}$ is selected from —S(=O)$R^{52}$, —S(=O)$_2R^{58}$, —S(=O)$_2$N($R^{52}$)$_2$, and —N$R^{52}$S(=O)$_2$ $R^{52}$, such as $R^{57}$ is selected from —S(=O)CH$_3$, —S(=O)$_2$ CH$_3$, —S(=O)$_2$NH$_2$, —NHS(=O)$_2$CH$_3$, and —S(=O)$_2$ NHCH$_3$. In some embodiments, C is selected from

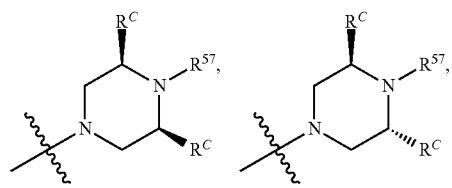

-continued

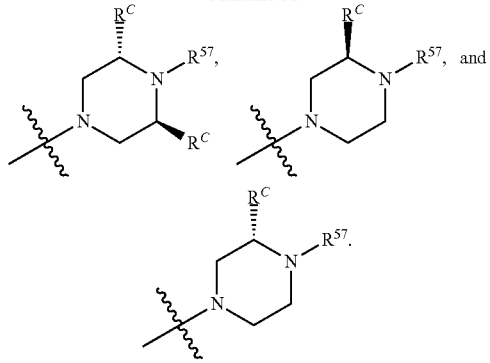

In some embodiments, $R^C$ is selected from —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, and —C(O) N$R^{53}R^{54}$. In some embodiments, $R^C$ is selected from —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N ($R^{52}$)$_2$, —C(O)N$R^{53}R^{54}$, $C_{1-6}$ alkyl, and $C_{1-6}$ alkyl substituted with —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O) O$R^{52}$, —N$R^{52}$C(O)N($R^{52}$)$_2$, —N$R^{52}$C(O)N$R^{53}R^{54}$, —C(O) N($R^{52}$)$_2$, or —C(O)N$R^{53}R^{54}$. In some embodiments, C is selected from

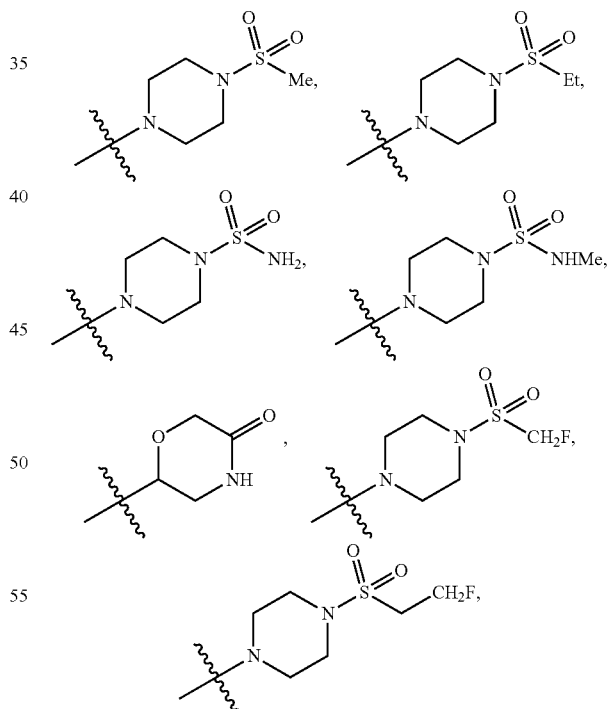

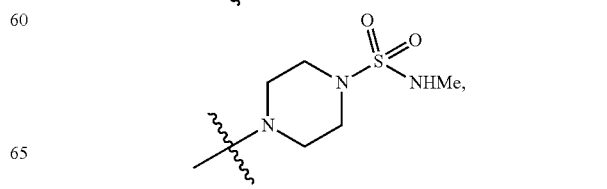

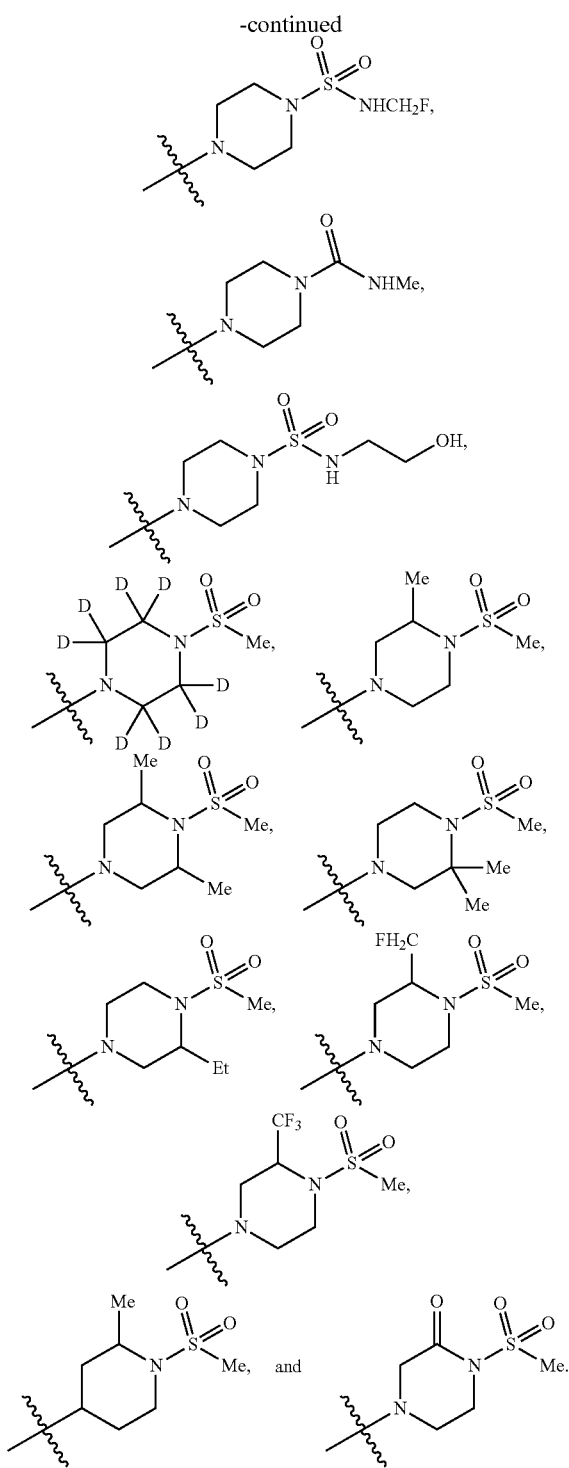

—NR$^{52}$S(=O)$_2$NR$^{53}$R$^{54}$, —S(=O)$_2$N(R$^{52}$)$_2$, —S(=O)$_2$NR$^{53}$R$^{54}$, —NR$^{52}$S(=O)$_2$R$^{52}$, C(O)NH(C$_{1-6}$ alkyl), —C(O)NR$^{53}$R$^{54}$; and C$_{1-6}$ alkyl and C$_{2-6}$ alkenyl, each of which is independently substituted at each occurrence with one or more substituents selected from —S(=O)$_2$R$^{58}$, —S(=O)$_2$N(R$^{52}$)$_2$, —S(=O)$_2$NR$^{53}$R$^{54}$, —NR$^{52}$S(=O)$_2$ R$^{52}$, —NR$^{52}$S(=O)$_2$N(R$^{52}$)$_2$, —NR$^{52}$S(=O)$_2$NR$^{53}$R$^{54}$, —C(O)NH(C$_{1-6}$ alkyl), —C(O)NR$^{53}$R$^{54}$. In some embodiments, R$^{57}$ is selected from —S(=O)$_2$R$^{58}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$ and C$_{1-6}$ alkyl substituted with one or more substituents selected from —S(=O)$_2$ R$^{58}$, —S(=O)$_2$N(R$^{52}$)$_2$, —S(=O)$_2$NR$^{53}$R$^{54}$, —NR$^{52}$S(=O)$_2$ R$^{52}$, —NR$^{52}$S(=O)$_2$N(R$^{52}$)$_2$, and —NR$^{52}$S(=O)$_2$NR$^{53}$R$^{54}$. In some embodiments, R$^{57}$ is selected from —S(=O)R$^{52}$, —S(=O)$_2$R$^{58}$, —S(=O)$_2$N(R$^{52}$)$_2$, and —NR$^{52}$S(=O)$_2$R$^{52}$. In some embodiments, R$^{57}$ is selected from —S(=O)CH$_3$, —S(=O)$_2$CH$_3$, —S(=O)$_2$NH$_2$, —NHS(=O)$_2$CH$_3$, and —S(=O)$_2$NHCH$_3$.

In certain aspects, a compound of Formula (I-A) may be represented by:

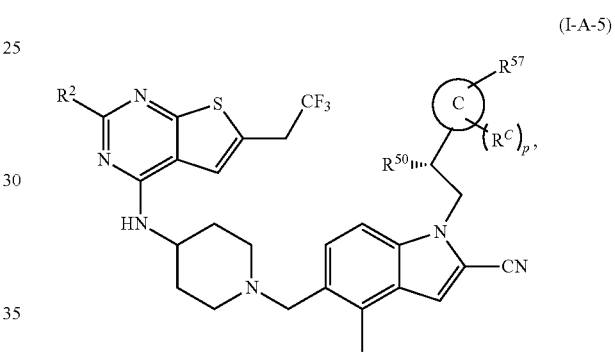

(I-A-5)

such as

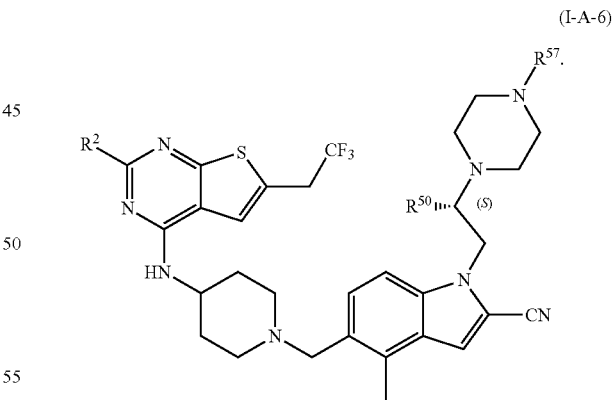

(I-A-6)

In some embodiments, C is selected from 5- to 7-membered monocyclic heterocycle, such as piperidinyl and piperazinyl. In some embodiments, R$^{50}$ is selected from deuterium, C$_{1-4}$ alkyl, C$_{1-4}$ haloalkyl, and —OR$^{52}$, such as R$^{50}$ is methyl. In some embodiments, R$^{57}$ is selected from —S(=O)R$^{52}$, —S(=O)$_2$R$^{58}$, —S(=O)$_2$N(R$^{52}$)$_2$, and —NR$^{52}$S(=O)$_2$ R$^{52}$, such as R$^{57}$ is selected from —S(=O)CH$_3$, —S(=O)$_2$ CH$_3$, —S(=O)$_2$NH$_2$, —NHS(=O)$_2$CH$_3$, and —S(=O)$_2$ NHCH$_3$. R$^{57}$ is —S(=O)$_2$CH$_3$. In some embodiments, R$^{50}$ is methyl and R$^{57}$ is —S(=O)$_2$ In some embodiments, R$^C$ is selected from —C(O)R$^{52}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, =O, C$_{1-3}$ alkyl, and C$_{1-3}$ haloalkyl, or two R$^C$ groups attached to different atoms can together form a C$_{1-3}$ bridge. In some embodiments, R$^C$ is selected from C$_{1-3}$ alkyl and C$_{1-3}$ haloalkyl, such as —CH$_3$. In some embodiments, p is selected from an integer 0 to 4, such as p is selected from an integer 0 to 2. In some embodiments, p is 0. In some embodiments, R$^{57}$ is selected from —S(=O)$_2$R$^{58}$, —NR$^{52}$S(=O)$_2$N(R$^{52}$)$_2$, CH₃. In some embodiments, R² is selected from hydrogen, halogen, —OH, —OR⁵², —NH₂, —N(R⁵²)₂, —CN, C₁₋₃ alkyl, —CH₂OH, —CH₂OR⁵², —CH₂NH₂, —CH₂N(R⁵²)₂, C₁₋₃ alkyl-N(R⁵²)₂, C₁₋₃ haloalkyl, C₂₋₃ alkenyl, and C₂₋₃ alkynyl, such as R² is selected from —OH, —OR⁵², —NH₂, —N(R⁵²)₂, —CN, and C₁₋₂ alkyl. In some embodiments, R² is methyl or —NHCH₃. In some embodiments, R² is H.

In certain aspects, a compound of Formula (I-A) may be represented by:

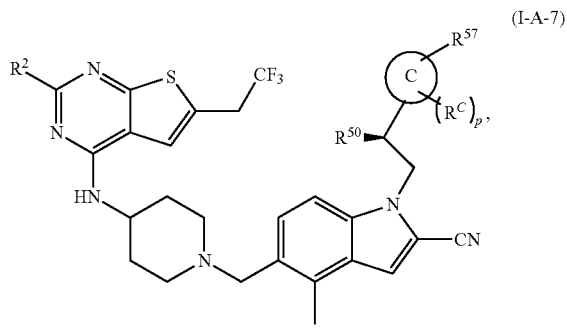
(I-A-7)

such as

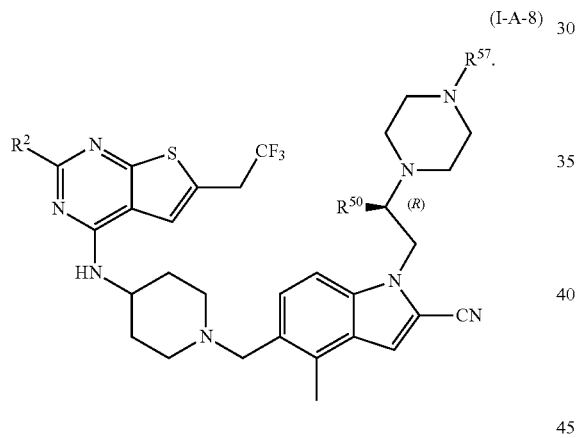
(I-A-8)

In some embodiments, C is selected from 5- to 7-membered monocyclic heterocycle, such as piperidinyl and piperazinyl. In some embodiments, R⁵⁰ is selected from deuterium, C₁₋₄ alkyl, C₁₋₄ haloalkyl, and —OR⁵², such as R⁵⁰ is methyl. In some embodiments, R⁵⁷ is selected from —S(=O)R⁵², —S(=O)₂R⁵⁸, —S(=O)₂N(R⁵²)₂, and —NR⁵²S(=O)₂ R⁵², such as R⁵⁷ is selected from —S(=O)CH₃, —S(=O)₂ CH₃, —S(=O)₂NH₂, —NHS(=O)₂CH₃, and —S(=O)₂ NHCH₃. In some embodiments, R⁵⁷ is —S(=O)₂CH₃. In some embodiments, R⁵⁰ is methyl and R⁵⁷ is —S(=O)₂ CH₃. In some embodiments, R² is selected from hydrogen, halogen, —OH, —OR⁵², —NH₂, —N(R⁵²)₂, —CN, C₁₋₃ alkyl, —CH₂OH, —CH₂OR⁵², —CH₂NH₂, —CH₂N(R⁵²)₂, C₁₋₃ alkyl-N(R⁵²)₂, C₁₋₃ haloalkyl, C₂₋₃ alkenyl, and C₂₋₃ alkynyl, such as R² is selected from —OH, —OR⁵², —NH₂, —N(R⁵²)₂, —CN, and C₁₋₂ alkyl. In some embodiments, R² is methyl or —NHCH₃. In some embodiments, R² is H.

In certain aspects, the present disclosure provides a compound of Formula (I-B):

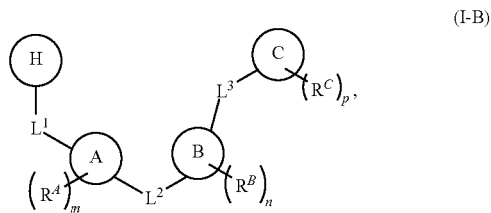
(I-B)

or a pharmaceutically acceptable salt thereof, wherein:
H is selected from C₅₋₁₂ carbocycle and 5- to 12-membered heterocycle, each of which is optionally substituted with one or more R⁵⁰;
A, B and C are each independently selected from C₃₋₁₂ carbocycle and 3- to 12-membered heterocycle;
L¹ and L² are each independently selected from bond, —O—, —S—, —N(R⁵¹)—, —N(R⁵¹)CH₂—, —C(O)—, —C(O)O—, —OC(O)—, —OC(O)O—, —C(O)N(R⁵¹)—, —C(O)N(R⁵¹)C(O)—, —C(O)N(R⁵¹)C(O)N(R⁵¹)—, —N(R⁵¹)C(O)—, —N(R⁵¹)C(O)N(R⁵¹)—, —N(R⁵¹)C(O)O—, —OC(O)N(R⁵¹)—, —C(NR⁵¹)—, —N(R⁵¹)C(NR⁵¹)—, —C(NR⁵¹)N(R⁵¹)—, —N(R⁵¹)C(NR⁵¹)N(R⁵¹)—, —S(O)₂—, —OS(O)—, —S(O)O—, —S(O)—, —OS(O)₂—, —S(O)₂O—, —N(R⁵¹)S(O)₂—, —S(O)₂N(R⁵¹)—, —N(R⁵¹)S(O)—, —S(O)N(R⁵¹)—, —N(R⁵¹)S(O)₂N(R⁵¹)—, —N(R⁵¹)S(O)N(R⁵¹)—; alkylene, alkenylene, alkynylene, heteroalkylene, heteroalkenylene, and heteroalkynylene, each of which is optionally substituted with one or more R⁵⁰;
L³ is selected from alkylene, alkenylene, and alkynylene, each of which is substituted with one or more R⁵⁶ and optionally further substituted with one or more R⁵⁰;
Rᴬ, Rᴮ and Rᶜ are each independently selected at each occurrence from R⁵⁰, or two Rᴬ groups, two Rᴮ groups or two Rᶜ groups attached to the same atom or different atoms can together optionally form a bridge or ring;
m, n and p are each independently an integer from 0 to 6;
R⁵⁰ is independently selected at each occurrence from:
halogen, —NO₂, —CN, —OR⁵², —SR⁵², —N(R⁵²)₂, —NR⁵³R⁵⁴, —S(=O)R⁵², —S(=O)₂R⁵², —S(=O)₂N(R⁵²)₂, —S(=O)₂NR⁵³R⁵⁴, —NR⁵²S(=O)₂R⁵², —NR⁵²S(=O)₂N(R⁵²)₂, —NR⁵²S(=O)₂ NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O)OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, —P(O)(OR⁵²)(R⁵²), —P(O)(NR⁵²)(R⁵²), —NR⁵²P(O)(R⁵²), P(O)(NR⁵²)(OR⁵²), —P(O)(NR⁵²)₂, =O, =S, =N(R⁵²);
C₁₋₁₀ alkyl, C₂₋₁₀ alkenyl, and C₂₋₁₀ alkynyl, each of which is independently optionally substituted at each occurrence with one or more substituents selected from halogen, —NO₂, —CN, —OR⁵², —SR⁵², —N(R⁵²)₂, —NR⁵³R⁵⁴, —S(=O)R⁵², —S(=O)₂ R⁵², —S(=O)₂N(R⁵²)₂, —S(=O)₂NR⁵³R⁵⁴, —NR⁵²S(=O)₂R⁵², —NR⁵²S(=O)₂N(R⁵²)₂, —NR⁵²S(=O)₂NR⁵³R⁵⁴, —C(O)R⁵², —C(O)OR⁵², —OC(O)R⁵², —OC(O)OR⁵², —OC(O)N(R⁵²)₂, —OC(O)NR⁵³R⁵⁴, —NR⁵²C(O)R⁵², —NR⁵²C(O) OR⁵², —NR⁵²C(O)N(R⁵²)₂, —NR⁵²C(O)NR⁵³R⁵⁴, —C(O)N(R⁵²)₂, —C(O)NR⁵³R⁵⁴, —P(O)(OR⁵²)₂, —P(O)(R⁵²)₂, —P(O)(OR⁵²)(R⁵²), —P(O)(NR⁵²) (R⁵²), —NR⁵²P(O)(R⁵²), P(O)(NR⁵²)(OR⁵²), —P(O)(NR$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from:
hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), P(O)(NR$^{52}$)(OR$^{52}$), —P(O)(NR$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{56}$ is independently selected at each occurrence from:
—NO$_2$, —SR$^{52}$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-10}$ alkyl, C$_{2-10}$ alkenyl, C$_{2-10}$ alkynyl, C$_{3-12}$ carbocycle and 3- to 12-membered heterocycle, wherein each C$_{1-10}$ alkyl, C$_{2-10}$ alkenyl, and C$_{2-10}$ alkynyl in R$^{56}$ is independently optionally substituted at each occurrence with one or more substituents selected from halogen, —NO$_2$, —CN, —OR$^{59}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle, and 3- to 12-membered heterocycle;

wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and further wherein R$^{56}$ optionally forms a bond to ring C; and R$^{59}$ is independently selected at each occurrence from C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle, wherein for a compound or salt of Formula (I-B), when R$^{56}$ is —CH$_3$, L$^3$ is not further substituted with —OH, —NH$_2$, or —CN.

In certain aspects, a compound of Formula (I-B) may be represented by:

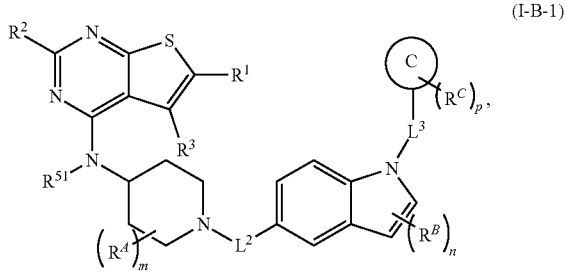

(I-B-1)

such as

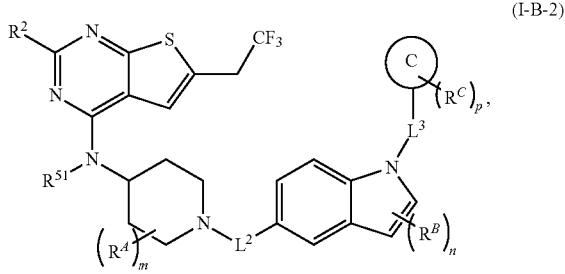

(I-B-2)

wherein $R^1$, $R^2$ and $R^3$ are each independently selected at each occurrence from hydrogen and $R^{50}$. In some embodiments, $R^1$ is selected from $R^{50}$. In some embodiments, $R^1$ is $C_{1-3}$ haloalkyl, such as —$CH_2CF_3$. In some embodiments, $R^2$ is selected from $R^{50}$. In some embodiments, $R^2$ is selected from hydrogen, halogen, —OH, —$OR^{52}$, —$NH_2$, —$N(R^{52})_2$, —CN, $C_{1-3}$ alkyl, $C_{1-3}$ alkyl-$OR^{52}$, $C_{1-3}$ alkyl-$N(R^{52})_2$, $C_{1-3}$ haloalkyl, $C_{2-3}$ alkenyl, and $C_{2-3}$ alkynyl. In some embodiments, $R^2$ is selected from halogen, —OH, —$OR^{52}$, —$NH_2$, —$N(R^{52})_2$, —CN, $C_{1-3}$ alkyl, —$CH_2OH$, —$CH_2OR^{52}$, —$CH_2NH_2$, —$CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from —OH, —$OR^{52}$, —$NH_2$, —$N(R^{52})_2$, —CN, and $C_{1-2}$ alkyl. Optionally, $R^2$ is selected from —$NH_2$, —$CH_3$, —$OCH_3$, —$CH_2OH$, and —$NHCH_3$. In some embodiments, $R^3$ is selected from hydrogen, halogen, —OH, —$N(R^{52})_2$, —CN, —$C(O)OR^{52}$, $C_{1-3}$ alkyl, and $C_{1-3}$ haloalkyl. In some embodiments, $R^{51}$ is selected from selected from hydrogen and alkyl, such as $R^{51}$ is hydrogen. In some embodiments, $R^A$ is selected from halogen, —CN, —$OR^{52}$, —$N(R^{52})_2$, —$NR^{53}R^{54}$, —$C(O)N(R^{52})_2$, —$C(O)NR^{53}R^{54}$, —$C(O)R^{52}$, $C(O)OR^{52}$, —$OC(O)R^{52}$, —$NR^{52}C(O)R^{52}$, —$C(O)N(R^{52})_2$, —$C(O)NR^{53}R^{54}$, =O, $C_{1-10}$ alkyl, $C_{2-10}$ alkenyl, $C_{2-10}$ alkynyl, optionally substituted $C_{1-10}$ alkyl, optionally substituted $C_{2-10}$ alkenyl, and optionally substituted $C_{2-10}$ alkynyl. In some embodiments, m is 0. In some embodiments, $L^2$ is selected from —O—, —$N(R^{51})$—, —$N(R^{51})CH_2$—, —$C(O)N(R^{51})$—, —$N(R^{51})C(O)$—, —$N(R^{51})S(O)_2$—, —$S(O)_2N(R^{51})$—, $C_{1-4}$ alkylene and $C_{1-4}$ heteroalkylene. In some embodiments, $L^2$ is $C_{1-4}$ alkylene, optionally substituted with one or more $R^{50}$. In some embodiments, $L^2$ is $C_{1-2}$ alkylene, optionally substituted with one or more $R^{50}$. In some embodiments, $L^2$ is selected from —$CH_2$—, —$N(R^{51})$—, —$N(R^{51})CH_2$—, —$N(R^{51})C(O)$—, and —$N(R^{51})S(O)_2$—. In some embodiments, $L^2$ is —$CH_2$—. In some embodiments, Ie is present at one or more positions of the indole, such as at position 2, 3, 4, or 6 of the indole. In some embodiments, $R^B$ is selected from halogen, —CN, —$OR^{52}$, —$N(R^{52})_2$, —$NR^{53}R^{54}$, —$C(O)R^{52}$, —$C(O)OR^{52}$, —$OC(O)R^{52}$, —$NR^{52}C(O)R^{52}$, —$C(O)N(R^{52})_2$, —$C(O)NR^{53}R^{54}$, =O, $C_{1-10}$ alkyl, $C_{2-10}$ alkenyl, $C_{2-10}$ alkynyl, optionally substituted $C_{1-10}$ alkyl, optionally substituted $C_{2-10}$ alkenyl, and optionally substituted $C_{2-10}$ alkynyl. In some embodiments, $R^B$ is selected from halogen, —CN, —$OR^{52}$, —$N(R^{52})_2$, —$NR^{53}R^{54}$, $C_{1-3}$ alkyl, and optionally substituted $C_{1-3}$ alkyl, such as $R^B$ is selected from halogen, —CN, —$OR^{52}$, —$N(R^{52})_2$, —$NR^{53}R^{54}$, and $C_{1-2}$ alkyl. In some embodiments, n is an integer from 1 to 4, such as an integer from 2 to 3. In some embodiments, n is 2. In some embodiments, $L^3$ is selected from alkylene, alkenylene, and alkynylene, each of which is substituted with one or more $R^{56}$ and optionally further substituted with one or more $R^{50}$. In some embodiments, $L^3$ is selected from $C_{1-6}$ alkylene, $C_{2-6}$ alkenylene, and $C_{2-6}$ alkynylene, each of which is substituted with one or more $R^{56}$ and optionally further substituted with one or more $R^{50}$. In some embodiments, $L^3$ is selected from $C_{1-6}$ alkylene, which is substituted with one or more $R^{56}$ and optionally further substituted with one or more $R^{50}$. In some embodiments, $L^3$ is C2 alkylene substituted with at least one $C_{1-3}$ alkyl or $C_{1-3}$ haloalkyl, and optionally further substituted with one or more $R^{50}$. In some embodiments, $L^3$ is substituted with =O, $C_{1-6}$ alkyl, $C_{1-6}$ haloalkyl, $C_{1-3}$ alkyl(cyclopropyl), $C_{1-3}$ alkyl($NR^{52}C(O)R^{52}$) or —$O(C_{1-6}$ alkyl). In some embodiments, $L^3$ is substituted with —$CH_3$. In some embodiments, $L^3$ is selected from

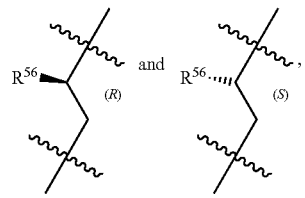

where $R^{56}$ is optionally methyl. In some embodiments, C is selected from $C_{3-12}$ carbocycle and 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

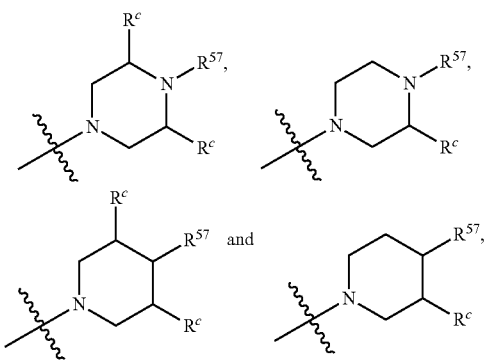

wherein R[57] is selected from hydrogen and R[50]. In some embodiments, C is selected from

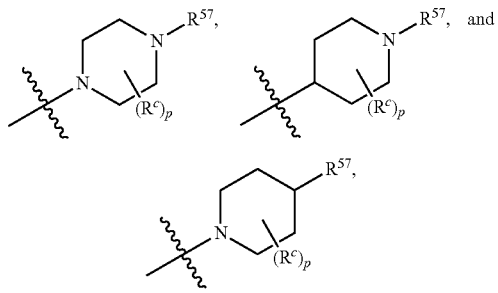

wherein R[57] is selected from hydrogen and R[50]. In some embodiments, C is selected from

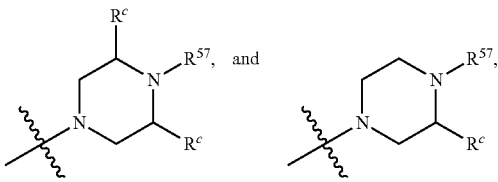

wherein R[57] is selected from hydrogen and R[50]. In some embodiments, C is selected from

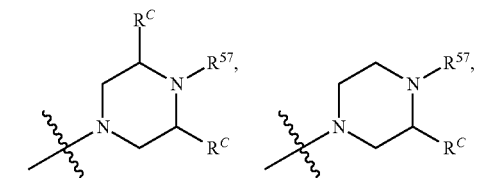

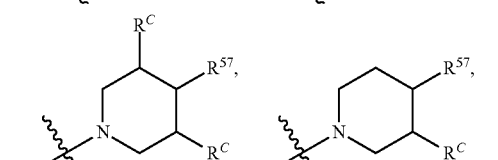

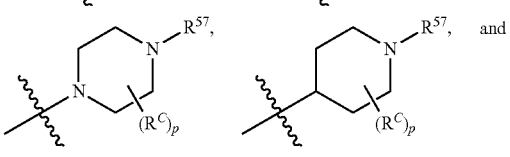

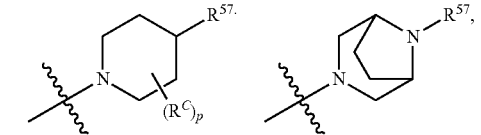

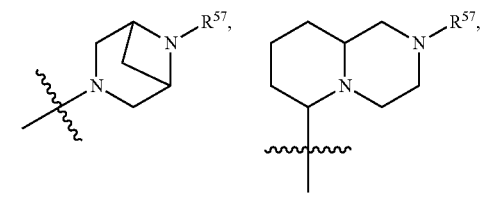

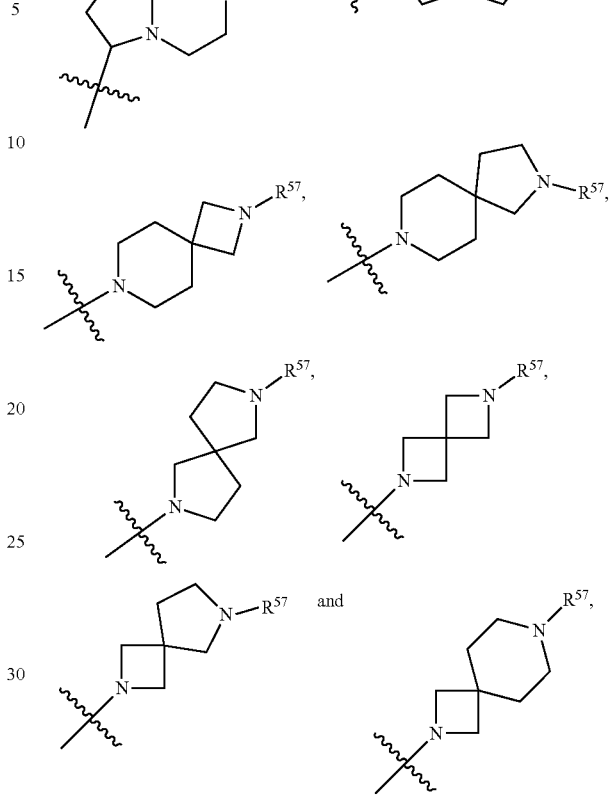

optionally substituted with one or more R[C], wherein R[57] is selected from hydrogen and R[50] In some embodiments, C is selected from

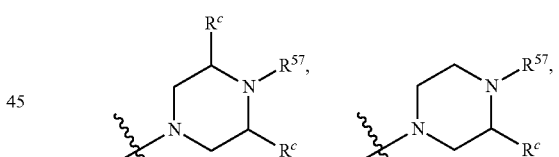

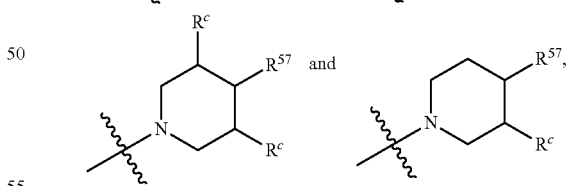

wherein R[57] is selected from —S(=O)R[52], —S(=O)$_2$R[52], —S(=O)$_2$N(R[52])$_2$, —S(=O)$_2$NR[53]R[54], —NR[52]S(=O)$_2$R[52]; and C$_{1-10}$ alkyl substituted with one or more substituents selected from —S(=O)R[52], —S(=O)$_2$R[52], —S(=O)$_2$N(R[52])$_2$, —S(=O)$_2$NR[53]R[54], and —NR[52]S(=O)$_2$R[52]. In some embodiments, R[57] is selected from —S(=O)R[52], —S(=O)$_2$R[52], —S(=O)$_2$N(R[52])$_2$, and —NR[52]S(=O)$_2$R[52], such as R[57] is selected from —S(=O)CH$_3$, —S(=O)$_2$CH$_3$, —S(=O)$_2$NH$_2$, —NHS(=O)$_2$CH$_3$, and —S(=O)$_2$NHCH$_3$. In some embodiments, C is selected from

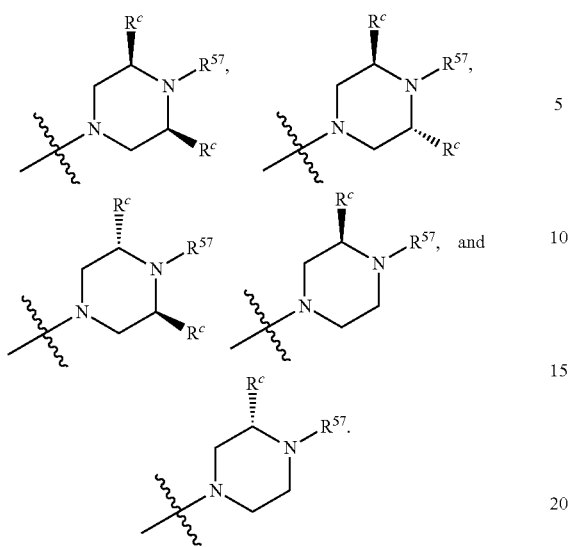

In some embodiments, $R^C$ is selected from —C(O)R$^{52}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, =O, C$_{1-3}$ alkyl, and C$_{1-3}$ haloalkyl, or two R$^C$ groups attached to different atoms can together form a C$_{1-3}$ bridge. In some embodiments, R$^C$ is selected from C$_{1-3}$ alkyl and C$_{1-3}$ haloalkyl, such as —CH$_3$. In some embodiments, p is selected from an integer 0 to 4, such as p is selected from an integer 0 to 2. In some embodiments, p is 0. In some embodiments, R$^C$ is 52)$_2$, —NR$^{53}$R$^{54}$, —NR$^{52}$S(=O)$_2$R$^{52}$, —C(O)R$^{52}$, selected from —N(R$^{52}$)$_2$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, and —C(O)NR$^{53}$R$^{54}$. In some embodiments, R$^C$ is selected from —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, NR$^{52}$C(O)NR$^{53}$R$^{54}$, —C(O)N(R$^{52}$)$_2$, —C(O)NR$^{53}$R$^{54}$, C$_{1-6}$ alkyl, and C$_{1-6}$ alkyl substituted with —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, or —C(O)NR$^{53}$R$^{54}$. In some embodiments, C is selected from

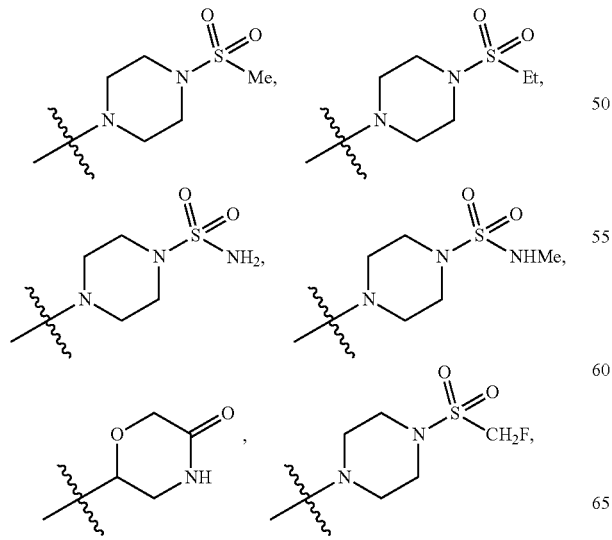

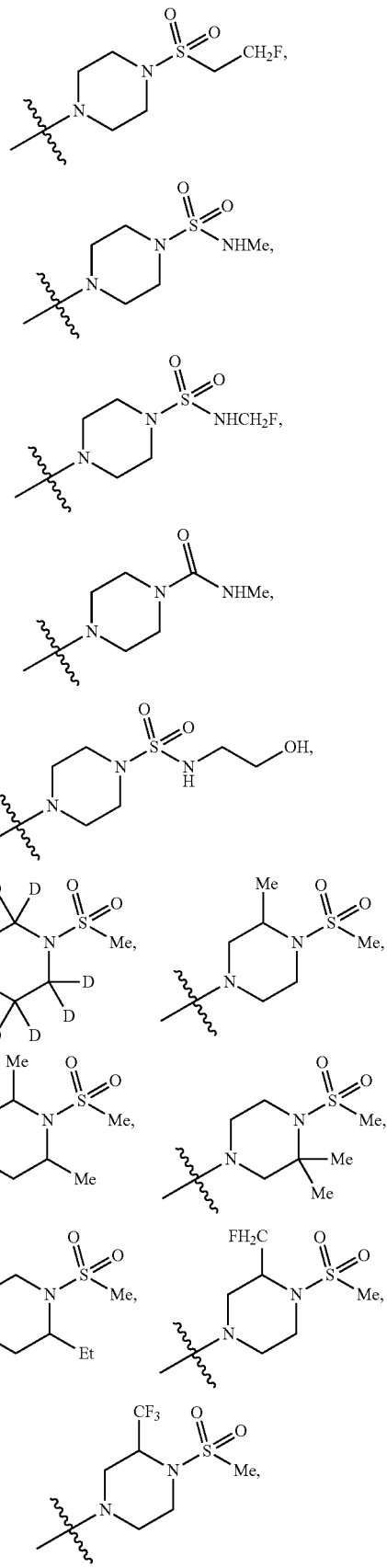

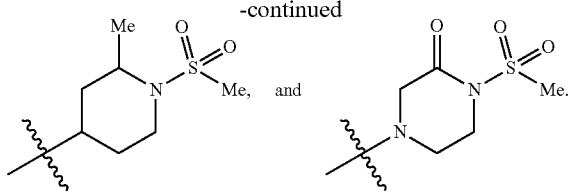

In certain aspects, a compound of Formula (I-B) may be represented by:

(I-B-3)

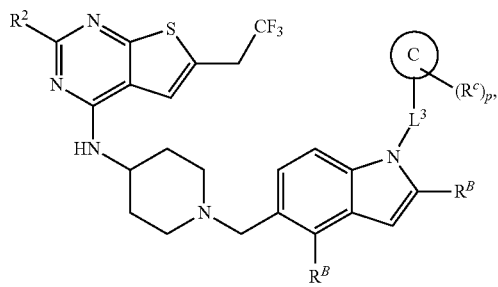

such as (I-B-4)

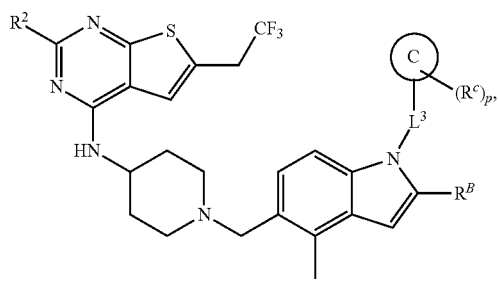

In some embodiments, $R^2$ is selected from $R^{50}$. In some embodiments, $R^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-OR$^{52}$, C$_{1-3}$ alkyl-N(R$^{52}$)$_2$, C$_{1-3}$ haloalkyl, C$_{2-3}$ alkenyl, and C$_{2-3}$ alkynyl. In some embodiments, $R^2$ is selected from halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl, such as $R^2$ is selected from —OH, —OR$^{52}$, —NH$_2$, —N(R$^{52}$)$_2$, —CN, and C$_{1-2}$ alkyl. Optionally, $R^2$ is selected from —NH$_2$, —CH$_3$, —OCH$_3$, —CH$_2$OH, and —NHCH$_3$. In some embodiments, $R^B$ is selected from halogen, —CN, —OR$^{52}$, —N(R$^{52}$)$_2$, —NR$^{53}$R$^{54}$, —C(O)R$^{52}$, —C(O)OR$^{52}$, —OC(O)R$^{52}$, —NR$^{52}$C(O)R$^{52}$, —C(O)N(R$^{52}$)$_2$, —C(O)NR$^{53}$R$^{54}$, =O, C$_{1-10}$ alkyl, C$_{2-10}$ alkenyl, C$_{2-10}$ alkynyl, optionally substituted C$_{1-10}$ alkyl, optionally substituted C$_{2-10}$ alkenyl, and optionally substituted C$_{2-10}$ alkynyl. In some embodiments, $R^B$ is selected from halogen, —CN, —OR$^{52}$, —N(R$^{52}$)$_2$, —NR$^{53}$R$^{54}$, C$_{1-3}$ alkyl, and optionally substituted C$_{1-3}$ alkyl, such as $R^B$ is selected from halogen, —CN, —OR$^{52}$, —N(R$^{52}$)$_2$, —NR$^{53}$R$^{54}$, and C$_{1-2}$ alkyl. In some embodiments, $L^3$ is selected from alkylene, alkenylene, and alkynylene, each of which is substituted with one or more $R^{56}$ and optionally further substituted with one or more $R^{50}$. In some embodiments, $L^3$ is selected from C$_{1-6}$ alkylene, C$_{2-6}$ alkenylene, and C$_{2-6}$ alkynylene, each of which is substituted with one or more $R^{56}$ and optionally further substituted with one or more $R^{50}$. In some embodiments, $L^3$ is selected from C$_{1-6}$ alkylene, which is substituted with one or more $R^{56}$ and optionally further substituted with one or more $R^{50}$. In some embodiments, $L^3$ is C2 alkylene substituted with at least one C$_{1-3}$ alkyl or C$_{1-3}$ haloalkyl, and optionally further substituted with one or more $R^{50}$. In some embodiments, $L^3$ is substituted with =O, C$_{1-6}$ alkyl, C$_{1-6}$ haloalkyl, C$_{1-3}$ alkyl(cyclopropyl), C$_{1-3}$ alkyl(NR$^{52}$C(O)R$^{52}$) or —O(C$_{1-6}$ alkyl). In some embodiments, $L^3$ is substituted with —CH$_3$. In some embodiments, $L^3$ is selected from

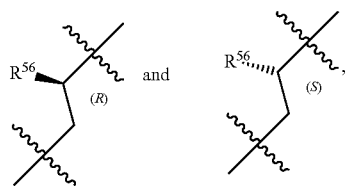

where $R^{56}$ is optionally methyl. In some embodiments, C is selected from C$_{3-12}$ carbocycle and 3- to 12-membered heterocycle, such as 5- to 12-membered heterocycle. In some embodiments, the heterocycle is saturated. In some embodiments, C is selected from 5- to 7-membered monocyclic heterocycle, 8- to 10-membered fused bicyclic heterocycle, and 7- to 12-membered spirocyclic heterocycle. In some embodiments, the heterocycle comprises at least one nitrogen atom, such as one or two nitrogen atoms. In some embodiments, C comprises at least one ring nitrogen. In some embodiments, C is selected from piperidinyl and piperazinyl, such as

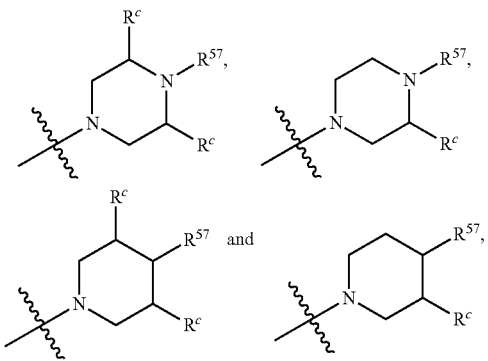

wherein $R^{57}$ is selected from hydrogen and $R^{50}$. In some embodiments, C is selected from

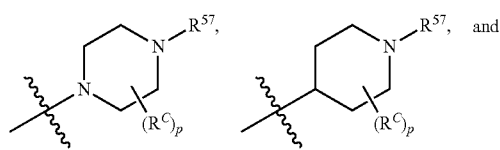

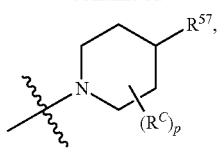

wherein $R^{57}$ is selected from hydrogen and $R^{50}$. In some embodiments, C is selected from

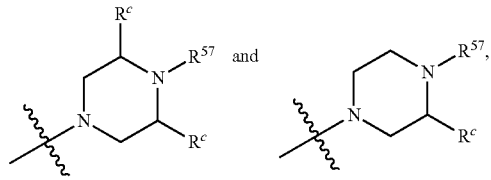

wherein $R^{57}$ is selected from hydrogen and $R^{50}$. In some embodiments, C is selected from

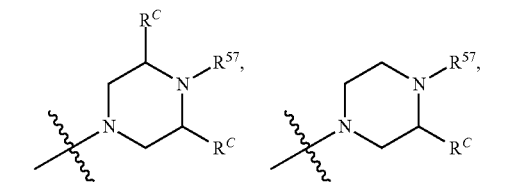

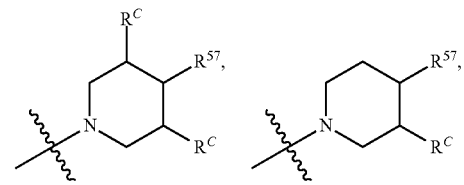

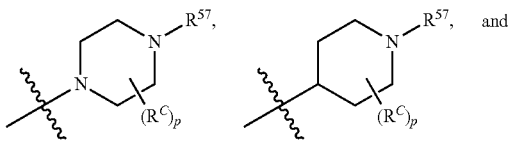

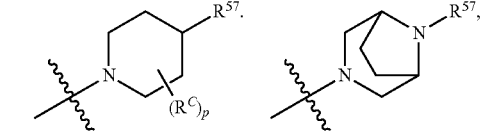

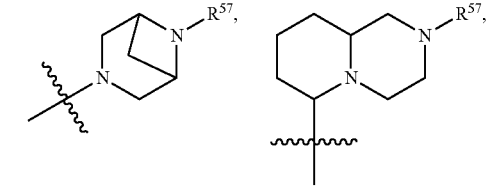

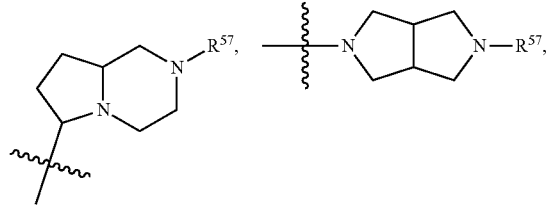

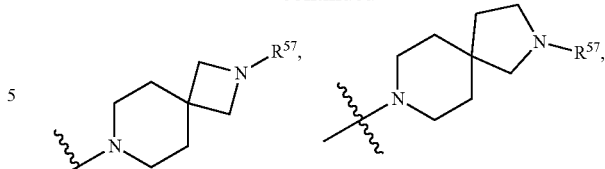

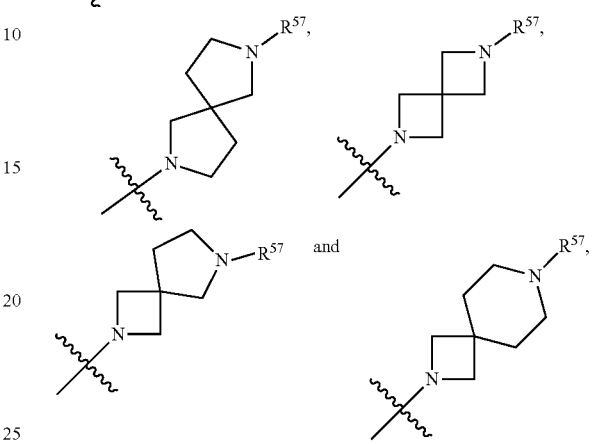

optionally substituted with one or more $R^C$, wherein $R^{57}$ is selected from hydrogen and $R^{50}$. In some embodiments, C is selected from

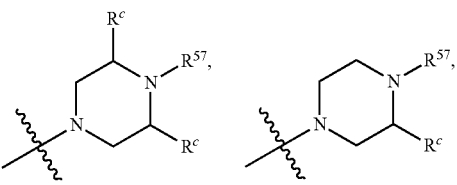

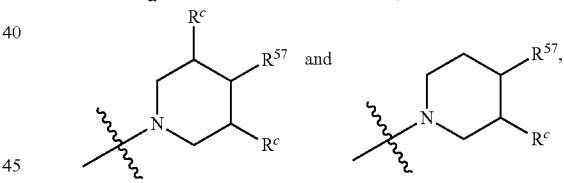

wherein $R^{57}$ is selected from —S(=O)$R^{52}$, —S(=O)$_2R^{52}$, —S(=O)$_2$N(R$^{52}$)$_2$, —S(=O)$_2$NR$^{53}$R$^{54}$, —NR$^{52}$S(=O)$_2$R$^{52}$; and $C_{1-10}$ alkyl substituted with one or more substituents selected from —S(=O)$R^{52}$, —S(=O)$_2R^{52}$, —S(=O)$_2$N(R$^{52}$)$_2$, —S(=O)$_2$NR$^{53}$R$^{54}$, and —NR$^{52}$S(=O)$_2$R$^{52}$. In some embodiments, $R^{57}$ is selected from —S(=O)$R^{52}$, —S(=O)$_2R^{52}$, —S(=O)$_2$N(R$^{52}$)$_2$, and —NR$^{52}$S(=O)$_2$R$^{52}$, such as $R^{57}$ is selected from —S(=O)CH$_3$, —S(=O)$_2$CH$_3$, —S(=O)$_2$NH$_2$, —NHS(=O)$_2$CH$_3$, and —S(=O)$_2$NHCH$_3$. In some embodiments, C is selected from

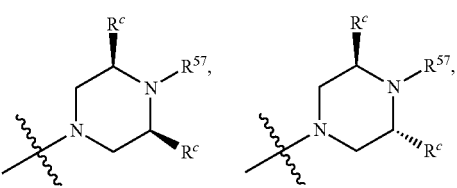

-continued

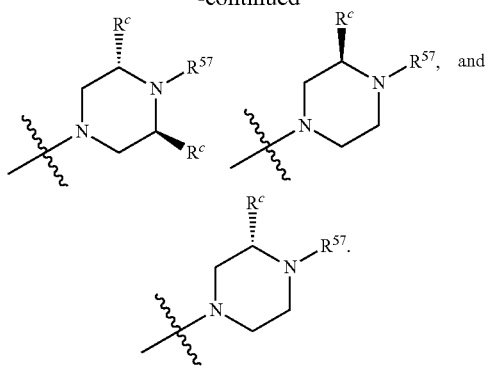

In some embodiments, $R^C$ is selected from —C(O)$R^{52}$, —S(=O)$R^{52}$, —S(=O)$_2R^{52}$, —S(=O)$_2$N($R^{52}$)$_2$, —S(=O)$_2$N$R^{53}R^{54}$, —N$R^{52}$S(=O)$_2R^{52}$, =O, $C_{1-3}$ alkyl, and $C_{1-3}$ haloalkyl, or two $R^C$ groups attached to different atoms can together form a $C_{1-3}$ bridge. In some embodiments, $R^C$ is selected from $C_{1-3}$ alkyl and $C_{1-3}$ haloalkyl, such as —CH$_3$. In some embodiments, p is selected from an integer 0 to 4, such as p is selected from an integer 0 to 2. In some embodiments, p is 0. In some embodiments, $R^C$ is selected from —N($R^{52}$)$_2$, —N$R^{53}R^{54}$, —N$R^{52}$S(=O)$_2R^{52}$, —C(O)$_R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, and —C(O)N$R^{53}R^{54}$. In some embodiments, $R^C$ is selected from —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, —C(O)N$R^{53}R^{54}$, $C_{1-6}$ alkyl, and $C_{1-6}$ alkyl substituted with —N($R^{52}$)$_2$, —N$R^{53}R^{54}$, —N$R^{52}$S(=O)$_2R^{52}$, —C(O)$R^{52}$, —C(O)O$R^{52}$, —N$R^{52}$C(O)$R^{52}$, —N$R^{52}$C(O)O$R^{52}$, —N$R^{52}$C(O)N($R^{52}$)$_2$, —N$R^{52}$C(O)N$R^{53}R^{54}$, —C(O)N($R^{52}$)$_2$, or —C(O)N$R^{53}R^{54}$. In some embodiments, C is selected from

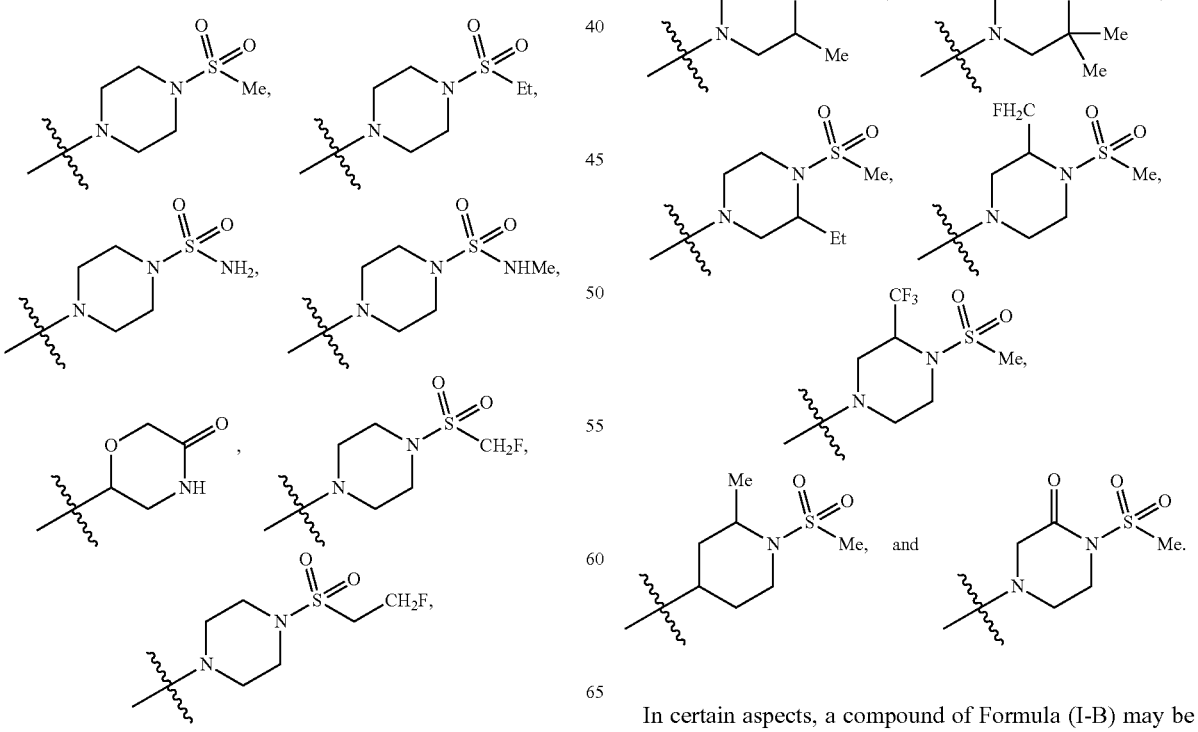

In certain aspects, a compound of Formula (I-B) may be represented by:

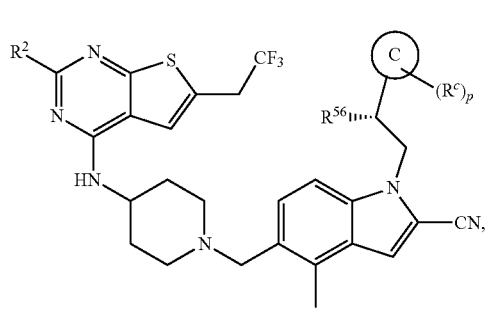
(I-B-5)

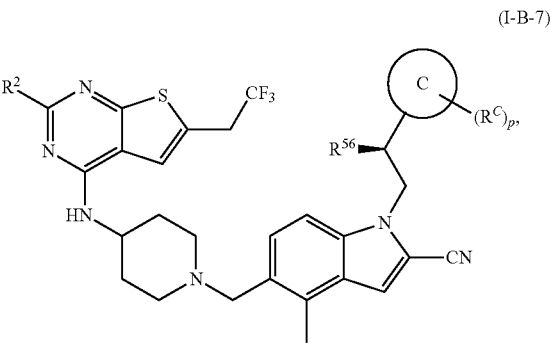
(I-B-7)

such as such as

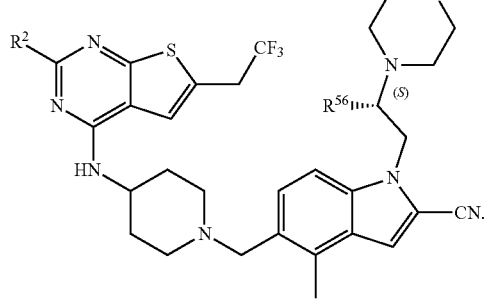
(I-B-6)

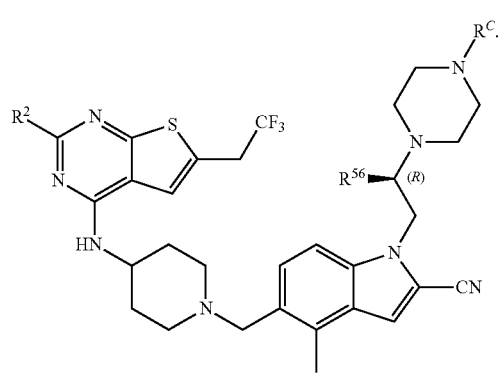
(I-B-8)

In some embodiments, C is selected from 5- to 7-membered monocyclic heterocycle, such as piperidinyl and piperazinyl. In some embodiments, $R^{56}$ is selected from deuterium, $C_{1-4}$ alkyl, $C_{1-4}$ haloalkyl, and —$OR^{59}$, such as $R^{56}$ is methyl. In some embodiments, $R^C$ is selected from —$S(=O)R^{52}$, —$S(=O)_2R^{52}$, —$S(=O)_2N(R^{52})_2$, and —$NR^{52}S(=O)_2R^{52}$, such as $R^C$ is selected from —$S(=O)CH_3$, —$S(=O)_2CH_3$, —$S(=O)_2NH_2$, —$NHS(=O)_2CH_3$, and —$S(=O)_2NHCH_3$. In some embodiments, p is an integer from 1 to 3, such asp is 1. In some embodiments, $R^C$ is —$S(=O)_2CH_3$. In some embodiments, $R^{56}$ is methyl and $R^C$ is —$S(=O)_2CH_3$. In some embodiments, $R^2$ is selected from hydrogen, halogen, —OH, —$OR^{52}$, —$NH_2$, —$N(R^{52})_2$, —CN, $C_{1-3}$ alkyl, —$CH_2OH$, —$CH_2OR^{52}$, —$CH_2NH_2$, —$CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from —OH, —$OR^{52}$, —$NH_2$, —$N(R^{52})_2$, —CN, and $C_{1-2}$ alkyl. In some embodiments, $R^2$ is methyl or —$NHCH_3$. In some embodiments, $R^2$ is H.

In some embodiments, C is selected from 5- to 7-membered monocyclic heterocycle, such as piperidinyl and piperazinyl. In some embodiments, $R^{56}$ is selected from deuterium, $C_{1-4}$ alkyl, $C_{1-4}$ haloalkyl, and —$OR^{59}$, such as $R^{56}$ is methyl. In some embodiments, $R^C$ is selected from —$S(=O)R^{52}$, —$S(=O)_2R^{52}$, —$S(=O)_2N(R^{52})_2$, and —$NR^{52}S(=O)_2R^{52}$, such as $R^C$ is selected from —$S(=O)CH_3$, —$S(=O)_2CH_3$, —$S(=O)_2NH_2$, —$NHS(=O)_2CH_3$, and —$S(=O)_2NHCH_3$. In some embodiments, p is an integer from 1 to 3, such asp is 1. In some embodiments, $R^C$ is —$S(=O)_2CH_3$. In some embodiments, $R^{56}$ is methyl and $R^C$ is —$S(=O)_2CH_3$. In some embodiments, $R^2$ is selected from hydrogen, halogen, —OH, —$OR^{52}$, —$NH_2$, —$N(R^{52})_2$, —CN, $C_{1-3}$ alkyl, —$CH_2OH$, —$CH_2OR^{52}$, —$CH_2NH_2$, —$CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from —OH, —$OR^{52}$, —$NH_2$, —$N(R^{52})_2$, —CN, and $C_{1-2}$ alkyl. In some embodiments, $R^2$ is methyl or —$NHCH_3$. In some embodiments, $R^2$ is H.

In certain aspects, the present disclosure provides a compound of Formula (II):

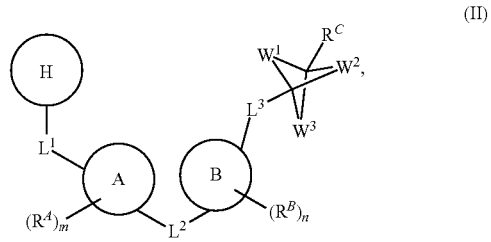
(II)

In certain aspects, a compound of Formula (I-B) may be represented by:

or a pharmaceutically acceptable salt or prodrug thereof, wherein:

H is selected from $C_{5-12}$ carbocycle and 5- to 12-membered heterocycle, each of which is optionally substituted with one or more $R^{59}$;

A is selected from bond, $C_{3-12}$ carbocycle and 3- to 12-membered heterocycle;

B is selected from $C_{3-12}$ carbocycle and 3- to 12-membered heterocycle;

$L^1$, $L^2$ and $L^3$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$;

$R^A$, $R^B$ and $R^C$ are each independently selected at each occurrence from $R^{50}$, or two $R^A$ groups or two $R^B$ groups attached to the same atom or different atoms can together optionally form a bridge or ring;

m and n are each independently an integer from 0 to 6;

$W^1$ is $C_{1-4}$ alkylene, optionally substituted with one or more $R^{50}$;

$W^2$ is selected from a bond; and $C_{1-4}$ alkylene, optionally substituted with one or more $R^{50}$;

$W^3$ is selected from absent; and $C_{1-4}$ alkylene, optionally substituted with one or more $R^{50}$;

$R^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from:
hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle; and $R^{53}$ and $R^{54}$ are taken together with the nitrogen atom to which they are attached to form a heterocycle, optionally substituted with one or more $R^{50}$, wherein for a compound or salt of Formula (II), when $W^3$ is absent:

$W^1$ is $C_1$ alkylene, $W^2$ is a bond, and $L^3$ is not a bond;

$W^1$ is $C_{2-4}$ alkylene and $W^2$ is a bond; or $W^1$ and $W^2$ are each $C_1$ alkylene and $L^3$ is not a bond, wherein each $C_1$ alkylene is independently optionally substituted with one or more $R^{50}$.

In certain aspects, a compound of Formula (II) may be represented by:

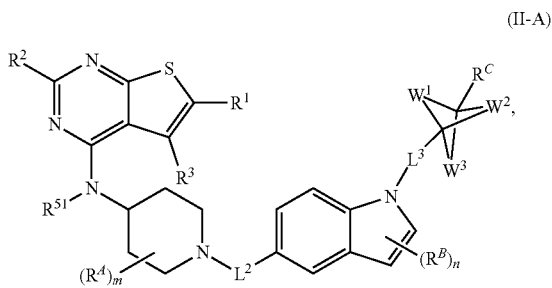

(II-A)

such as

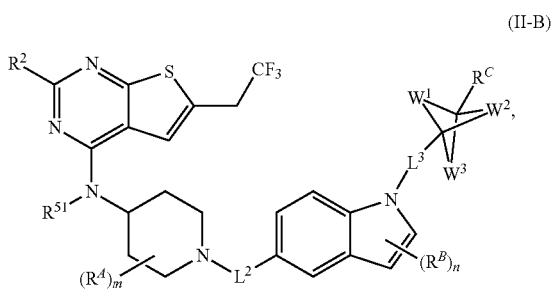

(II-B)

wherein $R^1$, $R^2$ and $R^3$ are each independently selected at each occurrence from hydrogen and $R^{50}$. In some embodiments, $R^1$ is selected from $R^{50}$. In some embodiments, $R^1$ is $C_{1-3}$ haloalkyl, such as —$CH_2CF_3$. In some embodiments, $R^2$ is selected from $R^{50}$. In some embodiments, $R^2$ is selected from hydrogen, halogen, —OH, —$OR^{52}$, —$NH_2$, —$N(R^{52})_2$, —CN, $C_{1-3}$ alkyl, $C_{1-3}$ alkyl-$OR^{52}$, $C_{1-3}$ alkyl-$N(R^{52})_2$, C13 haloalkyl, $C_{2-3}$ alkenyl, and $C_{2-3}$ alkynyl. In some embodiments, $R^2$ is selected from halogen, —OH, —$OR^{52}$, —$NH_2$, —$N(R^{52})_2$, —CN, $C_{1-3}$ alkyl, —$CH_2OH$, —$CH_2OR^{52}$, —$CH_2NH_2$, —$CH_2N(R^{52})_2$, $C_{1-3}$ alkyl-$N(R^{52})_2$, $C_{1-3}$ haloalkyl, $C_{2-3}$ alkenyl, and $C_{2-3}$ alkynyl, such as $R^2$ is selected from —OH, —$OR^{52}$, —$NH_2$, —$N(R^{52})_2$, —CN, and $C_{1-2}$ alkyl. Optionally, $R^2$ is selected from —$NH_2$, —$CH_3$, —$OCH_3$, —$CH_2OH$, and —$NHCH_3$. In some embodiments, $R^3$ is selected from hydrogen, halogen, —OH, —$N(R^{52})_2$, —CN, —$C(O)OR^{52}$, $C_{1-3}$ alkyl, and $C_{1-3}$ haloalkyl. In some embodiments, $R^{51}$ is selected from selected from hydrogen and alkyl, such as $R^{51}$ is hydrogen. In some embodiments, $R^A$ is selected from halogen, —CN, —$OR^{52}$, —$N(R^{52})_2$, —$NR^{53}R^{54}$, —$C(O)N(R^{52})_2$, —$C(O)NR^{53}R^{54}$, —$C(O)R^{52}$, $C(O)OR^{52}$, —$OC(O)R^{52}$, —$NR^{52}C(O)R^{52}$, —$C(O)N(R^{52})_2$, —$C(O)NR^{53}R^{54}$, =O, $C_{1-10}$ alkyl, $C_{2-10}$ alkenyl, $C_{2-10}$ alkynyl, optionally substituted $C_{1-10}$ alkyl, optionally substituted $C_{2-10}$ alkenyl, and optionally substituted $C_{2-10}$ alkynyl. In some embodiments, m is an integer from 0 to 3. In some embodiments, m is 0. In some embodiments, $L^2$ is selected from —O—, —$N(R^{51})$—, —$N(R^{51})CH_2$—, —$C(O)N(R^{51})$—, —$N(R^{51})C(O)$—, —$N(R^{51})S(O)_2$—, —$S(O)_2N(R^{51})$—, $C_{1-4}$ alkylene and $C_{1-4}$ heteroalkylene. In some embodiments, $L^2$ is $C_{1-4}$ alkylene, optionally substituted with one or more $R^{50}$. In some embodiments, $L^2$ is $C_{1-2}$ alkylene, optionally substituted with one or more $R^{50}$. In some embodiments, $L^2$ is selected from —$CH_2$—, —$N(R^{51})$—, —$N(R^{51})CH_2$—, —$N(R^{51})C(O)$—, and —$N(R^{51})S(O)_2$—. In some embodiments, $L^2$ is —$CH_2$—. In some embodiments, $R^B$ is present at one or more positions of the indole, such as at position 2, 3, 4, or 6 of the indole. In some embodiments, $R^B$ is selected from halogen, —CN, —$OR^{52}$, —$N(R^{52})_2$, —$NR^{53}R^{54}$, —$C(O)N(R^{52})_2$, —$C(O)NR^{53}R^{54}$, —$C(O)R^{52}$, $C(O)OR^{52}$, —$OC(O)R^{52}$, —$NR^{52}C(O)R^{52}$, —$C(O)N(R^{52})_2$, —$C(O)NR^{53}R^{54}$, =O, $C_{1-10}$ alkyl, $C_{2-10}$ alkenyl, $C_{2-10}$ alkynyl, optionally substituted $C_{1-10}$ alkyl, optionally substituted $C_{2-10}$ alkenyl, and optionally substituted $C_{2-10}$ alkynyl. In some embodiments, $R^B$ is selected from halogen, —CN, —$OR^{52}$, —$N(R^{52})_2$, —$NR^{53}R^{54}$, $C_{1-3}$ alkyl, and optionally substituted $C_{1-3}$ alkyl, such as $R^B$ is selected from halogen, —CN, —$OR^{52}$, —$N(R^{52})_2$, —$NR^{53}R^{54}$, and $C_{1-2}$ alkyl. In some embodiments, n is an integer from 1 to 4, such as an integer from 2 to 3. In some embodiments, n is 2. In some embodiments, $L^3$ is $C_{1-4}$ alkylene, optionally substituted with one or more $R^{50}$. In some embodiments, $L^3$ is $C_{1-2}$ alkylene, optionally substituted with one or more $R^{50}$. In some embodiments, $L^3$ is —$CH_2$—. In some embodiments, $W^1$ is $C_{1-4}$ alkylene, optionally substituted with one or more $R^{50}$. In some embodiments, $W^1$ is $C_{1-2}$ alkylene, optionally substituted with one or more $R^{50}$. In some embodiments, $W^1$ is $C_{1-2}$ alkylene, such as $C_1$ alkylene or —$CH_2$—. In some embodiments, $W^2$ is $C_{1-4}$ alkylene, optionally substituted with one or more $R^{50}$. In some embodiments, $W^2$ is $C_{1-2}$ alkylene, optionally substituted with one or more $R^{50}$. In some embodiments, $W^2$ is $C_{1-2}$ alkylene, such as $C_1$ alkylene or —$CH_2$—. In some embodiments, $W^3$ is absent. In some embodiments, $W^3$ is $C_{1-4}$ alkylene, optionally substituted with one or more $R^{50}$. In some embodiments, $W^3$ is $C_{1-2}$ alkylene, optionally substituted with one or more $R^{50}$. In some embodiments, $W^3$ is $C_{1-2}$ alkylene, such as $C_1$ alkylene or —$CH_2$—. In some embodiments, $R^C$ is selected from —$N(R^{52})_2$, —$NR^{53}R^{54}$, —$NR^{52}S(=O)_2R^{52}$, —$C(O)R^{52}$, —$C(O)OR^{52}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, and —$C(O)NR^{53}R^{54}$. In some embodiments, $R^C$ is selected from

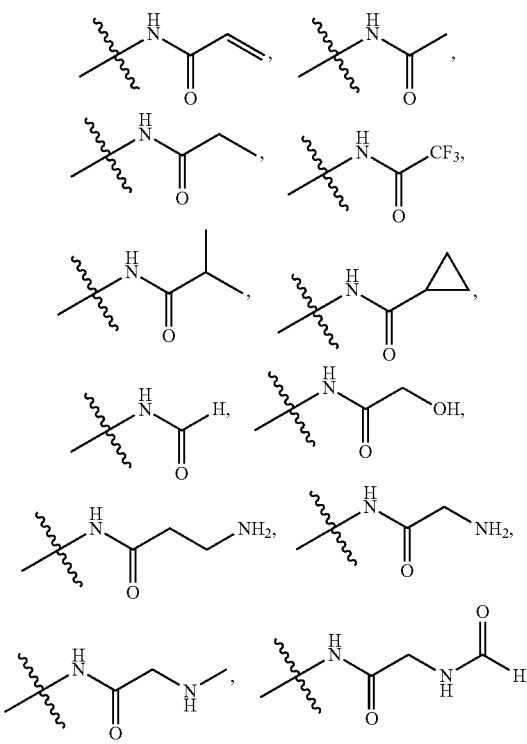

-continued

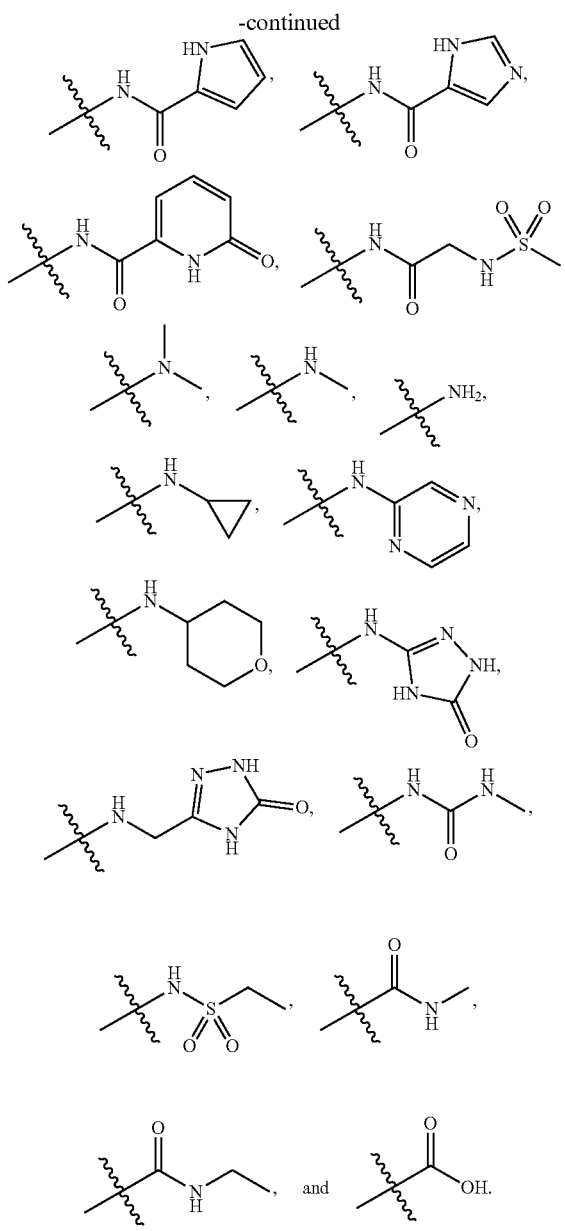

In certain aspects, a compound of Formula (II) may be represented by:

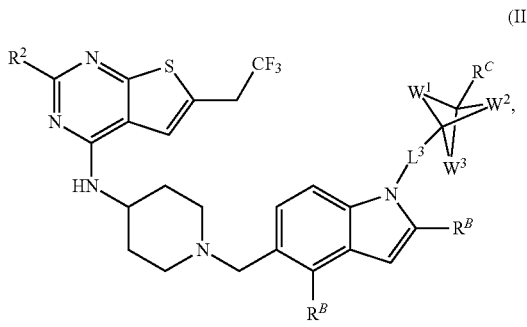

such as

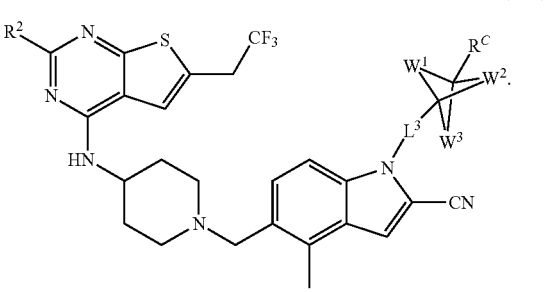

In some embodiments, $R^2$ is selected from $R^{50}$. In some embodiments, $R^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-OR$^{52}$, C$_{1-3}$ alkyl-N(R$^{52}$)$_2$, C$_{1-3}$ haloalkyl, C$_{2-3}$ alkenyl, and C$_{2-3}$ alkynyl. In some embodiments, $R^2$ is selected from halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl, such as $R^2$ is selected from —OH, —OR$^{52}$, —NH$_2$, —N(R$^{52}$)$_2$, —CN, and C$_{1-2}$ alkyl. Optionally, $R^2$ is selected from —NH$_2$, —CH$_3$, —OCH$_3$, —CH$_2$OH, and —NHCH$_3$. In some embodiments, $R^B$ is selected from halogen, —CN, —OR$^{52}$, —N(R$^{52}$)$_2$, —NR$^{53}$R$^{54}$, —C(O)R$^{52}$, —C(O)OR$^{52}$, —OC(O)R$^{52}$, —NR$^{52}$C(O)R$^{52}$, —C(O)N(R$^{52}$)$_2$, —C(O)NR$^{53}$R$^{54}$, =O, C$_{1-10}$ alkyl, C$_{2-10}$ alkenyl, C$_{2-10}$ alkynyl, optionally substituted C$_{1-10}$ alkyl, optionally substituted C$_{2-10}$ alkenyl, and optionally substituted C$_{2-10}$ alkynyl. In some embodiments, $R^B$ is selected from halogen, —CN, —OR$^{52}$, —N(R$^{52}$)$_2$, —NR$^{53}$R$^{54}$, C$_{1-3}$ alkyl, and optionally substituted C$_{1-3}$ alkyl, such as $R^B$ is selected from halogen, —CN, —OR$^{52}$, —N(R$^{52}$)$_2$, —NR$^{53}$R$^{54}$, and C$_{1-2}$ alkyl. In some embodiments, $L^3$ is C$_{1-4}$ alkylene, optionally substituted with one or more R$^{50}$. In some embodiments, $L^3$ is C$_{1-2}$ alkylene, optionally substituted with one or more R$^{50}$. In some embodiments, $L^3$ is —CH$_2$—. In some embodiments, $W^1$ is C$_{1-4}$ alkylene, optionally substituted with one or more R$^{50}$. In some embodiments, $W^1$ is C$_{1-2}$ alkylene, optionally substituted with one or more R$^{50}$. In some embodiments, $W^1$ is C$_{1-2}$ alkylene, such as C$_1$ alkylene or —CH$_2$—. In some embodiments, $W^2$ is C$_{1-4}$ alkylene, optionally substituted with one or more R$^{50}$. In some embodiments, $W^2$ is C$_{1-2}$ alkylene, optionally substituted with one or more R$^{50}$. In some embodiments, $W^2$ is C$_{1-2}$ alkylene, such as C$_1$ alkylene or —CH$_2$—. In some embodiments, $W^3$ is absent. In some embodiments, $W^3$ is C$_{1-4}$ alkylene, optionally substituted with one or more R$^{50}$. In some embodiments, $W^3$ is C$_{1-2}$ alkylene, optionally substituted with one or more R$^{50}$. In some embodiments, $W^3$ is C$_{1-2}$ alkylene, such as C$_1$ alkylene or —CH$_2$—. In some embodiments, $R^C$ is selected from —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, and —C(O)NR$^{53}$R$^{54}$. In some embodiments, $R^C$ is selected from

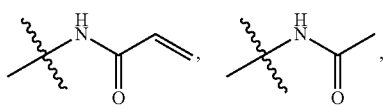

-continued

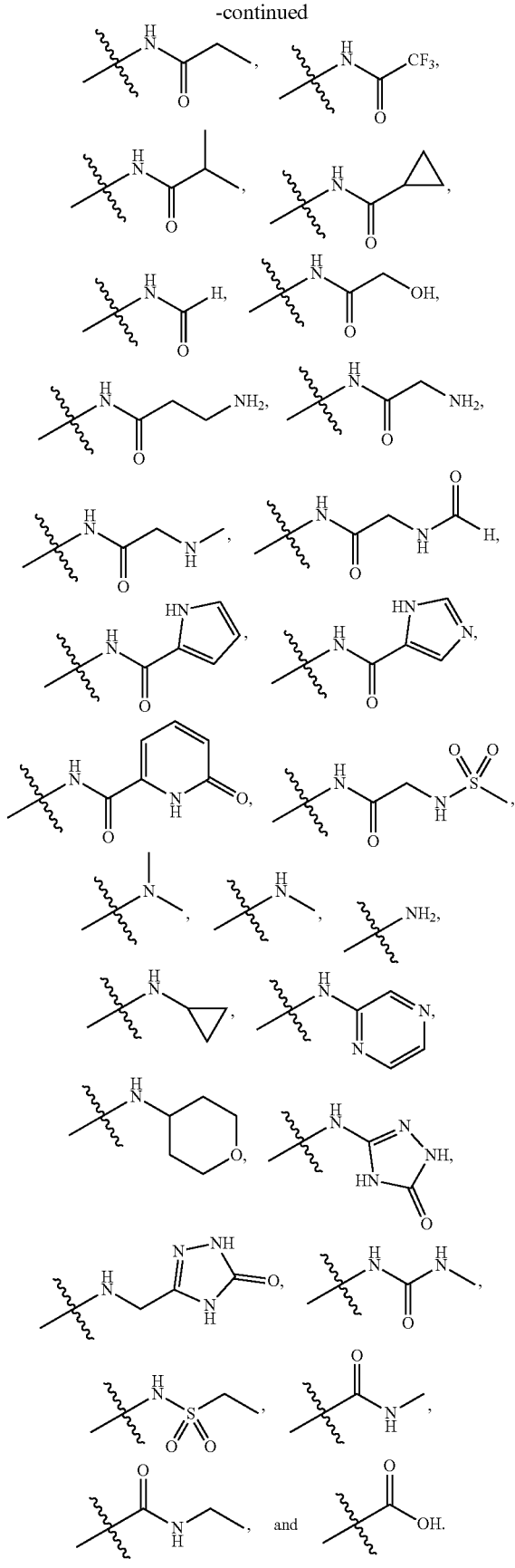

In certain aspects, a compound of Formula (II) may be represented by:

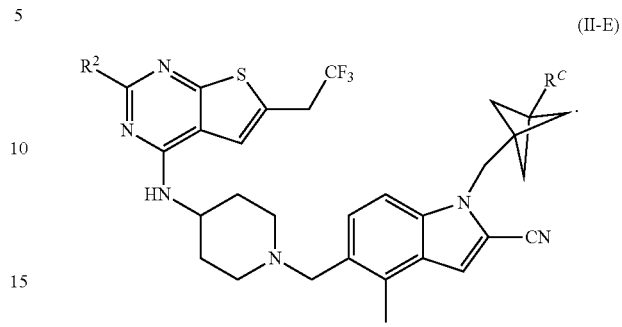

(II-E)

In some embodiments, $R^2$ is selected from $R^{50}$. In some embodiments, $R^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-OR$^{52}$, C$_{1-3}$ alkyl-N(R$^{52}$)$_2$, C$_{1-3}$ haloalkyl, C$_{2-3}$ alkenyl, and C$_{2-3}$ alkynyl. In some embodiments, $R^2$ is selected from halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl, such as $R^2$ is selected from —OH, —OR$^{52}$, —NH$_2$, —N(R$^{52}$)$_2$, —CN, and C$_{1-2}$ alkyl. Optionally, $R^2$ is selected from —NH$_2$, —CH$_3$, —OCH$_3$, —CH$_2$OH, and —NHCH$_3$.
In some embodiments, $R^C$ is selected from —N(R$^{52}$)$_2$, —NR$^{53}$R$^{54}$, —NR$^{52}$S(=O)$_2$R$^{52}$, —C(O)R$^{52}$, —C(O)OR$^{52}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, and —C(O)NR$^{53}$R$^{54}$. In some embodiments, $R^C$ is selected from

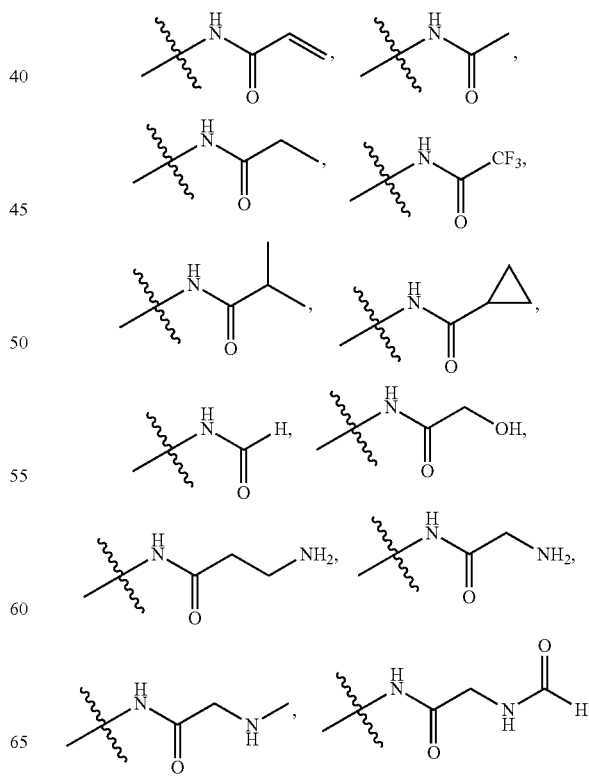

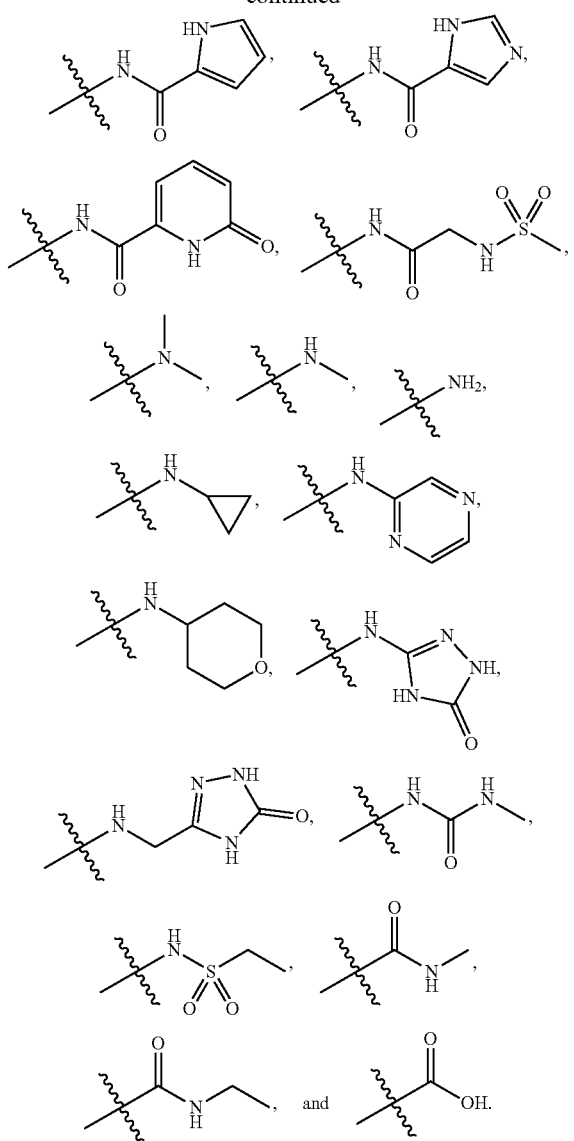

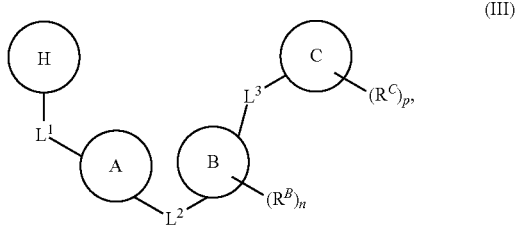

In certain aspects, the present disclosure provides a compound of Formula (III):

(III)

or a pharmaceutically acceptable salt or prodrug thereof, wherein:

H is selected from $C_{3-12}$ carbocycle and 3- to 12-membered heterocycle, each of which is optionally substituted with one or more $R^{50}$;

A is

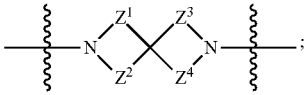

each of $Z^1$, $Z^2$, $Z^3$, and $Z^4$ is independently selected from —$C(R^{A1})(R^{A2})$—, —$C(R^{A1})(R^{A2})$—$C(R^{A1})(R^{A2})$—, —C(O)—, and —$C(R^{A1})(R^{A2})$—C(O)—, wherein no more than one of $Z^1$, $Z^2$, $Z^3$, and $Z^4$ is —C(O)— or —$C(R^{A1})(R^{A2})$—C(O)—;

B is selected from bond, $C_{3-12}$ carbocycle and 3- to 12-membered heterocycle;

C is selected from bond, $C_{3-12}$ carbocycle and 3- to 12-membered heterocycle;

$L^1$, $L^2$ and $L^3$ are each independently selected from bond, —O—, —S—, —$N(R^{51})$—, —$N(R^{51})CH_2$—, —C(O)—, —C(O)O—, —OC(O)—, —OC(O)O—, —$C(O)N(R^{51})$—, —$C(O)N(R^{51})C(O)$—, —$C(O)N(R^{51})C(O)N(R^{51})$—, —$N(R^{51})C(O)$—, $N(R^{51})C(O)$—, —$N(R^{51})C(O)N(R^{51})$—, —$N(R^{51})C(O)O$—, —$OC(O)N(R^{51})$—, —$C(NR^{51})$—, —$N(R^{51})C(NR^{51})$—, —$C(NR^{51})N(R^{51})$—, —$N(R^{51})C(NR^{51})N(R^{51})$—, —$S(O)_2$-, —OS(O)—, —S(O)O—, —S(O)—, —$OS(O)_2$—, —$S(O)_2O$—, —$N(R^{51})S(O)_2$—, —$S(O)_2N(R^{51})$—, —$N(R^{51})S(O)$—, —$S(O)N(R^{51})$—, —$N(R^{51})S(O)_2N(R^{51})$—, —$N(R^{51})S(O)N(R^{51})$—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^3$ can together optionally form a bridge or ring;

$R^B$ is independently selected at each occurrence from $R^{50}$, or two $R^B$ groups attached to the same atom or different atoms can together optionally form a bridge or ring;

$R^C$ is independently selected at each occurrence from hydrogen and $R^{50}$, or two $R^C$ groups attached to the same atom or different atoms can together optionally form a bridge or ring;

$R^{A1}$ and $R^{A2}$ are each independently selected at each occurrence from hydrogen and $R^{50}$;

n is an integer from 0 to 6;

p is an integer from 1 to 6;

$R^{50}$ is independently selected at each occurrence from: halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2 NR^{53}R^{54}$, —$C(O)R^{52}$, $C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(NR^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)$ OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(NR$^{52}$)(OR$^{52}$)), —P(O)(NR$^{52}$)$_2$, =O, =S, =N(R$^{52}$), C$_{3-12}$ carbocycle, and 3- to 12-membered heterocycle; and
C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S (=O)$_2$R$^{52}$, —NR$^{52}$S(=O)$_2$N(R$^{52}$)$_2$, —NR$^{52}$S (=O)$_2$ NR$^{53}$R$^{54}$, —C(O)R$^{52}$, —C(O)OR$^{52}$, —OC (O)R$^{52}$, —OC(O)OR$^{52}$, —OC(O)N(R$^{52}$)$_2$, —OC(O) NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;
R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;
C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$ R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O) OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle and 3- to 12-membered heterocycle; and
C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N (R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S (=O)$_2$R$^{52}$, —NR$^{52}$S(=O)$_2$N(R$^{52}$)$_2$, —NR$^{52}$S (=O)$_2$ NR$^{53}$R$^{54}$, —C(O)R$^{52}$, —C(O)OR$^{52}$, —OC (O)R$^{52}$, —OC(O)OR$^{52}$, —OC(O)N(R$^{52}$)$_2$, —OC(O) NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;
R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle; and R$^{53}$ and R$^{54}$ are taken together with the nitrogen atom to which they are attached to form a heterocycle, optionally substituted with one or more R$^{50}$.

In certain aspects, a compound of Formula (III) may be represented by:

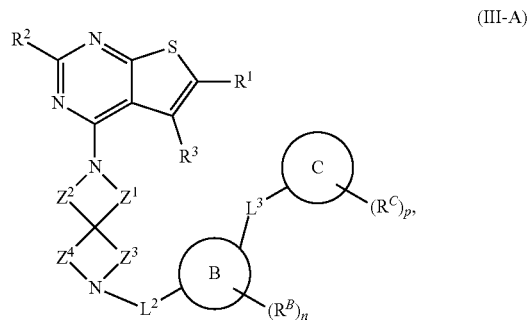

(III-A)

such as

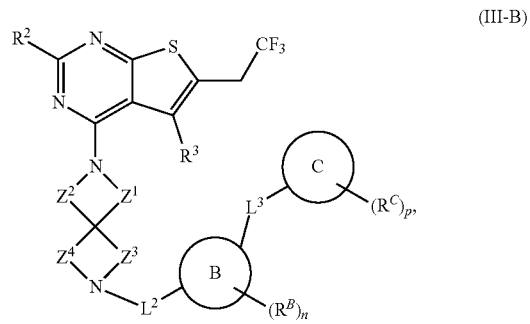

(III-B)

wherein R$^r$, R$^2$ and R$^3$ are each independently selected at each occurrence from hydrogen and R$^{50}$. In some embodiments, R$^1$ is selected from R$^{50}$. In some embodiments, R$^1$ is C$_{1-3}$ haloalkyl, such as —CH$_2$CF$_3$. In some embodiments, R$^2$ is selected from hydrogen and R$^{50}$. In some embodiments, R$^2$ is selected from hydrogen, halogen, —OH, —OR$^{52}$, —NH$_2$, —N(R$^{52}$)$_2$, —CN, C$_{1-3}$ alkyl, C$_{1-3}$ alkyl-OR$^{52}$, C$_{1-3}$ alkyl-N(R$^{52}$)$_2$, C$_{1-3}$ haloalkyl, C$_{2-3}$ alkenyl, and C$_{2-3}$ alkynyl. In some embodiments, R$^2$ is selected from halogen, —OH, —OR$^{52}$, —NH$_2$, —N(R$^{52}$)$_2$, —CN, C$_{1-3}$ alkyl, —CH$_2$OH, —CH$_2$OR$^{52}$, —CH$_2$NH$_2$, —CH$_2$N(R$^{52}$)$_2$, C$_{1-3}$ alkyl-N(R$^{52}$)$_2$, C$_{1-3}$ haloalkyl, C$_{2-3}$ alkenyl, and C$_{2-3}$ alkynyl, such as R$^2$ is selected from —OH, —OR$^{52}$, —NH$_2$, —N(R$^{52}$)$_2$, —CN, and C$_{1-2}$ alkyl. Optionally, R$^2$ is selected from —NH$_2$, —CH$_3$, —OCH$_3$, —CH$_2$OH, and —NHCH$_3$. In some embodiments, R$^3$ is selected from hydrogen, halogen, —OH, —N(R$^{52}$)$_2$, —CN, —C(O)OR$^{52}$, C$_{1-3}$ alkyl, and C$_{1-3}$ haloalkyl. In some embodiments, R$^{52}$ is selected from selected from hydrogen and alkyl, such as R$^{52}$ is hydrogen.

In some embodiments, for a compound of Formula (III), A is selected from

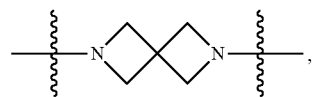

-continued

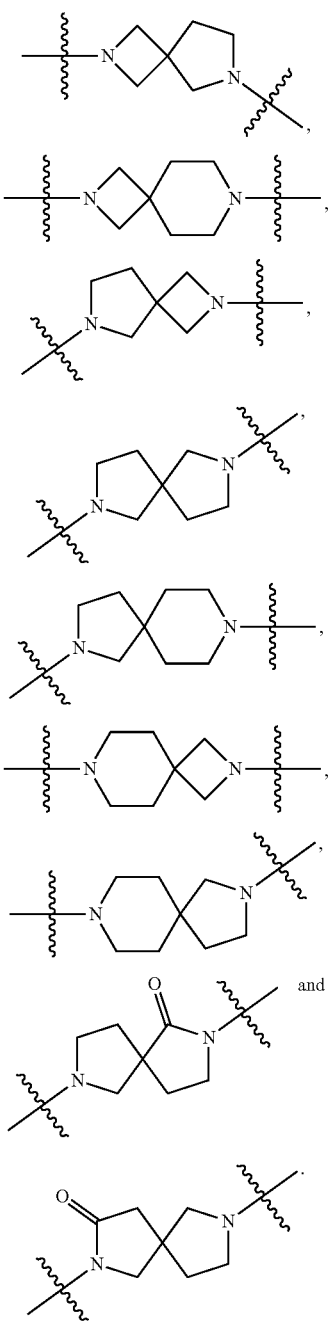

In certain aspects, the present disclosure provides a compound of Formula (IV):

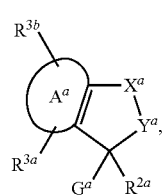

(IV)

or a pharmaceutically acceptable salt or prodrug thereof, wherein:

$A^a$ 

is a fused thienyl or fused phenyl group;

$G^a$ is selected from $C_{3-12}$ carbocycle and 3- to 12-membered heterocycle, each of which is substituted with $-E^1-R^{4a}$ and optionally further substituted with one or more $R^{50}$;

$R^{2a}$ is selected from hydrogen, alkyl, alkenyl, optionally substituted cycloalkyl, optionally substituted aryl, optionally substituted heterocyclo, optionally substituted heteroaryl, and aralkyl;

$R^{3a}$ and $R^{3b}$ are each independently selected from hydrogen, alkyl, halo, hydroxy, cyano, amino, alkylamino, dialkylamino, haloalkyl, alkoxy, and haloalkoxy;

$X^a-Y^a$ is selected from $-N(R^{52})-C(=O)-$, $-C(=O)-O-$, $-C(=O)-N(R^{52})-$, $-CH_2N(R^{52})-CH_2-$, $-C(=O)N(R^{52})-CH_2-$, $-CH_2CH_2-N(R^{52})-$, $-CH_2N(R^{52})-C(=O)-$, and $-CH_2O-CH_2-$; or $X^a$ and $Y^a$ do not form a chemical bond, wherein:

$X^a$ is selected from hydrogen, alkyl, halo, hydroxy, cyano, amino, alkylamino, dialkylamino, haloalkyl, alkoxy, and haloalkoxy; and $Y^a$ is selected from cyano, hydroxy, and $-CH_2R^{50}$;

$E^1$ is selected from absent, $-C(=O)-$, $-C(=O)N(R^{52})-$, $-[C(R^{14a})_2]_{1-5}O-$, $-[C(R^{14a})_2]_{1-5}NR^{52}-$, $-[C(R^{14a})_2]_{1-5}-$, $-CH_2(=O)-$, and $-S(=O)_2-$;

$R^{4a}$ is selected from hydrogen, alkyl, optionally substituted alkenyl, optionally substituted alkynyl, optionally substituted cycloalkyl, optionally substituted aryl, optionally substituted heterocyclo, optionally substituted heteroaryl, aralkyl, (heterocyclo)alkyl, and (heteroaryl)alkyl;

$R^{14a}$ is selected from hydrogen and alkyl;

$R^{50}$ is independently selected at each occurrence from: halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $-P(O)(OR^{52})(R^{52})$, $-P(O)(NR^{52})(R^{52})$, $-NR^{52}P(O)(R^{52})$, $P(O)(NR^{52})(OR^{52})$, $-P(O)(NR^{52})_2$, $=O$, $=S$, $=N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $-P(O)(OR^{52})(R^{52})$, $-P(O)(NR^{52})$ ($R^{52}$), —$NR^{52}P(O)(R^{52})$, $P(O)(NR^{52})(OR^{52})$, —$P(O)(NR^{52})_2$, =O, =S, =$N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2 NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, —$P(O)(OR^{52})(R^{52})$, —$P(O)(NR^{52})(R^{52})$, —$NR^{52}P(O)(R^{52})$, —$P(O)(NR^{52})(OR^{52})$, —$P(O)(NR^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle; and $R^{53}$ and $R^{54}$ are taken together with the nitrogen atom to which they are attached to form a heterocycle, optionally substituted with one or more $R^{50}$.

In some embodiments, for a compound of Formula (IV), $G^a$ is piperidinyl. In some embodiments, a compound of Formula (IV) is represented by:

(IV-A)

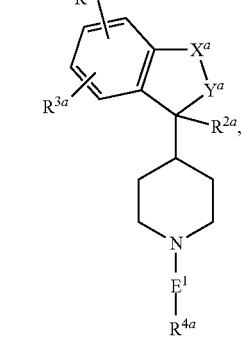

(IV-B)

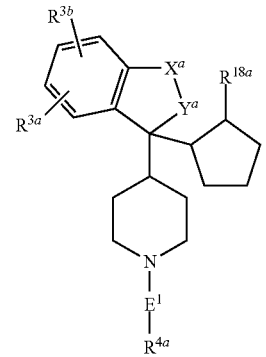

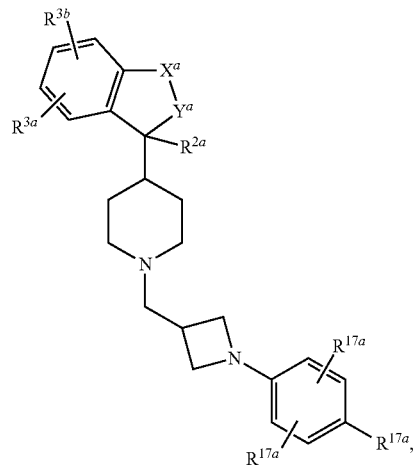

(IV-C)

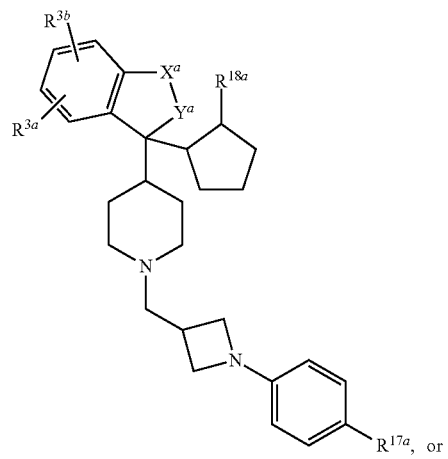

(IV-D)

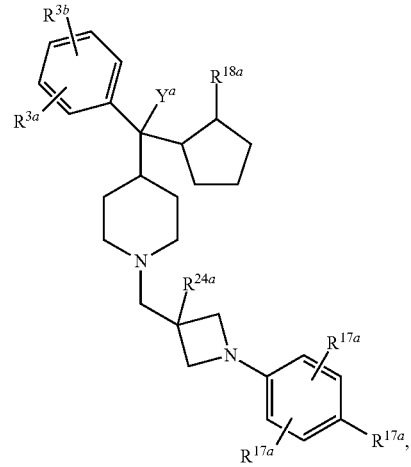

(IV-E)

wherein $R^{17a}$ and $R^{18a}$ is independently selected from hydrogen and $R^{50}$; and $R^{24a}$ is selected from hydrogen and fluoro.

In some embodiments, for a compound of Formula (IV), $R^{3a}$ and $R^{3b}$ are independently selected from hydrogen and halo. In some embodiments, $X^a$ and $Y^a$ do not form a chemical bond, and $X^a$ is hydrogen. In some embodiments, $R^{4a}$ is selected from hydrogen; and alkyl, alkenyl, alkynyl, cycloalkyl, aryl, heterocyclo, heteroaryl, aralkyl, (heterocyclo)alkyl, and (heteroaryl)alkyl, each of which is optionally substituted with one or more substituents selected from $R^{50}$. In some embodiments, $R^{4a}$ is $R^{50}$-substituted heterocyclo.

In certain aspects, the present disclosure provides a compound of Formula (VI):

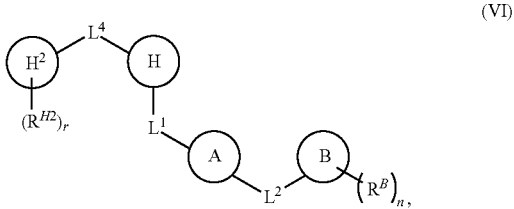

(VI)

or a pharmaceutically acceptable salt or prodrug thereof, wherein:
$H^2$ is selected from $C_{3-12}$ carbocycle and 3- to 12-membered heterocycle;
H is selected from $C_{3-12}$ carbocycle and 3- to 12-membered heterocycle, each of which is optionally substituted with one or more $R^{50}$;
A is

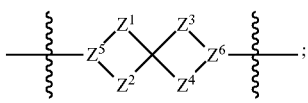

;

each of $Z^1$, $Z^2$, $Z^3$, and $Z^4$ is independently selected from —C($R^{A1}$)($R^{A2}$)—, —C($R^{A1}$)($R^{A2}$)—C($R^{A1}$)($R^{A2}$)—, —O—, —C($R^{A1}$)($R^{A2}$)—O—, —C($R^{A1}$)($R^{A2}$)—N($R^{51}$)—, —C(O)—, —C($R^{A1}$)($R^{A2}$)—C(O)—, and —N=C(NH$_2$)—, wherein no more than one of $Z^1$, $Z^2$, $Z^3$, and $Z^4$ is —O—, —C($R^{A1}$)($R^{A2}$)—O—, —C($R^{A1}$)($R^{A2}$)—N($R^{51}$)—, —C(O)—, —C($R^{A1}$)($R^{A2}$)—C(O)—, or —N=C(NH$_2$)—;
$Z^5$ and $Z^6$ are independently selected from —C($R^{A3}$)— and —N—;
B is selected from bond, $C_{3-12}$ carbocycle and 3- to 12-membered heterocycle;
$L^1$, $L^2$ and $L^4$ are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$-, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$, $L^2$ or $L^4$ can together optionally form a bridge or ring;
$R^B$ is independently selected at each occurrence from hydrogen and $R^{50}$, or two $R^B$ groups attached to the same atom or different atoms can together optionally form a bridge or ring;
$R^{H2}$ is independently selected at each occurrence from $R^{50}$, or two $R^{H2}$ groups attached to the same atom or different atoms can together optionally form a bridge or ring;

$R^{A1}$, $R^{A2}$ and $R^{A3}$ are each independently selected at each occurrence from hydrogen and $R^{50}$;
n is an integer from 0 to 6;
r is an integer from 1 to 6;
$R^{50}$ is independently selected at each occurrence from:
halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), P(O)(NR$^{52}$)(OR$^{52}$), —P(O)(NR$^{52}$)$_2$, =O, =S, =N($R^{52}$);
$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{3-12}$ carbocycle, and 3- to 12-membered heterocycle; and
$C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N($R^{52}$), $C_{1-6}$ alkyl, $C_{1-6}$ haloalkyl, $C_{2-6}$ alkenyl, and $C_{2-6}$ alkynyl;
$R^{51}$ is independently selected at each occurrence from:
hydrogen, —C(O)R$^{52}$, —C(O)OR$^{52}$, —C(O)N($R^{52}$)$_2$, —C(O)NR$^{53}$R$^{54}$;
$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N($R^{52}$)$_2$, —NR$^{53}$R$^{54}$, —S(=O)R$^{52}$, —S(=O)$_2$R$^{52}$, —S(=O)$_2$N($R^{52}$)$_2$, —S(=O)$_2$NR$^{53}$R$^{54}$, —NR$^{52}$S(=O)$_2$R$^{52}$, —NR$^{52}$S(=O)$_2$N($R^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N($R^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N($R^{52}$)$_2$, —NR$^{52}$C(O)NR$^{53}$R$^{54}$, —C(O)N($R^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle and 3- to 12-membered heterocycle; and
C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle; and R$^{53}$ and R$^{54}$ are taken together with the nitrogen atom to which they are attached to form a heterocycle, optionally substituted with one or more R$^{50}$.

In certain aspects, a compound of Formula (VI) may be represented by:

(VI-A)

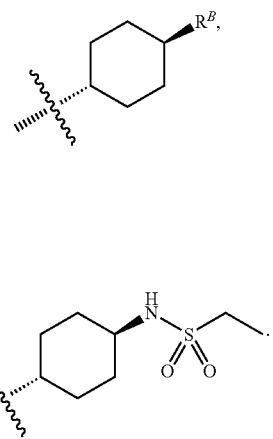

such as (VI-B)

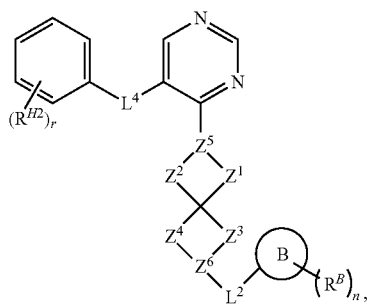

In some embodiments, L$^4$ is selected from —O— and —NH—. In some embodiments, Z$^5$ and Z$^6$ are each N. In some embodiments, B is C$_{3-12}$ carbocycle, such as cyclohexane. In some embodiments, B is

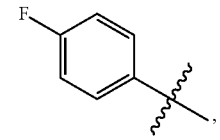 [SMILES: *c1ccc(F)cc1]

such as

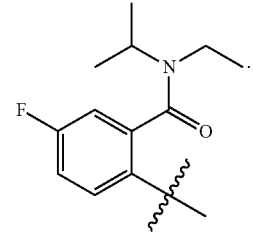 [SMILES: *c1ccc(F)cc1C(=O)N(CC)C(C)C]

In some embodiments, H$^2$ is

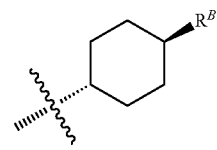

optionally further substituted with one or more R$^{H2}$. In some embodiments, H$^2$ is

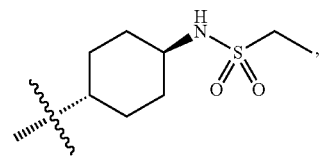

In some embodiments, L$^4$ is selected from —O— and —NH—, Z$^5$ and Z$^6$ are each N, B is B is

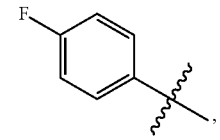 [SMILES: *c1ccc(F)cc1]

such as

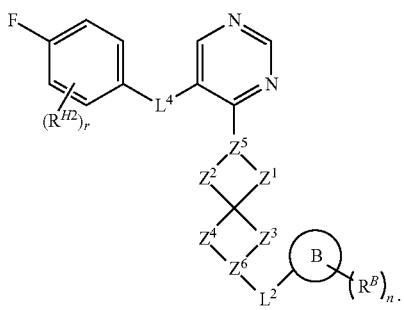

and $H^2$ is optionally $R^{H2}$-substituted

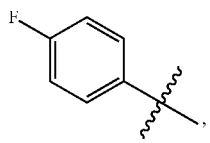

such as

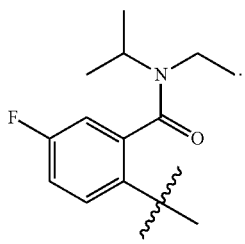 [SMILES: *c1ccc(F)cc1C(=O)N(CC)C(C)C]

In some embodiments, for a compound of Formula (VI), A is selected from

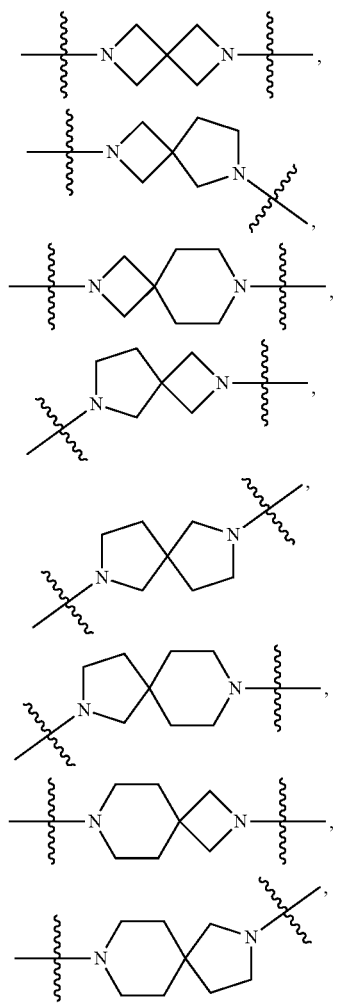

-continued

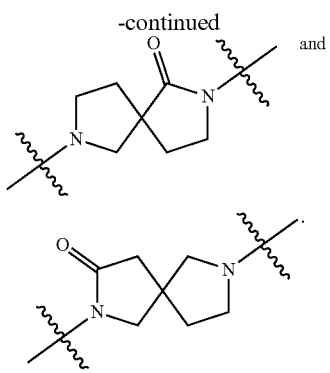

Any combination of the groups described above for the various variables is contemplated herein. Throughout the specification, groups and substituents thereof can be chosen to provide stable moieties and compounds.

The chemical entities described herein for use in the subject methods can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Scheme 1 and Examples 1-11, the steps in some cases may be performed in a different order than the order shown in Scheme 1 and Examples 1-11. Various modifications to these synthetic reaction schemes may be made and will be suggested to one skilled in the art having referred to the disclosure contained in this Application. Numberings or R groups in each scheme do not necessarily correspond to that of the claims or other schemes or tables herein.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure for use in the subject methods, including compounds of Formula (I-A), (I-B), (II), (III) and (VI), may be prepared by the following reaction scheme:

Scheme 1

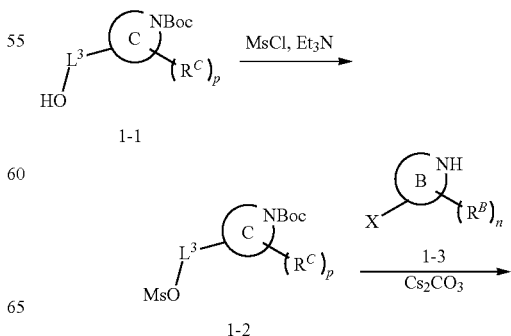

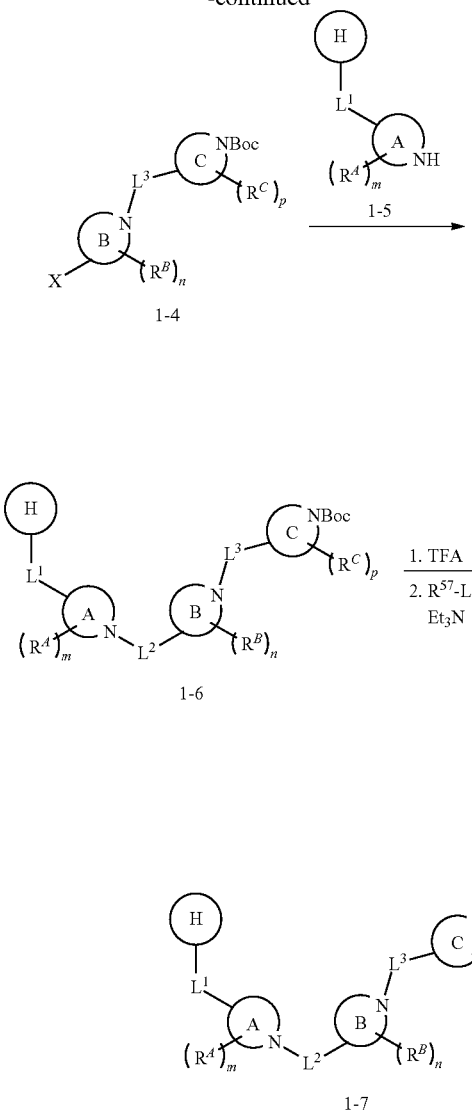

TABLE 1

| No. | Structure |
|---|---|
| I-1 | MW (calc'd) 687.78<br>m/z (found) 688.45 [M + H]⁺ |
| I-2 | MW (calc'd) 688.83<br>m/z (found) 689.40 [M + H]⁺ |
| I-3 | MW (calc'd) 687.84<br>m/z (found) 688.45 [M + H]⁺ |

In some embodiments, a compound of Formula 1-7 may be prepared according to Scheme 1. For example, methanesulfonyl chloride can be added to a solution of alcohol 1-1 and triethylamine to afford mesylate 1-2. Addition of mesylate 1-2 to a solution of $Cs_2CO_3$ and amine 1-3 can provide a compound of Formula 1-4. Coupling of 1-4 to amine 1-5 can proceed according to methods known in the art to give a compound of Formula 1-6. Addition of TFA can reveal the free amine, which can optionally be reacted with $R^{57}$-LG, wherein LG is a suitable leaving group, to afford a compound of Formula 1-7.

In some embodiments, a compound of the present disclosure for use in the subject methods, for example, a compound of a formula given in Table 1, Table 2, Table 3, Table 4, Table 5, Table 6 or Table 7, is synthesized according to one of the general routes outlined in Scheme 1, Examples 1-11, or by methods generally known in the art. In some embodiments, exemplary compounds for use in the subject methods may include, but are not limited to, a compound or salt thereof selected from Table 1, Table 2, Table 3, Table 4, Table 5, Table 6 or Table 7.

TABLE 1-continued
| No. | Structure |
|---|---|
| I-4 | 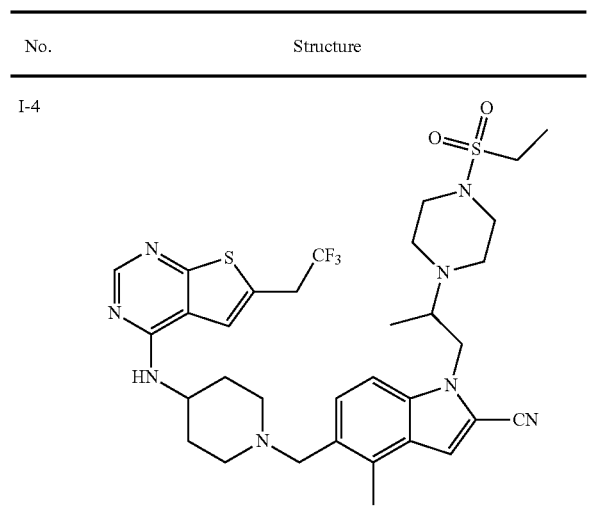
MW (calc'd) 702.86
m/z (found) 703.55 [M + H]+ |
| I-5 | 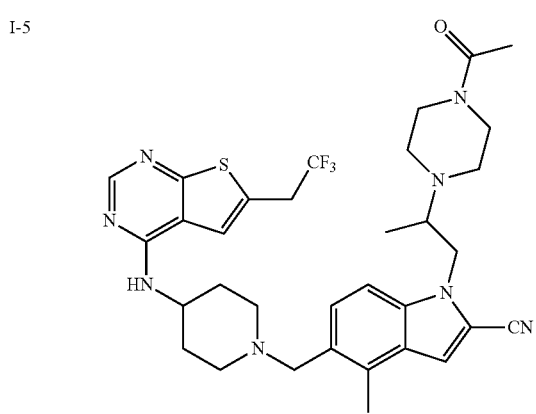
MW (calc'd) 652.78
m/z (found) 653.55 [M + H]+ |
| I-6 | 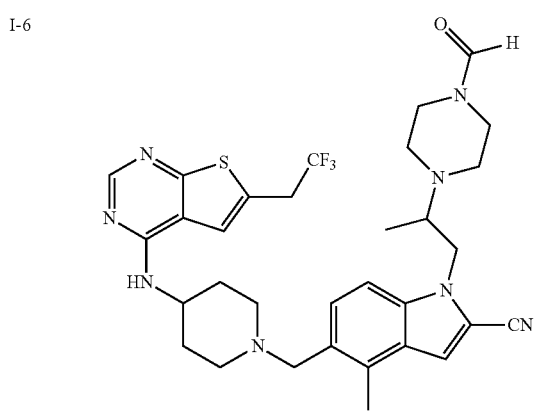
MW (calc'd) 638.75
m/z (found) 639.50 [M + H]+ |
| I-7 | 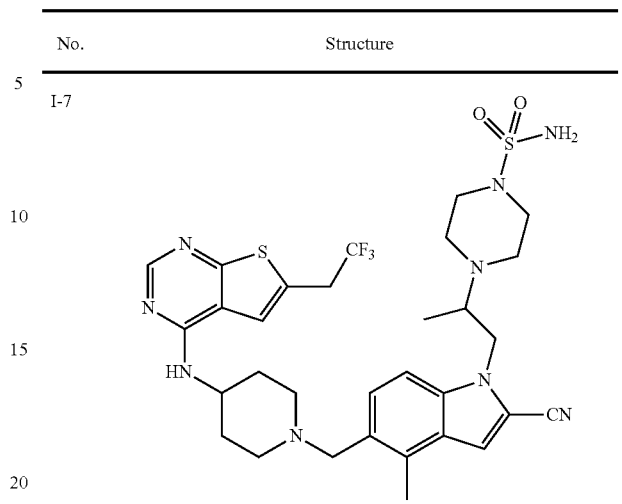
MW (calc'd) 689.82
m/z (found) 690.50 [M + H]+ |
| I-8 | 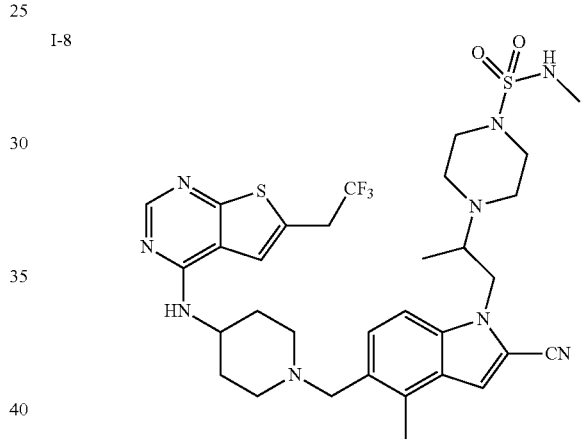
MW (calc'd) 703.84
m/z (found) 704.55 [M + H]+ |
| I-9 | 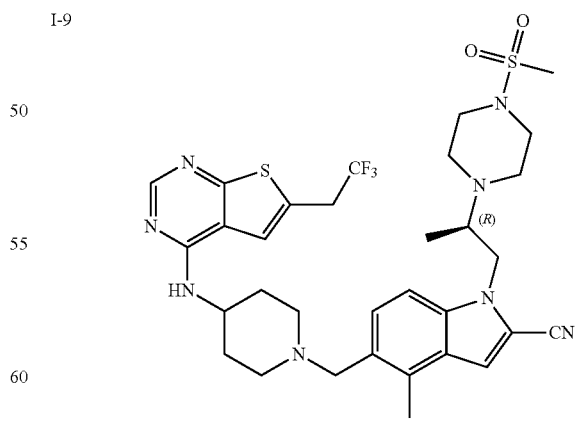
MW (calc'd) 688.83
m/z (found) 689.45 [M + H]+ |

TABLE 1-continued

| No. | Structure |
|-----|-----------|
| I-10 | MW (calc'd) 688.83<br>m/z (found) 689.40 [M + H]⁺ |
| I-11 | MW (calc'd) 702.86<br>m/z (found) 703.55 [M + H]⁺ |
| I-12 | MW (calc'd) 716.88<br>m/z (found) 717.55 [M + H]⁺ |
| I-13 | MW (calc'd) 702.86<br>m/z (found) 703.55 [M + H]⁺ |
| I-14 | MW (calc'd) 702.86<br>m/z (found) 703.55 [M + H]⁺ |
| I-15 | MW (calc'd) 702.86<br>m/z (found) 703.50 [M + H]⁺ |

TABLE 1-continued
| No. | Structure |
|---|---|
| I-16 | 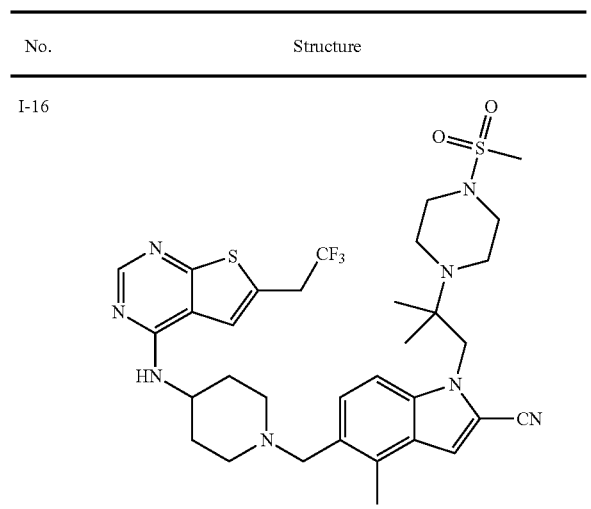 MW (calc'd) 702.86<br>m/z (found) 703.60 [M + H]⁺ |
| I-17 | 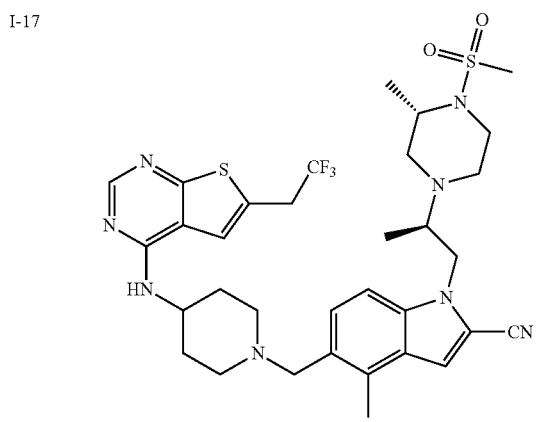 MW (calc'd) 702.86<br>m/z (found) 703.35 [M + H]⁺ |
| I-18 | 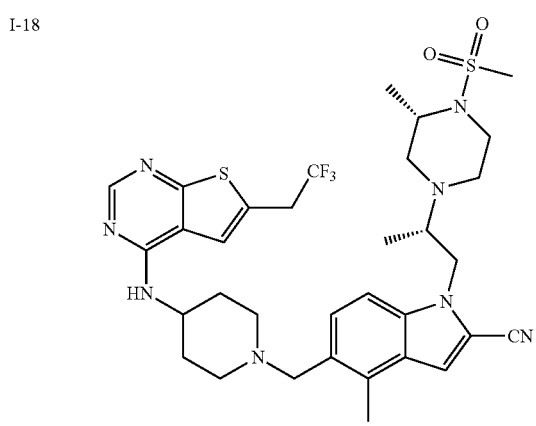 MW (calc'd) 702.86<br>m/z (found) 703.35 [M + H]⁺ |
| I-19 | 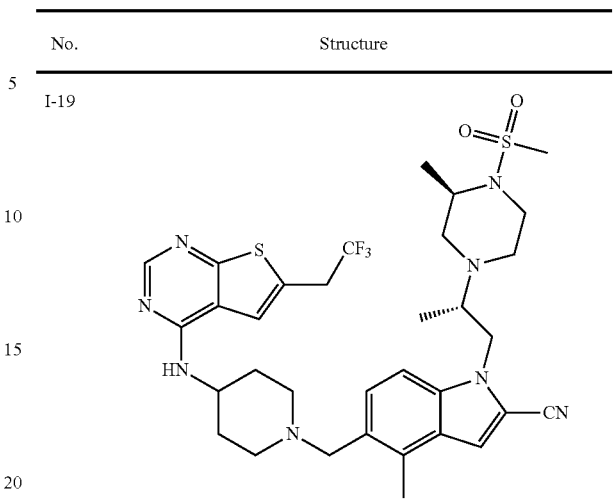 MW (calc'd) 702.86<br>m/z (found) 703.35 [M + H]⁺ |
| I-20 | 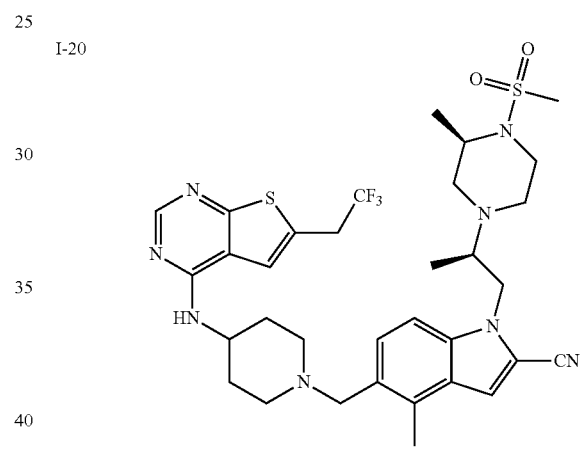 MW (calc'd) 702.86<br>m/z (found) 703.35 [M + H]⁺ |
| I-21 | 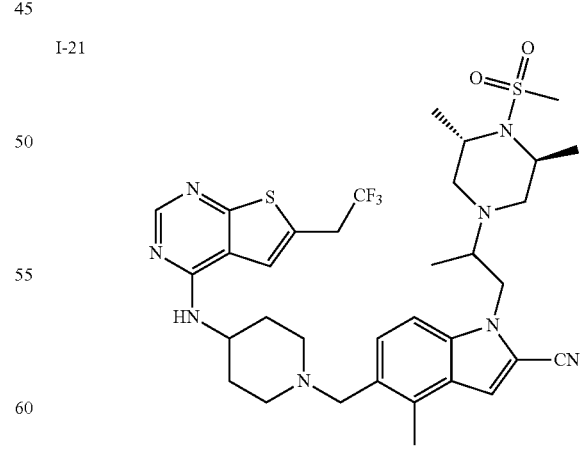 MW (calc'd) 716.88<br>m/z (found) 717.35 [M + H]⁺ |

TABLE 1-continued
| No. | Structure |
|---|---|
| I-22 | 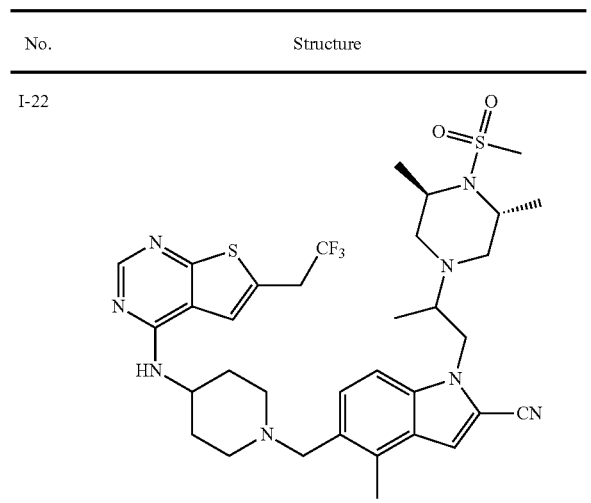<br>MW (calc'd) 716.88<br>m/z (found) 717.35 [M + H]+ |
| I-23 | 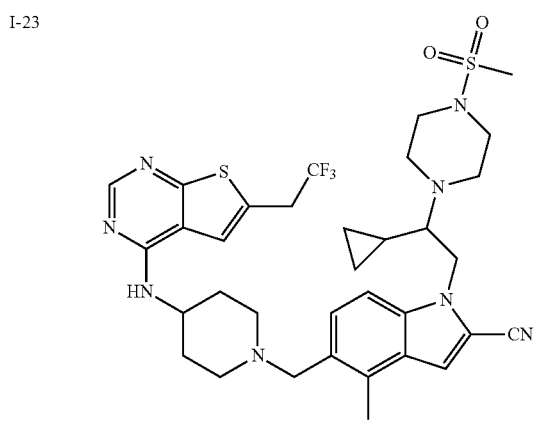<br>MW (calc'd) 714.87<br>m/z (found) 715.25 [M + H]+ |
| I-24 | 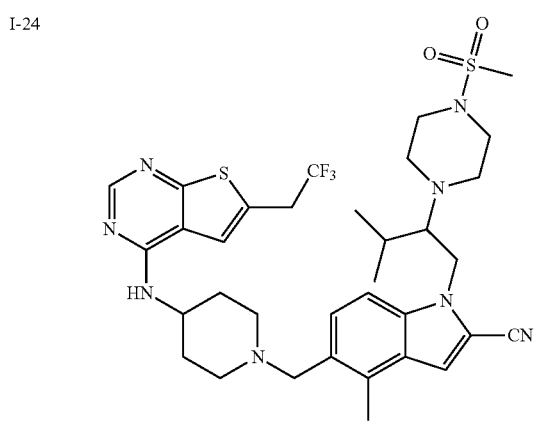<br>MW (calc'd) 716.88<br>m/z (found) 717.45 [M + H]+ |
TABLE 1-continued
| No. | Structure |
|---|---|
| I-25 | 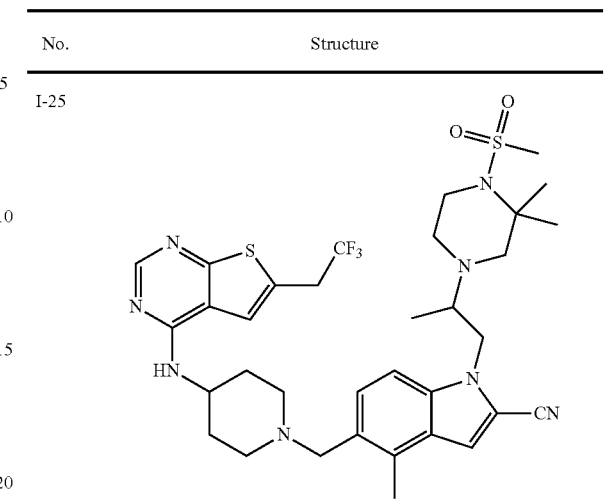<br>MW (calc'd) 716.88<br>m/z (found) 717.40 [M + H]+ |
| I-26 | 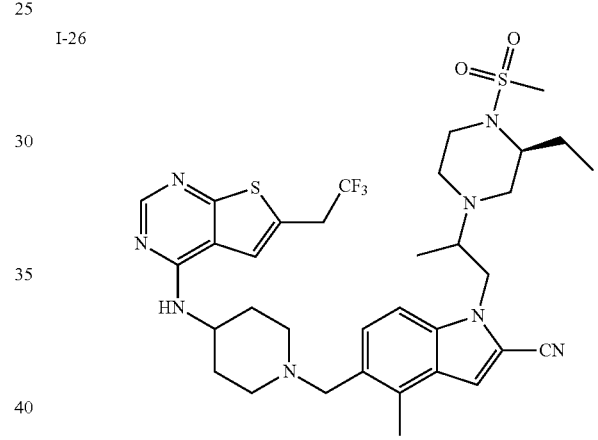<br>MW (calc'd) 716.88<br>m/z (found) 717.40 [M + H]+ |
| I-28 | 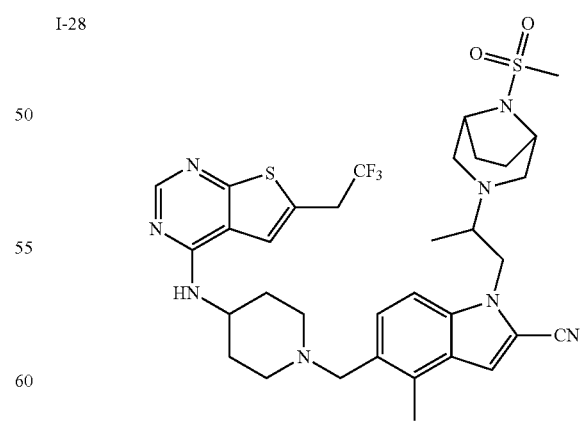<br>MW (calc'd) 714.87<br>m/z (found) 715.35 [M + H]+ |

TABLE 1-continued

| No. | Structure |
|---|---|
| I-29 | MW (calc'd) 716.88<br>m/z (found) 717.40 [M + H]+ |
| I-30 | MW (calc'd) 700.84<br>m/z (found) 701.35 [M + H]+ |
| I-35 | MW (calc'd) 688.79<br>m/z (found) 689.15 [M + H]+ |
| I-43 | MW (calc'd) 688.83<br>m/z (found) 689.45 [M + H]+ |
| I-44 | MW (calc'd) 702.86<br>m/z (found) 703.45 [M + H]+ |
| I-45 | MW (calc'd) 688.83<br>m/z (found) 689.40 [M + H]+ |

TABLE 1-continued
| No. | Structure |
|---|---|
| I-46 | 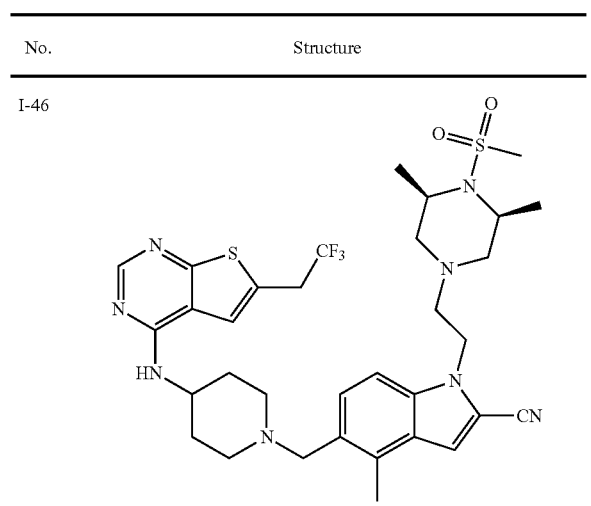<br>MW (calc'd) 702.86<br>m/z (found) 703.45 [M + H]⁺ |
| I-47 | 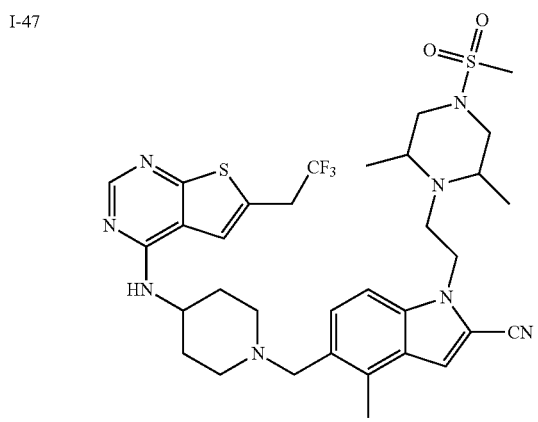<br>MW (calc'd) 702.86<br>m/z (found) 703.50 [M + H]⁺ |
| I-48 | 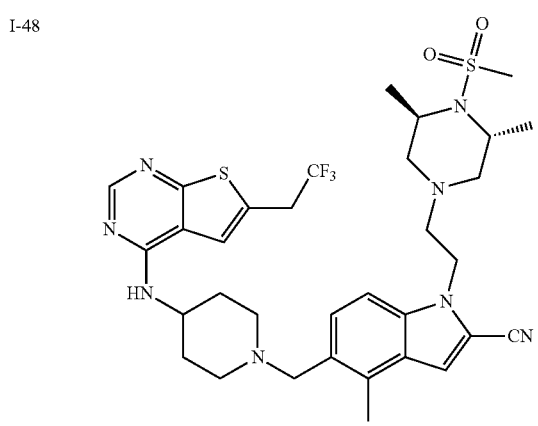<br>MW (calc'd) 702.86<br>m/z (found) 703.55 [M + H]⁺ |
| I-49 | 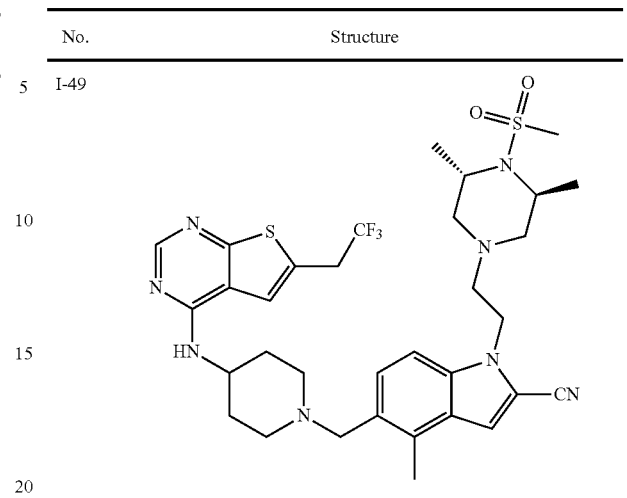<br>MW (calc'd) 702.86<br>m/z (found) 703.55 [M + H]⁺ |
| I-52 | 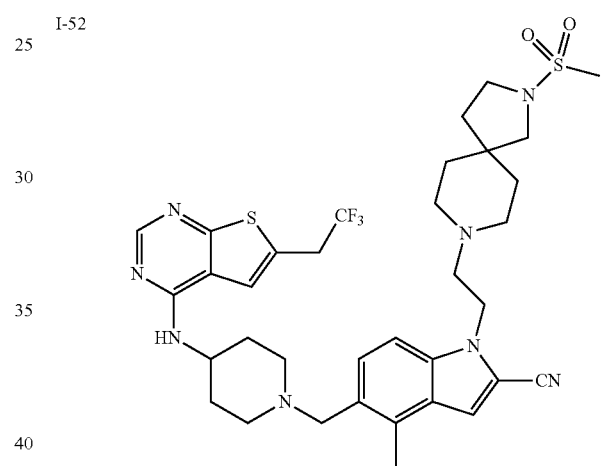<br>MW (calc'd) 728.89<br>m/z (found) 729.55 [M + H]⁺ |
| I-53 | 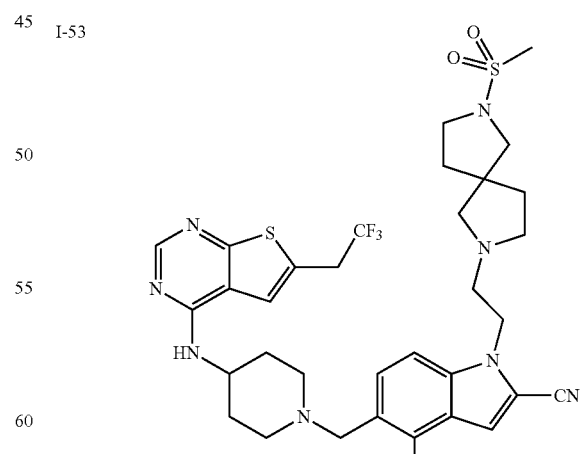<br>MW (calc'd) 714.87<br>m/z (found) 715.30 [M + H]⁺ |

TABLE 1-continued

| No. | Structure |
|---|---|
| I-54 | MW (calc'd) 714.87<br>m/z (found) 715.30 [M + H]+ |
| I-55 | MW (calc'd) 700.84<br>m/z (found) 701.30 [M + H]+ |
| I-56 | MW (calc'd) 714.87<br>m/z (found) 715.35 [M + H]+ |
| I-57 | MW (calc'd) 686.81<br>m/z (found) 687.25 [M + H]+ |
| I-58 | MW (calc'd) 700.84<br>m/z (found) 701.35 [M + H]+ |
| I-59 | MW (calc'd) 687.84<br>m/z (found) 688.45 [M + H]+ |

TABLE 1-continued
| No. | Structure |
|---|---|
| I-60 | 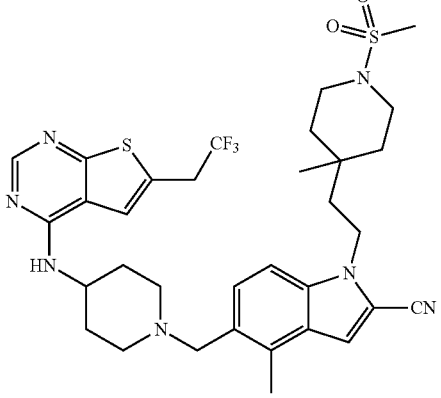 [SMILES: CC(=O)N1CCN(C(C)Cn2c(C#N)cc3c(C)c(CN4CCC(Nc5ncnc6sc(CC(F)(F)F)cc56)CC4)ccc32)CC1] MW (calc'd) 687.84<br>m/z (found) 688.50 [M + H]⁺ |
| I-61 | 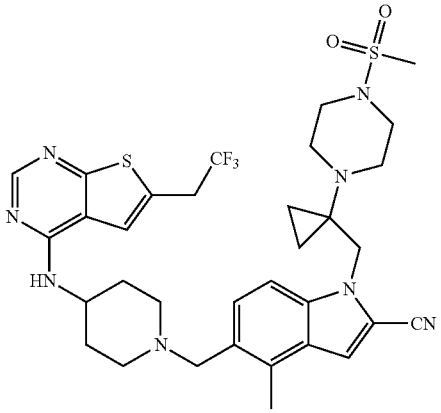 [SMILES: Cc1c(CN2CCC(Nc3ncnc4sc(CC(F)(F)F)cc34)CC2)ccc2c1cc(C#N)n2CC1(N2CCN(S(C)(=O)=O)CC2)CC1] MW (calc'd) 700.84<br>m/z (found) 701.30 [M + H]⁺ |
| I-62 | 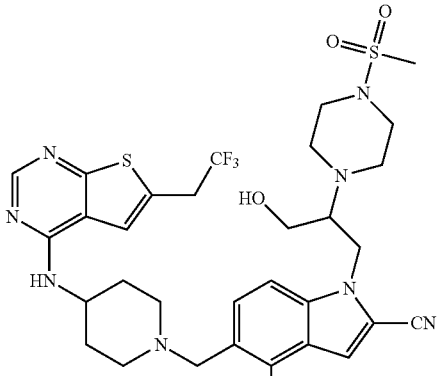 |
TABLE 1-continued
| No. | Structure |
|---|---|
| I-64 | 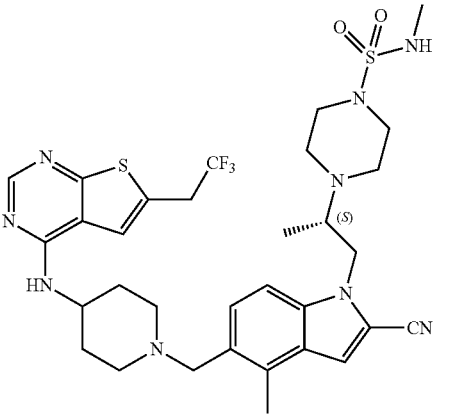 MW (calc'd) 703.84<br>m/z (found) 704.25 [M + H]⁺ |
| I-65 | 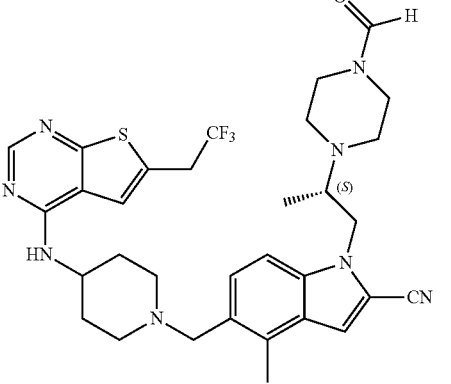 MW (calc'd) 638.75<br>m/z (found) 639.20 [M + H]⁺ |
| I-66 | 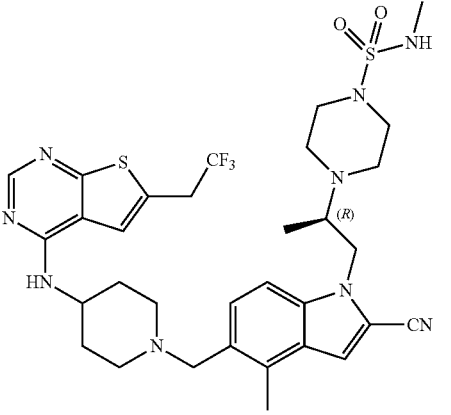 MW (calc'd) 703.84<br>m/z (found) 704.25 [M + H]⁺ |

TABLE 1-continued
| No. | Structure |
|---|---|
| I-67 | 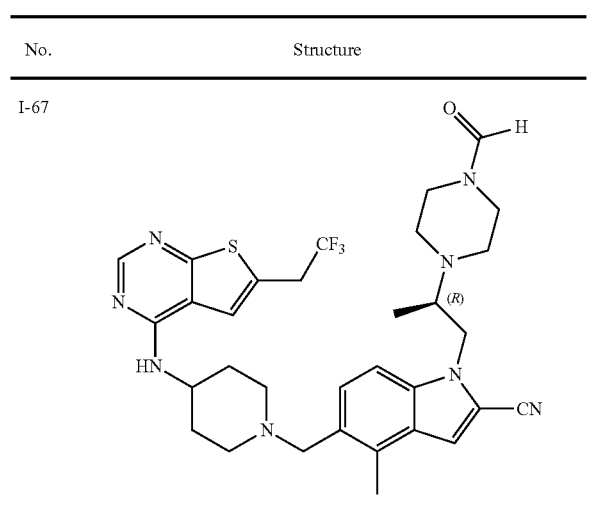<br>MW (calc'd) 638.75<br>m/z (found) 639.25 [M + H]⁺ |
| I-68 | 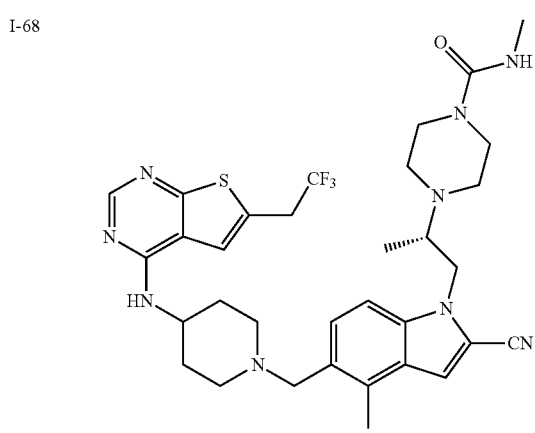<br>MW (calc'd) 667.79<br>m/z (found) 668.35 [M + H]⁺ |
| I-72 | 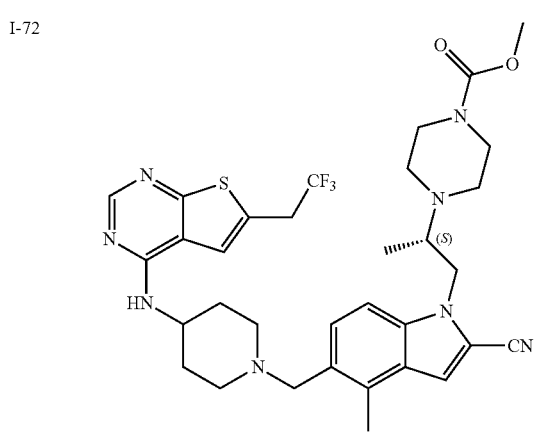<br>MW (calc'd) 668.29<br>m/z (found) 689.2 |
TABLE 1-continued
| No. | Structure |
|---|---|
| I-73 | 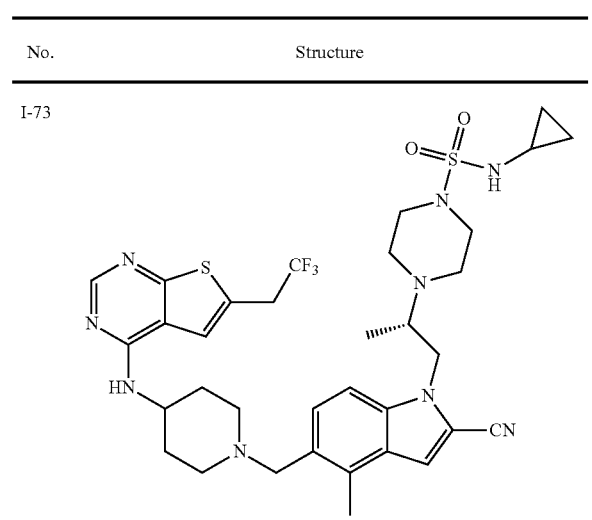<br>MW (calc'd) 729.88<br>m/z (found) 730.30 [M + H]⁺ |
| I-74 | 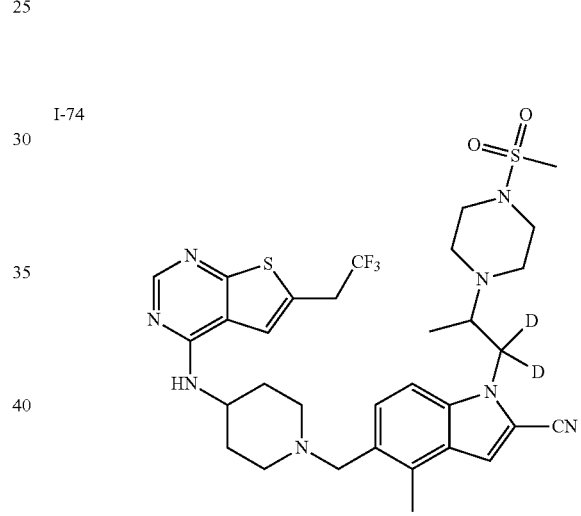 |
| I-80 | 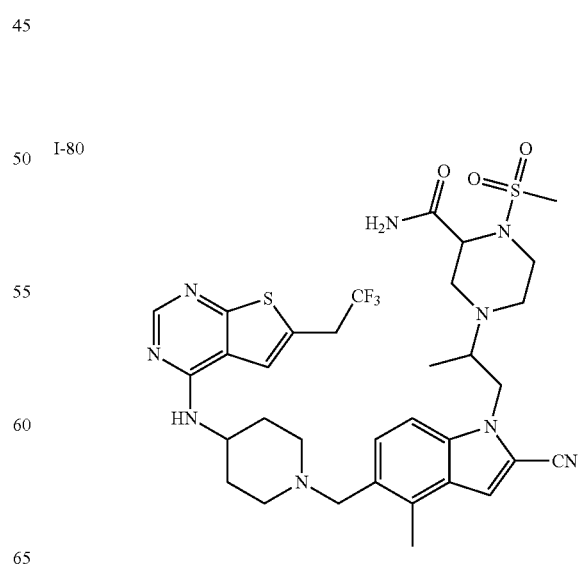 |

TABLE 1-continued
| No. | Structure |
|---|---|
| I-82 | 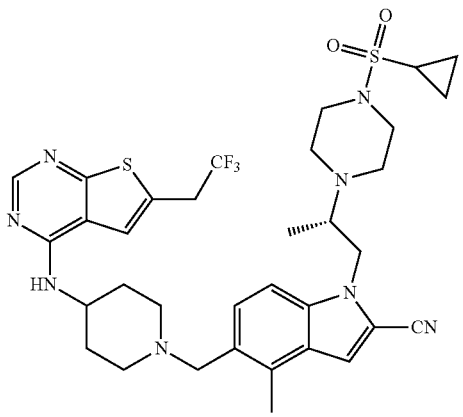 |
| I-87 | 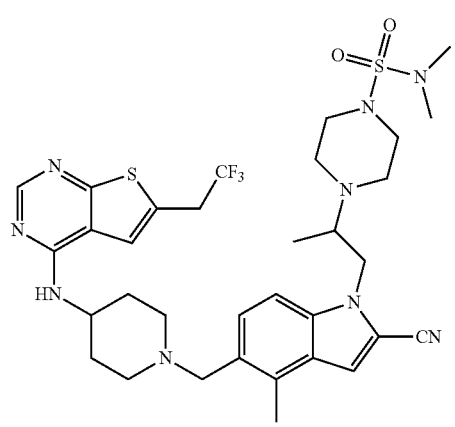 [SMILES: Cc1c(CN2CCC(Nc3ncnc4sc(CC(F)(F)F)cc34)CC2)ccc2c1cc(C#N)n2CC(C)N1CCN(S(=O)(=O)N(C)C)CC1]
MW (calc'd) 717.29
m/z (found) 718.35 [M + H]⁺ |
| I-89 | 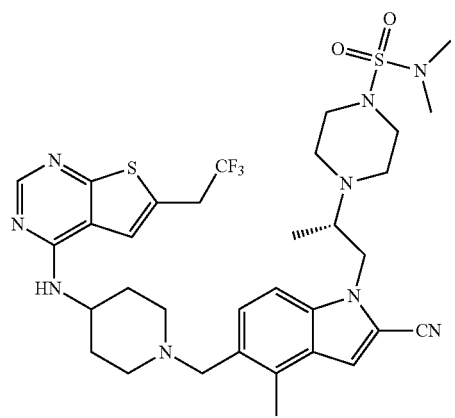 [SMILES: Cc1c(CN2CCC(Nc3ncnc4sc(CC(F)(F)F)cc34)CC2)ccc2c1cc(C#N)n2C[C@H](C)N1CCN(S(=O)(=O)N(C)C)CC1]
MW (calc'd) 717.29
m/z (found) 718.25 [M + H]⁺ |
| I-115 | 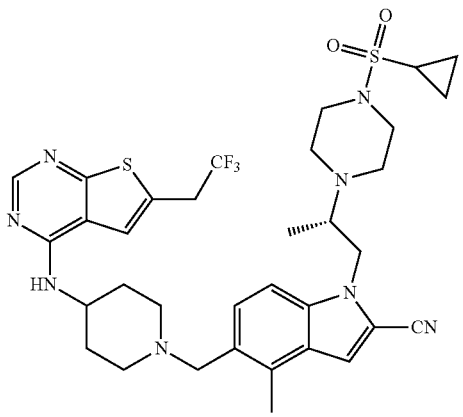
MW (calc'd) 714.27
m/z (found) 715.45 [M + H]⁺ |
| I-116 | 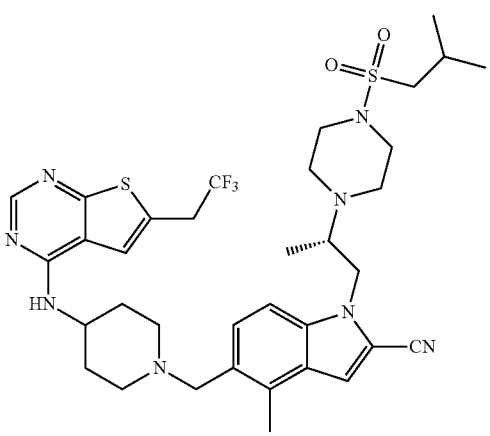 [SMILES: Cc1c(CN2CCC(Nc3ncnc4sc(CC(F)(F)F)cc34)CC2)ccc2c1cc(C#N)n2C[C@H](C)N1CCN(S(=O)(=O)CC(C)C)CC1]
MW (calc'd) 730.31
m/z (found) 731.50 [M + H]⁺ |
| I-117 | 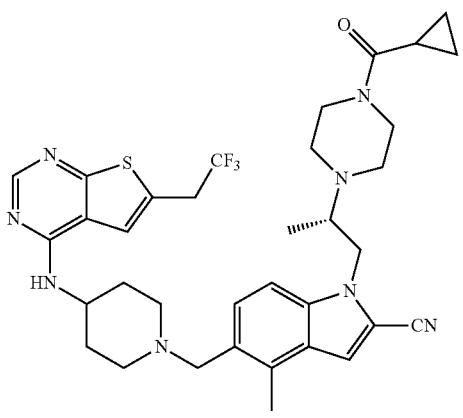 [SMILES: Cc1c(CN2CCC(Nc3ncnc4sc(CC(F)(F)F)cc34)CC2)ccc2c1cc(C#N)n2C[C@H](C)N1CCN(C(=O)C2CC2)CC1]
MW (calc'd) 678.31
m/z (found) 679.50 [M + H]⁺ |

TABLE 1-continued
| No. | Structure |
|---|---|
| I-118 | 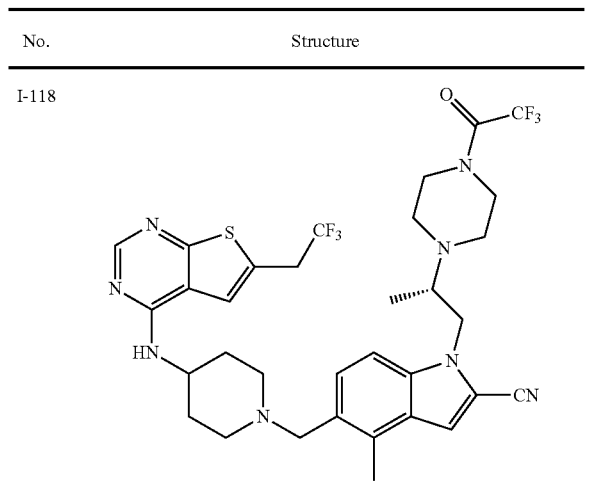<br>MW (calc'd) 706.26<br>m/z (found) 707.40 [M + H]⁺ |
| I-119 | 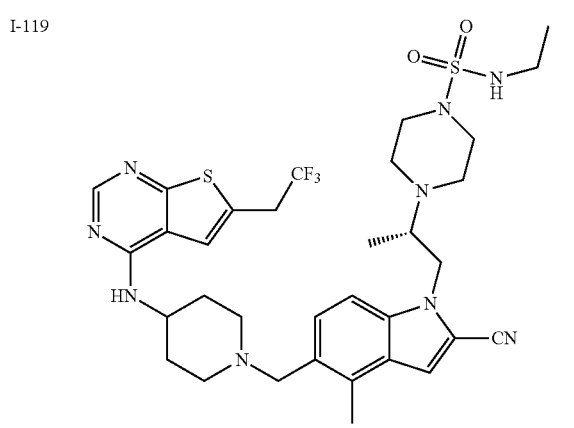<br>MW (calc'd) 717.29<br>m/z (found) 718.25 [M + H]⁺ |
| I-120 | 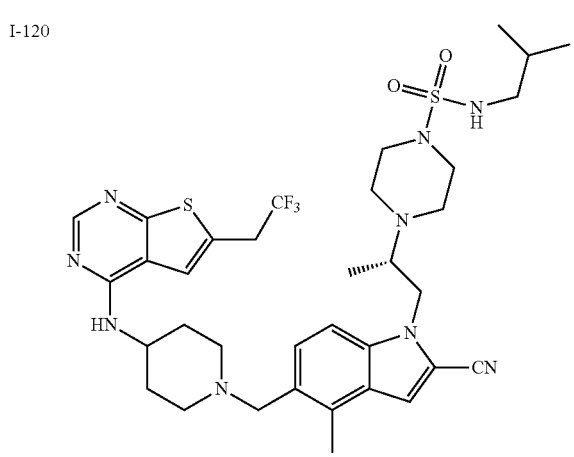<br>MW (calc'd) 745.32<br>m/z (found) 746.30 [M + H]⁺ |
TABLE 1-continued
| No. | Structure |
|---|---|
| I-121 | 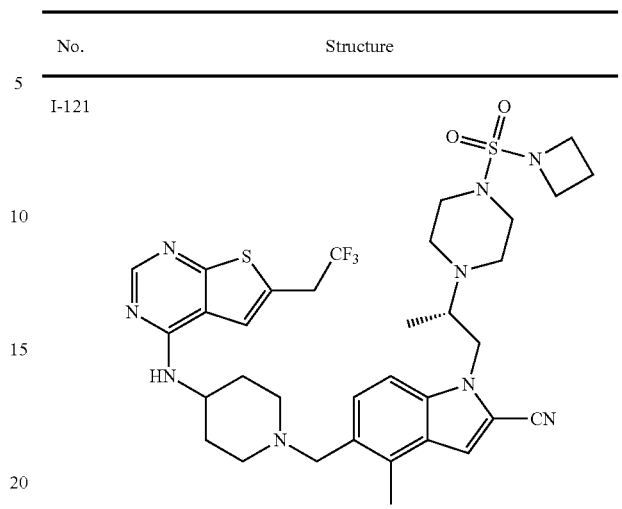<br>MW (calc'd) 729.29<br>m/z (found) 730.45 [M + H]⁺ |
| I-122 | 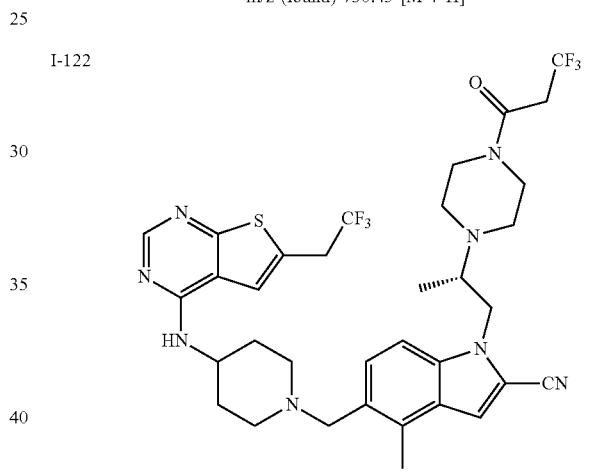<br>MW (calc'd) 720.28<br>m/z (found) 721.40 [M + H]⁺ |
| I-123 | 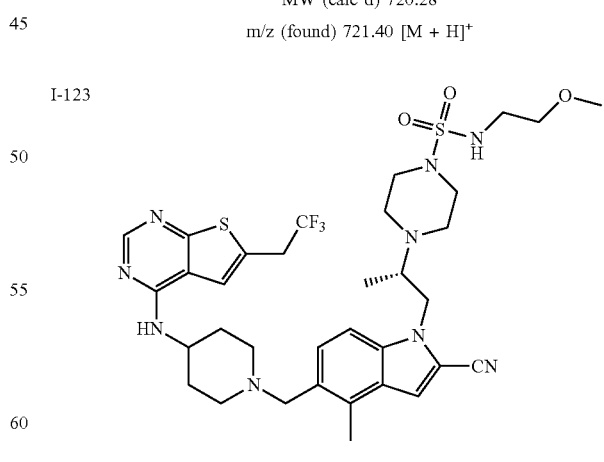<br>MW (calc'd) 747.30<br>m/z (found) 748.45 [M + H]⁺ |

TABLE 1-continued
| No. | Structure |
|---|---|
| I-127 | 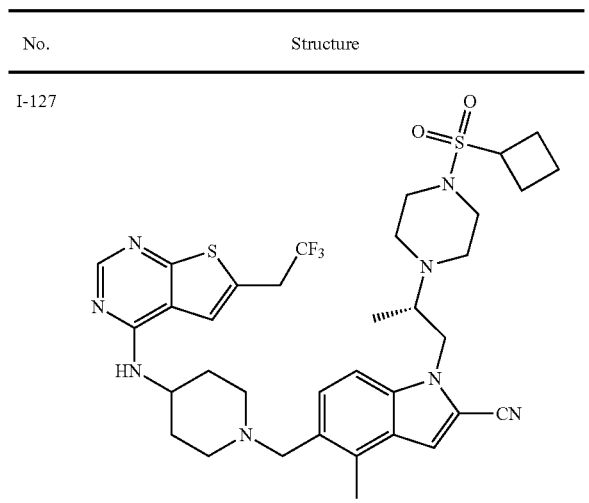 |
MW (calc'd) 728.29
m/z (found) 729.45 [M + H]+
| I-128 | 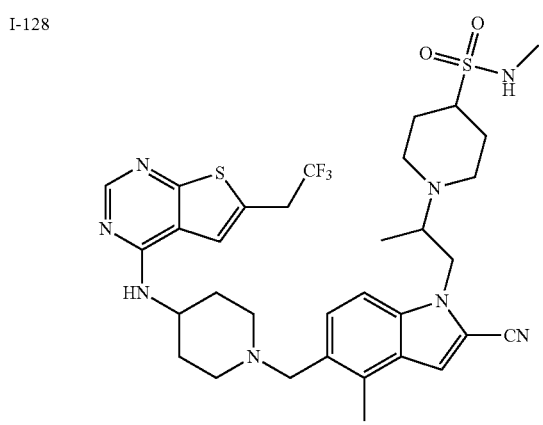 |
MW (calc'd) 702.27
m/z (found) 703.35 [M + H]+
| I-131 | 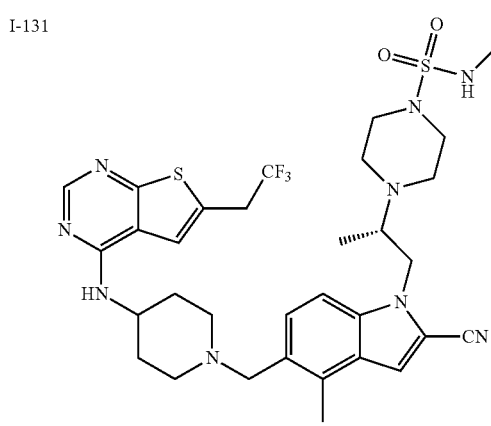 |
MW (calc'd) 733.28
m/z (found) 734.45 [M + H]+
TABLE 1-continued
| No. | Structure |
|---|---|
| I-132 | 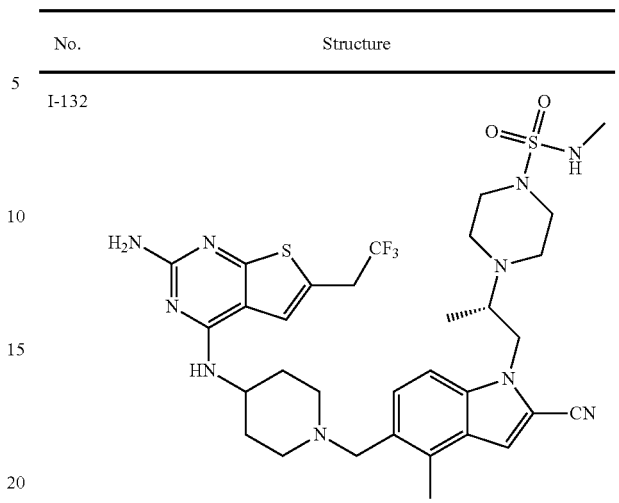 |
MW (calc'd) 718.28
m/z (found) 719.45 [M + H]+
| I-133 | 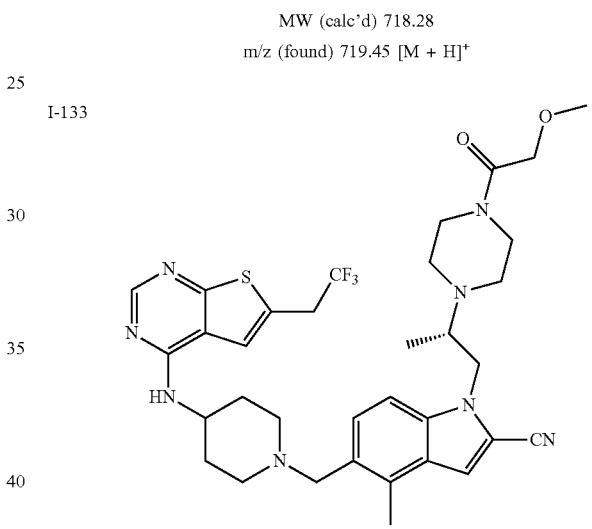 |
MW (calc'd) 682.30
m/z (found) 683.50 [M + H]+
| I-134 | 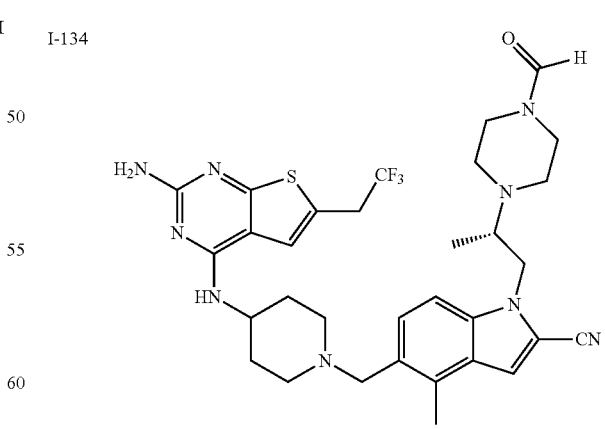 |
MW (calc'd) 653.29
m/z (found) 654.40 [M + H]+

TABLE 1-continued
| No. | Structure |
|---|---|
| I-135 | 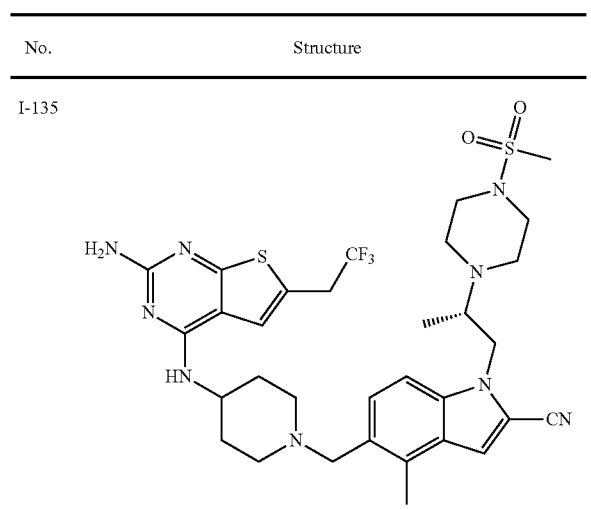<br>MW (calc'd) 703.27<br>m/z (found) 704.40 [M + H]+ |
| I-136 | 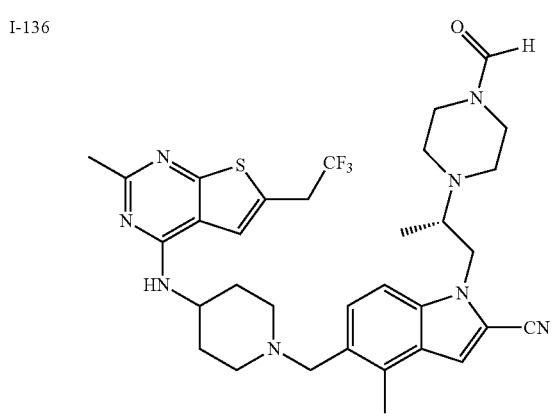<br>MW (calc'd) 652.29<br>m/z (found) 653.45 [M + H]+ |
| I-138 | 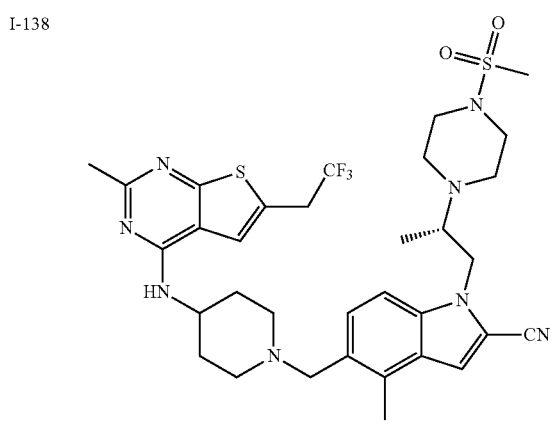<br>MW (calc'd) 702.27<br>m/z (found) 703.50 [M + H]+ |
| I-139 | 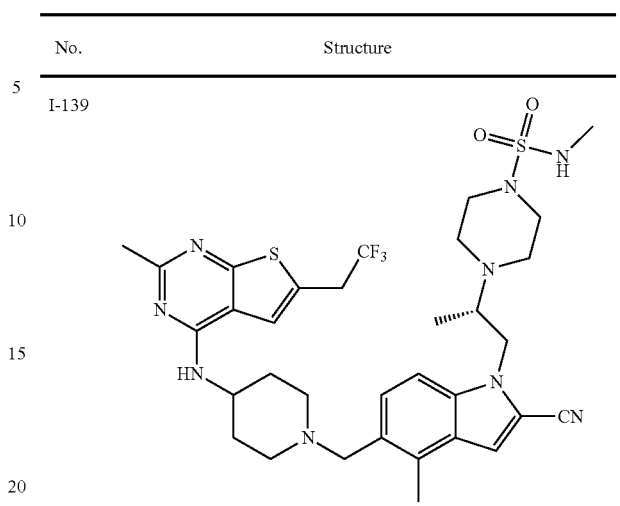<br>MW (calc'd) 717.29<br>m/z (found) 718.50 [M + H]+ |
| I-140 | 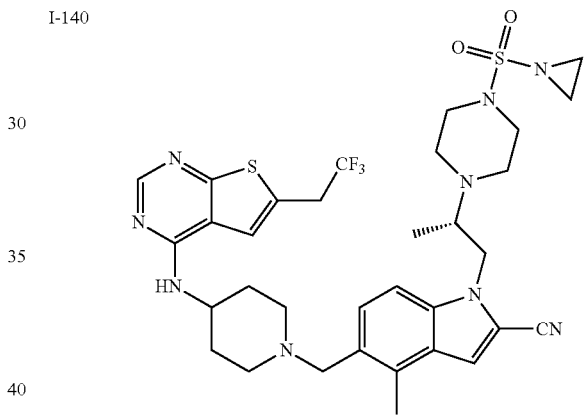<br>MW (calc'd) 715.27<br>m/z (found) 716.40 [M + H]+ |
| I-141 | 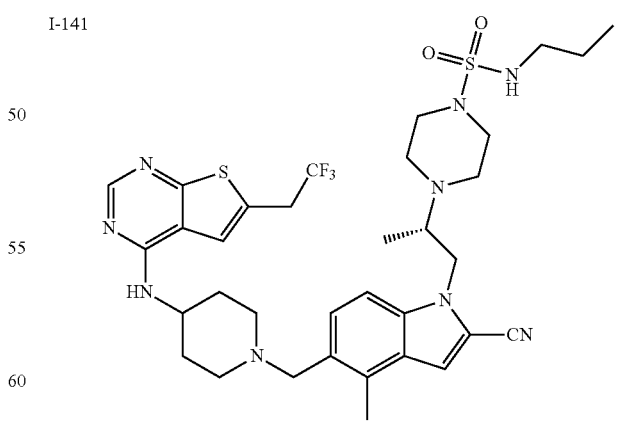<br>MW (calc'd) 731.30<br>m/z (found) 732.45 [M + H]+ |

TABLE 1-continued
| No. | Structure |
|---|---|
| I-142 | 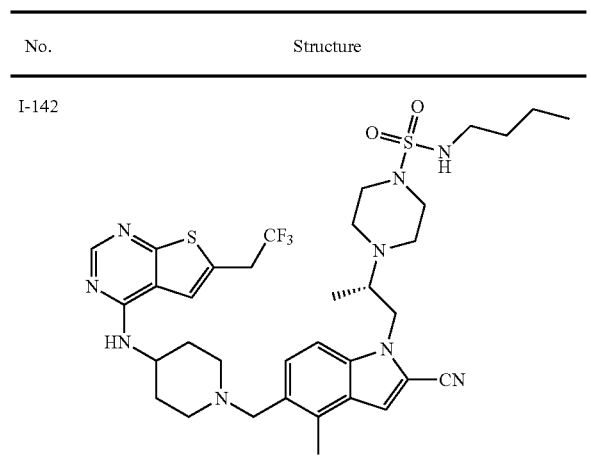 MW (calc'd) 745.32<br>m/z (found) 746.40 [M + H]⁺ |
| I-143 | 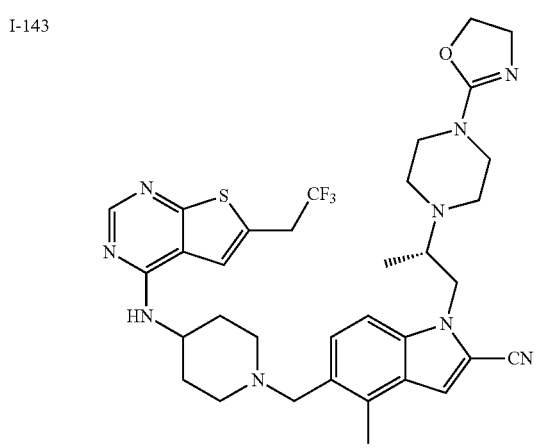 MW (calc'd) 679.30<br>m/z (found) 680.50 [M + H]⁺ |
| I-146 | 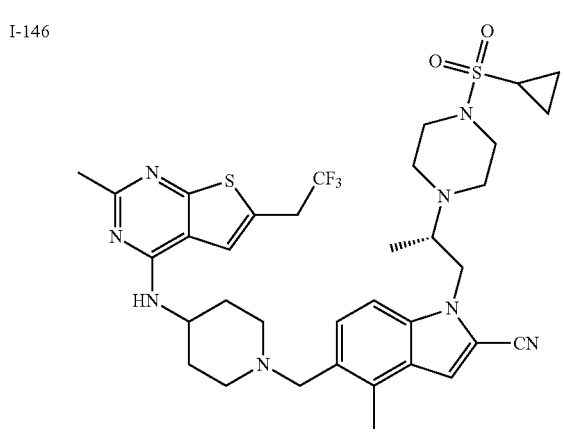 MW (calc'd) 728.29<br>m/z (found) 729.45 [M + H]⁺ |
TABLE 1-continued
| No. | Structure |
|---|---|
| I-147 | 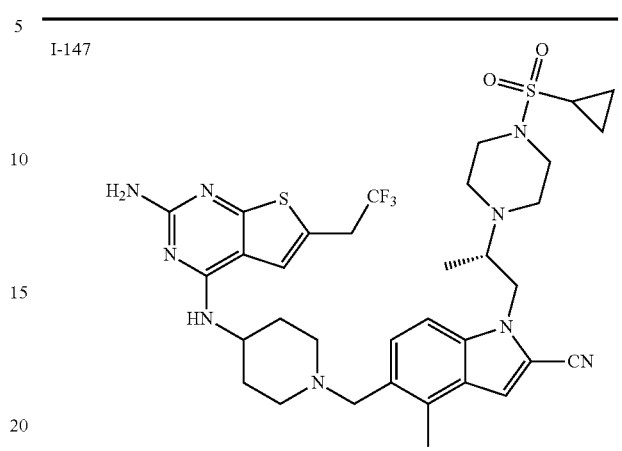 MW (calc'd) 729.29<br>m/z (found) 730.40 [M + H]⁺ |
| I-148 | 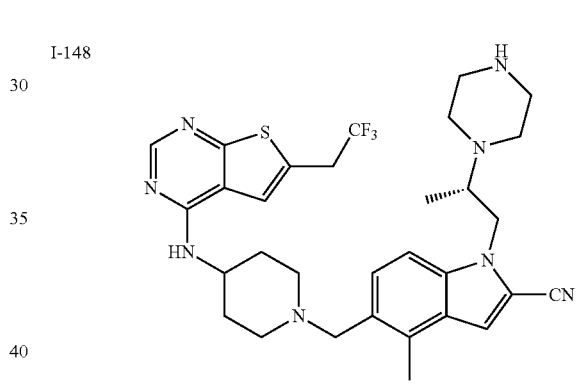 MW (calc'd) 610.28<br>m/z (found) 611.3 [M + H]⁺ |
| I-150 | 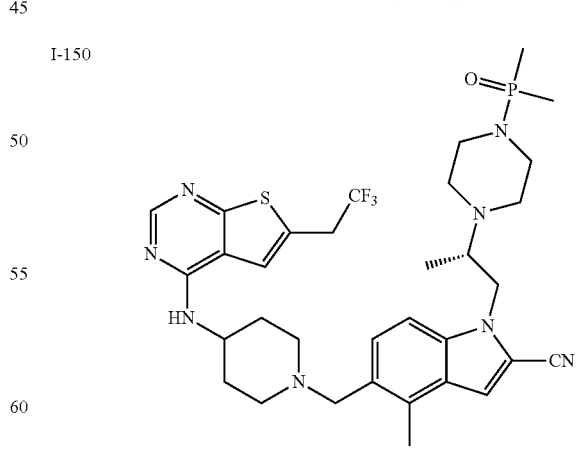 MW (calc'd) 686.29<br>m/z (found) 687.3 [M + H]⁺ |

TABLE 1-continued
| No. | Structure |
|---|---|
| I-151 | 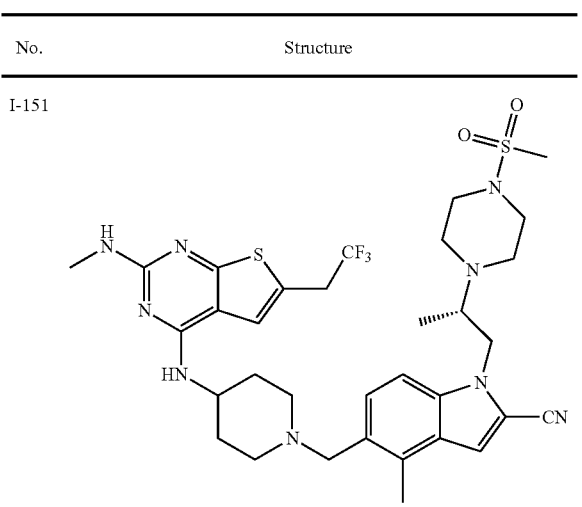<br>MW (calc'd) 717.29<br>m/z (found) 718.55 [M + H]+ |
| I-153 | 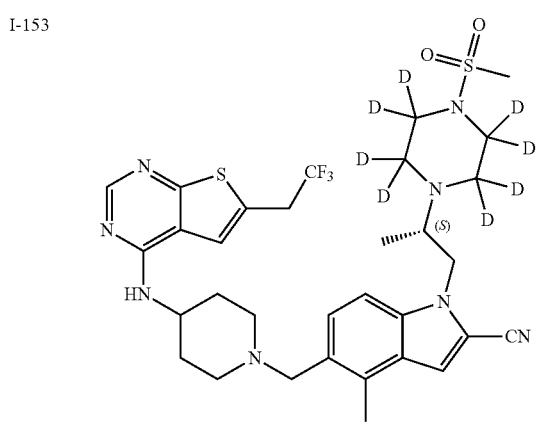<br>MW (calc'd) 696.31 |
| I-154 | 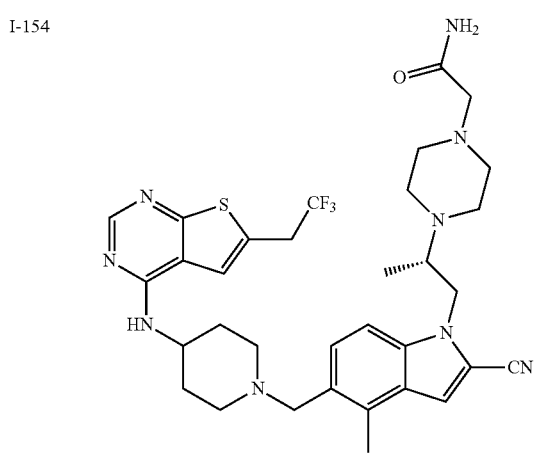<br>MW (calc'd) 667.30<br>m/z (found) 668.35 [M + H]+ |
TABLE 1-continued
| No. | Structure |
|---|---|
| I-155 | 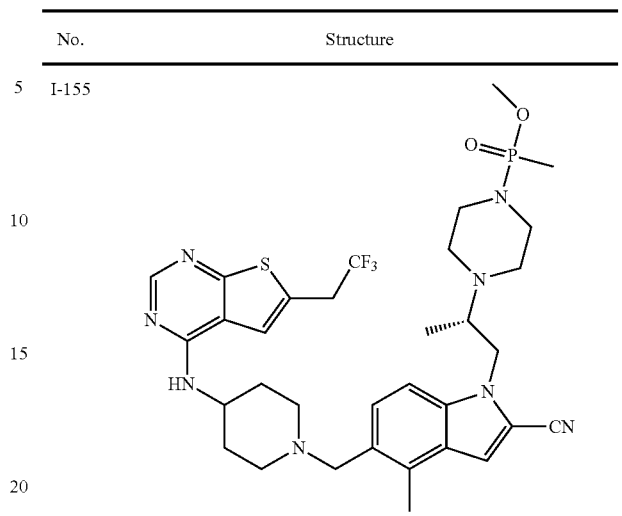<br>MW (calc'd) 702.28<br>m/z (found) 703.35 [M + H]+ |
| I-156 | 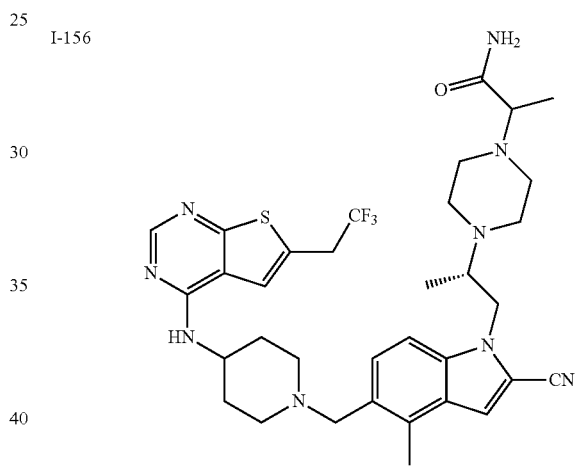<br>MW (calc'd) 681.32<br>m/z (found) 682.45 [M + H]+ |
| I-157 | 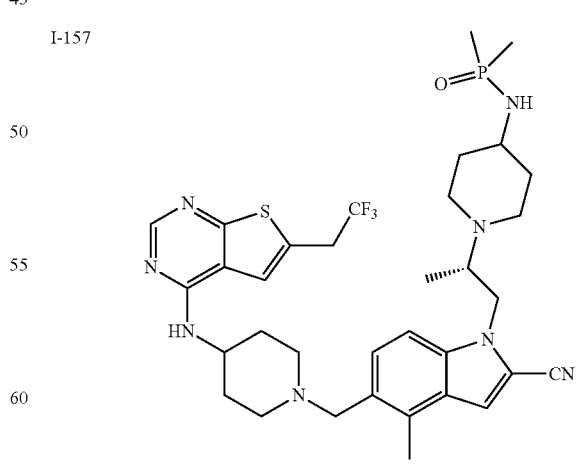<br>MW (calc'd) 700.30<br>m/z (found) 701.40 [M + H]+ |

TABLE 1-continued
| No. | Structure |
|---|---|
| I-158 | 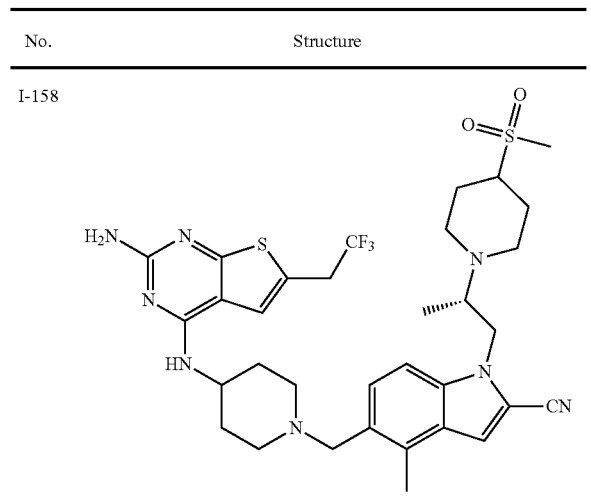<br>MW (calc'd) 702.27<br>m/z (found) 703.40 [M + H]⁺ |
| I-159 | 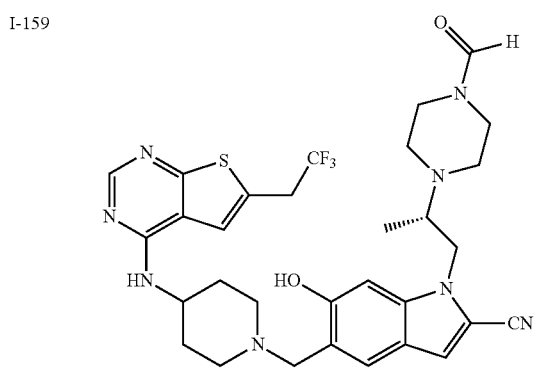<br>MW (calc'd) 640.26<br>m/z (found) 641.40 [M + H]⁺ |
| I-160 | 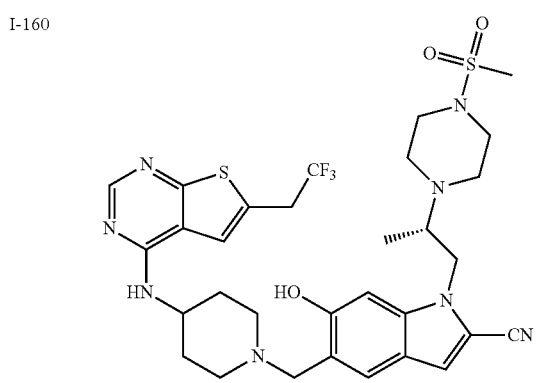<br>MW (calc'd) 690.24<br>m/z (found) 691.35 [M + H]⁺ |
| I-161 | 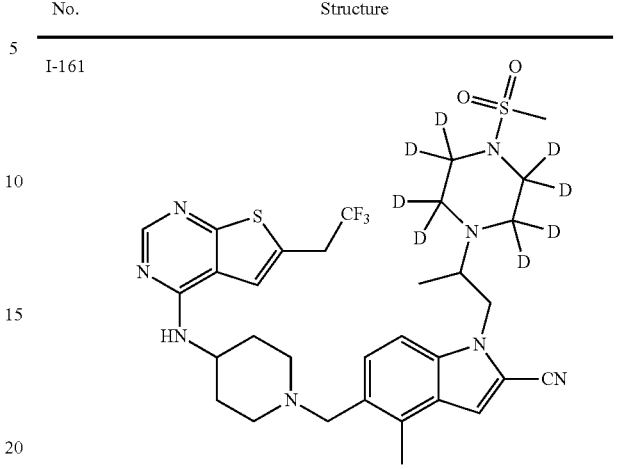<br>MW (calc'd) 696.31<br>m/z (found) 697.3 [M + H]⁺ |
| I-162 | 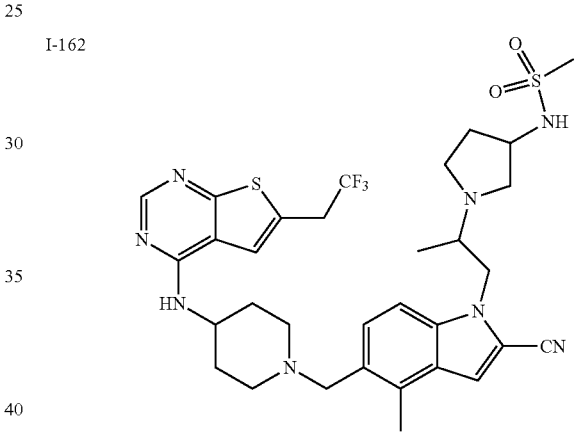<br>MW (calc'd) 659.23<br>m/z (found) 660.2 [M + H]⁺ |
| I-163 | 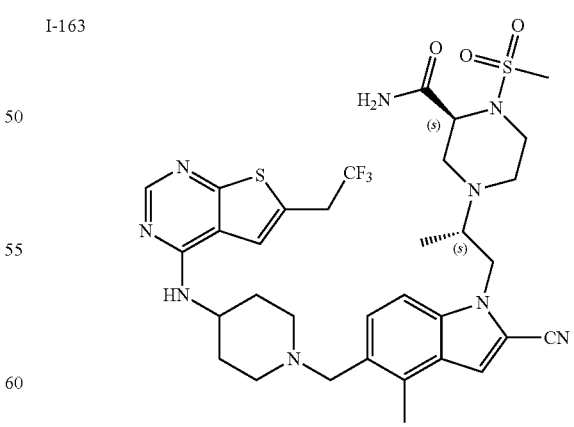<br>MW (calc'd) 731.26<br>m/z (found) 732.40 [M + H]⁺ |

TABLE 1-continued

| No. | Structure |
|---|---|
| I-164 | MW (calc'd) 731.26<br>m/z (found) 732.35 [M + H]⁺ |
| I-165 | MW (calc'd) 701.28<br>m/z (found) 702.40 [M + H]⁺ |
| I-166 | MW (calc'd) 667.34<br>m/z (found) 668.45 [M + H]⁺ |
| I-167 | MW (calc'd) 703.27<br>m/z (found) 704.40 [M + H]⁺ |
| I-168 | MW (calc'd) 660.28<br>m/z (found) 661.40 [M + H]⁺ |
| I-170 | MW (calc'd) 731.30<br>m/z (found) 732.40 [M + H]⁺ |

TABLE 1-continued
| No. | Structure |
|---|---|
| I-171 | 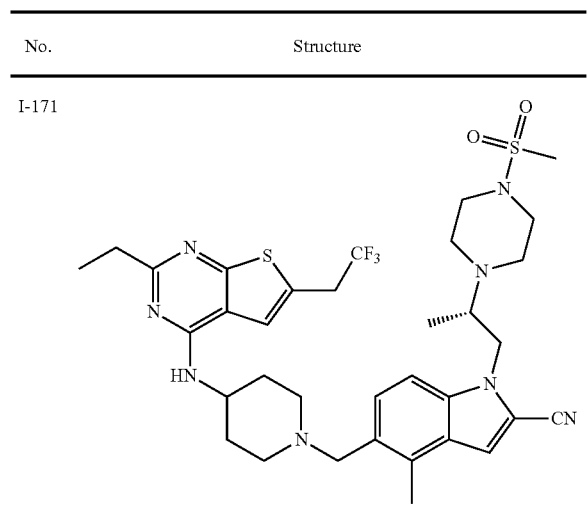 MW (calc'd) 716.29<br>m/z (found) 717.45 [M + H]+ |
| I-172 | 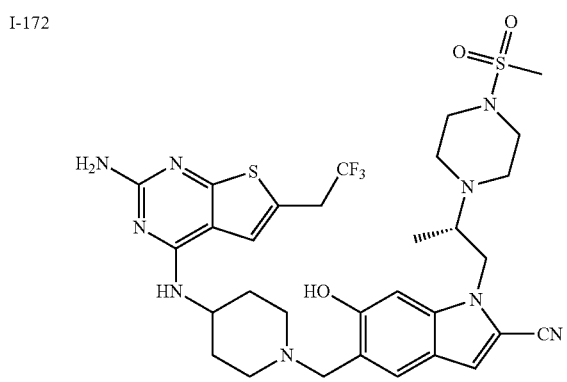 MW (calc'd) 705.25<br>m/z (found) 706.45 [M + H]+ |
| I-173 | 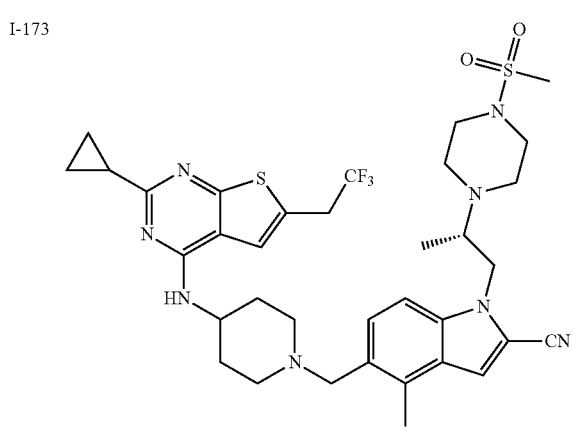 MW (calc'd) 728.29<br>m/z (found) 729.45 [M + H]+ |
| I-174 | 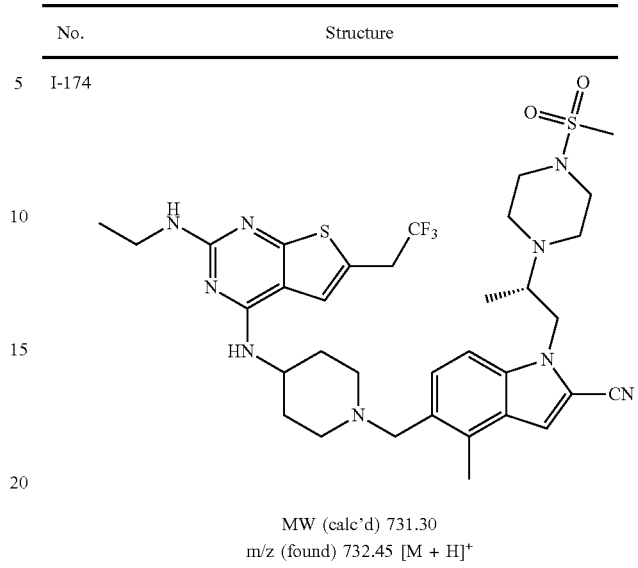 MW (calc'd) 731.30<br>m/z (found) 732.45 [M + H]+ |
| I-175 | 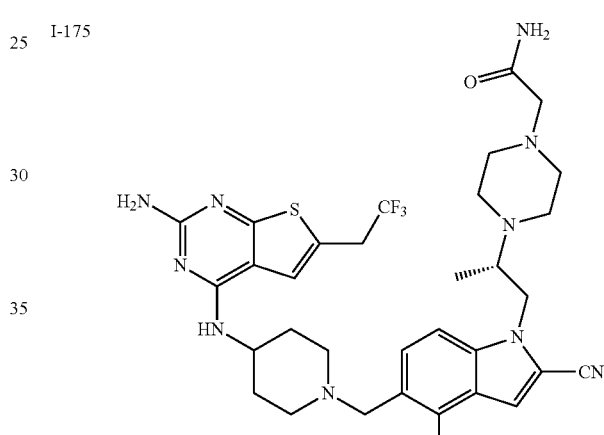 MW (calc'd) 682.31<br>m/z (found) 683.45 [M + H]+ |
| I-176 | 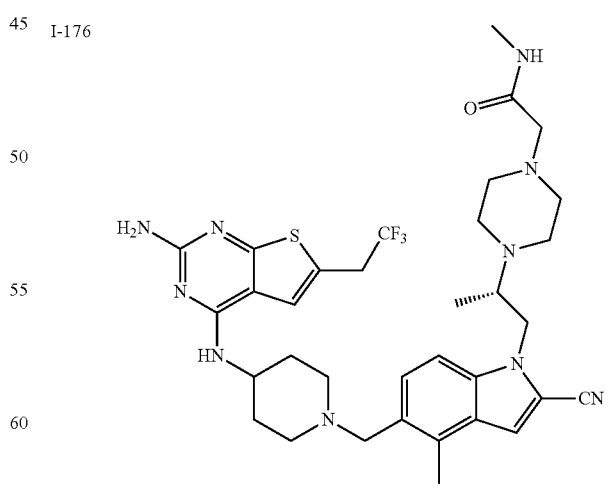 MW (calc'd) 696.33<br>m/z (found) 697.60 [M + H]+ |

TABLE 1-continued
| No. | Structure |
|---|---|
| I-177 | 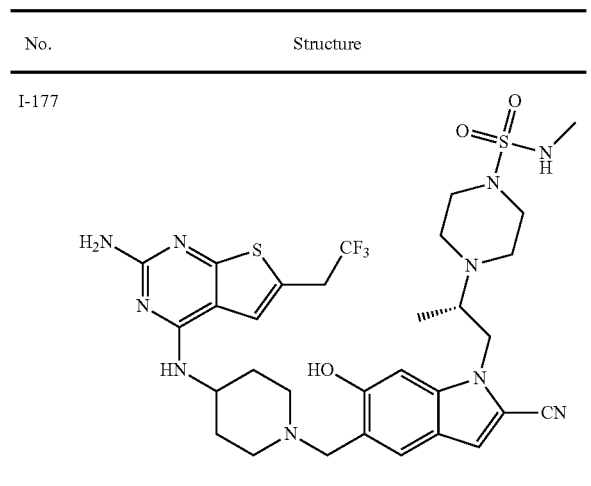<br>MW (calc'd) 720.26<br>m/z (found) 721.50 [M + H]+ |
| I-178 | 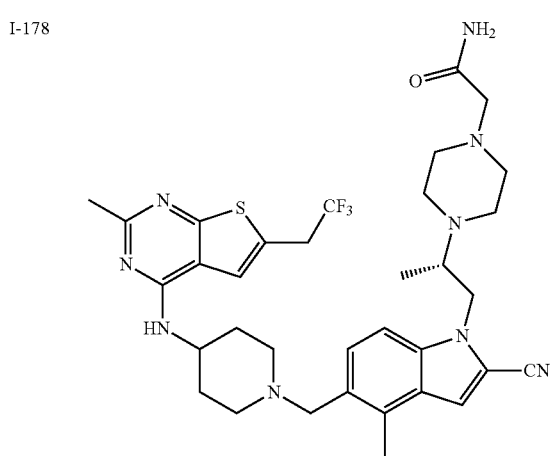<br>MW (calc'd) 681.32<br>m/z (found) 682.45 [M + H]+ |
| I-179 | 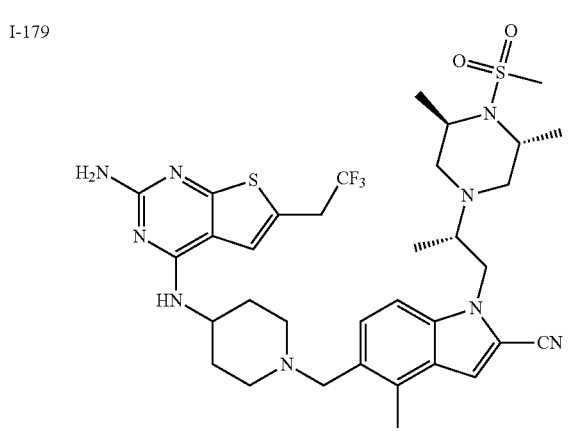<br>MW (calc'd) 731.30<br>m/z (found) 732.50 [M + H]+ |
TABLE 1-continued
| No. | Structure |
|---|---|
| I-180 | 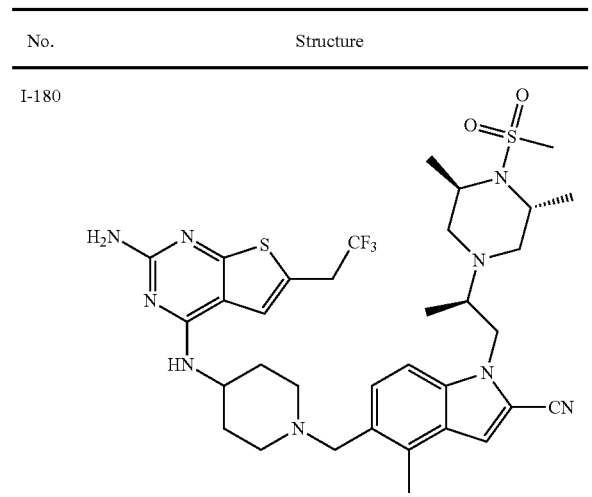<br>MW (calc'd) 731.30<br>m/z (found) 732.50 [M + H]+ |
| I-181 | 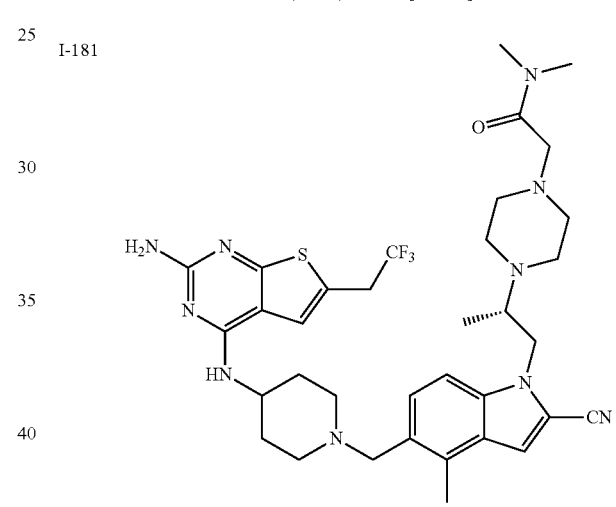<br>MW (calc'd) 710.35<br>m/z (found) 711.50 [M + H]+ |
| I-182 | 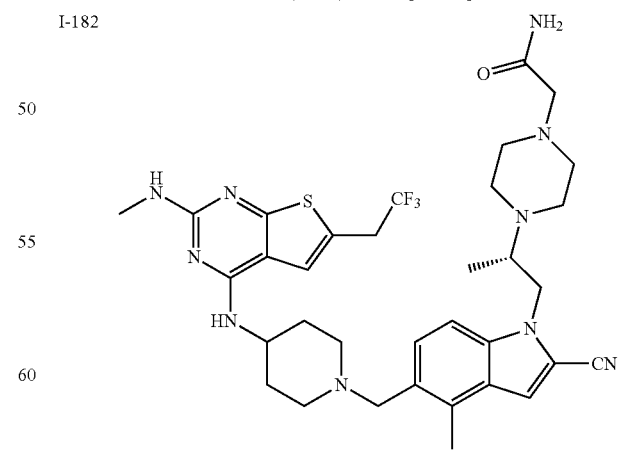<br>MW (calc'd) 696.33<br>m/z (found) 697.60 [M + H]+ |

TABLE 1-continued
| No. | Structure |
|---|---|
| I-183 | 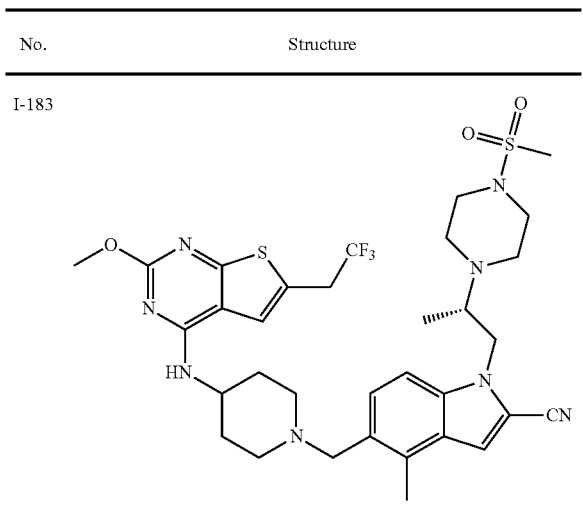 |
MW (calc'd) 718.27
m/z (found) 719.45 [M + H]+
| I-184 | 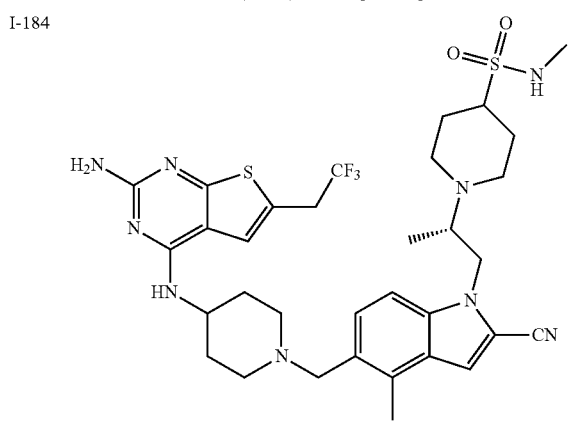 |
MW (calc'd) 717.29
m/z (found) 718.45 [M + H]+
| I-185 | 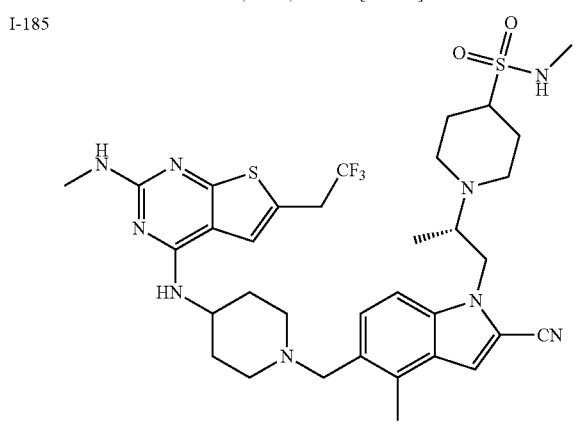 |
MW (calc'd) 731.30
m/z (found) 732.45 [M + H]+
TABLE 1-continued
| No. | Structure |
|---|---|
| I-186 | 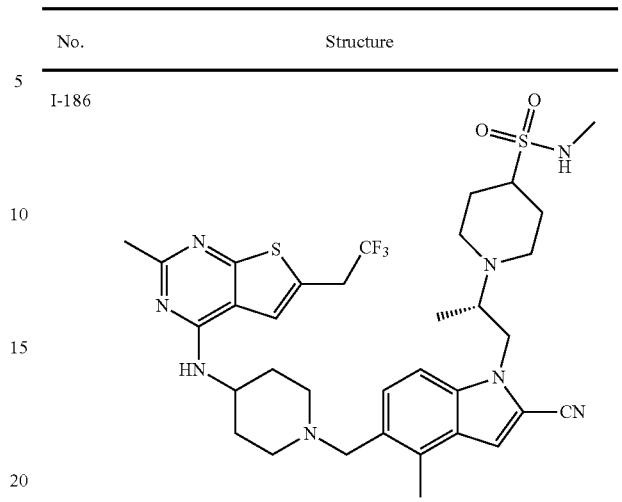 |
MW (calc'd) 716.29
m/z (found) 717.45 [M + H]+
| I-187 | 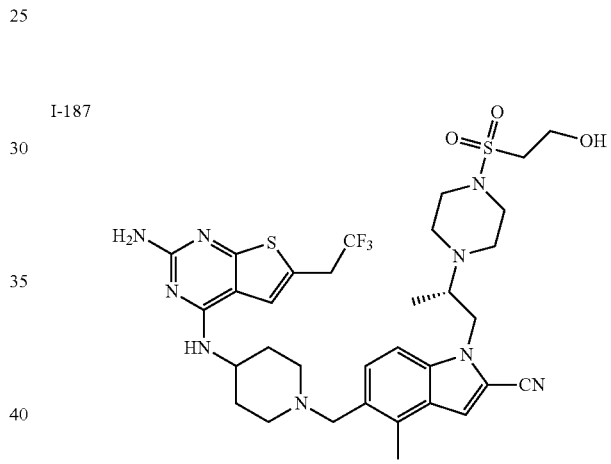 |
MW (calc'd) 733.28
m/z (found) 734.45 [M + H]+
| I-188 | 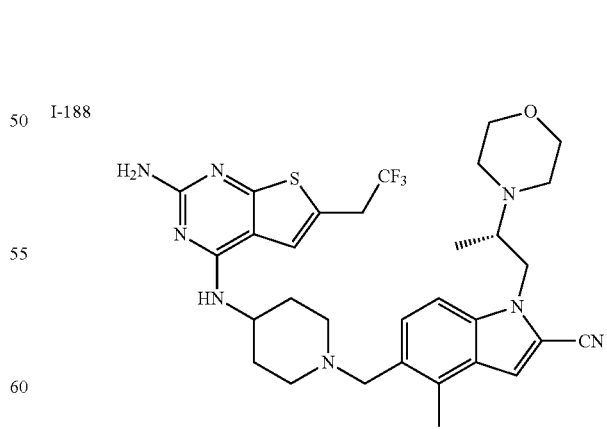 |
MW (calc'd) 626.28
m/z (found) 627.40 [M + H]+

TABLE 1-continued
| No. | Structure |
|---|---|
| I-189 | 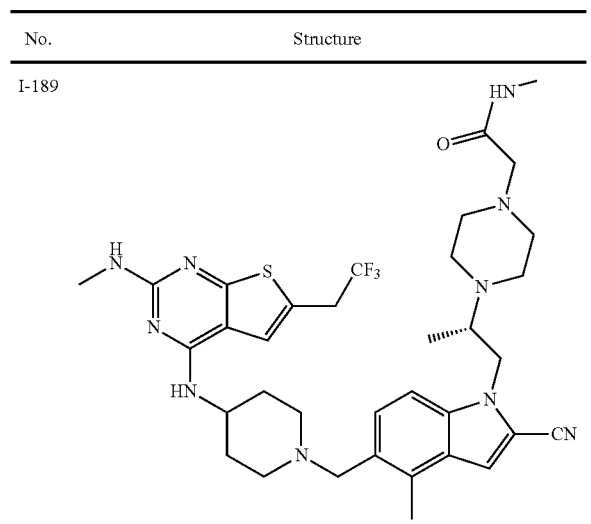 MW (calc'd) 710.35<br>m/z (found) 711.45 [M + H]+ |
| I-190 | 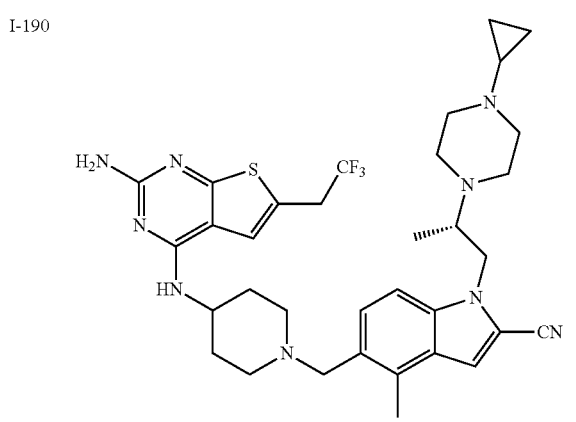 MW (calc'd) 665.32<br>m/z (found) 666.45 [M + H]+ |
| I-191 | 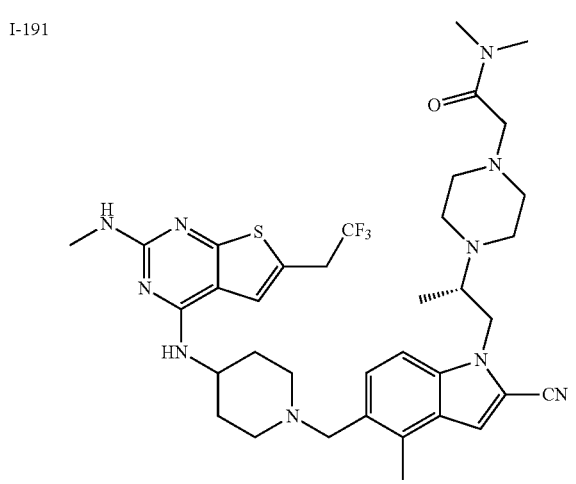 MW (calc'd) 724.36<br>m/z (found) 725.45 [M + H]+ |
| I-192 | 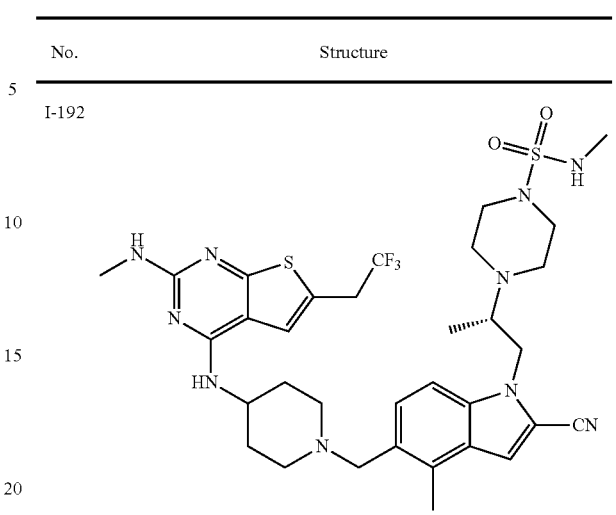 MW (calc'd) 732.30<br>m/z (found) 733.45 [M + H]+ |
| I-193 | 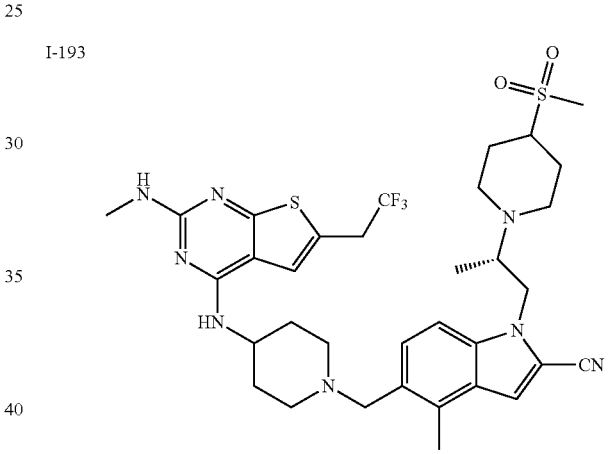 MW (calc'd) 716.29<br>m/z (found) 717.45 [M + H]+ |
| I-194 | 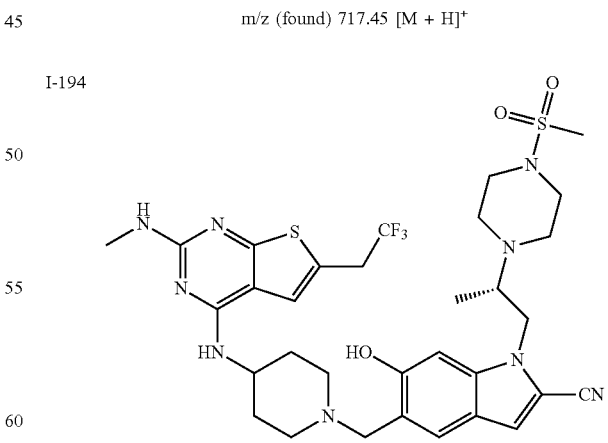 MW (calc'd) 719.26<br>m/z (found) 720.55 [M + H]+ |

TABLE 1-continued
| No. | Structure |
|---|---|
| I-195 | 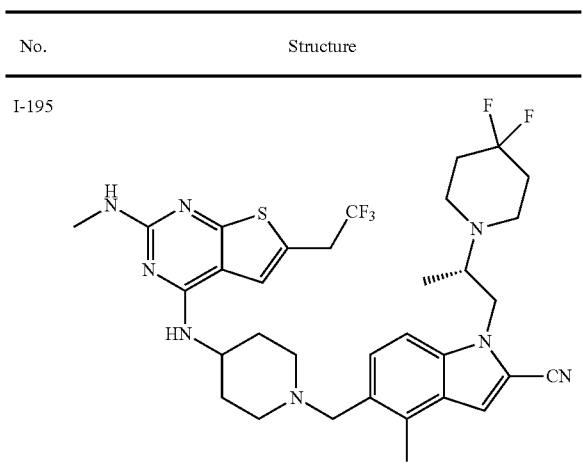 MW (calc'd) 674.29<br>m/z (found) 675.50 [M + H]+ |
| I-196 | 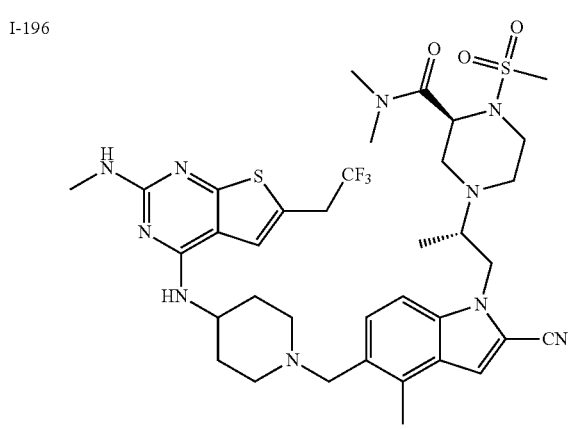 MW (calc'd) 788.32<br>m/z (found) 789.45 [M + H]+ |
| I-197 | 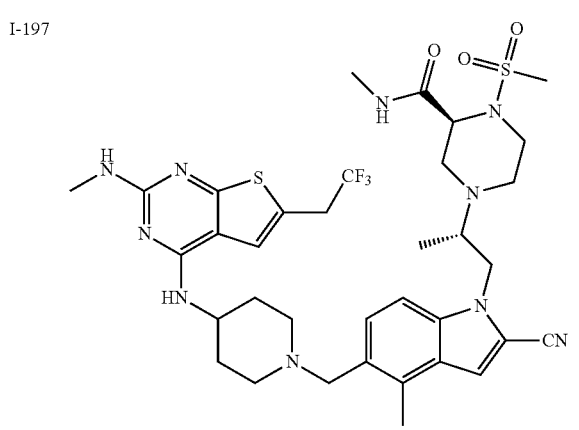 MW (calc'd) 774.31<br>m/z (found) 775.3 [M + H]+ |
| I-199 | 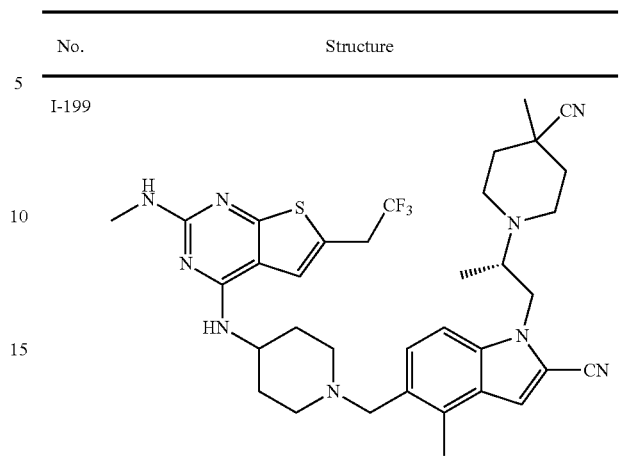 MW (calc'd) 677.32<br>m/z (found) 678.55 [M + H]+ |
| I-200 | 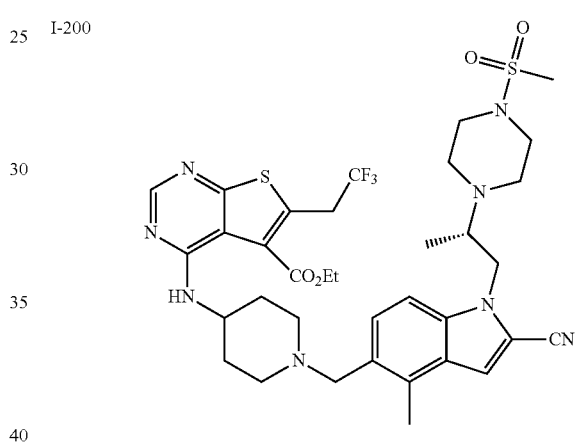 MW (calc'd) 760.28<br>m/z (found) 761.40 [M + H]+ |
| I-201 | 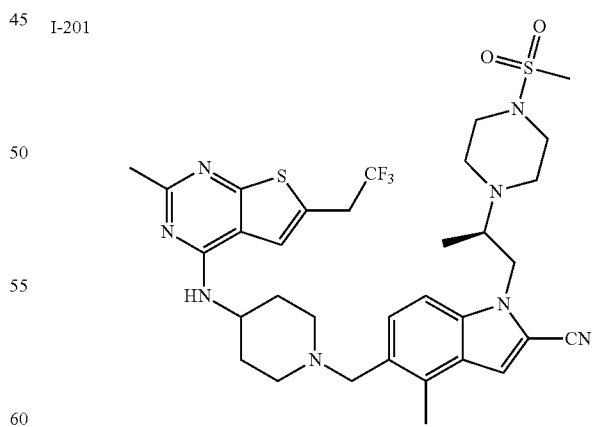 MW (calc'd) 702.27<br>m/z (found) 703.45 [M + H]+ |

TABLE 1-continued

| No. | Structure |
|---|---|
| I-202 | MW (calc'd) 723.37; m/z (found) 724.55 [M + H]+ |
| I-203 | MW (calc'd) 688.26; m/z (found) 689.40 [M + H]+ |
| I-204 | MW (calc'd) 695.33; m/z (found) 696.60 [M + H]+ |
| I-205 | MW (calc'd) 733.28; m/z (found) 734.55 [M + H]+ |
| I-206 | MW (calc'd) 709.35; m/z (found) 710.55 [M + H]+ |
| I-207 | MW (calc'd) 668.32; m/z (found) 669.55 [M + H]+ |

TABLE 1-continued
| No. | Structure |
|---|---|
| I-208 | 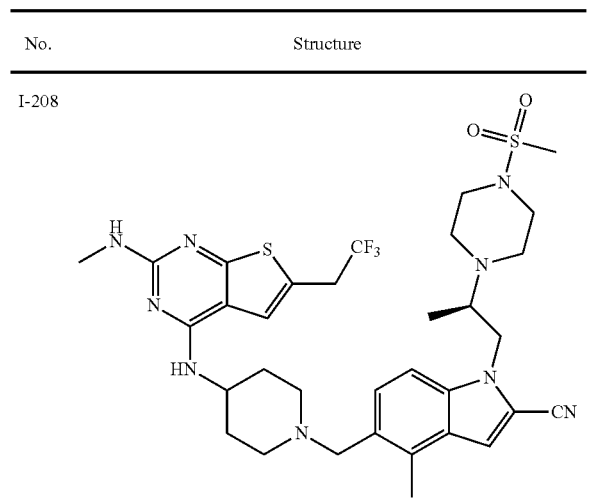 |
MW (calc'd) 717.29
m/z (found) 718.40 [M + H]+
| No. | Structure |
|---|---|
| I-209 | 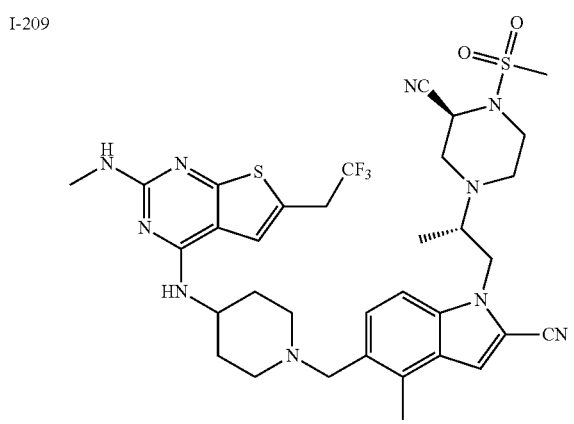 |
MW (calc'd) 742.28
m/z (found) 743.40 [M + H]+
| No. | Structure |
|---|---|
| I-210 | 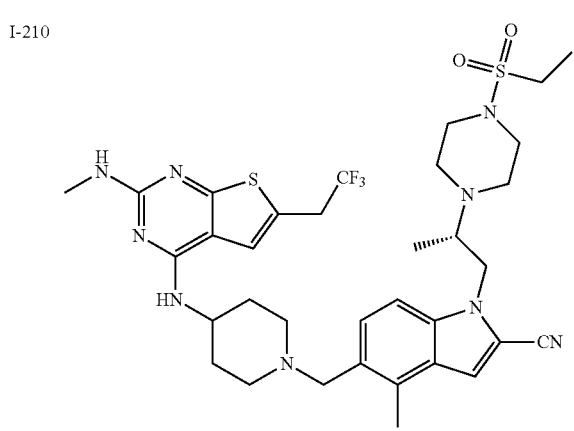 |
MW (calc'd) 731.30
m/z (found) 732.40 [M + H]+
| No. | Structure |
|---|---|
| I-211 | 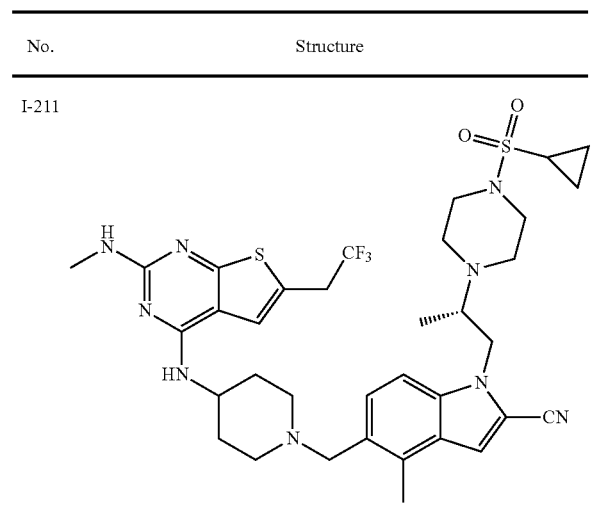 |
MW (calc'd) 743.30
m/z (found) 744.40 [M + H]+
| No. | Structure |
|---|---|
| I-212 | 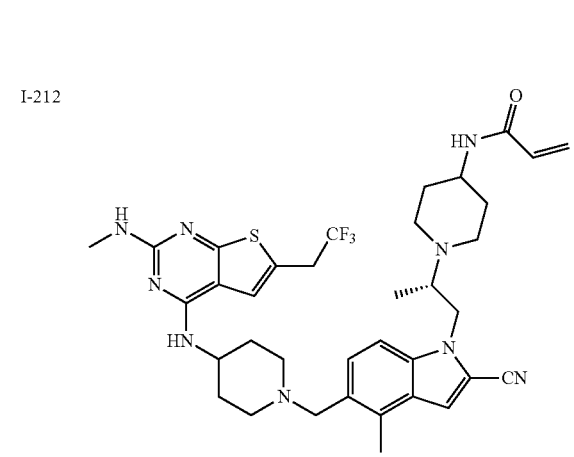 |
MW (calc'd) 707.33
m/z (found) 708.45 [M + H]+
| No. | Structure |
|---|---|
| I-213 | 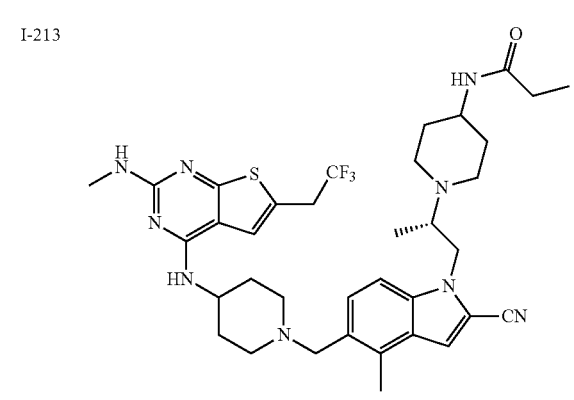 |
MW (calc'd) 709.35
m/z (found) 710.50 [M + H]+

TABLE 1-continued
| No. | Structure |
|---|---|
| I-214 | 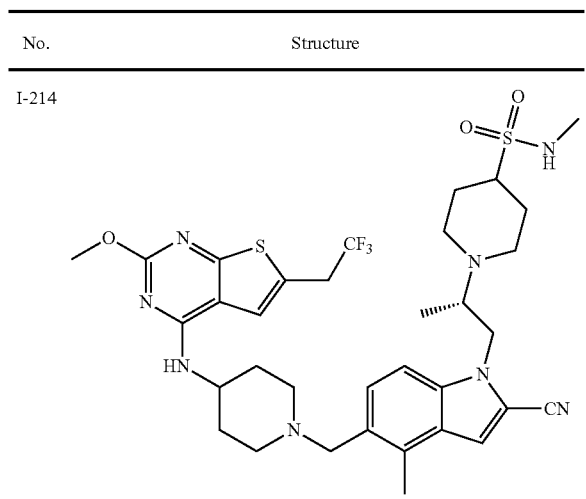<br>MW (calc'd) 732.29<br>m/z (found) 733.40 [M + H]⁺ |
| I-215 | 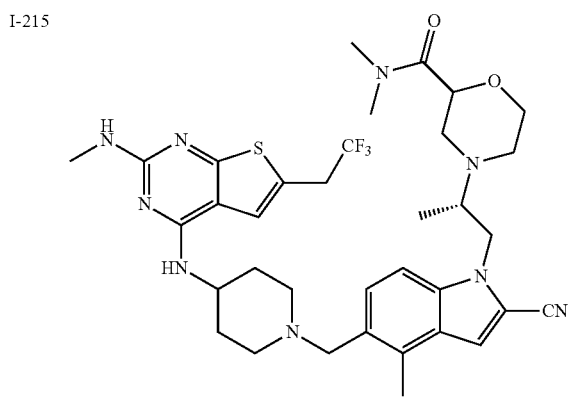<br>MW (calc'd) 711.33<br>m/z (found) 712.45 [M + H]⁺ |
| I-216 | 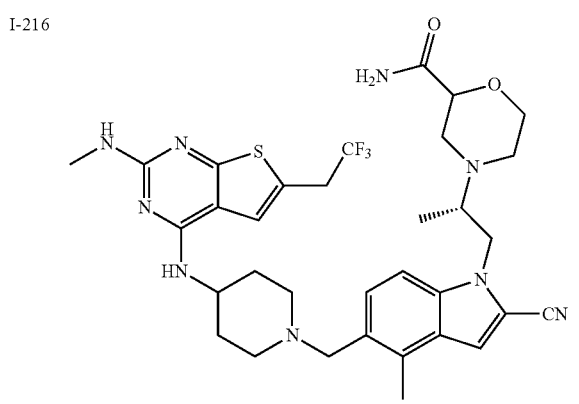<br>MW (calc'd) 683.30<br>m/z (found) 684.45 [M + H]⁺ |
| I-217 | 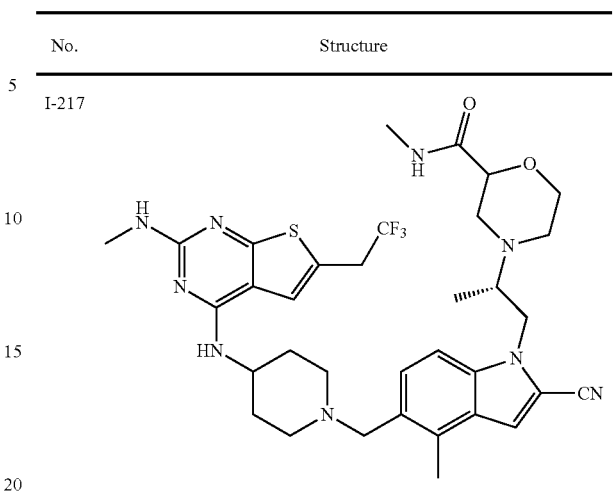<br>MW (calc'd) 697.31<br>m/z (found) 698.3 [M + H]⁺ |
| I-218 | 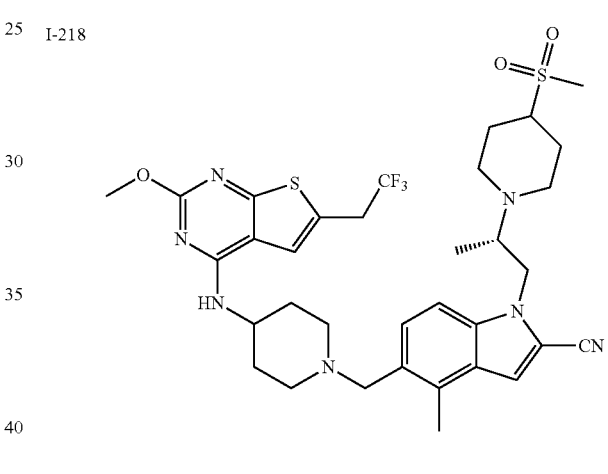<br>MW (calc'd) 717.27<br>m/z (found) 718.45 [M + H]⁺ |
| I-219 | 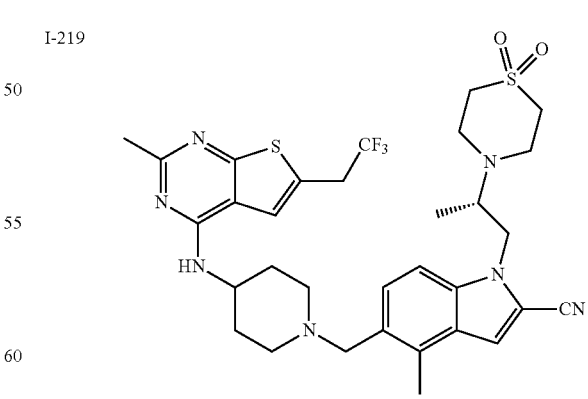<br>MW (calc'd) 673.25<br>m/z (found) 674.2 [M + H]⁺ |

TABLE 1-continued
| No. | Structure |
|---|---|
| I-220 | 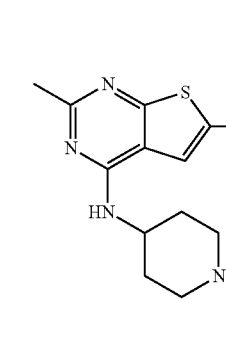<br>MW (calc'd) 694.34<br>m/z (found) 695.50 [M + H]+ |
| I-221 | 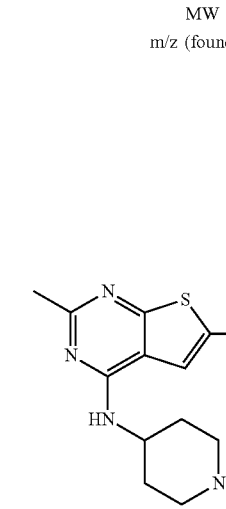<br>MW (calc'd) 708.35<br>m/z (found) 709.50 [M + H]+ |
| I-235 | 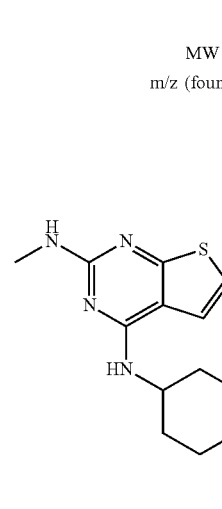<br>MW (calc'd) 688.26<br>m/z (found) 689.40 [M + H]+ |
| I-243 | 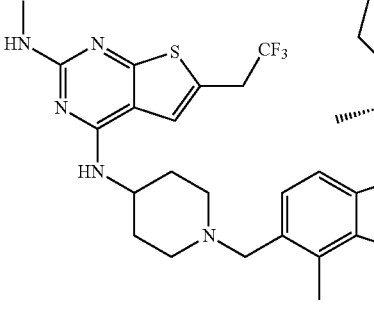<br>MW (calc'd) 667.30<br>m/z (found) 668.45 [M + H]+ |
| I-244 | 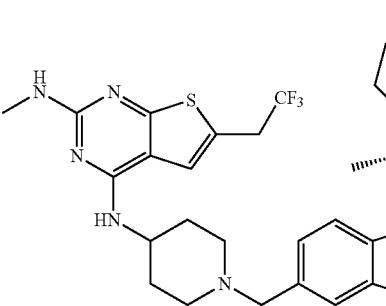<br>MW (calc'd) 653.29<br>m/z (found) 654.45 [M + H]+ |
| I-247 | 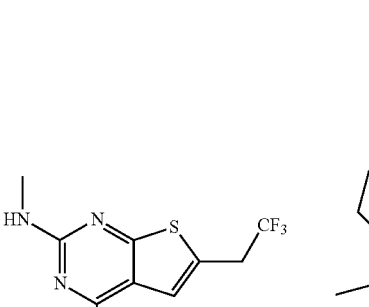<br>MW (calc'd) 716.29<br>m/z (found) 717.56 [M + H]+ |

TABLE 1-continued
| No. | Structure |
|---|---|
| I-248 | 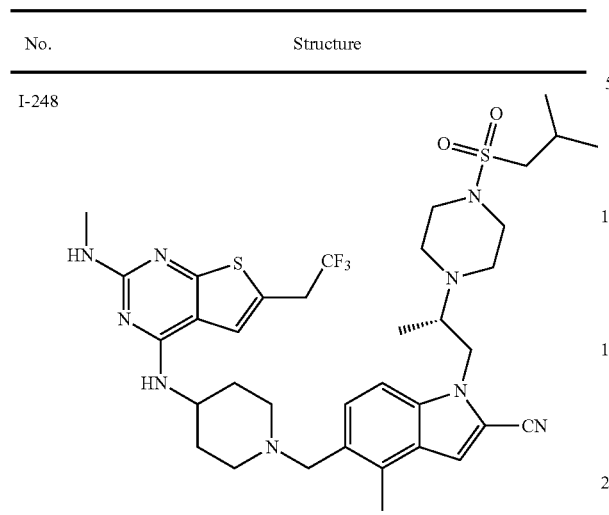 MW (calc'd) 759.33<br>m/z (found) 760.50 [M + H]+ |
| I-249 | 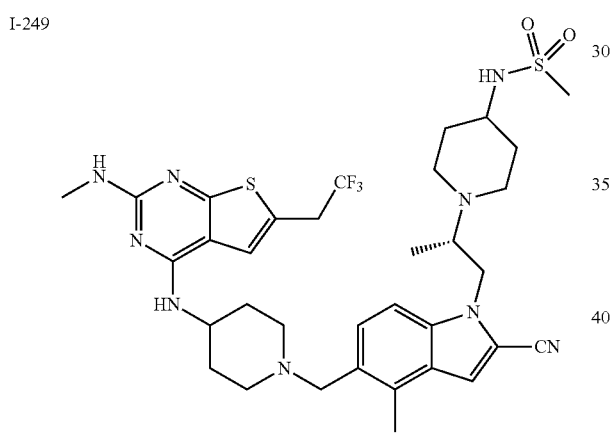 MW (calc'd) 731.30<br>m/z (found) 732.45 [M + H]+ |
| I-250 | 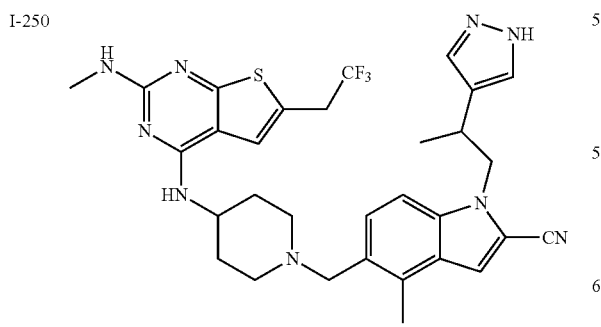 MW (calc'd) 621.26<br>m/z (found) 622.2 [M + H]+ |
| I-251 | 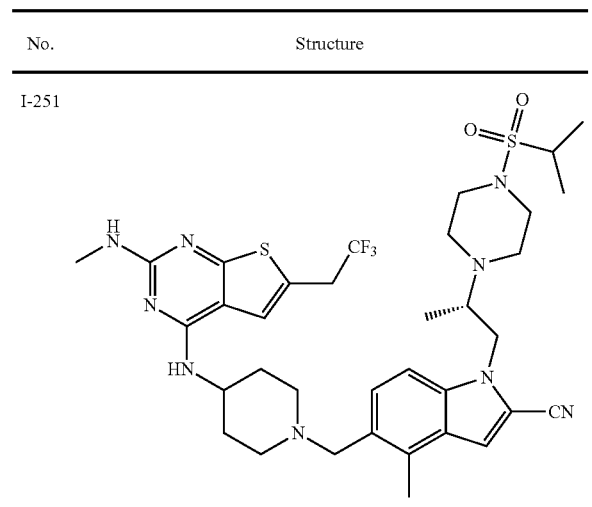 MW (calc'd) 745.32<br>m/z (found) 746.3 [M + H]+ |
| I-252 | 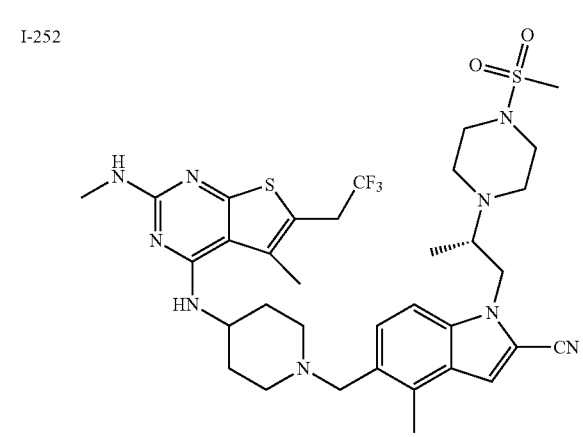 MW (calc'd) 731.30<br>m/z (found) 732.3 [M + H]+ |
| I-253 | 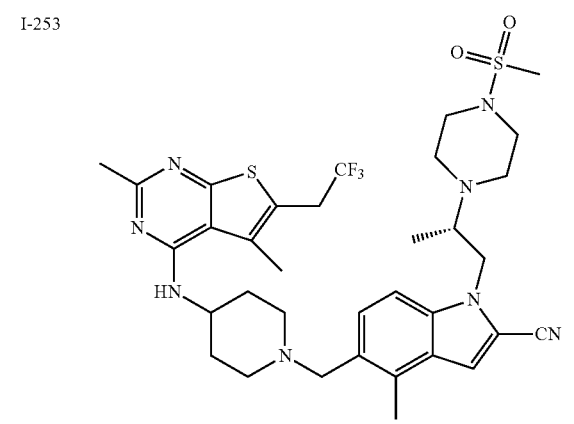 MW (calc'd) 716.29<br>m/z (found) 717.3 [M + H]+ |

TABLE 2
| No. | Structure |
|---|---|
| II-1 | |
| II-2 | |
| II-3 | |
| II-4 | |
| II-5 | 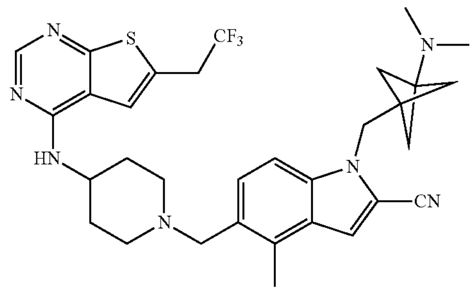 [SMILES: Cc1c(CN2CCC(Nc3ncnc4sc(CC(F)(F)F)cc34)CC2)ccc2c1cc(C#N)n2CC12CC(N(C)C)(C1)C2] |
| II-6 | 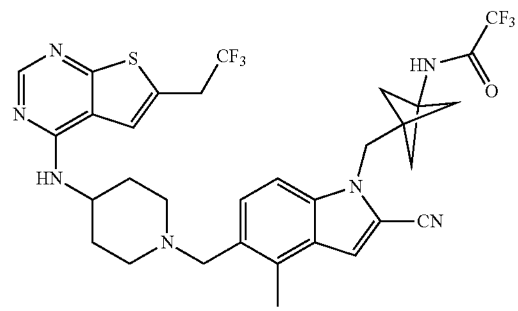 [SMILES: Cc1c(CN2CCC(Nc3ncnc4sc(CC(F)(F)F)cc34)CC2)ccc2c1cc(C#N)n2CC12CC(NC(=O)C(F)(F)F)(C1)C2] |
| II-7 | 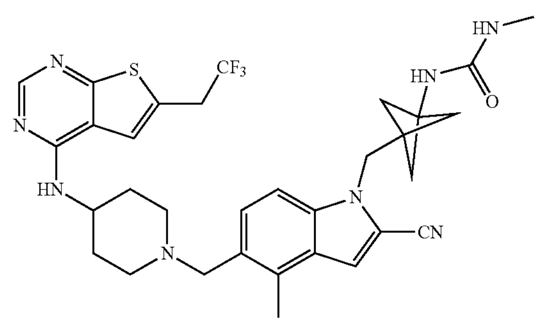 [SMILES: CNC(=O)NC12CC(Cn3c(C#N)cc4c(C)c(CN5CCC(Nc6ncnc7sc(CC(F)(F)F)cc67)CC5)ccc43)(C1)C2] |
| II-8 | 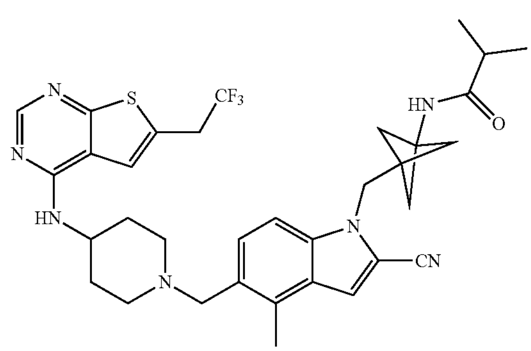 [SMILES: Cc1c(CN2CCC(Nc3ncnc4sc(CC(F)(F)F)cc34)CC2)ccc2c1cc(C#N)n2CC12CC(NC(=O)C(C)C)(C1)C2] |
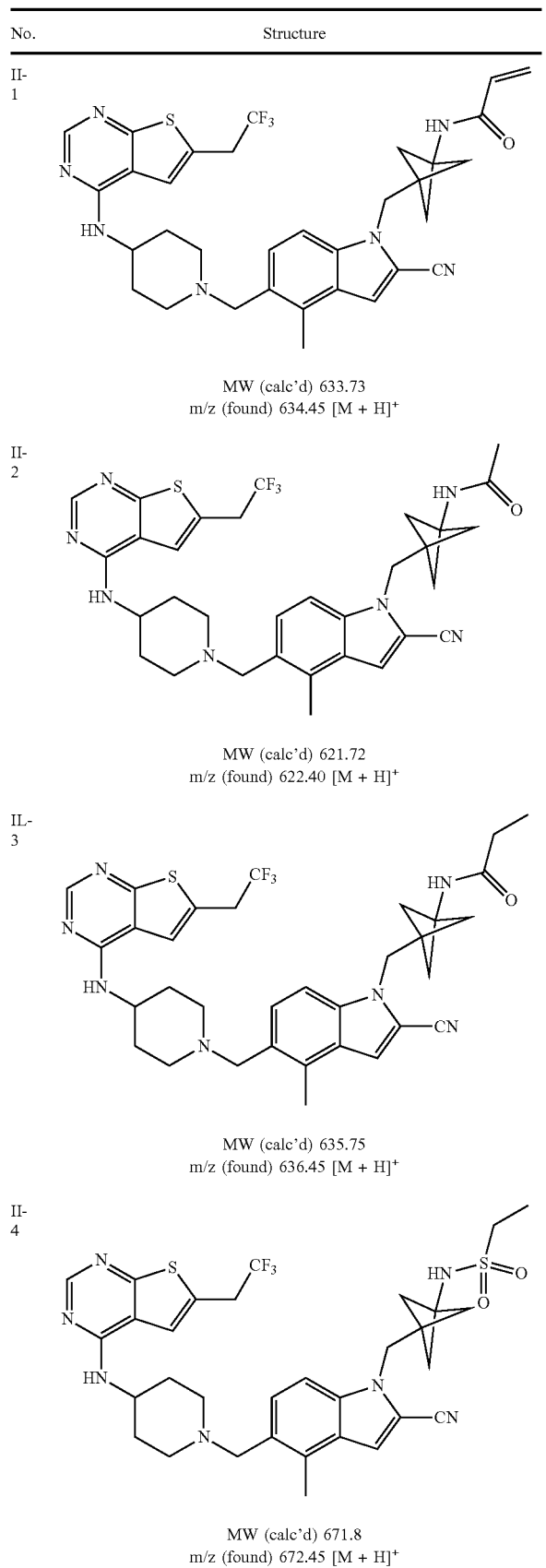
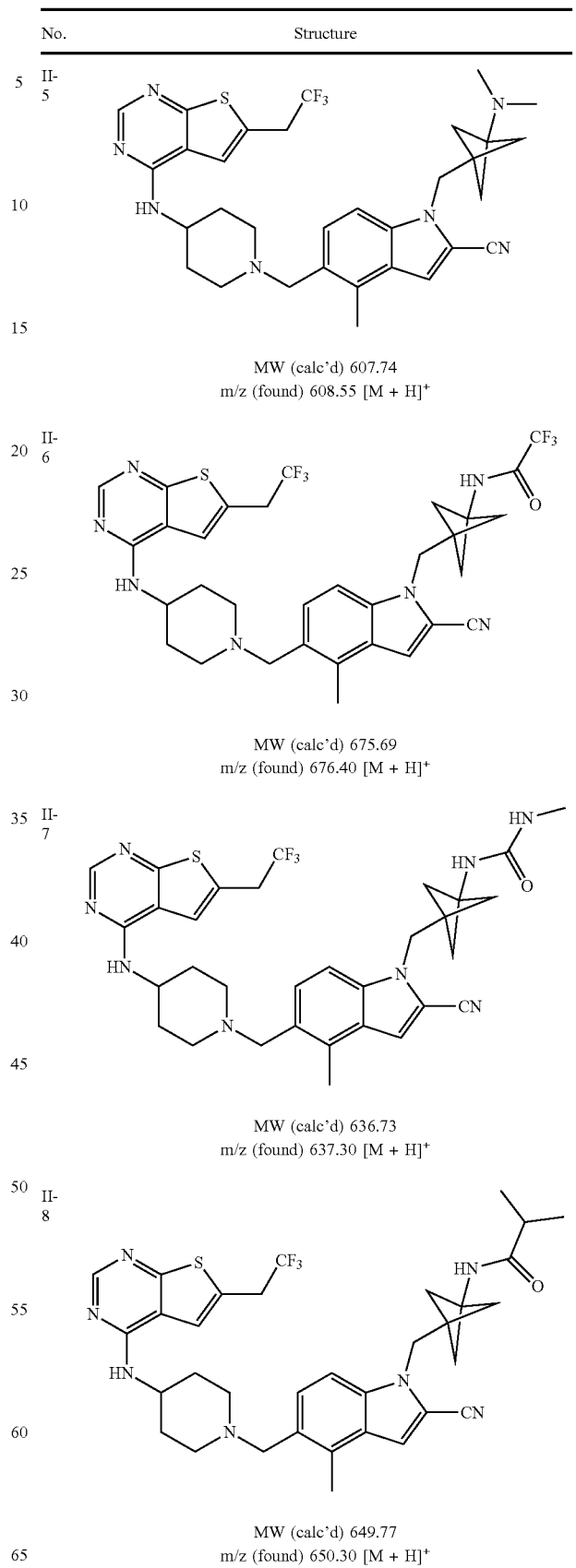
II-1: MW (calc'd) 633.73; m/z (found) 634.45 [M + H]⁺
II-2: MW (calc'd) 621.72; m/z (found) 622.40 [M + H]⁺
II-3: MW (calc'd) 635.75; m/z (found) 636.45 [M + H]⁺
II-4: MW (calc'd) 671.8; m/z (found) 672.45 [M + H]⁺
II-5: MW (calc'd) 607.74; m/z (found) 608.55 [M + H]⁺
II-6: MW (calc'd) 675.69; m/z (found) 676.40 [M + H]⁺
II-7: MW (calc'd) 636.73; m/z (found) 637.30 [M + H]⁺
II-8: MW (calc'd) 649.77; m/z (found) 650.30 [M + H]⁺

TABLE 2-continued

| No. | Structure |
|---|---|
| II-9 | MW (calc'd) 647.76<br>m/z (found) 648.30 [M + H]+ |
| II-10 | MW (calc'd) 593.71<br>m/z (found) 594.30 [M + H]+ |
| II-11 | MW (calc'd) 593.71<br>m/z (found) 594.35 [M + H]+ |
| II-12 | MW (calc'd) 649.77<br>m/z (found) 650.35 [M + H]+ |
| II-13 | MW (calc'd) 579.68<br>m/z (found) 580.25 [M + H]+ |
| II-14 | MW (calc'd) 647.76<br>m/z (found) 648.35 [M + H]+ |
| II-15 | MW (calc'd) 607.69<br>m/z (found) 608.30 [M + H]+ |
| II-16 | MW (calc'd) 637.72<br>m/z (found) 638.30 [M + H]+ |

TABLE 2-continued
| No. | Structure |
|---|---|
| II-17 | 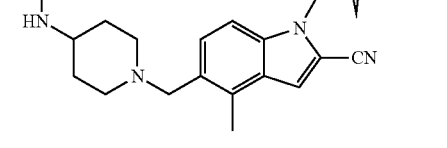<br>MW (calc'd) 636.73<br>m/z (found) 637.30 [M + H]+ |
| II-18 | MW (calc'd) 621.72<br>m/z (found) 622.35 [M + H]+ |
| II-20 | MW (calc'd) 608.68<br>m/z (found) 609.20 [M + H]+ |
| II-29 | MW (calc'd) 621.72<br>m/z (found) 622.40 [M + H]+ |
| II-30 | 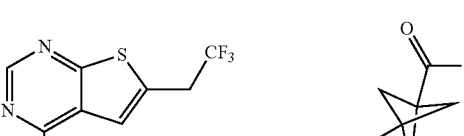<br>MW (calc'd) 621.72<br>m/z (found) 622.40 [M + H]+ |
| II-31 | MW (calc'd) 609.71<br>m/z (found) 610.40 [M + H]+ |
| II-32 | MW (calc'd) 609.71<br>m/z (found) 610.40 [M + H]+ |
| II-33 | MW (calc'd) 664.74<br>m/z (found) 665.55 [M + H]+ |

TABLE 2-continued
| No. | Structure |
|---|---|
| II-34 | 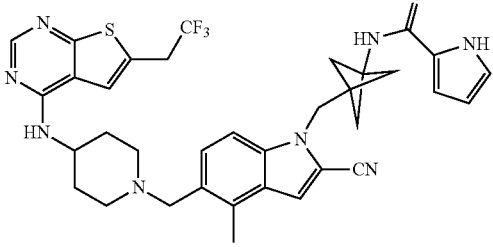<br>MW (calc'd) 672.77<br>m/z (found) 673.45 [M + H]⁺ |
| II-35 | 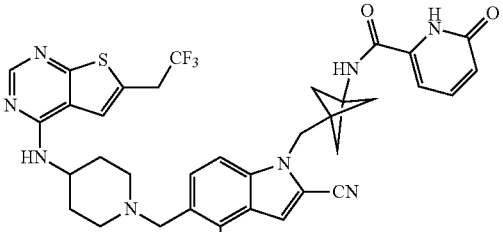<br>MW (calc'd) 700.78<br>m/z (found) 699.45 [M − H]⁻ |
| II-36 | 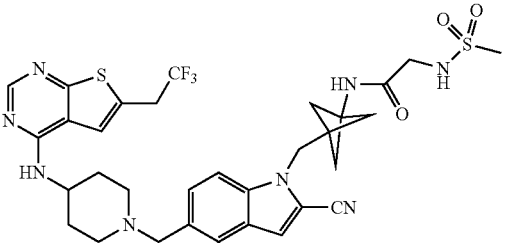<br>MW (calc'd) 714.82<br>m/z (found) 715.40 [M + H]⁺ |
| II-37 | 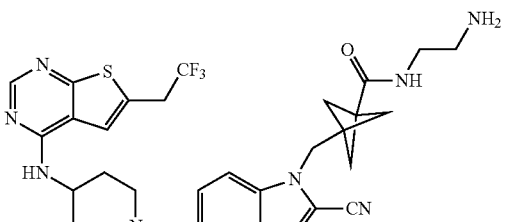<br>MW (calc'd) 650.76<br>m/z (found) 651.45 [M + H]⁺ |
TABLE 2-continued
| No. | Structure |
|---|---|
| II-38 | 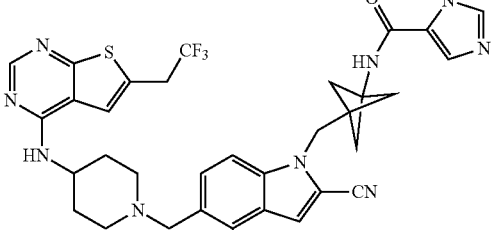<br>MW (calc'd) 673.75<br>m/z (found) 674.35 [M + H]⁺ |
| II-39 | 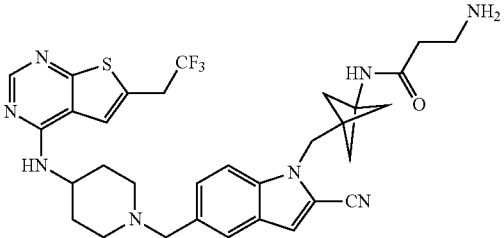<br>MW (calc'd) 650.76<br>m/z (found) 651.25 [M + H]⁺ |
TABLE 3
| No. | Structure |
|---|---|
| III-1 | 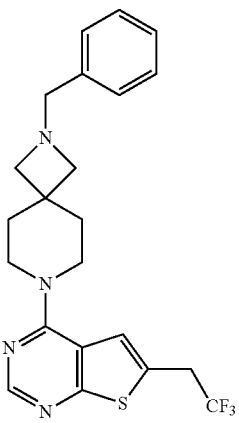 [SMILES: FC(F)(F)Cc1cc2c(N3CCC4(CC3)CN(Cc3ccccc3)C4)ncnc2s1] |

TABLE 3-continued

| No. | Structure |
|---|---|
| III-2 | 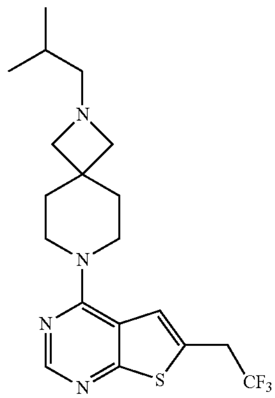 [SMILES: CC(C)CN1CC2(CCN(c3ncnc4sc(CC(F)(F)F)cc34)CC2)C1] |
| III-3 | 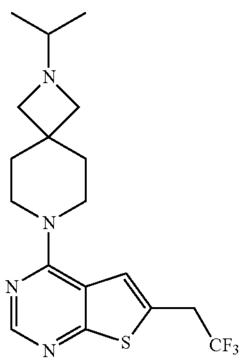 [SMILES: CC(C)N1CC2(CCN(c3ncnc4sc(CC(F)(F)F)cc34)CC2)C1] |
| III-4 | 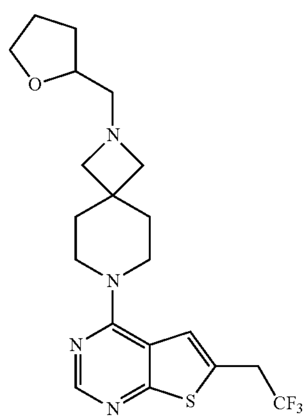 [SMILES: FC(F)(F)Cc1cc2c(N3CCC4(CC3)CN(CC3CCCO3)C4)ncnc2s1] |
| III-5 | 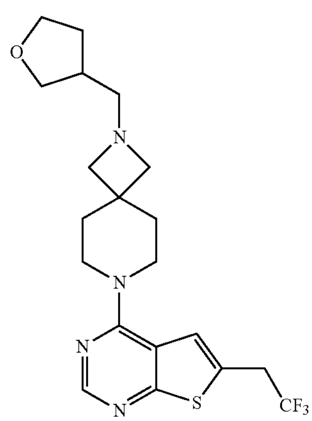 [SMILES: FC(F)(F)Cc1cc2c(N3CCC4(CC3)CN(CC3CCOC3)C4)ncnc2s1] |
| III-6 | 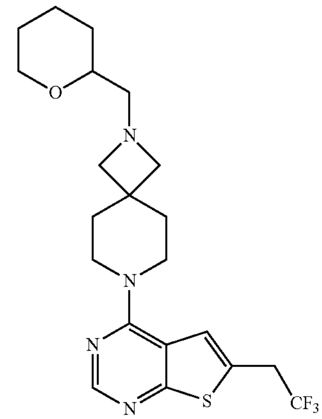 [SMILES: FC(F)(F)Cc1cc2c(N3CCC4(CC3)CN(CC3CCCCO3)C4)ncnc2s1] |
| III-7 | 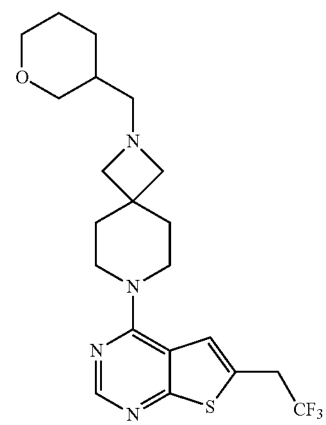 [SMILES: FC(F)(F)Cc1cc2c(N3CCC4(CC3)CN(CC3CCCOC3)C4)ncnc2s1] |
| III-8 | 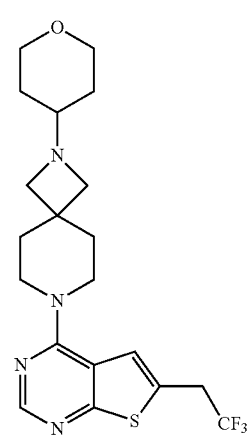 [SMILES: FC(F)(F)Cc1cc2c(N3CCC4(CC3)CN(C3CCOCC3)C4)ncnc2s1] |

TABLE 3-continued
| No. | Structure |
|---|---|
| III-9 | 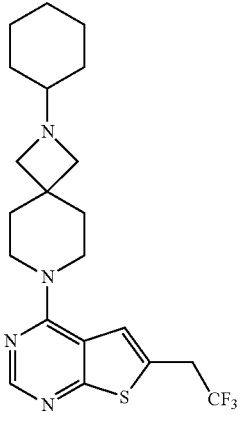 [SMILES: FC(F)(F)Cc1cc2c(N3CCC4(CC3)CN(C3CCCCC3)C4)ncnc2s1] |
| III-10 | 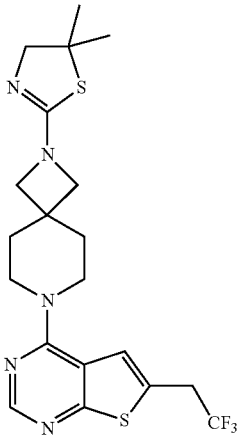 [SMILES: CC1(C)CN=C(N2CC3(CCN(c4ncnc5sc(CC(F)(F)F)cc45)CC3)C2)S1] |
| III-11 | 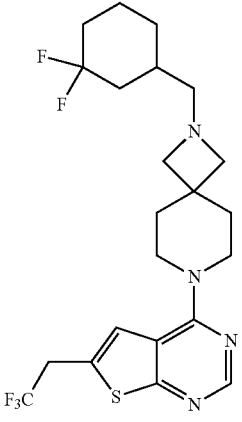 [SMILES: FC(F)(F)Cc1cc2c(N3CCC4(CC3)CN(CC3CCCC(F)(F)C3)C4)ncnc2s1] |
| III-12 | 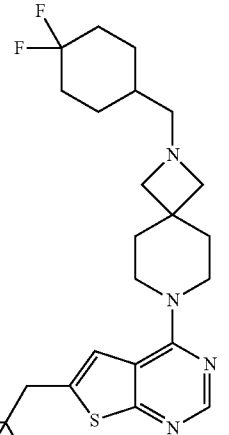 |
| III-13 | 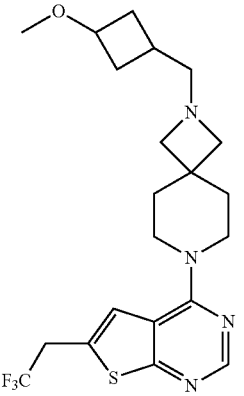 [SMILES: COC1CC(CN2CC3(CCN(c4ncnc5sc(CC(F)(F)F)cc45)CC3)C2)C1] |
| III-14 | 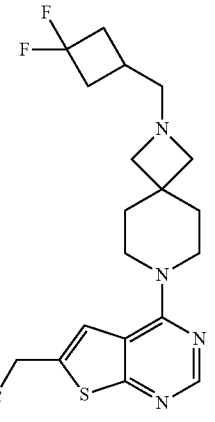 |

TABLE 3-continued
| No. | Structure |
|---|---|
| III-15 | 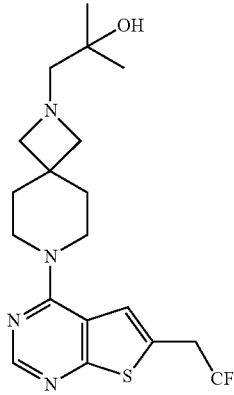 |
| III-16 | 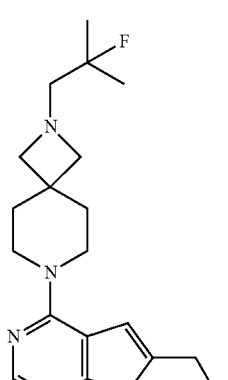 |
| III-17 | 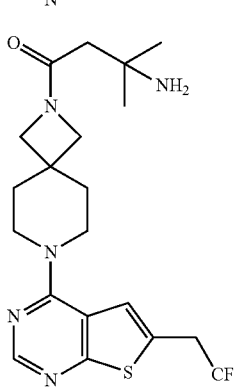 |
| III-18 | 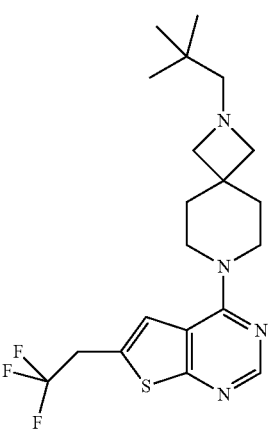 [SMILES: CC(C)(C)CN1CC2(CCN(c3ncnc4sc(CC(F)(F)F)cc34)CC2)C1] |
| III-19 | 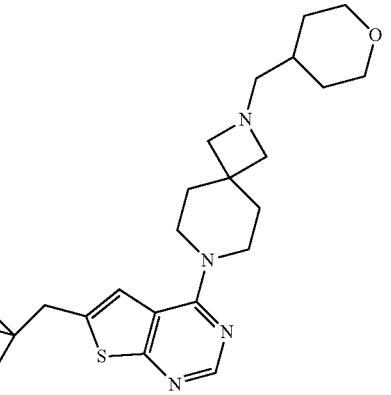 |
| III-20 | 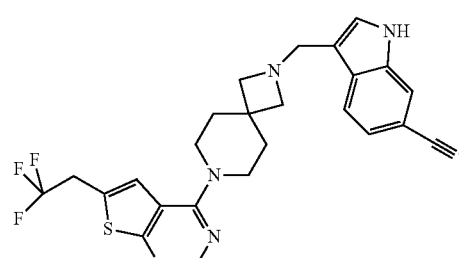 |
| III-21 | 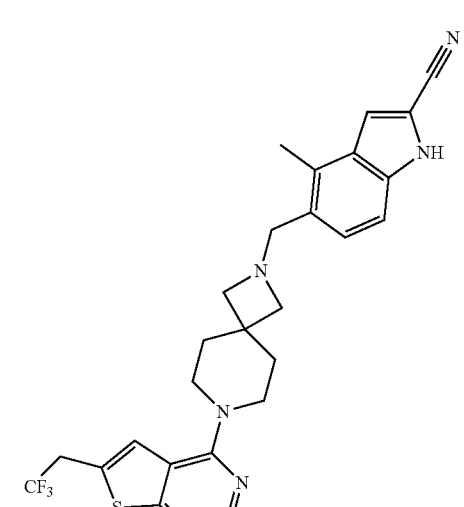 |
| III-22 | 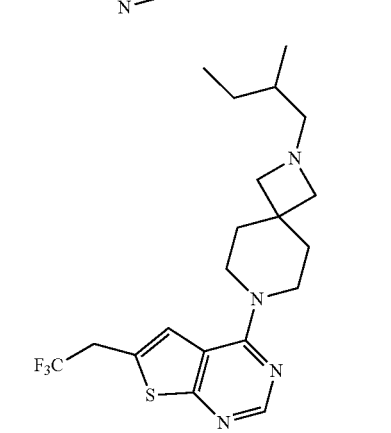 |

TABLE 3-continued
| No. | Structure |
|---|---|
| III-23 | 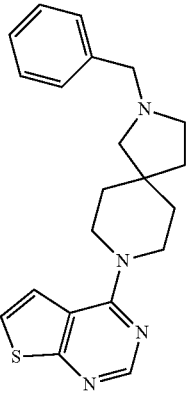 |
| III-24 | 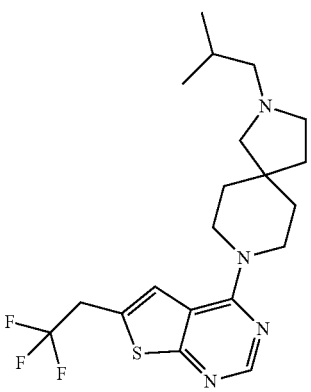 [SMILES: CC(C)CN1CCC2(CCN(c3ncnc4sc(CC(F)(F)F)cc34)CC2)C1] |
| III-25 | 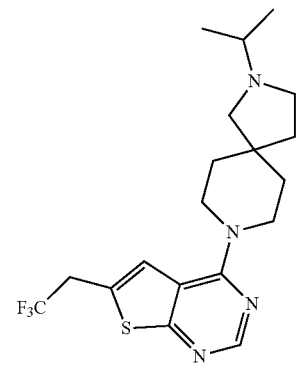 [SMILES: CC(C)N1CCC2(CCN(c3ncnc4sc(CC(F)(F)F)cc34)CC2)C1] |
| III-26 | 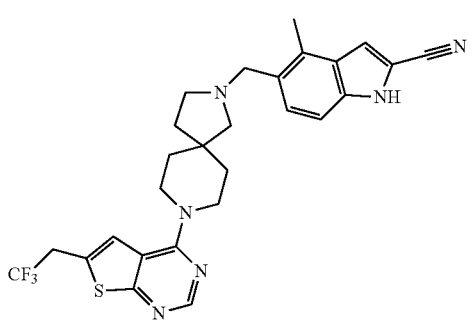 [SMILES: Cc1c(CN2CCC3(CCN(c4ncnc5sc(CC(F)(F)F)cc45)CC3)C2)ccc2[nH]c(C#N)cc12] |
| III-27 | 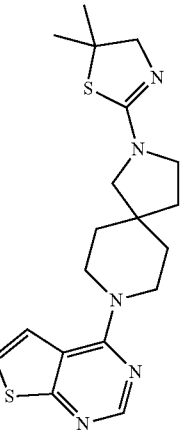 |
| III-28 | 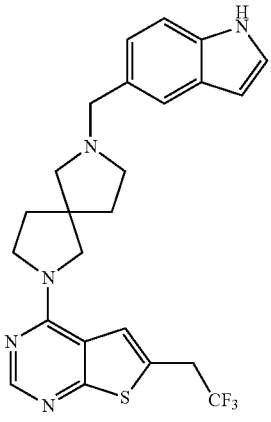 [SMILES: FC(F)(F)Cc1cc2c(N3CCC4(CCN(Cc5ccc6[nH]ccc6c5)C4)C3)ncnc2s1] |
| III-29 | 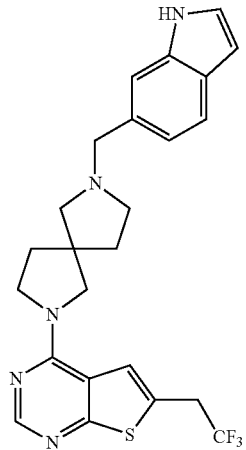 [SMILES: FC(F)(F)Cc1cc2c(N3CCC4(CCN(Cc5ccc6cc[nH]c6c5)C4)C3)ncnc2s1] |

TABLE 3-continued
| No. | Structure |
|---|---|
| III-30a | 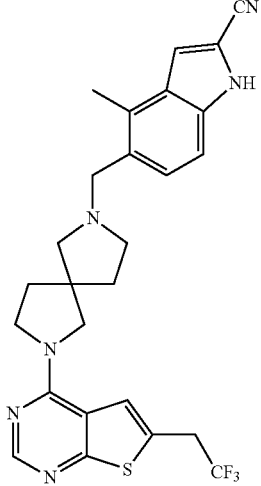 [SMILES: Cc1c(CN2CCC3(CCN(c4ncnc5sc(CC(F)(F)F)cc45)C3)C2)ccc2[nH]c(C#N)cc12] |
| III-30b | 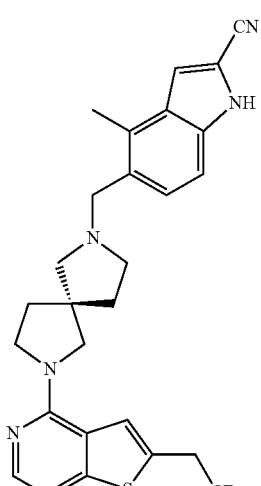 |
| III-30c | 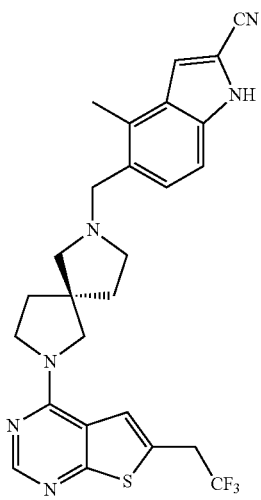 [SMILES: Cc1c(CN2CC[C@]3(CCN(c4ncnc5sc(CC(F)(F)F)cc45)C3)C2)ccc2[nH]c(C#N)cc12] |
| III-31 | 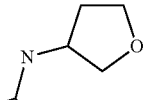 |
| III-32 | 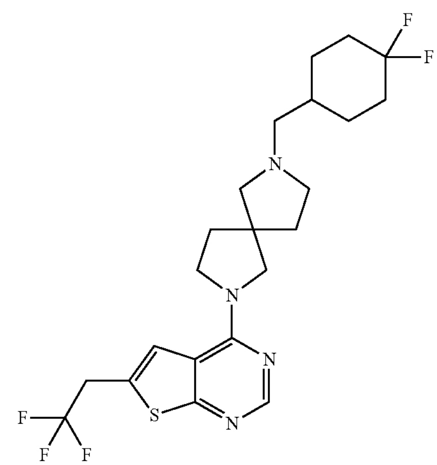 [SMILES: FC(F)(F)Cc1cc2c(N3CCC4(CCN(CC5CCC(F)(F)CC5)C4)C3)ncnc2s1] |
| III-33 | 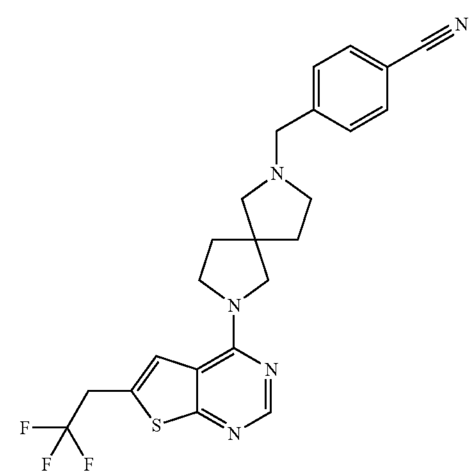 [SMILES: N#Cc1ccc(CN2CCC3(CCN(c4ncnc5sc(CC(F)(F)F)cc45)C3)C2)cc1] |
| III-34 | 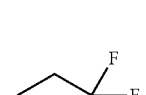 |

TABLE 3-continued
| No. | Structure |
|---|---|
| III-35 | 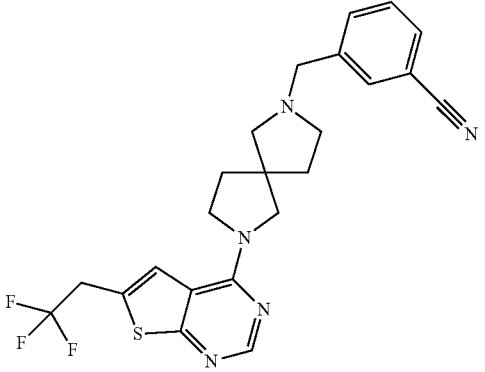 [SMILES: N#Cc1cccc(CN2CCC3(CCN(c4ncnc5sc(CC(F)(F)F)cc45)C3)C2)c1] |
| III-36 | 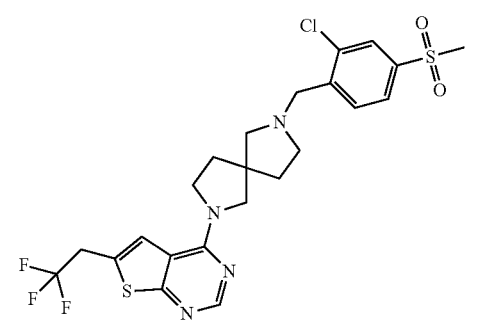 [SMILES: CS(=O)(=O)c1ccc(CN2CCC3(CCN(c4ncnc5sc(CC(F)(F)F)cc45)C3)C2)c(Cl)c1] |
| III-37 | 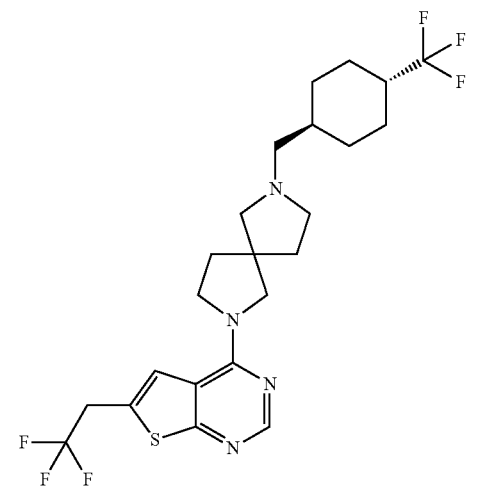 [SMILES: FC(F)(F)Cc1cc2c(N3CCC4(CCN(C[C@H]5CC[C@H](C(F)(F)F)CC5)C4)C3)ncnc2s1] |
| III-38 | 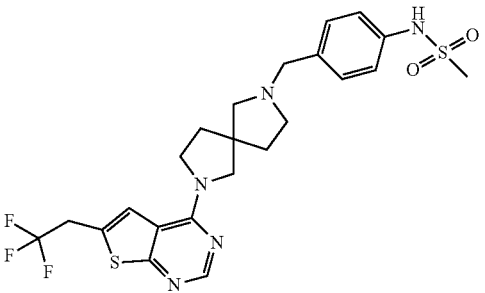 [SMILES: CS(=O)(=O)Nc1ccc(CN2CCC3(CCN(c4ncnc5sc(CC(F)(F)F)cc45)C3)C2)cc1] |
| III-39 | 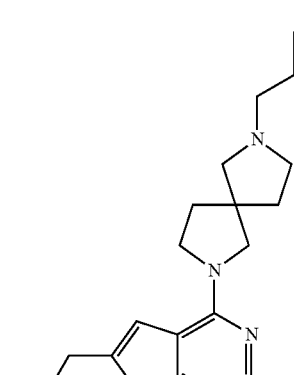 |
| III-40 | 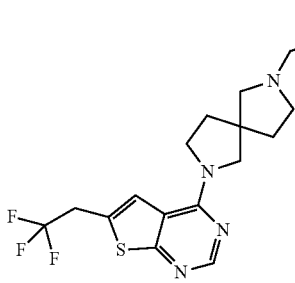 |
| III-41a | 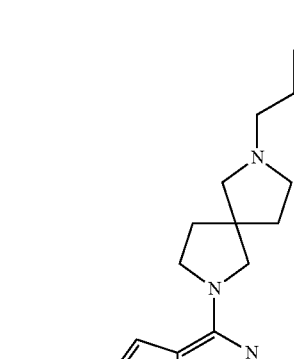 |

TABLE 3-continued

| No. | Structure |
|---|---|
| III-41b | 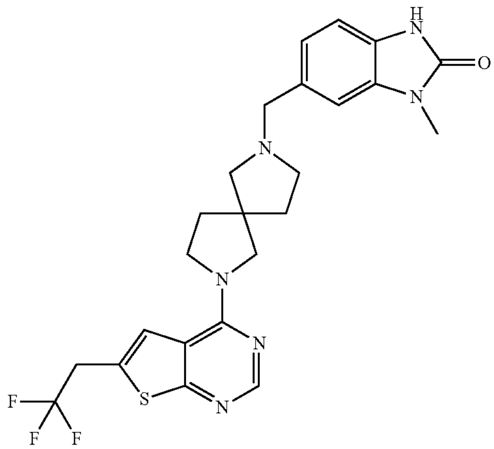 [SMILES: Cn1c(=O)[nH]c2ccc(CN3CCC4(CCN(c5ncnc6sc(CC(F)(F)F)cc56)C4)C3)cc21] |
| III-42 | 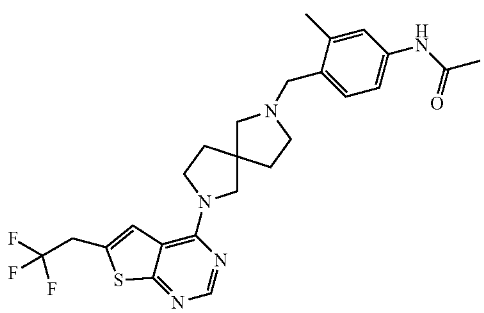 [SMILES: CC(=O)Nc1ccc(CN2CCC3(CCN(c4ncnc5sc(CC(F)(F)F)cc45)C3)C2)c(C)c1] |
| III-43 | 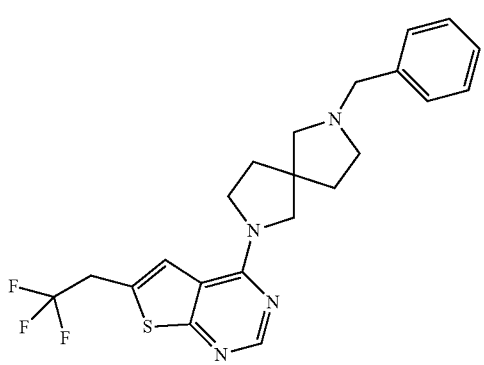 [SMILES: FC(F)(F)Cc1cc2c(N3CCC4(CCN(Cc5ccccc5)C4)C3)ncnc2s1] |
| III-44 | 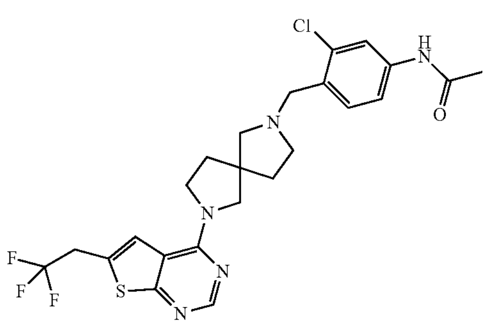 [SMILES: CC(=O)Nc1ccc(CN2CCC3(CCN(c4ncnc5sc(CC(F)(F)F)cc45)C3)C2)c(Cl)c1] |
| III-45 | |
| III-46 | |
| III-47 | |
| III-48 | |

TABLE 3-continued

| No. | Structure |
|---|---|
| III-49 | 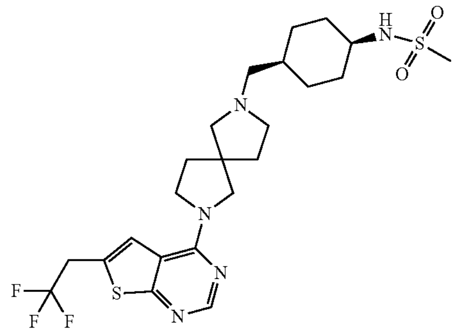 [SMILES: CS(=O)(=O)N[C@H]1CC[C@@H](CN2CCC3(CCN(c4ncnc5sc(CC(F)(F)F)cc45)C3)C2)CC1] |
| III-50 | 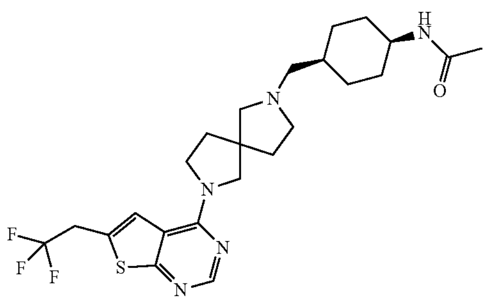 [SMILES: CC(=O)N[C@H]1CC[C@@H](CN2CCC3(CCN(c4ncnc5sc(CC(F)(F)F)cc45)C3)C2)CC1] |
| III-51 | 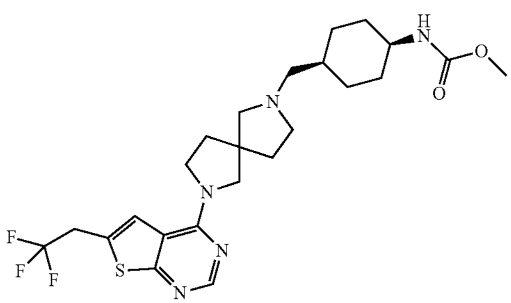 [SMILES: COC(=O)N[C@H]1CC[C@@H](CN2CCC3(CCN(c4ncnc5sc(CC(F)(F)F)cc45)C3)C2)CC1] |
| III-52 | 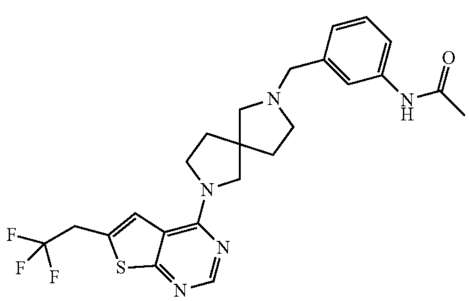 [SMILES: CC(=O)Nc1cccc(CN2CCC3(CCN(c4ncnc5sc(CC(F)(F)F)cc45)C3)C2)c1] |
| III-53 | 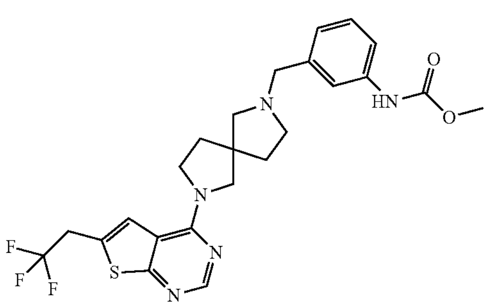 [SMILES: COC(=O)Nc1cccc(CN2CCC3(CCN(c4ncnc5sc(CC(F)(F)F)cc45)C3)C2)c1] |
| III-54 | |
| III-55 | |
| III-56 | |
| III-57 | |

TABLE 3-continued

| No. | Structure |
|---|---|
| III-58 | 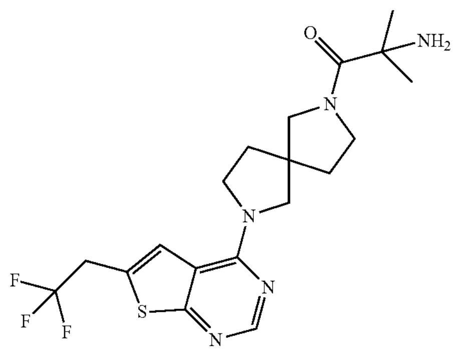 [SMILES: CC(C)(N)C(=O)N1CCC2(CCN(c3ncnc4sc(CC(F)(F)F)cc34)C2)C1] |
| III-59 | 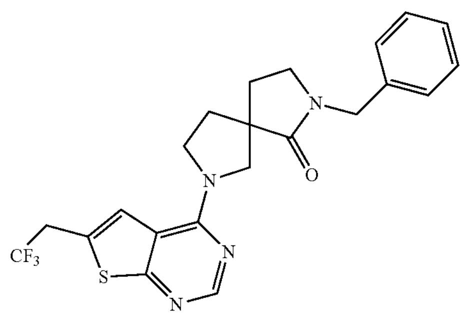 [SMILES: O=C1N(Cc2ccccc2)CCC12CCN(c1ncnc3sc(CC(F)(F)F)cc13)C2] |
| III-60a | 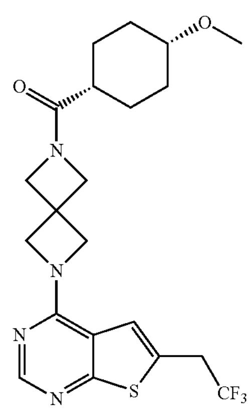 [SMILES: CO[C@H]1CC[C@@H](C(=O)N2CC3(CN(c4ncnc5sc(CC(F)(F)F)cc45)C3)C2)CC1] |
| III-60b | 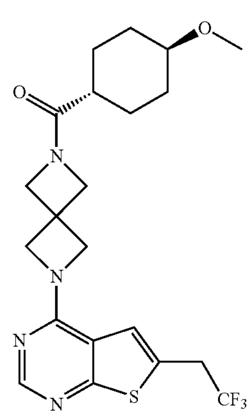 [SMILES: CO[C@H]1CC[C@H](C(=O)N2CC3(CN(c4ncnc5sc(CC(F)(F)F)cc45)C3)C2)CC1] |
| III-61 | |
| III-62 | |
| III-63 | |
| III-64 | |

TABLE 3-continued
| No. | Structure |
|---|---|
| III-65 | 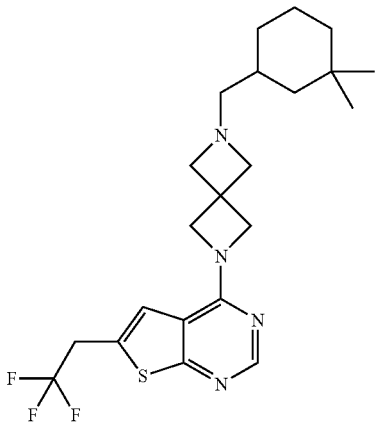 [SMILES: CC1(C)CCCC(CN2CC3(C2)CN(c2ncnc4sc(CC(F)(F)F)cc24)C3)C1] |
| III-66 | 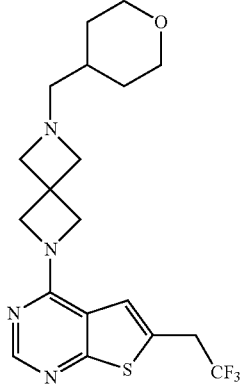 |
| III-67 | 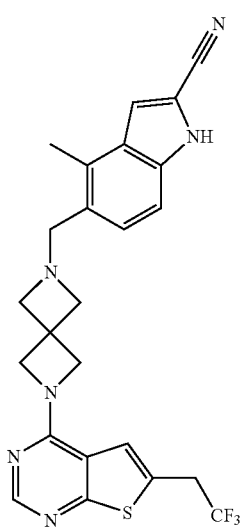 [SMILES: Cc1c(CN2CC3(C2)CN(c2ncnc4sc(CC(F)(F)F)cc24)C3)ccc2[nH]c(C#N)cc12] |
| III-68 | 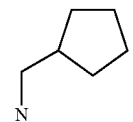 |
| III-69 | 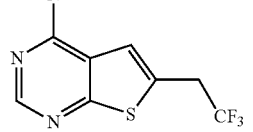 |
| III-70 | 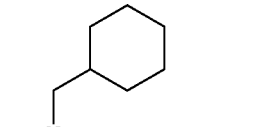 |
| III-71 | 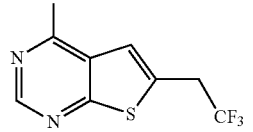 |

TABLE 3-continued

| No. | Structure |
|---|---|
| III-72 | |
| III-73 | |
| III-74 | |
| III-75 | 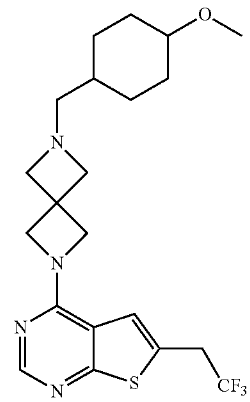 [SMILES: COC1CCC(CN2CC3(C2)CN(c2ncnc4sc(CC(F)(F)F)cc24)C3)CC1] |
| III-76 | 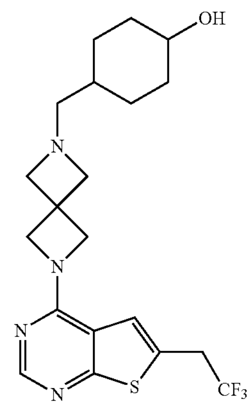 [SMILES: OC1CCC(CN2CC3(C2)CN(c2ncnc4sc(CC(F)(F)F)cc24)C3)CC1] |
| III-77 | 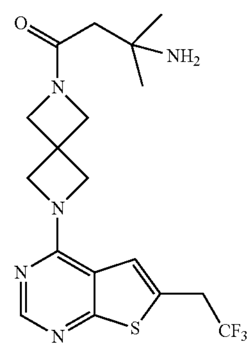 [SMILES: CC(C)(N)CC(=O)N1CC2(C1)CN(c1ncnc3sc(CC(F)(F)F)cc13)C2] |
| III-78 | 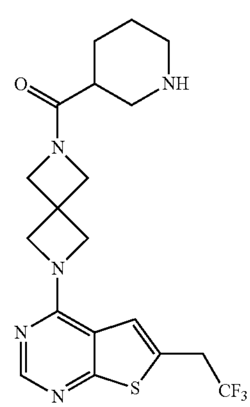 [SMILES: O=C(C1CCCNC1)N1CC2(C1)CN(c1ncnc3sc(CC(F)(F)F)cc13)C2] |

TABLE 3-continued
| No. | Structure |
|---|---|
| III-79 | 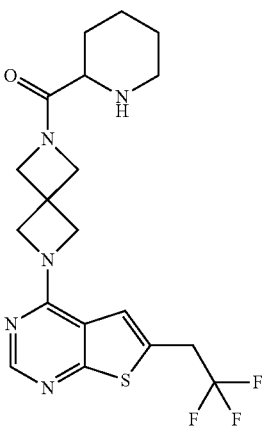 [SMILES: O=C(C1CCCCN1)N1CC2(C1)CN(c1ncnc3sc(CC(F)(F)F)cc13)C2] |
| III-80 | 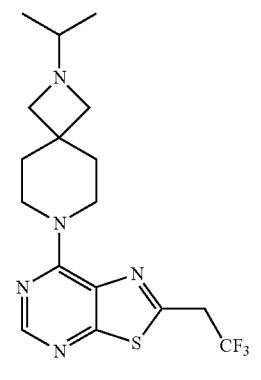 |
| III-81 | 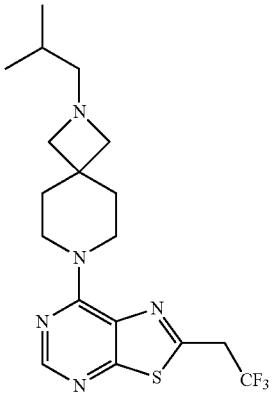 |
| III-82 | 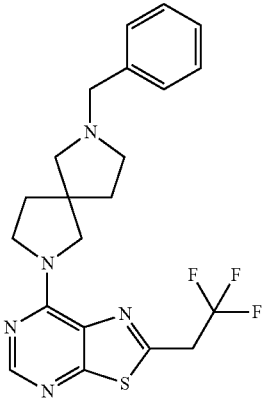 [SMILES: FC(F)(F)Cc1nc2c(N3CCC4(CCN(Cc5ccccc5)C4)C3)ncnc2s1] |
| III-83 | 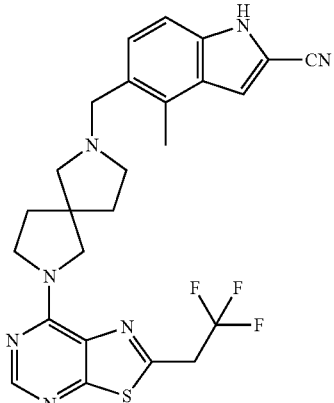 |
| III-84 | 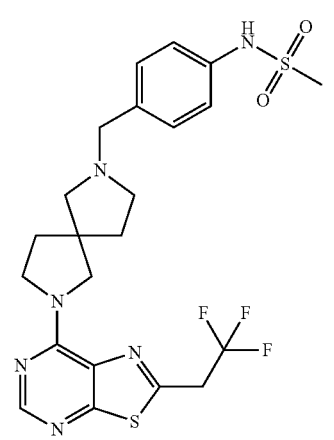 [SMILES: CS(=O)(=O)Nc1ccc(CN2CCC3(CCN(c4ncnc5sc(CC(F)(F)F)nc45)C3)C2)cc1] |
| III-85 | 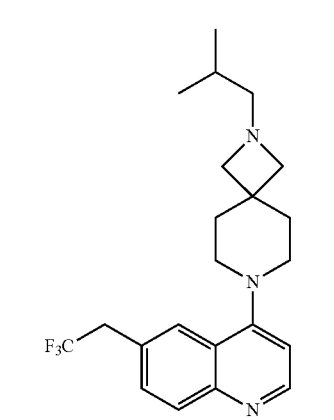 [SMILES: CC(C)CN1CC2(CCN(c3ccnc4ccc(CC(F)(F)F)cc34)CC2)C1] |
| III-86a | 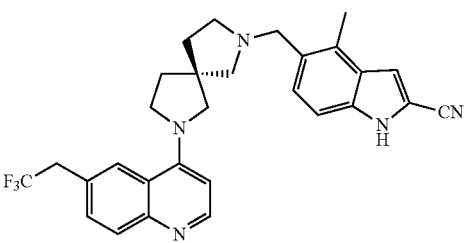 [SMILES: Cc1c(CN2CC[C@@]3(CCN(c4ccnc5ccc(CC(F)(F)F)cc45)C3)C2)ccc2[nH]c(C#N)cc12] |

TABLE 3-continued

| No. | Structure |
|---|---|
| III-86b | 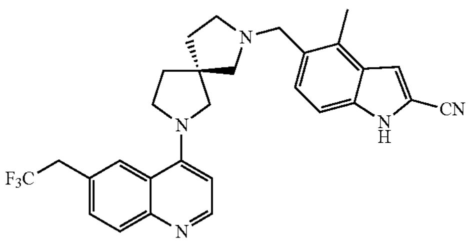 [SMILES: Cc1c(CN2CC[C@]3(CCN(c4ccnc5ccc(CC(F)(F)F)cc45)C3)C2)ccc2[nH]c(C#N)cc12] |
| III-87 | 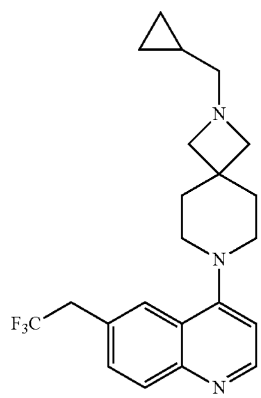 [SMILES: FC(F)(F)Cc1ccc2nccc(N3CCC4(CC3)CN(CC3CC3)C4)c2c1] |
| III-88 | 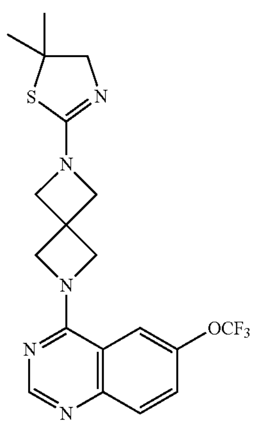 [SMILES: CC1(C)CN=C(N2CC3(C2)CN(c2ncnc4ccc(OC(F)(F)F)cc24)C3)S1] |
| III-89 | 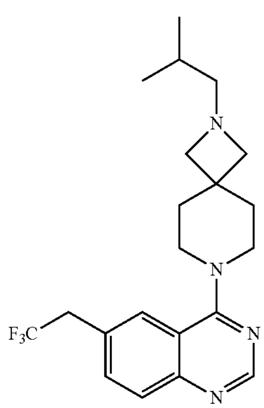 [SMILES: CC(C)CN1CC2(CCN(c3ncnc4ccc(CC(F)(F)F)cc34)CC2)C1] |
| III-90 | |
| III-91 | |
| III-92 | |
| III-93 | |

TABLE 3-continued

| No. | Structure |
|---|---|
| III-94 | 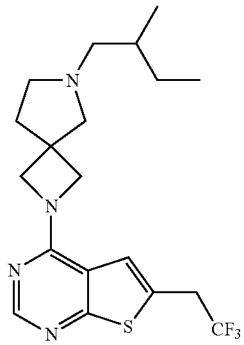 [SMILES: CCC(C)CN1CCC2(C1)CN(c1ncnc3sc(CC(F)(F)F)cc13)C2] |
| III-95 | 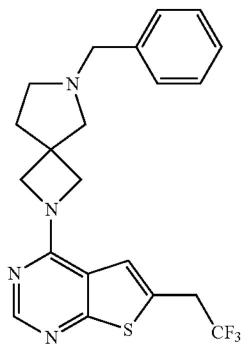 [SMILES: FC(F)(F)Cc1cc2c(N3CC4(CCN(Cc5ccccc5)C4)C3)ncnc2s1] |
| III-96 | 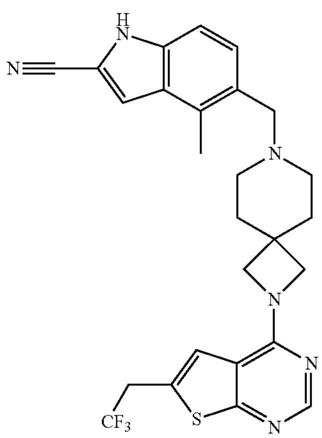 [SMILES: Cc1c(CN2CCC3(CC2)CN(c2ncnc4sc(CC(F)(F)F)cc24)C3)ccc2[nH]c(C#N)cc12] |
| III-97 | 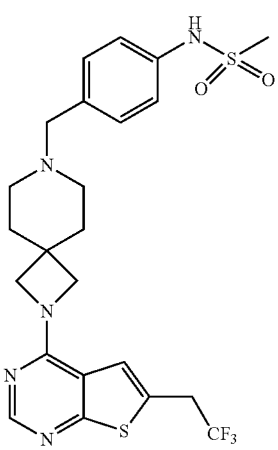 [SMILES: CS(=O)(=O)Nc1ccc(CN2CCC3(CC2)CN(c2ncnc4sc(CC(F)(F)F)cc24)C3)cc1] |
| III-98 | |
| III-99 | |
| III-100 | |

TABLE 3-continued
| No. | Structure |
|---|---|
| III-101 | 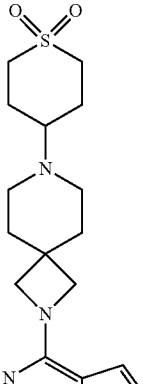 |
| III-102 | 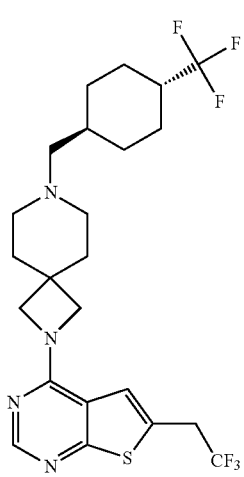 [SMILES: FC(F)(F)Cc1cc2c(N3CC4(CCN(C[C@H]5CC[C@H](C(F)(F)F)CC5)CC4)C3)ncnc2s1] |
| III-103 | 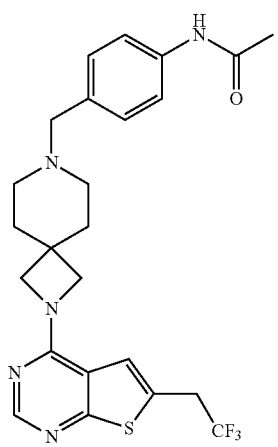 [SMILES: CC(=O)Nc1ccc(CN2CCC3(CC2)CN(c2ncnc4sc(CC(F)(F)F)cc24)C3)cc1] |
TABLE 3-continued
| No. | Structure |
|---|---|
| III-104 | 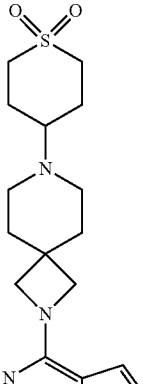 |
| III-105 | 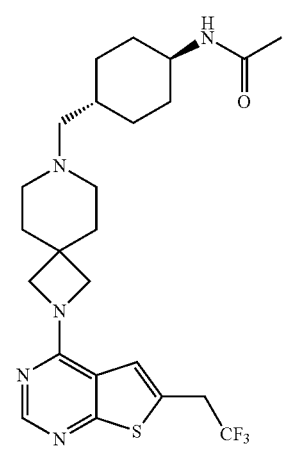 [SMILES: CC(=O)N[C@H]1CC[C@H](CN2CCC3(CC2)CN(c2ncnc4sc(CC(F)(F)F)cc24)C3)CC1] |
| III-106 | 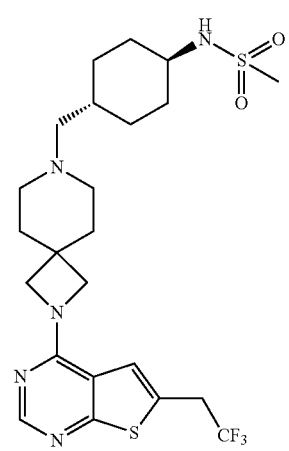 [SMILES: CS(=O)(=O)N[C@H]1CC[C@H](CN2CCC3(CC2)CN(c2ncnc4sc(CC(F)(F)F)cc24)C3)CC1] |

TABLE 3-continued

| No. | Structure |
|---|---|
| III-107 | 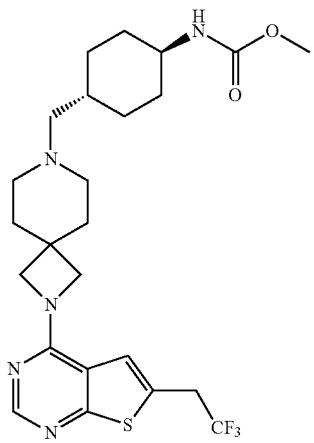 [SMILES: COC(=O)N[C@H]1CC[C@H](CN2CCC3(CC2)CN(c2ncnc4sc(CC(F)(F)F)cc24)C3)CC1] |
| III-108 | 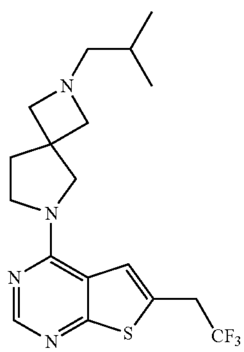 [SMILES: CC(C)CN1CC2(CCN(c3ncnc4sc(CC(F)(F)F)cc34)C2)C1] |
| III-109 | 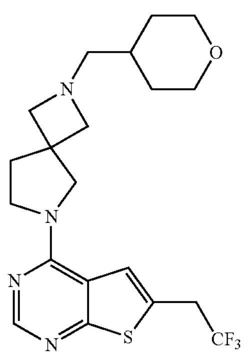 [SMILES: FC(F)(F)Cc1cc2c(N3CCC4(CN(CC5CCOCC5)C4)C3)ncnc2s1] |
| III-110 | 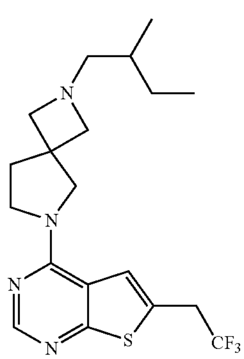 [SMILES: CCC(C)CN1CC2(CCN(c3ncnc4sc(CC(F)(F)F)cc34)C2)C1] |
| III-111 | |
| III-112 | |
| III-113 | |
| III-114 | |

TABLE 3-continued
| No. | Structure |
|---|---|
| III-115 | 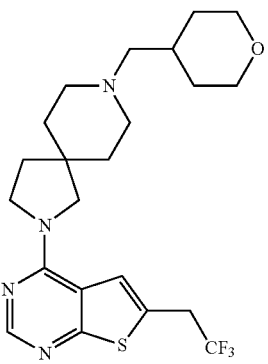 [SMILES: FC(F)(F)Cc1cc2c(N3CCC4(CCN(CC5CCOCC5)CC4)C3)ncnc2s1] |
| III-116 | 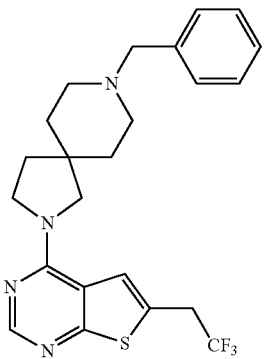 [SMILES: FC(F)(F)Cc1cc2c(N3CCC4(CCN(Cc5ccccc5)CC4)C3)ncnc2s1] |
| III-117 | 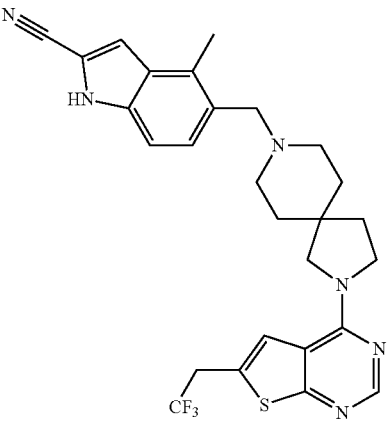 [SMILES: Cc1c(CN2CCC3(CC2)CCN(c2ncnc4sc(CC(F)(F)F)cc24)C3)ccc2[nH]c(C#N)cc12] |
| III-118 | 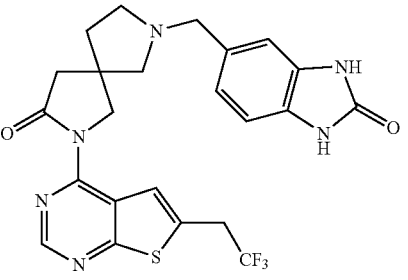 [SMILES: O=C1CC2(CCN(Cc3ccc4[nH]c(=O)[nH]c4c3)C2)CN1c1ncnc2sc(CC(F)(F)F)cc12] |
| III-119 | 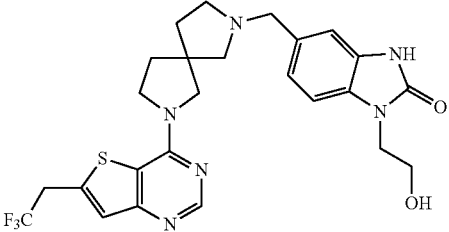 [SMILES: O=c1[nH]c2cc(CN3CCC4(CCN(c5ncnc6cc(CC(F)(F)F)sc56)C4)C3)ccc2n1CCO] |
| III-120 | 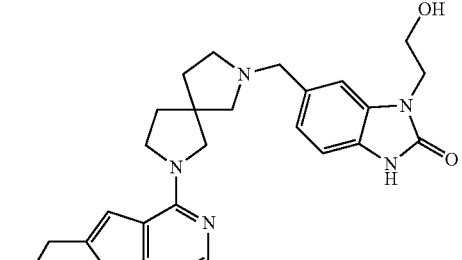 |
TABLE 4
| No. | Structure |
|---|---|
| IV-1 | 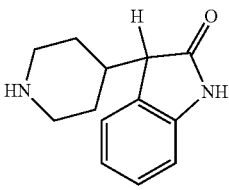 |

TABLE 4-continued

| No. | Structure |
|---|---|
| IV-2 | 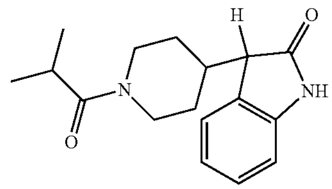 [SMILES: CC(C)C(=O)N1CCC(C2C(=O)Nc3ccccc32)CC1] |
| IV-3 | 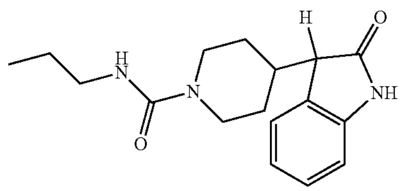 [SMILES: CCCNC(=O)N1CCC(C2C(=O)Nc3ccccc32)CC1] |
| IV-4 | 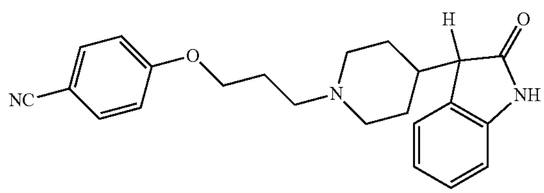 [SMILES: N#Cc1ccc(OCCCN2CCC(C3C(=O)Nc4ccccc43)CC2)cc1] |
| IV-5 | 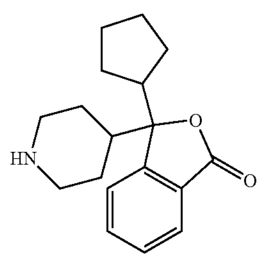 [SMILES: O=C1OC(C2CCCC2)(C2CCNCC2)c2ccccc21] |
| IV-6 | 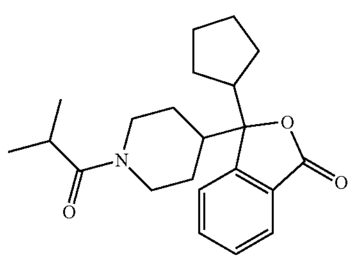 [SMILES: CC(C)C(=O)N1CCC(C2(C3CCCC3)OC(=O)c3ccccc32)CC1] |
| IV-7 | 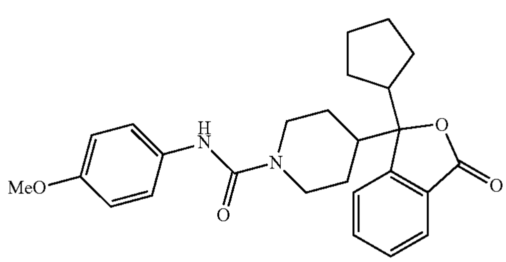 [SMILES: COc1ccc(NC(=O)N2CCC(C3(C4CCCC4)OC(=O)c4ccccc43)CC2)cc1] |

TABLE 4-continued
| No. | Structure |
|---|---|
| IV-8 | 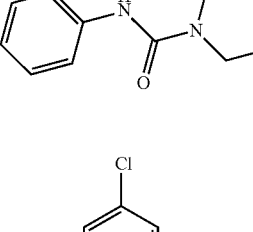 |
| IV-9 | 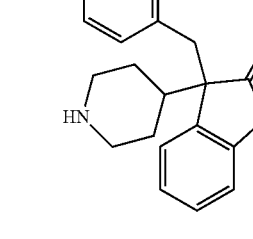 |
| IV-10 | 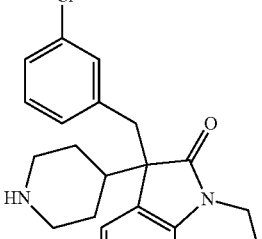 |
| IV-11 | 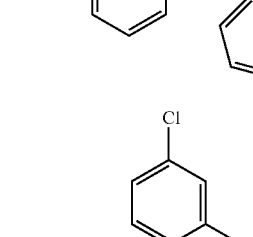 |
| IV-12 | 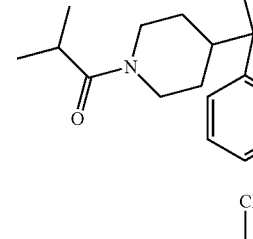 |

TABLE 4-continued

| No. | Structure |
|---|---|
| IV-13 | 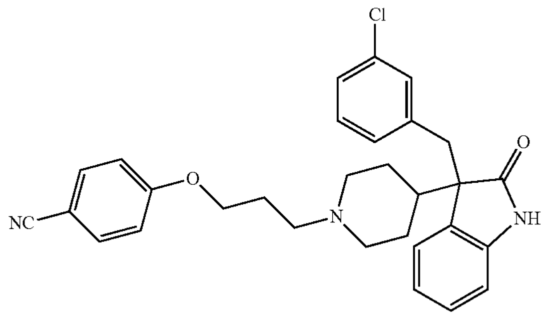 [SMILES: N#Cc1ccc(OCCCN2CCC(C3(Cc4cccc(Cl)c4)C(=O)Nc4ccccc43)CC2)cc1] |
| IV-14 | 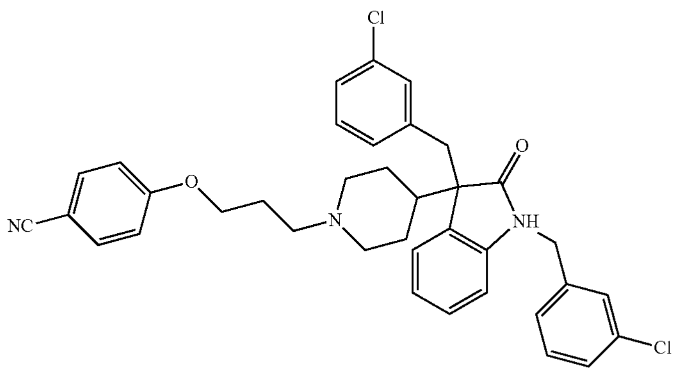 [SMILES: N#Cc1ccc(OCCCN2CCC(C3(Cc4cccc(Cl)c4)C(=O)N(Cc4cccc(Cl)c4)c4ccccc43)CC2)cc1] |
| IV-15 | 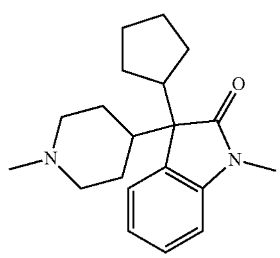 |
| IV-16 | 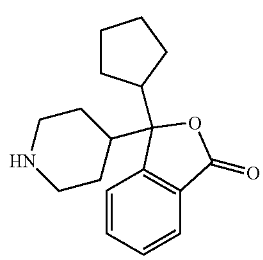 [SMILES: O=C1OC(C2CCCC2)(C2CCNCC2)c2ccccc21] |
| IV-17 | 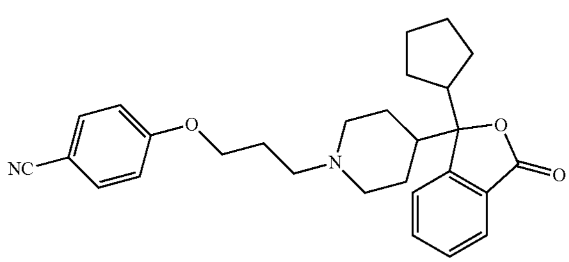 [SMILES: N#Cc1ccc(OCCCN2CCC(C3(C4CCCC4)OC(=O)c4ccccc43)CC2)cc1] |

US 11,944,627 B2
227                                                                                                         228
TABLE 4-continued
| No. | Structure |
|-----|-----------|
| IV-18 | 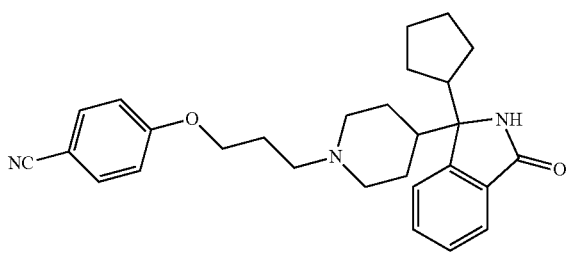 [SMILES: N#Cc1ccc(OCCCN2CCC(C3(C4CCCC4)NC(=O)c4ccccc43)CC2)cc1] |
| IV-19 | 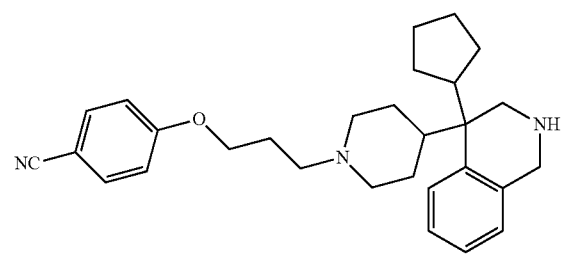 [SMILES: N#Cc1ccc(OCCCN2CCC(C3(C4CCCC4)CNCc4ccccc43)CC2)cc1] |
| IV-20 | 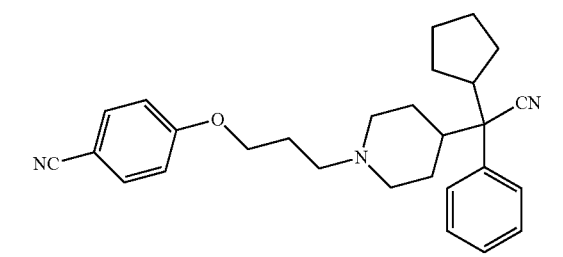 [SMILES: N#Cc1ccc(OCCCN2CCC(C(C#N)(c3ccccc3)C3CCCC3)CC2)cc1] |
| IV-21 | 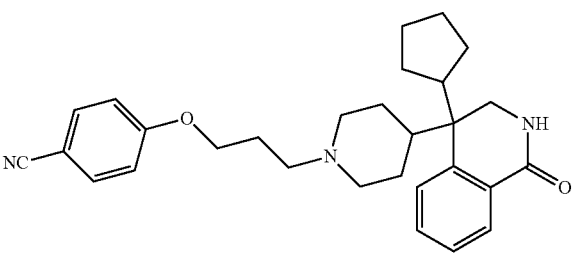 [SMILES: N#Cc1ccc(OCCCN2CCC(C3(C4CCCC4)CNC(=O)c4ccccc43)CC2)cc1] |
| IV-22 | 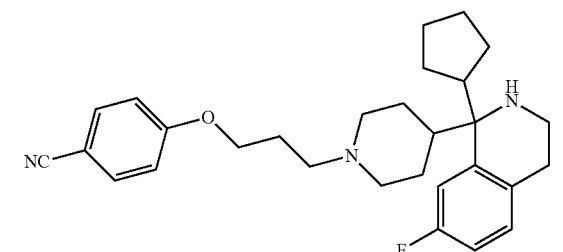 |
| IV-23 | 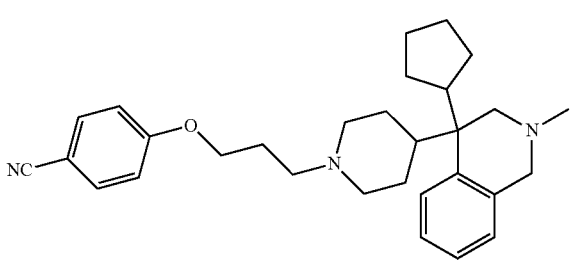 [SMILES: CN1Cc2ccccc2C(C2CCCC2)(C2CCN(CCCOc3ccc(C#N)cc3)CC2)C1] |

TABLE 4-continued

| No. | Structure |
|---|---|
| IV-24 | 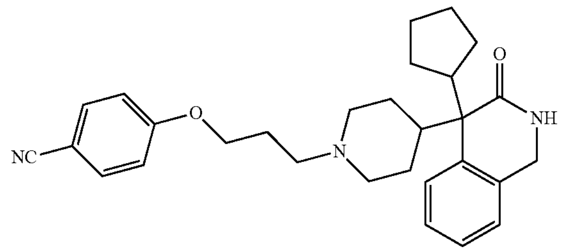 [SMILES: N#Cc1ccc(OCCCN2CCC(C3(C4CCCC4)C(=O)NCc4ccccc43)CC2)cc1] |
| IV-25 | 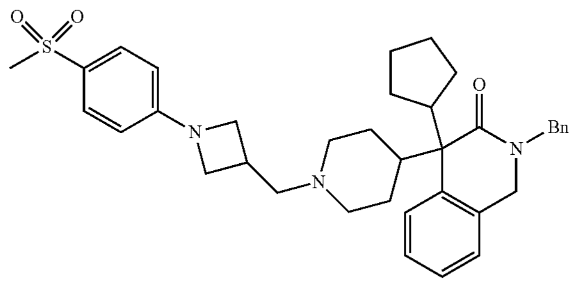 [SMILES: CS(=O)(=O)c1ccc(N2CC(CN3CCC(C4(C5CCCC5)C(=O)N(Cc5ccccc5)Cc5ccccc54)CC3)C2)cc1] |
| IV-26 | 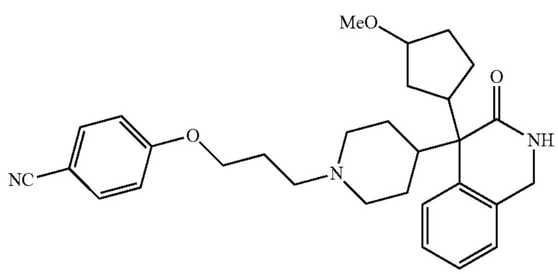 [SMILES: COC1CCC(C2(C3CCN(CCCOc4ccc(C#N)cc4)CC3)C(=O)NCc3ccccc32)C1] |
| IV-27 | 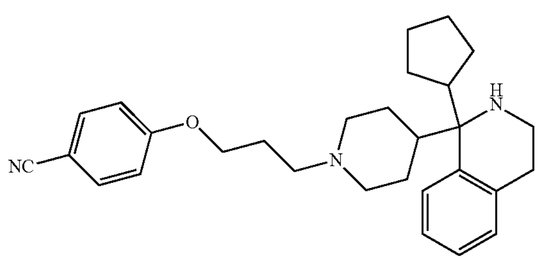 [SMILES: N#Cc1ccc(OCCCN2CCC(C3(C4CCCC4)NCCc4ccccc43)CC2)cc1] |
| IV-28 | 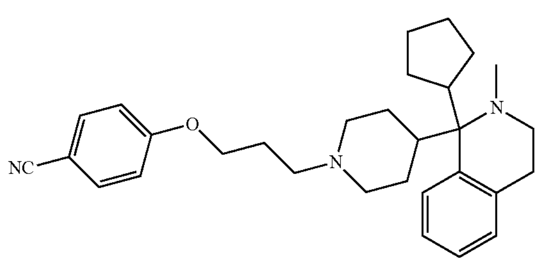 [SMILES: CN1CCc2ccccc2C1(C1CCCC1)C1CCN(CCCOc2ccc(C#N)cc2)CC1] |
| IV-29 | 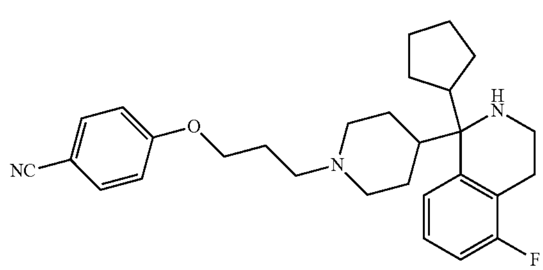 [SMILES: N#Cc1ccc(OCCCN2CCC(C3(C4CCCC4)NCCc4c(F)cccc43)CC2)cc1] |

TABLE 4-continued
| No. | Structure |
|---|---|
| IV-30 | 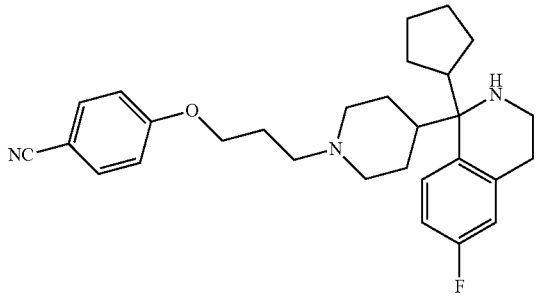 [SMILES: N#Cc1ccc(OCCCN2CCC(C3(C4CCCC4)NCCc4cc(F)ccc43)CC2)cc1] |
| IV-31 | 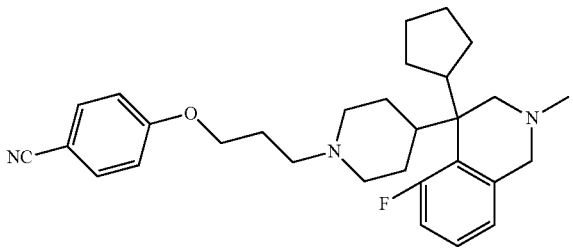 |
| IV-32 | 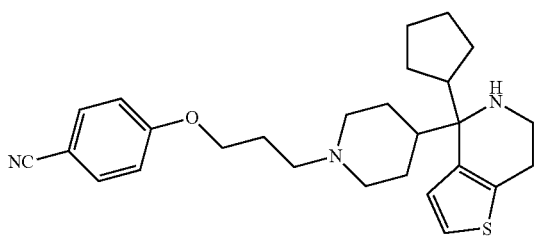 [SMILES: N#Cc1ccc(OCCCN2CCC(C3(C4CCCC4)NCCc4sccc43)CC2)cc1] |
| IV-33 | 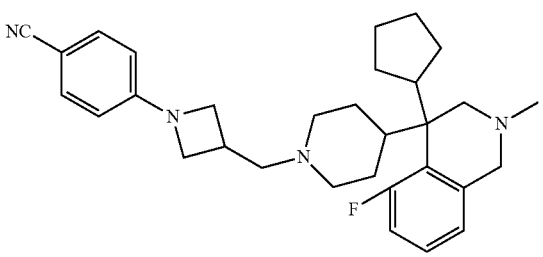 [SMILES: CN1Cc2cccc(F)c2C(C2CCCC2)(C2CCN(CC3CN(c4ccc(C#N)cc4)C3)CC2)C1] |
| IV-34 | 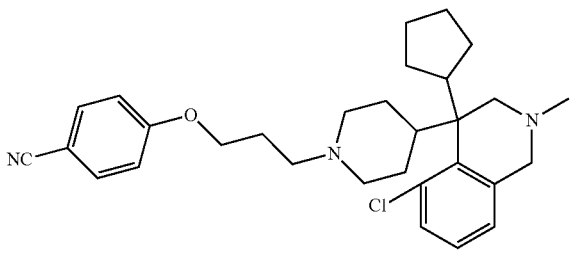 [SMILES: CN1Cc2cccc(Cl)c2C(C2CCCC2)(C2CCN(CCCOc3ccc(C#N)cc3)CC2)C1] |
| IV-35 | 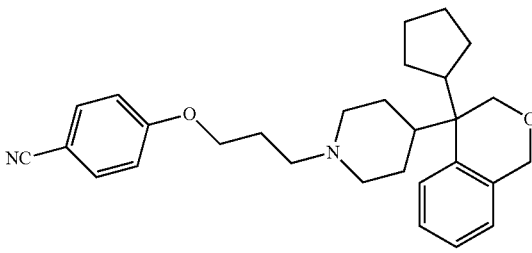 |

TABLE 4-continued

| No. | Structure |
|---|---|
| IV-36 | 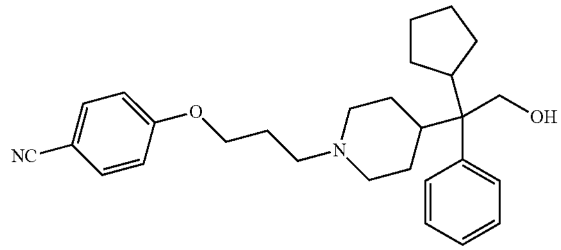 [SMILES: N#Cc1ccc(OCCCN2CCC(C(CO)(c3ccccc3)C3CCCC3)CC2)cc1] |
| IV-37 | 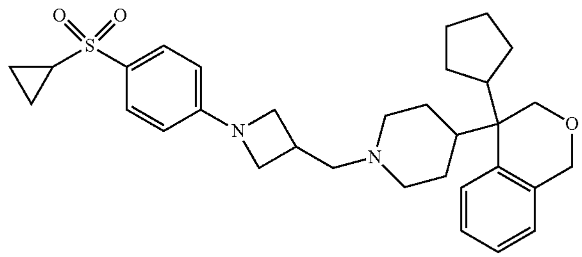 [SMILES: O=S(=O)(c1ccc(N2CC(CN3CCC(C4(C5CCCC5)COCc5ccccc54)CC3)C2)cc1)C1CC1] |
| IV-38 | 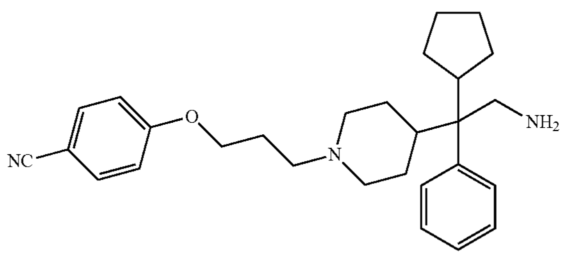 [SMILES: N#Cc1ccc(OCCCN2CCC(C(CN)(c3ccccc3)C3CCCC3)CC2)cc1] |
| IV-39 | 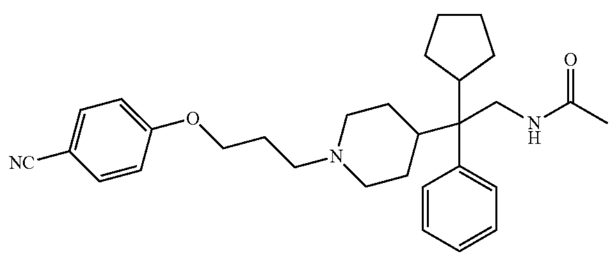 [SMILES: CC(=O)NCC(c1ccccc1)(C1CCCC1)C1CCN(CCCOc2ccc(C#N)cc2)CC1] |
| IV-40 | 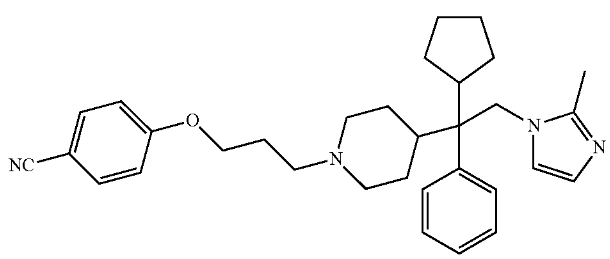 [SMILES: Cc1nccn1CC(c1ccccc1)(C1CCCC1)C1CCN(CCCOc2ccc(C#N)cc2)CC1] |
| IV-41 | 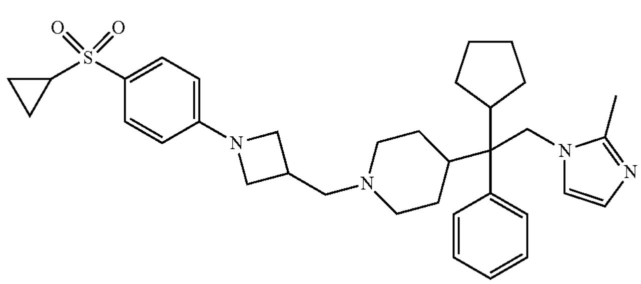 [SMILES: Cc1nccn1CC(c1ccccc1)(C1CCCC1)C1CCN(CC2CN(c3ccc(S(=O)(=O)C4CC4)cc3)C2)CC1] |

TABLE 4-continued

| No. | Structure |
|---|---|
| IV-42 | 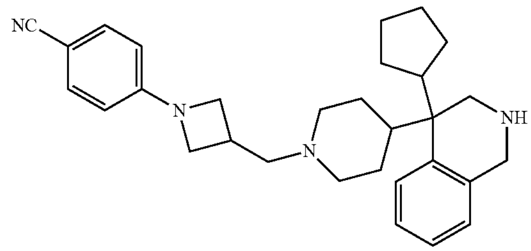 [SMILES: N#Cc1ccc(N2CC(CN3CCC(C4(C5CCCC5)CNCc5ccccc54)CC3)C2)cc1] |
| IV-43 | 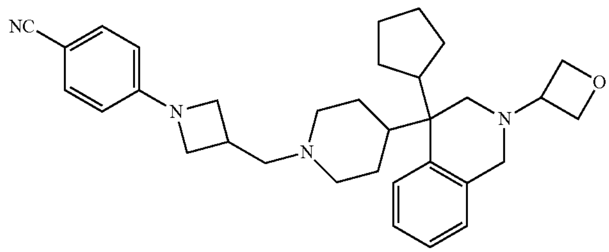 [SMILES: N#Cc1ccc(N2CC(CN3CCC(C4(C5CCCC5)CN(C5COC5)Cc5ccccc54)CC3)C2)cc1] |
| IV-44 | 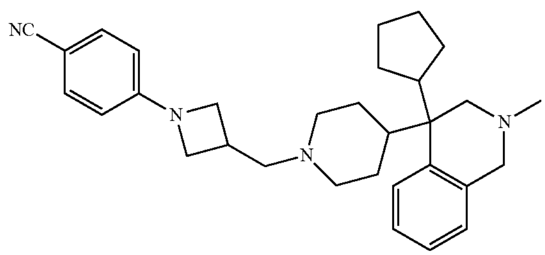 [SMILES: CN1Cc2ccccc2C(C2CCCC2)(C2CCN(CC3CN(c4ccc(C#N)cc4)C3)CC2)C1] |
| IV-45 | 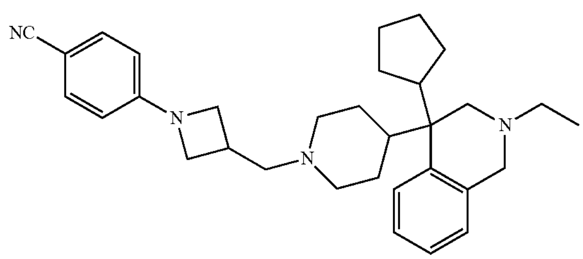 [SMILES: CCN1Cc2ccccc2C(C2CCCC2)(C2CCN(CC3CN(c4ccc(C#N)cc4)C3)CC2)C1] |
| IV-46 | 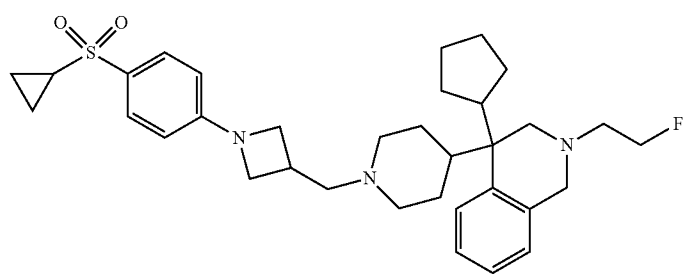 [SMILES: O=S(=O)(c1ccc(N2CC(CN3CCC(C4(C5CCCC5)CN(CCF)Cc5ccccc54)CC3)C2)cc1)C1CC1] |
| IV-47 | 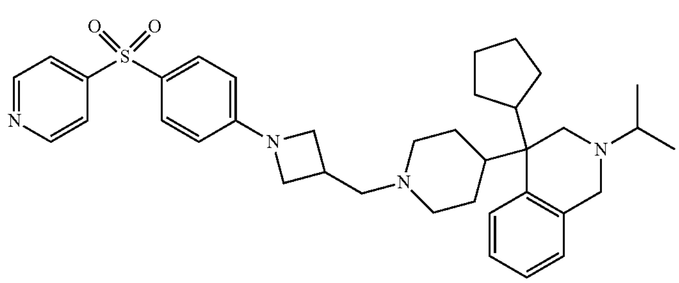 [SMILES: CC(C)N1Cc2ccccc2C(C2CCCC2)(C2CCN(CC3CN(c4ccc(S(=O)(=O)c5ccncc5)cc4)C3)CC2)C1] |

TABLE 4-continued

| No. | Structure |
|---|---|
| IV-48 | 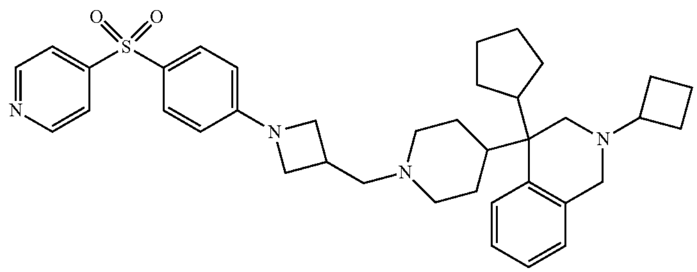 [SMILES: O=S(=O)(c1ccncc1)c1ccc(N2CC(CN3CCC(C4(C5CCCC5)CN(C5CCC5)Cc5ccccc54)CC3)C2)cc1] |
| IV-49 | 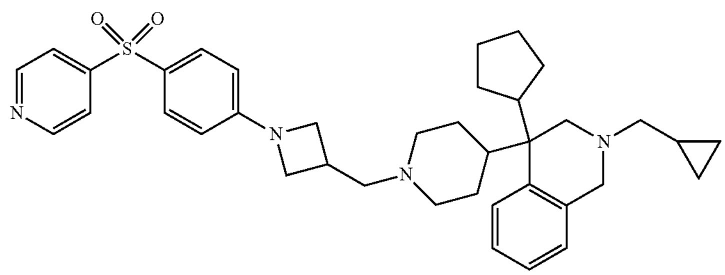 [SMILES: O=S(=O)(c1ccncc1)c1ccc(N2CC(CN3CCC(C4(C5CCCC5)CN(CC5CC5)Cc5ccccc54)CC3)C2)cc1] |
| IV-50 | 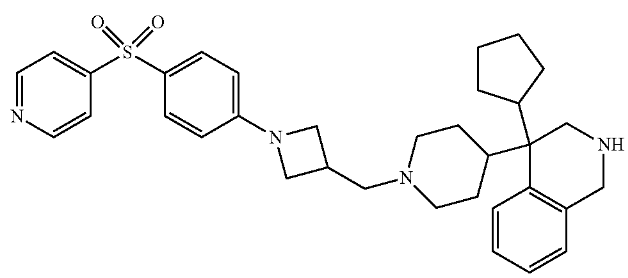 [SMILES: O=S(=O)(c1ccncc1)c1ccc(N2CC(CN3CCC(C4(C5CCCC5)CNCc5ccccc54)CC3)C2)cc1] |
| IV-51 | 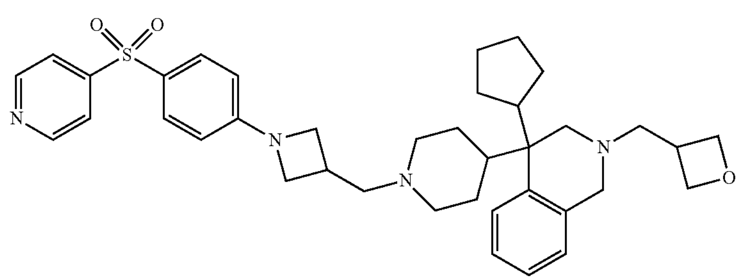 [SMILES: O=S(=O)(c1ccncc1)c1ccc(N2CC(CN3CCC(C4(C5CCCC5)CN(CC5COC5)Cc5ccccc54)CC3)C2)cc1] |
| IV-52 | 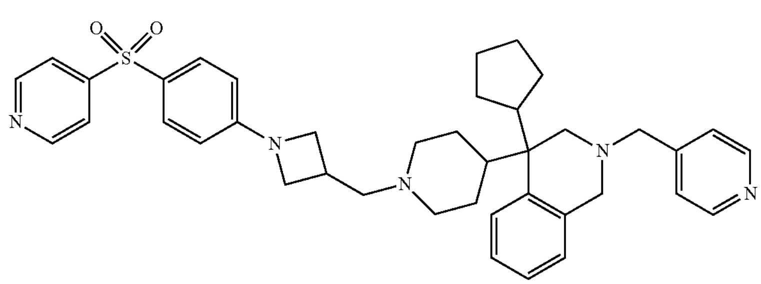 [SMILES: O=S(=O)(c1ccncc1)c1ccc(N2CC(CN3CCC(C4(C5CCCC5)CN(Cc5ccncc5)Cc5ccccc54)CC3)C2)cc1] |

TABLE 4-continued

| No. | Structure |
|---|---|
| IV-53 | 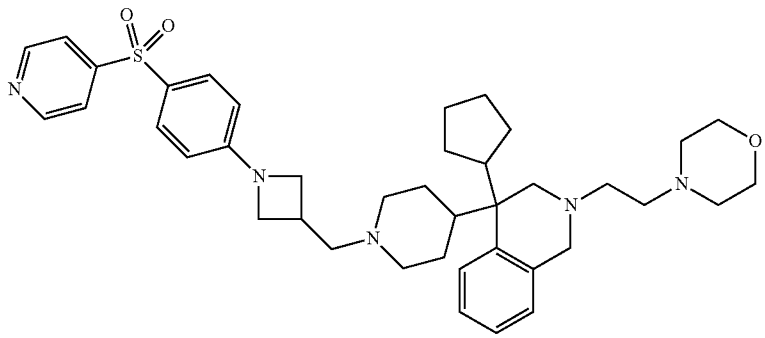 [SMILES: O=S(=O)(c1ccncc1)c1ccc(N2CC(CN3CCC(C4(C5CCCC5)CN(CCN5CCOCC5)Cc5ccccc54)CC3)C2)cc1] |
| IV-54 | 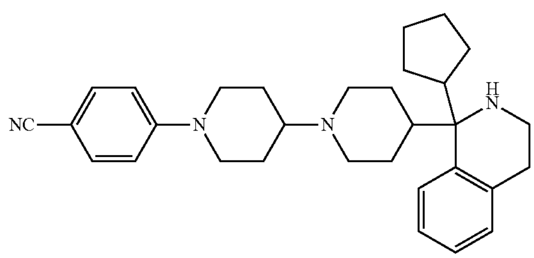 [SMILES: N#Cc1ccc(N2CCC(N3CCC(C4(C5CCCC5)NCCc5ccccc54)CC3)CC2)cc1] |
| IV-55 | 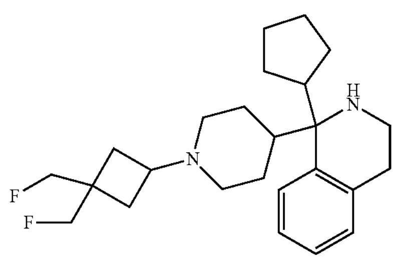 [SMILES: FCC1(CF)CC(N2CCC(C3(C4CCCC4)NCCc4ccccc43)CC2)C1] |
| IV-56 | 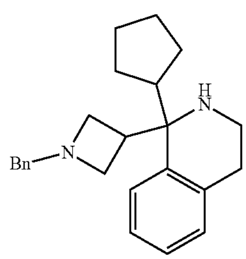 [SMILES: c1ccc(CN2CC(C3(C4CCCC4)NCCc4ccccc43)C2)cc1] |
| IV-57 | 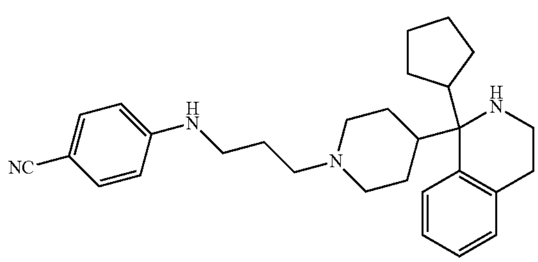 [SMILES: N#Cc1ccc(NCCCN2CCC(C3(C4CCCC4)NCCc4ccccc43)CC2)cc1] |

TABLE 4-continued
| No. | Structure |
|---|---|
| IV-58 | 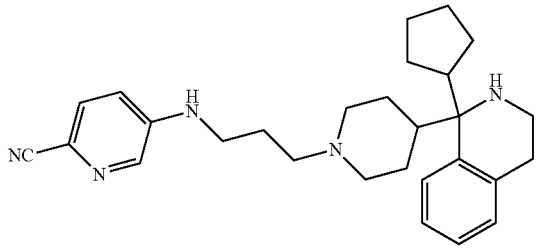 [SMILES: N#Cc1ccc(NCCCN2CCC(C3(C4CCCC4)NCCc4ccccc43)CC2)cn1] |
| IV-59 | 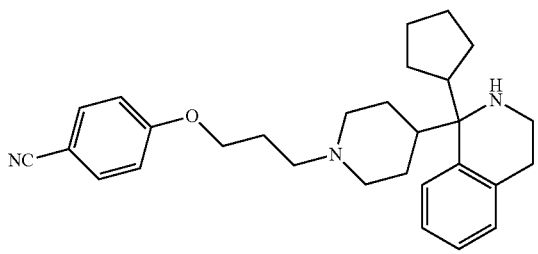 |
| IV-60 | 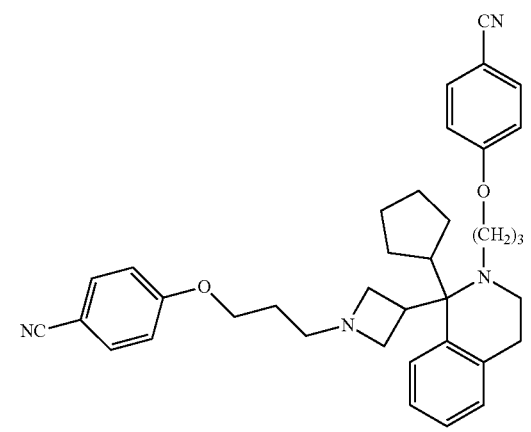 |
| IV-61 | 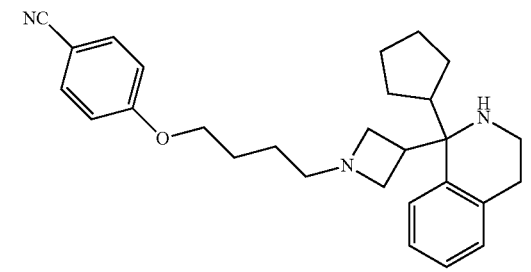 [SMILES: N#Cc1ccc(OCCCCN2CC(C3(C4CCCC4)NCCc4ccccc43)C2)cc1] |
| IV-62 | 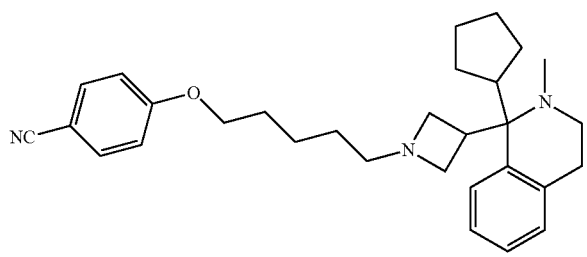 [SMILES: CN1CCc2ccccc2C1(C1CCCC1)C1CN(CCCCCOc2ccc(C#N)cc2)C1] |

TABLE 4-continued

| No. | Structure |
|---|---|
| IV-63 | 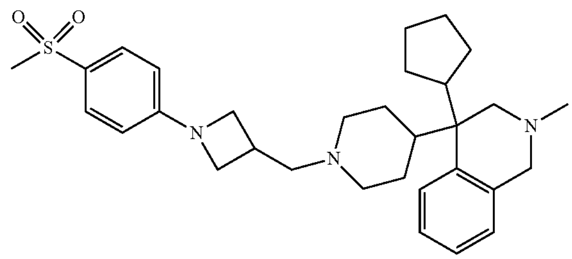 |
| IV-64 | 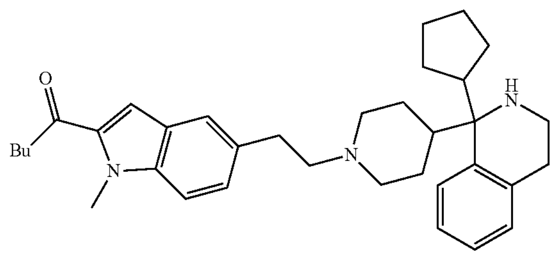 |
| IV-65 | 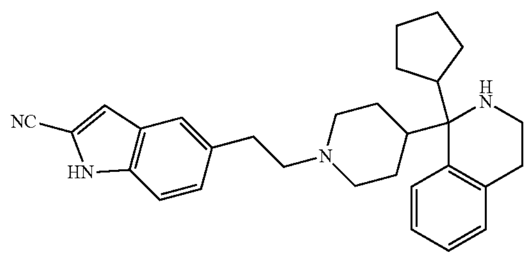 [SMILES: N#Cc1cc2cc(CCN3CCC(C4(C5CCCC5)NCCc5ccccc54)CC3)ccc2[nH]1] |
| IV-66 | 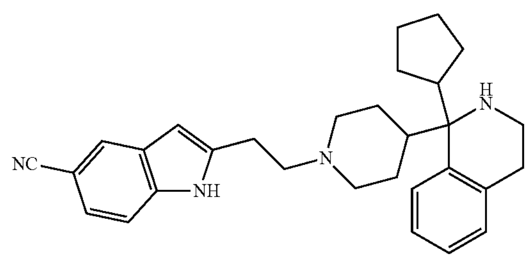 [SMILES: N#Cc1ccc2[nH]c(CCN3CCC(C4(C5CCCC5)NCCc5ccccc54)CC3)cc2c1] |
| IV-67 | 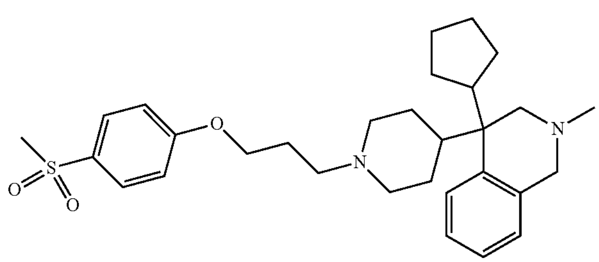 [SMILES: CN1Cc2ccccc2C(C2CCCC2)(C2CCN(CCCOc3ccc(S(C)(=O)=O)cc3)CC2)C1] |
| IV-68 | 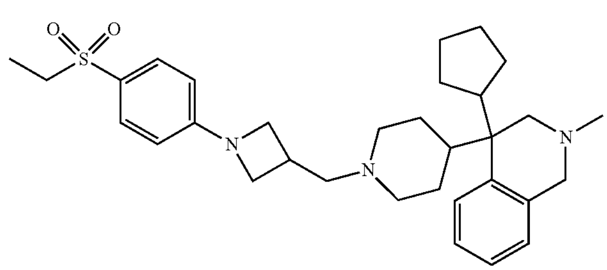 [SMILES: CCS(=O)(=O)c1ccc(N2CC(CN3CCC(C4(C5CCCC5)CN(C)Cc5ccccc54)CC3)C2)cc1] |

TABLE 4-continued

| No. | Structure |
|---|---|
| IV-69 | 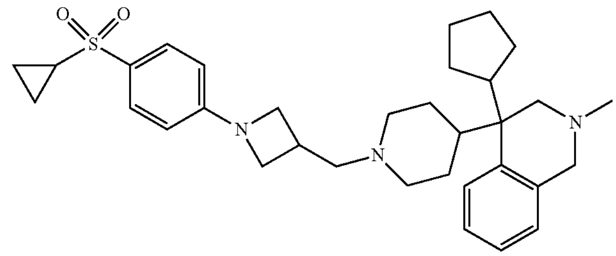 [SMILES: CN1Cc2ccccc2C(C2CCCC2)(C2CCN(CC3CN(c4ccc(S(=O)(=O)C5CC5)cc4)C3)CC2)C1] |
| IV-70 | 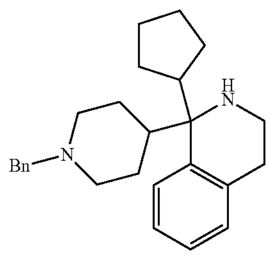 [SMILES: c1ccc(CN2CCC(C3(C4CCCC4)NCCc4ccccc43)CC2)cc1] |
| IV-71 | 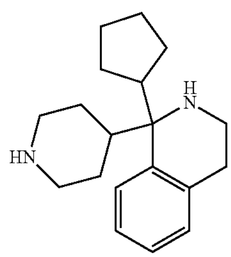 [SMILES: c1ccc2c(c1)CCNC2(C1CCCC1)C1CCNCC1] |
| IV-72 | 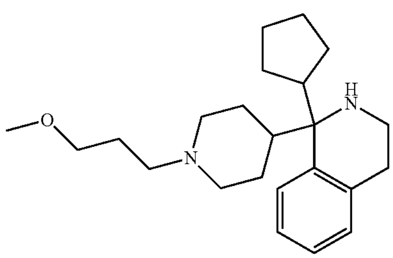 [SMILES: COCCCN1CCC(C2(C3CCCC3)NCCc3ccccc32)CC1] |
| IV-73 | 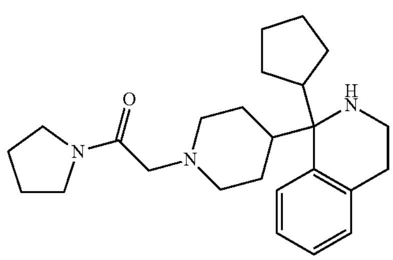 [SMILES: O=C(CN1CCC(C2(C3CCCC3)NCCc3ccccc32)CC1)N1CCCC1] |
| IV-74 | 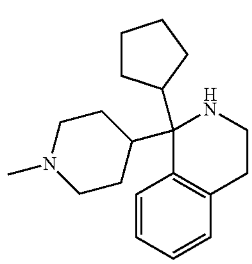 [SMILES: CN1CCC(C2(C3CCCC3)NCCc3ccccc32)CC1] |

TABLE 4-continued

| No. | Structure |
|---|---|
| IV-75 | 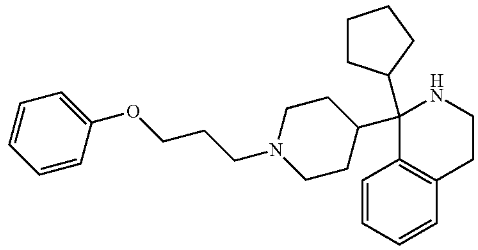 [SMILES: c1ccc(OCCCN2CCC(C3(C4CCCC4)NCCc4ccccc43)CC2)cc1] |
| IV-76 | 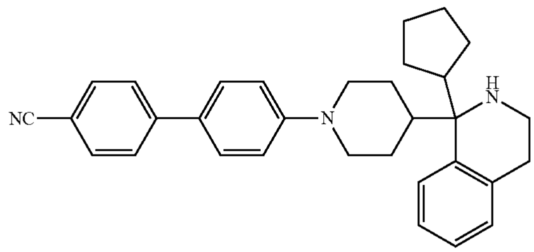 [SMILES: N#Cc1ccc(-c2ccc(N3CCC(C4(C5CCCC5)NCCc5ccccc54)CC3)cc2)cc1] |
| IV-77 | 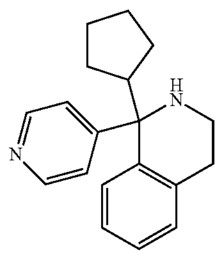 [SMILES: c1ccc2c(c1)CCNC2(c1ccncc1)C1CCCC1] |
| IV-78 | 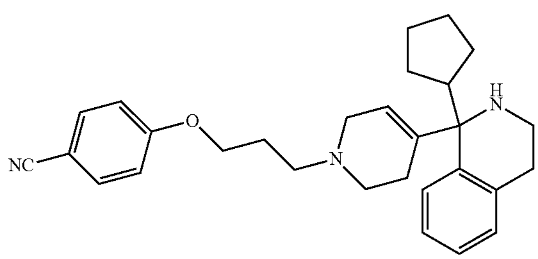 [SMILES: N#Cc1ccc(OCCCN2CC=C(C3(C4CCCC4)NCCc4ccccc43)CC2)cc1] |
| IV-79 | 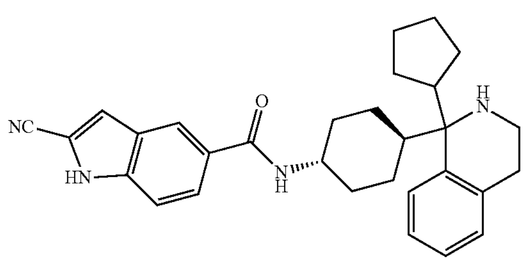 [SMILES: N#Cc1cc2cc(C(=O)N[C@H]3CC[C@H](C4(C5CCCC5)NCCc5ccccc54)CC3)ccc2[nH]1] |
| IV-80 | 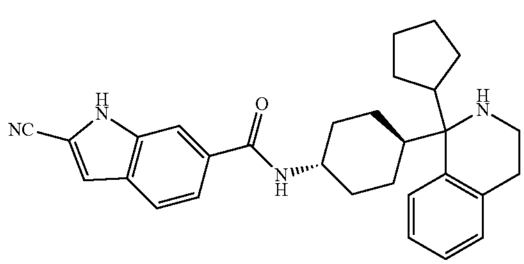 [SMILES: N#Cc1cc2ccc(C(=O)N[C@H]3CC[C@H](C4(C5CCCC5)NCCc5ccccc54)CC3)cc2[nH]1] |

TABLE 4-continued

| No. | Structure |
|---|---|
| IV-81 | 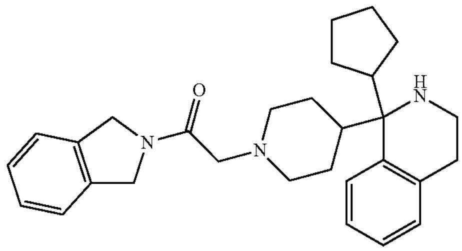 [SMILES: O=C(CN1CCC(C2(C3CCCC3)NCCc3ccccc32)CC1)N1Cc2ccccc2C1] |
| IV-82 | 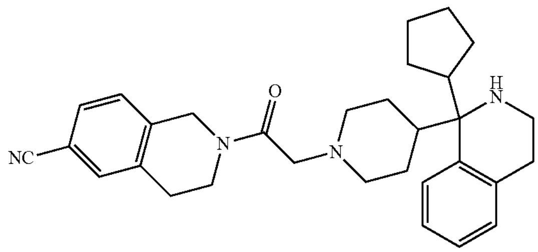 [SMILES: N#Cc1ccc2c(c1)CCN(C(=O)CN1CCC(C3(C4CCCC4)NCCc4ccccc43)CC1)C2] |
| IV-83 | 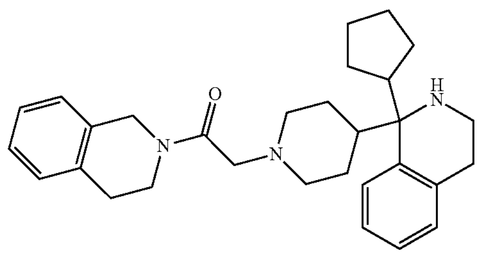 [SMILES: O=C(CN1CCC(C2(C3CCCC3)NCCc3ccccc32)CC1)N1CCc2ccccc2C1] |
| IV-84 | 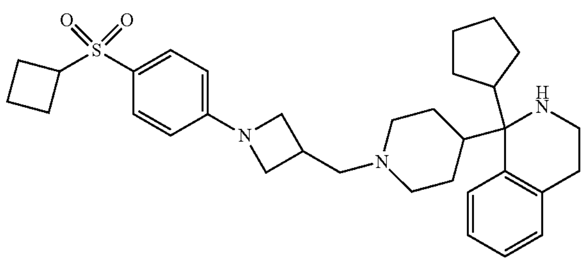 [SMILES: O=S(=O)(c1ccc(N2CC(CN3CCC(C4(C5CCCC5)NCCc5ccccc54)CC3)C2)cc1)C1CCC1] |
| IV-85 | 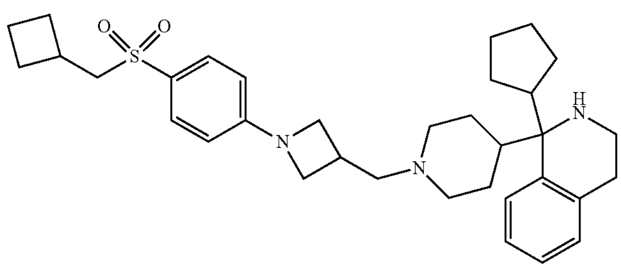 [SMILES: O=S(=O)(CC1CCC1)c1ccc(N2CC(CN3CCC(C4(C5CCCC5)NCCc5ccccc54)CC3)C2)cc1] |
| IV-86 | 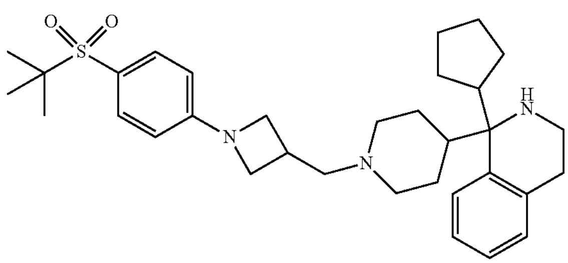 [SMILES: CC(C)(C)S(=O)(=O)c1ccc(N2CC(CN3CCC(C4(C5CCCC5)NCCc5ccccc54)CC3)C2)cc1] |

TABLE 4-continued

| No. | Structure |
|---|---|
| IV-87 | 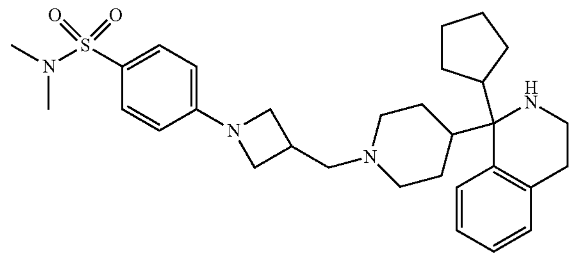 [SMILES: CN(C)S(=O)(=O)c1ccc(N2CC(CN3CCC(C4(C5CCCC5)NCCc5ccccc54)CC3)C2)cc1] |
| IV-88 | 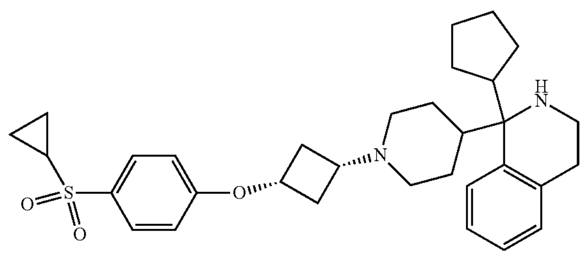 [SMILES: O=S(=O)(c1ccc(O[C@H]2C[C@@H](N3CCC(C4(C5CCCC5)NCCc5ccccc54)CC3)C2)cc1)C1CC1] |
| IV-89 | 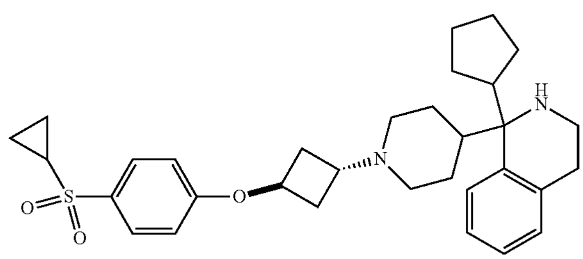 [SMILES: O=S(=O)(c1ccc(O[C@H]2C[C@H](N3CCC(C4(C5CCCC5)NCCc5ccccc54)CC3)C2)cc1)C1CC1] |
| IV-90 | 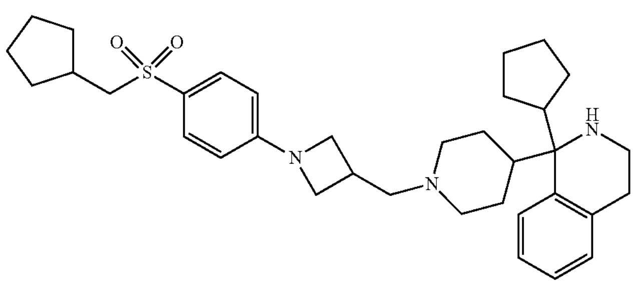 [SMILES: O=S(=O)(CC1CCCC1)c1ccc(N2CC(CN3CCC(C4(C5CCCC5)NCCc5ccccc54)CC3)C2)cc1] |
| IV-91 | 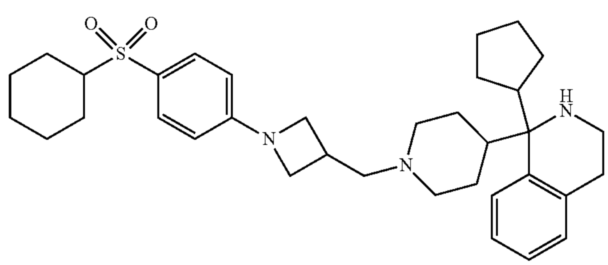 [SMILES: O=S(=O)(c1ccc(N2CC(CN3CCC(C4(C5CCCC5)NCCc5ccccc54)CC3)C2)cc1)C1CCCCC1] |
| IV-92 | 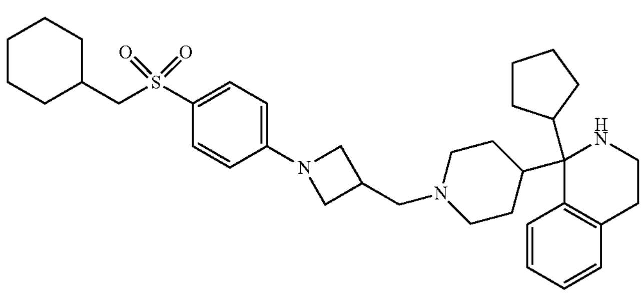 [SMILES: O=S(=O)(CC1CCCCC1)c1ccc(N2CC(CN3CCC(C4(C5CCCC5)NCCc5ccccc54)CC3)C2)cc1] |

TABLE 4-continued

| No. | Structure |
|---|---|
| IV-93 | 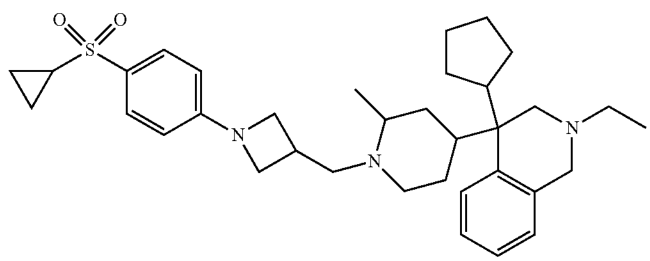 [SMILES: CCN1Cc2ccccc2C(C2CCCC2)(C2CCN(CC3CN(c4ccc(S(=O)(=O)C5CC5)cc4)C3)C(C)C2)C1] |
| IV-94 | 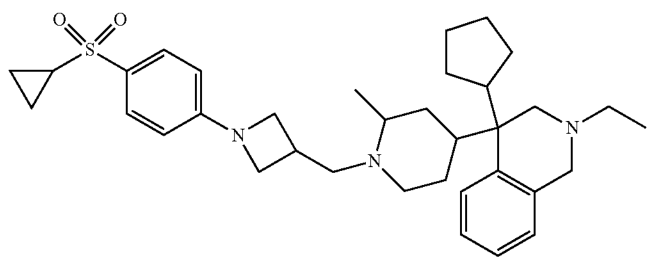 [SMILES: CCN1Cc2ccccc2C(C2CCCC2)(C2CCN(CC3CN(c4ccc(S(=O)(=O)C5CC5)cc4)C3)C(C)C2)C1] |
| IV-95 | 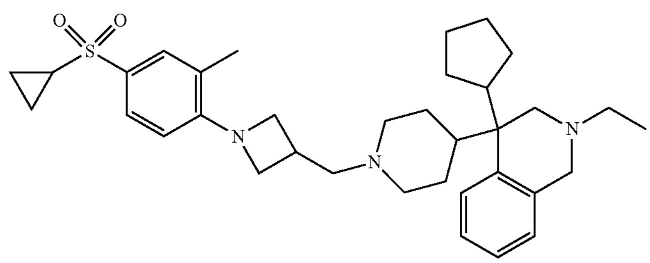 [SMILES: CCN1Cc2ccccc2C(C2CCCC2)(C2CCN(CC3CN(c4ccc(S(=O)(=O)C5CC5)cc4C)C3)CC2)C1] |
| IV-96 | 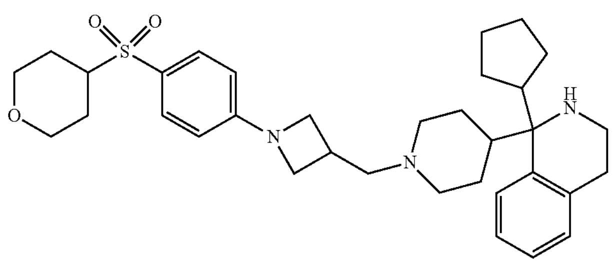 [SMILES: O=S(=O)(c1ccc(N2CC(CN3CCC(C4(C5CCCC5)NCCc5ccccc54)CC3)C2)cc1)C1CCOCC1] |
| IV-97 | 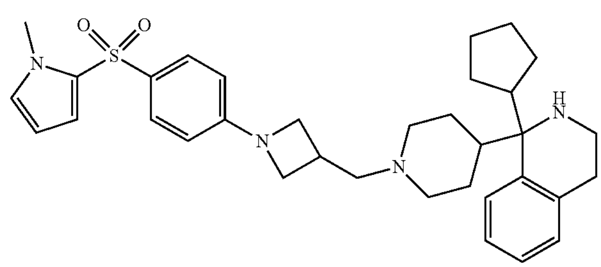 [SMILES: Cn1cccc1S(=O)(=O)c1ccc(N2CC(CN3CCC(C4(C5CCCC5)NCCc5ccccc54)CC3)C2)cc1] |
| IV-98 | 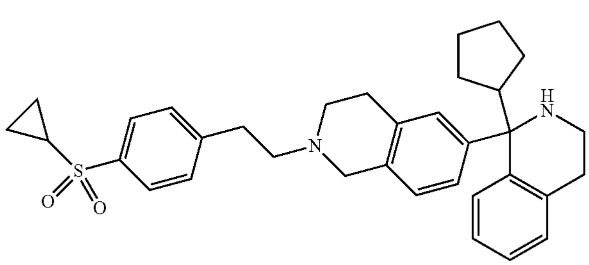 [SMILES: O=S(=O)(c1ccc(CCN2CCc3cc(C4(C5CCCC5)NCCc5ccccc54)ccc3C2)cc1)C1CC1] |

TABLE 4-continued

| No. | Structure |
|---|---|
| IV-99 | 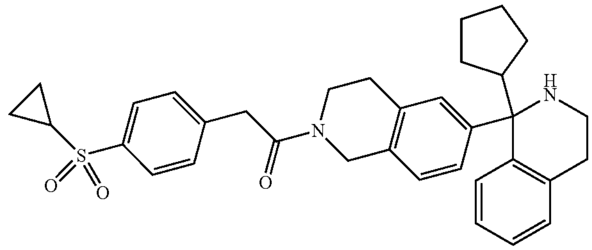 [SMILES: O=C(Cc1ccc(S(=O)(=O)C2CC2)cc1)N1CCc2cc(C3(C4CCCC4)NCCc4ccccc43)ccc2C1] |
| IV-100 | 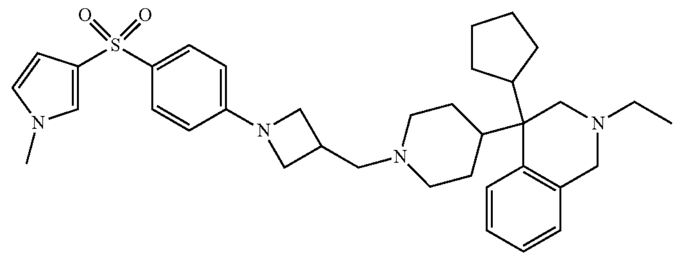 [SMILES: CCN1Cc2ccccc2C(C2CCCC2)(C2CCN(CC3CN(c4ccc(S(=O)(=O)c5ccn(C)c5)cc4)C3)CC2)C1] |
| IV-101 | 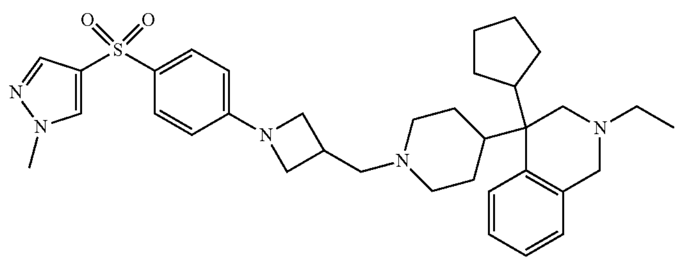 [SMILES: CCN1Cc2ccccc2C(C2CCCC2)(C2CCN(CC3CN(c4ccc(S(=O)(=O)c5cnn(C)c5)cc4)C3)CC2)C1] |
| IV-102 | 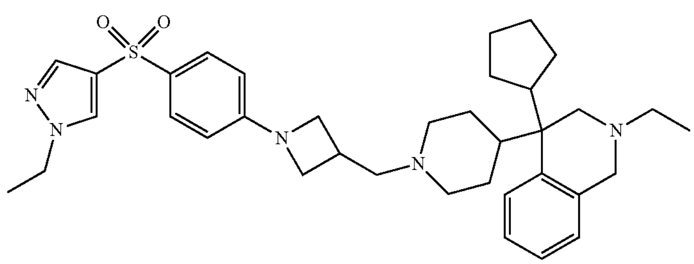 [SMILES: CCN1Cc2ccccc2C(C2CCCC2)(C2CCN(CC3CN(c4ccc(S(=O)(=O)c5cnn(CC)c5)cc4)C3)CC2)C1] |
| IV-103 | 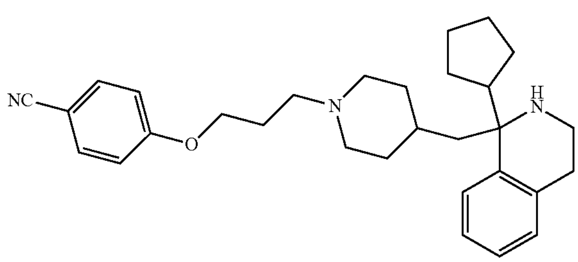 [SMILES: N#Cc1ccc(OCCCN2CCC(CC3(C4CCCC4)NCCc4ccccc43)CC2)cc1] |
| IV-104 | 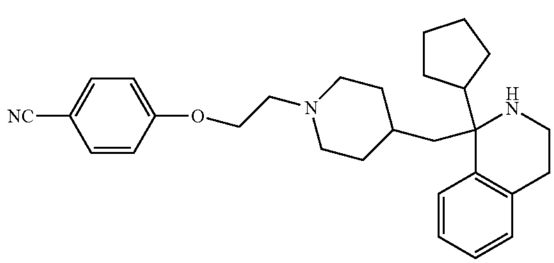 [SMILES: N#Cc1ccc(OCCN2CCC(CC3(C4CCCC4)NCCc4ccccc43)CC2)cc1] |

TABLE 4-continued

| No. | Structure |
|---|---|
| IV-105 | 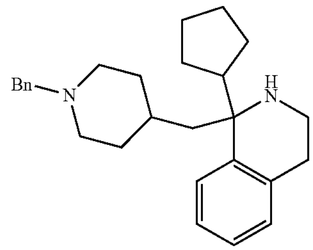 [SMILES: c1ccc(CN2CCC(CC3(C4CCCC4)NCCc4ccccc43)CC2)cc1] |
| IV-106 | 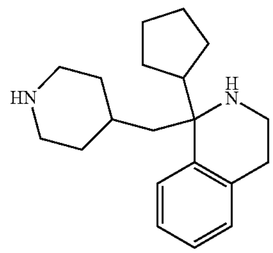 [SMILES: c1ccc2c(c1)CCNC2(CC1CCNCC1)C1CCCC1] |
| IV-107 | 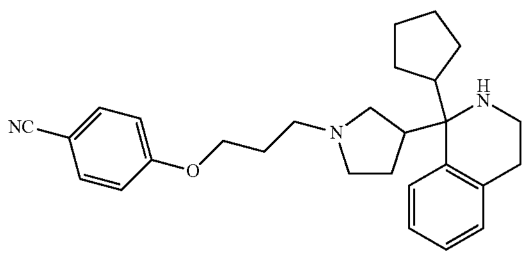 [SMILES: N#Cc1ccc(OCCCN2CCC(C3(C4CCCC4)NCCc4ccccc43)C2)cc1] |
| IV-108 | 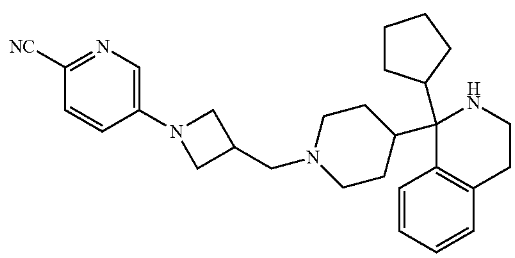 [SMILES: N#Cc1ccc(N2CC(CN3CCC(C4(C5CCCC5)NCCc5ccccc54)CC3)C2)cn1] |
| IV-109 | 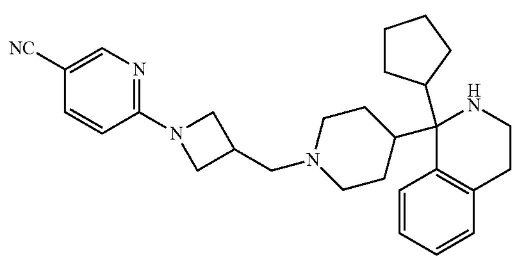 [SMILES: N#Cc1ccc(N2CC(CN3CCC(C4(C5CCCC5)NCCc5ccccc54)CC3)C2)nc1] |
| IV-110 | 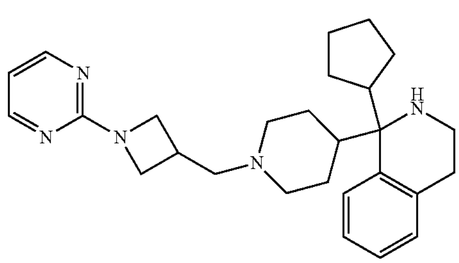 [SMILES: c1cnc(N2CC(CN3CCC(C4(C5CCCC5)NCCc5ccccc54)CC3)C2)nc1] |

TABLE 4-continued

| No. | Structure |
|---|---|
| IV-111 | 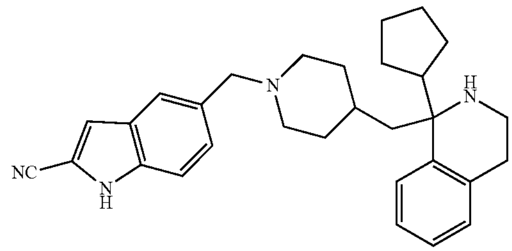 [SMILES: N#Cc1cc2cc(CN3CCC(CC4(C5CCCC5)NCCc5ccccc54)CC3)ccc2[nH]1] |
| IV-112 | 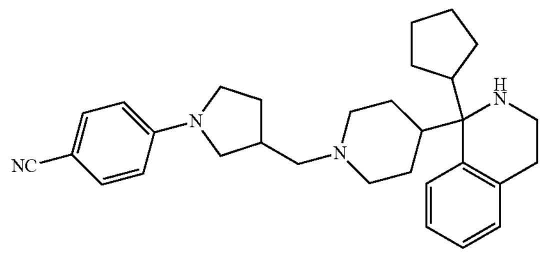 [SMILES: N#Cc1ccc(N2CCC(CN3CCC(C4(C5CCCC5)NCCc5ccccc54)CC3)C2)cc1] |
| IV-113 | 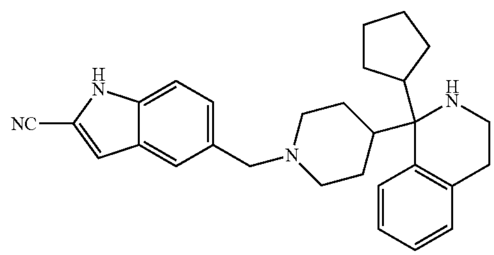 [SMILES: N#Cc1cc2cc(CN3CCC(C4(C5CCCC5)NCCc5ccccc54)CC3)ccc2[nH]1] |
| IV-114 | 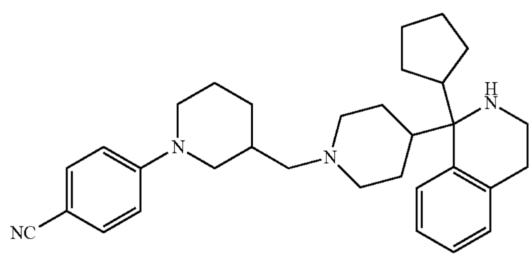 [SMILES: N#Cc1ccc(N2CCCC(CN3CCC(C4(C5CCCC5)NCCc5ccccc54)CC3)C2)cc1] |
| IV-115 | 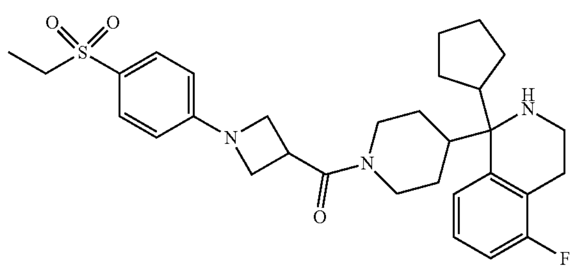 [SMILES: CCS(=O)(=O)c1ccc(N2CC(C(=O)N3CCC(C4(C5CCCC5)NCCc5c(F)cccc54)CC3)C2)cc1] |
| IV-116 | 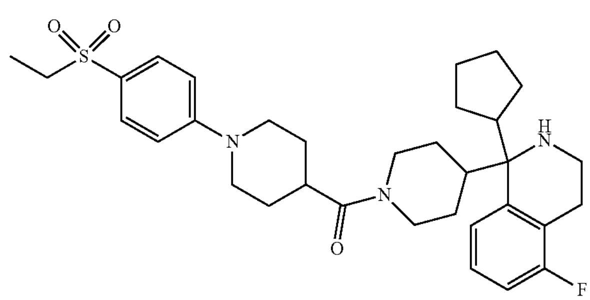 [SMILES: CCS(=O)(=O)c1ccc(N2CCC(C(=O)N3CCC(C4(C5CCCC5)NCCc5c(F)cccc54)CC3)CC2)cc1] |

TABLE 4-continued

| No. | Structure |
|---|---|
| IV-117 | 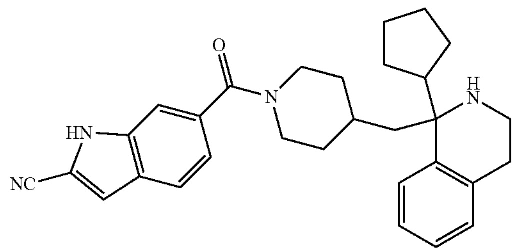 [SMILES: N#Cc1cc2ccc(C(=O)N3CCC(CC4(C5CCCC5)NCCc5ccccc54)CC3)cc2[nH]1] |
| IV-118 | 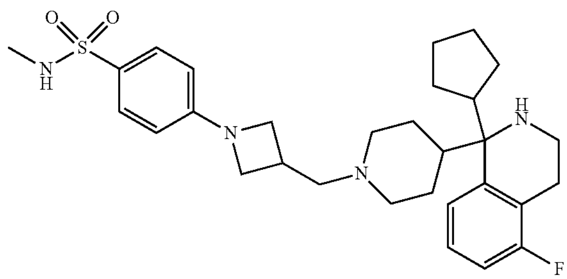 [SMILES: CNS(=O)(=O)c1ccc(N2CC(CN3CCC(C4(C5CCCC5)NCCc5c(F)cccc54)CC3)C2)cc1] |
| IV-119 | 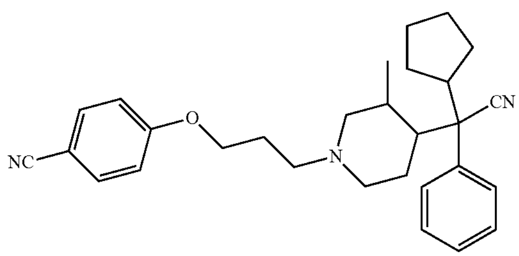 [SMILES: CC1CN(CCCOc2ccc(C#N)cc2)CCC1C(C#N)(c1ccccc1)C1CCCC1] |
| IV-120 | 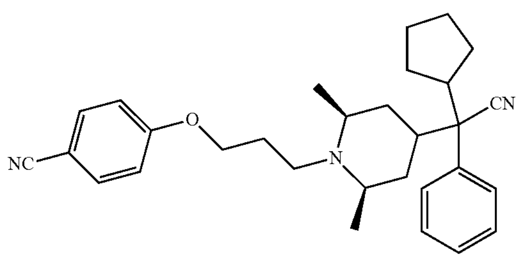 [SMILES: C[C@@H]1CC(C(C#N)(c2ccccc2)C2CCCC2)C[C@H](C)N1CCCOc1ccc(C#N)cc1] |
| IV-121 | 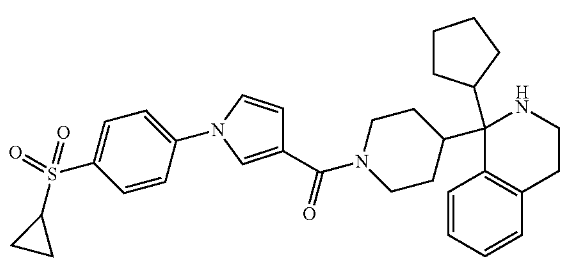 [SMILES: O=C(c1ccn(-c2ccc(S(=O)(=O)C3CC3)cc2)c1)N1CCC(C2(C3CCCC3)NCCc3ccccc32)CC1] |
| IV-122 | 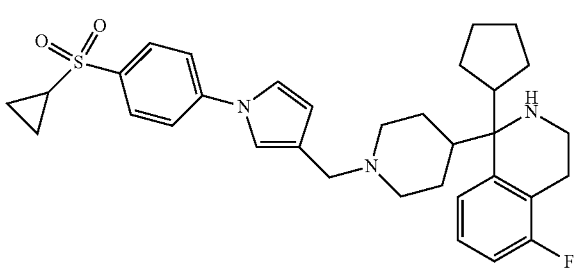 [SMILES: O=S(=O)(c1ccc(-n2ccc(CN3CCC(C4(C5CCCC5)NCCc5c(F)cccc54)CC3)c2)cc1)C1CC1] |

TABLE 4-continued

| No. | Structure |
|---|---|
| IV-123 | 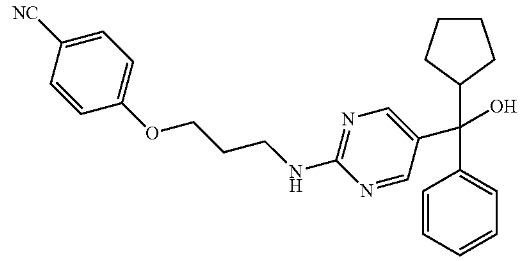 [SMILES: N#Cc1ccc(OCCCNc2ncc(C(O)(c3ccccc3)C3CCCC3)cn2)cc1] |
| IV-124 | 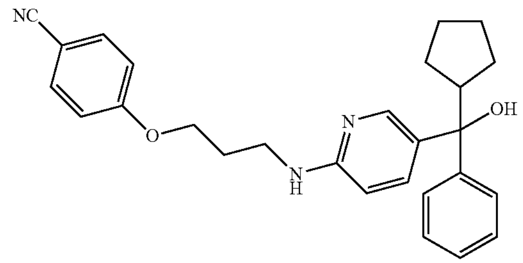 [SMILES: N#Cc1ccc(OCCCNc2ccc(C(O)(c3ccccc3)C3CCCC3)cn2)cc1] |
| IV-125 | 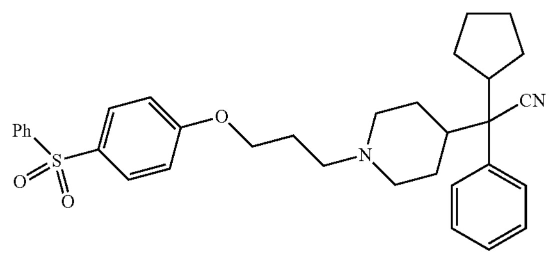 [SMILES: N#CC(c1ccccc1)(C1CCCC1)C1CCN(CCCOc2ccc(S(=O)(=O)c3ccccc3)cc2)CC1] |
| IV-126 | 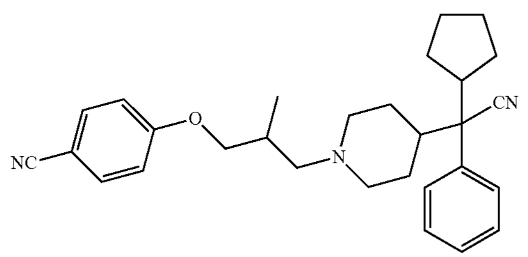 [SMILES: CC(COc1ccc(C#N)cc1)CN1CCC(C(C#N)(c2ccccc2)C2CCCC2)CC1] |
| IV-127 | 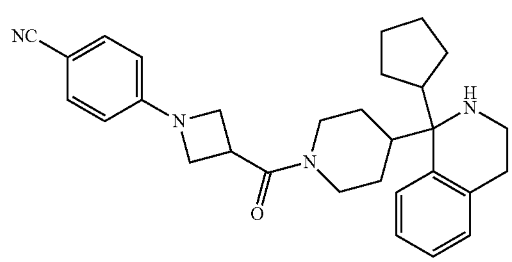 [SMILES: N#Cc1ccc(N2CC(C(=O)N3CCC(C4(C5CCCC5)NCCc5ccccc54)CC3)C2)cc1] |
| IV-128 | 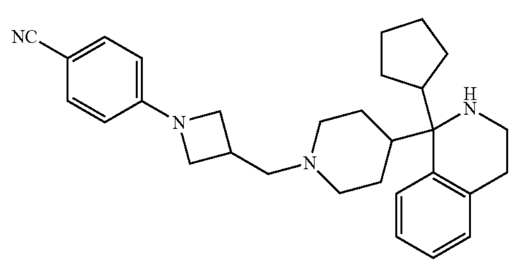 [SMILES: N#Cc1ccc(N2CC(CN3CCC(C4(C5CCCC5)NCCc5ccccc54)CC3)C2)cc1] |

TABLE 4-continued
| No. | Structure |
|---|---|
| IV-129 | 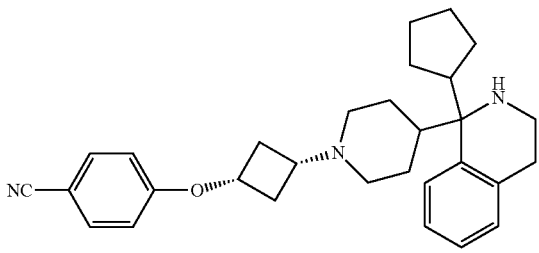 [SMILES: N#Cc1ccc(O[C@H]2C[C@@H](N3CCC(C4(C5CCCC5)NCCc5ccccc54)CC3)C2)cc1] |
| IV-130 | 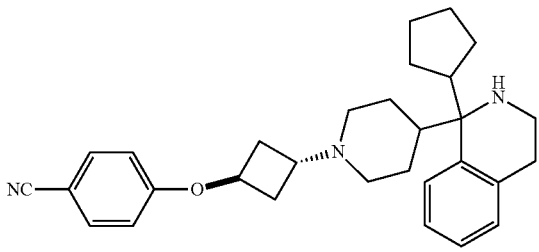 [SMILES: N#Cc1ccc(O[C@H]2C[C@H](N3CCC(C4(C5CCCC5)NCCc5ccccc54)CC3)C2)cc1] |
| IV-131 | 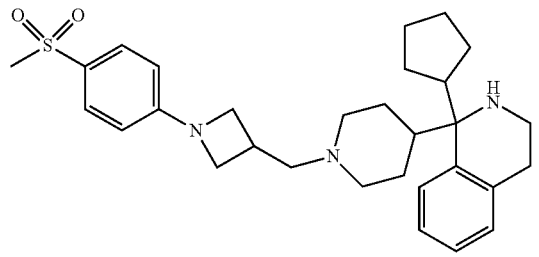 [SMILES: CS(=O)(=O)c1ccc(N2CC(CN3CCC(C4(C5CCCC5)NCCc5ccccc54)CC3)C2)cc1] |
| IV-132 | 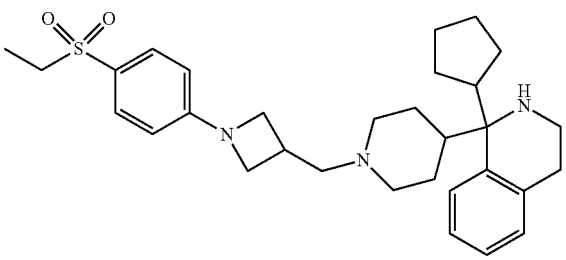 [SMILES: CCS(=O)(=O)c1ccc(N2CC(CN3CCC(C4(C5CCCC5)NCCc5ccccc54)CC3)C2)cc1] |
| IV-133 | 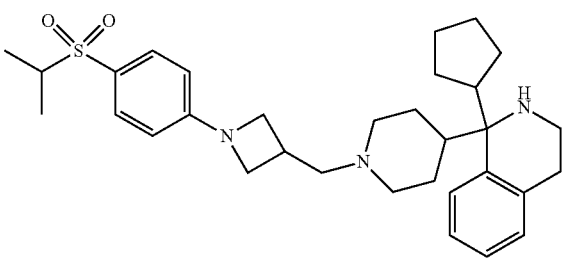 |
| IV-134 | 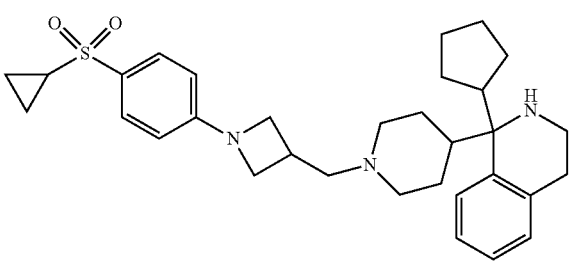 |

TABLE 4-continued

| No. | Structure |
|---|---|
| IV-135 | 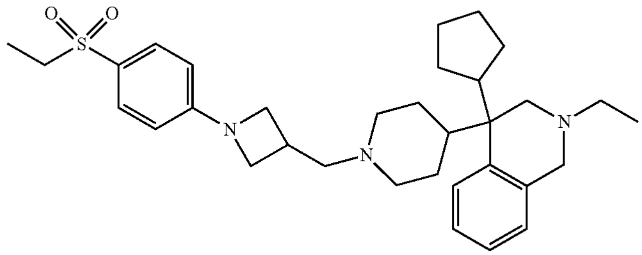 [SMILES: CCN1Cc2ccccc2C(C2CCCC2)(C2CCN(CC3CN(c4ccc(S(=O)(=O)CC)cc4)C3)CC2)C1] |
| IV-136 | 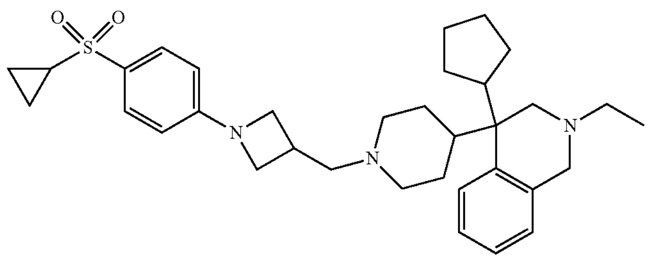 [SMILES: CCN1Cc2ccccc2C(C2CCCC2)(C2CCN(CC3CN(c4ccc(S(=O)(=O)C5CC5)cc4)C3)CC2)C1] |
| IV-137 | 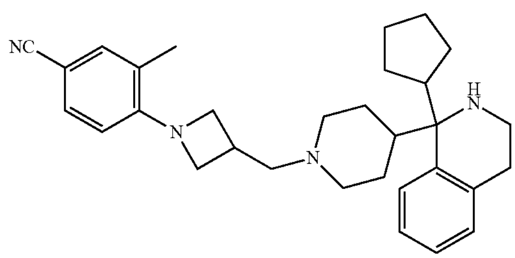 [SMILES: Cc1cc(C#N)ccc1N1CC(CN2CCC(C3(C4CCCC4)NCCc4ccccc43)CC2)C1] |
| IV-138 | 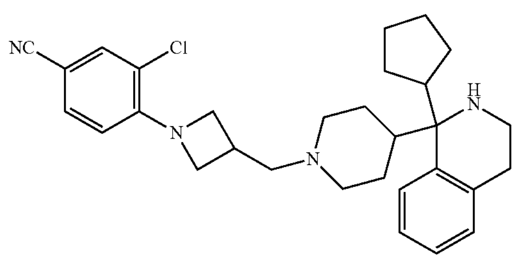 [SMILES: N#Cc1ccc(N2CC(CN3CCC(C4(C5CCCC5)NCCc5ccccc54)CC3)C2)c(Cl)c1] |
| IV-139 | 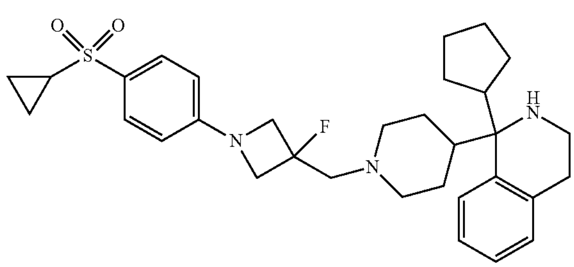 [SMILES: O=S(=O)(c1ccc(N2CC(F)(CN3CCC(C4(C5CCCC5)NCCc5ccccc54)CC3)C2)cc1)C1CC1] |
| IV-140 | 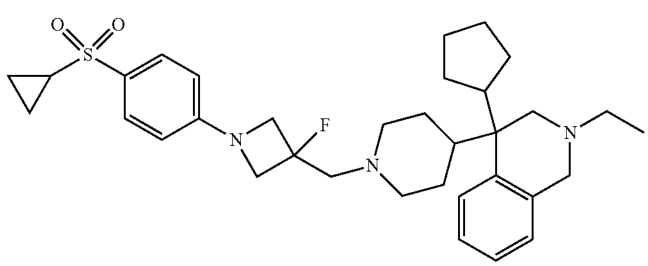 [SMILES: CCN1Cc2ccccc2C(C2CCCC2)(C2CCN(CC3(F)CN(c4ccc(S(=O)(=O)C5CC5)cc4)C3)CC2)C1] |

TABLE 4-continued

| No. | Structure |
|---|---|
| IV-141 | 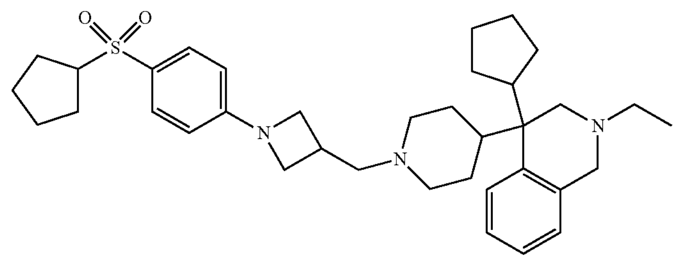 [SMILES: CCN1Cc2ccccc2C(C2CCCC2)(C2CCN(CC3CN(c4ccc(S(=O)(=O)C5CCCC5)cc4)C3)CC2)C1] |
| IV-142 | 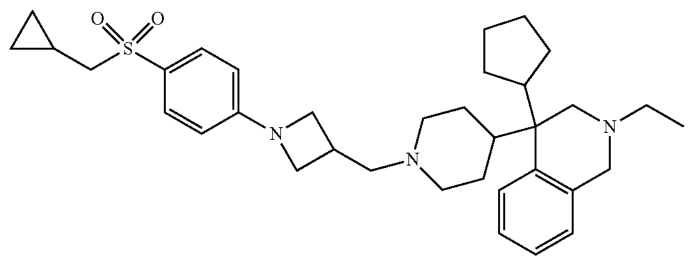 [SMILES: CCN1Cc2ccccc2C(C2CCCC2)(C2CCN(CC3CN(c4ccc(S(=O)(=O)CC5CC5)cc4)C3)CC2)C1] |
| IV-143 | 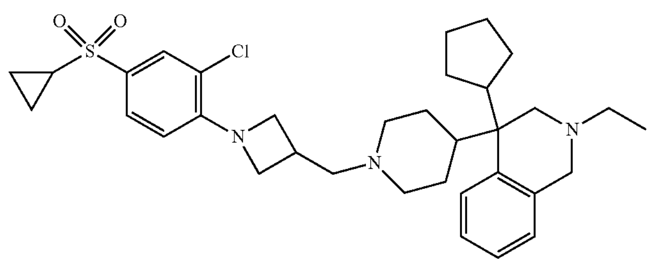 [SMILES: CCN1Cc2ccccc2C(C2CCCC2)(C2CCN(CC3CN(c4ccc(S(=O)(=O)C5CC5)cc4Cl)C3)CC2)C1] |
| IV-144 | 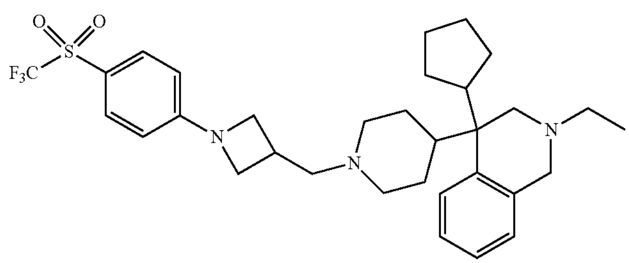 [SMILES: CCN1Cc2ccccc2C(C2CCCC2)(C2CCN(CC3CN(c4ccc(S(=O)(=O)C(F)(F)F)cc4)C3)CC2)C1] |
| IV-145 | 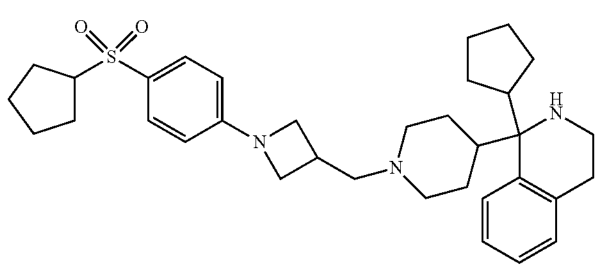 [SMILES: O=S(=O)(c1ccc(N2CC(CN3CCC(C4(C5CCCC5)NCCc5ccccc54)CC3)C2)cc1)C1CCCC1] |
| IV-146 | 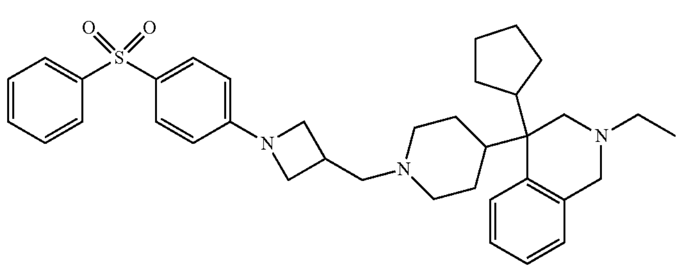 [SMILES: CCN1Cc2ccccc2C(C2CCCC2)(C2CCN(CC3CN(c4ccc(S(=O)(=O)c5ccccc5)cc4)C3)CC2)C1] |

TABLE 4-continued

| No. | Structure |
|---|---|
| IV-147 | 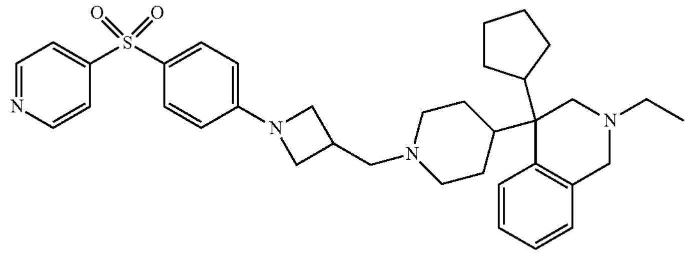 [SMILES: CCN1Cc2ccccc2C(C2CCCC2)(C2CCN(CC3CN(c4ccc(S(=O)(=O)c5ccncc5)cc4)C3)CC2)C1] |
| IV-148 | 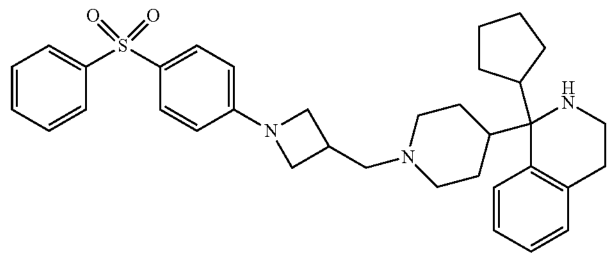 [SMILES: O=S(=O)(c1ccccc1)c1ccc(N2CC(CN3CCC(C4(C5CCCC5)NCCc5ccccc54)CC3)C2)cc1] |
| IV-149 | 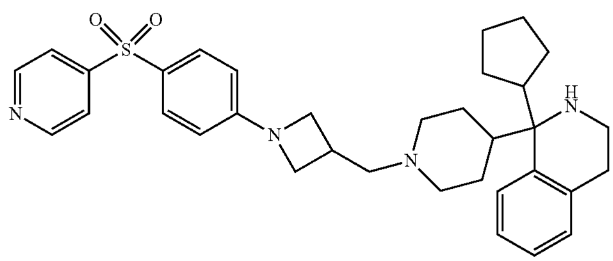 [SMILES: O=S(=O)(c1ccncc1)c1ccc(N2CC(CN3CCC(C4(C5CCCC5)NCCc5ccccc54)CC3)C2)cc1] |
| IV-150 | 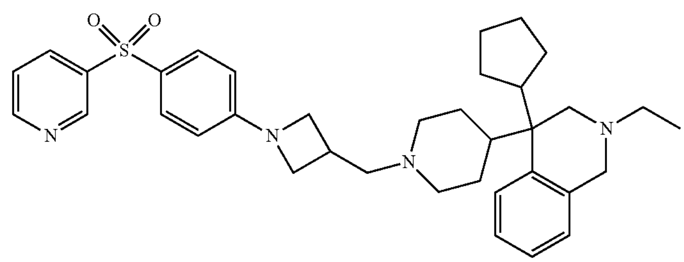 [SMILES: CCN1Cc2ccccc2C(C2CCCC2)(C2CCN(CC3CN(c4ccc(S(=O)(=O)c5cccnc5)cc4)C3)CC2)C1] |
| IV-151 | 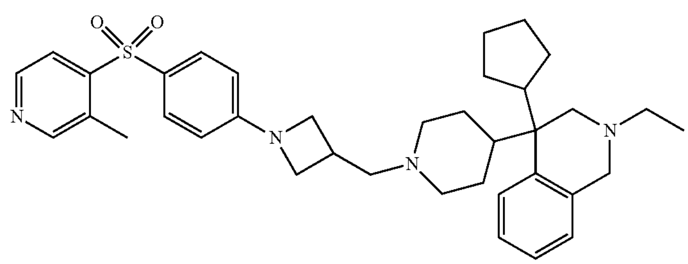 [SMILES: CCN1Cc2ccccc2C(C2CCCC2)(C2CCN(CC3CN(c4ccc(S(=O)(=O)c5ccncc5C)cc4)C3)CC2)C1] |
| IV-152 | 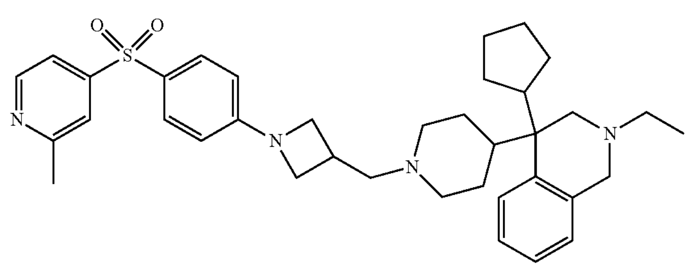 [SMILES: CCN1Cc2ccccc2C(C2CCCC2)(C2CCN(CC3CN(c4ccc(S(=O)(=O)c5ccnc(C)c5)cc4)C3)CC2)C1] |

TABLE 4-continued
| No. | Structure |
|---|---|
| IV-153 | 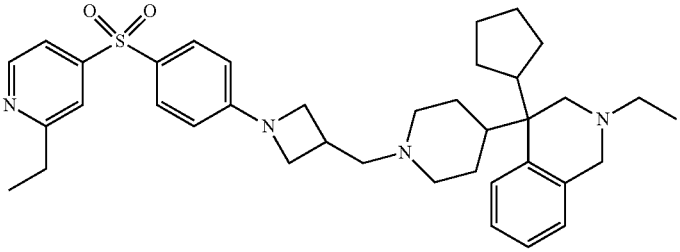 [SMILES: CCc1cc(S(=O)(=O)c2ccc(N3CC(CN4CCC(C5(C6CCCC6)CN(CC)Cc6ccccc65)CC4)C3)cc2)ccn1] |
| IV-154 | 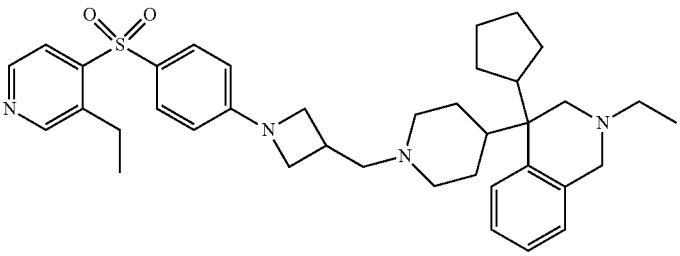 [SMILES: CCc1cnccc1S(=O)(=O)c1ccc(N2CC(CN3CCC(C4(C5CCCC5)CN(CC)Cc5ccccc54)CC3)C2)cc1] |
| IV-155 | 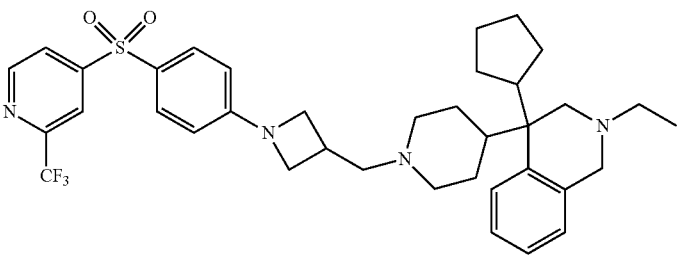 |
| IV-156 | 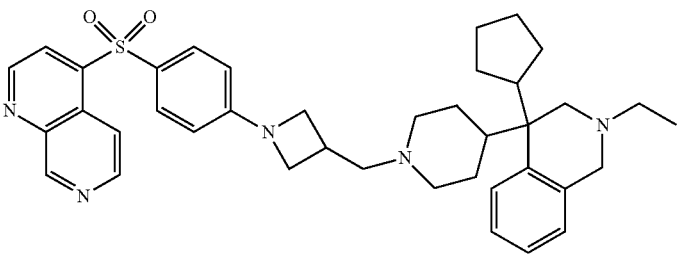 [SMILES: CCN1Cc2ccccc2C(C2CCCC2)(C2CCN(CC3CN(c4ccc(S(=O)(=O)c5ccnc6cnccc56)cc4)C3)CC2)C1] |
| IV-157 | 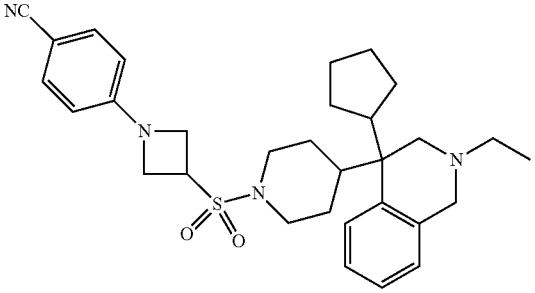 [SMILES: CCN1Cc2ccccc2C(C2CCCC2)(C2CCN(S(=O)(=O)C3CN(c4ccc(C#N)cc4)C3)CC2)C1] |

TABLE 4-continued

| No. | Structure |
|---|---|
| IV-158 | 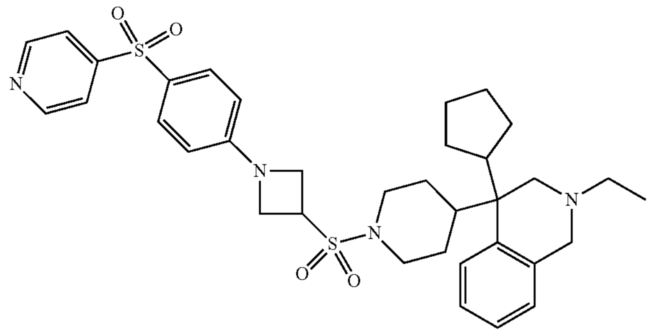 [SMILES: CCN1Cc2ccccc2C(C2CCCC2)(C2CCN(S(=O)(=O)C3CN(c4ccc(S(=O)(=O)c5ccncc5)cc4)C3)CC2)C1] |
| IV-159 | 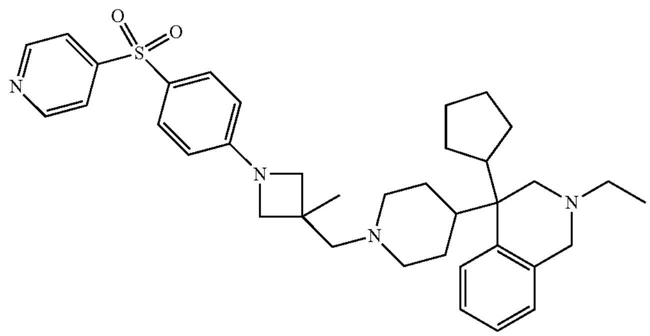 [SMILES: CCN1Cc2ccccc2C(C2CCCC2)(C2CCN(CC3(C)CN(c4ccc(S(=O)(=O)c5ccncc5)cc4)C3)CC2)C1] |
| IV-160 | 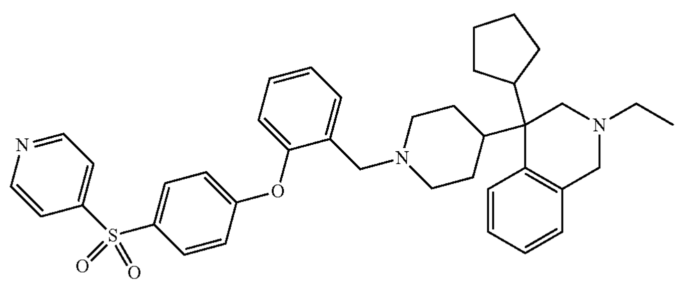 [SMILES: CCN1Cc2ccccc2C(C2CCCC2)(C2CCN(Cc3ccccc3Oc3ccc(S(=O)(=O)c4ccncc4)cc3)CC2)C1] |
| IV-161 | 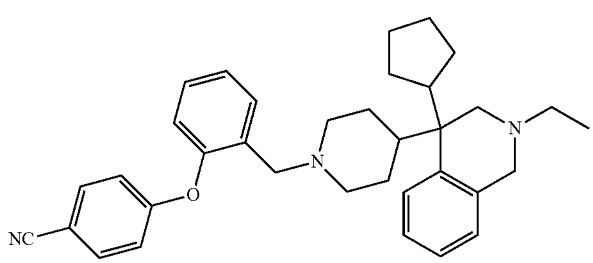 [SMILES: CCN1Cc2ccccc2C(C2CCCC2)(C2CCN(Cc3ccccc3Oc3ccc(C#N)cc3)CC2)C1] |
| IV-162 | 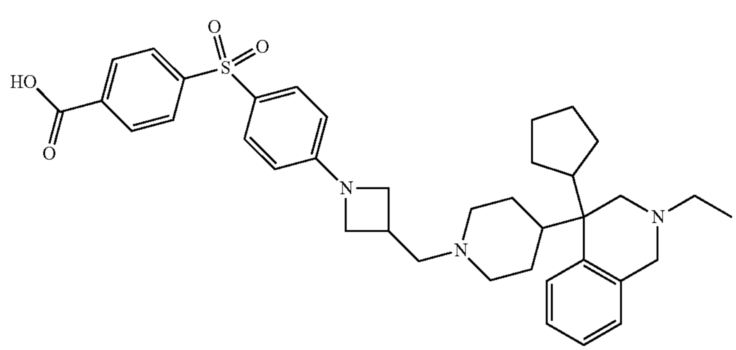 [SMILES: CCN1Cc2ccccc2C(C2CCCC2)(C2CCN(CC3CN(c4ccc(S(=O)(=O)c5ccc(C(=O)O)cc5)cc4)C3)CC2)C1] |

TABLE 4-continued

| No. | Structure |
|---|---|
| IV-163 | 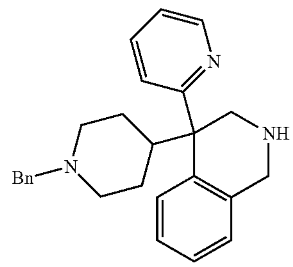 [SMILES: c1ccc(CN2CCC(C3(c4ccccn4)CNCc4ccccc43)CC2)cc1] |
| IV-164 | 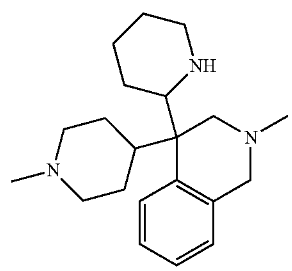 |
| IV-165 | 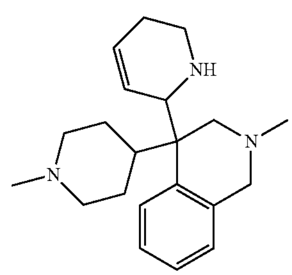 |
| IV-166 | 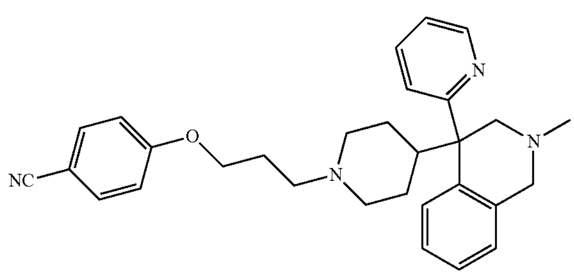 [SMILES: CN1Cc2ccccc2C(c2ccccn2)(C2CCN(CCCOc3ccc(C#N)cc3)CC2)C1] |
| IV-167 | 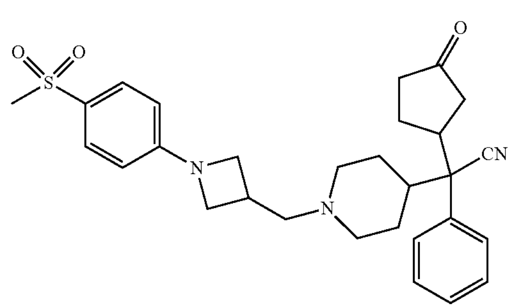 [SMILES: CS(=O)(=O)c1ccc(N2CC(CN3CCC(C(C#N)(c4ccccc4)C4CCC(=O)C4)CC3)C2)cc1] |

TABLE 4-continued

| No. | Structure |
|---|---|
| IV-168 | 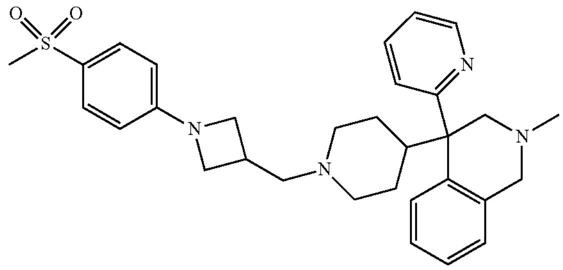 |
| IV-169 | 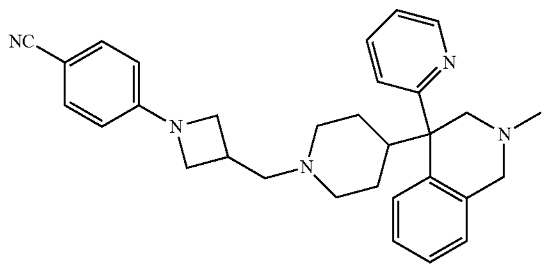 [SMILES: CN1Cc2ccccc2C(c2ccccn2)(C2CCN(CC3CN(c4ccc(C#N)cc4)C3)CC2)C1] |
| IV-170 | 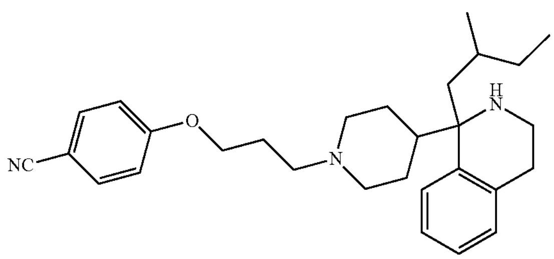 [SMILES: CCC(C)CC1(C2CCN(CCCOc3ccc(C#N)cc3)CC2)NCCc2ccccc21] |
| IV-171 | 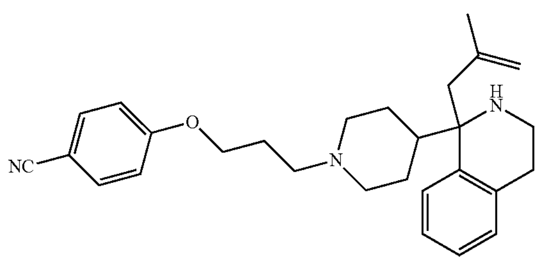 [SMILES: C=C(C)CC1(C2CCN(CCCOc3ccc(C#N)cc3)CC2)NCCc2ccccc21] |
| IV-172 | 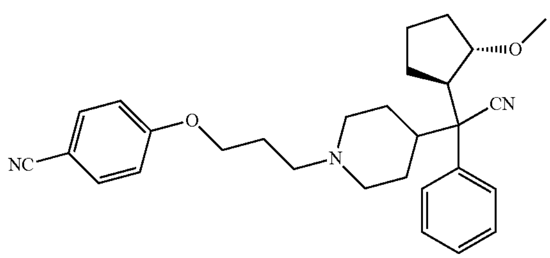 [SMILES: CO[C@H]1CCC[C@@H]1C(C#N)(c1ccccc1)C1CCN(CCCOc2ccc(C#N)cc2)CC1] |
| IV-173 | 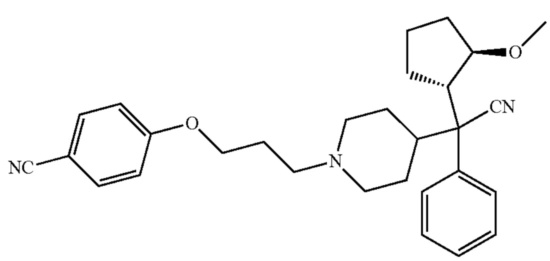 [SMILES: CO[C@@H]1CCC[C@H]1C(C#N)(c1ccccc1)C1CCN(CCCOc2ccc(C#N)cc2)CC1] |

TABLE 4-continued

| No. | Structure |
|---|---|
| IV-174 | 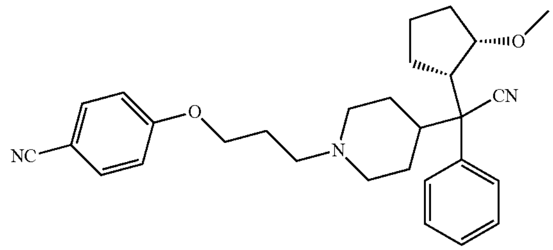 [SMILES: CO[C@H]1CCC[C@H]1C(C#N)(c1ccccc1)C1CCN(CCCOc2ccc(C#N)cc2)CC1] |
| IV-175 | 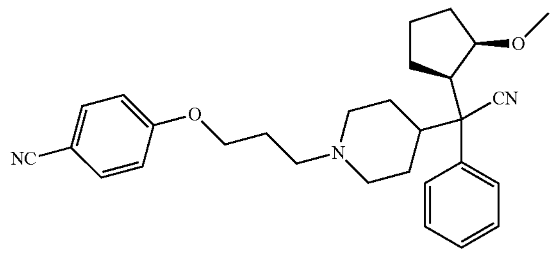 [SMILES: CO[C@@H]1CCC[C@@H]1C(C#N)(c1ccccc1)C1CCN(CCCOc2ccc(C#N)cc2)CC1] |
| IV-176 | 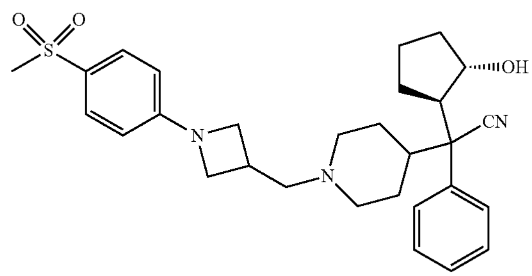 [SMILES: CS(=O)(=O)c1ccc(N2CC(CN3CCC(C(C#N)(c4ccccc4)[C@H]4CCC[C@@H]4O)CC3)C2)cc1] |
| IV-177 | 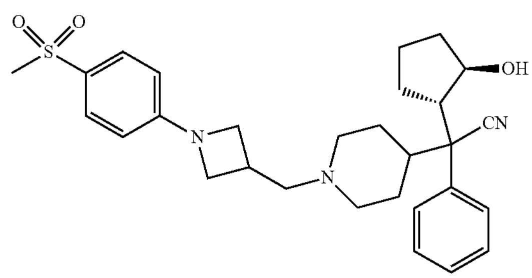 [SMILES: CS(=O)(=O)c1ccc(N2CC(CN3CCC(C(C#N)(c4ccccc4)[C@@H]4CCC[C@H]4O)CC3)C2)cc1] |
| IV-178 | 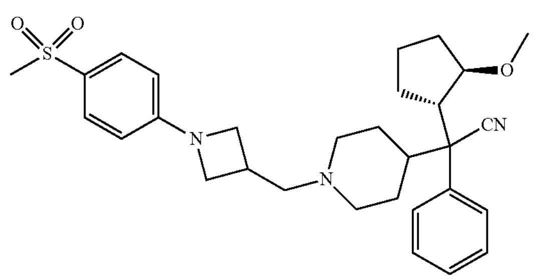 |
| IV-179 | 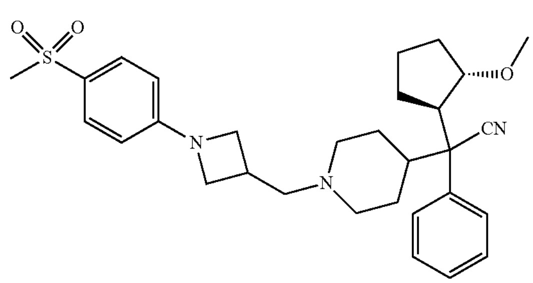 |

TABLE 4-continued

| No. | Structure |
|---|---|
| IV-180 | 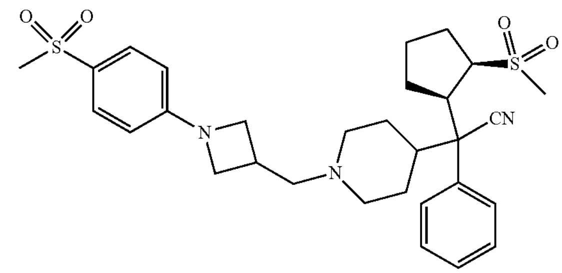 [SMILES: CS(=O)(=O)c1ccc(N2CC(CN3CCC(C(C#N)(c4ccccc4)[C@H]4CCC[C@H]4S(C)(=O)=O)CC3)C2)cc1] |
| IV-181 | 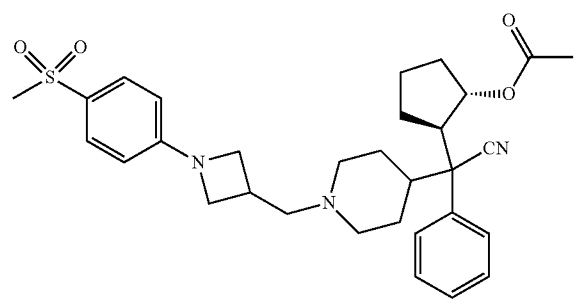 [SMILES: CC(=O)O[C@H]1CCC[C@@H]1C(C#N)(c1ccccc1)C1CCN(CC2CN(c3ccc(S(C)(=O)=O)cc3)C2)CC1] |
| IV-182 | 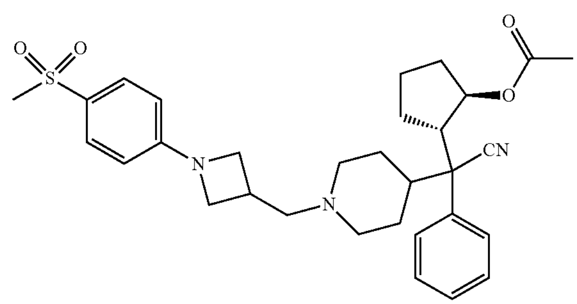 [SMILES: CC(=O)O[C@@H]1CCC[C@H]1C(C#N)(c1ccccc1)C1CCN(CC2CN(c3ccc(S(C)(=O)=O)cc3)C2)CC1] |
| IV-183 | 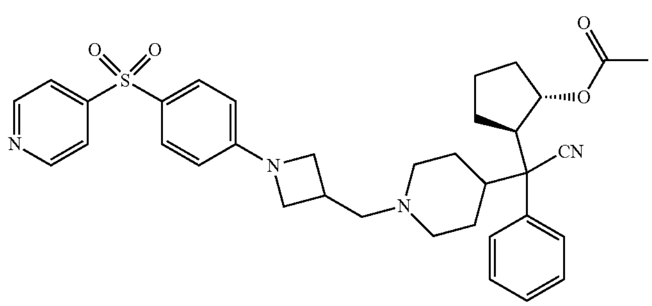 [SMILES: CC(=O)O[C@H]1CCC[C@@H]1C(C#N)(c1ccccc1)C1CCN(CC2CN(c3ccc(S(=O)(=O)c4ccncc4)cc3)C2)CC1] |
| IV-184 | 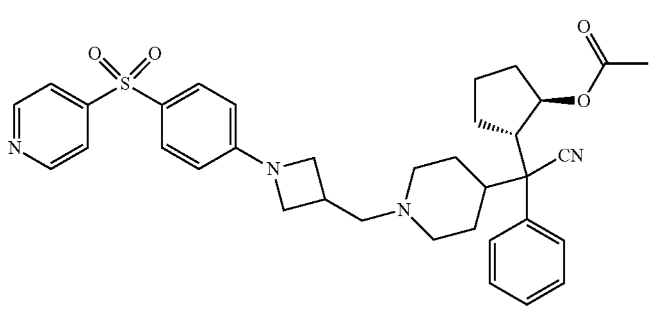 [SMILES: CC(=O)O[C@@H]1CCC[C@H]1C(C#N)(c1ccccc1)C1CCN(CC2CN(c3ccc(S(=O)(=O)c4ccncc4)cc3)C2)CC1] |

TABLE 4-continued

| No. | Structure |
|---|---|
| IV-185 | 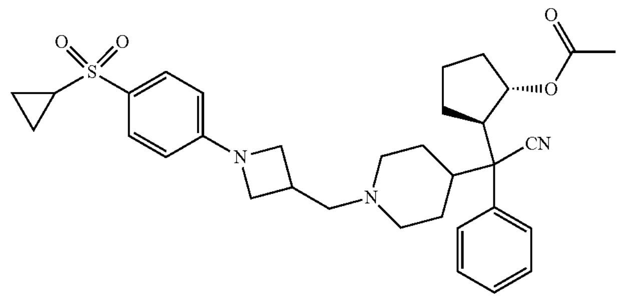 [SMILES: CC(=O)O[C@H]1CCC[C@@H]1C(C#N)(c1ccccc1)C1CCN(CC2CN(c3ccc(S(=O)(=O)C4CC4)cc3)C2)CC1] |
| IV-186 | 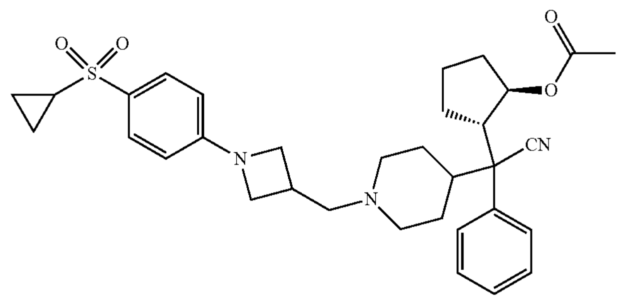 [SMILES: CC(=O)O[C@@H]1CCC[C@H]1C(C#N)(c1ccccc1)C1CCN(CC2CN(c3ccc(S(=O)(=O)C4CC4)cc3)C2)CC1] |
| IV-187 | 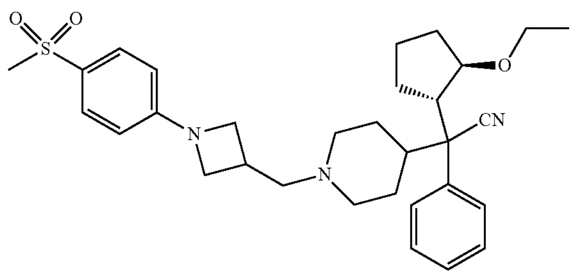 [SMILES: CCO[C@@H]1CCC[C@H]1C(C#N)(c1ccccc1)C1CCN(CC2CN(c3ccc(S(C)(=O)=O)cc3)C2)CC1] |
| IV-188 | 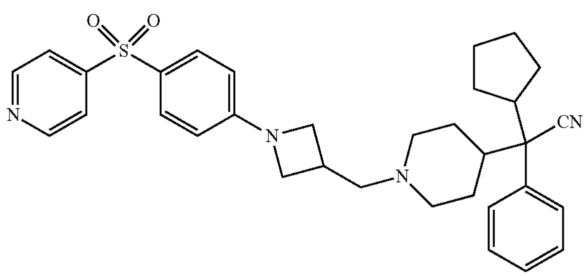 [SMILES: N#CC(c1ccccc1)(C1CCCC1)C1CCN(CC2CN(c3ccc(S(=O)(=O)c4ccncc4)cc3)C2)CC1] |
| IV-189 | 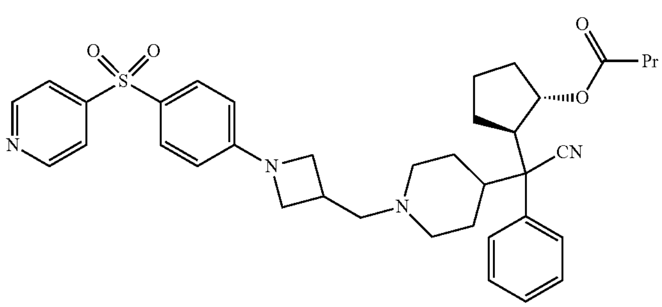 |

TABLE 4-continued

| No. | Structure |
|---|---|
| IV-190 | 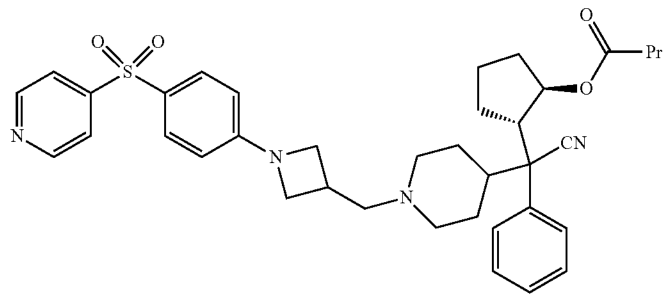 |
| IV-191 | 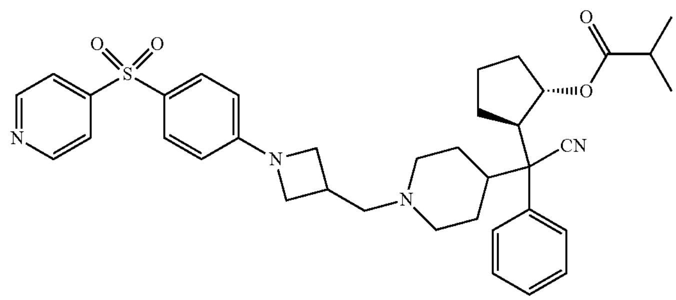 [SMILES: CC(C)C(=O)O[C@H]1CCC[C@@H]1C(C#N)(c1ccccc1)C1CCN(CC2CN(c3ccc(S(=O)(=O)c4ccncc4)cc3)C2)CC1] |
| IV-192 | 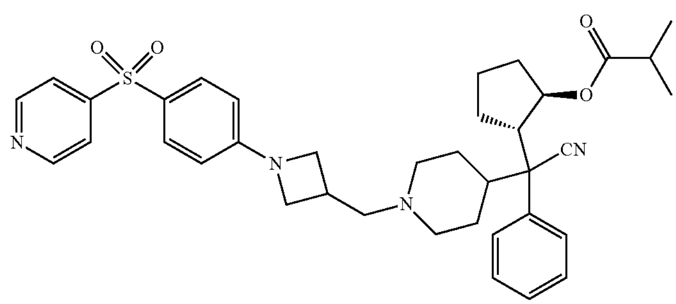 [SMILES: CC(C)C(=O)O[C@@H]1CCC[C@H]1C(C#N)(c1ccccc1)C1CCN(CC2CN(c3ccc(S(=O)(=O)c4ccncc4)cc3)C2)CC1] |
| IV-193 | 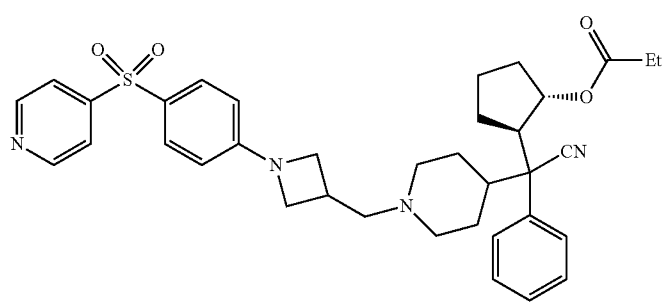 |
| IV-194 | 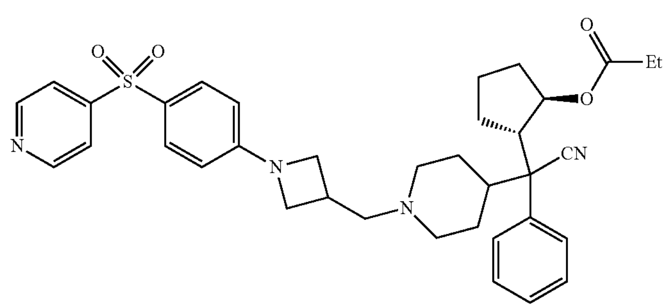 [SMILES: CCC(=O)O[C@@H]1CCC[C@H]1C(C#N)(c1ccccc1)C1CCN(CC2CN(c3ccc(S(=O)(=O)c4ccncc4)cc3)C2)CC1] |

TABLE 4-continued

| No. | Structure |
|---|---|
| IV-195 | 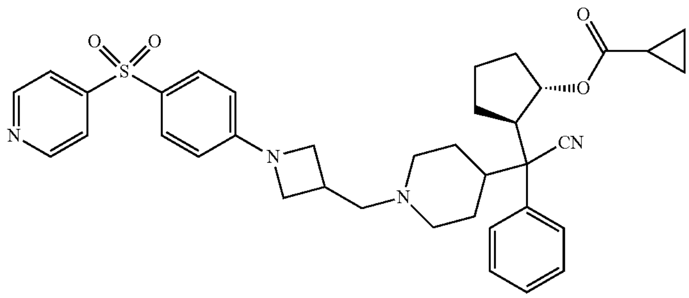 [SMILES: N#CC(c1ccccc1)(C1CCN(CC2CN(c3ccc(S(=O)(=O)c4ccncc4)cc3)C2)CC1)[C@H]1CCC[C@@H]1OC(=O)C1CC1] |
| IV-196 | 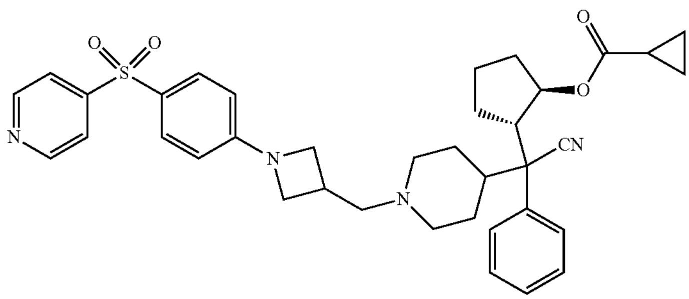 [SMILES: N#CC(c1ccccc1)(C1CCN(CC2CN(c3ccc(S(=O)(=O)c4ccncc4)cc3)C2)CC1)[C@@H]1CCC[C@H]1OC(=O)C1CC1] |
| IV-197 | 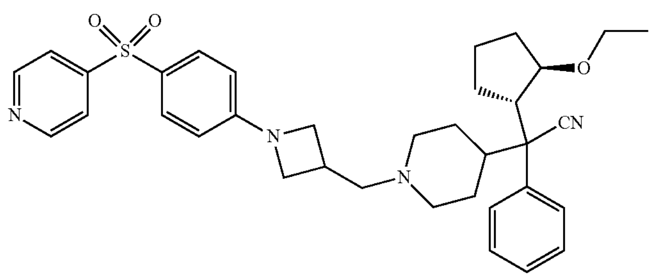 [SMILES: CCO[C@@H]1CCC[C@H]1C(C#N)(c1ccccc1)C1CCN(CC2CN(c3ccc(S(=O)(=O)c4ccncc4)cc3)C2)CC1] |
| IV-198 | 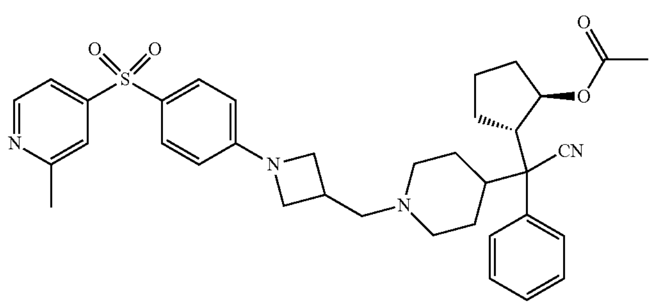 [SMILES: CC(=O)O[C@@H]1CCC[C@H]1C(C#N)(c1ccccc1)C1CCN(CC2CN(c3ccc(S(=O)(=O)c4ccnc(C)c4)cc3)C2)CC1] |
| IV-199 | 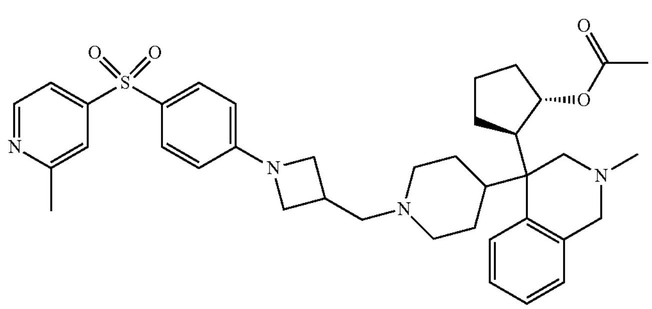 [SMILES: CC(=O)O[C@H]1CCC[C@@H]1C1(C2CCN(CC3CN(c4ccc(S(=O)(=O)c5ccnc(C)c5)cc4)C3)CC2)CN(C)Cc2ccccc21] |

TABLE 4-continued

| No. | Structure |
|---|---|
| IV-200 | 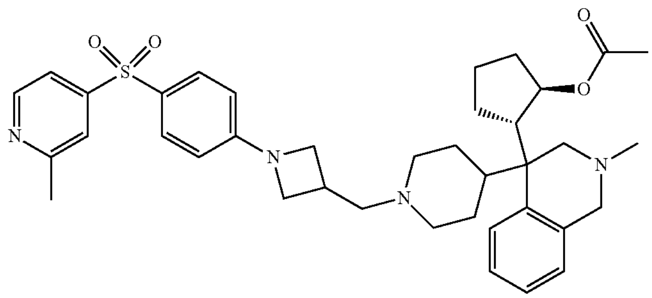 [SMILES: CC(=O)O[C@@H]1CCC[C@H]1C1(C2CCN(CC3CN(c4ccc(S(=O)(=O)c5ccnc(C)c5)cc4)C3)CC2)CN(C)Cc2ccccc21] |
| IV-201 | 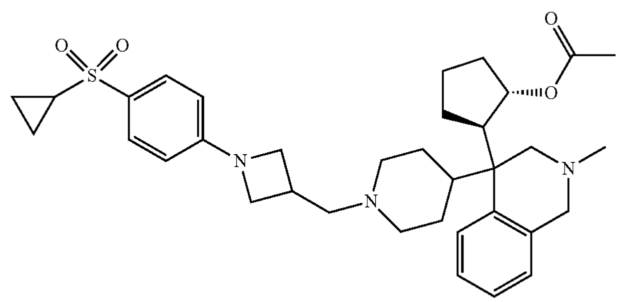 [SMILES: CC(=O)O[C@H]1CCC[C@@H]1C1(C2CCN(CC3CN(c4ccc(S(=O)(=O)C5CC5)cc4)C3)CC2)CN(C)Cc2ccccc21] |
| IV-202 | 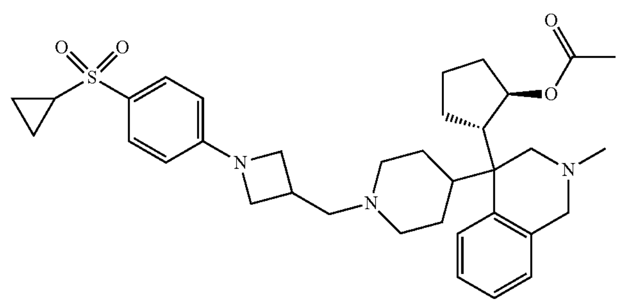 [SMILES: CC(=O)O[C@@H]1CCC[C@H]1C1(C2CCN(CC3CN(c4ccc(S(=O)(=O)C5CC5)cc4)C3)CC2)CN(C)Cc2ccccc21] |
| IV-203 | 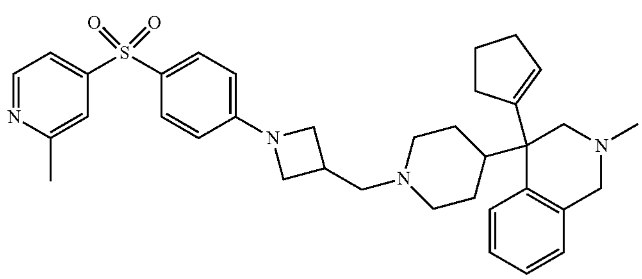 [SMILES: Cc1cc(S(=O)(=O)c2ccc(N3CC(CN4CCC(C5(C6=CCCC6)CN(C)Cc6ccccc65)CC4)C3)cc2)ccn1] |
| IV-204 | 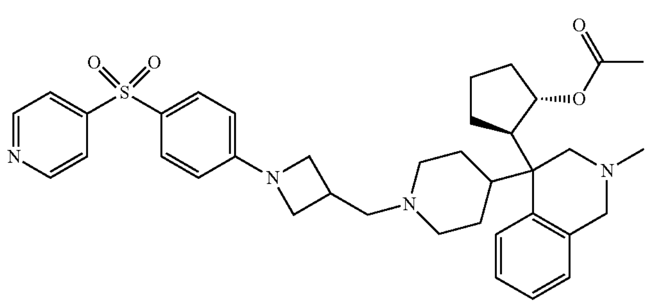 [SMILES: CC(=O)O[C@H]1CCC[C@@H]1C1(C2CCN(CC3CN(c4ccc(S(=O)(=O)c5ccncc5)cc4)C3)CC2)CN(C)Cc2ccccc21] |

TABLE 4-continued

| No. | Structure |
| --- | --- |
| IV-205 | 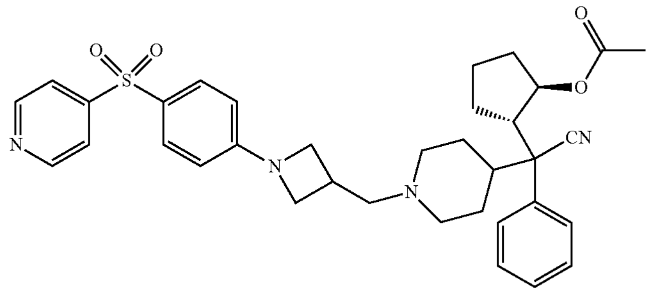 [SMILES: CC(=O)O[C@@H]1CCC[C@H]1C(C#N)(c1ccccc1)C1CCN(CC2CN(c3ccc(S(=O)(=O)c4ccncc4)cc3)C2)CC1] |
| IV-206 | 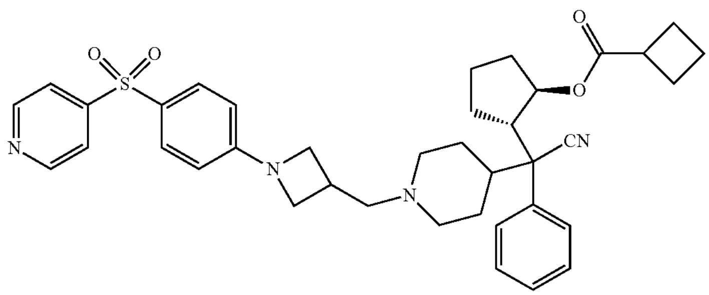 [SMILES: N#CC(c1ccccc1)(C1CCN(CC2CN(c3ccc(S(=O)(=O)c4ccncc4)cc3)C2)CC1)[C@@H]1CCC[C@H]1OC(=O)C1CCC1] |
| IV-207 | 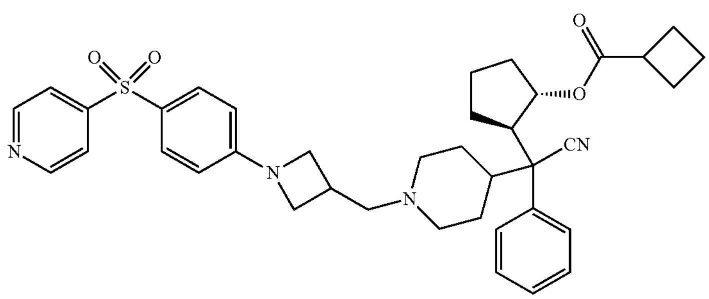 [SMILES: N#CC(c1ccccc1)(C1CCN(CC2CN(c3ccc(S(=O)(=O)c4ccncc4)cc3)C2)CC1)[C@H]1CCC[C@@H]1OC(=O)C1CCC1] |
| IV-208 | 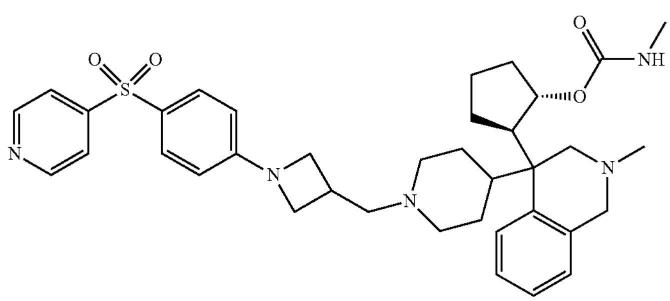 [SMILES: CNC(=O)O[C@H]1CCC[C@@H]1C1(C2CCN(CC3CN(c4ccc(S(=O)(=O)c5ccncc5)cc4)C3)CC2)CN(C)Cc2ccccc21] |
| IV-209 | 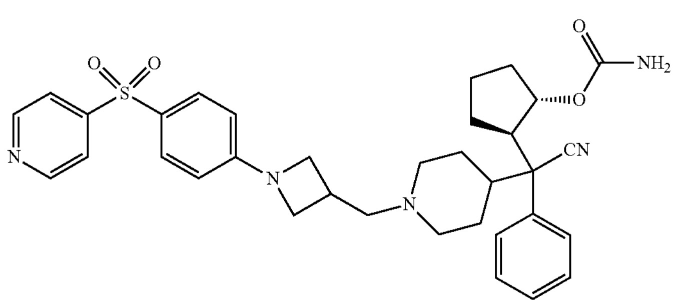 [SMILES: N#CC(c1ccccc1)(C1CCN(CC2CN(c3ccc(S(=O)(=O)c4ccncc4)cc3)C2)CC1)[C@H]1CCC[C@@H]1OC(N)=O] |

TABLE 4-continued

| No. | Structure |
|---|---|
| IV-210 | 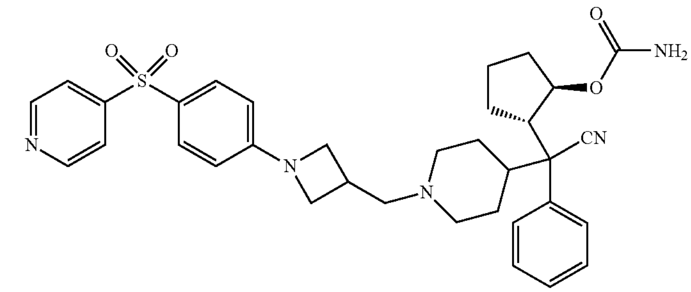 [SMILES: N#CC(c1ccccc1)(C1CCN(CC2CN(c3ccc(S(=O)(=O)c4ccncc4)cc3)C2)CC1)[C@@H]1CCC[C@H]1OC(N)=O] |
| IV-211 | 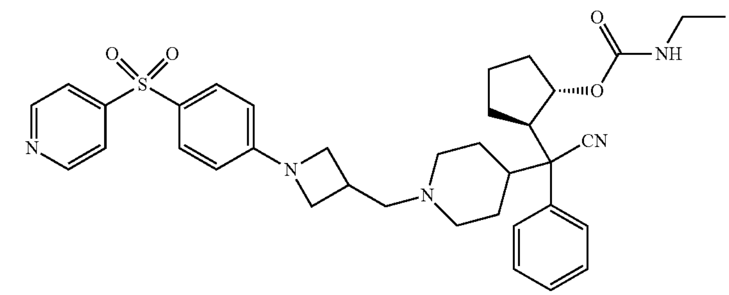 [SMILES: CCNC(=O)O[C@H]1CCC[C@@H]1C(C#N)(c1ccccc1)C1CCN(CC2CN(c3ccc(S(=O)(=O)c4ccncc4)cc3)C2)CC1] |
| IV-212 | 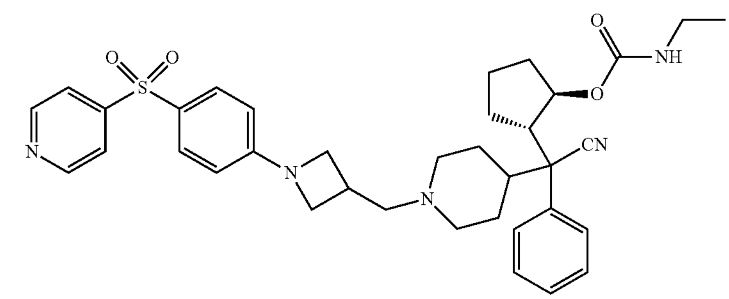 [SMILES: CCNC(=O)O[C@@H]1CCC[C@H]1C(C#N)(c1ccccc1)C1CCN(CC2CN(c3ccc(S(=O)(=O)c4ccncc4)cc3)C2)CC1] |
| IV-213 | 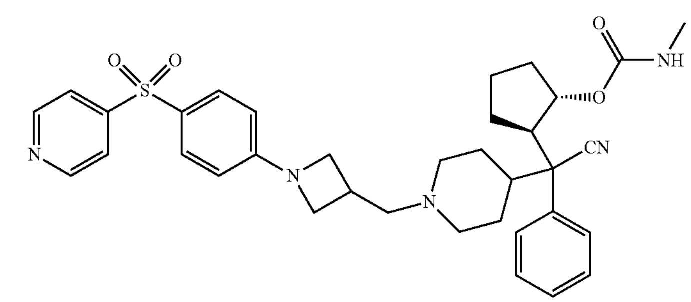 [SMILES: CNC(=O)O[C@H]1CCC[C@@H]1C(C#N)(c1ccccc1)C1CCN(CC2CN(c3ccc(S(=O)(=O)c4ccncc4)cc3)C2)CC1] |
| IV-214 | 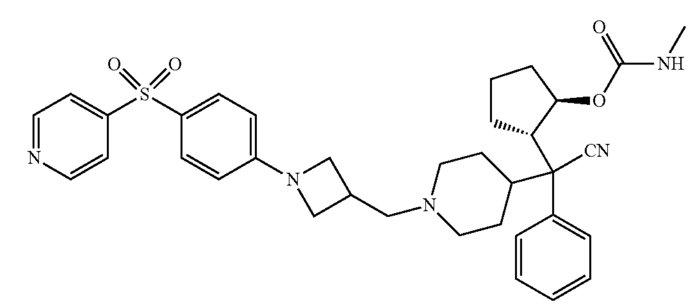 [SMILES: CNC(=O)O[C@@H]1CCC[C@H]1C(C#N)(c1ccccc1)C1CCN(CC2CN(c3ccc(S(=O)(=O)c4ccncc4)cc3)C2)CC1] |

TABLE 4-continued

| No. | Structure |
|---|---|
| IV-215 | 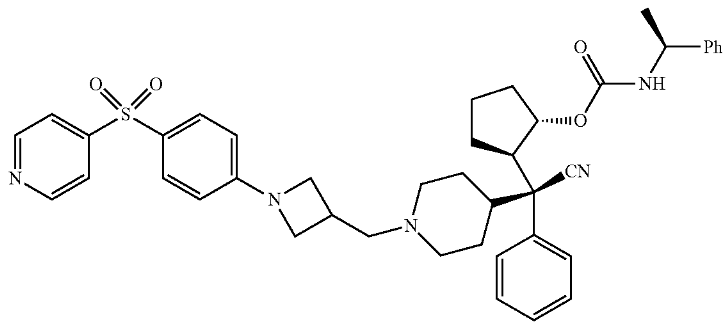 |
| IV-216 | 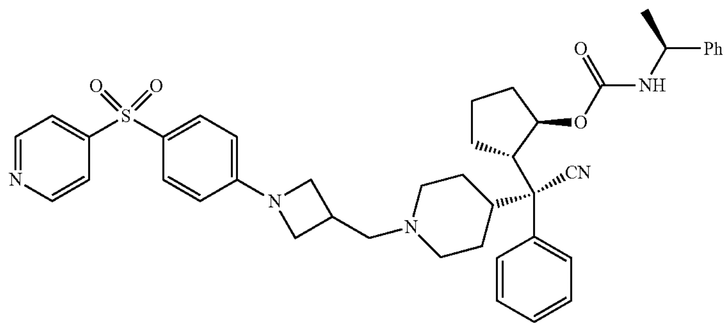 |
| IV-217 | 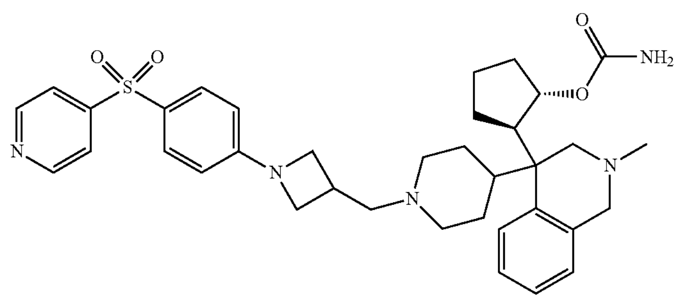 [SMILES: CN1Cc2ccccc2C(C2CCN(CC3CN(c4ccc(S(=O)(=O)c5ccncc5)cc4)C3)CC2)([C@H]2CCC[C@@H]2OC(N)=O)C1] |
| IV-218 | 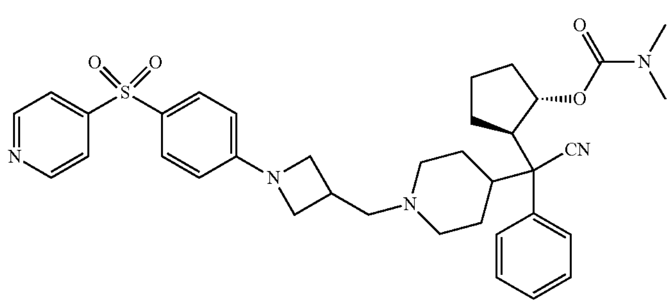 [SMILES: CN(C)C(=O)O[C@H]1CCC[C@@H]1C(C#N)(c1ccccc1)C1CCN(CC2CN(c3ccc(S(=O)(=O)c4ccncc4)cc3)C2)CC1] |
| IV-219 | 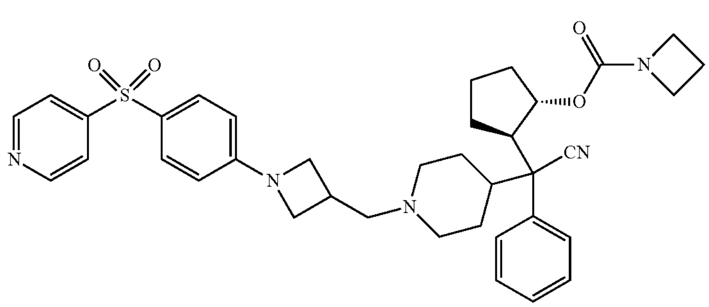 [SMILES: N#CC(c1ccccc1)(C1CCN(CC2CN(c3ccc(S(=O)(=O)c4ccncc4)cc3)C2)CC1)[C@H]1CCC[C@@H]1OC(=O)N1CCC1] |

TABLE 4-continued

| No. | Structure |
|---|---|
| IV-220 | 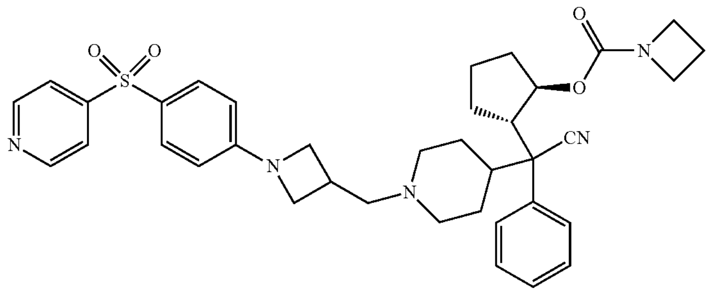 [SMILES: N#CC(c1ccccc1)(C1CCN(CC2CN(c3ccc(S(=O)(=O)c4ccncc4)cc3)C2)CC1)[C@@H]1CCC[C@H]1OC(=O)N1CCC1] |
| IV-221 | 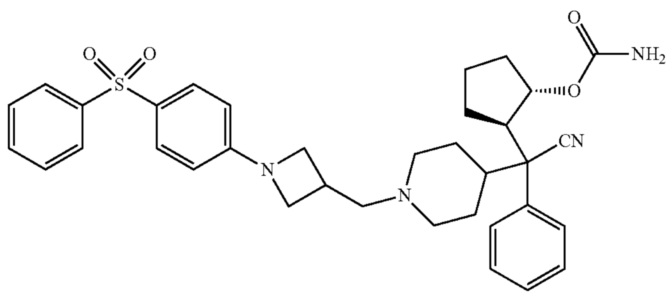 [SMILES: N#CC(c1ccccc1)(C1CCN(CC2CN(c3ccc(S(=O)(=O)c4ccccc4)cc3)C2)CC1)[C@H]1CCC[C@@H]1OC(N)=O] |
| IV-222 | 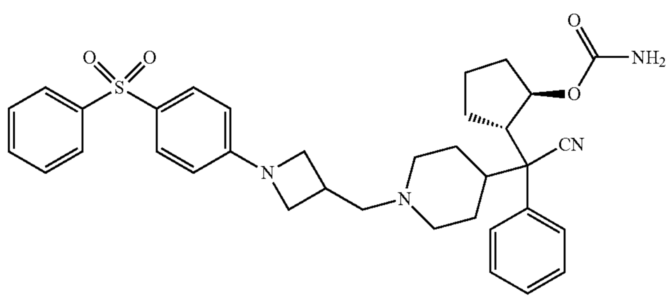 [SMILES: N#CC(c1ccccc1)(C1CCN(CC2CN(c3ccc(S(=O)(=O)c4ccccc4)cc3)C2)CC1)[C@@H]1CCC[C@H]1OC(N)=O] |
| IV-223 | 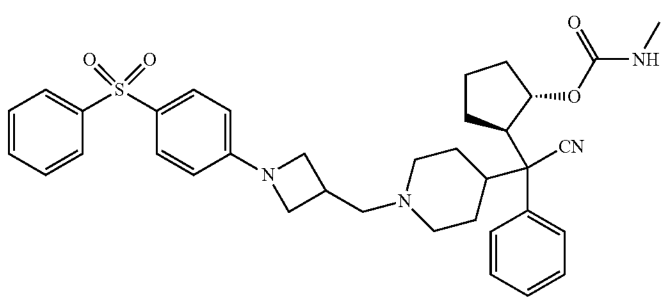 [SMILES: CNC(=O)O[C@H]1CCC[C@@H]1C(C#N)(c1ccccc1)C1CCN(CC2CN(c3ccc(S(=O)(=O)c4ccccc4)cc3)C2)CC1] |
| IV-224 | 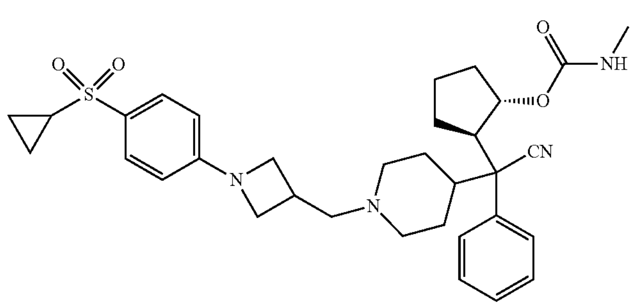 [SMILES: CNC(=O)O[C@H]1CCC[C@@H]1C(C#N)(c1ccccc1)C1CCN(CC2CN(c3ccc(S(=O)(=O)C4CC4)cc3)C2)CC1] |

TABLE 4-continued

| No. | Structure |
|---|---|
| IV-225 | 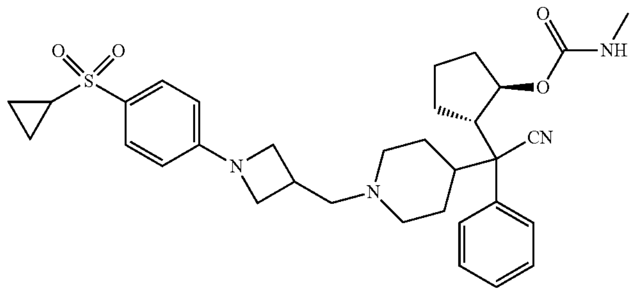 [SMILES: CNC(=O)O[C@@H]1CCC[C@H]1C(C#N)(c1ccccc1)C1CCN(CC2CN(c3ccc(S(=O)(=O)C4CC4)cc3)C2)CC1] |
| IV-226 | 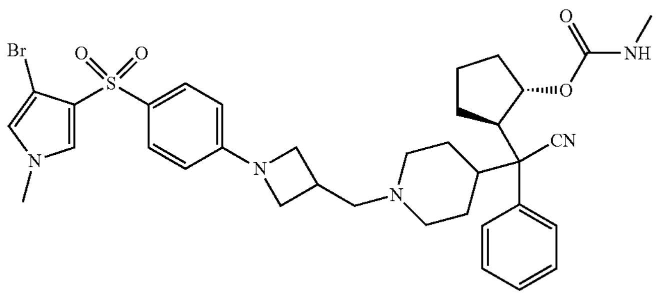 [SMILES: CNC(=O)O[C@H]1CCC[C@@H]1C(C#N)(c1ccccc1)C1CCN(CC2CN(c3ccc(S(=O)(=O)c4cn(C)cc4Br)cc3)C2)CC1] |
| IV-227 | 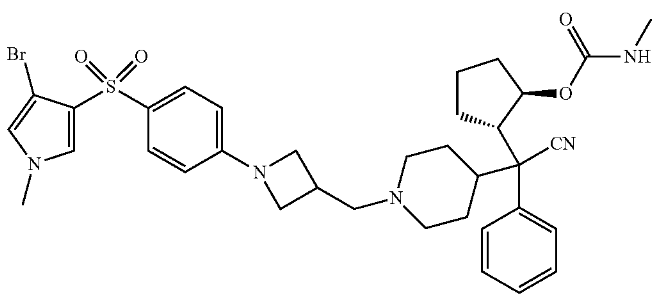 [SMILES: CNC(=O)O[C@@H]1CCC[C@H]1C(C#N)(c1ccccc1)C1CCN(CC2CN(c3ccc(S(=O)(=O)c4cn(C)cc4Br)cc3)C2)CC1] |
| IV-228 | 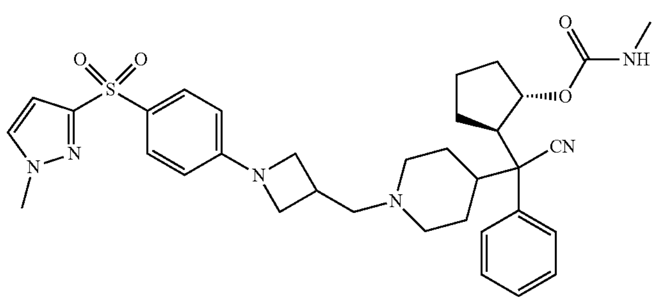 [SMILES: CNC(=O)O[C@H]1CCC[C@@H]1C(C#N)(c1ccccc1)C1CCN(CC2CN(c3ccc(S(=O)(=O)c4ccn(C)n4)cc3)C2)CC1] |
| IV-229 | 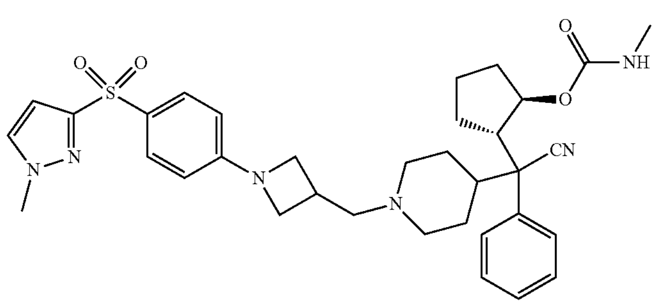 [SMILES: CNC(=O)O[C@@H]1CCC[C@H]1C(C#N)(c1ccccc1)C1CCN(CC2CN(c3ccc(S(=O)(=O)c4ccn(C)n4)cc3)C2)CC1] |

TABLE 4-continued

| No. | Structure |
|---|---|
| IV-230 | 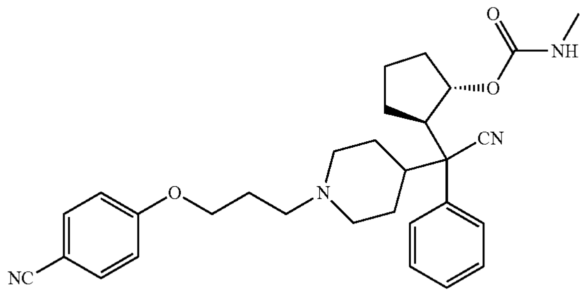 [SMILES: CNC(=O)O[C@H]1CCC[C@@H]1C(C#N)(c1ccccc1)C1CCN(CCCOc2ccc(C#N)cc2)CC1] |
| IV-231 | 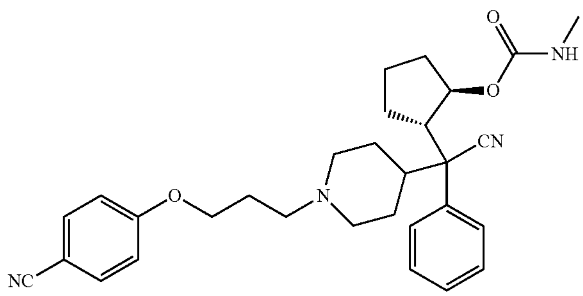 [SMILES: CNC(=O)O[C@@H]1CCC[C@H]1C(C#N)(c1ccccc1)C1CCN(CCCOc2ccc(C#N)cc2)CC1] |
| IV-232 | 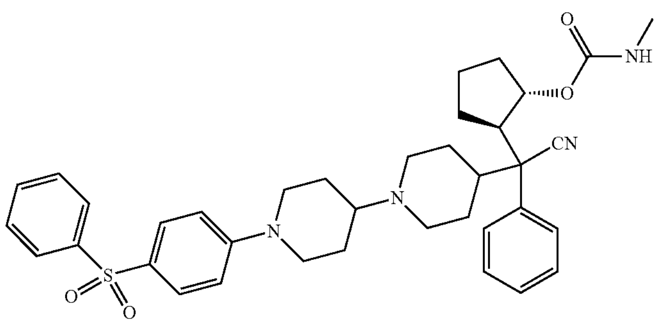 [SMILES: CNC(=O)O[C@H]1CCC[C@@H]1C(C#N)(c1ccccc1)C1CCN(C2CCN(c3ccc(S(=O)(=O)c4ccccc4)cc3)CC2)CC1] |
| IV-233 | 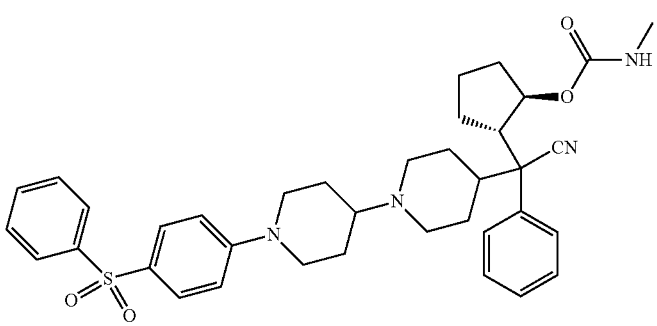 [SMILES: CNC(=O)O[C@@H]1CCC[C@H]1C(C#N)(c1ccccc1)C1CCN(C2CCN(c3ccc(S(=O)(=O)c4ccccc4)cc3)CC2)CC1] |
| IV-234 | 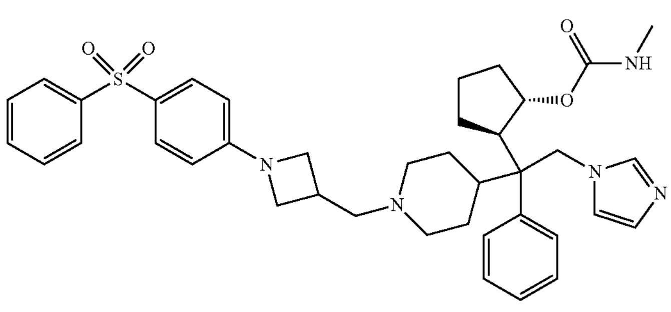 [SMILES: CNC(=O)O[C@H]1CCC[C@@H]1C(Cn1ccnc1)(c1ccccc1)C1CCN(CC2CN(c3ccc(S(=O)(=O)c4ccccc4)cc3)C2)CC1] |

TABLE 4-continued

| No. | Structure |
|---|---|
| IV-235 | 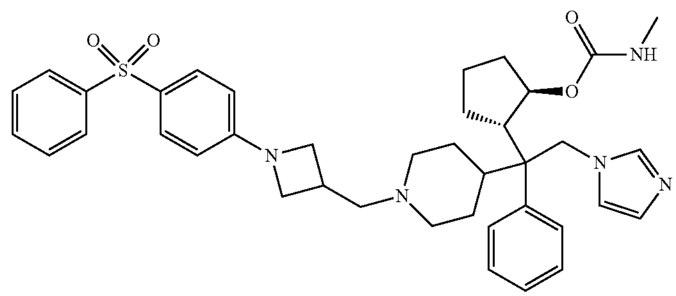 [SMILES: CNC(=O)O[C@@H]1CCC[C@H]1C(Cn1ccnc1)(c1ccccc1)C1CCN(CC2CN(c3ccc(S(=O)(=O)c4ccccc4)cc3)C2)CC1] |
| IV-236 | 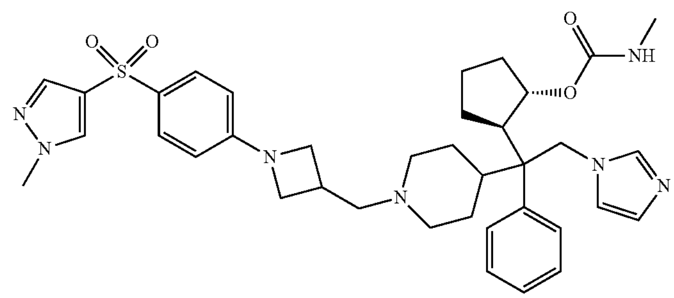 [SMILES: CNC(=O)O[C@H]1CCC[C@@H]1C(Cn1ccnc1)(c1ccccc1)C1CCN(CC2CN(c3ccc(S(=O)(=O)c4cnn(C)c4)cc3)C2)CC1] |
| IV-237 | 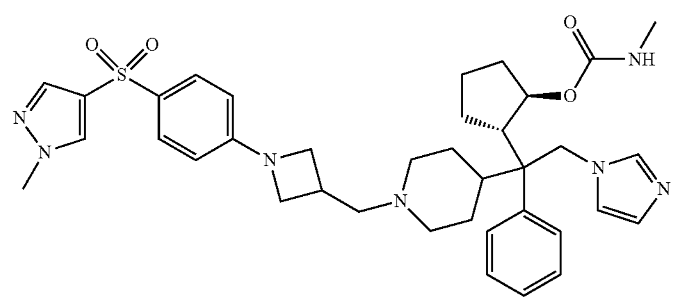 [SMILES: CNC(=O)O[C@@H]1CCC[C@H]1C(Cn1ccnc1)(c1ccccc1)C1CCN(CC2CN(c3ccc(S(=O)(=O)c4cnn(C)c4)cc3)C2)CC1] |
| IV-238 | 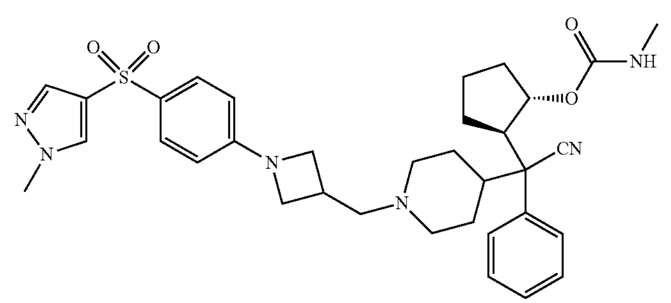 [SMILES: CNC(=O)O[C@H]1CCC[C@@H]1C(C#N)(c1ccccc1)C1CCN(CC2CN(c3ccc(S(=O)(=O)c4cnn(C)c4)cc3)C2)CC1] |
| IV-239 | 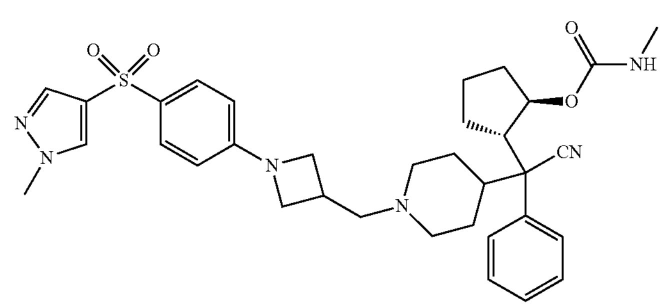 [SMILES: CNC(=O)O[C@@H]1CCC[C@H]1C(C#N)(c1ccccc1)C1CCN(CC2CN(c3ccc(S(=O)(=O)c4cnn(C)c4)cc3)C2)CC1] |

TABLE 4-continued
| No. | Structure |
|---|---|
| IV-240 | 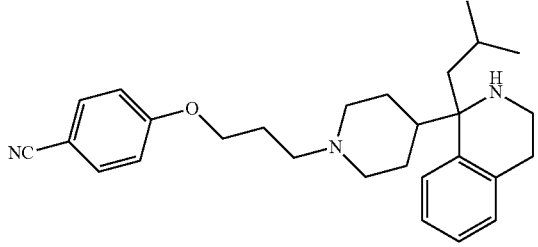 [SMILES: CC(C)CC1(C2CCN(CCCOc3ccc(C#N)cc3)CC2)NCCc2ccccc21] |
| IV-241 | 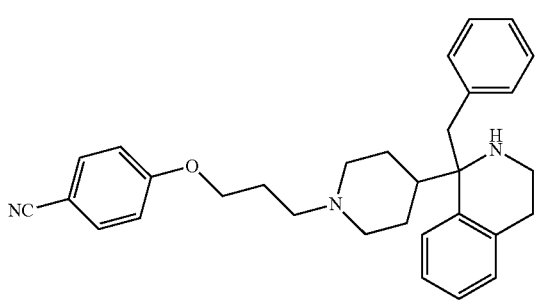 [SMILES: N#Cc1ccc(OCCCN2CCC(C3(Cc4ccccc4)NCCc4ccccc43)CC2)cc1] |
| IV-242 | 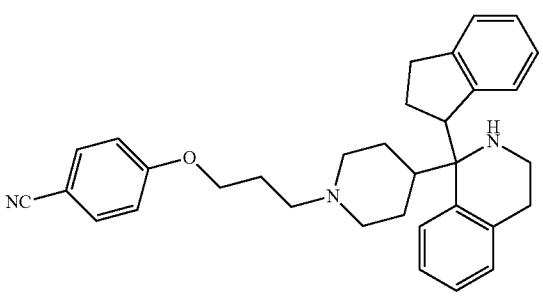 [SMILES: N#Cc1ccc(OCCCN2CCC(C3(C4CCc5ccccc54)NCCc4ccccc43)CC2)cc1] |
| IV-243 | 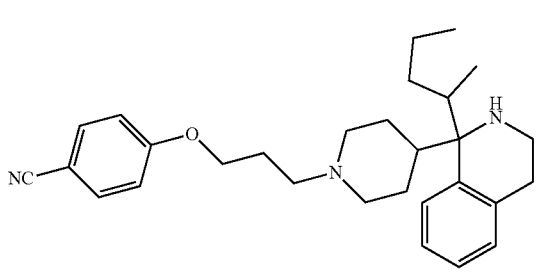 [SMILES: CCCC(C)C1(C2CCN(CCCOc3ccc(C#N)cc3)CC2)NCCc2ccccc21] |
| IV-244 | 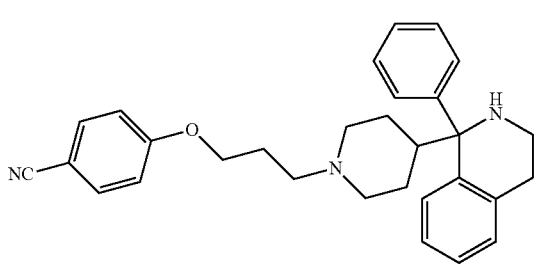 [SMILES: N#Cc1ccc(OCCCN2CCC(C3(c4ccccc4)NCCc4ccccc43)CC2)cc1] |
| IV-245 | 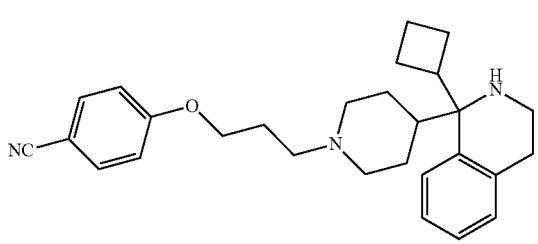 [SMILES: N#Cc1ccc(OCCCN2CCC(C3(C4CCC4)NCCc4ccccc43)CC2)cc1] |

TABLE 4-continued

| No. | Structure |
|---|---|
| IV-246 | 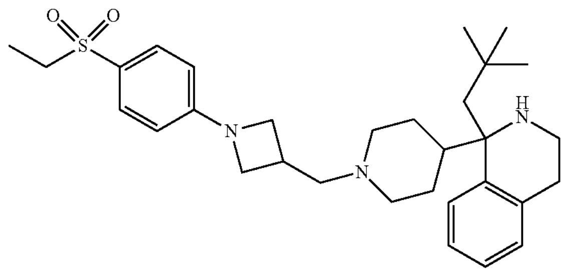 [SMILES: CCS(=O)(=O)c1ccc(N2CC(CN3CCC(C4(CC(C)(C)C)NCCc5ccccc54)CC3)C2)cc1] |
| IV-247 | 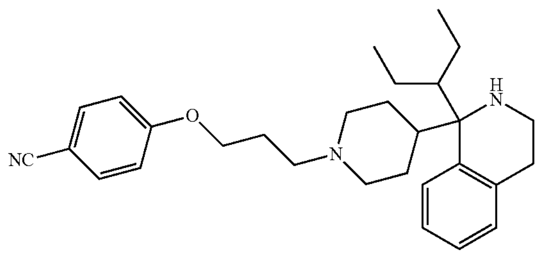 [SMILES: CCC(CC)C1(C2CCN(CCCOc3ccc(C#N)cc3)CC2)NCCc2ccccc21] |
| IV-248 | 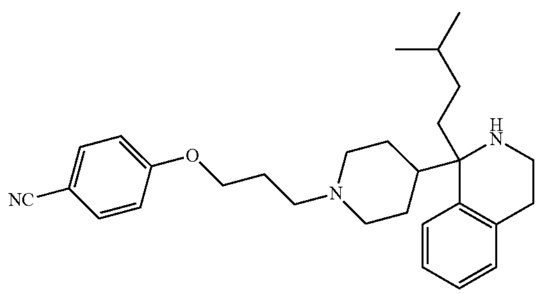 [SMILES: CC(C)CCC1(C2CCN(CCCOc3ccc(C#N)cc3)CC2)NCCc2ccccc21] |
| IV-249 | 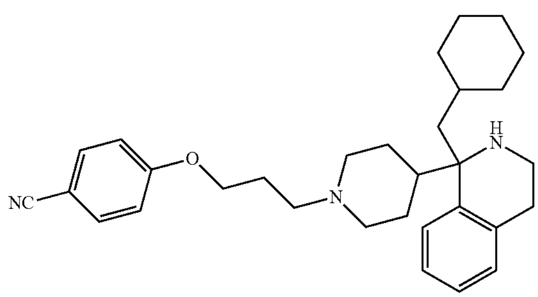 [SMILES: N#Cc1ccc(OCCCN2CCC(C3(CC4CCCCC4)NCCc4ccccc43)CC2)cc1] |
| IV-250 | 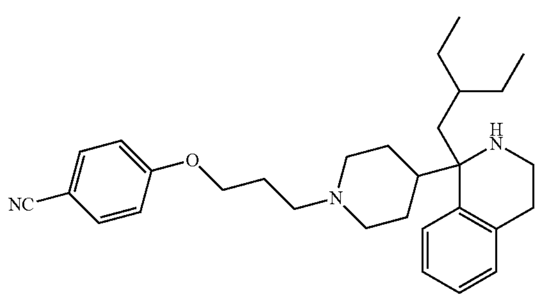 [SMILES: CCC(CC)CC1(C2CCN(CCCOc3ccc(C#N)cc3)CC2)NCCc2ccccc21] |

TABLE 4-continued

| No. | Structure |
|---|---|
| IV-251 | 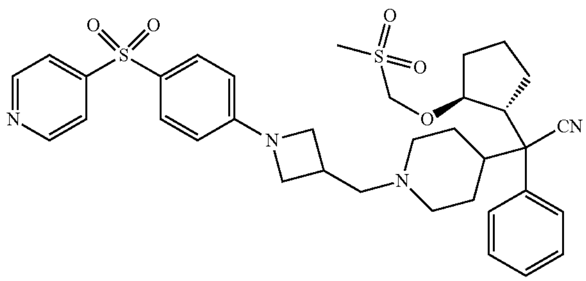 [SMILES: CS(=O)(=O)CO[C@H]1CCC[C@@H]1C(C#N)(c1ccccc1)C1CCN(CC2CN(c3ccc(S(=O)(=O)c4ccncc4)cc3)C2)CC1] |
| IV-252 | 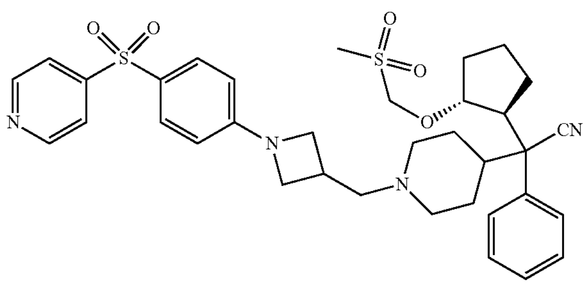 [SMILES: CS(=O)(=O)CO[C@@H]1CCC[C@H]1C(C#N)(c1ccccc1)C1CCN(CC2CN(c3ccc(S(=O)(=O)c4ccncc4)cc3)C2)CC1] |
| IV-253 | 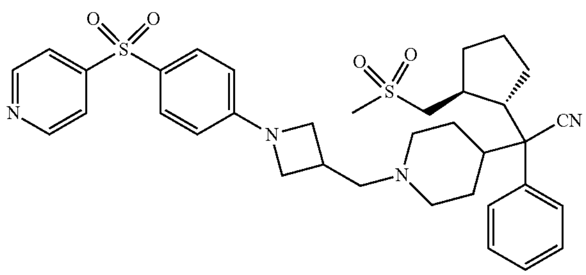 [SMILES: CS(=O)(=O)C[C@H]1CCC[C@@H]1C(C#N)(c1ccccc1)C1CCN(CC2CN(c3ccc(S(=O)(=O)c4ccncc4)cc3)C2)CC1] |
| IV-254 | 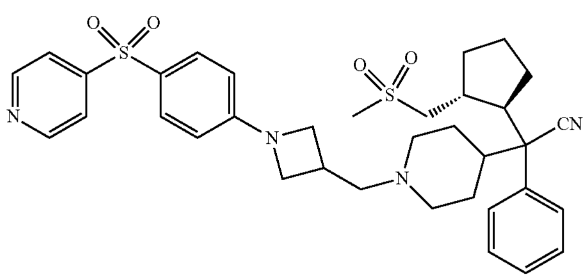 [SMILES: CS(=O)(=O)C[C@@H]1CCC[C@H]1C(C#N)(c1ccccc1)C1CCN(CC2CN(c3ccc(S(=O)(=O)c4ccncc4)cc3)C2)CC1] |
| IV-255 | 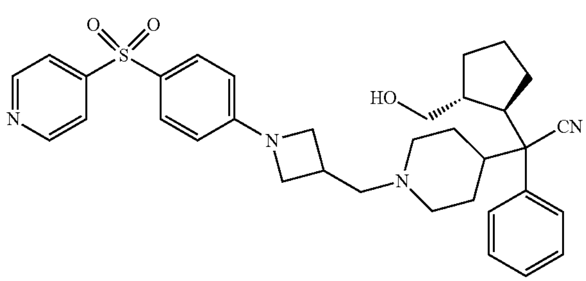 [SMILES: N#CC(c1ccccc1)(C1CCN(CC2CN(c3ccc(S(=O)(=O)c4ccncc4)cc3)C2)CC1)[C@@H]1CCC[C@H]1CO] |

TABLE 4-continued

| No. | Structure |
|---|---|
| IV-256 | 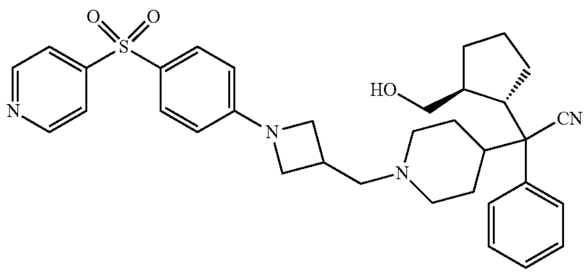 [SMILES: N#CC(c1ccccc1)(C1CCN(CC2CN(c3ccc(S(=O)(=O)c4ccncc4)cc3)C2)CC1)[C@H]1CCC[C@@H]1CO] |
| IV-257 | 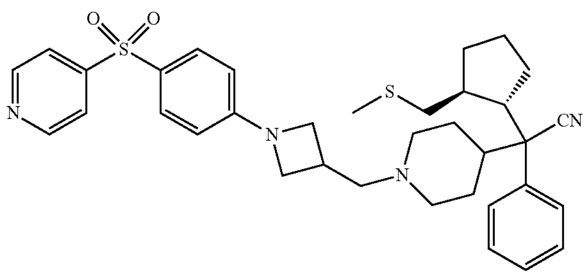 [SMILES: CSC[C@H]1CCC[C@@H]1C(C#N)(c1ccccc1)C1CCN(CC2CN(c3ccc(S(=O)(=O)c4ccncc4)cc3)C2)CC1] |
| IV-258 | 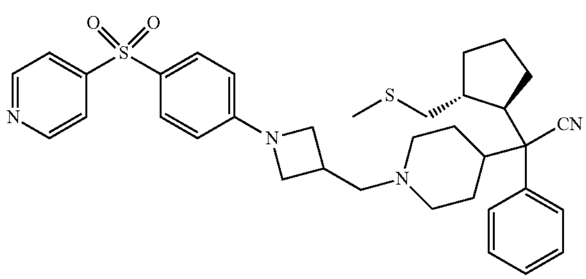 [SMILES: CSC[C@@H]1CCC[C@H]1C(C#N)(c1ccccc1)C1CCN(CC2CN(c3ccc(S(=O)(=O)c4ccncc4)cc3)C2)CC1] |
| IV-259 | 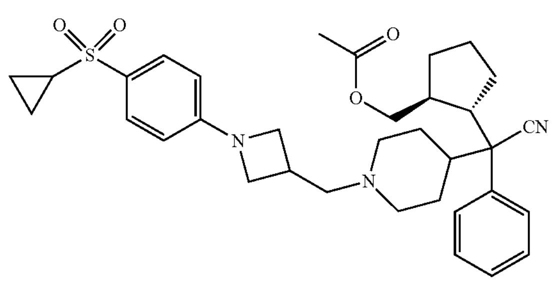 [SMILES: CC(=O)OC[C@H]1CCC[C@@H]1C(C#N)(c1ccccc1)C1CCN(CC2CN(c3ccc(S(=O)(=O)C4CC4)cc3)C2)CC1] |
| IV-260 | 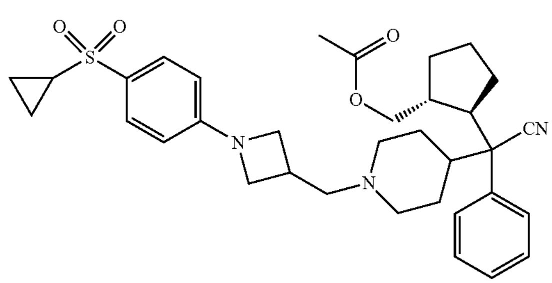 [SMILES: CC(=O)OC[C@@H]1CCC[C@H]1C(C#N)(c1ccccc1)C1CCN(CC2CN(c3ccc(S(=O)(=O)C4CC4)cc3)C2)CC1] |

TABLE 4-continued

| No. | Structure |
|---|---|
| IV-261 | 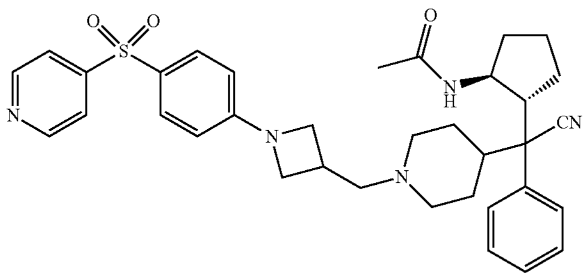 [SMILES: CC(=O)N[C@H]1CCC[C@@H]1C(C#N)(c1ccccc1)C1CCN(CC2CN(c3ccc(S(=O)(=O)c4ccncc4)cc3)C2)CC1] |
| IV-262 | 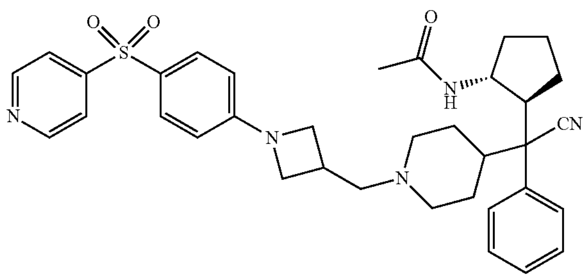 [SMILES: CC(=O)N[C@@H]1CCC[C@H]1C(C#N)(c1ccccc1)C1CCN(CC2CN(c3ccc(S(=O)(=O)c4ccncc4)cc3)C2)CC1] |
| IV-263 | 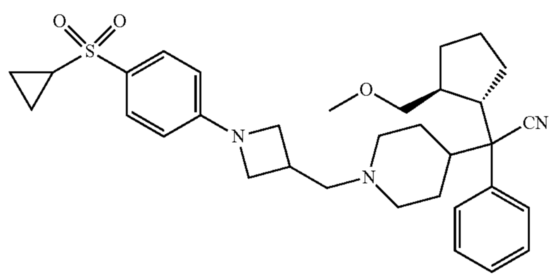 [SMILES: COC[C@H]1CCC[C@@H]1C(C#N)(c1ccccc1)C1CCN(CC2CN(c3ccc(S(=O)(=O)C4CC4)cc3)C2)CC1] |
| IV-264 | 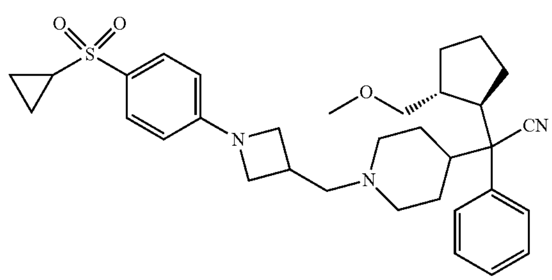 [SMILES: COC[C@@H]1CCC[C@H]1C(C#N)(c1ccccc1)C1CCN(CC2CN(c3ccc(S(=O)(=O)C4CC4)cc3)C2)CC1] |
| IV-265 | 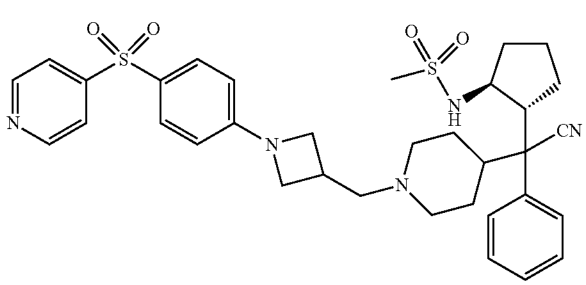 [SMILES: CS(=O)(=O)N[C@H]1CCC[C@@H]1C(C#N)(c1ccccc1)C1CCN(CC2CN(c3ccc(S(=O)(=O)c4ccncc4)cc3)C2)CC1] |

TABLE 4-continued
| No. | Structure |
|---|---|
| IV-266 | 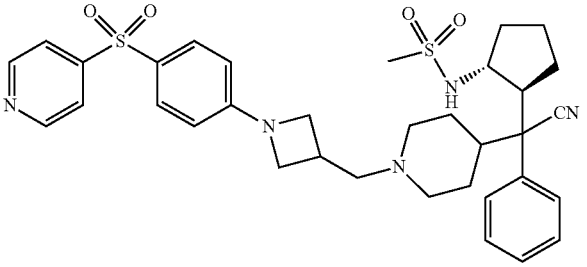 [SMILES: CS(=O)(=O)N[C@@H]1CCC[C@H]1C(C#N)(c1ccccc1)C1CCN(CC2CN(c3ccc(S(=O)(=O)c4ccncc4)cc3)C2)CC1] |
| IV-267 | 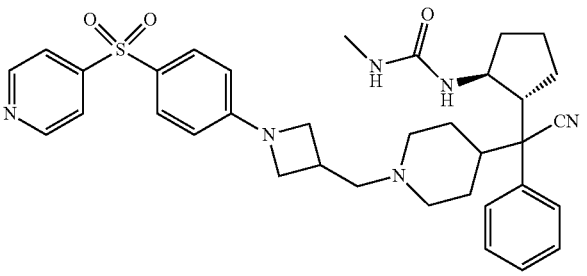 [SMILES: CNC(=O)N[C@H]1CCC[C@@H]1C(C#N)(c1ccccc1)C1CCN(CC2CN(c3ccc(S(=O)(=O)c4ccncc4)cc3)C2)CC1] |
| IV-268 | 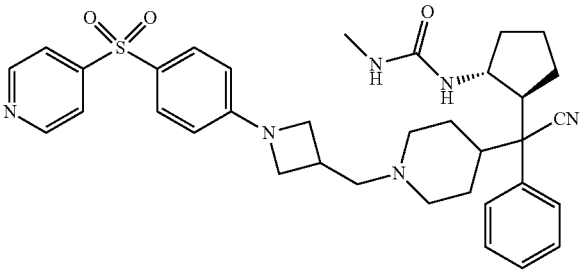 [SMILES: CNC(=O)N[C@@H]1CCC[C@H]1C(C#N)(c1ccccc1)C1CCN(CC2CN(c3ccc(S(=O)(=O)c4ccncc4)cc3)C2)CC1] |
| IV-269 | 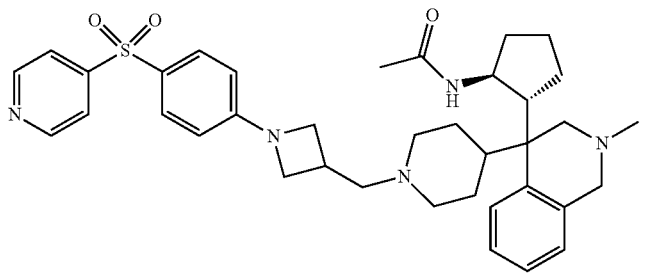 [SMILES: CC(=O)N[C@H]1CCC[C@@H]1C1(C2CCN(CC3CN(c4ccc(S(=O)(=O)c5ccncc5)cc4)C3)CC2)CN(C)Cc2ccccc21] |
| IV-270 | 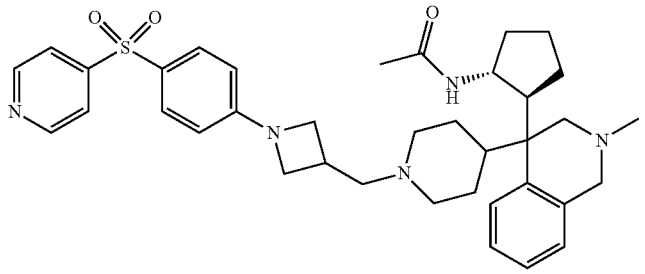 [SMILES: CC(=O)N[C@@H]1CCC[C@H]1C1(C2CCN(CC3CN(c4ccc(S(=O)(=O)c5ccncc5)cc4)C3)CC2)CN(C)Cc2ccccc21] |

TABLE 4-continued
| No. | Structure |
|---|---|
| IV-271 | 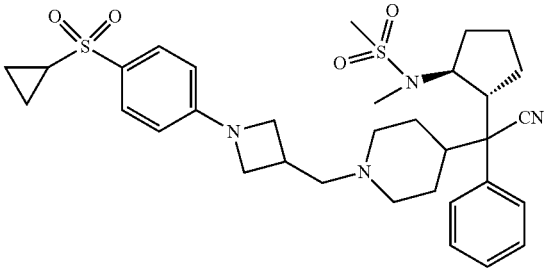 [SMILES: CN([C@H]1CCC[C@@H]1C(C#N)(c1ccccc1)C1CCN(CC2CN(c3ccc(S(=O)(=O)C4CC4)cc3)C2)CC1)S(C)(=O)=O] |
| IV-272 | 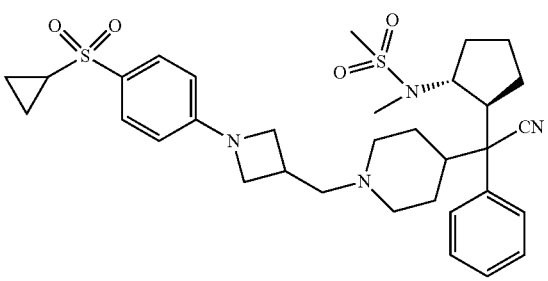 [SMILES: CN([C@@H]1CCC[C@H]1C(C#N)(c1ccccc1)C1CCN(CC2CN(c3ccc(S(=O)(=O)C4CC4)cc3)C2)CC1)S(C)(=O)=O] |
| IV-273 | 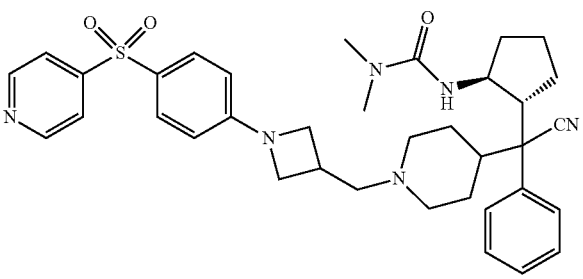 [SMILES: CN(C)C(=O)N[C@H]1CCC[C@@H]1C(C#N)(c1ccccc1)C1CCN(CC2CN(c3ccc(S(=O)(=O)c4ccncc4)cc3)C2)CC1] |
| IV-274 | 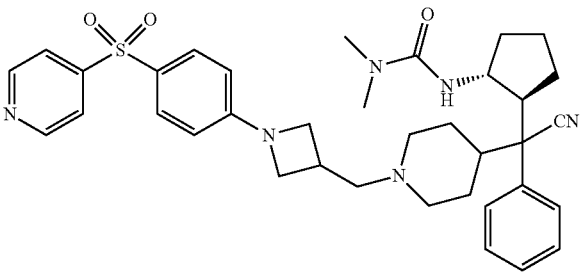 [SMILES: CN(C)C(=O)N[C@@H]1CCC[C@H]1C(C#N)(c1ccccc1)C1CCN(CC2CN(c3ccc(S(=O)(=O)c4ccncc4)cc3)C2)CC1] |
| IV-275 | 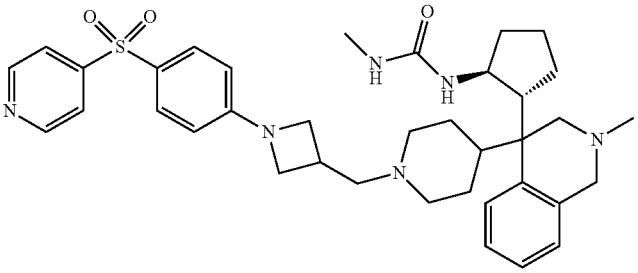 [SMILES: CNC(=O)N[C@H]1CCC[C@@H]1C1(C2CCN(CC3CN(c4ccc(S(=O)(=O)c5ccncc5)cc4)C3)CC2)CN(C)Cc2ccccc21] |

TABLE 4-continued

| No. | Structure |
|---|---|
| IV-276 | 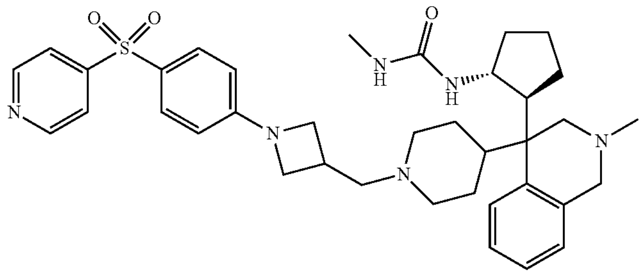 [SMILES: CNC(=O)N[C@@H]1CCC[C@H]1C1(C2CCN(CC3CN(c4ccc(S(=O)(=O)c5ccncc5)cc4)C3)CC2)CN(C)Cc2ccccc21] |
| IV-277 | 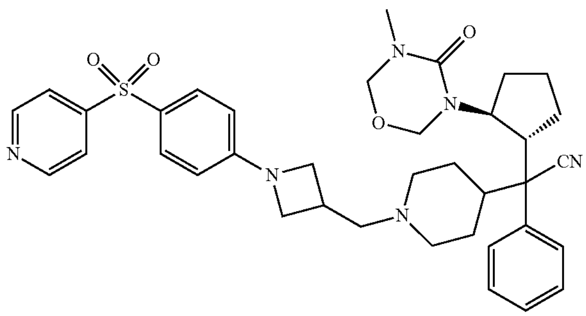 [SMILES: CN1COCN([C@H]2CCC[C@@H]2C(C#N)(c2ccccc2)C2CCN(CC3CN(c4ccc(S(=O)(=O)c5ccncc5)cc4)C3)CC2)C1=O] |
| IV-278 | 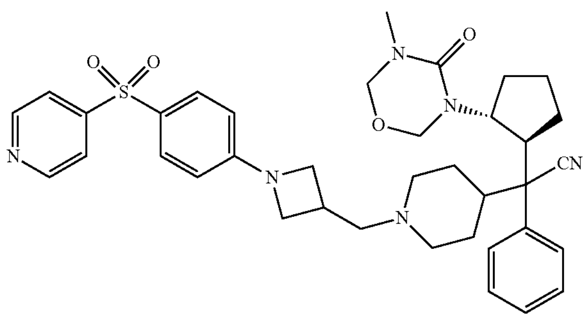 [SMILES: CN1COCN([C@@H]2CCC[C@H]2C(C#N)(c2ccccc2)C2CCN(CC3CN(c4ccc(S(=O)(=O)c5ccncc5)cc4)C3)CC2)C1=O] |
| IV-279 | 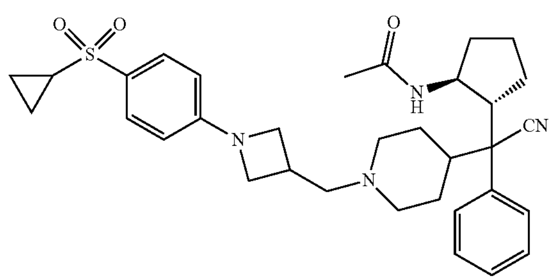 [SMILES: CC(=O)N[C@H]1CCC[C@@H]1C(C#N)(c1ccccc1)C1CCN(CC2CN(c3ccc(S(=O)(=O)C4CC4)cc3)C2)CC1] |
| IV-280 | 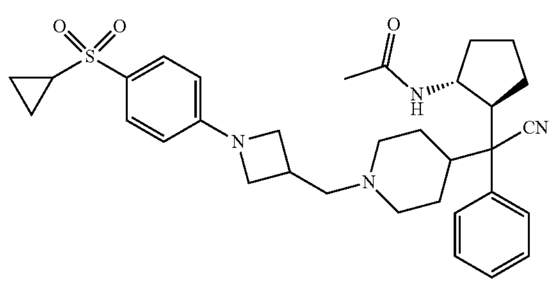 [SMILES: CC(=O)N[C@@H]1CCC[C@H]1C(C#N)(c1ccccc1)C1CCN(CC2CN(c3ccc(S(=O)(=O)C4CC4)cc3)C2)CC1] |

TABLE 4-continued
| No. | Structure |
|---|---|
| IV-281 | 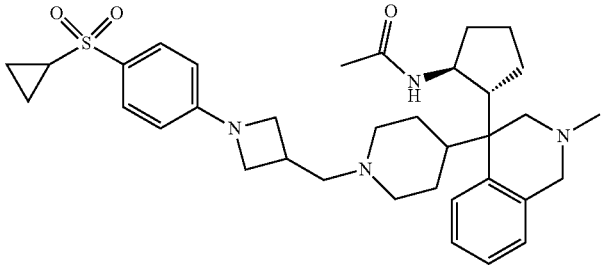 [SMILES: CC(=O)N[C@H]1CCC[C@@H]1C1(C2CCN(CC3CN(c4ccc(S(=O)(=O)C5CC5)cc4)C3)CC2)CN(C)Cc2ccccc21] |
| IV-282 | 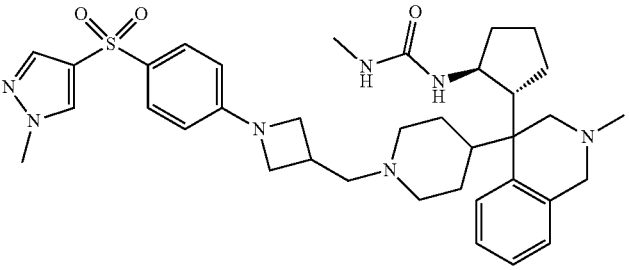 [SMILES: CNC(=O)N[C@H]1CCC[C@@H]1C1(C2CCN(CC3CN(c4ccc(S(=O)(=O)c5cnn(C)c5)cc4)C3)CC2)CN(C)Cc2ccccc21] |
| IV-283 | 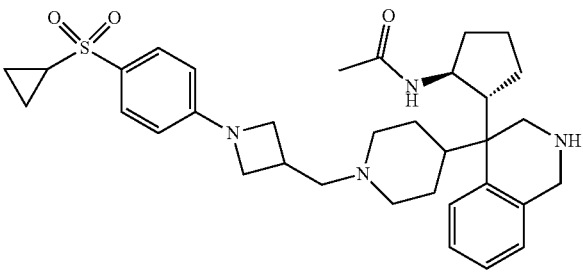 [SMILES: CC(=O)N[C@H]1CCC[C@@H]1C1(C2CCN(CC3CN(c4ccc(S(=O)(=O)C5CC5)cc4)C3)CC2)CNCc2ccccc21] |
| IV-284 | 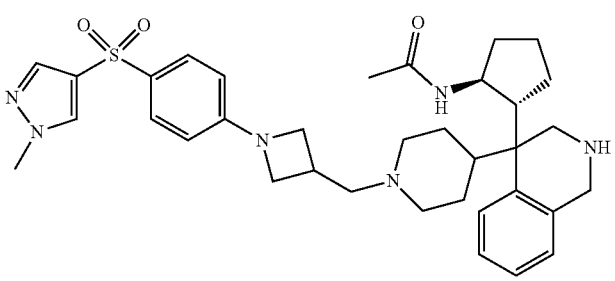 [SMILES: CC(=O)N[C@H]1CCC[C@@H]1C1(C2CCN(CC3CN(c4ccc(S(=O)(=O)c5cnn(C)c5)cc4)C3)CC2)CNCc2ccccc21] |
| IV-285 | 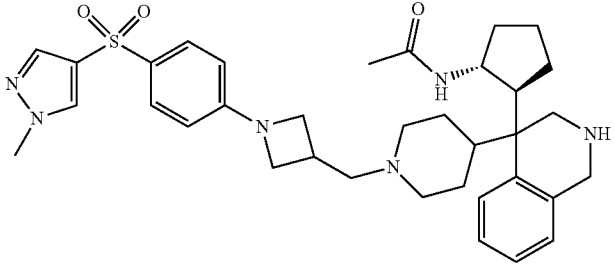 [SMILES: CC(=O)N[C@@H]1CCC[C@H]1C1(C2CCN(CC3CN(c4ccc(S(=O)(=O)c5cnn(C)c5)cc4)C3)CC2)CNCc2ccccc21] |

TABLE 4-continued

| No. | Structure |
|---|---|
| IV-286 | 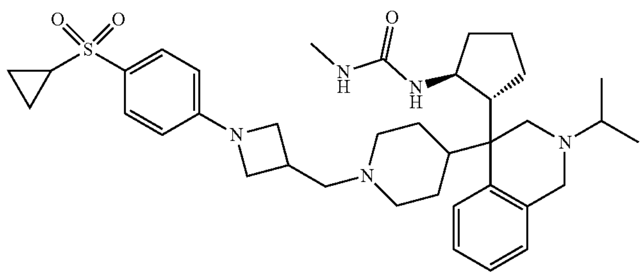 [SMILES: CNC(=O)N[C@H]1CCC[C@@H]1C1(C2CCN(CC3CN(c4ccc(S(=O)(=O)C5CC5)cc4)C3)CC2)CN(C(C)C)Cc2ccccc21] |
| IV-287 | 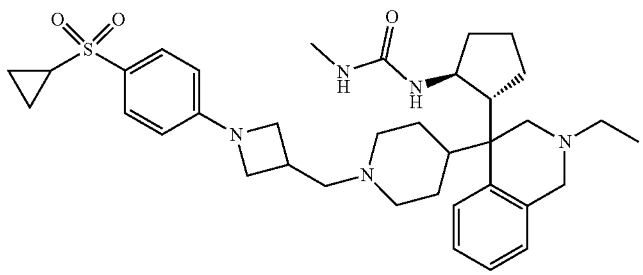 [SMILES: CCN1Cc2ccccc2C(C2CCN(CC3CN(c4ccc(S(=O)(=O)C5CC5)cc4)C3)CC2)([C@H]2CCC[C@@H]2NC(=O)NC)C1] |
| IV-288 | 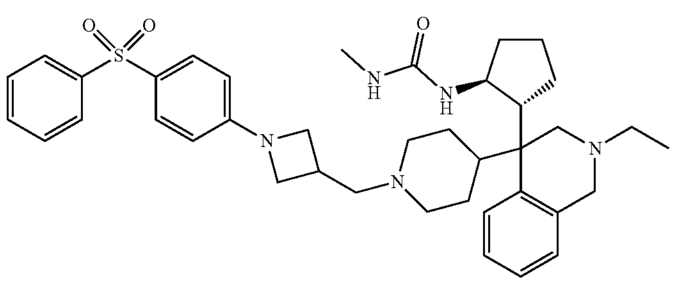 [SMILES: CCN1Cc2ccccc2C(C2CCN(CC3CN(c4ccc(S(=O)(=O)c5ccccc5)cc4)C3)CC2)([C@H]2CCC[C@@H]2NC(=O)NC)C1] |
| IV-289 | 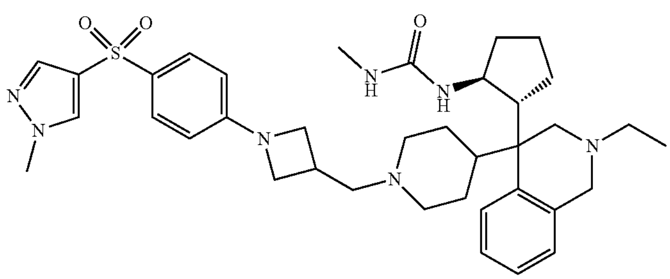 [SMILES: CCN1Cc2ccccc2C(C2CCN(CC3CN(c4ccc(S(=O)(=O)c5cnn(C)c5)cc4)C3)CC2)([C@H]2CCC[C@@H]2NC(=O)NC)C1] |
| IV-290 | 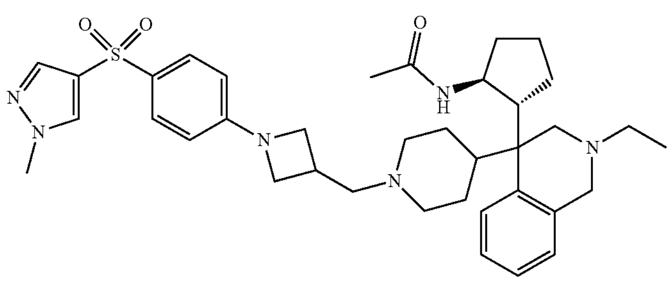 [SMILES: CCN1Cc2ccccc2C(C2CCN(CC3CN(c4ccc(S(=O)(=O)c5cnn(C)c5)cc4)C3)CC2)([C@H]2CCC[C@@H]2NC(C)=O)C1] |

TABLE 4-continued

| No. | Structure |
|---|---|
| IV-291 | 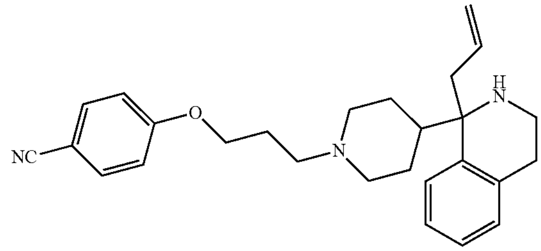 [SMILES: C=CCC1(C2CCN(CCCOc3ccc(C#N)cc3)CC2)NCCc2ccccc21] |
| IV-292 | 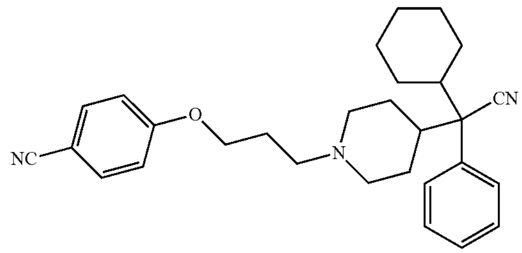 [SMILES: N#Cc1ccc(OCCCN2CCC(C(C#N)(c3ccccc3)C3CCCCC3)CC2)cc1] |
| IV-293 | 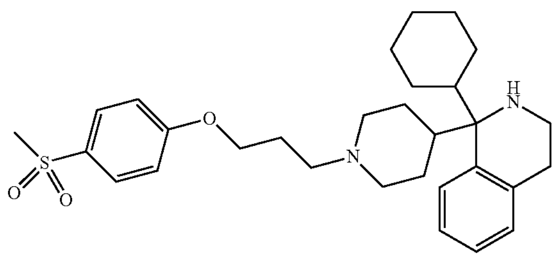 [SMILES: CS(=O)(=O)c1ccc(OCCCN2CCC(C3(C4CCCCC4)NCCc4ccccc43)CC2)cc1] |
| IV-294 | 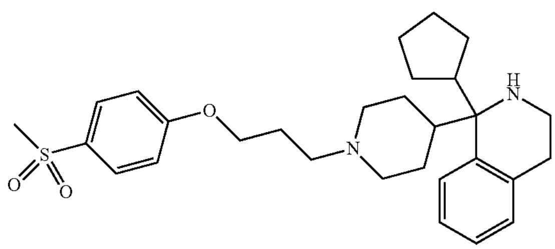 [SMILES: CS(=O)(=O)c1ccc(OCCCN2CCC(C3(C4CCCC4)NCCc4ccccc43)CC2)cc1] |
| IV-295 | 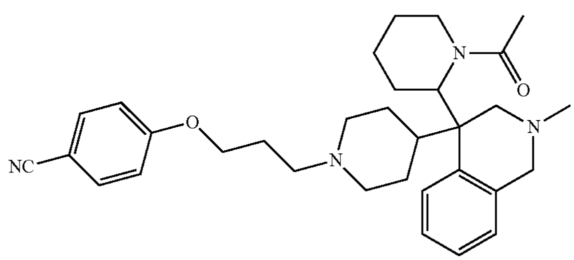 [SMILES: CC(=O)N1CCCCC1C1(C2CCN(CCCOc3ccc(C#N)cc3)CC2)CN(C)Cc2ccccc21] |
| IV-296 | 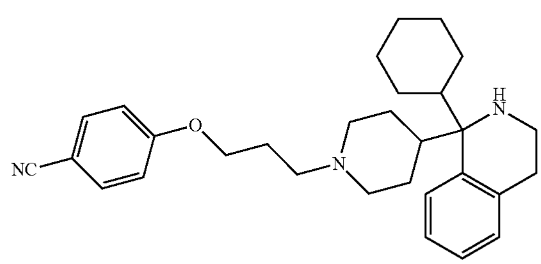 [SMILES: N#Cc1ccc(OCCCN2CCC(C3(C4CCCCC4)NCCc4ccccc43)CC2)cc1] |

TABLE 4-continued

| No. | Structure |
|---|---|
| IV-297 | 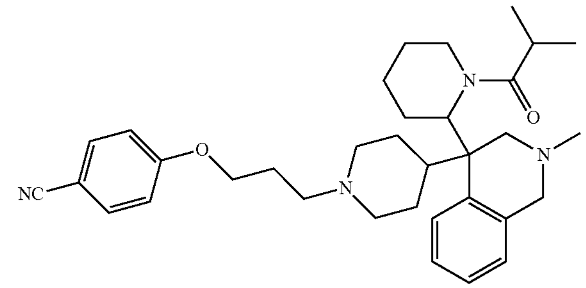 [SMILES: CC(C)C(=O)N1CCCCC1C1(C2CCN(CCCOc3ccc(C#N)cc3)CC2)CN(C)Cc2ccccc21] |
| IV-298 | 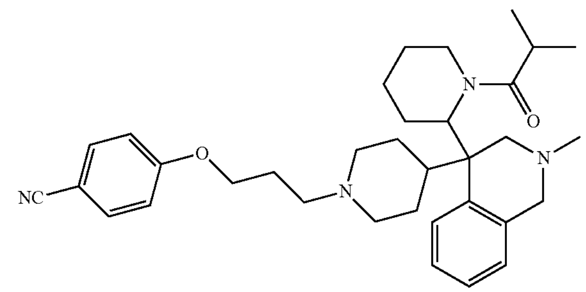 [SMILES: CC(C)C(=O)N1CCCCC1C1(C2CCN(CCCOc3ccc(C#N)cc3)CC2)CN(C)Cc2ccccc21] |
| IV-299 | 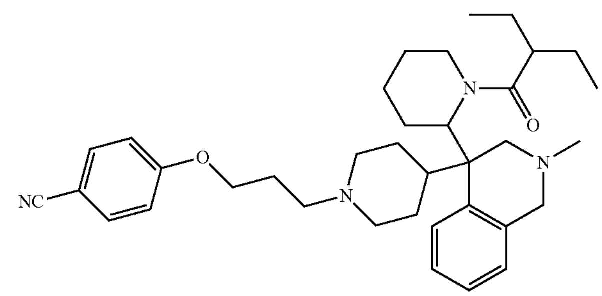 [SMILES: CCC(CC)C(=O)N1CCCCC1C1(C2CCN(CCCOc3ccc(C#N)cc3)CC2)CN(C)Cc2ccccc21] |
| IV-300 | 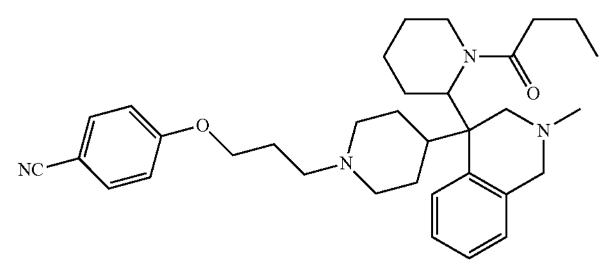 [SMILES: CCCC(=O)N1CCCCC1C1(C2CCN(CCCOc3ccc(C#N)cc3)CC2)CN(C)Cc2ccccc21] |
| IV-301 | 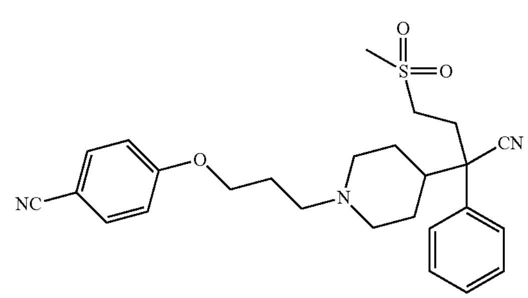 [SMILES: CS(=O)(=O)CCC(C#N)(c1ccccc1)C1CCN(CCCOc2ccc(C#N)cc2)CC1] |

TABLE 4-continued

| No. | Structure |
|---|---|
| IV-302 | 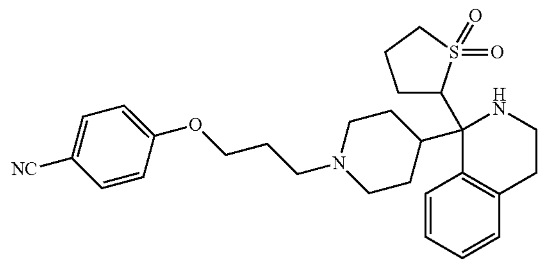 [SMILES: N#Cc1ccc(OCCCN2CCC(C3(C4CCCS4(=O)=O)NCCc4ccccc43)CC2)cc1] |
| IV-303 | 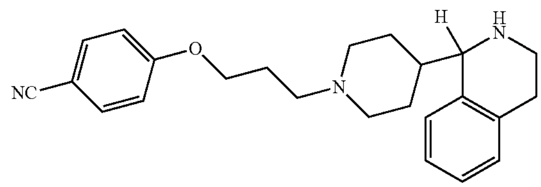 [SMILES: N#Cc1ccc(OCCCN2CCC(C3NCCc4ccccc43)CC2)cc1] |
| IV-304 | 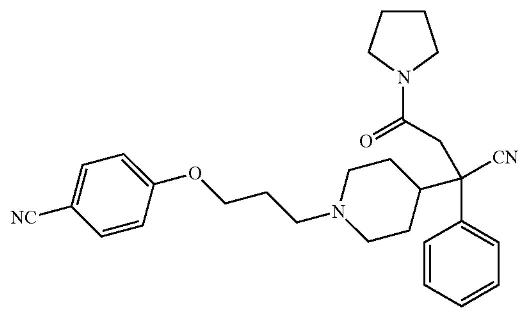 [SMILES: N#Cc1ccc(OCCCN2CCC(C(C#N)(CC(=O)N3CCCC3)c3ccccc3)CC2)cc1] |
| IV-305 | 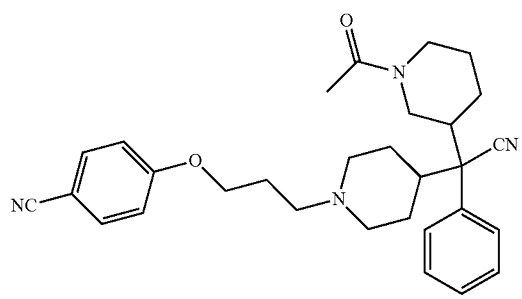 [SMILES: CC(=O)N1CCCC(C(C#N)(c2ccccc2)C2CCN(CCCOc3ccc(C#N)cc3)CC2)C1] |
| IV-306 | 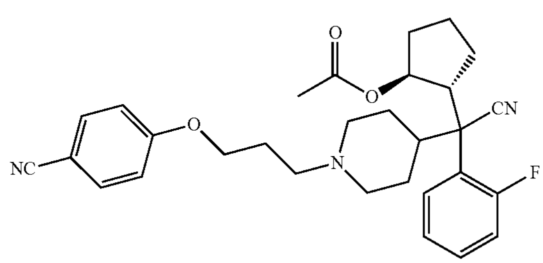 [SMILES: CC(=O)O[C@H]1CCC[C@@H]1C(C#N)(c1ccccc1F)C1CCN(CCCOc2ccc(C#N)cc2)CC1] |
| IV-307 | 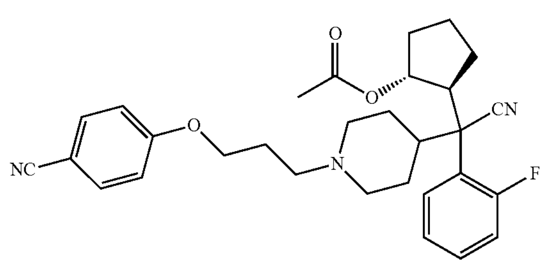 [SMILES: CC(=O)O[C@@H]1CCC[C@H]1C(C#N)(c1ccccc1F)C1CCN(CCCOc2ccc(C#N)cc2)CC1] |

TABLE 4-continued

| No. | Structure |
|---|---|
| IV-308 | 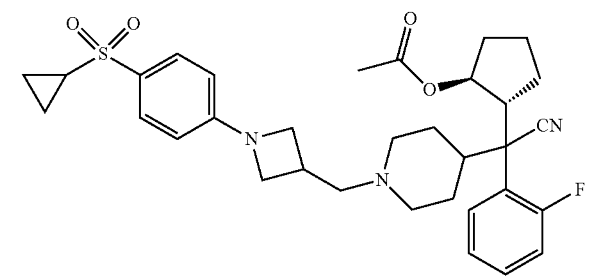 [SMILES: CC(=O)O[C@H]1CCC[C@@H]1C(C#N)(c1ccccc1F)C1CCN(CC2CN(c3ccc(S(=O)(=O)C4CC4)cc3)C2)CC1] |
| IV-309 | 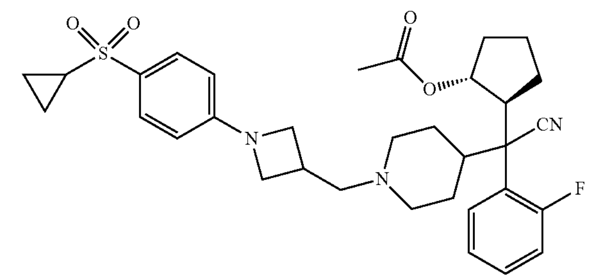 [SMILES: CC(=O)O[C@@H]1CCC[C@H]1C(C#N)(c1ccccc1F)C1CCN(CC2CN(c3ccc(S(=O)(=O)C4CC4)cc3)C2)CC1] |
| IV-310 | 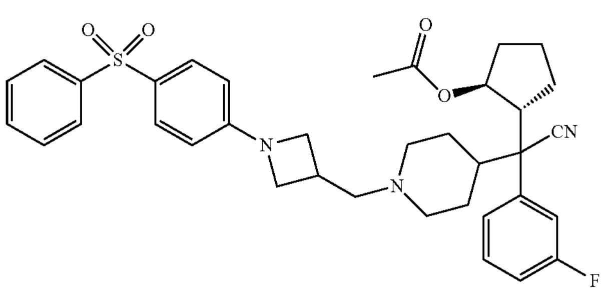 [SMILES: CC(=O)O[C@H]1CCC[C@@H]1C(C#N)(c1cccc(F)c1)C1CCN(CC2CN(c3ccc(S(=O)(=O)c4ccccc4)cc3)C2)CC1] |
| IV-311 | 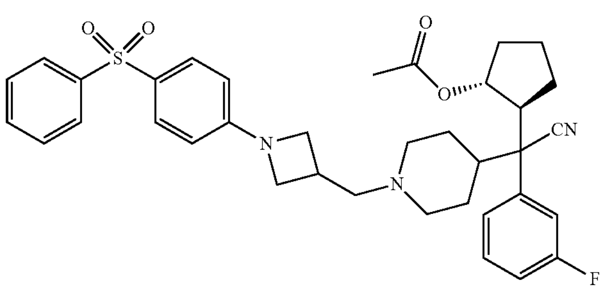 [SMILES: CC(=O)O[C@@H]1CCC[C@H]1C(C#N)(c1cccc(F)c1)C1CCN(CC2CN(c3ccc(S(=O)(=O)c4ccccc4)cc3)C2)CC1] |
| IV-312 | 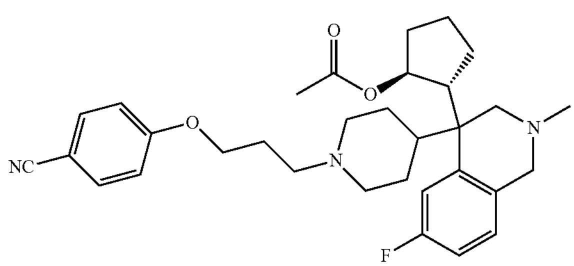 [SMILES: CC(=O)O[C@H]1CCC[C@@H]1C1(C2CCN(CCCOc3ccc(C#N)cc3)CC2)CN(C)Cc2ccc(F)cc21] |

TABLE 4-continued

| No. | Structure |
|---|---|
| IV-313 | 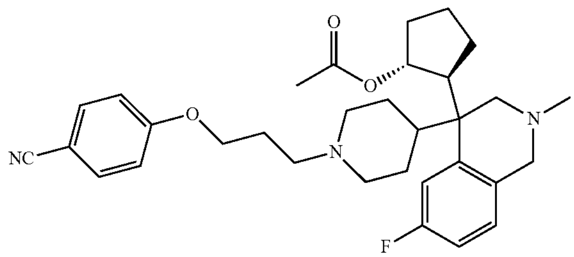 [SMILES: CC(=O)O[C@@H]1CCC[C@H]1C1(C2CCN(CCCOc3ccc(C#N)cc3)CC2)CN(C)Cc2ccc(F)cc21] |
| IV-314 | 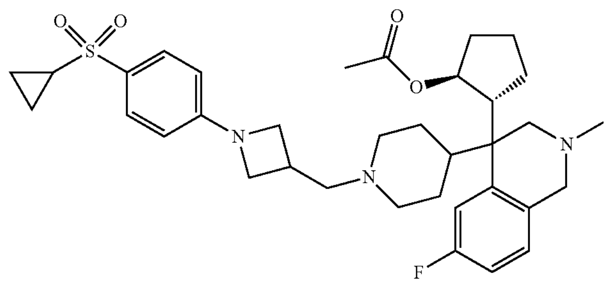 [SMILES: CC(=O)O[C@H]1CCC[C@@H]1C1(C2CCN(CC3CN(c4ccc(S(=O)(=O)C5CC5)cc4)C3)CC2)CN(C)Cc2ccc(F)cc21] |
| IV-315 | 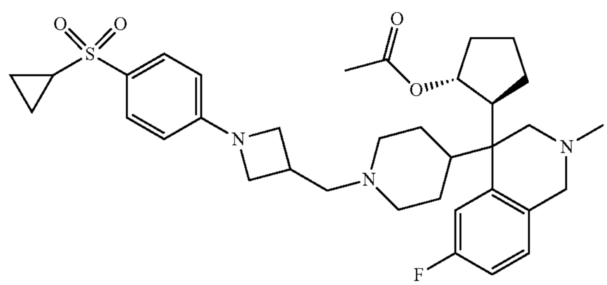 [SMILES: CC(=O)O[C@@H]1CCC[C@H]1C1(C2CCN(CC3CN(c4ccc(S(=O)(=O)C5CC5)cc4)C3)CC2)CN(C)Cc2ccc(F)cc21] |
| IV-316 | 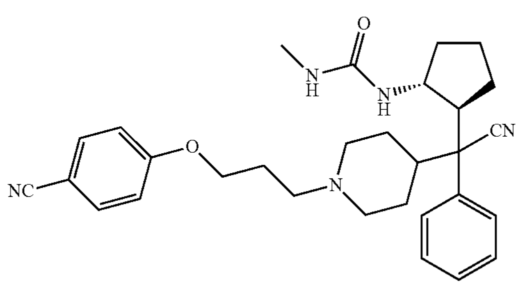 [SMILES: CNC(=O)N[C@@H]1CCC[C@H]1C(C#N)(c1ccccc1)C1CCN(CCCOc2ccc(C#N)cc2)CC1] |
| IV-317 | 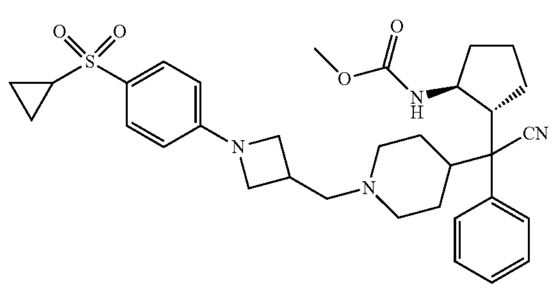 [SMILES: COC(=O)N[C@H]1CCC[C@@H]1C(C#N)(c1ccccc1)C1CCN(CC2CN(c3ccc(S(=O)(=O)C4CC4)cc3)C2)CC1] |

TABLE 4-continued

| No. | Structure |
|---|---|
| IV-318 | 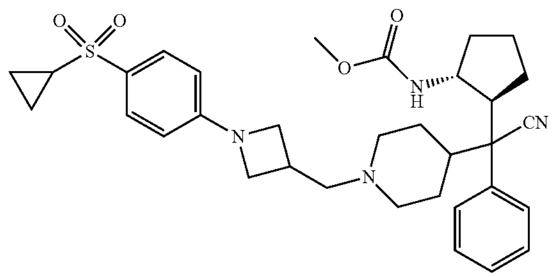 [SMILES: COC(=O)N[C@@H]1CCC[C@H]1C(C#N)(c1ccccc1)C1CCN(CC2CN(c3ccc(S(=O)(=O)C4CC4)cc3)C2)CC1] |
| IV-319 | 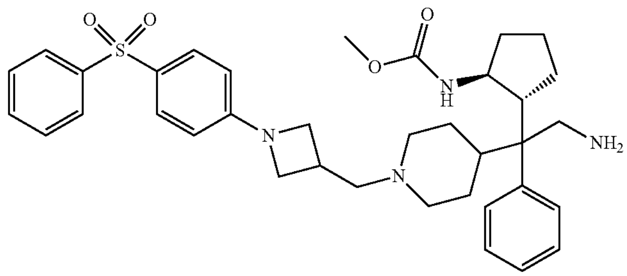 [SMILES: COC(=O)N[C@H]1CCC[C@@H]1C(CN)(c1ccccc1)C1CCN(CC2CN(c3ccc(S(=O)(=O)c4ccccc4)cc3)C2)CC1] |
| IV-320 | 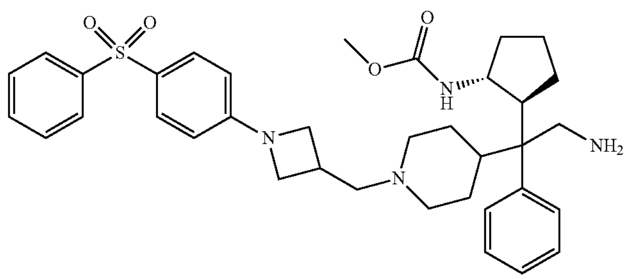 [SMILES: COC(=O)N[C@@H]1CCC[C@H]1C(CN)(c1ccccc1)C1CCN(CC2CN(c3ccc(S(=O)(=O)c4ccccc4)cc3)C2)CC1] |
| IV-321 | 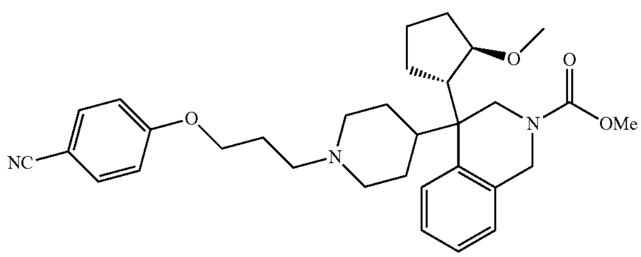 [SMILES: COC(=O)N1Cc2ccccc2C(C2CCN(CCCOc3ccc(C#N)cc3)CC2)([C@@H]2CCC[C@H]2OC)C1] |
| IV-322 | 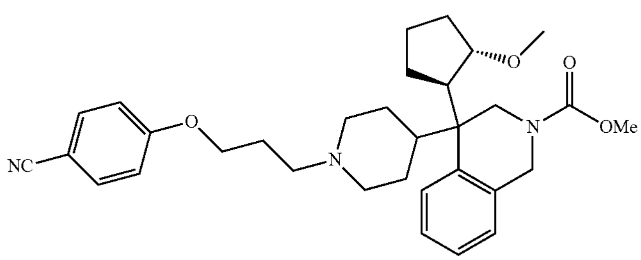 [SMILES: COC(=O)N1Cc2ccccc2C(C2CCN(CCCOc3ccc(C#N)cc3)CC2)([C@H]2CCC[C@@H]2OC)C1] |
| IV-323 | 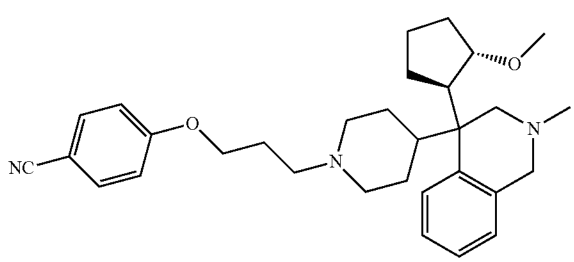 [SMILES: CO[C@H]1CCC[C@@H]1C1(C2CCN(CCCOc3ccc(C#N)cc3)CC2)CN(C)Cc2ccccc21] |

TABLE 4-continued
| No. | Structure |
|---|---|
| IV-324 | 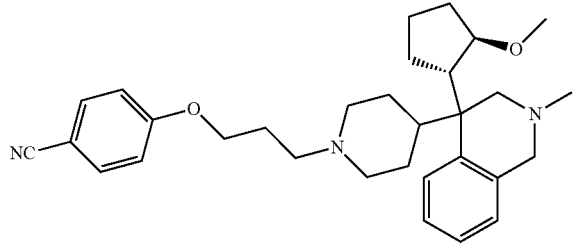 [SMILES: CO[C@@H]1CCC[C@H]1C1(C2CCN(CCCOc3ccc(C#N)cc3)CC2)CN(C)Cc2ccccc21] |
| IV-325 | 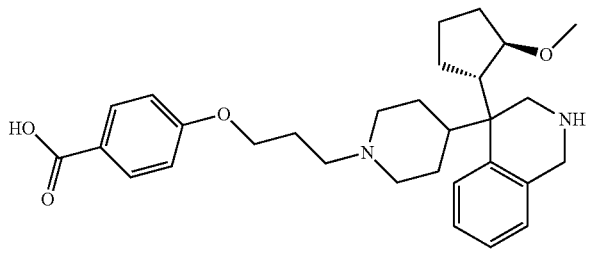 [SMILES: CO[C@@H]1CCC[C@H]1C1(C2CCN(CCCOc3ccc(C(=O)O)cc3)CC2)CNCc2ccccc21] |
| IV-326 | 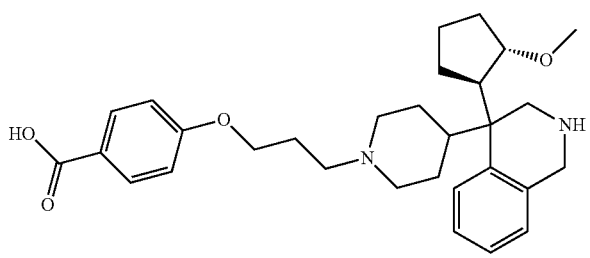 [SMILES: CO[C@H]1CCC[C@@H]1C1(C2CCN(CCCOc3ccc(C(=O)O)cc3)CC2)CNCc2ccccc21] |
| IV-327 | 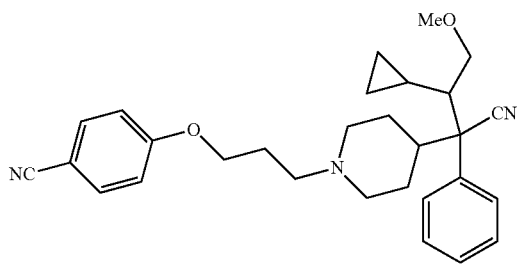 [SMILES: COCC(C1CC1)C(C#N)(c1ccccc1)C1CCN(CCCOc2ccc(C#N)cc2)CC1] |
| IV-328 | 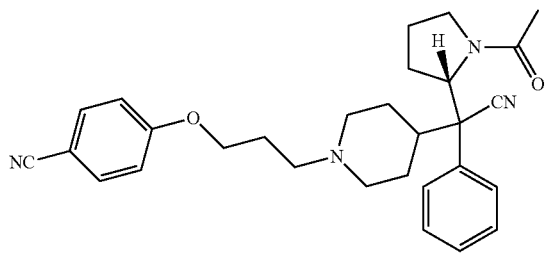 |
| IV-329 | 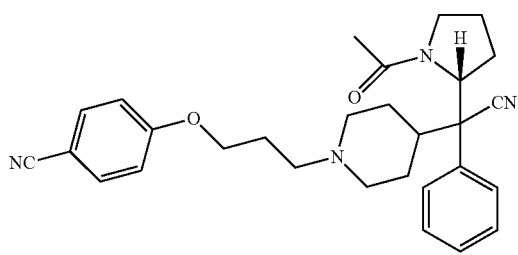 |

TABLE 4-continued

| No. | Structure |
|---|---|
| IV-330 | 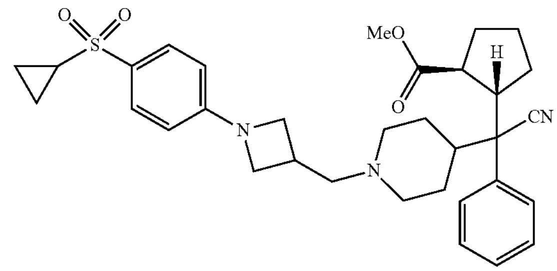 |
| IV-331 | 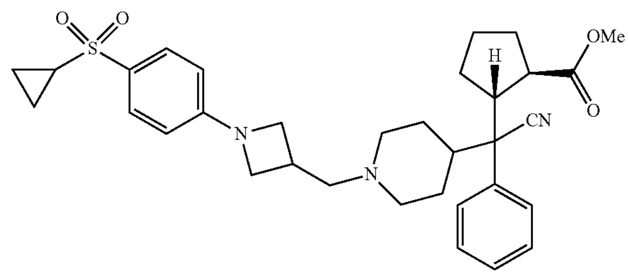 |
| IV-332 | 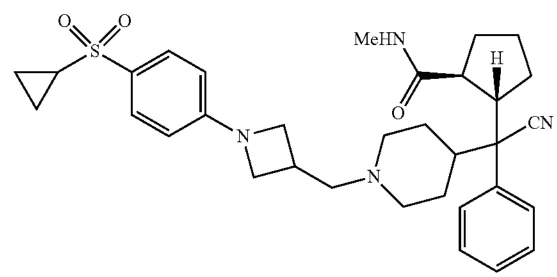 |
| IV-333 | 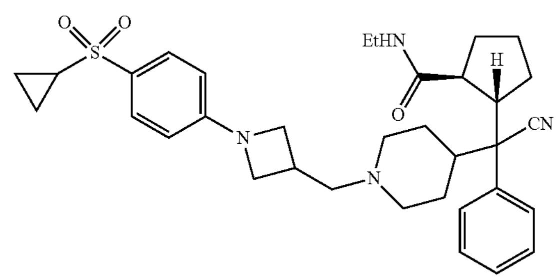 |
| IV-334 | 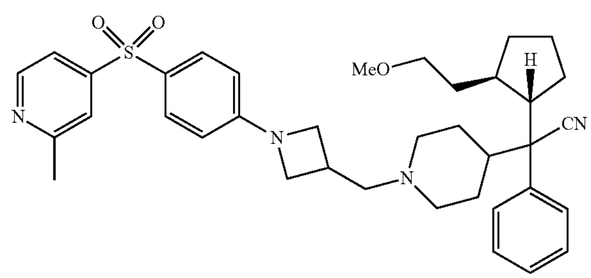 |

TABLE 4-continued

| No. | Structure |
|---|---|
| IV-335 | 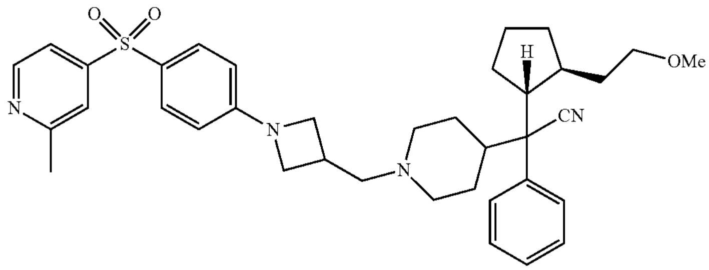 |
| IV-336 | 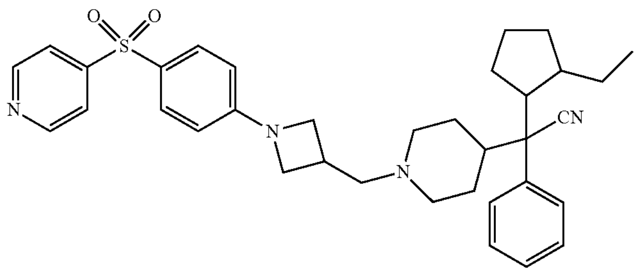 [SMILES: CCC1CCCC1C(C#N)(c1ccccc1)C1CCN(CC2CN(c3ccc(S(=O)(=O)c4ccncc4)cc3)C2)CC1] |
| IV-337 | 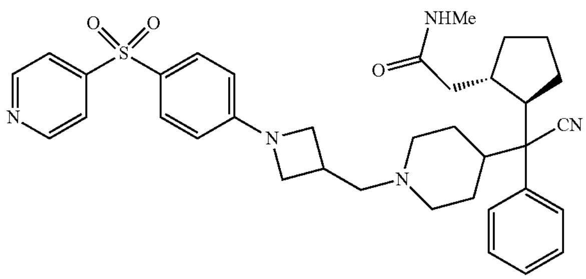 [SMILES: CNC(=O)C[C@@H]1CCC[C@H]1C(C#N)(c1ccccc1)C1CCN(CC2CN(c3ccc(S(=O)(=O)c4ccncc4)cc3)C2)CC1] |
| IV-338 | 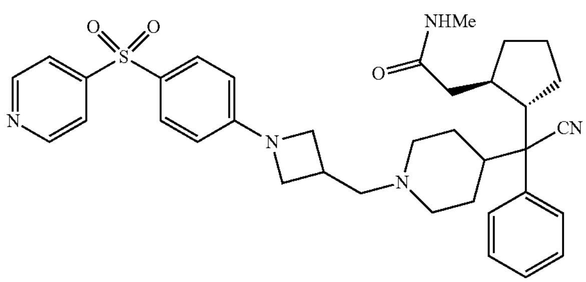 [SMILES: CNC(=O)C[C@H]1CCC[C@@H]1C(C#N)(c1ccccc1)C1CCN(CC2CN(c3ccc(S(=O)(=O)c4ccncc4)cc3)C2)CC1] |
| IV-339 | 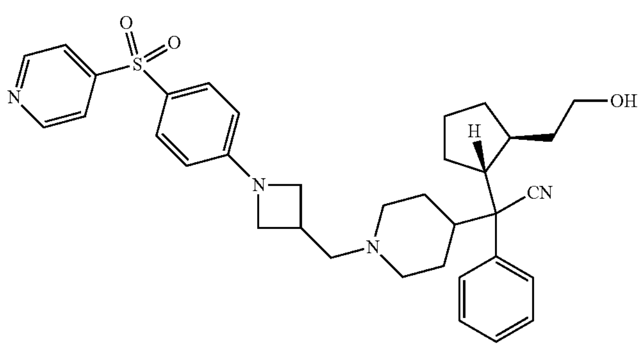 |

TABLE 4-continued

| No. | Structure |
|---|---|
| IV-340 | 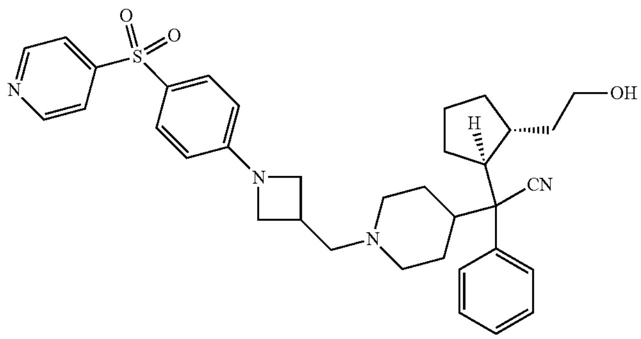 |
| IV-341 | 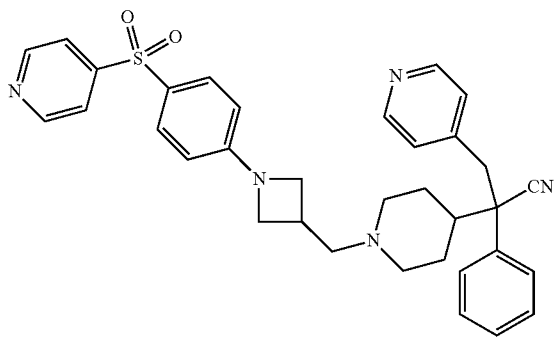 [SMILES: N#CC(Cc1ccncc1)(c1ccccc1)C1CCN(CC2CN(c3ccc(S(=O)(=O)c4ccncc4)cc3)C2)CC1] |
| IV-342 | 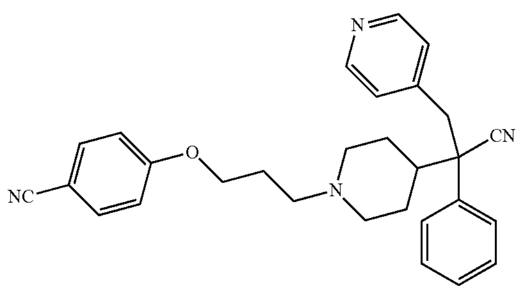 [SMILES: N#Cc1ccc(OCCCN2CCC(C(C#N)(Cc3ccncc3)c3ccccc3)CC2)cc1] |
| IV-343 | 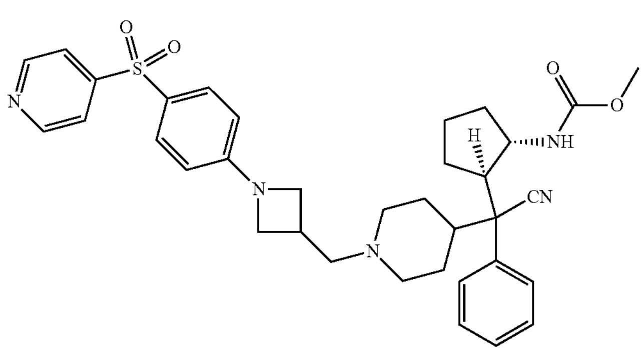 |

TABLE 4-continued
| No. | Structure |
|---|---|
| IV-344 | 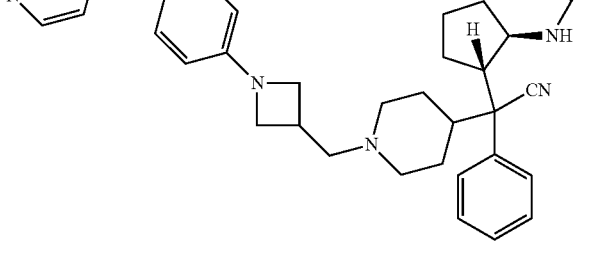 |
| IV-345 | 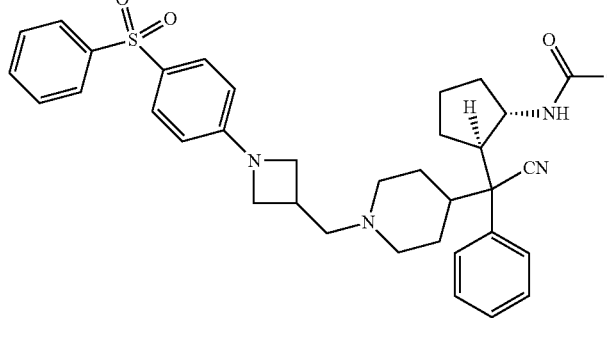 |
| IV-346 | 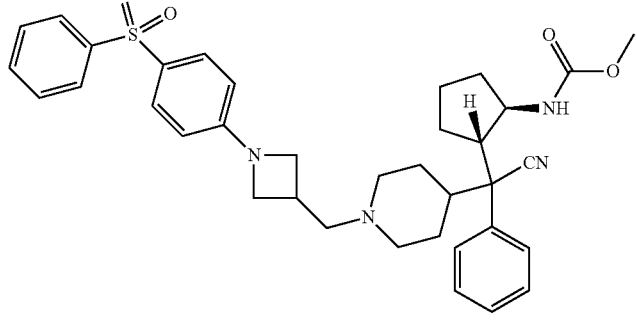 |
| IV-347 | 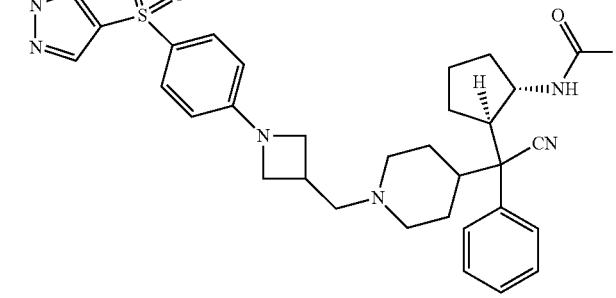 |

TABLE 4-continued

| No. | Structure |
|---|---|
| IV-348 | 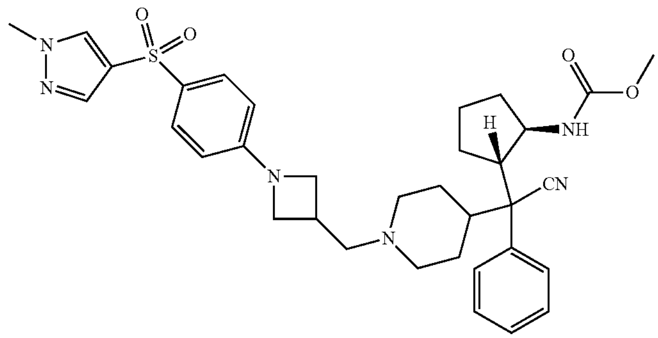 |
| IV-349 | 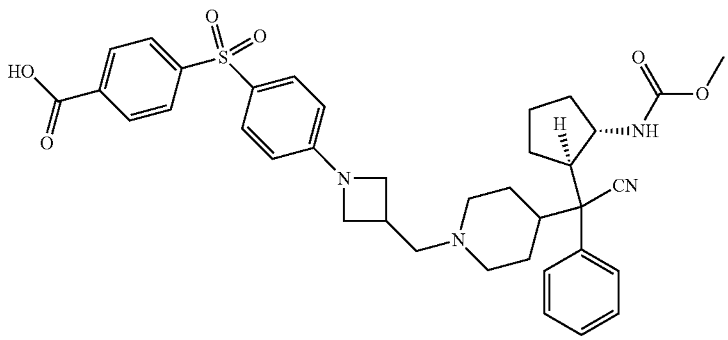 |
| IV-350 | 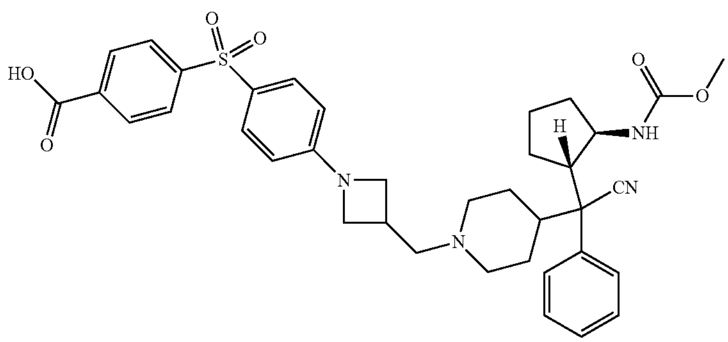 |
| IV-351 | 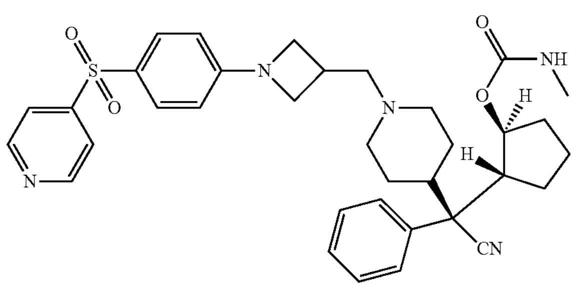 [SMILES: CNC(=O)O[C@H]1CCC[C@@H]1[C@](C#N)(c1ccccc1)C1CCN(CC2CN(c3ccc(S(=O)(=O)c4ccncc4)cc3)C2)CC1] |
| IV-352 | 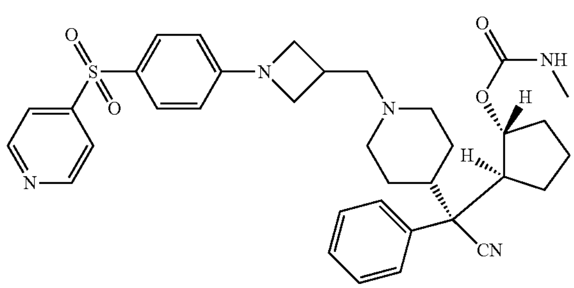 [SMILES: CNC(=O)O[C@@H]1CCC[C@H]1[C@@](C#N)(c1ccccc1)C1CCN(CC2CN(c3ccc(S(=O)(=O)c4ccncc4)cc3)C2)CC1] |

TABLE 4-continued

| No. | Structure |
|---|---|
| IV-353 | 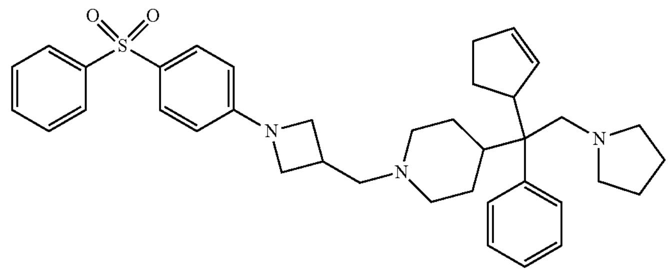 [SMILES: O=S(=O)(c1ccccc1)c1ccc(N2CC(CN3CCC(C(CN4CCCC4)(c4ccccc4)C4C=CCC4)CC3)C2)cc1] |
| IV-354 | 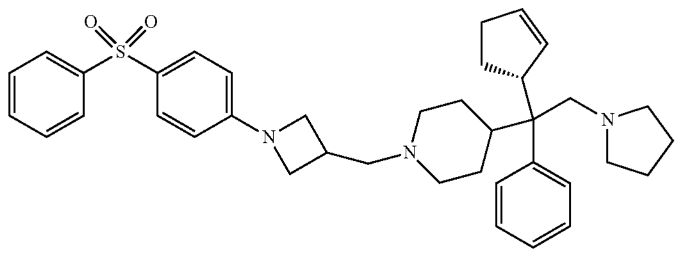 [SMILES: O=S(=O)(c1ccccc1)c1ccc(N2CC(CN3CCC(C(CN4CCCC4)(c4ccccc4)[C@H]4C=CCC4)CC3)C2)cc1] |
| IV-355 | 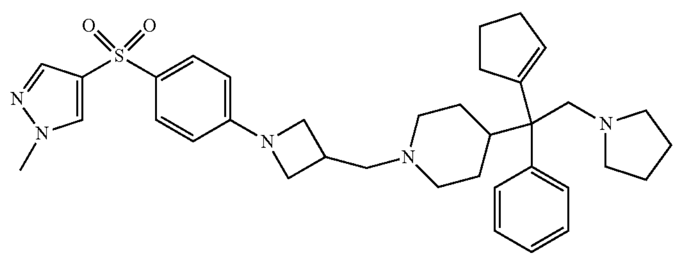 [SMILES: Cn1cc(S(=O)(=O)c2ccc(N3CC(CN4CCC(C(CN5CCCC5)(C5=CCCC5)c5ccccc5)CC4)C3)cc2)cn1] |
| IV-356 | 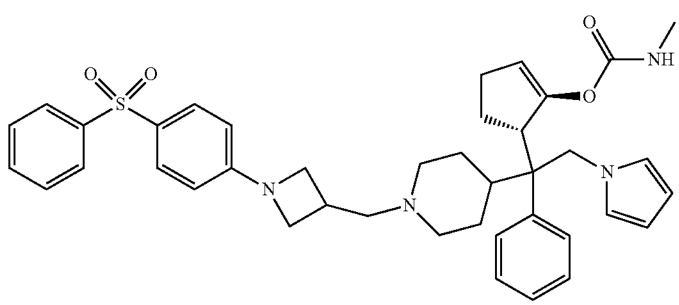 |
| IV-357 | 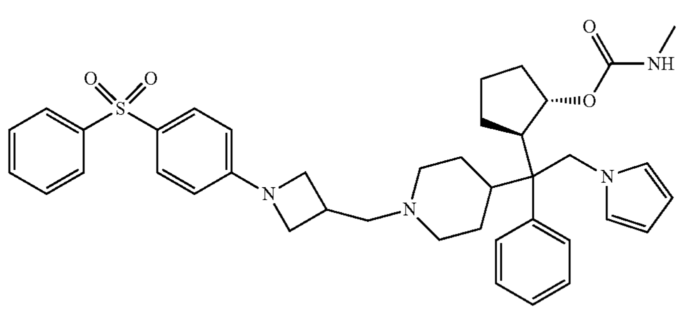 [SMILES: CNC(=O)O[C@H]1CCC[C@@H]1C(Cn1cccc1)(c1ccccc1)C1CCN(CC2CN(c3ccc(S(=O)(=O)c4ccccc4)cc3)C2)CC1] |

TABLE 4-continued
| No. | Structure |
|---|---|
| IV-358 | 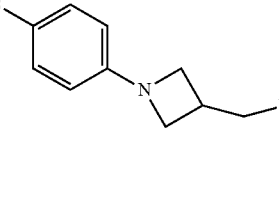 |
| IV-359 | 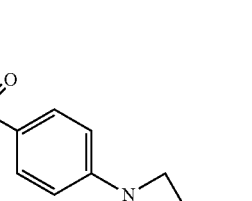 |
| IV-360 | 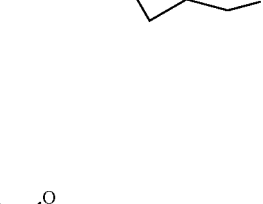 |
| IV-361 | 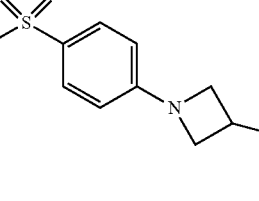 |
| IV-362 | 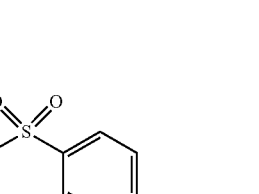 |

TABLE 4-continued

| No. | Structure |
|---|---|
| IV-363 | 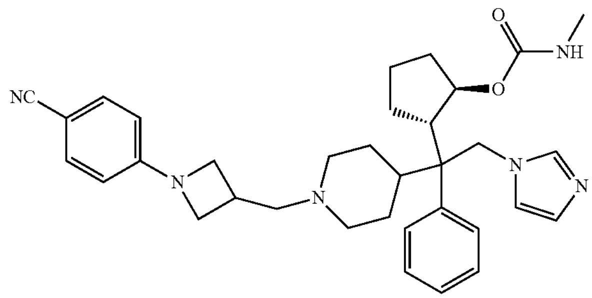 [SMILES: CNC(=O)O[C@@H]1CCC[C@H]1C(Cn1ccnc1)(c1ccccc1)C1CCN(CC2CN(c3ccc(C#N)cc3)C2)CC1] |
| IV-364 | 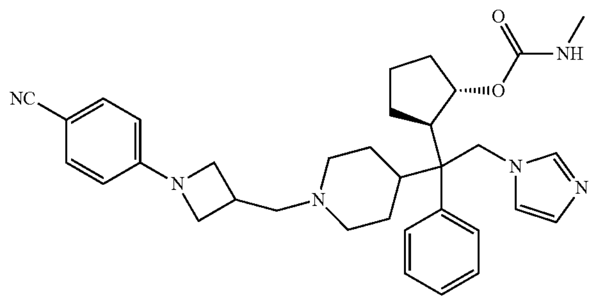 [SMILES: CNC(=O)O[C@H]1CCC[C@@H]1C(Cn1ccnc1)(c1ccccc1)C1CCN(CC2CN(c3ccc(C#N)cc3)C2)CC1] |
| IV-365 | 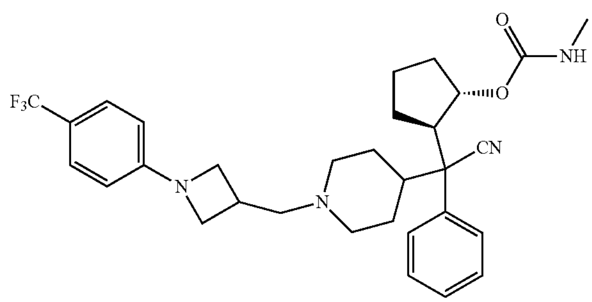 [SMILES: CNC(=O)O[C@H]1CCC[C@@H]1C(C#N)(c1ccccc1)C1CCN(CC2CN(c3ccc(C(F)(F)F)cc3)C2)CC1] |
| IV-366 | 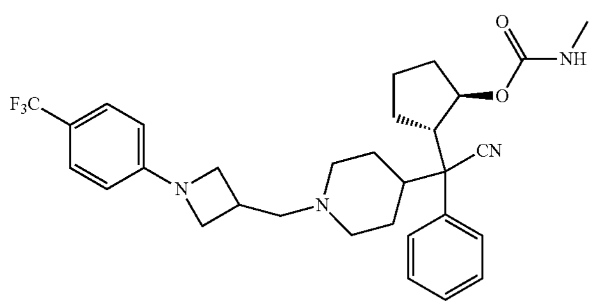 [SMILES: CNC(=O)O[C@@H]1CCC[C@H]1C(C#N)(c1ccccc1)C1CCN(CC2CN(c3ccc(C(F)(F)F)cc3)C2)CC1] |
| IV-367 | 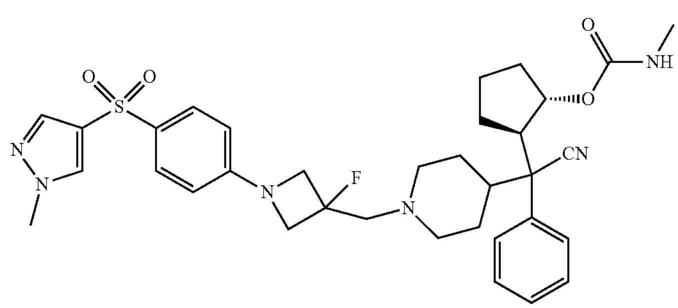 [SMILES: CNC(=O)O[C@H]1CCC[C@@H]1C(C#N)(c1ccccc1)C1CCN(CC2(F)CN(c3ccc(S(=O)(=O)c4cnn(C)c4)cc3)C2)CC1] |

TABLE 4-continued
| No. | Structure |
|---|---|
| IV-368 | 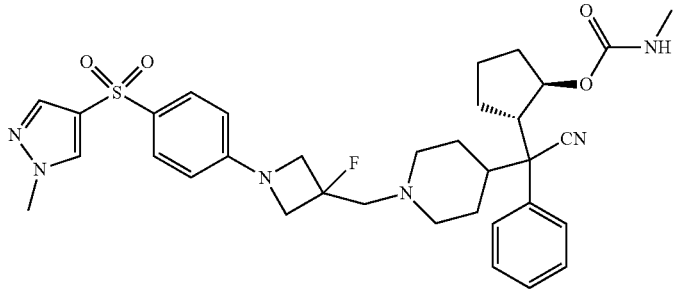 [SMILES: CNC(=O)O[C@@H]1CCC[C@H]1C(C#N)(c1ccccc1)C1CCN(CC2(F)CN(c3ccc(S(=O)(=O)c4cnn(C)c4)cc3)C2)CC1] |
| IV-369 | 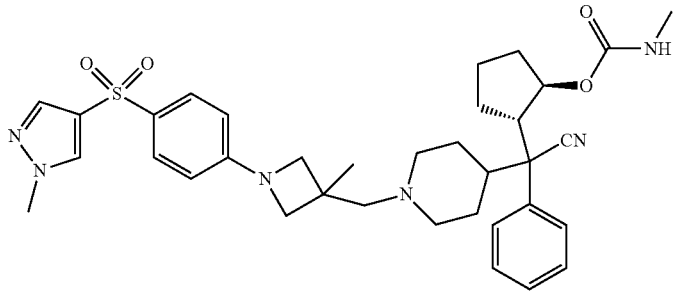 [SMILES: CNC(=O)O[C@@H]1CCC[C@H]1C(C#N)(c1ccccc1)C1CCN(CC2(C)CN(c3ccc(S(=O)(=O)c4cnn(C)c4)cc3)C2)CC1] |
| IV-370 | 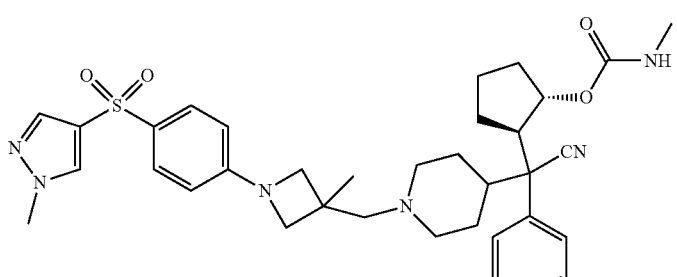 |
| IV-371 | 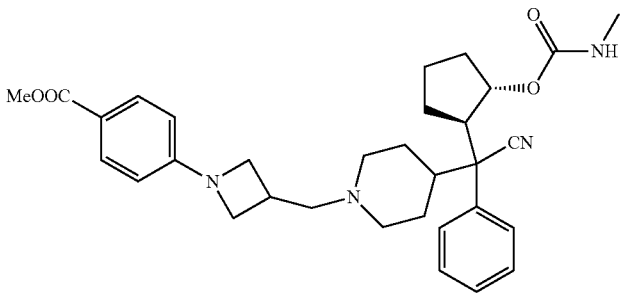 [SMILES: CNC(=O)O[C@H]1CCC[C@@H]1C(C#N)(c1ccccc1)C1CCN(CC2CN(c3ccc(C(=O)OC)cc3)C2)CC1] |
| IV-372 | 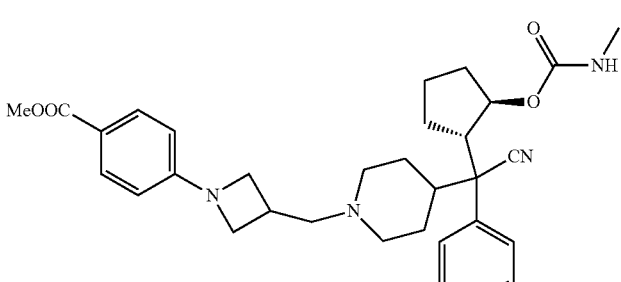 |

TABLE 4-continued

| No. | Structure |
|---|---|
| IV-373 | 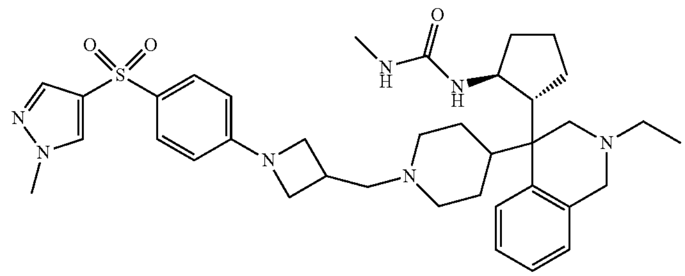 [SMILES: CCN1Cc2ccccc2C(C2CCN(CC3CN(c4ccc(S(=O)(=O)c5cnn(C)c5)cc4)C3)CC2)([C@H]2CCC[C@@H]2NC(=O)NC)C1] |
| IV-374 | 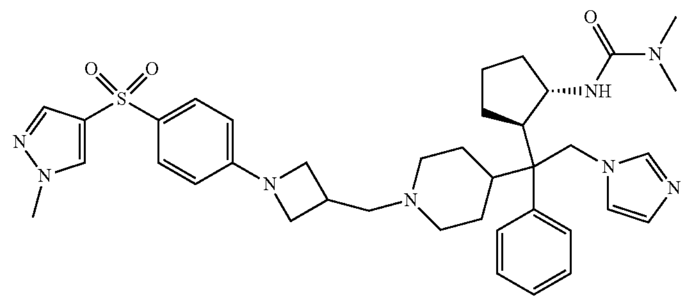 [SMILES: CN(C)C(=O)N[C@H]1CCC[C@@H]1C(Cn1ccnc1)(c1ccccc1)C1CCN(CC2CN(c3ccc(S(=O)(=O)c4cnn(C)c4)cc3)C2)CC1] |
| IV-375 | 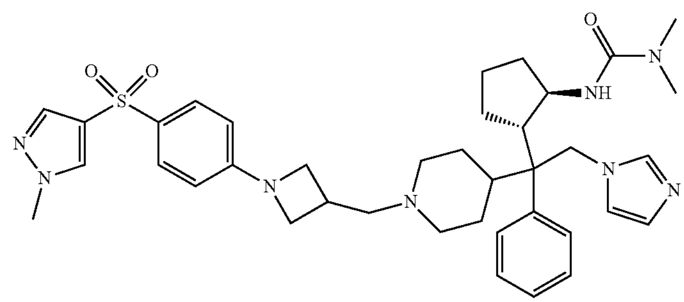 [SMILES: CN(C)C(=O)N[C@@H]1CCC[C@H]1C(Cn1ccnc1)(c1ccccc1)C1CCN(CC2CN(c3ccc(S(=O)(=O)c4cnn(C)c4)cc3)C2)CC1] |
| IV-376 | 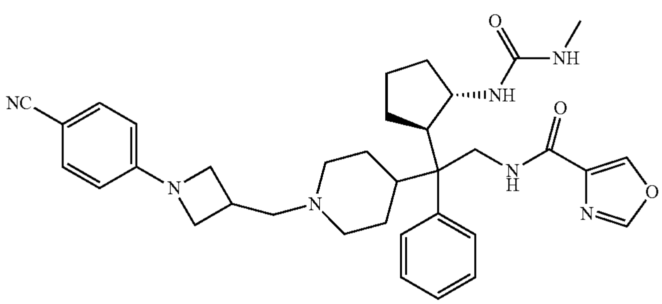 [SMILES: CNC(=O)N[C@H]1CCC[C@@H]1C(CNC(=O)c1cocn1)(c1ccccc1)C1CCN(CC2CN(c3ccc(C#N)cc3)C2)CC1] |
| IV-377 | 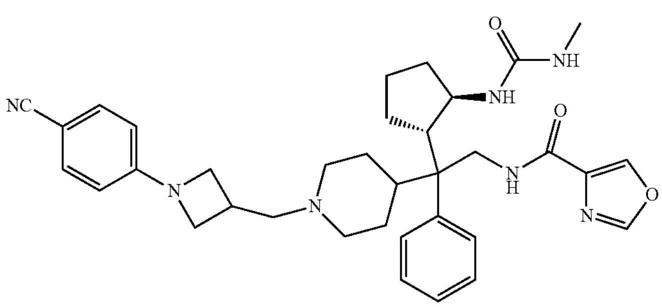 [SMILES: CNC(=O)N[C@@H]1CCC[C@H]1C(CNC(=O)c1cocn1)(c1ccccc1)C1CCN(CC2CN(c3ccc(C#N)cc3)C2)CC1] |

TABLE 4-continued

| No. | Structure |
|---|---|
| IV-378 | 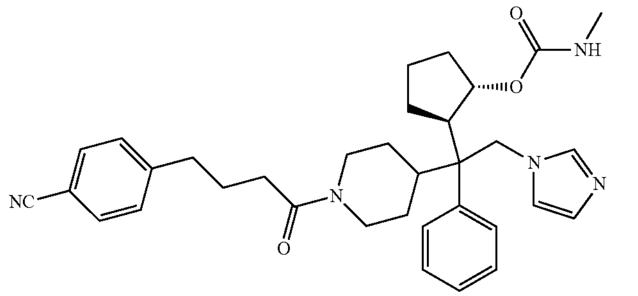 [SMILES: CNC(=O)O[C@H]1CCC[C@@H]1C(Cn1ccnc1)(c1ccccc1)C1CCN(C(=O)CCCc2ccc(C#N)cc2)CC1] |
| IV-379 | 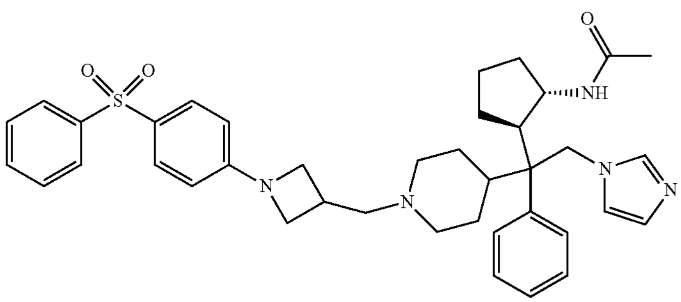 [SMILES: CC(=O)N[C@H]1CCC[C@@H]1C(Cn1ccnc1)(c1ccccc1)C1CCN(CC2CN(c3ccc(S(=O)(=O)c4ccccc4)cc3)C2)CC1] |
| IV-380 | 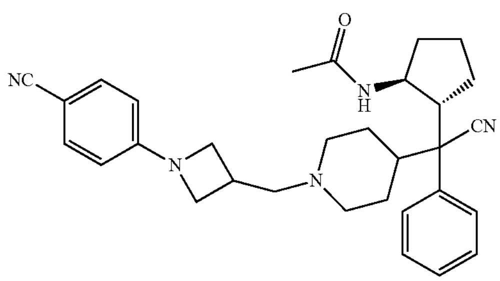 [SMILES: CC(=O)N[C@H]1CCC[C@@H]1C(C#N)(c1ccccc1)C1CCN(CC2CN(c3ccc(C#N)cc3)C2)CC1] |
| IV-381 | 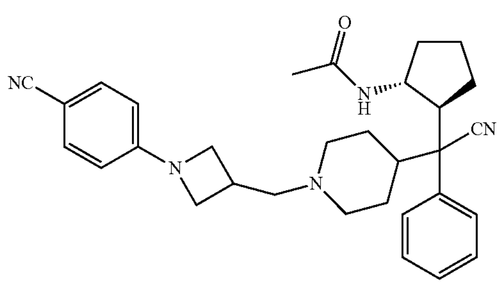 [SMILES: CC(=O)N[C@@H]1CCC[C@H]1C(C#N)(c1ccccc1)C1CCN(CC2CN(c3ccc(C#N)cc3)C2)CC1] |
| IV-382 | 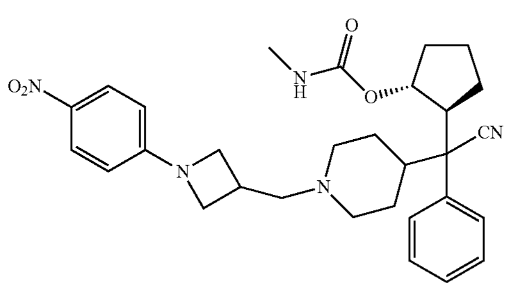 [SMILES: CNC(=O)O[C@@H]1CCC[C@H]1C(C#N)(c1ccccc1)C1CCN(CC2CN(c3ccc([N+](=O)[O-])cc3)C2)CC1] |

TABLE 4-continued

| No. | Structure |
|---|---|
| IV-383 | 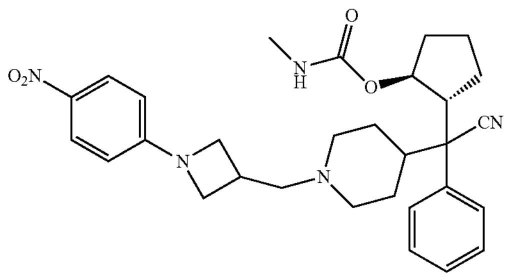 [SMILES: CNC(=O)O[C@H]1CCC[C@@H]1C(C#N)(c1ccccc1)C1CCN(CC2CN(c3ccc([N+](=O)[O-])cc3)C2)CC1] |
| IV-384 | 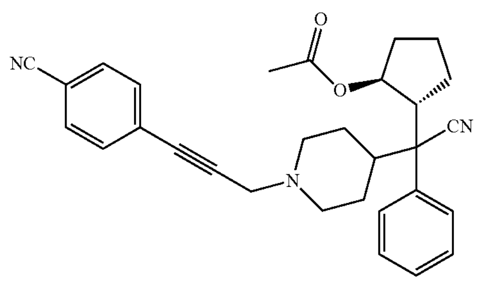 [SMILES: CC(=O)O[C@H]1CCC[C@@H]1C(C#N)(c1ccccc1)C1CCN(CC#Cc2ccc(C#N)cc2)CC1] |
| IV-385 | 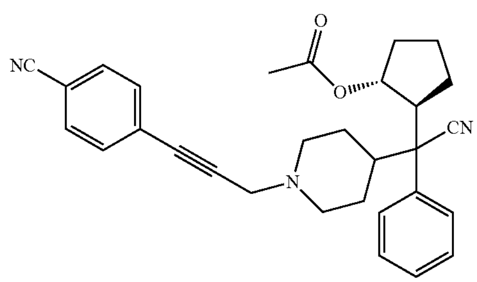 [SMILES: CC(=O)O[C@@H]1CCC[C@H]1C(C#N)(c1ccccc1)C1CCN(CC#Cc2ccc(C#N)cc2)CC1] |
| IV-386 | 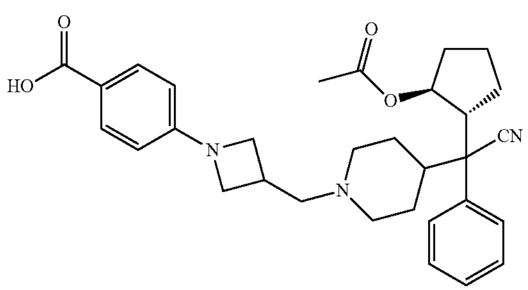 [SMILES: CC(=O)O[C@H]1CCC[C@@H]1C(C#N)(c1ccccc1)C1CCN(CC2CN(c3ccc(C(=O)O)cc3)C2)CC1] |
| IV-387 | 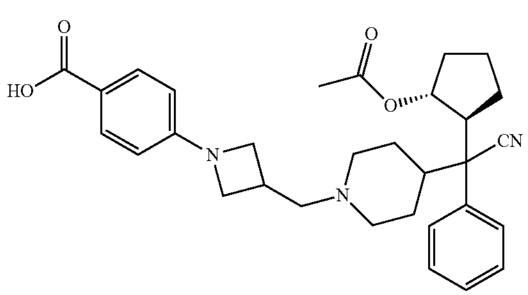 [SMILES: CC(=O)O[C@@H]1CCC[C@H]1C(C#N)(c1ccccc1)C1CCN(CC2CN(c3ccc(C(=O)O)cc3)C2)CC1] |

TABLE 4-continued
| No. | Structure |
|---|---|
| IV-388 | 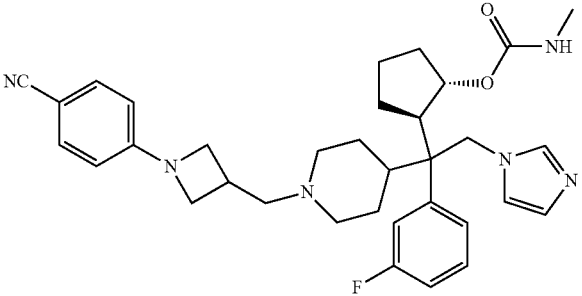 [SMILES: CNC(=O)O[C@H]1CCC[C@@H]1C(Cn1ccnc1)(c1cccc(F)c1)C1CCN(CC2CN(c3ccc(C#N)cc3)C2)CC1] |
| IV-389 | 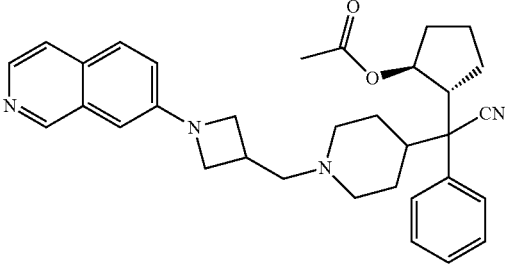 [SMILES: CC(=O)O[C@H]1CCC[C@@H]1C(C#N)(c1ccccc1)C1CCN(CC2CN(c3ccc4ccncc4c3)C2)CC1] |
| IV-390 | 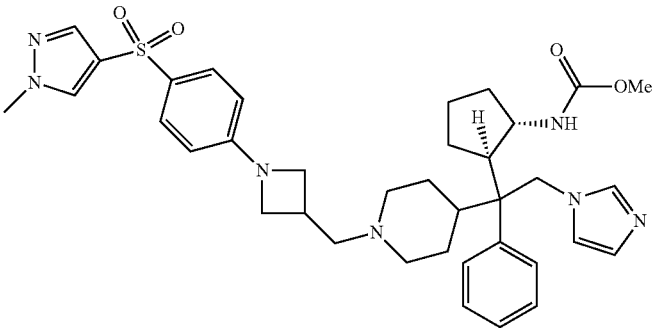 |
| IV-391 | 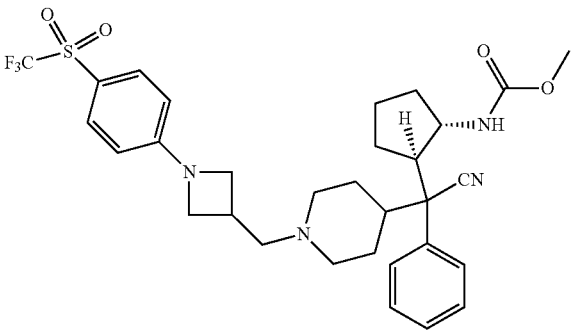 |
| IV-392 | 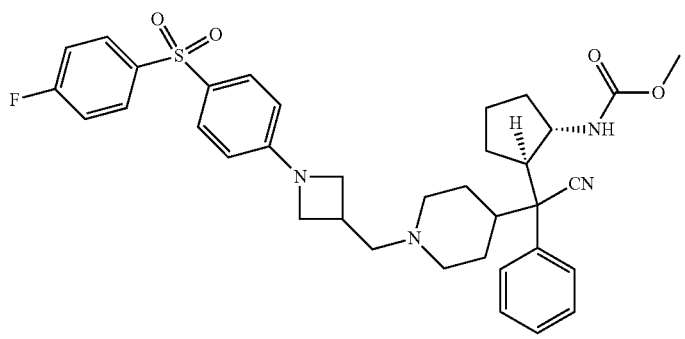 |

TABLE 4-continued

| No. | Structure |
| --- | --- |
| IV-393 | 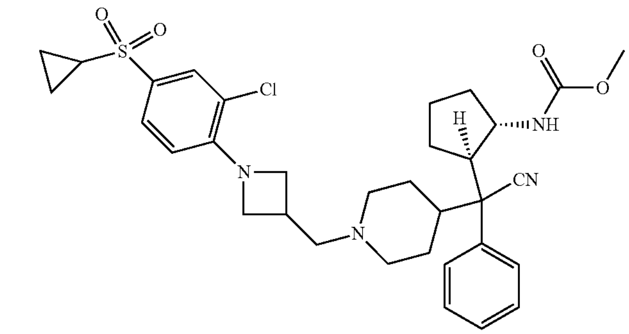 |
| IV-394 | 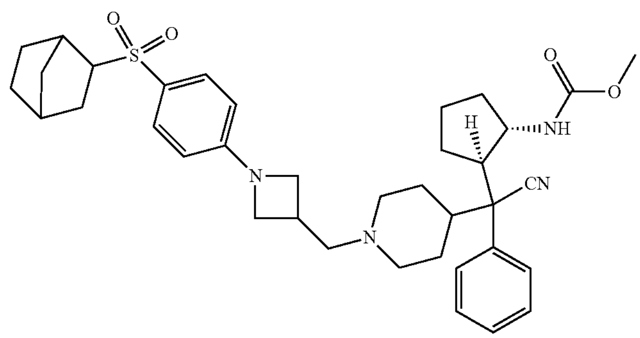 |
| IV-395 | 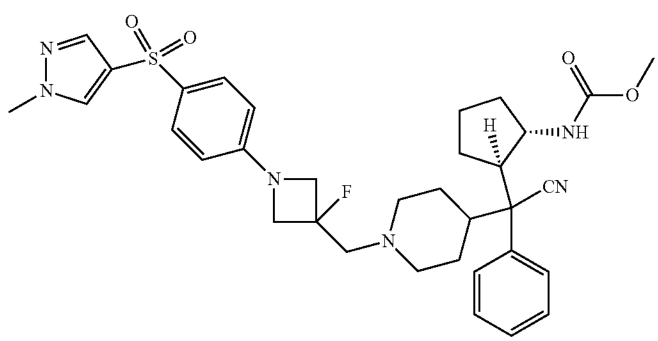 |
| IV-396 | 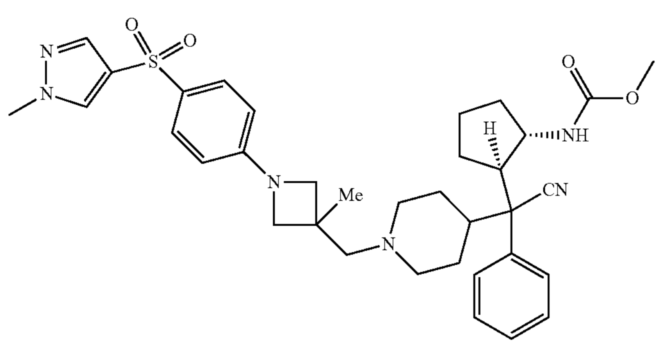 |

TABLE 4-continued

| No. | Structure |
|---|---|
| IV-397 | 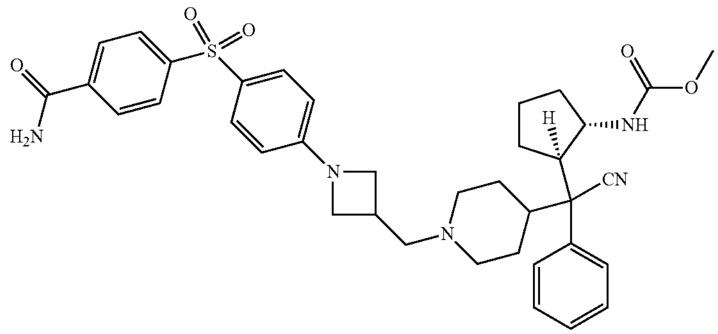 |
| IV-398 | 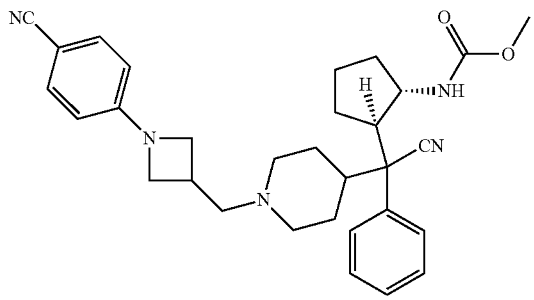 |
| IV-399 | 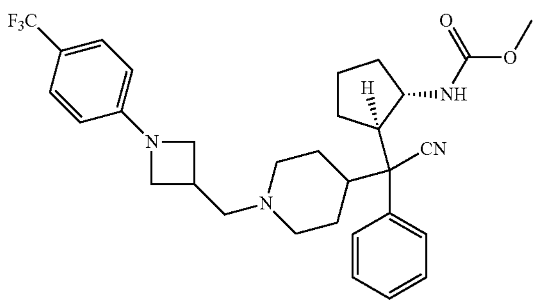 |
| IV-400 | 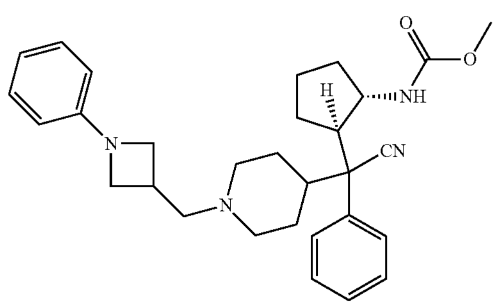 |
| IV-401 | 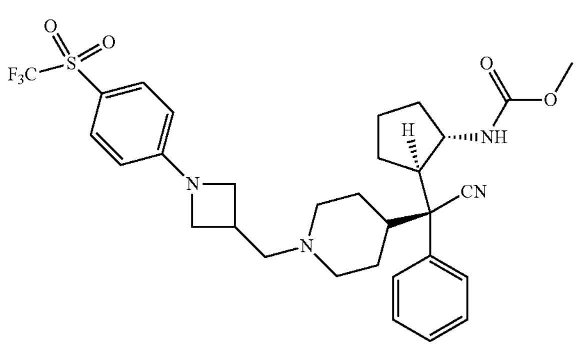 |

TABLE 4-continued

| No. | Structure |
|---|---|
| IV-402 | 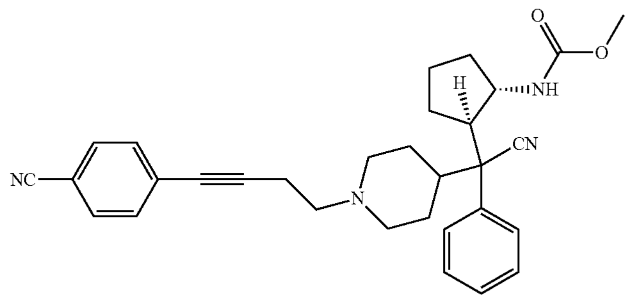 |
| IV-403 | 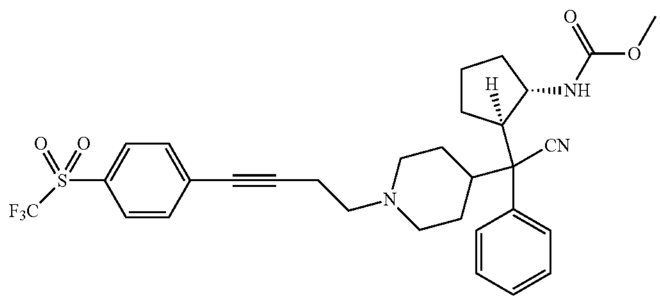 |
| IV-404 | 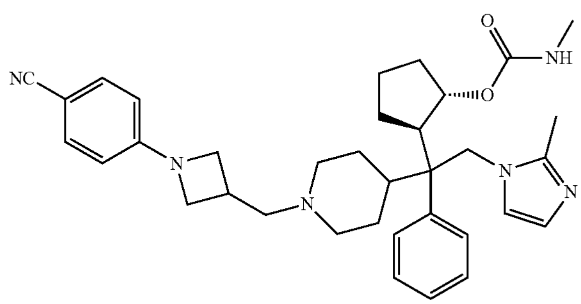 [SMILES: CNC(=O)O[C@H]1CCC[C@@H]1C(Cn1ccnc1C)(c1ccccc1)C1CCN(CC2CN(c3ccc(C#N)cc3)C2)CC1] |
| IV-405 | 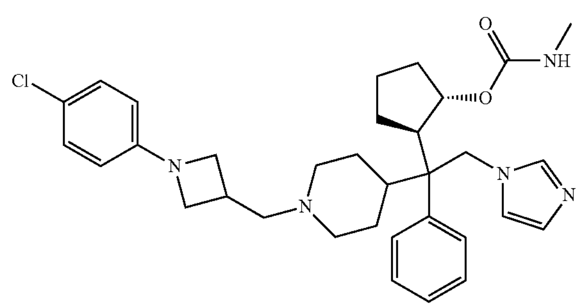 [SMILES: CNC(=O)O[C@H]1CCC[C@@H]1C(Cn1ccnc1)(c1ccccc1)C1CCN(CC2CN(c3ccc(Cl)cc3)C2)CC1] |
| IV-406 | 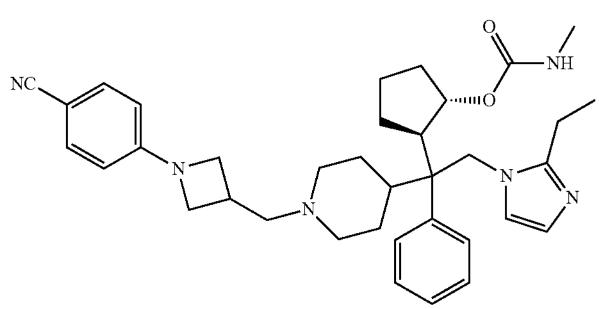 [SMILES: CCc1nccn1CC(c1ccccc1)(C1CCN(CC2CN(c3ccc(C#N)cc3)C2)CC1)[C@H]1CCC[C@@H]1OC(=O)NC] |

TABLE 4-continued

| No. | Structure |
|---|---|
| IV-407 | 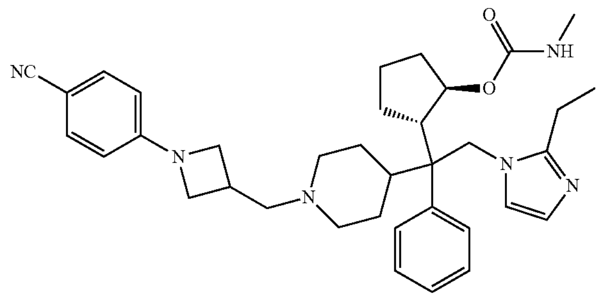 [SMILES: CCc1nccn1CC(c1ccccc1)(C1CCN(CC2CN(c3ccc(C#N)cc3)C2)CC1)[C@@H]1CCC[C@H]1OC(=O)NC] |
| IV-408 | 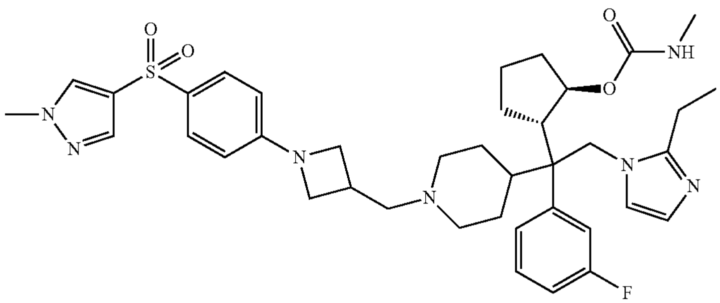 [SMILES: CCc1nccn1CC(c1cccc(F)c1)(C1CCN(CC2CN(c3ccc(S(=O)(=O)c4cnn(C)c4)cc3)C2)CC1)[C@@H]1CCC[C@H]1OC(=O)NC] |
| IV-409 | 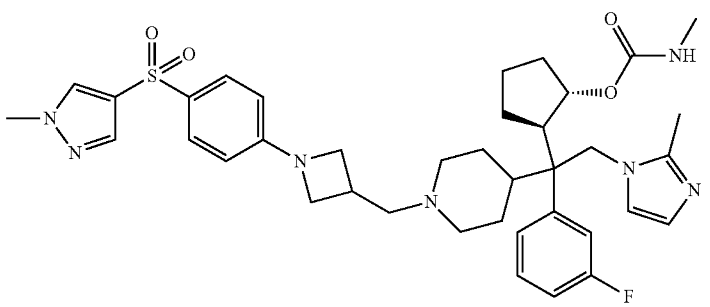 |
| IV-410 | 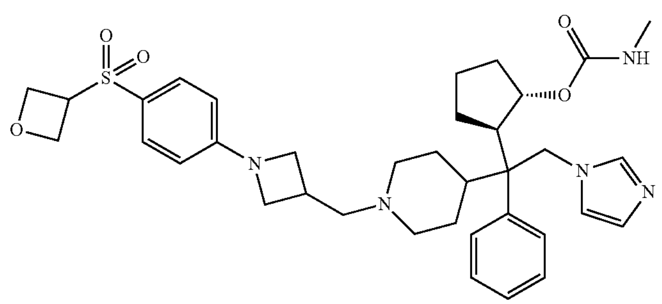 [SMILES: CNC(=O)O[C@H]1CCC[C@@H]1C(Cn1ccnc1)(c1ccccc1)C1CCN(CC2CN(c3ccc(S(=O)(=O)C4COC4)cc3)C2)CC1] |
| IV-411 | 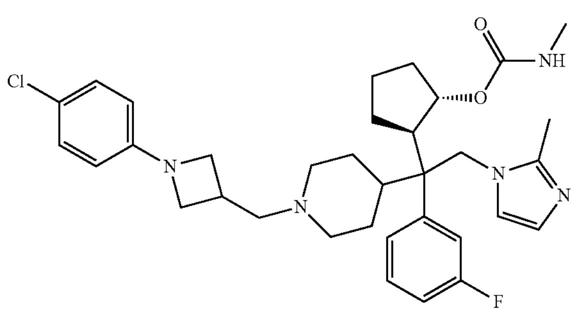 [SMILES: CNC(=O)O[C@H]1CCC[C@@H]1C(Cn1ccnc1C)(c1cccc(F)c1)C1CCN(CC2CN(c3ccc(Cl)cc3)C2)CC1] |

TABLE 4-continued

| No. | Structure |
| --- | --- |
| IV-412 | 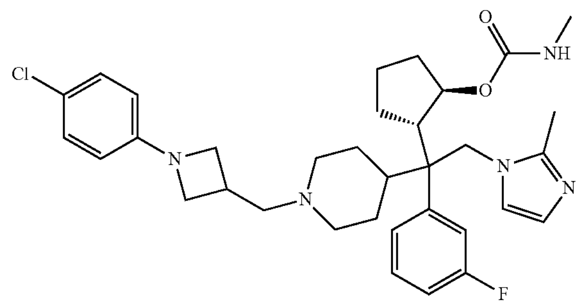 [SMILES: CNC(=O)O[C@@H]1CCC[C@H]1C(Cn1ccnc1C)(c1cccc(F)c1)C1CCN(CC2CN(c3ccc(Cl)cc3)C2)CC1] |
| IV-413 | 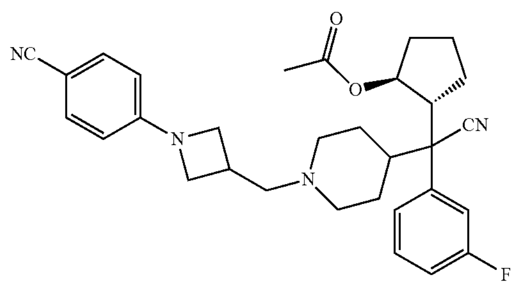 [SMILES: CC(=O)O[C@H]1CCC[C@@H]1C(C#N)(c1cccc(F)c1)C1CCN(CC2CN(c3ccc(C#N)cc3)C2)CC1] |
| IV-414 | 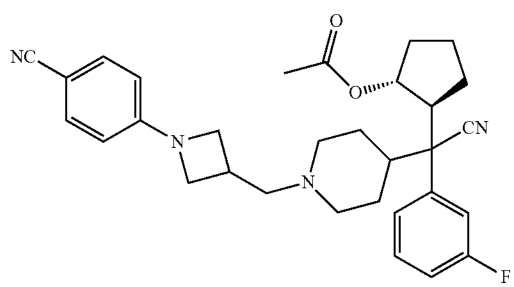 [SMILES: CC(=O)O[C@@H]1CCC[C@H]1C(C#N)(c1cccc(F)c1)C1CCN(CC2CN(c3ccc(C#N)cc3)C2)CC1] |
| IV-415 | 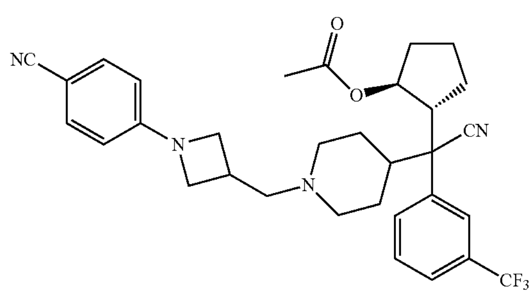 [SMILES: CC(=O)O[C@H]1CCC[C@@H]1C(C#N)(c1cccc(C(F)(F)F)c1)C1CCN(CC2CN(c3ccc(C#N)cc3)C2)CC1] |
| IV-416 | 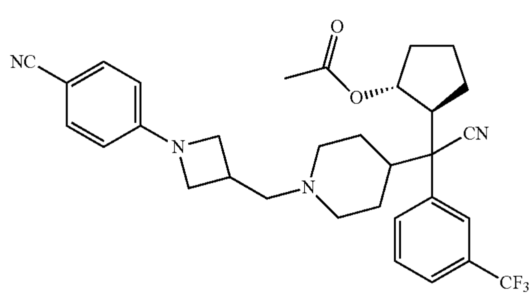 [SMILES: CC(=O)O[C@@H]1CCC[C@H]1C(C#N)(c1cccc(C(F)(F)F)c1)C1CCN(CC2CN(c3ccc(C#N)cc3)C2)CC1] |

TABLE 4-continued

| No. | Structure |
|-----|-----------|
| IV-417 | 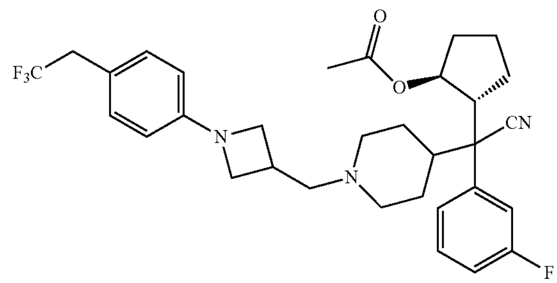 [SMILES: CC(=O)O[C@H]1CCC[C@@H]1C(C#N)(c1cccc(F)c1)C1CCN(CC2CN(c3ccc(CC(F)(F)F)cc3)C2)CC1] |
| IV-418 | 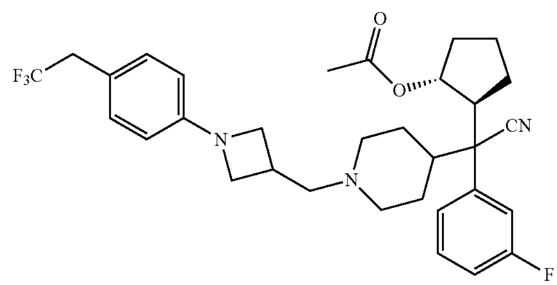 [SMILES: CC(=O)O[C@@H]1CCC[C@H]1C(C#N)(c1cccc(F)c1)C1CCN(CC2CN(c3ccc(CC(F)(F)F)cc3)C2)CC1] |
| IV-419 | 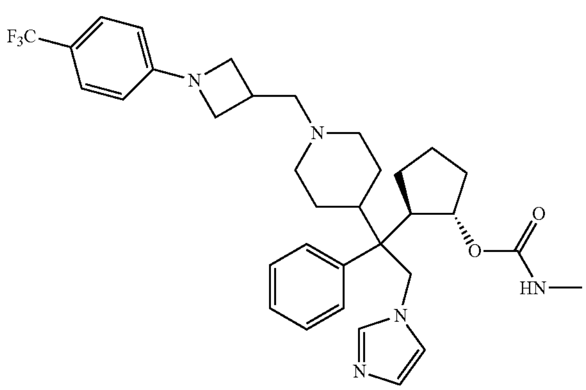 [SMILES: CNC(=O)O[C@H]1CCC[C@@H]1C(Cn1ccnc1)(c1ccccc1)C1CCN(CC2CN(c3ccc(C(F)(F)F)cc3)C2)CC1] |
| IV-420 | 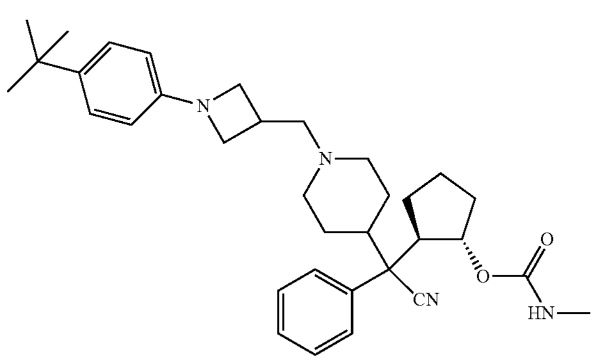 [SMILES: CNC(=O)O[C@H]1CCC[C@@H]1C(C#N)(c1ccccc1)C1CCN(CC2CN(c3ccc(C(C)(C)C)cc3)C2)CC1] |

TABLE 4-continued
| No. | Structure |
|---|---|
| IV-421 | 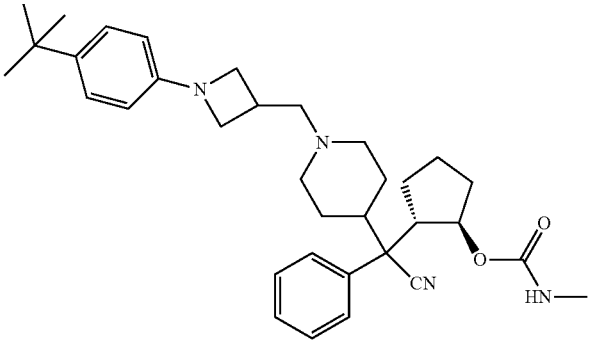 [SMILES: CNC(=O)O[C@@H]1CCC[C@H]1C(C#N)(c1ccccc1)C1CCN(CC2CN(c3ccc(C(C)(C)C)cc3)C2)CC1] |
| IV-422 | 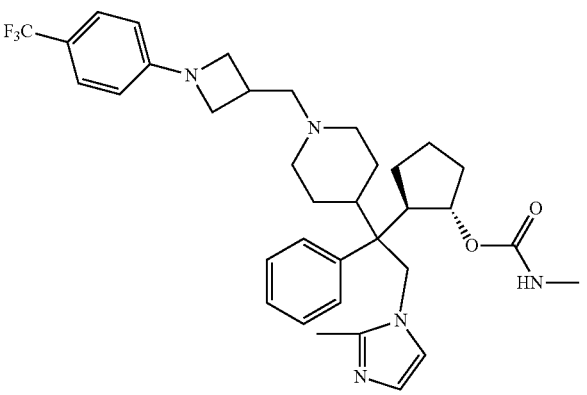 [SMILES: CNC(=O)O[C@H]1CCC[C@@H]1C(Cn1ccnc1C)(c1ccccc1)C1CCN(CC2CN(c3ccc(C(F)(F)F)cc3)C2)CC1] |
| IV-423 | 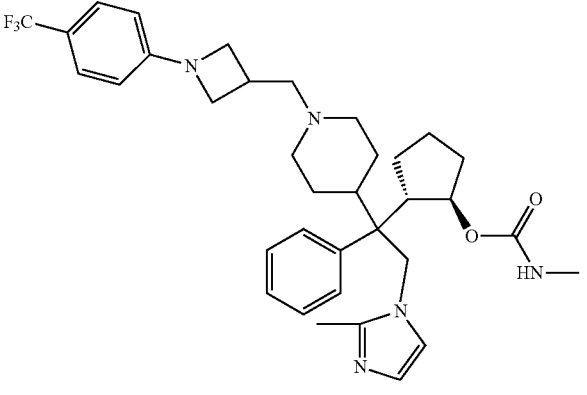 [SMILES: CNC(=O)O[C@@H]1CCC[C@H]1C(Cn1ccnc1C)(c1ccccc1)C1CCN(CC2CN(c3ccc(C(F)(F)F)cc3)C2)CC1] |
| IV-424 | 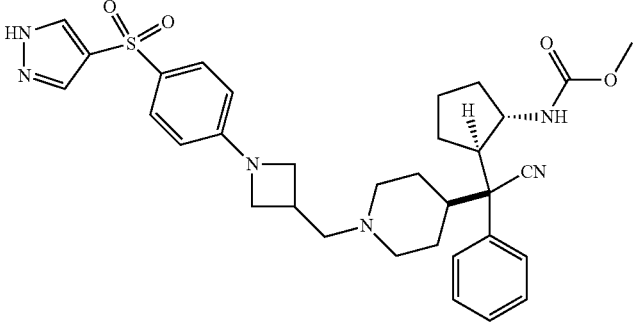 |

TABLE 4-continued

| No. | Structure |
|---|---|
| IV-425 | 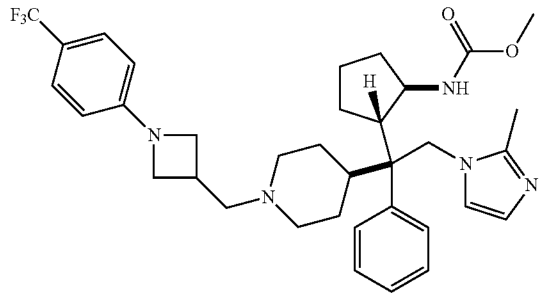 |
| IV-426 | 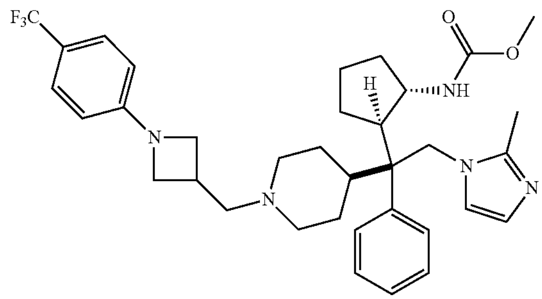 |
| IV-427 | 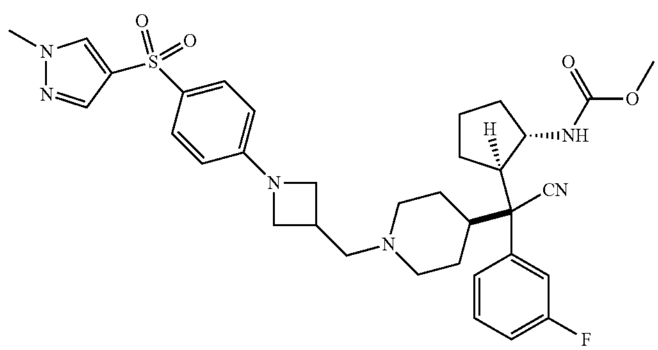 |
| IV-428 | 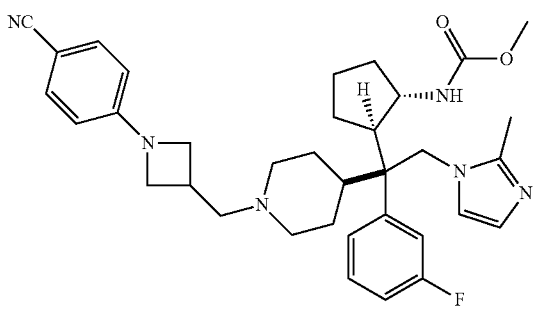 |
| IV-429 | 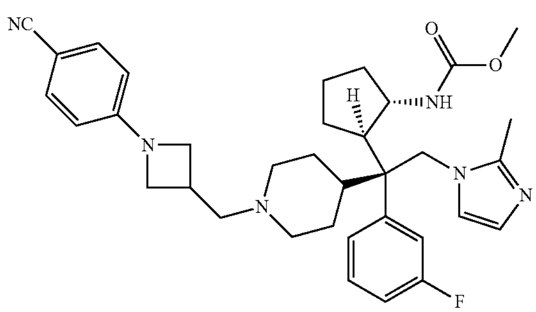 |

TABLE 4-continued

| No. | Structure |
|---|---|
| IV-430 | 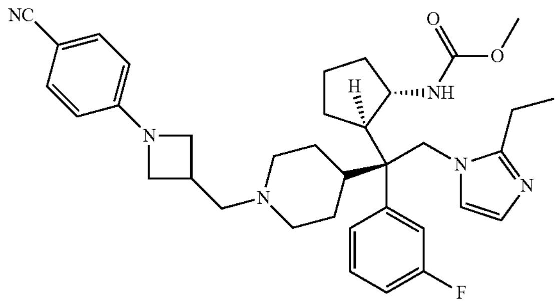 |
| IV-431 | 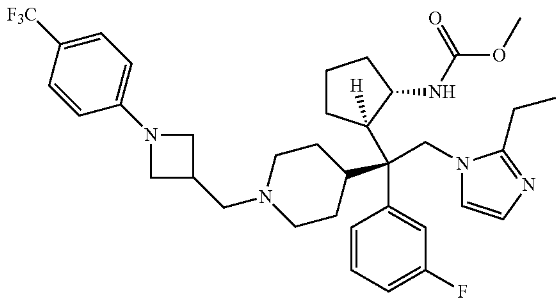 |
| IV-432 | 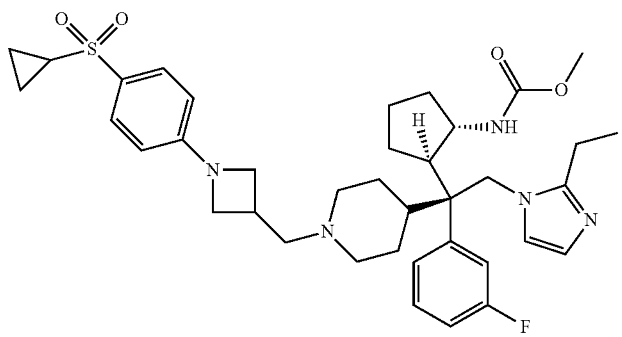 |
| IV-433 | 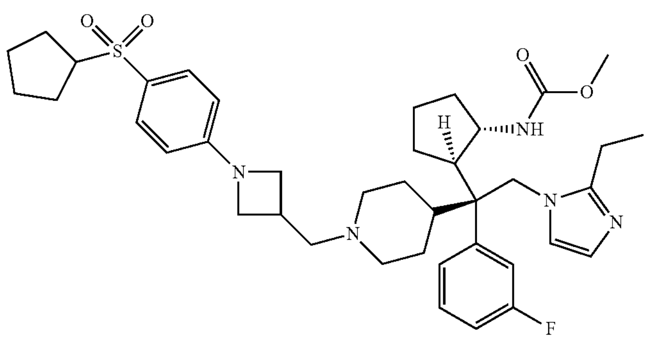 |
| IV-434 | 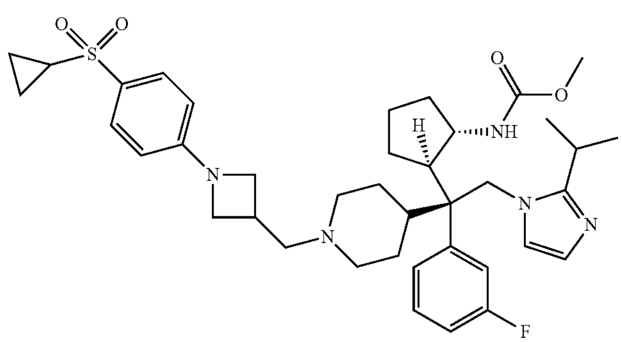 |

TABLE 4-continued
| No. | Structure |
|---|---|
| IV-435 | 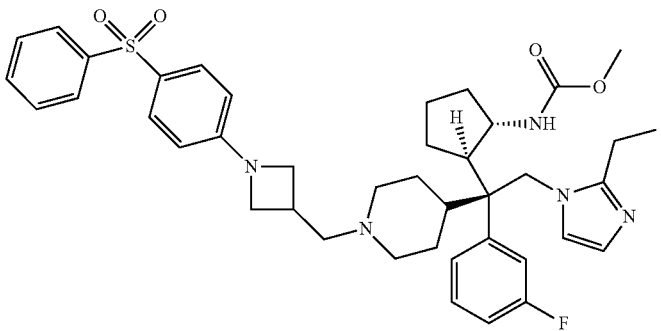 |
| IV-436 | 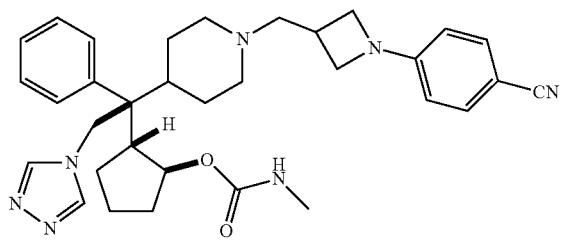 [SMILES: CNC(=O)O[C@H]1CCC[C@@H]1[C@](Cn1cnnc1)(c1ccccc1)C1CCN(CC2CN(c3ccc(C#N)cc3)C2)CC1] |
| IV-437 | 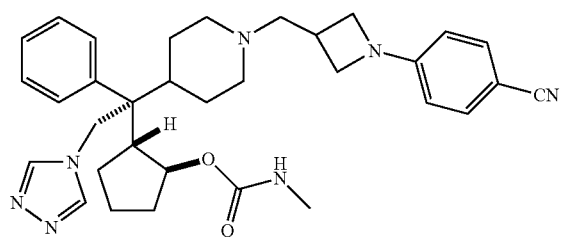 [SMILES: CNC(=O)O[C@H]1CCC[C@@H]1[C@@](Cn1cnnc1)(c1ccccc1)C1CCN(CC2CN(c3ccc(C#N)cc3)C2)CC1] |
| IV-438 | 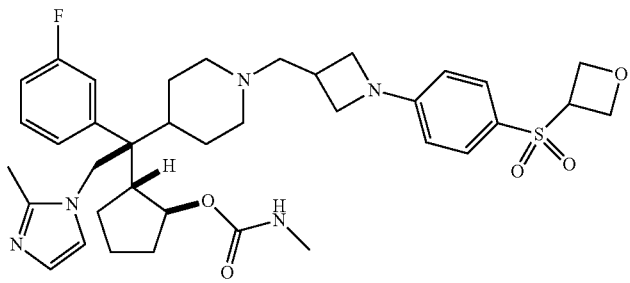 [SMILES: CNC(=O)O[C@H]1CCC[C@@H]1[C@](Cn1ccnc1C)(c1cccc(F)c1)C1CCN(CC2CN(c3ccc(S(=O)(=O)C4COC4)cc3)C2)CC1] |
| IV-439 | 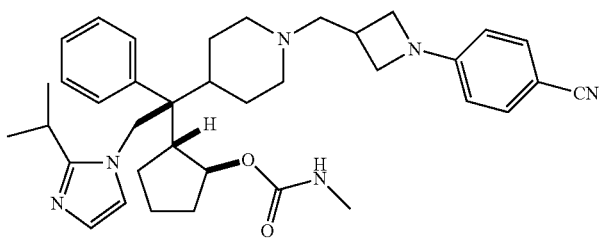 [SMILES: CNC(=O)O[C@H]1CCC[C@@H]1[C@](Cn1ccnc1C(C)C)(c1ccccc1)C1CCN(CC2CN(c3ccc(C#N)cc3)C2)CC1] |

TABLE 4-continued
| No. | Structure |
|---|---|
| IV-440 | 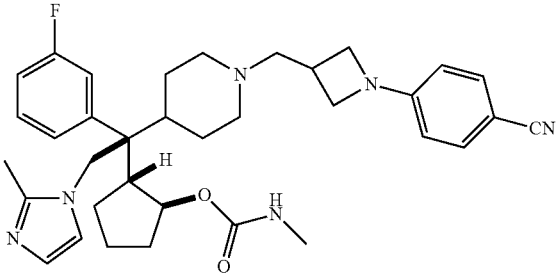 [SMILES: CNC(=O)O[C@H]1CCC[C@@H]1[C@](Cn1ccnc1C)(c1cccc(F)c1)C1CCN(CC2CN(c3ccc(C#N)cc3)C2)CC1] |
| IV-441 | 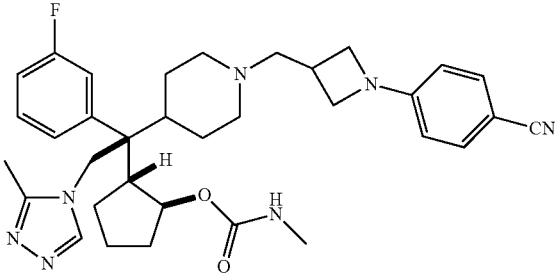 [SMILES: CNC(=O)O[C@H]1CCC[C@@H]1[C@](Cn1cnnc1C)(c1cccc(F)c1)C1CCN(CC2CN(c3ccc(C#N)cc3)C2)CC1] |
| IV-442 | 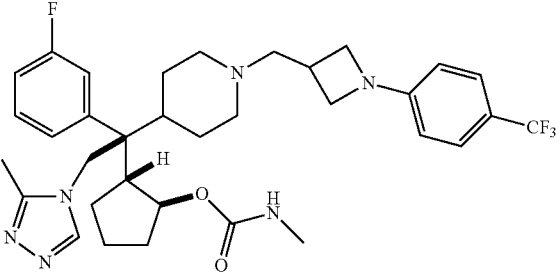 [SMILES: CNC(=O)O[C@H]1CCC[C@@H]1[C@](Cn1cnnc1C)(c1cccc(F)c1)C1CCN(CC2CN(c3ccc(C(F)(F)F)cc3)C2)CC1] |
| IV-443 | 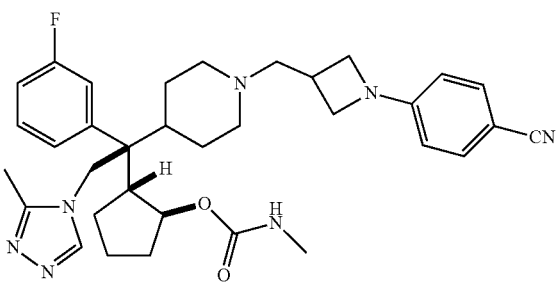 [SMILES: CNC(=O)O[C@H]1CCC[C@@H]1[C@](Cn1cnnc1C)(c1cccc(F)c1)C1CCN(CC2CN(c3ccc(C#N)cc3)C2)CC1] |
| IV-444 | 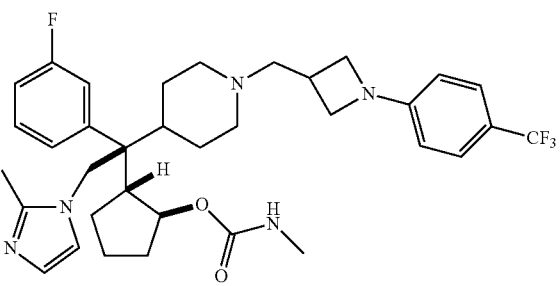 [SMILES: CNC(=O)O[C@H]1CCC[C@@H]1[C@](Cn1ccnc1C)(c1cccc(F)c1)C1CCN(CC2CN(c3ccc(C(F)(F)F)cc3)C2)CC1] |

TABLE 4-continued
| No. | Structure |
|---|---|
| IV-445 | 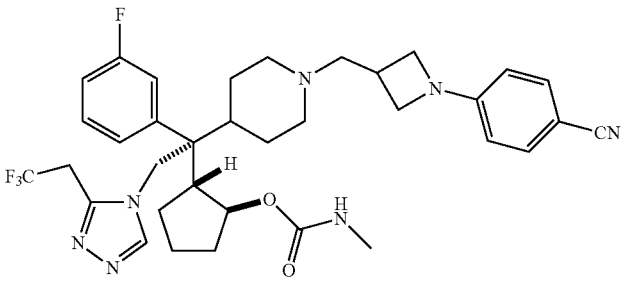 [SMILES: CNC(=O)O[C@H]1CCC[C@@H]1[C@@](Cn1cnnc1CC(F)(F)F)(c1cccc(F)c1)C1CCN(CC2CN(c3ccc(C#N)cc3)C2)CC1] |
| IV-446 | 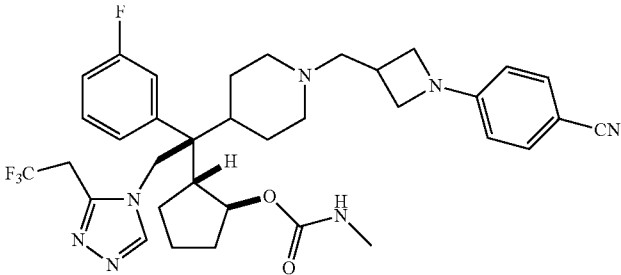 [SMILES: CNC(=O)O[C@H]1CCC[C@@H]1[C@](Cn1cnnc1CC(F)(F)F)(c1cccc(F)c1)C1CCN(CC2CN(c3ccc(C#N)cc3)C2)CC1] |
| IV-447 | 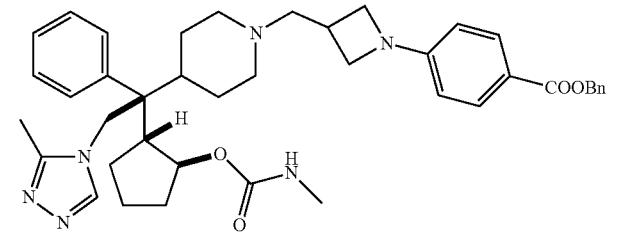 |
| IV-448 | 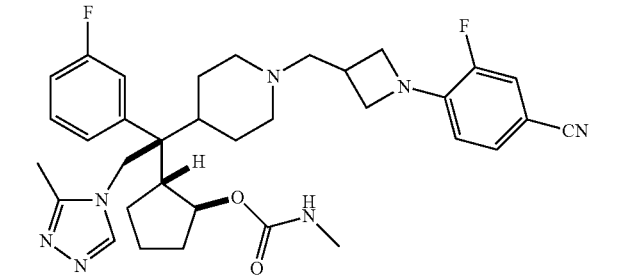 [SMILES: CNC(=O)O[C@H]1CCC[C@@H]1[C@](Cn1cnnc1C)(c1cccc(F)c1)C1CCN(CC2CN(c3ccc(C#N)cc3F)C2)CC1] |
| IV-449 | 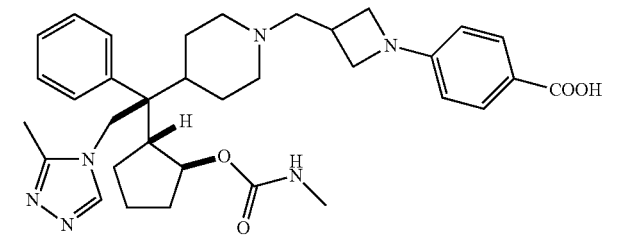 [SMILES: CNC(=O)O[C@H]1CCC[C@@H]1[C@](Cn1cnnc1C)(c1ccccc1)C1CCN(CC2CN(c3ccc(C(=O)O)cc3)C2)CC1] |

TABLE 4-continued
| No. | Structure |
|---|---|
| IV-450 | 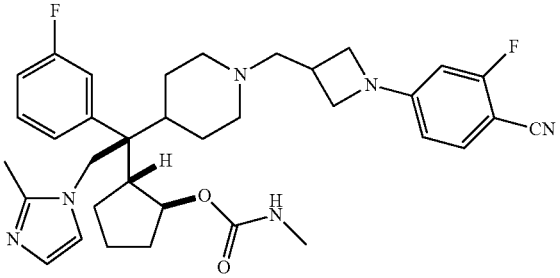 [SMILES: CNC(=O)O[C@H]1CCC[C@@H]1[C@](Cn1ccnc1C)(c1cccc(F)c1)C1CCN(CC2CN(c3ccc(C#N)c(F)c3)C2)CC1] |
| IV-451 | 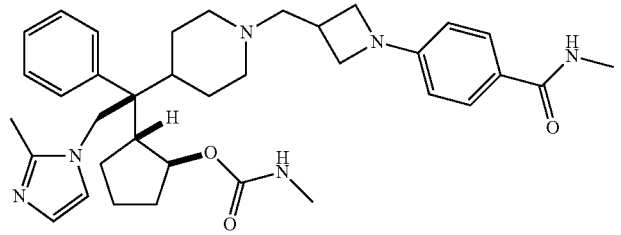 |
| IV-452 | 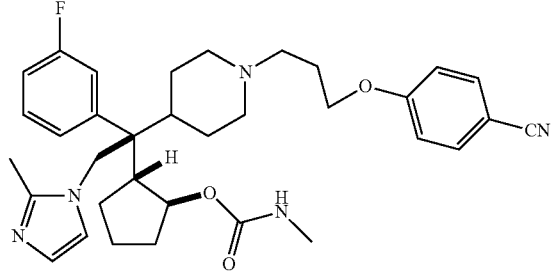 [SMILES: CNC(=O)O[C@H]1CCC[C@@H]1[C@](Cn1ccnc1C)(c1cccc(F)c1)C1CCN(CCCOc2ccc(C#N)cc2)CC1] |
| IV-453 | 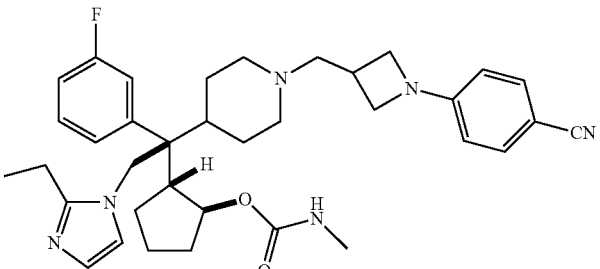 |
| IV-454 | 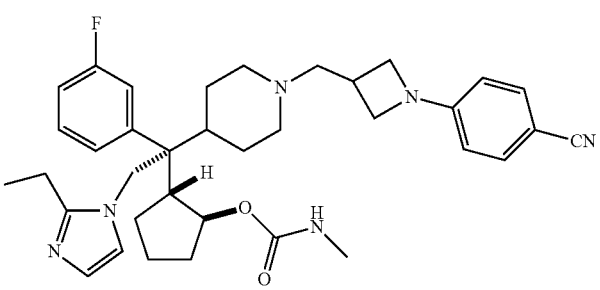 [SMILES: CCc1nccn1C[C@](c1cccc(F)c1)(C1CCN(CC2CN(c3ccc(C#N)cc3)C2)CC1)[C@H]1CCC[C@@H]1OC(=O)NC] |

TABLE 4-continued

| No. | Structure |
|---|---|
| IV-455 | 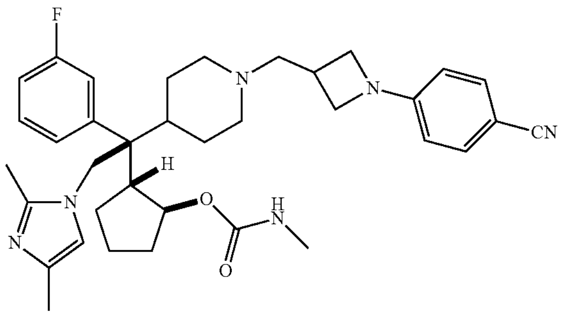 [SMILES: CNC(=O)O[C@H]1CCC[C@@H]1[C@](Cn1cc(C)nc1C)(c1cccc(F)c1)C1CCN(CC2CN(c3ccc(C#N)cc3)C2)CC1] |
| IV-456 | 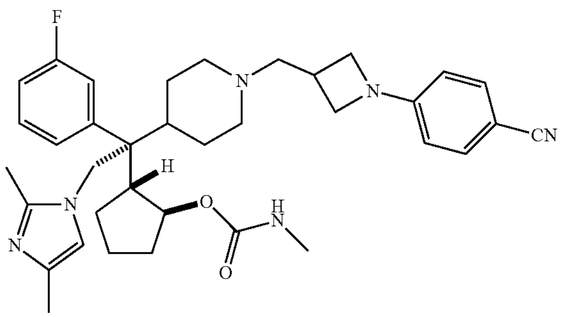 [SMILES: CNC(=O)O[C@H]1CCC[C@@H]1[C@@](Cn1cc(C)nc1C)(c1cccc(F)c1)C1CCN(CC2CN(c3ccc(C#N)cc3)C2)CC1] |
| IV-457 | 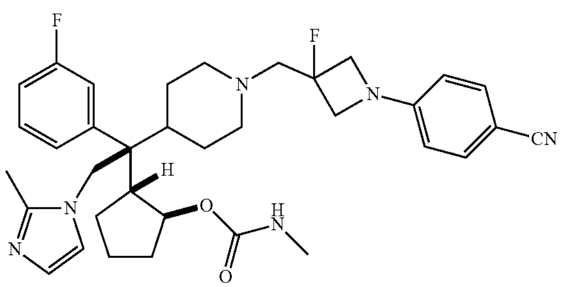 [SMILES: CNC(=O)O[C@H]1CCC[C@@H]1[C@](Cn1ccnc1C)(c1cccc(F)c1)C1CCN(CC2(F)CN(c3ccc(C#N)cc3)C2)CC1] |
| IV-458 | 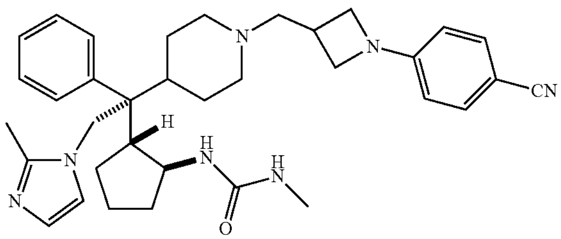 [SMILES: CNC(=O)N[C@H]1CCC[C@@H]1[C@@](Cn1ccnc1C)(c1ccccc1)C1CCN(CC2CN(c3ccc(C#N)cc3)C2)CC1] |
| IV-459 | 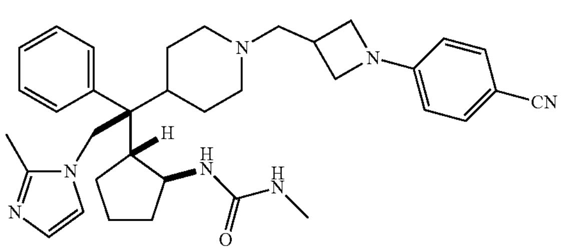 [SMILES: CNC(=O)N[C@H]1CCC[C@@H]1[C@](Cn1ccnc1C)(c1ccccc1)C1CCN(CC2CN(c3ccc(C#N)cc3)C2)CC1] |

TABLE 4-continued

| No. | Structure |
|---|---|
| IV-460 | 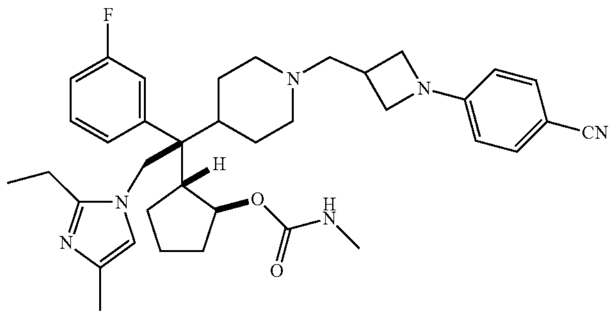 [SMILES: CCc1nc(C)cn1C[C@@](c1cccc(F)c1)(C1CCN(CC2CN(c3ccc(C#N)cc3)C2)CC1)[C@H]1CCC[C@@H]1OC(=O)NC] |
| IV-461 | 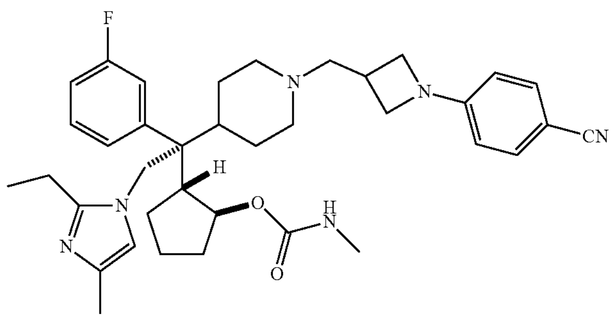 [SMILES: CCc1nc(C)cn1C[C@](c1cccc(F)c1)(C1CCN(CC2CN(c3ccc(C#N)cc3)C2)CC1)[C@H]1CCC[C@@H]1OC(=O)NC] |
| IV-462 | 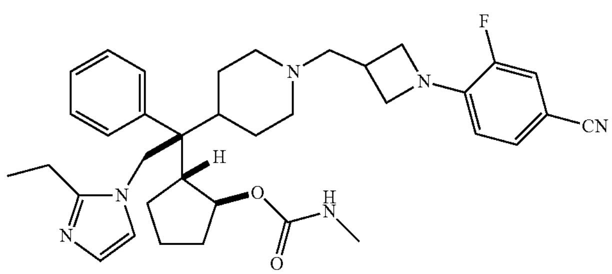 [SMILES: CCc1nccn1C[C@@](c1ccccc1)(C1CCN(CC2CN(c3ccc(C#N)cc3F)C2)CC1)[C@H]1CCC[C@@H]1OC(=O)NC] |
| IV-463 | 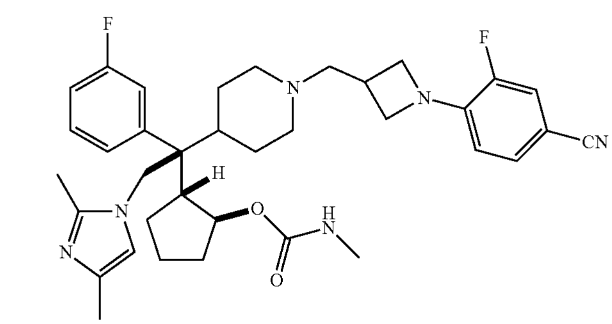 [SMILES: CNC(=O)O[C@H]1CCC[C@@H]1[C@](Cn1cc(C)nc1C)(c1cccc(F)c1)C1CCN(CC2CN(c3ccc(C#N)cc3F)C2)CC1] |
| IV-464 | 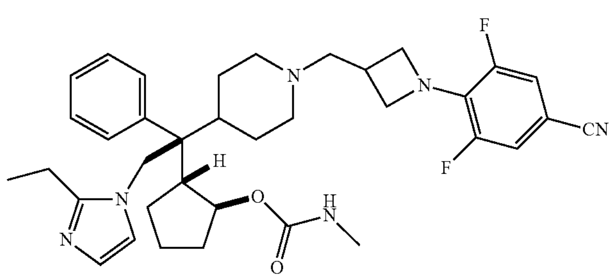 [SMILES: CCc1nccn1C[C@@](c1ccccc1)(C1CCN(CC2CN(c3c(F)cc(C#N)cc3F)C2)CC1)[C@H]1CCC[C@@H]1OC(=O)NC] |

TABLE 4-continued

| No. | Structure |
|---|---|
| IV-465 | 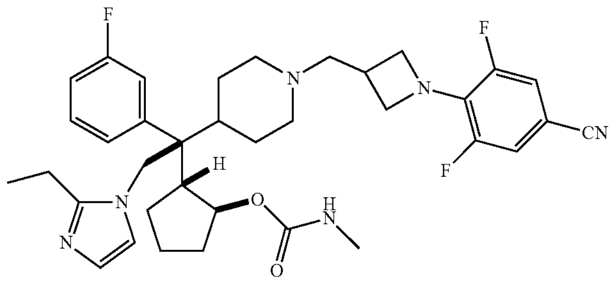 [SMILES: CCc1nccn1C[C@@](c1cccc(F)c1)(C1CCN(CC2CN(c3c(F)cc(C#N)cc3F)C2)CC1)[C@H]1CCC[C@@H]1OC(=O)NC] |
| IV-466 | 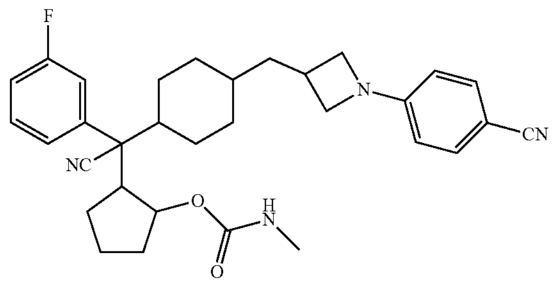 [SMILES: CNC(=O)OC1CCCC1C(C#N)(c1cccc(F)c1)C1CCC(CC2CN(c3ccc(C#N)cc3)C2)CC1] |
| IV-467 | 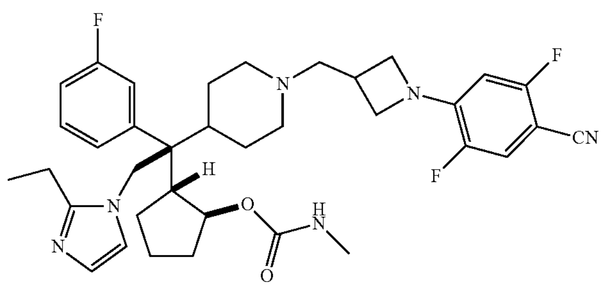 [SMILES: CCc1nccn1C[C@@](c1cccc(F)c1)(C1CCN(CC2CN(c3cc(F)c(C#N)cc3F)C2)CC1)[C@H]1CCC[C@@H]1OC(=O)NC] |
| IV-468 | 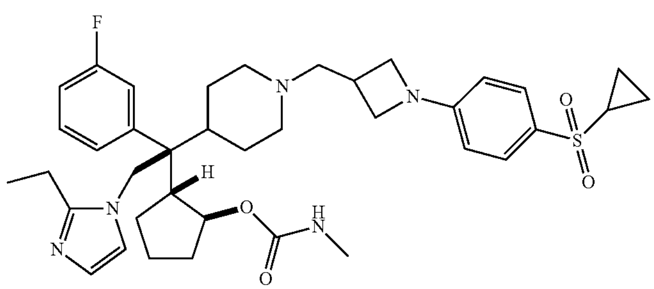 [SMILES: CCc1nccn1C[C@@](c1cccc(F)c1)(C1CCN(CC2CN(c3ccc(S(=O)(=O)C4CC4)cc3)C2)CC1)[C@H]1CCC[C@@H]1OC(=O)NC] |
| IV-469 | 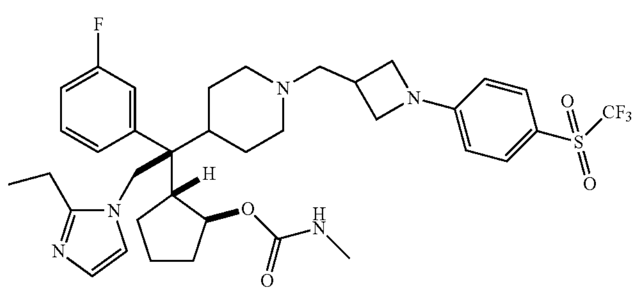 [SMILES: CCc1nccn1C[C@@](c1cccc(F)c1)(C1CCN(CC2CN(c3ccc(S(=O)(=O)C(F)(F)F)cc3)C2)CC1)[C@H]1CCC[C@@H]1OC(=O)NC] |

TABLE 4-continued
| No. | Structure |
|---|---|
| IV-470 | 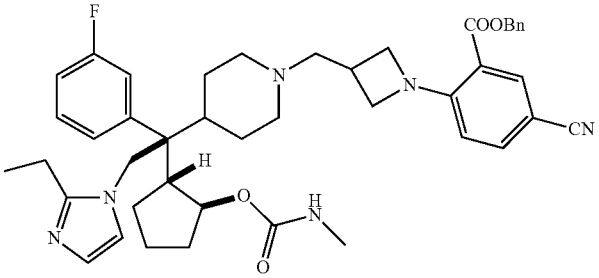 |
| IV-471 | 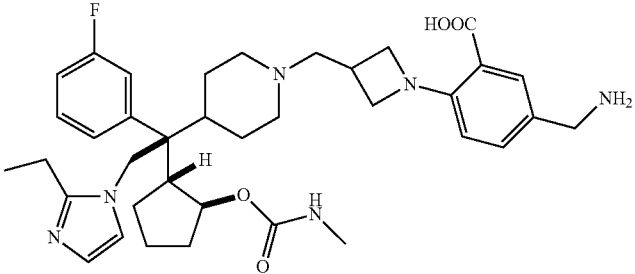 [SMILES: CCc1nccn1C[C@@](c1cccc(F)c1)(C1CCN(CC2CN(c3ccc(CN)cc3C(=O)O)C2)CC1)[C@H]1CCC[C@@H]1OC(=O)NC] |
| IV-472 | 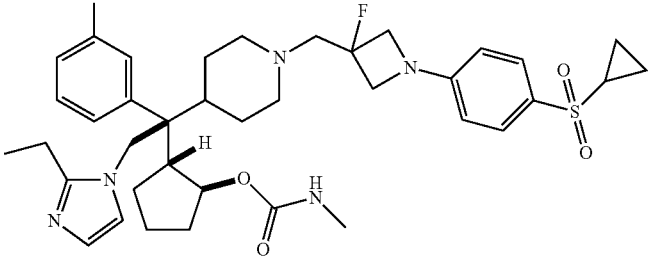 |
| IV-473 | 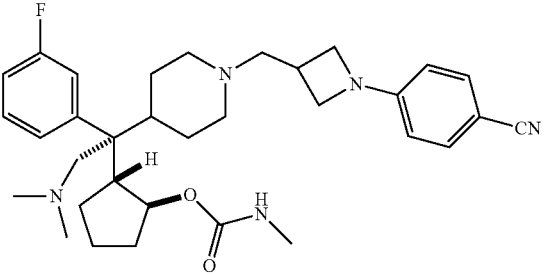 [SMILES: CNC(=O)O[C@H]1CCC[C@@H]1[C@@](CN(C)C)(c1cccc(F)c1)C1CCN(CC2CN(c3ccc(C#N)cc3)C2)CC1] |
| IV-474 | 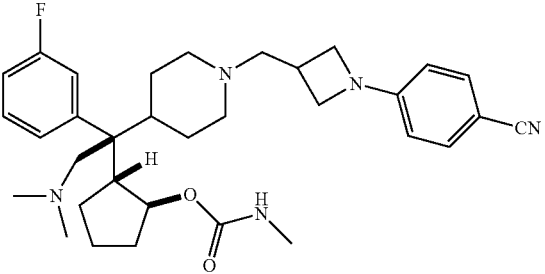 [SMILES: CNC(=O)O[C@H]1CCC[C@@H]1[C@](CN(C)C)(c1cccc(F)c1)C1CCN(CC2CN(c3ccc(C#N)cc3)C2)CC1] |

TABLE 4-continued

| No. | Structure |
|---|---|
| IV-475 | 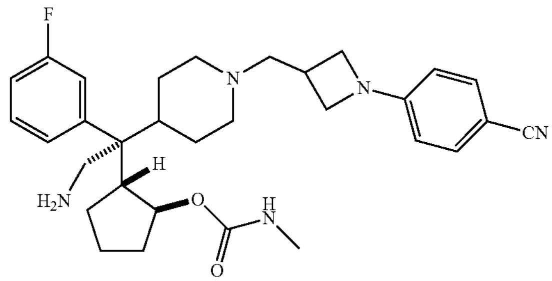 [SMILES: CNC(=O)O[C@H]1CCC[C@@H]1[C@@](CN)(c1cccc(F)c1)C1CCN(CC2CN(c3ccc(C#N)cc3)C2)CC1] |
| IV-476 | 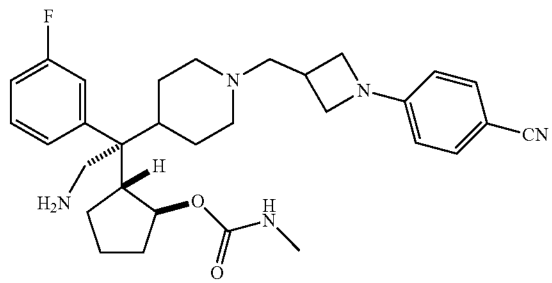 [SMILES: CNC(=O)O[C@H]1CCC[C@@H]1[C@@](CN)(c1cccc(F)c1)C1CCN(CC2CN(c3ccc(C#N)cc3)C2)CC1] |
| IV-477 | 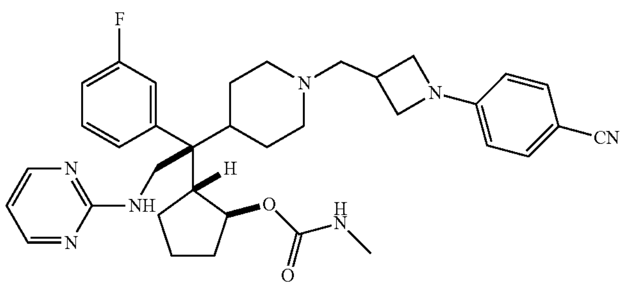 [SMILES: CNC(=O)O[C@H]1CCC[C@@H]1[C@](CNc1ncccn1)(c1cccc(F)c1)C1CCN(CC2CN(c3ccc(C#N)cc3)C2)CC1] |
| IV-478 | 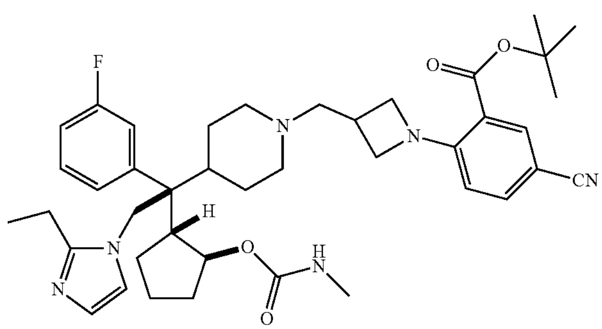 [SMILES: CCc1nccn1C[C@@](c1cccc(F)c1)(C1CCN(CC2CN(c3ccc(C#N)cc3C(=O)OC(C)(C)C)C2)CC1)[C@H]1CCC[C@@H]1OC(=O)NC] |
| IV-479 | 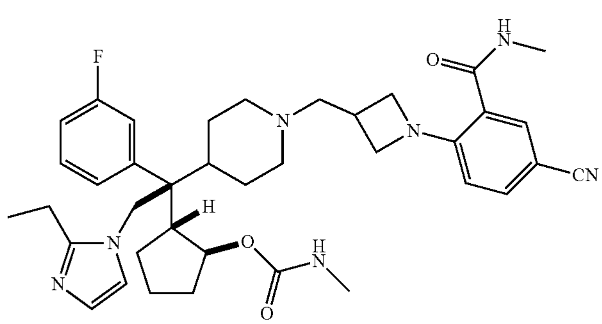 [SMILES: CCc1nccn1C[C@@](c1cccc(F)c1)(C1CCN(CC2CN(c3ccc(C#N)cc3C(=O)NC)C2)CC1)[C@H]1CCC[C@@H]1OC(=O)NC] |

TABLE 4-continued

| No. | Structure |
|---|---|
| IV-480 | 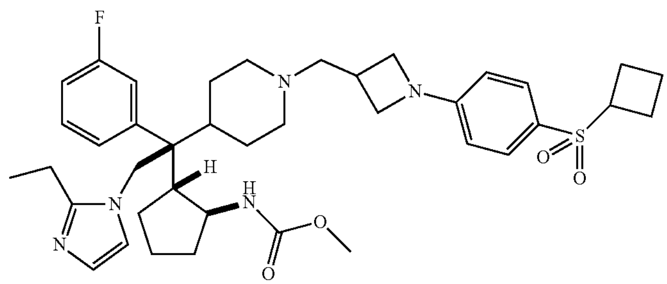 [SMILES: CCc1nccn1C[C@@](c1cccc(F)c1)(C1CCN(CC2CN(c3ccc(S(=O)(=O)C4CCC4)cc3)C2)CC1)[C@H]1CCC[C@@H]1NC(=O)OC] |
| IV-481 | 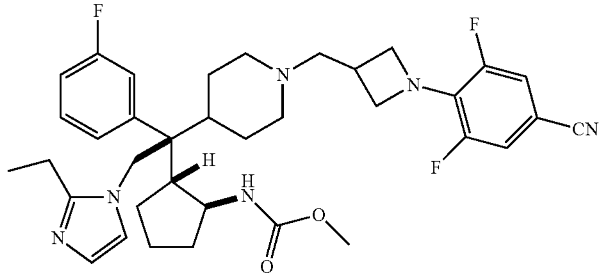 [SMILES: CCc1nccn1C[C@@](c1cccc(F)c1)(C1CCN(CC2CN(c3c(F)cc(C#N)cc3F)C2)CC1)[C@H]1CCC[C@@H]1NC(=O)OC] |
| IV-482 | 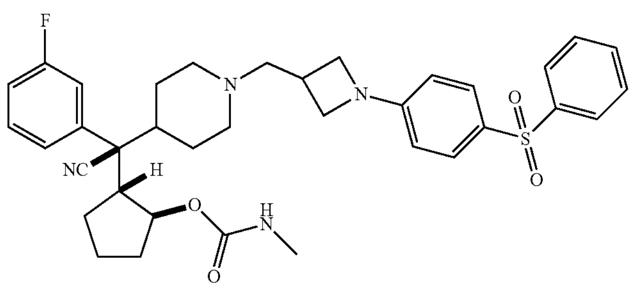 [SMILES: CNC(=O)O[C@H]1CCC[C@@H]1[C@](C#N)(c1cccc(F)c1)C1CCN(CC2CN(c3ccc(S(=O)(=O)c4ccccc4)cc3)C2)CC1] |
| IV-483 | 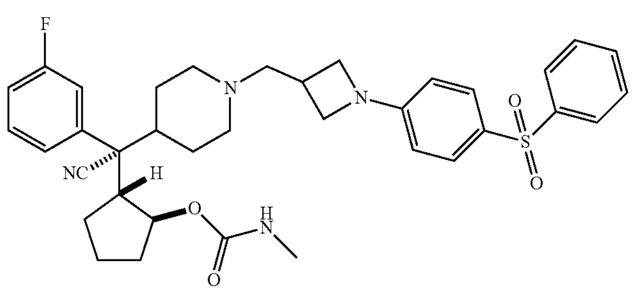 [SMILES: CNC(=O)O[C@H]1CCC[C@@H]1[C@@](C#N)(c1cccc(F)c1)C1CCN(CC2CN(c3ccc(S(=O)(=O)c4ccccc4)cc3)C2)CC1] |
| IV-484 | 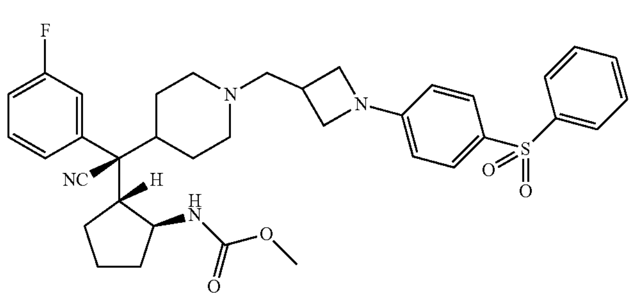 [SMILES: COC(=O)N[C@H]1CCC[C@@H]1[C@](C#N)(c1cccc(F)c1)C1CCN(CC2CN(c3ccc(S(=O)(=O)c4ccccc4)cc3)C2)CC1] |

TABLE 4-continued

| No. | Structure |
|---|---|
| IV-485 | 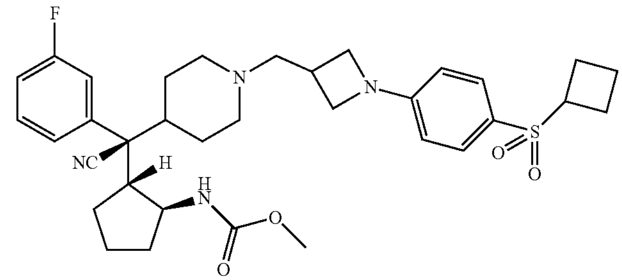 [SMILES: COC(=O)N[C@H]1CCC[C@@H]1[C@](C#N)(c1cccc(F)c1)C1CCN(CC2CN(c3ccc(S(=O)(=O)C4CCC4)cc3)C2)CC1] |
| IV-486 | 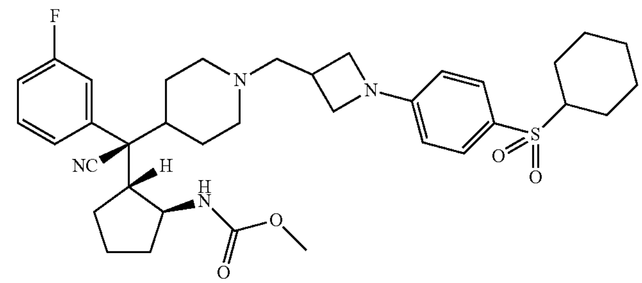 [SMILES: COC(=O)N[C@H]1CCC[C@@H]1[C@](C#N)(c1cccc(F)c1)C1CCN(CC2CN(c3ccc(S(=O)(=O)C4CCCCC4)cc3)C2)CC1] |
| IV-487 | 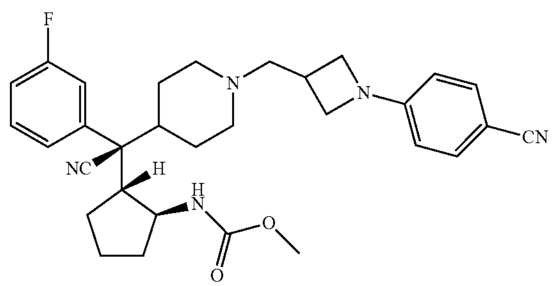 [SMILES: COC(=O)N[C@H]1CCC[C@@H]1[C@](C#N)(c1cccc(F)c1)C1CCN(CC2CN(c3ccc(C#N)cc3)C2)CC1] |
| IV-488 | 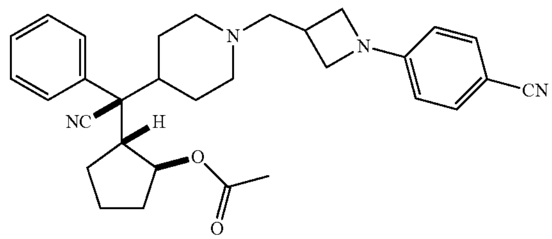 [SMILES: CC(=O)O[C@H]1CCC[C@@H]1[C@](C#N)(c1ccccc1)C1CCN(CC2CN(c3ccc(C#N)cc3)C2)CC1] |
| IV-489 | 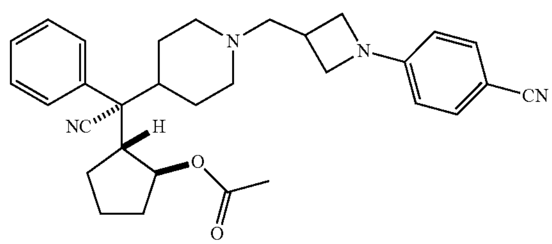 [SMILES: CC(=O)O[C@H]1CCC[C@@H]1[C@@](C#N)(c1ccccc1)C1CCN(CC2CN(c3ccc(C#N)cc3)C2)CC1] |
| IV-490 | 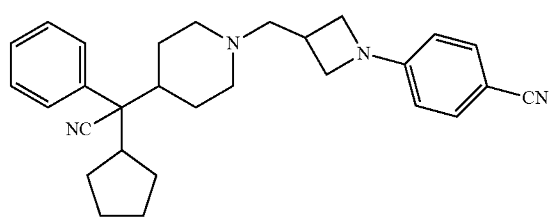 [SMILES: N#Cc1ccc(N2CC(CN3CCC(C(C#N)(c4ccccc4)C4CCCC4)CC3)C2)cc1] |

TABLE 4-continued

| No. | Structure |
|---|---|
| IV-491 | 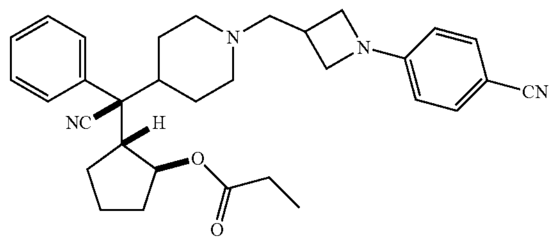 [SMILES: CCC(=O)O[C@H]1CCC[C@@H]1[C@](C#N)(c1ccccc1)C1CCN(CC2CN(c3ccc(C#N)cc3)C2)CC1] |
| IV-492 | 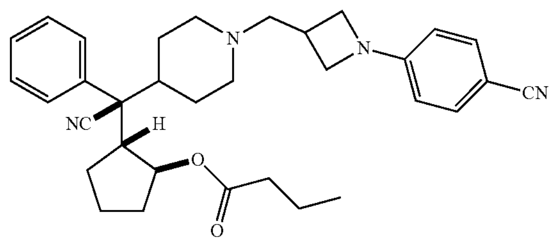 [SMILES: CCCC(=O)O[C@H]1CCC[C@@H]1[C@](C#N)(c1ccccc1)C1CCN(CC2CN(c3ccc(C#N)cc3)C2)CC1] |
| IV-493 | 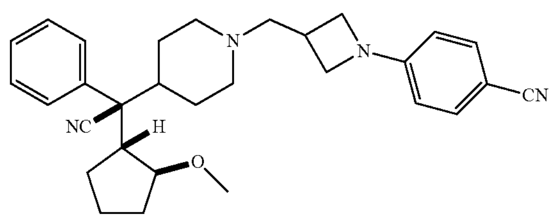 [SMILES: CO[C@H]1CCC[C@@H]1[C@](C#N)(c1ccccc1)C1CCN(CC2CN(c3ccc(C#N)cc3)C2)CC1] |
| IV-494 | 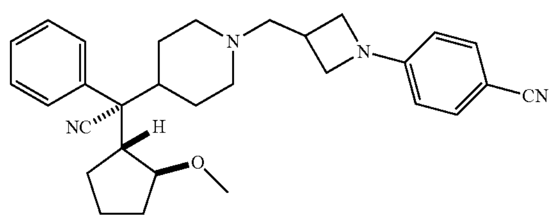 [SMILES: CO[C@H]1CCC[C@@H]1[C@@](C#N)(c1ccccc1)C1CCN(CC2CN(c3ccc(C#N)cc3)C2)CC1] |
| IV-495 | 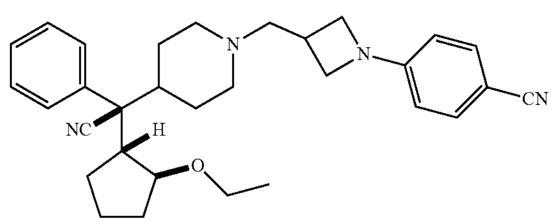 [SMILES: CCO[C@H]1CCC[C@@H]1[C@](C#N)(c1ccccc1)C1CCN(CC2CN(c3ccc(C#N)cc3)C2)CC1] |
| IV-496 | 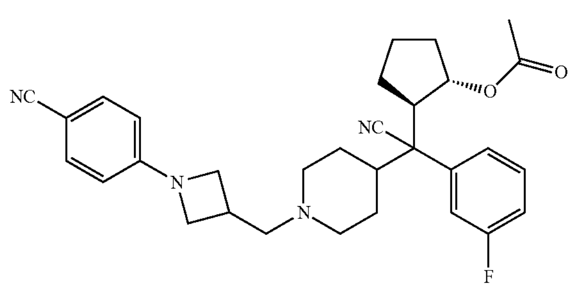 [SMILES: CC(=O)O[C@H]1CCC[C@@H]1C(C#N)(c1cccc(F)c1)C1CCN(CC2CN(c3ccc(C#N)cc3)C2)CC1] |

TABLE 4-continued

| No. | Structure |
|---|---|
| IV-497 | 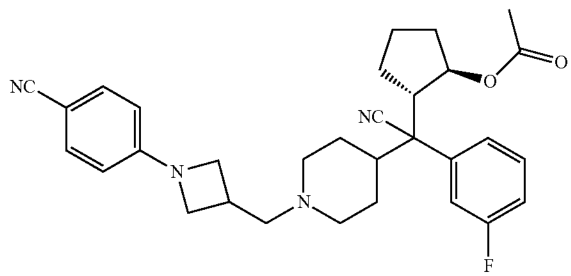 [SMILES: CC(=O)O[C@@H]1CCC[C@H]1C(C#N)(c1cccc(F)c1)C1CCN(CC2CN(c3ccc(C#N)cc3)C2)CC1] |
| IV-498 | 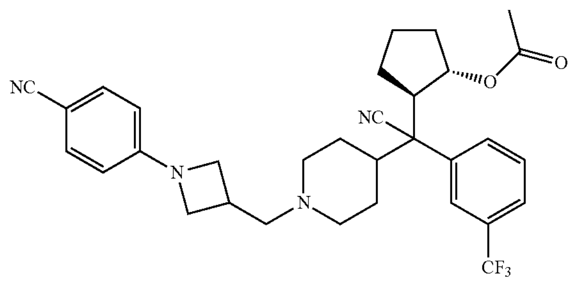 [SMILES: CC(=O)O[C@H]1CCC[C@@H]1C(C#N)(c1cccc(C(F)(F)F)c1)C1CCN(CC2CN(c3ccc(C#N)cc3)C2)CC1] |
| IV-499 | 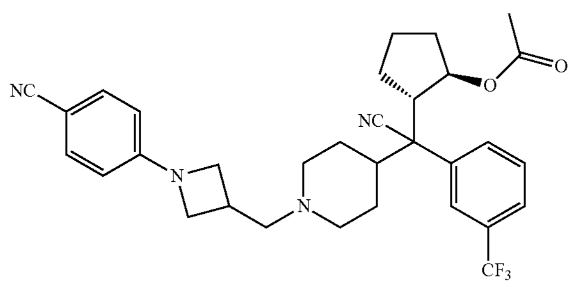 [SMILES: CC(=O)O[C@@H]1CCC[C@H]1C(C#N)(c1cccc(C(F)(F)F)c1)C1CCN(CC2CN(c3ccc(C#N)cc3)C2)CC1] |
| IV-500 | 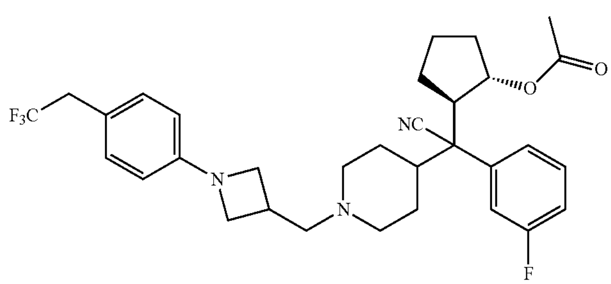 [SMILES: CC(=O)O[C@H]1CCC[C@@H]1C(C#N)(c1cccc(F)c1)C1CCN(CC2CN(c3ccc(CC(F)(F)F)cc3)C2)CC1] |
| IV-501 | 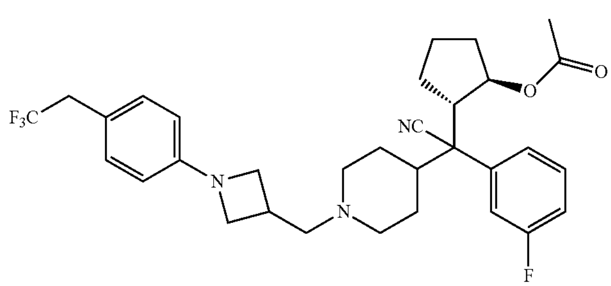 [SMILES: CC(=O)O[C@@H]1CCC[C@H]1C(C#N)(c1cccc(F)c1)C1CCN(CC2CN(c3ccc(CC(F)(F)F)cc3)C2)CC1] |

TABLE 4-continued

| No. | Structure |
|---|---|
| IV-502 | 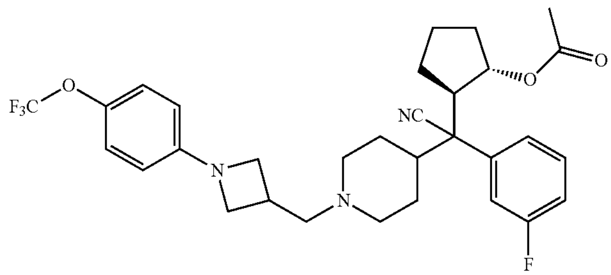 [SMILES: CC(=O)O[C@H]1CCC[C@@H]1C(C#N)(c1cccc(F)c1)C1CCN(CC2CN(c3ccc(OC(F)(F)F)cc3)C2)CC1] |
| IV-503 | 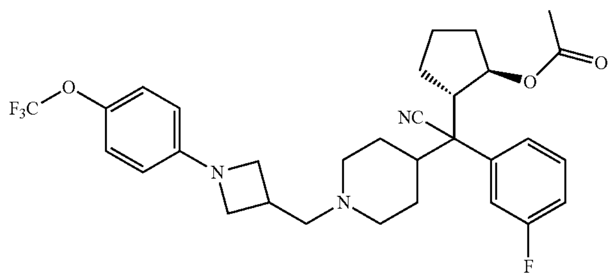 [SMILES: CC(=O)O[C@@H]1CCC[C@H]1C(C#N)(c1cccc(F)c1)C1CCN(CC2CN(c3ccc(OC(F)(F)F)cc3)C2)CC1] |
| IV-504 | 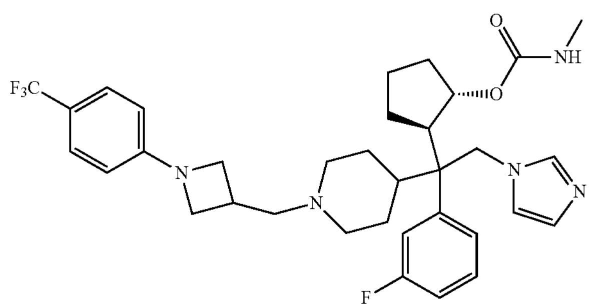 [SMILES: CNC(=O)O[C@H]1CCC[C@@H]1C(Cn1ccnc1)(c1cccc(F)c1)C1CCN(CC2CN(c3ccc(C(F)(F)F)cc3)C2)CC1] |
| IV-505 | 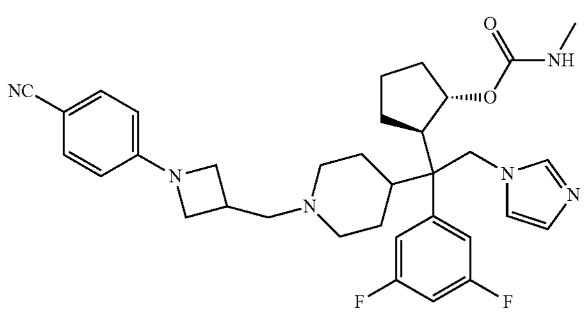 [SMILES: CNC(=O)O[C@H]1CCC[C@@H]1C(Cn1ccnc1)(c1cc(F)cc(F)c1)C1CCN(CC2CN(c3ccc(C#N)cc3)C2)CC1] |
| IV-506 | 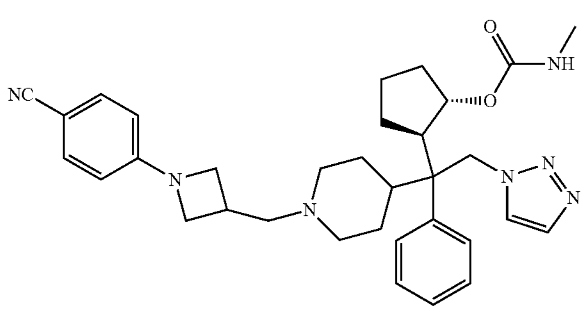 [SMILES: CNC(=O)O[C@H]1CCC[C@@H]1C(Cn1ccnn1)(c1ccccc1)C1CCN(CC2CN(c3ccc(C#N)cc3)C2)CC1] |

TABLE 4-continued

| No. | Structure |
|---|---|
| IV-507 | 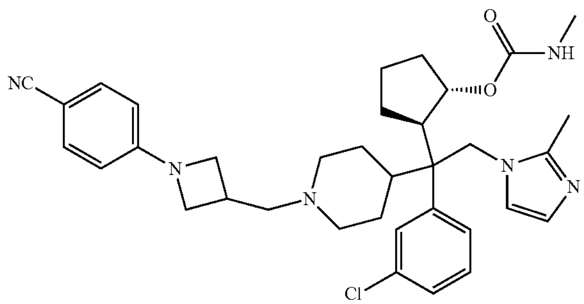 [SMILES: CNC(=O)O[C@H]1CCC[C@@H]1C(Cn1ccnc1C)(c1cccc(Cl)c1)C1CCN(CC2CN(c3ccc(C#N)cc3)C2)CC1] |
| IV-508 | 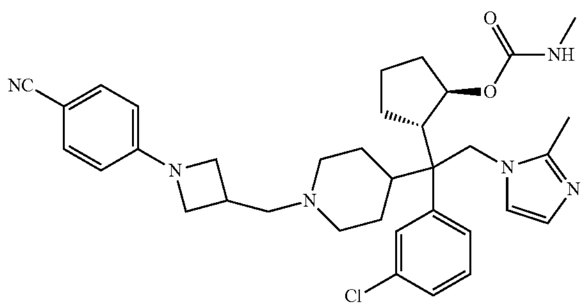 [SMILES: CNC(=O)O[C@@H]1CCC[C@H]1C(Cn1ccnc1C)(c1cccc(Cl)c1)C1CCN(CC2CN(c3ccc(C#N)cc3)C2)CC1] |
| IV-509 | 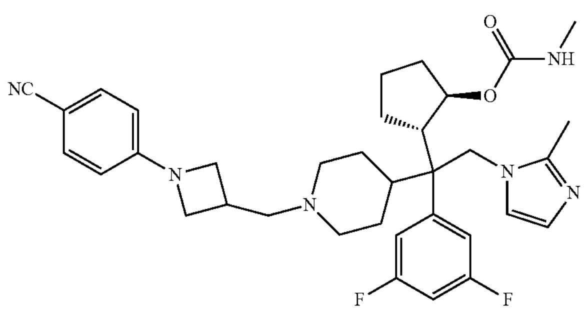 [SMILES: CNC(=O)O[C@@H]1CCC[C@H]1C(Cn1ccnc1C)(c1cc(F)cc(F)c1)C1CCN(CC2CN(c3ccc(C#N)cc3)C2)CC1] |
| IV-510 | 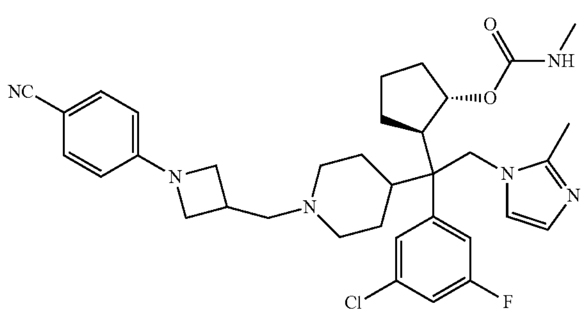 [SMILES: CNC(=O)O[C@H]1CCC[C@@H]1C(Cn1ccnc1C)(c1cc(F)cc(Cl)c1)C1CCN(CC2CN(c3ccc(C#N)cc3)C2)CC1] |
| IV-511 | 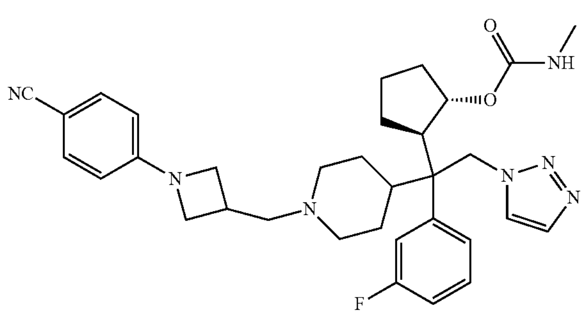 [SMILES: CNC(=O)O[C@H]1CCC[C@@H]1C(Cn1ccnn1)(c1cccc(F)c1)C1CCN(CC2CN(c3ccc(C#N)cc3)C2)CC1] |

TABLE 4-continued

| No. | Structure |
|---|---|
| IV-512 | 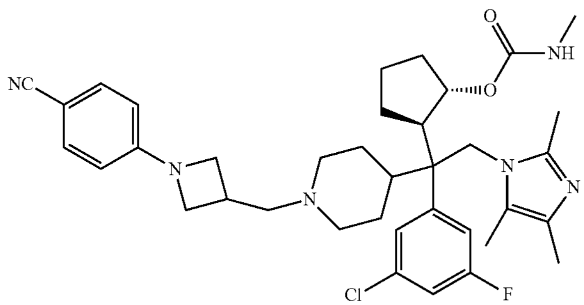 [SMILES: CNC(=O)O[C@H]1CCC[C@@H]1C(Cn1c(C)nc(C)c1C)(c1cc(F)cc(Cl)c1)C1CCN(CC2CN(c3ccc(C#N)cc3)C2)CC1] |
| IV-513 | 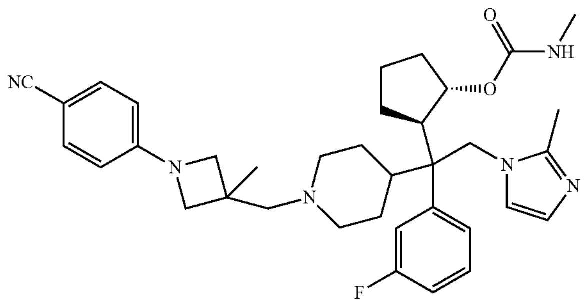 [SMILES: CNC(=O)O[C@H]1CCC[C@@H]1C(Cn1ccnc1C)(c1cccc(F)c1)C1CCN(CC2(C)CN(c3ccc(C#N)cc3)C2)CC1] |
| IV-514 | 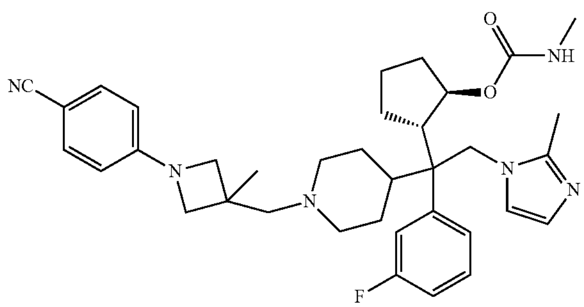 [SMILES: CNC(=O)O[C@@H]1CCC[C@H]1C(Cn1ccnc1C)(c1cccc(F)c1)C1CCN(CC2(C)CN(c3ccc(C#N)cc3)C2)CC1] |
| IV-515 | 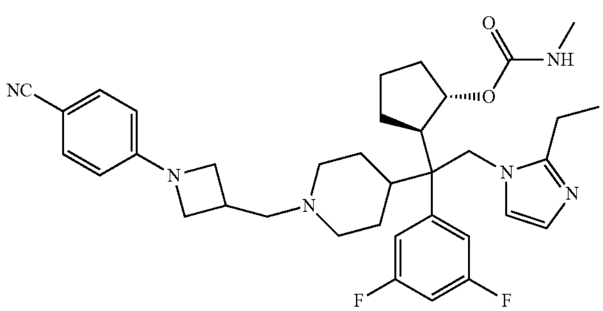 [SMILES: CCc1nccn1CC(c1cc(F)cc(F)c1)(C1CCN(CC2CN(c3ccc(C#N)cc3)C2)CC1)[C@H]1CCC[C@@H]1OC(=O)NC] |
| IV-516 | 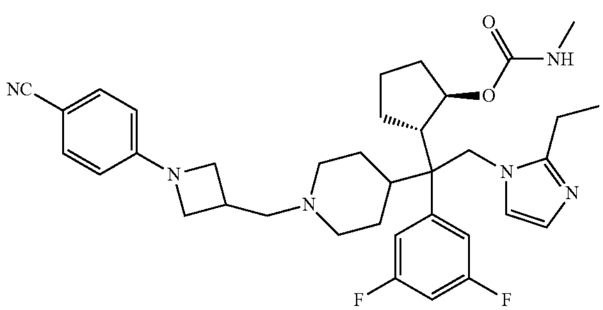 [SMILES: CCc1nccn1CC(c1cc(F)cc(F)c1)(C1CCN(CC2CN(c3ccc(C#N)cc3)C2)CC1)[C@@H]1CCC[C@H]1OC(=O)NC] |

TABLE 4-continued

| No. | Structure |
|---|---|
| IV-517 | 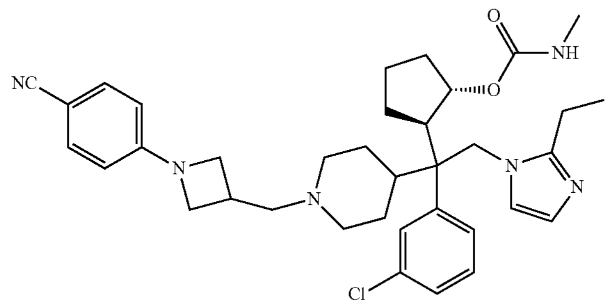 [SMILES: CCc1nccn1CC(c1cccc(Cl)c1)(C1CCN(CC2CN(c3ccc(C#N)cc3)C2)CC1)[C@H]1CCC[C@@H]1OC(=O)NC] |
| IV-518 | 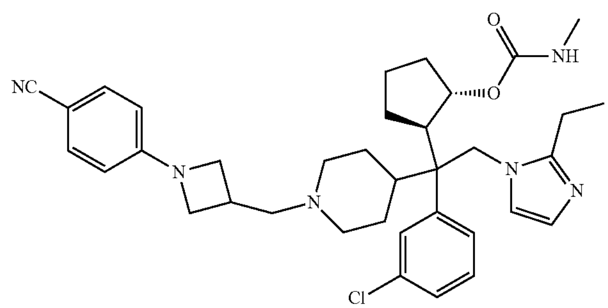 [SMILES: CCc1nccn1CC(c1cccc(Cl)c1)(C1CCN(CC2CN(c3ccc(C#N)cc3)C2)CC1)[C@H]1CCC[C@@H]1OC(=O)NC] |
| IV-519 | 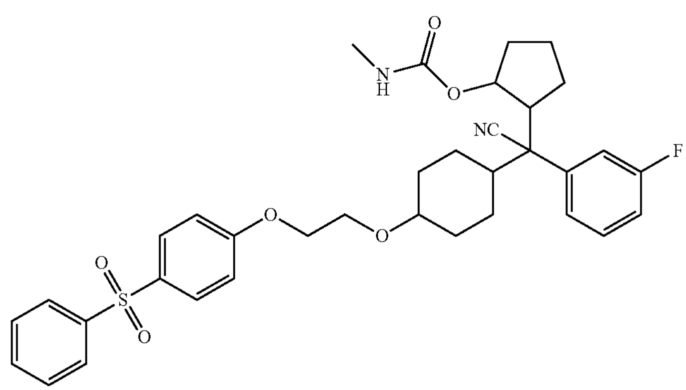 [SMILES: CNC(=O)OC1CCCC1C(C#N)(c1cccc(F)c1)C1CCC(OCCOc2ccc(S(=O)(=O)c3ccccc3)cc2)CC1] |
| IV-520 | 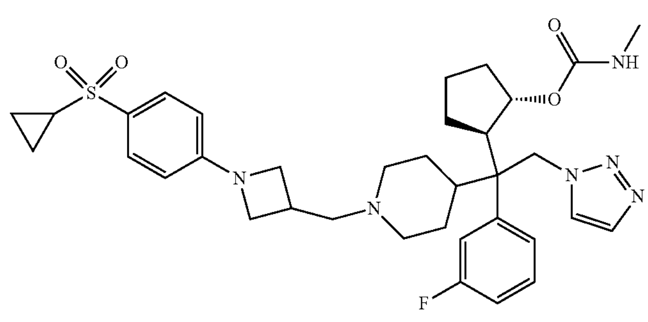 [SMILES: CNC(=O)O[C@H]1CCC[C@@H]1C(Cn1ccnn1)(c1cccc(F)c1)C1CCN(CC2CN(c3ccc(S(=O)(=O)C4CC4)cc3)C2)CC1] |

TABLE 5

| No. | Structure |
|---|---|
| V-1 | 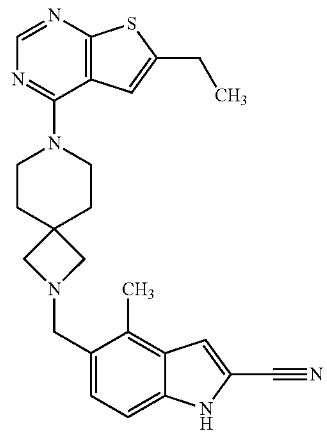 [SMILES: CCc1cc2c(N3CCC4(CC3)CN(Cc3ccc5[nH]c(C#N)cc5c3C)C4)ncnc2s1] |
| V-2 | 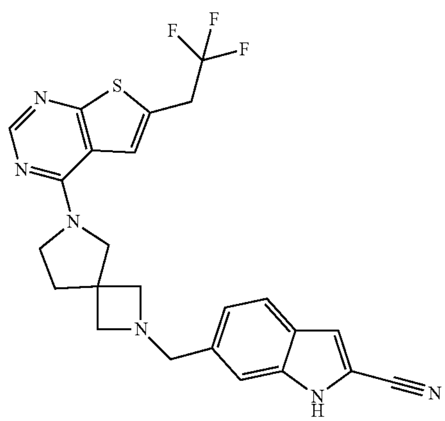 [SMILES: N#Cc1cc2ccc(CN3CC4(CCN(c5ncnc6sc(CC(F)(F)F)cc56)C4)C3)cc2[nH]1] |
| V-3 | 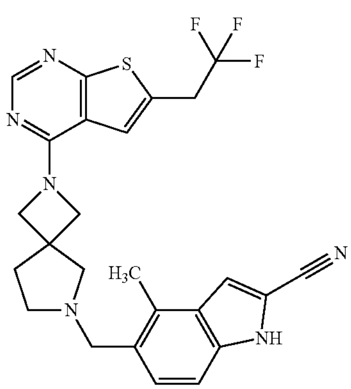 [SMILES: Cc1c(CN2CCC3(C2)CN(c2ncnc4sc(CC(F)(F)F)cc24)C3)ccc2[nH]c(C#N)cc12] |
| V-4 | |
| V-5 | |
| V-6 | |

TABLE 5-continued

| No. | Structure |
|---|---|
| V-7 | *(structure)* |
| V-8 | *(structure)* |
| V-9 | *(structure)* |
| V-10 | *(structure)* |
| V-11 | *(structure)* |
| V-12 | *(structure)* |
| V-13 | *(structure)* |
| V-14 | *(structure)* |

TABLE 5-continued

| No. | Structure |
|---|---|
| V-15 | |
| V-16 | |
| V-17 | |
| V-18 | 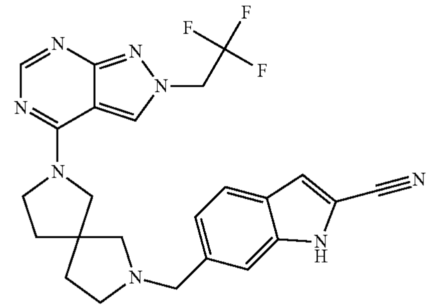 [SMILES: N#Cc1cc2ccc(CN3CCC4(CCN(c5ncnc6nn(CC(F)(F)F)cc56)C4)C3)cc2[nH]1] |
| V-19 | 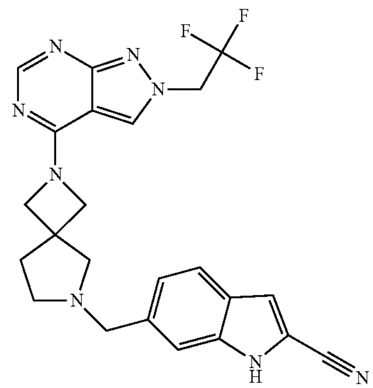 [SMILES: N#Cc1cc2ccc(CN3CCC4(C3)CN(c3ncnc5nn(CC(F)(F)F)cc35)C4)cc2[nH]1] |
| V-20 | 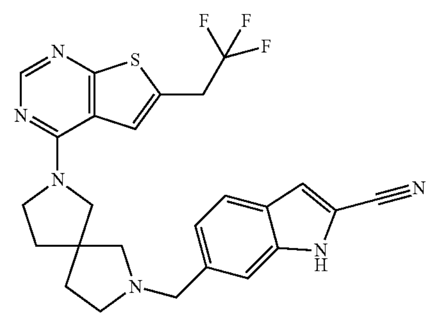 [SMILES: N#Cc1cc2ccc(CN3CCC4(CCN(c5ncnc6sc(CC(F)(F)F)cc56)C4)C3)cc2[nH]1] |
| V-21 | 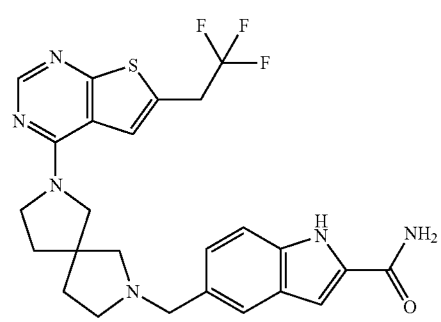 [SMILES: NC(=O)c1cc2cc(CN3CCC4(CCN(c5ncnc6sc(CC(F)(F)F)cc56)C4)C3)ccc2[nH]1] |

TABLE 5-continued
| No. | Structure |
|---|---|
| V-22 | 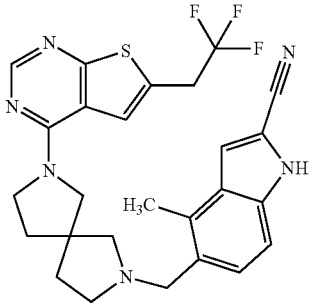 [SMILES: Cc1c(CN2CCC3(CCN(c4ncnc5sc(CC(F)(F)F)cc45)C3)C2)ccc2[nH]c(C#N)cc12] |
| V-23 | 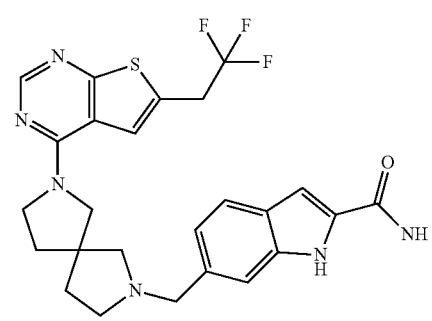 [SMILES: NC(=O)c1cc2ccc(CN3CCC4(CCN(c5ncnc6sc(CC(F)(F)F)cc56)C4)C3)cc2[nH]1] |
| V-24 | 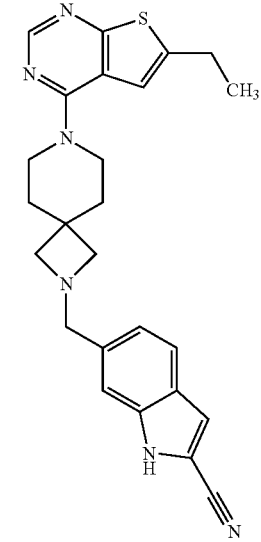 [SMILES: CCc1cc2c(N3CCC4(CC3)CN(Cc3ccc5cc(C#N)[nH]c5c3)C4)ncnc2s1] |
| V-25 | 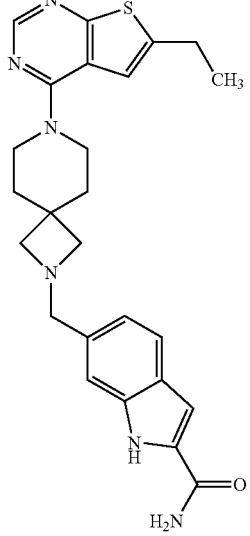 |
| V-26 | 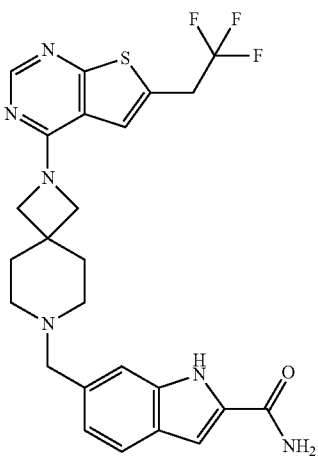 [SMILES: NC(=O)c1cc2ccc(CN3CCC4(CC3)CN(c3ncnc5sc(CC(F)(F)F)cc35)C4)cc2[nH]1] |
| V-27 | 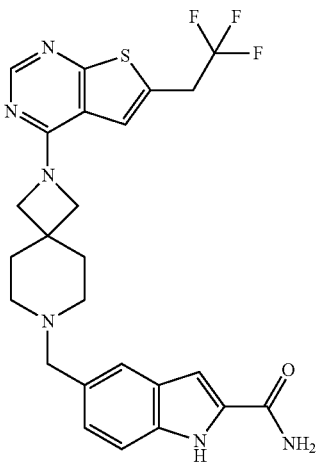 [SMILES: NC(=O)c1cc2cc(CN3CCC4(CC3)CN(c3ncnc5sc(CC(F)(F)F)cc35)C4)ccc2[nH]1] |

TABLE 5-continued

| No. | Structure |
|---|---|
| V-28 | 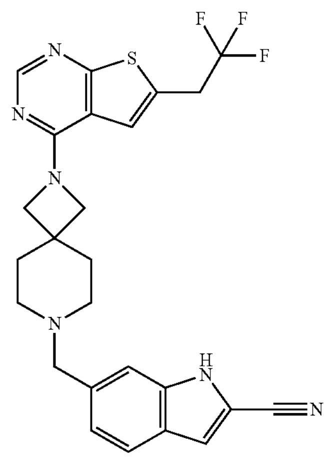 [SMILES: N#Cc1cc2ccc(CN3CCC4(CC3)CN(c3ncnc5sc(CC(F)(F)F)cc35)C4)cc2[nH]1] |
| V-29 | 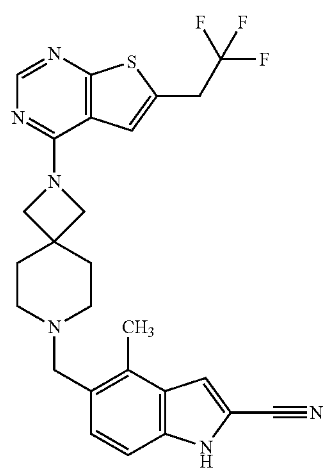 [SMILES: Cc1c(CN2CCC3(CC2)CN(c2ncnc4sc(CC(F)(F)F)cc24)C3)ccc2[nH]c(C#N)cc12] |
| V-30 | 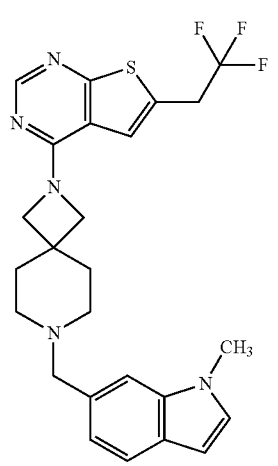 [SMILES: Cn1ccc2ccc(CN3CCC4(CC3)CN(c3ncnc5sc(CC(F)(F)F)cc35)C4)cc21] |
| V-31 | |
| V-32 | |
| V-33 | |

TABLE 5-continued

| No. | Structure |
|-----|-----------|
| V-34 | 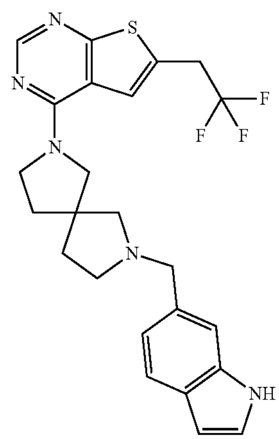 [SMILES: FC(F)(F)Cc1cc2c(N3CCC4(CCN(Cc5ccc6cc[nH]c6c5)C4)C3)ncnc2s1] |
| V-35 | 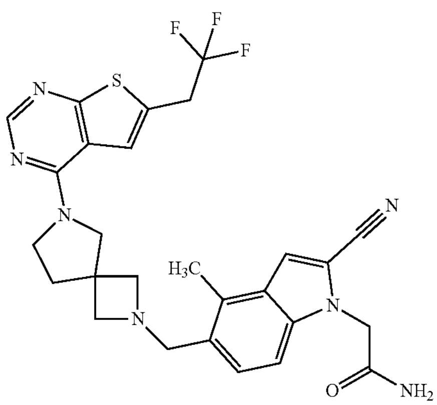 [SMILES: Cc1c(CN2CC3(CCN(c4ncnc5sc(CC(F)(F)F)cc45)C3)C2)ccc2c1cc(C#N)n2CC(N)=O] |
| V-36 | 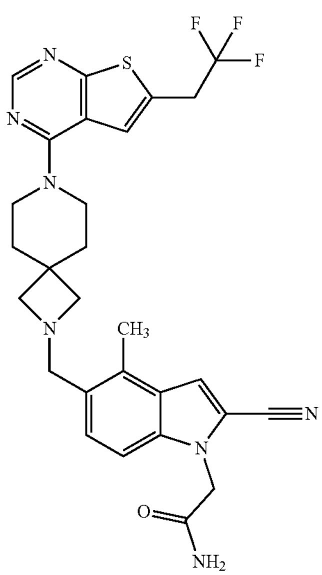 [SMILES: Cc1c(CN2CC3(CCN(c4ncnc5sc(CC(F)(F)F)cc45)CC3)C2)ccc2c1cc(C#N)n2CC(N)=O] |
| V-37 | 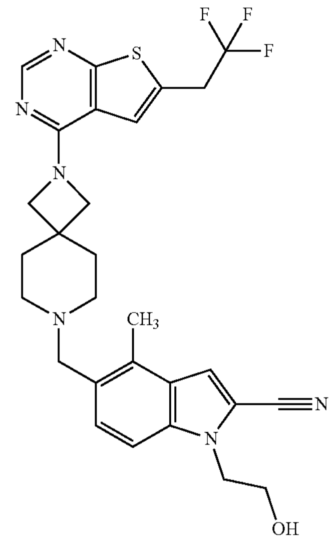 [SMILES: Cc1c(CN2CCC3(CC2)CN(c2ncnc4sc(CC(F)(F)F)cc24)C3)ccc2c1cc(C#N)n2CCO] |
| V-38 | 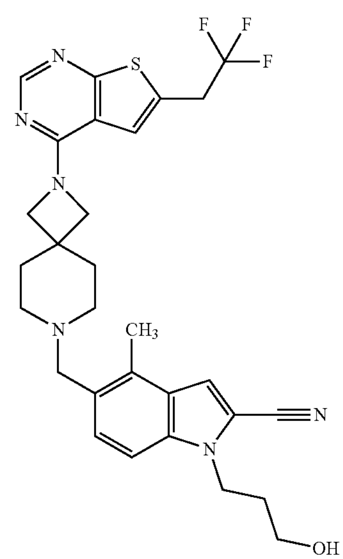 [SMILES: Cc1c(CN2CCC3(CC2)CN(c2ncnc4sc(CC(F)(F)F)cc24)C3)ccc2c1cc(C#N)n2CCCO] |

TABLE 5-continued
| No. | Structure |
|---|---|
| V-39 | 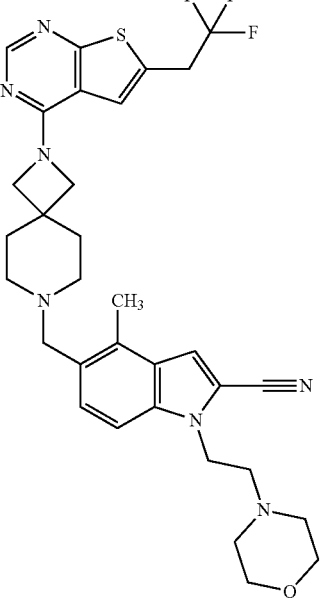 |
| V-40 | |
| V-41 | 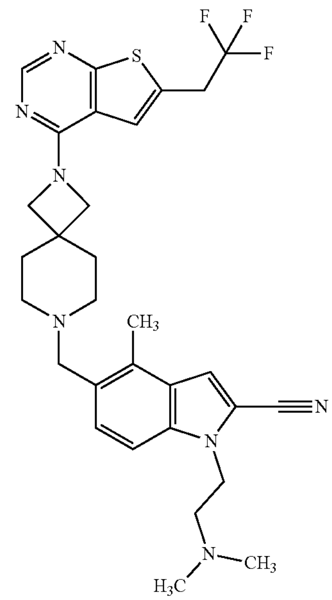 [SMILES: Cc1c(CN2CCC3(CC2)CN(c2ncnc4sc(CC(F)(F)F)cc24)C3)ccc2c1cc(C#N)n2CCN(C)C] |
| V-42 | 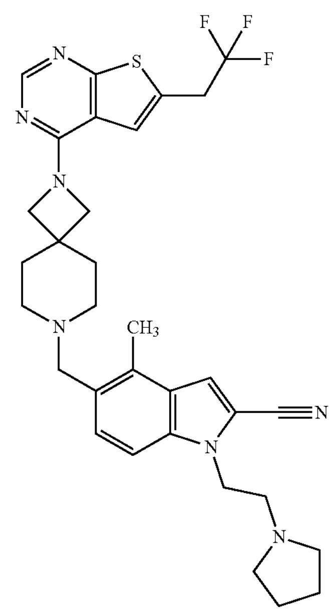 [SMILES: Cc1c(CN2CCC3(CC2)CN(c2ncnc4sc(CC(F)(F)F)cc24)C3)ccc2c1cc(C#N)n2CCN1CCCC1] |
| V-43 | 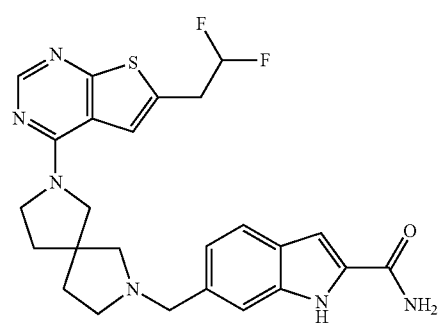 [SMILES: NC(=O)c1cc2ccc(CN3CCC4(CCN(c5ncnc6sc(CC(F)F)cc56)C4)C3)cc2[nH]1] |

TABLE 5-continued

| No. | Structure |
|---|---|
| V-44 | 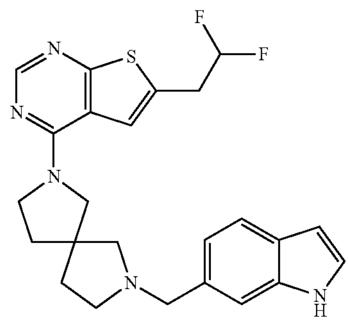 [SMILES: FC(F)Cc1cc2c(N3CCC4(CCN(Cc5ccc6cc[nH]c6c5)C4)C3)ncnc2s1] |
| V-45 | 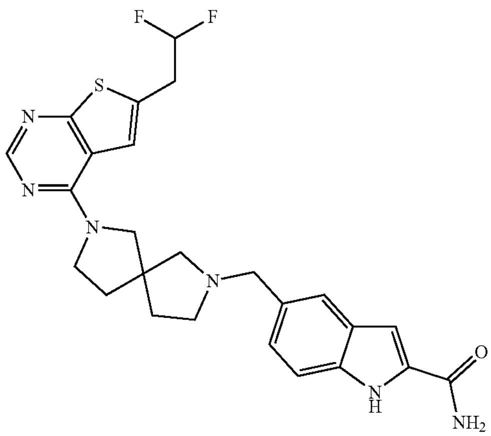 [SMILES: NC(=O)c1cc2cc(CN3CCC4(CCN(c5ncnc6sc(CC(F)F)cc56)C4)C3)ccc2[nH]1] |
| V-46 | 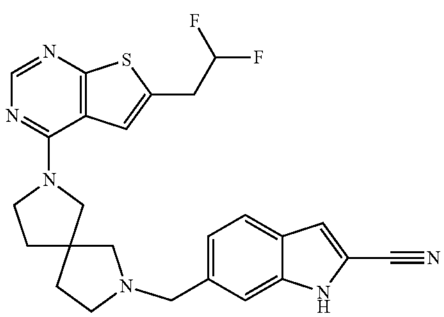 [SMILES: N#Cc1cc2ccc(CN3CCC4(CCN(c5ncnc6sc(CC(F)F)cc56)C4)C3)cc2[nH]1] |
| V-47 | 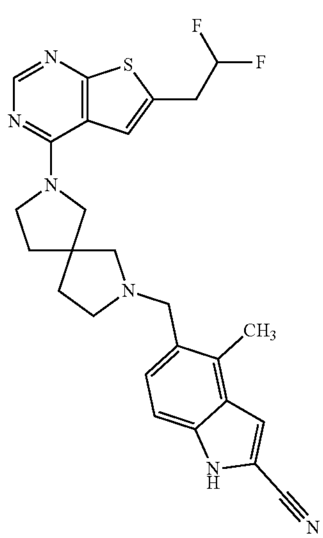 [SMILES: Cc1c(CN2CCC3(CCN(c4ncnc5sc(CC(F)F)cc45)C3)C2)ccc2[nH]c(C#N)cc12] |
| V-48 | |
| V-49 | |
| V-50 | |

TABLE 5-continued

| No. | Structure |
|---|---|
| V-51 | 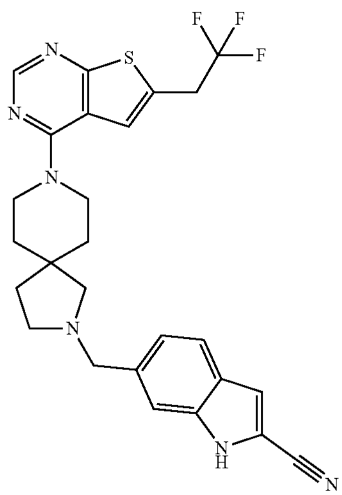 [SMILES: N#Cc1cc2ccc(CN3CCC4(CCN(c5ncnc6sc(CC(F)(F)F)cc56)CC4)C3)cc2[nH]1] |
| V-52 | 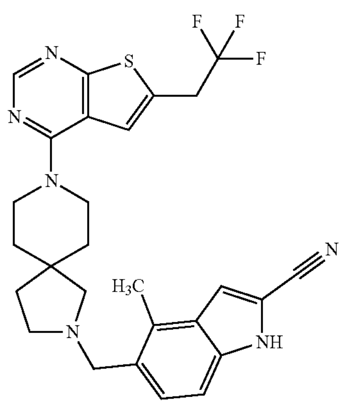 [SMILES: Cc1c(CN2CCC3(CCN(c4ncnc5sc(CC(F)(F)F)cc45)CC3)C2)ccc2[nH]c(C#N)cc12] |
| V-53 | 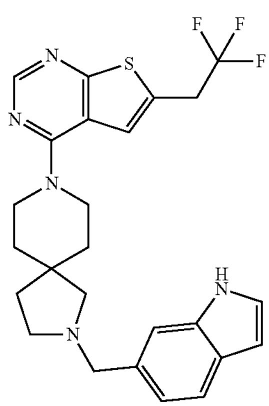 [SMILES: FC(F)(F)Cc1cc2c(N3CCC4(CCN(Cc5ccc6cc[nH]c6c5)C4)CC3)ncnc2s1] |
| V-54 | |
| V-55 | |
| V-56 | |

TABLE 5-continued

| No. | Structure |
|---|---|
| V-57 | 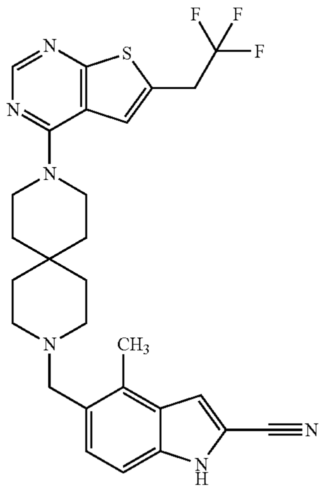 [SMILES: Cc1c(CN2CCC3(CC2)CCN(c2ncnc4sc(CC(F)(F)F)cc24)CC3)ccc2[nH]c(C#N)cc12] |
| V-58 | 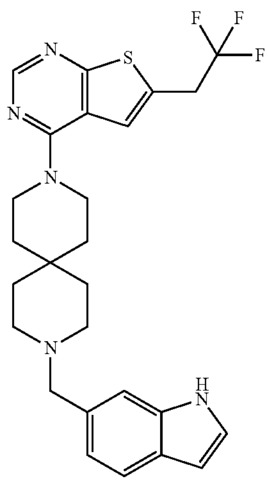 [SMILES: FC(F)(F)Cc1cc2c(N3CCC4(CCN(Cc5ccc6cc[nH]c6c5)CC4)CC3)ncnc2s1] |
| V-59 | 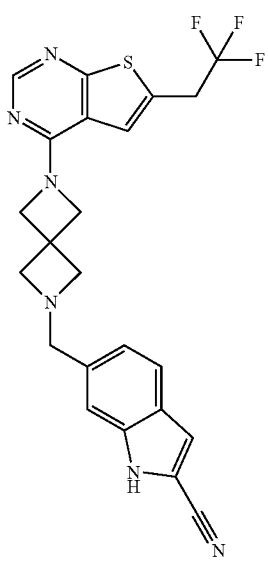 [SMILES: N#Cc1cc2ccc(CN3CC4(C3)CN(c3ncnc5sc(CC(F)(F)F)cc35)C4)cc2[nH]1] |
| V-60 | |
| V-61 | |
| V-62 | |

TABLE 5-continued

| No. | Structure |
|---|---|
| V-63 | 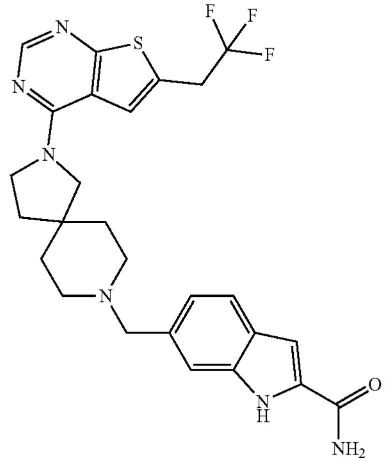 [SMILES: NC(=O)c1cc2ccc(CN3CCC4(CC3)CCN(c3ncnc5sc(CC(F)(F)F)cc35)C4)cc2[nH]1] |
| V-64 | 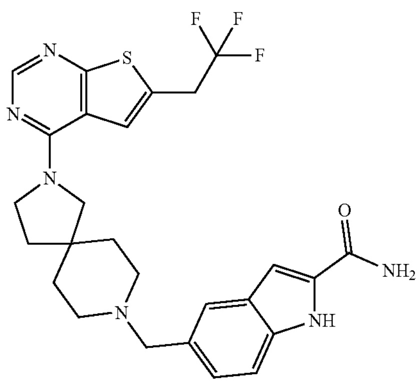 [SMILES: NC(=O)c1cc2cc(CN3CCC4(CC3)CCN(c3ncnc5sc(CC(F)(F)F)cc35)C4)ccc2[nH]1] |
| V-65 | 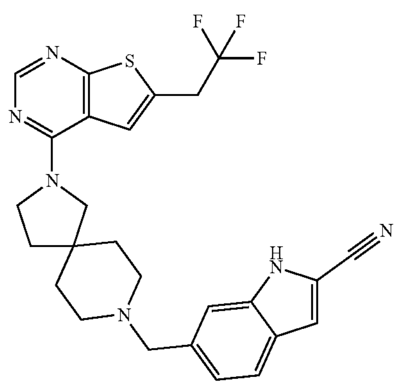 [SMILES: N#Cc1cc2ccc(CN3CCC4(CC3)CCN(c3ncnc5sc(CC(F)(F)F)cc35)C4)cc2[nH]1] |
| V-66 | 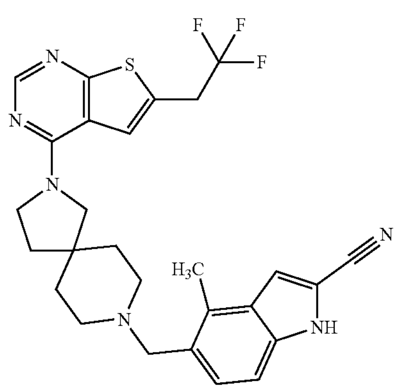 [SMILES: Cc1c(CN2CCC3(CC2)CCN(c2ncnc4sc(CC(F)(F)F)cc24)C3)ccc2[nH]c(C#N)cc12] |
| V-67 | |
| V-68 | |
| V-69 | |
| V-70 | |

TABLE 5-continued

| No. | Structure |
|---|---|
| V-71 | 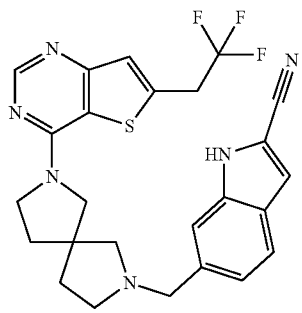 [SMILES: N#Cc1cc2ccc(CN3CCC4(CCN(c5ncnc6cc(CC(F)(F)F)sc56)C4)C3)cc2[nH]1] |
| V-72 | 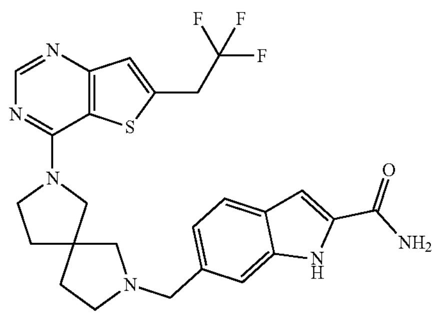 [SMILES: NC(=O)c1cc2ccc(CN3CCC4(CCN(c5ncnc6cc(CC(F)(F)F)sc56)C4)C3)cc2[nH]1] |
| V-73 | 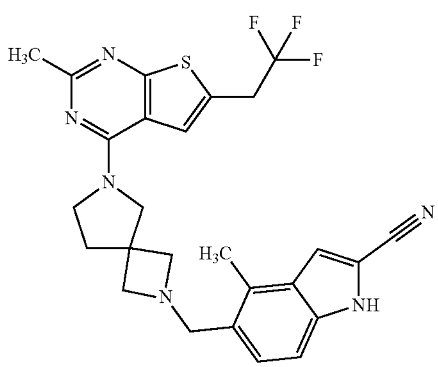 [SMILES: Cc1nc(N2CCC3(CN(Cc4ccc5[nH]c(C#N)cc5c4C)C3)C2)c2cc(CC(F)(F)F)sc2n1] |
| V-74 | 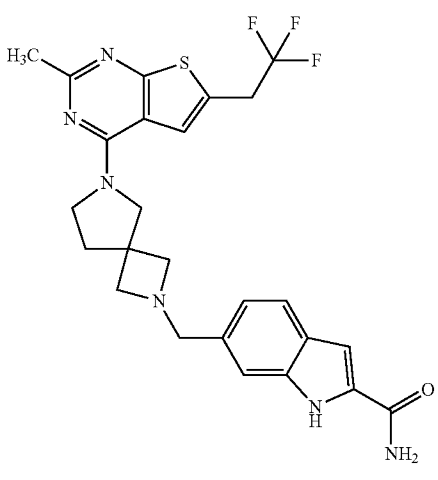 [SMILES: Cc1nc(N2CCC3(CN(Cc4ccc5cc(C(N)=O)[nH]c5c4)C3)C2)c2cc(CC(F)(F)F)sc2n1] |
| V-75 | |
| V-76 | |
| V-77 | |
| V-78 | |

TABLE 5-continued

| No. | Structure |
|---|---|
| V-79 | 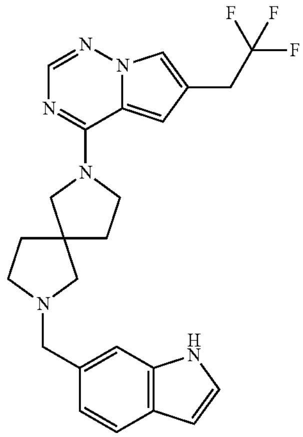 [SMILES: FC(F)(F)Cc1cc2c(N3CCC4(CCN(Cc5ccc6cc[nH]c6c5)C4)C3)ncnn2c1] |
| V-80 | 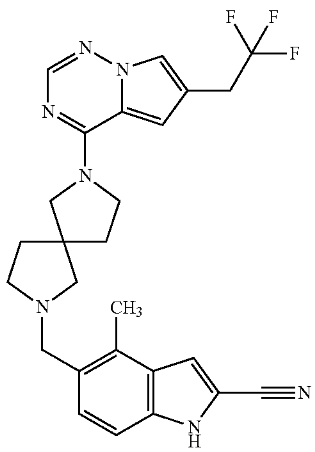 [SMILES: Cc1c(CN2CCC3(CCN(c4ncnn5cc(CC(F)(F)F)cc45)C3)C2)ccc2[nH]c(C#N)cc12] |
| V-81 | 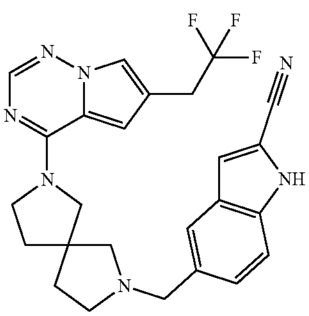 [SMILES: N#Cc1cc2cc(CN3CCC4(CCN(c5ncnn6cc(CC(F)(F)F)cc56)C4)C3)ccc2[nH]1] |
| V-82 | |("structures not transcribable")

TABLE 5-continued

| No. | Structure |
|---|---|
| V-83 | 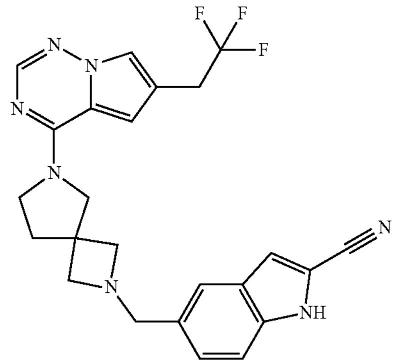 [SMILES: N#Cc1cc2cc(CN3CC4(CCN(c5ncnn6cc(CC(F)(F)F)cc56)C4)C3)ccc2[nH]1] |
| V-84 | 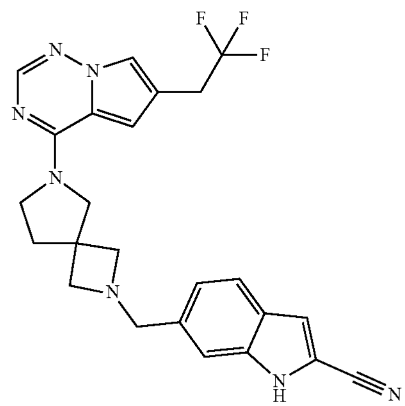 [SMILES: N#Cc1cc2ccc(CN3CC4(CCN(c5ncnn6cc(CC(F)(F)F)cc56)C4)C3)cc2[nH]1] |
| V-85 | 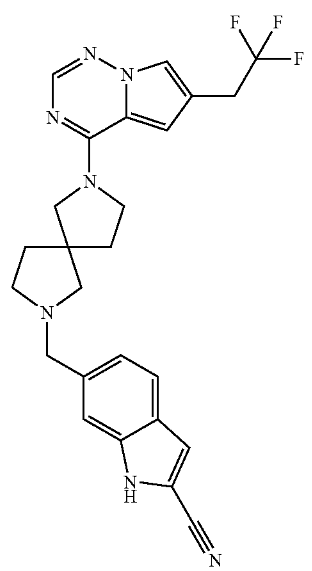 [SMILES: N#Cc1cc2ccc(CN3CCC4(CCN(c5ncnn6cc(CC(F)(F)F)cc56)C4)C3)cc2[nH]1] |

TABLE 5-continued
| No. | Structure |
|---|---|
| V-86 | 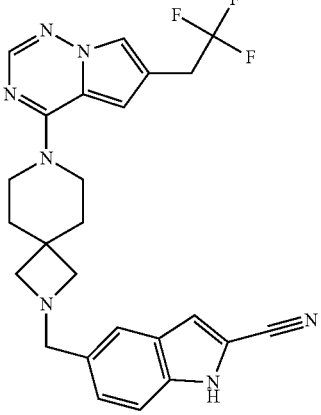 |
| V-87 | 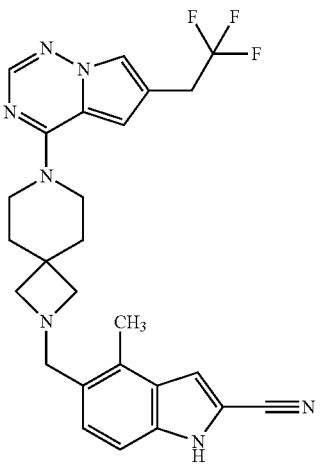 [SMILES: Cc1c(CN2CC3(CCN(c4ncnn5cc(CC(F)(F)F)cc45)CC3)C2)ccc2[nH]c(C#N)cc12] |
| V-88 | 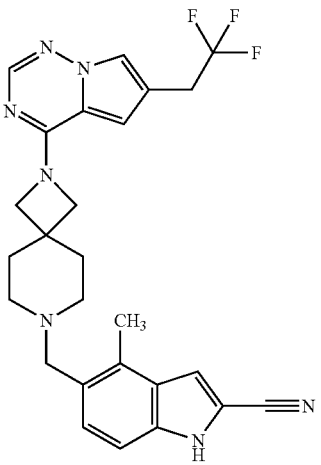 [SMILES: Cc1c(CN2CCC3(CC2)CN(c2ncnn4cc(CC(F)(F)F)cc24)C3)ccc2[nH]c(C#N)cc12] |
| V-89 | 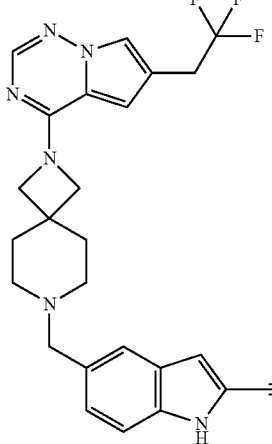 |
| V-90 | 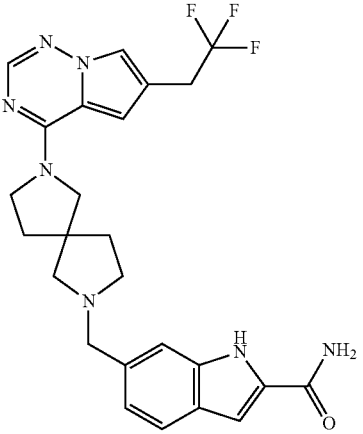 [SMILES: NC(=O)c1cc2ccc(CN3CCC4(CCN(c5ncnn6cc(CC(F)(F)F)cc56)C4)C3)cc2[nH]1] |
| V-91 | 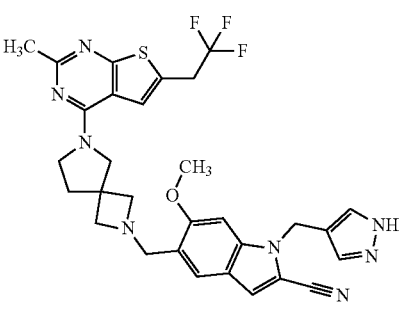 [SMILES: COc1cc2c(cc1CN1CC3(CCN(c4nc(C)nc5sc(CC(F)(F)F)cc45)C3)C1)cc(C#N)n2Cc1cn[nH]c1] |
| V-92 | 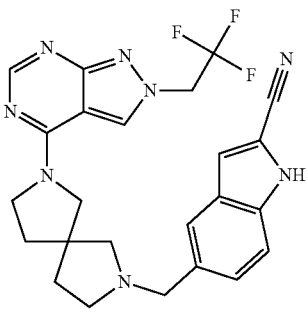 [SMILES: N#Cc1cc2cc(CN3CCC4(CCN(c5ncnc6nn(CC(F)(F)F)cc56)C4)C3)ccc2[nH]1] |

TABLE 5-continued

| No. | Structure |
|---|---|
| V-93 | 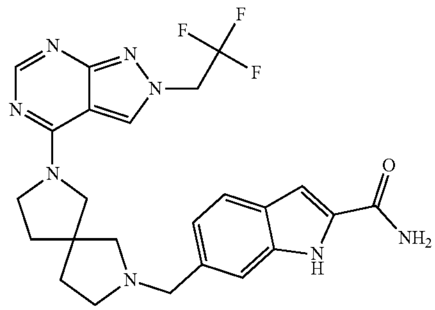 [SMILES: NC(=O)c1cc2ccc(CN3CCC4(CCN(c5ncnc6nn(CC(F)(F)F)cc56)C4)C3)cc2[nH]1] |
| V-94 | 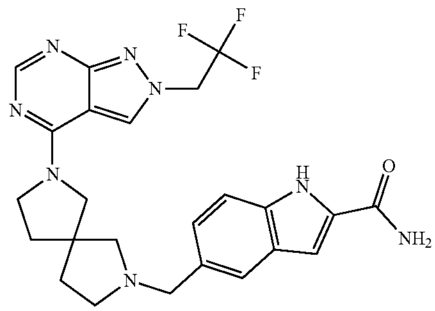 [SMILES: NC(=O)c1cc2cc(CN3CCC4(CCN(c5ncnc6nn(CC(F)(F)F)cc56)C4)C3)ccc2[nH]1] |
| V-95 | 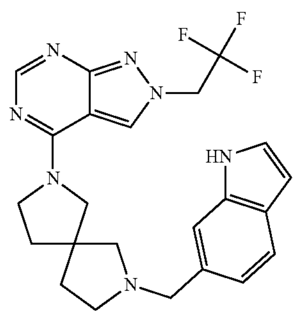 [SMILES: FC(F)(F)Cn1cc2c(N3CCC4(CCN(Cc5ccc6cc[nH]c6c5)C4)C3)ncnc2n1] |
| V-96 | 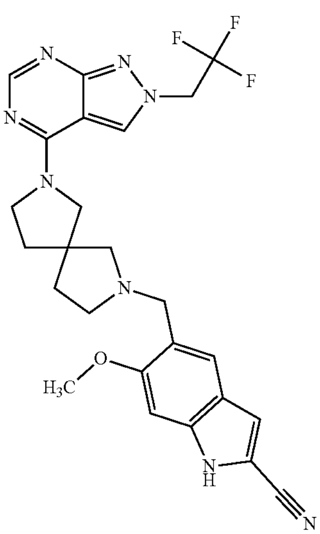 [SMILES: COc1cc2[nH]c(C#N)cc2cc1CN1CCC2(CCN(c3ncnc4nn(CC(F)(F)F)cc34)C2)C1] |
| V-97 | |
| V-98 | |
| V-99 | |

TABLE 5-continued
| No. | Structure |
|---|---|
| V-100 | 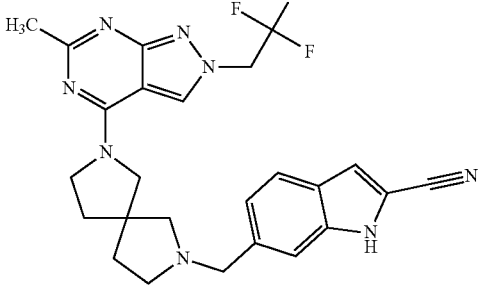 |
| V-101 | 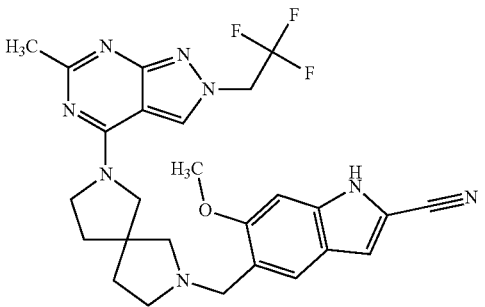 [SMILES: COc1cc2[nH]c(C#N)cc2cc1CN1CCC2(CCN(c3nc(C)nc4nn(CC(F)(F)F)cc34)C2)C1] |
| V-102 | 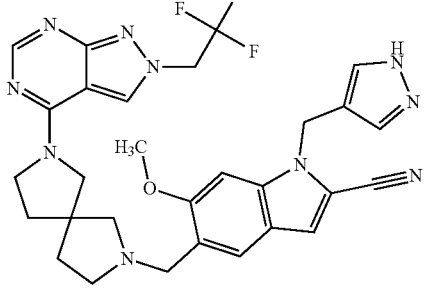 |
| V-103 | 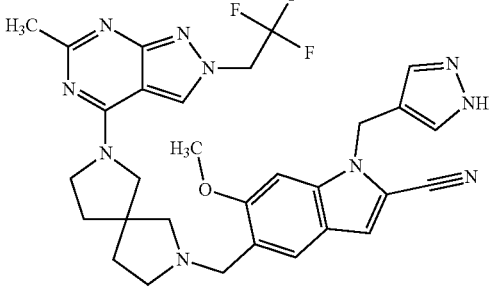 |
| V-104 | 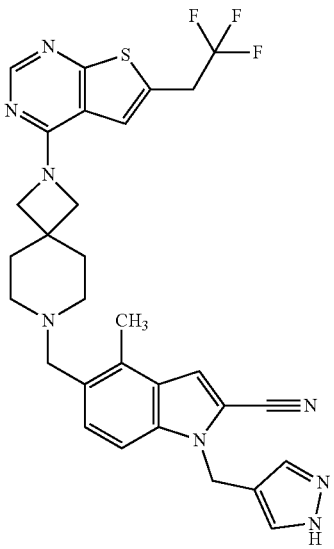 [SMILES: Cc1c(CN2CCC3(CC2)CN(c2ncnc4sc(CC(F)(F)F)cc24)C3)ccc2c1cc(C#N)n2Cc1cn[nH]c1] |
| V-105 | 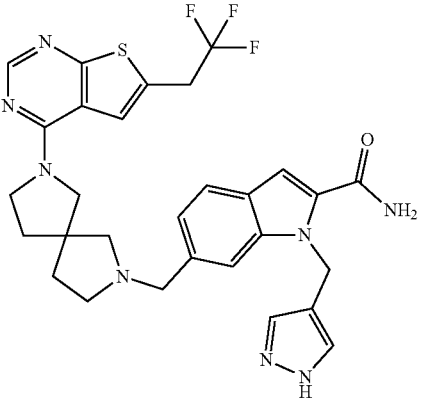 [SMILES: NC(=O)c1cc2ccc(CN3CCC4(CCN(c5ncnc6sc(CC(F)(F)F)cc56)C4)C3)cc2n1Cc1cn[nH]c1] |
| V-106 | 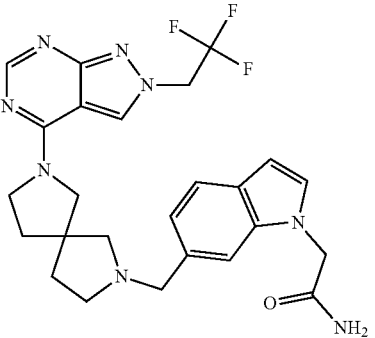 [SMILES: NC(=O)Cn1ccc2ccc(CN3CCC4(CCN(c5ncnc6nn(CC(F)(F)F)cc56)C4)C3)cc21] |

TABLE 5-continued

| No. | Structure |
|---|---|
| V-107 | 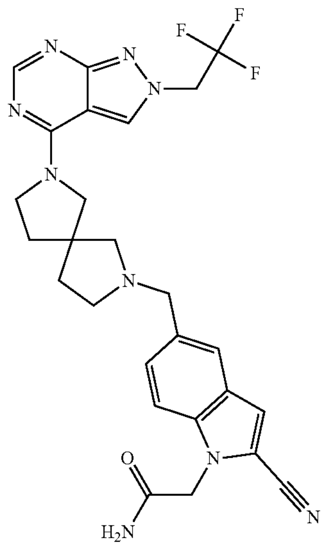 [SMILES: N#Cc1cc2cc(CN3CCC4(CCN(c5ncnc6nn(CC(F)(F)F)cc56)C4)C3)ccc2n1CC(N)=O] |
| V-108 | 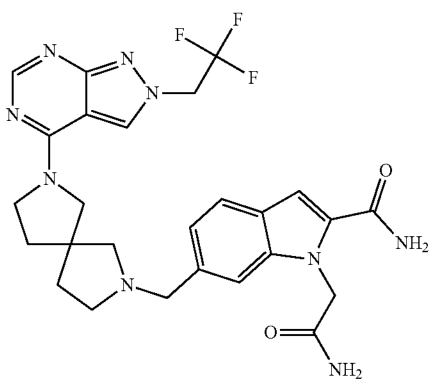 [SMILES: NC(=O)Cn1c(C(N)=O)cc2ccc(CN3CCC4(CCN(c5ncnc6nn(CC(F)(F)F)cc56)C4)C3)cc21] |
| V-109 | 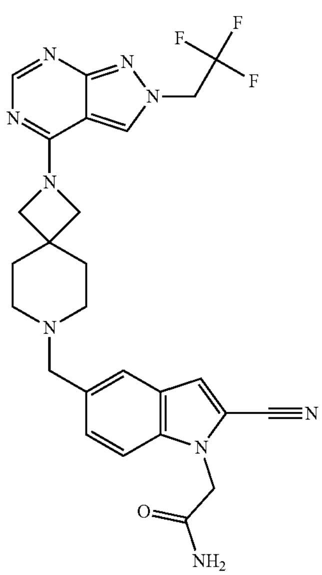 [SMILES: N#Cc1cc2cc(CN3CCC4(CC3)CN(c3ncnc5nn(CC(F)(F)F)cc35)C4)ccc2n1CC(N)=O] |
| V-110 | |
| V-111 | |

TABLE 5-continued

| No. | Structure |
|---|---|
| V-112 | |
| V-113 | |
| V-114 | |
| V-115 | 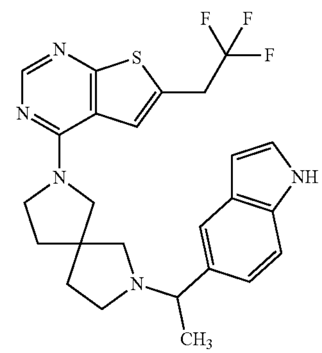 [SMILES: CC(c1ccc2[nH]ccc2c1)N1CCC2(CCN(c3ncnc4sc(CC(F)(F)F)cc34)C2)C1] |
| V-116 | 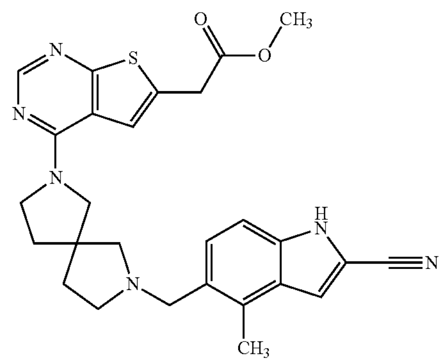 [SMILES: COC(=O)Cc1cc2c(N3CCC4(CCN(Cc5ccc6[nH]c(C#N)cc6c5C)C4)C3)ncnc2s1] |
| V-117 | 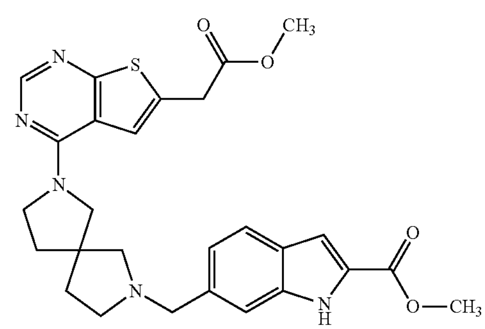 [SMILES: COC(=O)Cc1cc2c(N3CCC4(CCN(Cc5ccc6cc(C(=O)OC)[nH]c6c5)C4)C3)ncnc2s1] |
| V-118 | 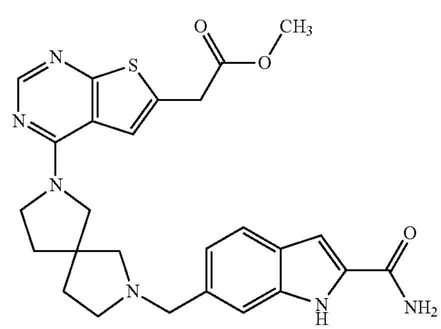 [SMILES: COC(=O)Cc1cc2c(N3CCC4(CCN(Cc5ccc6cc(C(N)=O)[nH]c6c5)C4)C3)ncnc2s1] |

TABLE 5-continued

| No. | Structure |
|---|---|
| V-119 | 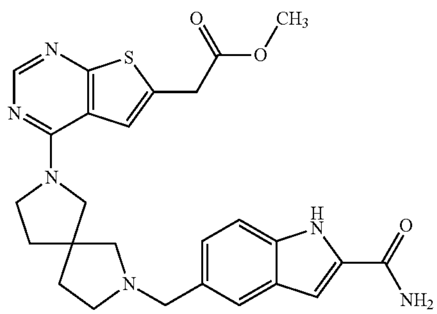 [SMILES: COC(=O)Cc1cc2c(N3CCC4(CCN(Cc5ccc6[nH]c(C(N)=O)cc6c5)C4)C3)ncnc2s1] |
| V-120 | 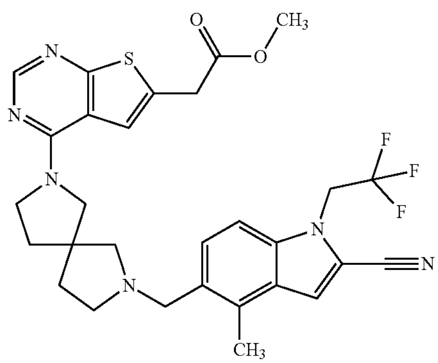 [SMILES: COC(=O)Cc1cc2c(N3CCC4(CCN(Cc5ccc6c(cc(C#N)n6CC(F)(F)F)c5C)C4)C3)ncnc2s1] |
| V-121 | 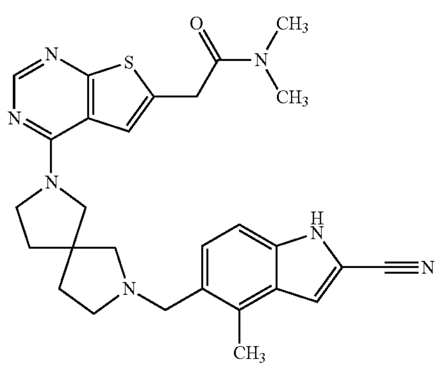 [SMILES: Cc1c(CN2CCC3(CCN(c4ncnc5sc(CC(=O)N(C)C)cc45)C3)C2)ccc2[nH]c(C#N)cc12] |
| V-122 | 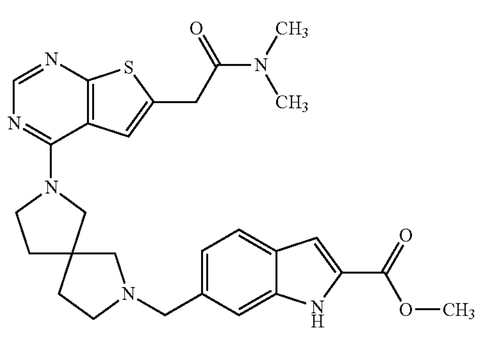 [SMILES: COC(=O)c1cc2ccc(CN3CCC4(CCN(c5ncnc6sc(CC(=O)N(C)C)cc56)C4)C3)cc2[nH]1] |
| V-123 | |
| V-124 | |
| V-125 | |
| V-126 | |

TABLE 5-continued
| No. | Structure |
|---|---|
| V-127 | 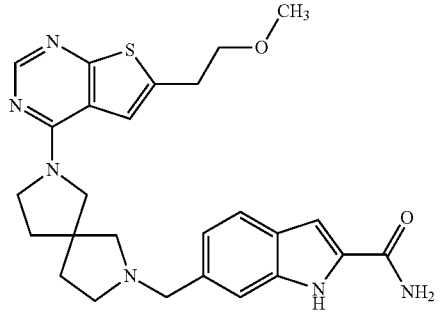 [SMILES: COCCc1cc2c(N3CCC4(CCN(Cc5ccc6cc(C(N)=O)[nH]c6c5)C4)C3)ncnc2s1] |
| V-128 | 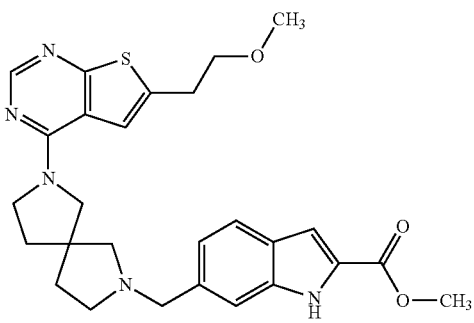 [SMILES: COCCc1cc2c(N3CCC4(CCN(Cc5ccc6cc(C(=O)OC)[nH]c6c5)C4)C3)ncnc2s1] |
| V-129 | 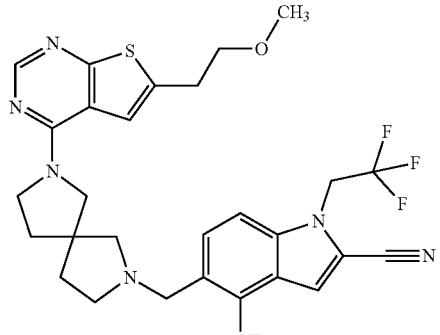 |
| V-130 | 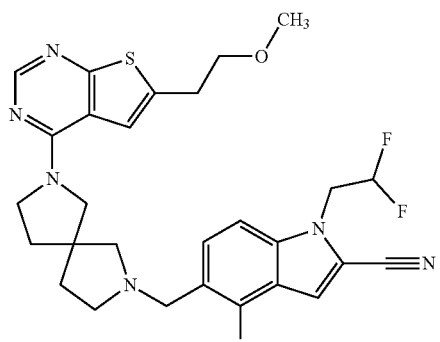 |
| V-131 | 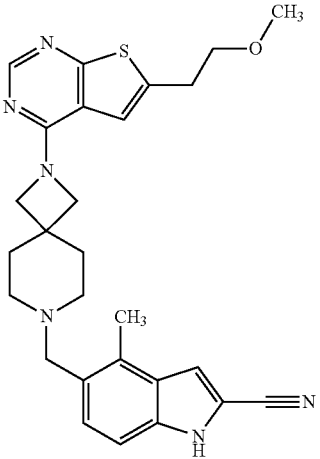 [SMILES: COCCc1cc2c(N3CC4(CCN(Cc5ccc6[nH]c(C#N)cc6c5C)CC4)C3)ncnc2s1] |
| V-132 | 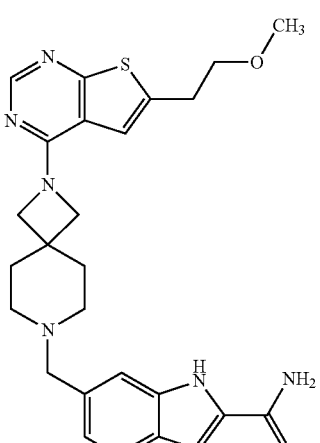 |
| V-133 | 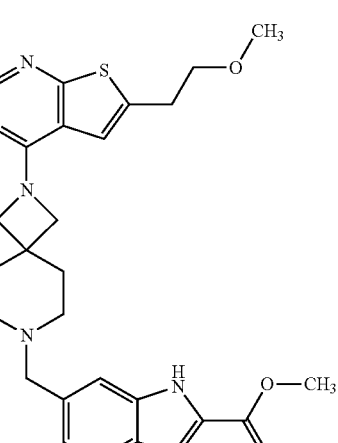 |

TABLE 5-continued
| No. | Structure |
|---|---|
| V-134 | 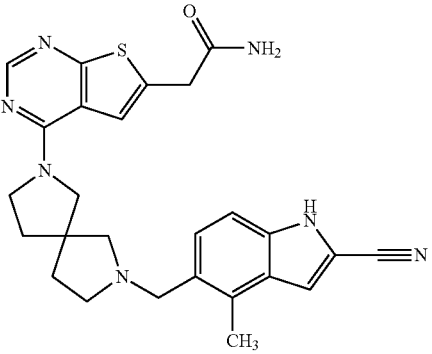 [SMILES: Cc1c(CN2CCC3(CCN(c4ncnc5sc(CC(N)=O)cc45)C3)C2)ccc2[nH]c(C#N)cc12] |
| V-135 | 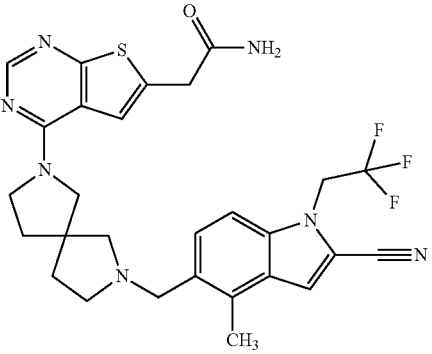 [SMILES: Cc1c(CN2CCC3(CCN(c4ncnc5sc(CC(N)=O)cc45)C3)C2)ccc2c1cc(C#N)n2CC(F)(F)F] |
| V-136 | 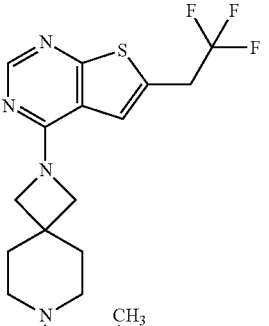 |
| V-137 |  |
| V-138 | 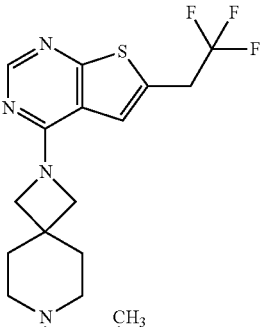 |

TABLE 5-continued
| No. | Structure |
|---|---|
| V-139 | 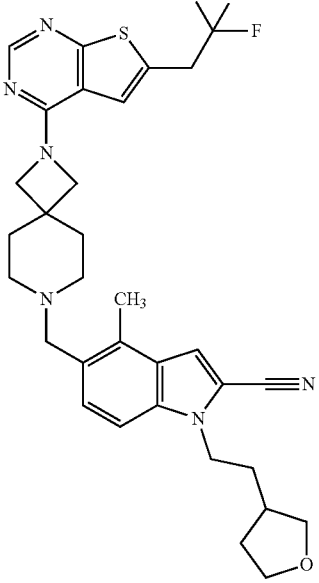 |
| V-140 | 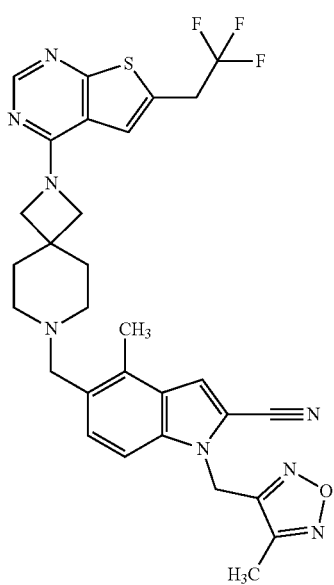 [SMILES: Cc1nonc1Cn1c(C#N)cc2c(C)c(CN3CCC4(CC3)CN(c3ncnc5sc(CC(F)(F)F)cc35)C4)ccc21] |
| V-141 | 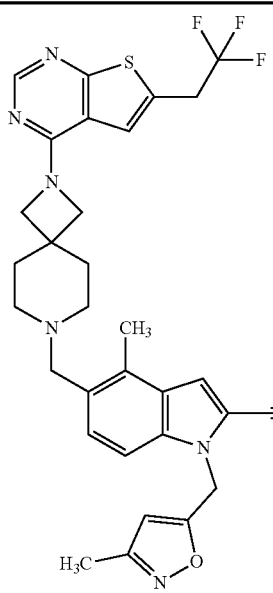 |
| V-142 | 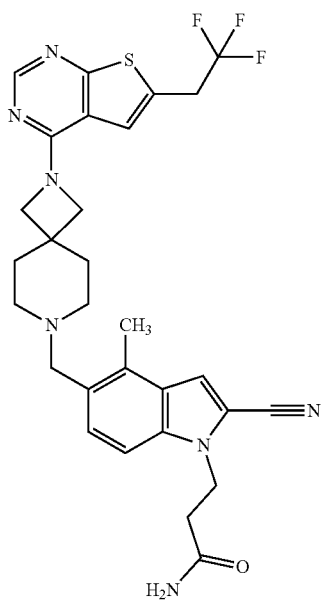 [SMILES: Cc1c(CN2CCC3(CC2)CN(c2ncnc4sc(CC(F)(F)F)cc24)C3)ccc2c1cc(C#N)n2CCC(N)=O] |

TABLE 5-continued

| No. | Structure |
|---|---|
| V-143 | |
| V-144 | |
| V-145 | 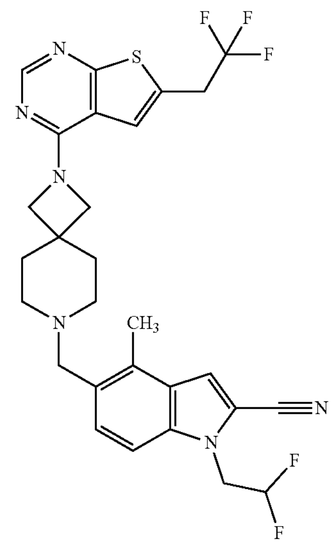 [SMILES: Cc1c(CN2CCC3(CC2)CN(c2ncnc4sc(CC(F)(F)F)cc24)C3)ccc2c1cc(C#N)n2CC(F)F] |
| V-146 | 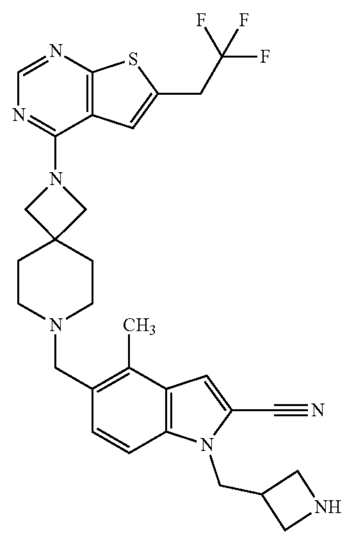 [SMILES: Cc1c(CN2CCC3(CC2)CN(c2ncnc4sc(CC(F)(F)F)cc24)C3)ccc2c1cc(C#N)n2CC1CNC1] |
| V-147 | 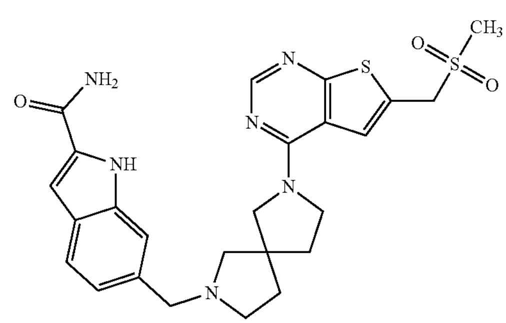 [SMILES: CS(=O)(=O)Cc1cc2c(N3CCC4(CCN(Cc5ccc6cc(C(N)=O)[nH]c6c5)C4)C3)ncnc2s1] |

TABLE 5-continued
| No. | Structure |
|---|---|
| V-148 | 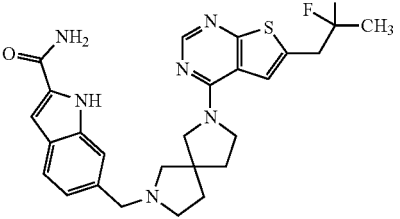 |
| V-149 | 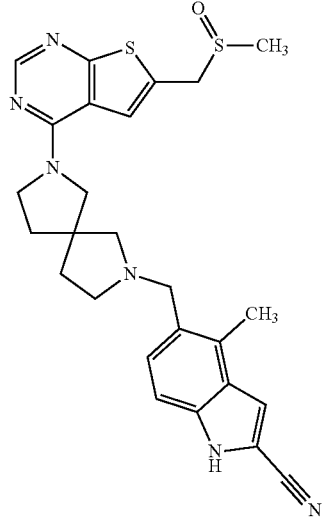 [SMILES: Cc1c(CN2CCC3(CCN(c4ncnc5sc(CS(C)=O)cc45)C3)C2)ccc2[nH]c(C#N)cc12] |
| V-150 | 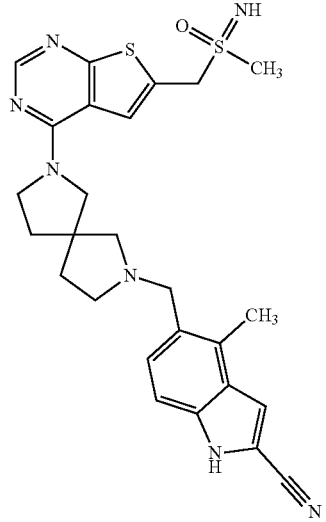 [SMILES: Cc1c(CN2CCC3(CCN(c4ncnc5sc(CS(C)(=N)=O)cc45)C3)C2)ccc2[nH]c(C#N)cc12] |
| V-151 | 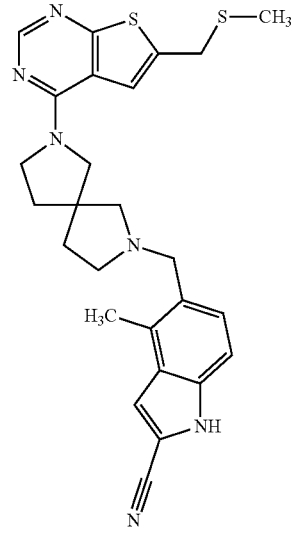 [SMILES: CSCc1cc2c(N3CCC4(CCN(Cc5ccc6[nH]c(C#N)cc6c5C)C4)C3)ncnc2s1] |
| V-152 | 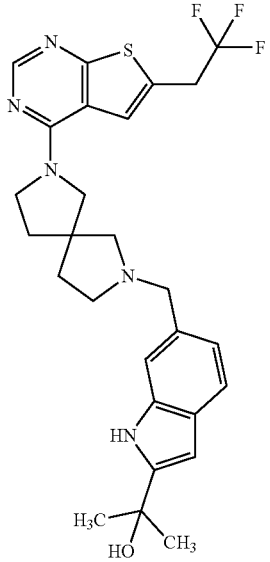 [SMILES: CC(C)(O)c1cc2ccc(CN3CCC4(CCN(c5ncnc6sc(CC(F)(F)F)cc56)C4)C3)cc2[nH]1] |
| V-153 | 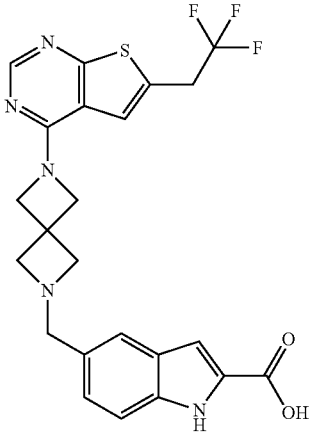 [SMILES: O=C(O)c1cc2cc(CN3CC4(C3)CN(c3ncnc5sc(CC(F)(F)F)cc35)C4)ccc2[nH]1] |

TABLE 6
| No. | Structure |
|---|---|
| VI-1 | 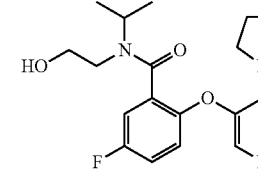 |
| VI-2 | 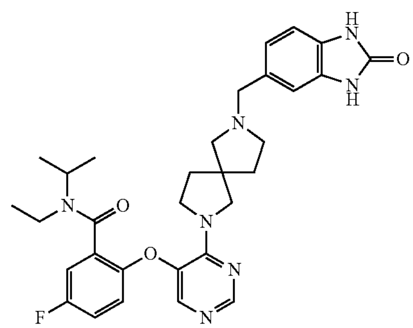 [SMILES: CCN(C(=O)c1cc(F)ccc1Oc1cncnc1N1CCC2(CCN(Cc3ccc4[nH]c(=O)[nH]c4c3)C2)C1)C(C)C] |
| VI-3 | 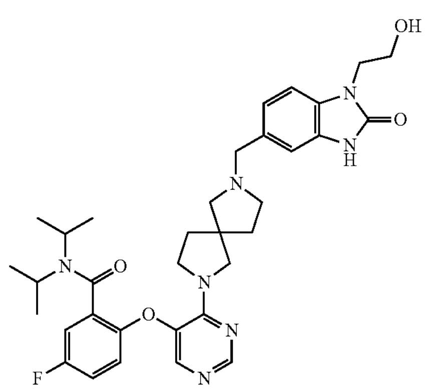 [SMILES: CC(C)N(C(=O)c1cc(F)ccc1Oc1cncnc1N1CCC2(CCN(Cc3ccc4c(c3)[nH]c(=O)n4CCO)C2)C1)C(C)C] |
| VI-4 | 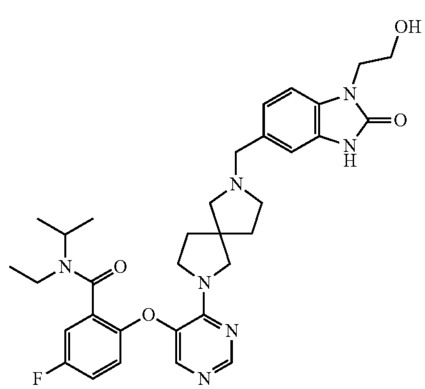 [SMILES: CCN(C(=O)c1cc(F)ccc1Oc1cncnc1N1CCC2(CCN(Cc3ccc4c(c3)[nH]c(=O)n4CCO)C2)C1)C(C)C] |
| VI-5 | 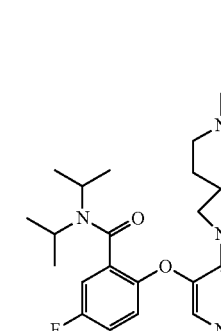 |
| VI-6 | |
| VI-7 | |
| VI-8 | |

TABLE 6-continued
| No. | Structure |
|---|---|
| VI-9 | 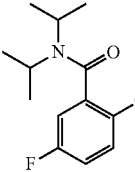 |
| VI-10 | |
| VI-11 | |
| VI-12 | 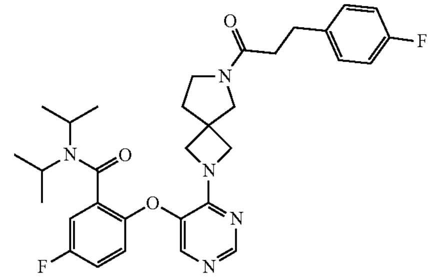 [SMILES: CC(C)N(C(=O)c1cc(F)ccc1Oc1cncnc1N1CC2(CCN(C(=O)CCc3ccc(F)cc3)C2)C1)C(C)C] |
| VI-13 | 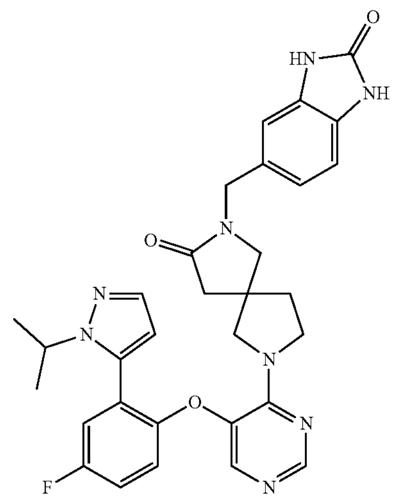 [SMILES: CC(C)n1nccc1-c1cc(F)ccc1Oc1cncnc1N1CCC2(CC(=O)N(Cc3ccc4[nH]c(=O)[nH]c4c3)C2)C1] |
| VI-14 | 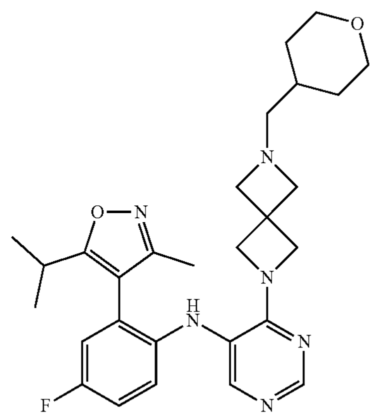 [SMILES: Cc1noc(C(C)C)c1-c1cc(F)ccc1Nc1cncnc1N1CC2(CN(CC3CCOCC3)C2)C1] |
| VI-15 | 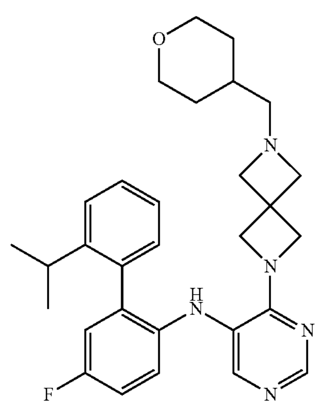 [SMILES: CC(C)c1ccccc1-c1cc(F)ccc1Nc1cncnc1N1CC2(CN(CC3CCOCC3)C2)C1] |

TABLE 6-continued

| No. | Structure |
|---|---|
| VI-16 | 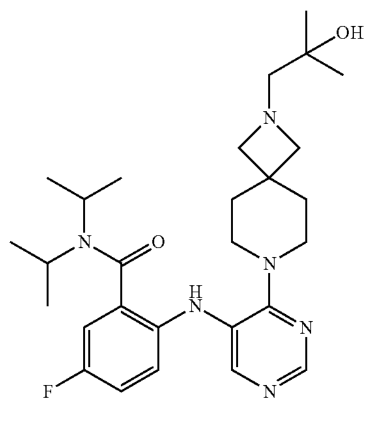 [SMILES: CC(C)N(C(=O)c1cc(F)ccc1Nc1cncnc1N1CCC2(CC1)CN(CC(C)(C)O)C2)C(C)C] |
| VI-17 | 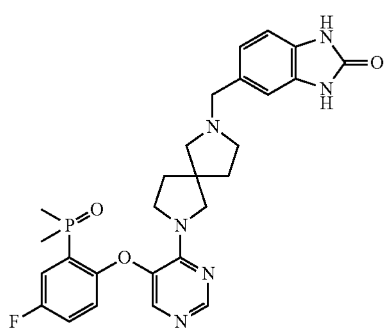 [SMILES: CP(C)(=O)c1cc(F)ccc1Oc1cncnc1N1CCC2(CCN(Cc3ccc4[nH]c(=O)[nH]c4c3)C2)C1] |
| VI-18 | 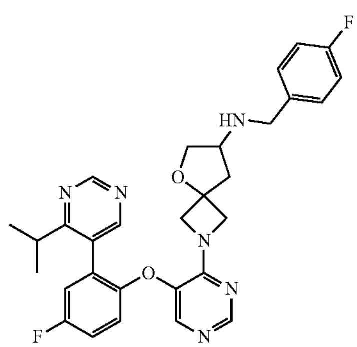 [SMILES: CC(C)c1ncncc1-c1cc(F)ccc1Oc1cncnc1N1CC2(CC(NCc3ccc(F)cc3)CO2)C1] |
| VI-19 | 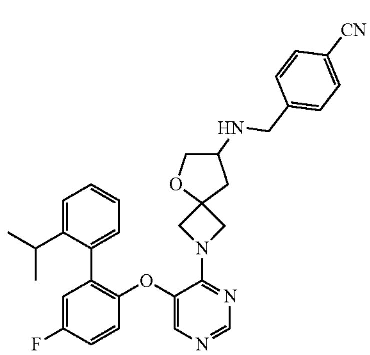 [SMILES: CC(C)c1ccccc1-c1cc(F)ccc1Oc1cncnc1N1CC2(CC(NCc3ccc(C#N)cc3)CO2)C1] |
| VI-20 | |
| VI-21 | |
| VI-22 | |
| VI-23 | |

TABLE 6-continued

| No. | Structure |
|---|---|
| VI-24 | 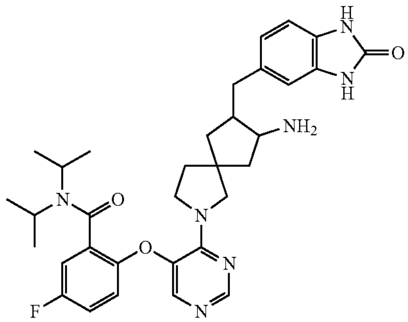 [SMILES: CC(C)N(C(=O)c1cc(F)ccc1Oc1cncnc1N1CCC2(CC(N)C(Cc3ccc4[nH]c(=O)[nH]c4c3)C2)C1)C(C)C] |
| VI-25 | 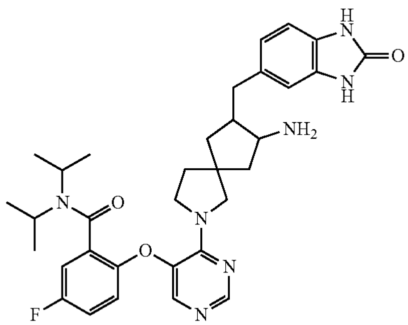 [SMILES: CC(C)N(C(=O)c1cc(F)ccc1Oc1cncnc1N1CCC2(CC(N)C(Cc3ccc4[nH]c(=O)[nH]c4c3)C2)C1)C(C)C] |
| VI-26 | 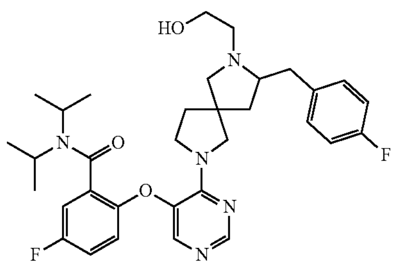 [SMILES: CC(C)N(C(=O)c1cc(F)ccc1Oc1cncnc1N1CCC2(CC(Cc3ccc(F)cc3)N(CCO)C2)C1)C(C)C] |
| VI-27 | 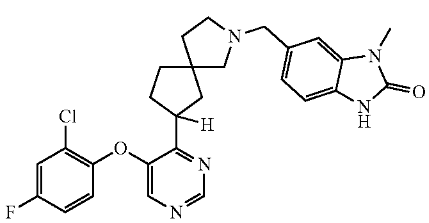 [SMILES: Cn1c(=O)[nH]c2ccc(CN3CCC4(CCC(c5ncncc5Oc5ccc(F)cc5Cl)C4)C3)cc21] |
| VI-28 | 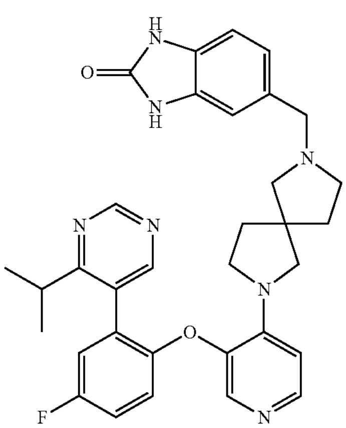 [SMILES: CC(C)c1ncncc1-c1cc(F)ccc1Oc1cnccc1N1CCC2(CCN(Cc3ccc4[nH]c(=O)[nH]c4c3)C2)C1] |
| VI-29 | |
| VI-30 | |
| VI-31 | |
| VI-32 | |

TABLE 6-continued
| No. | Structure |
|---|---|
| VI-33 | 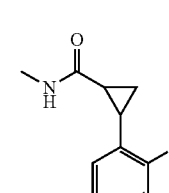 |
| VI-34 | 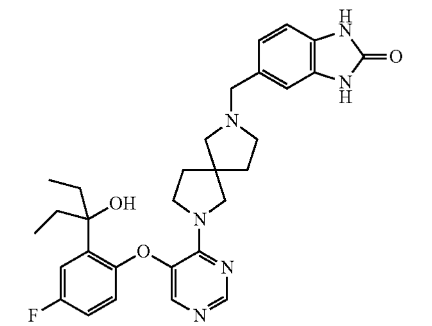 [SMILES: CCC(O)(CC)c1cc(F)ccc1Oc1cncnc1N1CCC2(CCN(Cc3ccc4[nH]c(=O)[nH]c4c3)C2)C1] |
| VI-35 | 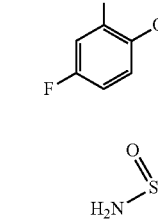 |
| VI-36 | 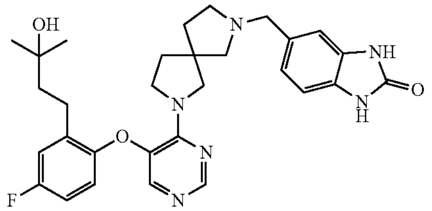 [SMILES: CC(C)(O)CCc1cc(F)ccc1Oc1cncnc1N1CCC2(CCN(Cc3ccc4[nH]c(=O)[nH]c4c3)C2)C1] |
| VI-37 | 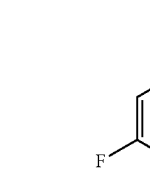 |
| VI-38 | 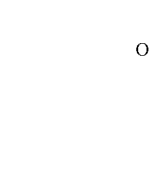 |
| VI-39 | 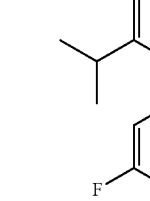 |
| VI-40 | |
| VI-41 | |

TABLE 6-continued

| No. | Structure |
|---|---|
| VI-42 | (structure) |
| VI-43 | (structure) |
| VI-44 | (structure) |
| VI-45 | (structure) |
| VI-46 | (structure) |
| VI-47 | (structure) |
| VI-48 | (structure) |
| VI-49 | (structure) |

TABLE 6-continued

| No. | Structure |
|---|---|
| VI-50 | 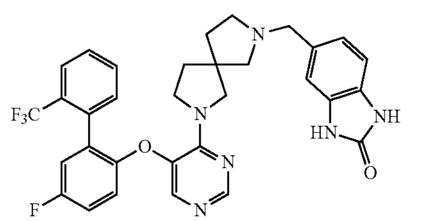 [SMILES: O=c1[nH]c2ccc(CN3CCC4(CCN(c5ncncc5Oc5ccc(F)cc5-c5ccccc5C(F)(F)F)C4)C3)cc2[nH]1] |
| VI-51 | 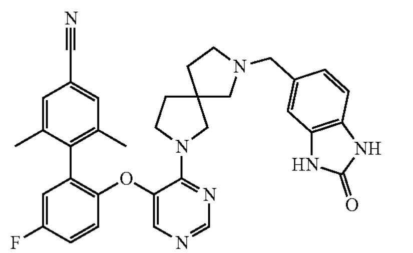 [SMILES: Cc1cc(C#N)cc(C)c1-c1cc(F)ccc1Oc1cncnc1N1CCC2(CCN(Cc3ccc4[nH]c(=O)[nH]c4c3)C2)C1] |
| VI-52 | 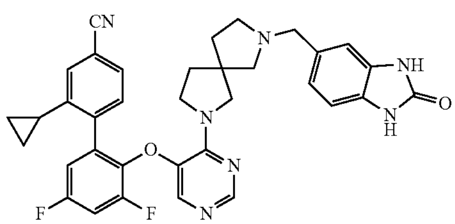 [SMILES: N#Cc1ccc(-c2cc(F)cc(F)c2Oc2cncnc2N2CCC3(CCN(Cc4ccc5[nH]c(=O)[nH]c5c4)C3)C2)c(C2CC2)c1] |
| VI-53 | 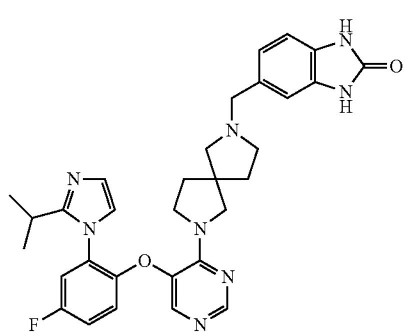 [SMILES: CC(C)c1nccn1-c1cc(F)ccc1Oc1cncnc1N1CCC2(CCN(Cc3ccc4[nH]c(=O)[nH]c4c3)C2)C1] |
| VI-54 | 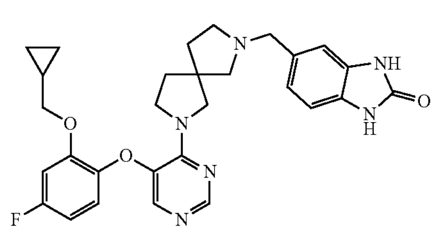 [SMILES: O=c1[nH]c2ccc(CN3CCC4(CCN(c5ncncc5Oc5ccc(F)cc5OCC5CC5)C4)C3)cc2[nH]1] |
| VI-55 | |
| VI-56 | |
| VI-57 | |

TABLE 6-continued

| No. | Structure |
|---|---|
| VI-58 | 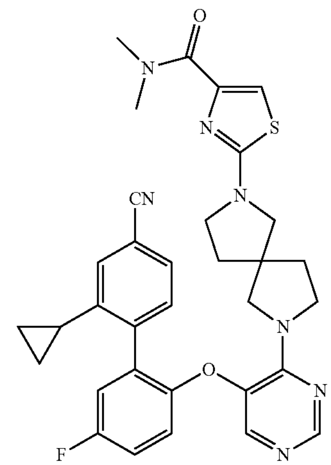 [SMILES: CN(C)C(=O)c1csc(N2CCC3(CCN(c4ncncc4Oc4ccc(F)cc4-c4ccc(C#N)cc4C4CC4)C3)C2)n1] |
| VI-59 | 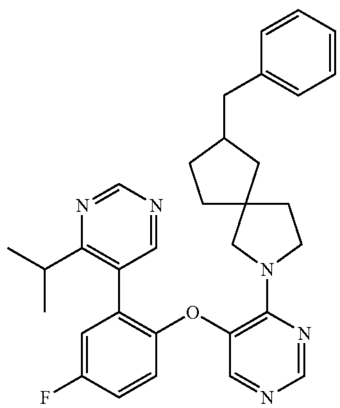 [SMILES: CC(C)c1ncncc1-c1cc(F)ccc1Oc1cncnc1N1CCC2(CCC(Cc3ccccc3)C2)C1] |
| VI-60 | 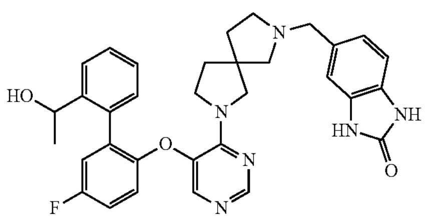 [SMILES: CC(O)c1ccccc1-c1cc(F)ccc1Oc1cncnc1N1CCC2(CCN(Cc3ccc4[nH]c(=O)[nH]c4c3)C2)C1] |
| VI-61 | 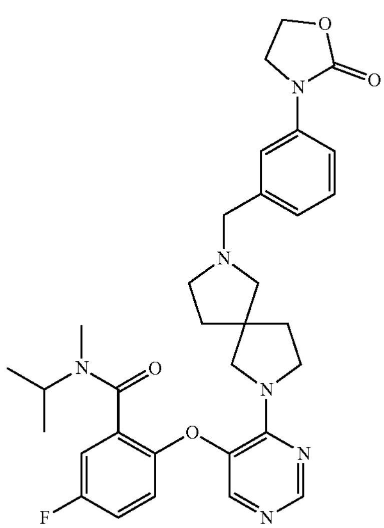 [SMILES: CC(C)N(C)C(=O)c1cc(F)ccc1Oc1cncnc1N1CCC2(CCN(Cc3cccc(N4CCOC4=O)c3)C2)C1] |
| VI-62 | |
| VI-63 | |
| VI-64 | |
| VI-65 | |

TABLE 6-continued
| No. | Structure |
|---|---|
| VI-66 | 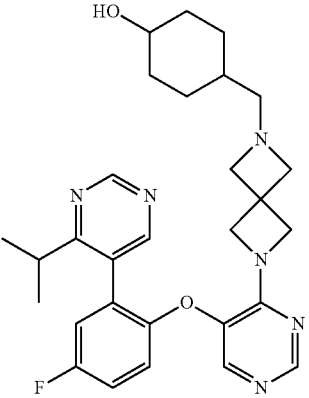 [SMILES: CC(C)c1ncncc1-c1cc(F)ccc1Oc1cncnc1N1CC2(CN(CC3CCC(O)CC3)C2)C1] |
| VI-67 | 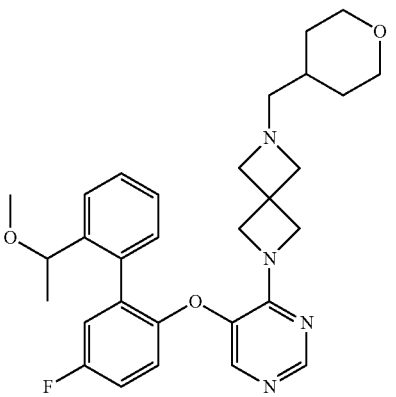 [SMILES: COC(C)c1ccccc1-c1cc(F)ccc1Oc1cncnc1N1CC2(CN(CC3CCOCC3)C2)C1] |
| VI-68 | 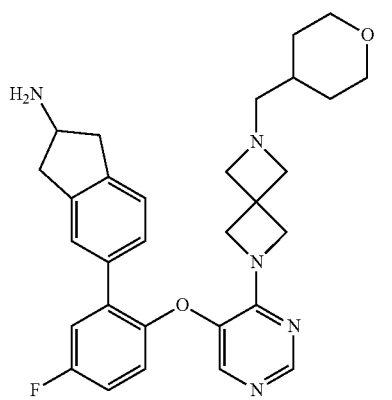 [SMILES: NC1Cc2ccc(-c3cc(F)ccc3Oc3cncnc3N3CC4(CN(CC5CCOCC5)C4)C3)cc2C1] |
| VI-69 | 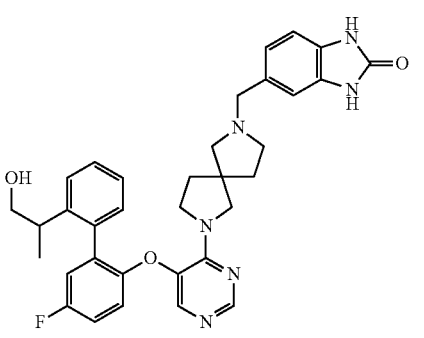 [SMILES: CC(CO)c1ccccc1-c1cc(F)ccc1Oc1cncnc1N1CCC2(CCN(Cc3ccc4[nH]c(=O)[nH]c4c3)C2)C1] |
| VI-70 | 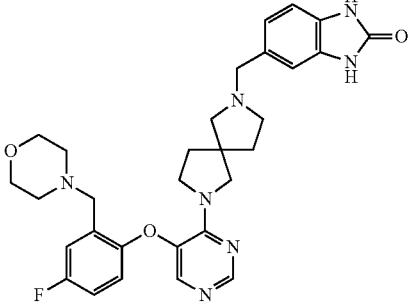 |
| VI-71 | 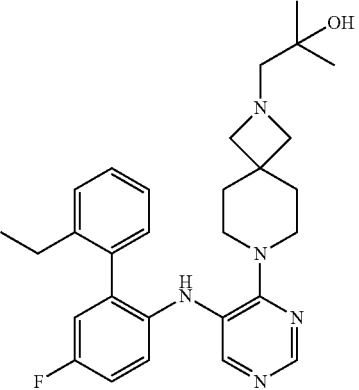 [SMILES: CCc1ccccc1-c1cc(F)ccc1Nc1cncnc1N1CCC2(CC1)CN(CC(C)(C)O)C2] |
| VI-72 | 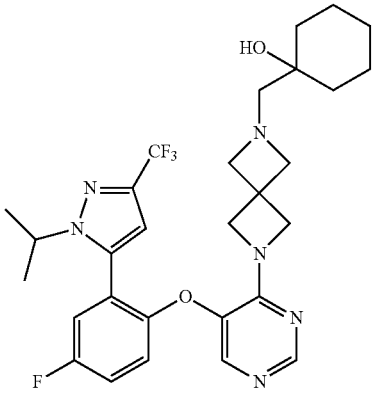 [SMILES: CC(C)n1nc(C(F)(F)F)cc1-c1cc(F)ccc1Oc1cncnc1N1CC2(CN(CC3(O)CCCCC3)C2)C1] |
| VI-73 | 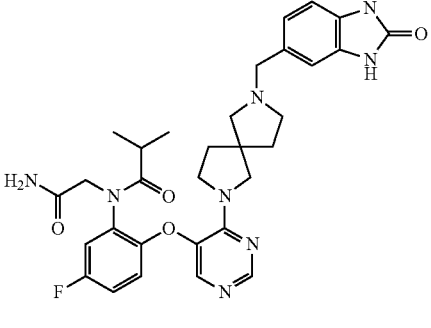 |

TABLE 6-continued

| No. | Structure |
|---|---|
| VI-74 | 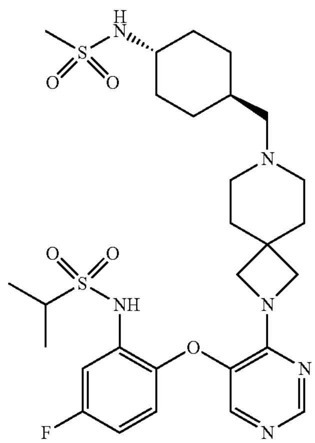 [SMILES: CC(C)S(=O)(=O)Nc1cc(F)ccc1Oc1cncnc1N1CC2(CCN(C[C@H]3CC[C@H](NS(C)(=O)=O)CC3)CC2)C1] |
| VI-75 | 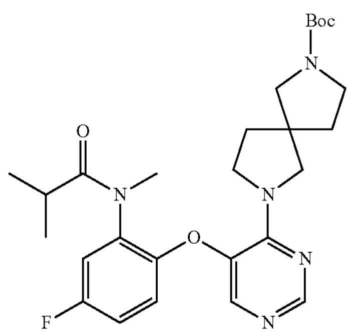 [SMILES: CC(C)C(=O)N(C)c1cc(F)ccc1Oc1cncnc1N1CCC2(CCN(C(=O)OC(C)(C)C)C2)C1] |
| VI-76 | 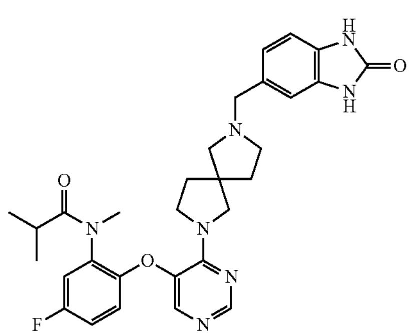 [SMILES: CC(C)C(=O)N(C)c1cc(F)ccc1Oc1cncnc1N1CCC2(CCN(Cc3ccc4[nH]c(=O)[nH]c4c3)C2)C1] |
| VI-77 | 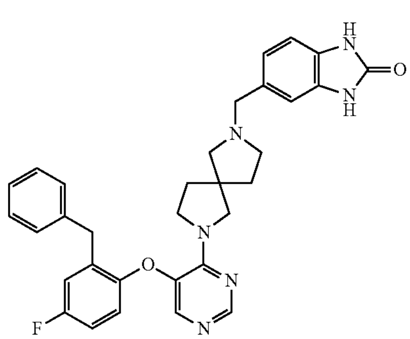 [SMILES: O=c1[nH]c2ccc(CN3CCC4(CCN(c5ncncc5Oc5ccc(F)cc5Cc5ccccc5)C4)C3)cc2[nH]1] |
| VI-78 | |
| VI-79 | |
| VI-80 | |
| VI-81 | |

TABLE 6-continued

| No. | Structure |
|---|---|
| VI-82 | 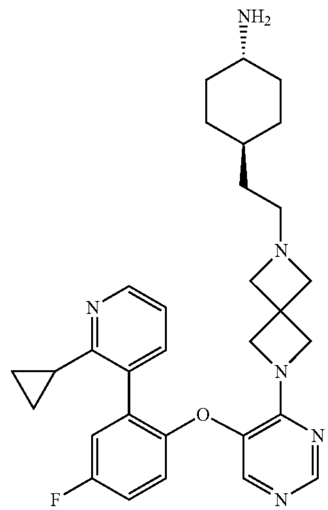 [SMILES: N[C@H]1CC[C@H](CCN2CC3(C2)CN(c2ncncc2Oc2ccc(F)cc2-c2cccnc2C2CC2)C3)CC1] |
| VI-83 | 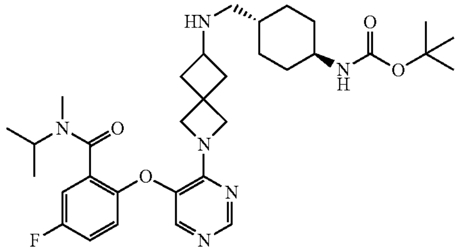 [SMILES: CC(C)N(C)C(=O)c1cc(F)ccc1Oc1cncnc1N1CC2(CC(NC[C@H]3CC[C@H](NC(=O)OC(C)(C)C)CC3)C2)C1] |
| VI-84 | 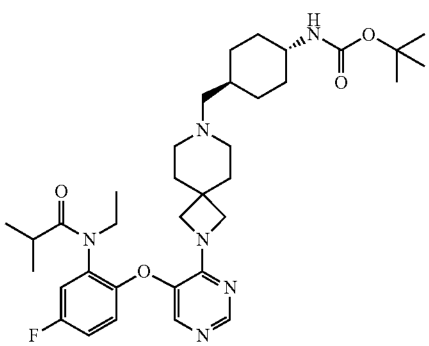 [SMILES: CCN(C(=O)C(C)C)c1cc(F)ccc1Oc1cncnc1N1CC2(CCN(C[C@H]3CC[C@H](NC(=O)OC(C)(C)C)CC3)CC2)C1] |
| VI-85 | 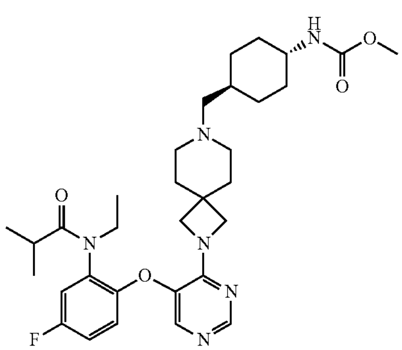 [SMILES: CCN(C(=O)C(C)C)c1cc(F)ccc1Oc1cncnc1N1CC2(CCN(C[C@H]3CC[C@H](NC(=O)OC)CC3)CC2)C1] |
| VI-86 | |
| VI-87 | |
| VI-88 | |
| VI-89 | |

TABLE 6-continued

| No. | Structure |
|---|---|
| VI-90 | 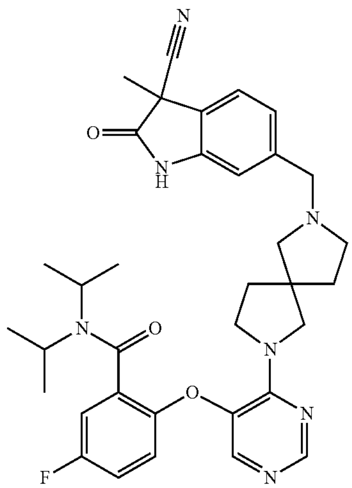 [SMILES: CC(C)N(C(=O)c1cc(F)ccc1Oc1cncnc1N1CCC2(CCN(Cc3ccc4c(c3)NC(=O)C4(C)C#N)C2)C1)C(C)C] |
| VI-91 | 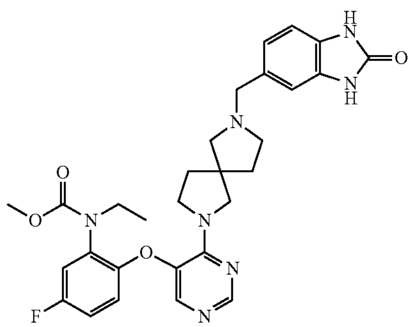 [SMILES: CCN(C(=O)OC)c1cc(F)ccc1Oc1cncnc1N1CCC2(CCN(Cc3ccc4[nH]c(=O)[nH]c4c3)C2)C1] |
| VI-92 | 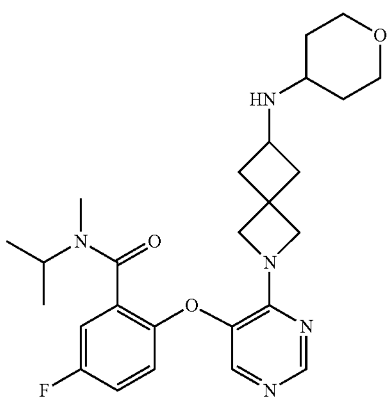 [SMILES: CC(C)N(C)C(=O)c1cc(F)ccc1Oc1cncnc1N1CC2(CC(NC3CCOCC3)C2)C1] |
| VI-93 | 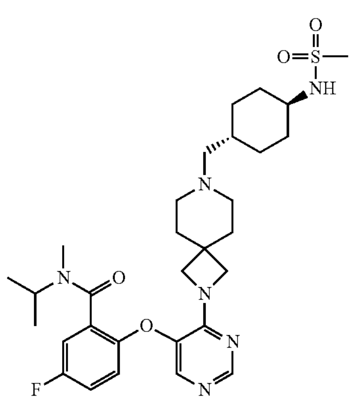 [SMILES: CC(C)N(C)C(=O)c1cc(F)ccc1Oc1cncnc1N1CC2(CCN(C[C@H]3CC[C@H](NS(C)(=O)=O)CC3)CC2)C1] |
| VI-94 | |
| VI-95 | |
| VI-96 | |
| VI-97 | |

TABLE 6-continued

| No. | Structure |
|---|---|
| VI-98 | 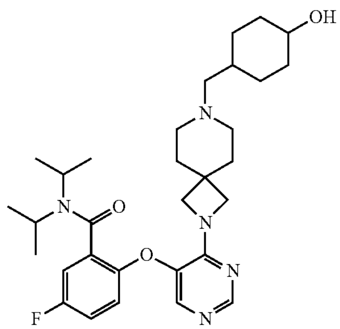 [SMILES: CC(C)N(C(=O)c1cc(F)ccc1Oc1cncnc1N1CC2(CCN(CC3CCC(O)CC3)CC2)C1)C(C)C] |
| VI-99 | 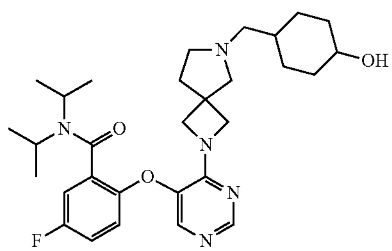 [SMILES: CC(C)N(C(=O)c1cc(F)ccc1Oc1cncnc1N1CC2(CCN(CC3CCC(O)CC3)C2)C1)C(C)C] |
| VI-100 | 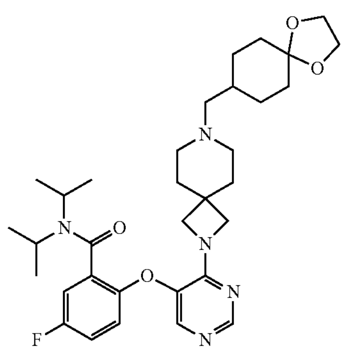 [SMILES: CC(C)N(C(=O)c1cc(F)ccc1Oc1cncnc1N1CC2(CCN(CC3CCC4(CC3)OCCO4)CC2)C1)C(C)C] |
| VI-101 | 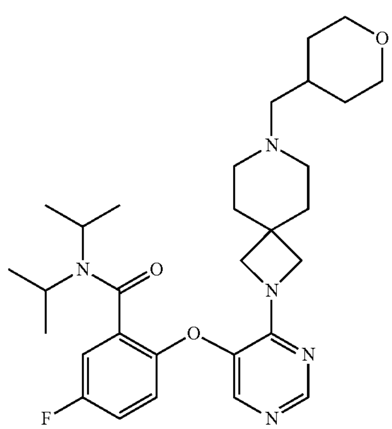 [SMILES: CC(C)N(C(=O)c1cc(F)ccc1Oc1cncnc1N1CC2(CCN(CC3CCOCC3)CC2)C1)C(C)C] |
| VI-102 | 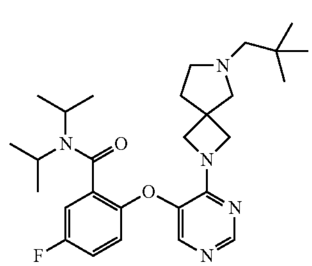 [SMILES: CC(C)N(C(=O)c1cc(F)ccc1Oc1cncnc1N1CC2(CCN(CC(C)(C)C)C2)C1)C(C)C] |
| VI-103 | |
| VI-104 | |
| VI-105 | |
| VI-106 | |
| VI-107 | |

TABLE 6-continued

| No. | Structure |
|---|---|
| VI-108 | 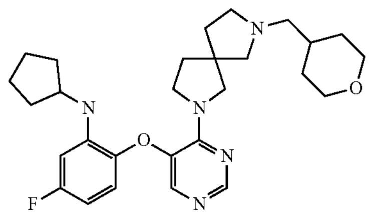 [SMILES: Fc1ccc(Oc2cncnc2N2CCC3(CCN(CC4CCOCC4)C3)C2)c(NC2CCCC2)c1] |
| VI-109 | 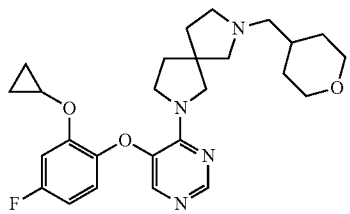 [SMILES: Fc1ccc(Oc2cncnc2N2CCC3(CCN(CC4CCOCC4)C3)C2)c(OC2CC2)c1] |
| VI-110 | 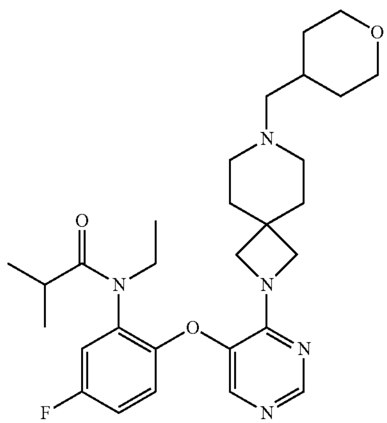 [SMILES: CCN(C(=O)C(C)C)c1cc(F)ccc1Oc1cncnc1N1CC2(CCN(CC3CCOCC3)CC2)C1] |
| VI-111 | 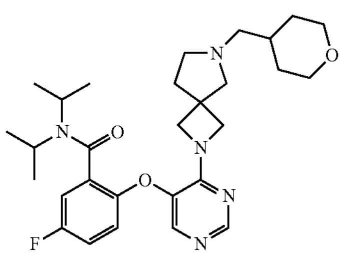 [SMILES: CC(C)N(C(=O)c1cc(F)ccc1Oc1cncnc1N1CC2(CCN(CC3CCOCC3)C2)C1)C(C)C] |
| VI-112 | 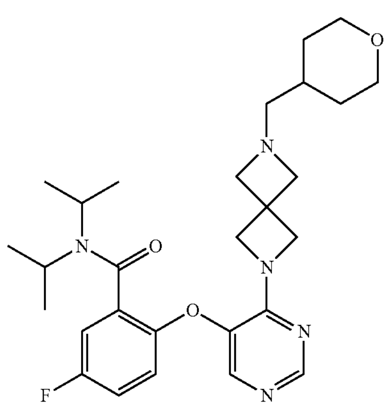 [SMILES: CC(C)N(C(=O)c1cc(F)ccc1Oc1cncnc1N1CC2(CN(CC3CCOCC3)C2)C1)C(C)C] |
| VI-113 | |
| VI-114 | |
| VI-115 | |
| VI-116 | |
| VI-117 | |

TABLE 6-continued

| No. | Structure |
|---|---|
| VI-118 | 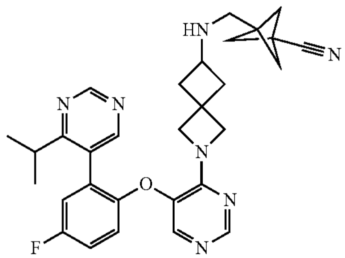 [SMILES: CC(C)c1ncncc1-c1cc(F)ccc1Oc1cncnc1N1CC2(CC(NCC34CC(C#N)(C3)C4)C2)C1] |
| VI-119 | 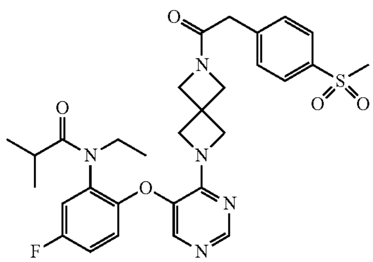 [SMILES: CCN(C(=O)C(C)C)c1cc(F)ccc1Oc1cncnc1N1CC2(CN(C(=O)Cc3ccc(S(C)(=O)=O)cc3)C2)C1] |
| VI-120 | 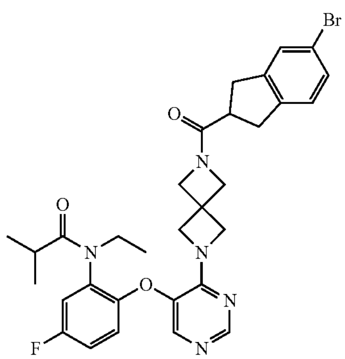 [SMILES: CCN(C(=O)C(C)C)c1cc(F)ccc1Oc1cncnc1N1CC2(CN(C(=O)C3Cc4ccc(Br)cc4C3)C2)C1] |
| VI-121 | 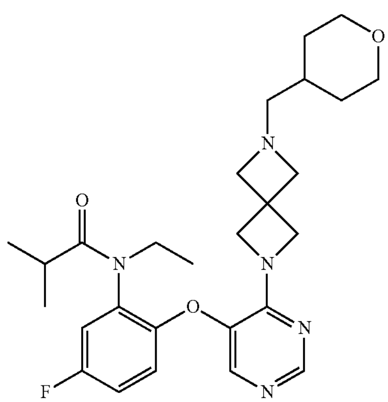 [SMILES: CCN(C(=O)C(C)C)c1cc(F)ccc1Oc1cncnc1N1CC2(CN(CC3CCOCC3)C2)C1] |
| VI-122 | 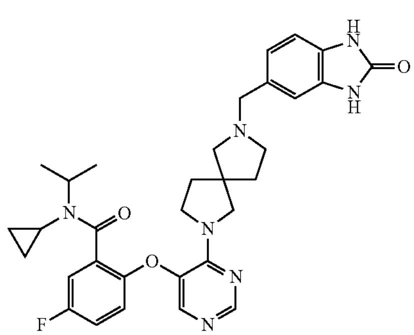 [SMILES: CC(C)N(C(=O)c1cc(F)ccc1Oc1cncnc1N1CCC2(CCN(Cc3ccc4[nH]c(=O)[nH]c4c3)C2)C1)C1CC1] |
| VI-123 | |
| VI-124 | |
| VI-125 | |
| VI-126 | |

TABLE 6-continued

| No. | Structure |
|---|---|
| VI-127 | 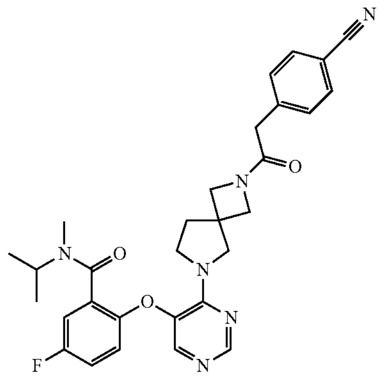 [SMILES: CC(C)N(C)C(=O)c1cc(F)ccc1Oc1cncnc1N1CCC2(CN(C(=O)Cc3ccc(C#N)cc3)C2)C1] |
| VI-128 | 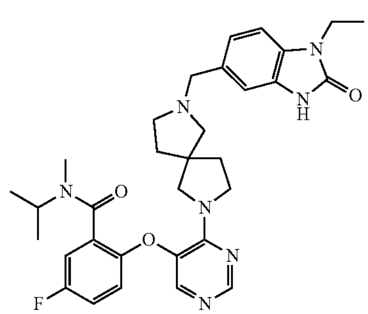 [SMILES: CCn1c(=O)[nH]c2cc(CN3CCC4(CCN(c5ncncc5Oc5ccc(F)cc5C(=O)N(C)C(C)C)C4)C3)ccc21] |
| VI-129 | 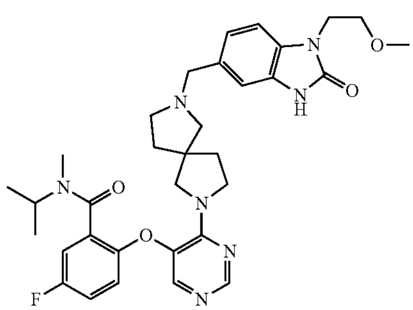 [SMILES: COCCn1c(=O)[nH]c2cc(CN3CCC4(CCN(c5ncncc5Oc5ccc(F)cc5C(=O)N(C)C(C)C)C4)C3)ccc21] |
| VI-130 | 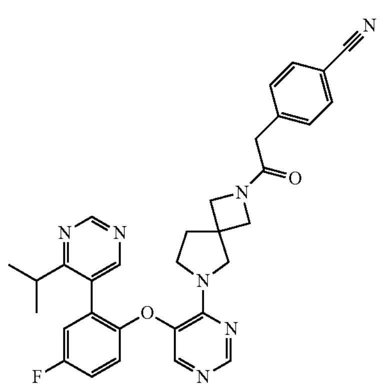 [SMILES: CC(C)c1ncncc1-c1cc(F)ccc1Oc1cncnc1N1CCC2(CN(C(=O)Cc3ccc(C#N)cc3)C2)C1] |
| VI-131 | 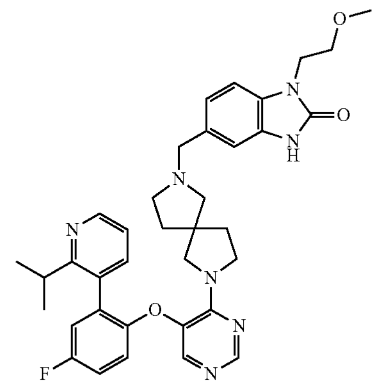 [SMILES: COCCn1c(=O)[nH]c2cc(CN3CCC4(CCN(c5ncncc5Oc5ccc(F)cc5-c5cccnc5C(C)C)C4)C3)ccc21] |
| VI-132 | 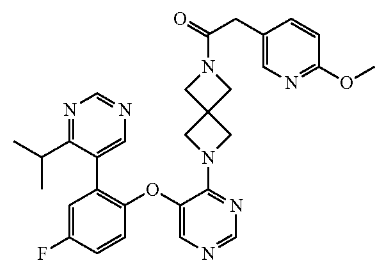 [SMILES: COc1ccc(CC(=O)N2CC3(C2)CN(c2ncncc2Oc2ccc(F)cc2-c2cncnc2C(C)C)C3)cn1] |
| VI-133 | 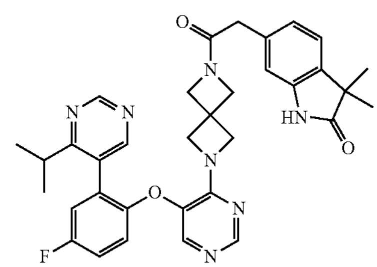 [SMILES: CC(C)c1ncncc1-c1cc(F)ccc1Oc1cncnc1N1CC2(CN(C(=O)Cc3ccc4c(c3)NC(=O)C4(C)C)C2)C1] |
| VI-134 | 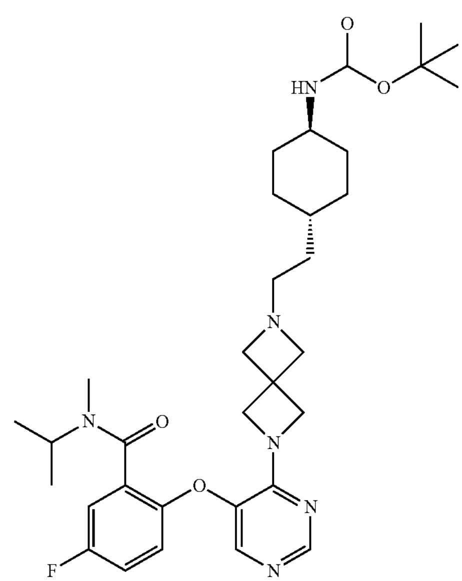 [SMILES: CC(C)N(C)C(=O)c1cc(F)ccc1Oc1cncnc1N1CC2(CN(CC[C@H]3CC[C@H](NC(O)OC(C)(C)C)CC3)C2)C1] |

TABLE 6-continued

| No. | Structure |
|---|---|
| VI-135 | 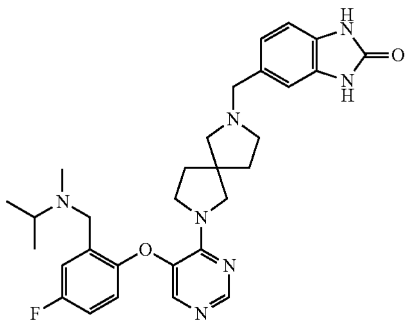 [SMILES: CC(C)N(C)Cc1cc(F)ccc1Oc1cncnc1N1CCC2(CCN(Cc3ccc4[nH]c(=O)[nH]c4c3)C2)C1] |
| VI-136 | 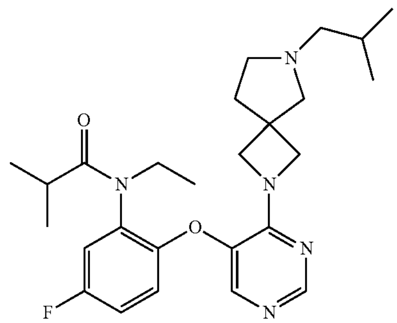 [SMILES: CCN(C(=O)C(C)C)c1cc(F)ccc1Oc1cncnc1N1CC2(CCN(CC(C)C)C2)C1] |
| VI-137 | 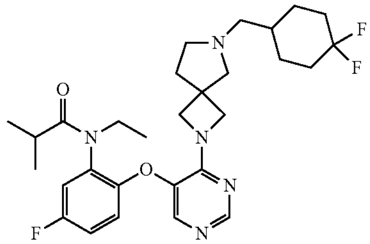 [SMILES: CCN(C(=O)C(C)C)c1cc(F)ccc1Oc1cncnc1N1CC2(CCN(CC3CCC(F)(F)CC3)C2)C1] |
| VI-138 | 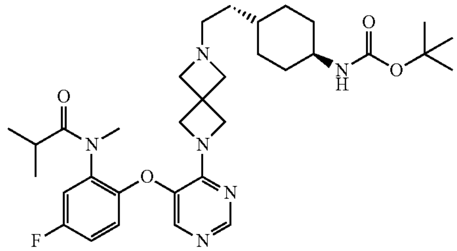 |
| VI-139 | 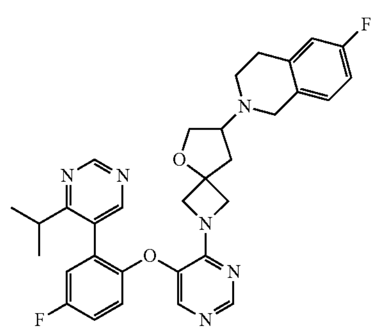 [SMILES: CC(C)c1ncncc1-c1cc(F)ccc1Oc1cncnc1N1CC2(CC(N3CCc4cc(F)ccc4C3)CO2)C1] |
| VI-140 | |
| VI-141 | |
| VI-142 | |
| VI-143 | |

TABLE 6-continued

| No. | Structure |
|---|---|
| VI-144 | |
| VI-145 | |
| VI-146 | |
| VI-147 | 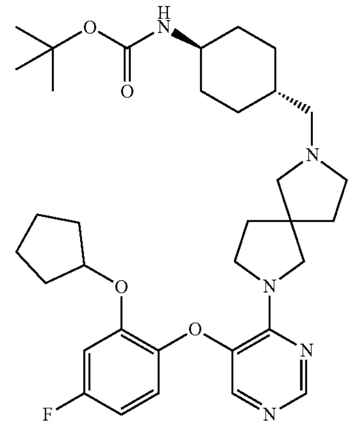 [SMILES: CC(C)(C)OC(=O)N[C@H]1CC[C@H](CN2CCC3(CCN(c4ncncc4Oc4ccc(F)cc4OC4CCCC4)C3)C2)CC1] |
| VI-148 | 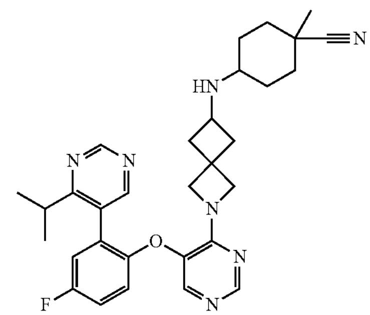 [SMILES: CC(C)c1ncncc1-c1cc(F)ccc1Oc1cncnc1N1CC2(CC(NC3CCC(C)(C#N)CC3)C2)C1] |
| VI-149 | 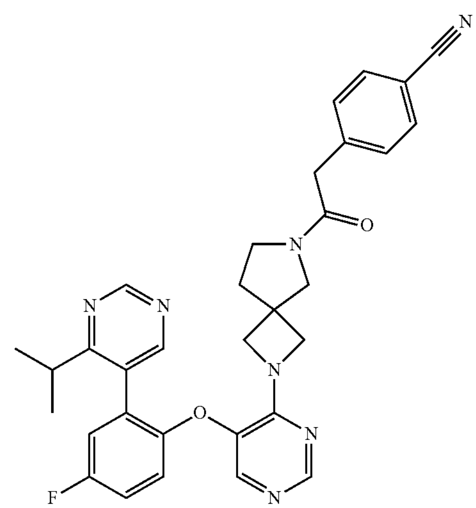 [SMILES: CC(C)c1ncncc1-c1cc(F)ccc1Oc1cncnc1N1CC2(CCN(C(=O)Cc3ccc(C#N)cc3)C2)C1] |
| VI-150 | 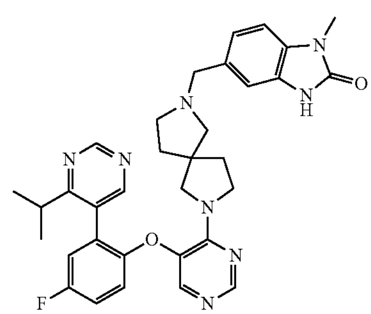 [SMILES: CC(C)c1ncncc1-c1cc(F)ccc1Oc1cncnc1N1CCC2(CCN(Cc3ccc4c(c3)[nH]c(=O)n4C)C2)C1] |

TABLE 6-continued

| No. | Structure |
|-----|-----------|
| VI-151 | 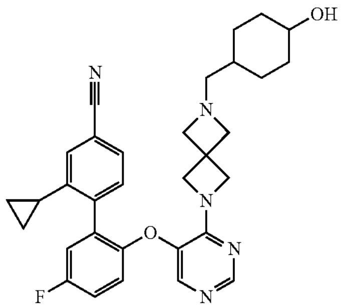 [SMILES: N#Cc1ccc(-c2cc(F)ccc2Oc2cncnc2N2CC3(CN(CC4CCC(O)CC4)C3)C2)c(C2CC2)c1] |
| VI-152 | 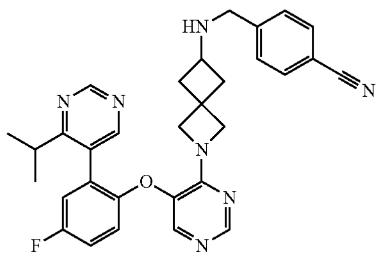 [SMILES: CC(C)c1ncncc1-c1cc(F)ccc1Oc1cncnc1N1CC2(CC(NCc3ccc(C#N)cc3)C2)C1] |
| VI-153 | 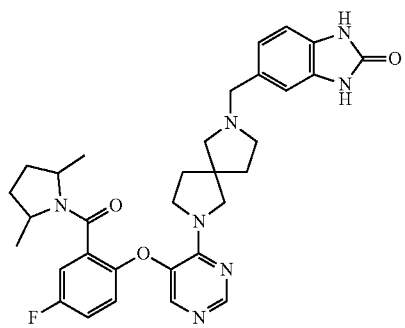 [SMILES: CC1CCC(C)N1C(=O)c1cc(F)ccc1Oc1cncnc1N1CCC2(CCN(Cc3ccc4[nH]c(=O)[nH]c4c3)C2)C1] |
| VI-154 | 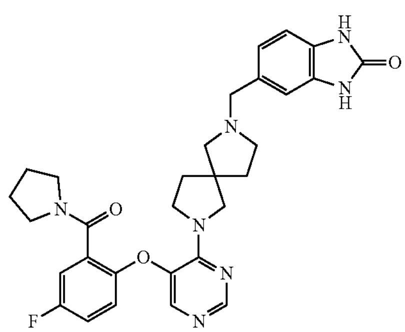 [SMILES: O=C(c1cc(F)ccc1Oc1cncnc1N1CCC2(CCN(Cc3ccc4[nH]c(=O)[nH]c4c3)C2)C1)N1CCCC1] |
| VI-155 | 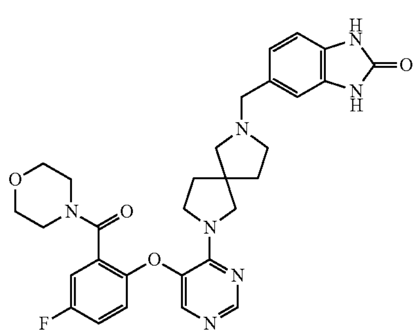 [SMILES: O=C(c1cc(F)ccc1Oc1cncnc1N1CCC2(CCN(Cc3ccc4[nH]c(=O)[nH]c4c3)C2)C1)N1CCOCC1] |
| VI-156 | |
| VI-157 | |
| VI-158 | |
| VI-159 | |
| VI-160 | |

TABLE 6-continued
| No. | Structure |
|---|---|
| VI-161 | 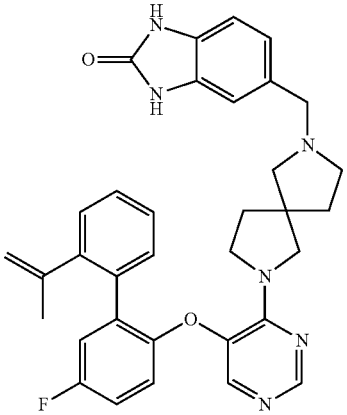 [SMILES: C=C(C)c1ccccc1-c1cc(F)ccc1Oc1cncnc1N1CCC2(CCN(Cc3ccc4[nH]c(=O)[nH]c4c3)C2)C1] |
| VI-162 | 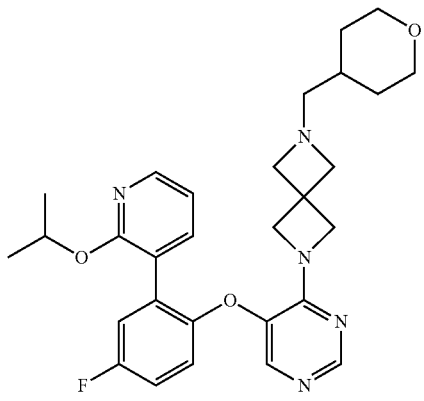 [SMILES: CC(C)Oc1ncccc1-c1cc(F)ccc1Oc1cncnc1N1CC2(CN(CC3CCOCC3)C2)C1] |
| VI-163 | 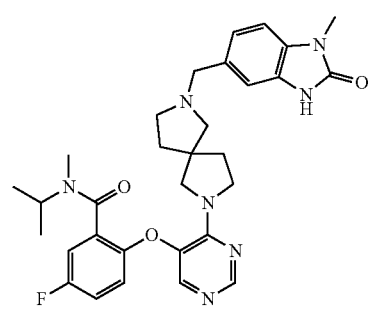 [SMILES: CC(C)N(C)C(=O)c1cc(F)ccc1Oc1cncnc1N1CCC2(CCN(Cc3ccc4c(c3)[nH]c(=O)n4C)C2)C1] |
| VI-164 | 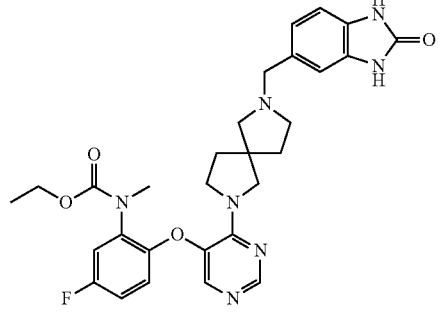 |
| VI-165 | 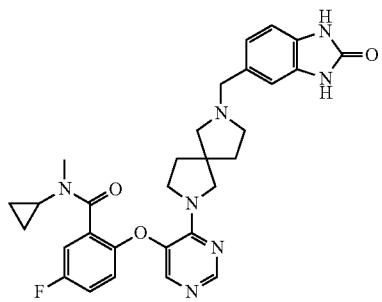 [SMILES: CN(C(=O)c1cc(F)ccc1Oc1cncnc1N1CCC2(CCN(Cc3ccc4[nH]c(=O)[nH]c4c3)C2)C1)C1CC1] |
| VI-166 | 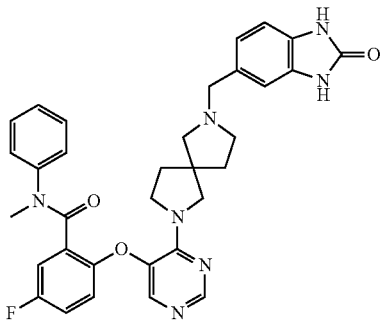 [SMILES: CN(C(=O)c1cc(F)ccc1Oc1cncnc1N1CCC2(CCN(Cc3ccc4[nH]c(=O)[nH]c4c3)C2)C1)c1ccccc1] |
| VI-167 | 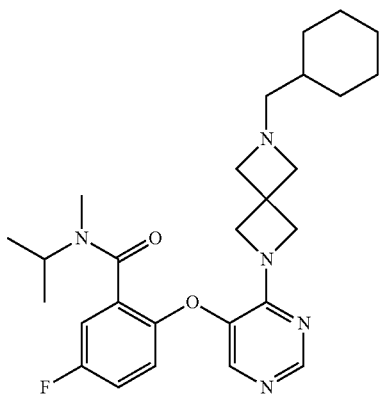 [SMILES: CC(C)N(C)C(=O)c1cc(F)ccc1Oc1cncnc1N1CC2(CN(CC3CCCCC3)C2)C1] |
| VI-168 | 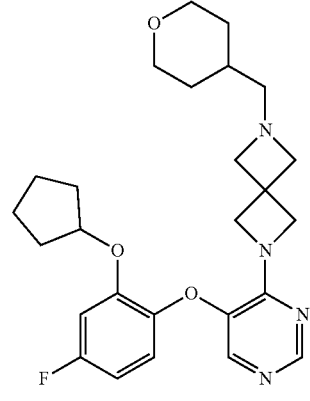 [SMILES: Fc1ccc(Oc2cncnc2N2CC3(CN(CC4CCOCC4)C3)C2)c(OC2CCCC2)c1] |

TABLE 6-continued

| No. | Structure |
|---|---|
| VI-169 | 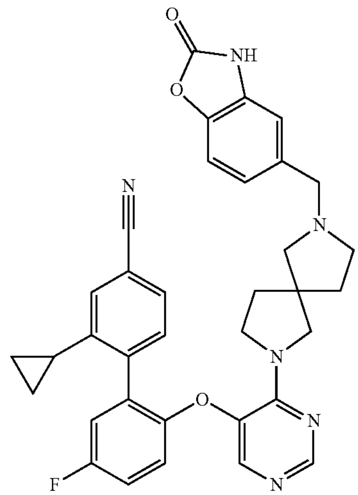 [SMILES: N#Cc1ccc(-c2cc(F)ccc2Oc2cncnc2N2CCC3(CCN(Cc4ccc5oc(=O)[nH]c5c4)C3)C2)c(C2CC2)c1] |
| VI-170 | 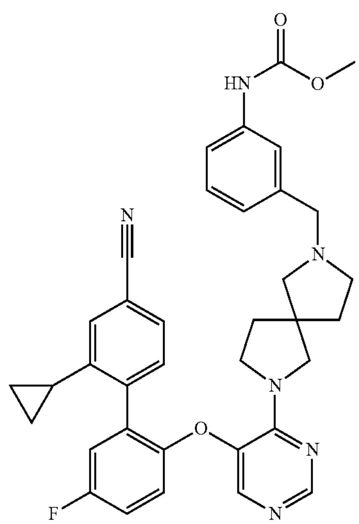 [SMILES: COC(=O)Nc1cccc(CN2CCC3(CCN(c4ncncc4Oc4ccc(F)cc4-c4ccc(C#N)cc4C4CC4)C3)C2)c1] |
| VI-171 | 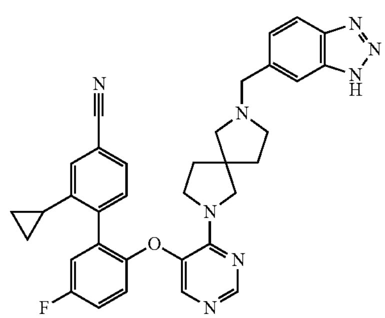 [SMILES: N#Cc1ccc(-c2cc(F)ccc2Oc2cncnc2N2CCC3(CCN(Cc4ccc5nn[nH]c5c4)C3)C2)c(C2CC2)c1] |
| VI-172 | 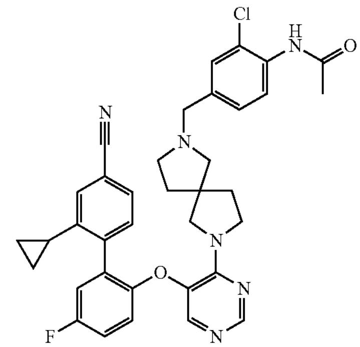 [SMILES: CC(=O)Nc1ccc(CN2CCC3(CCN(c4ncncc4Oc4ccc(F)cc4-c4ccc(C#N)cc4C4CC4)C3)C2)cc1Cl] |
| VI-173 | 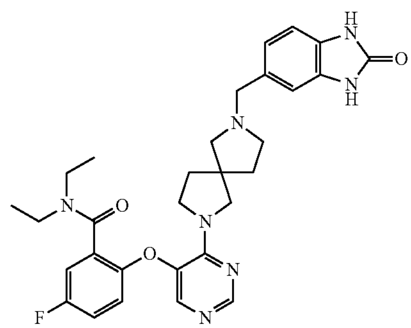 [SMILES: CCN(CC)C(=O)c1cc(F)ccc1Oc1cncnc1N1CCC2(CCN(Cc3ccc4[nH]c(=O)[nH]c4c3)C2)C1] |
| VI-174 | 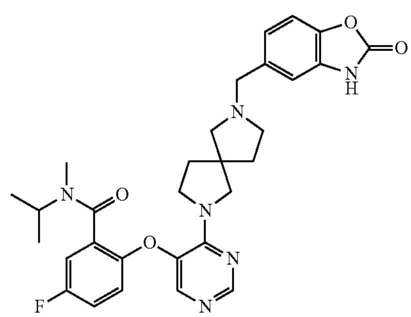 [SMILES: CC(C)N(C)C(=O)c1cc(F)ccc1Oc1cncnc1N1CCC2(CCN(Cc3ccc4oc(=O)[nH]c4c3)C2)C1] |
| VI-175 | 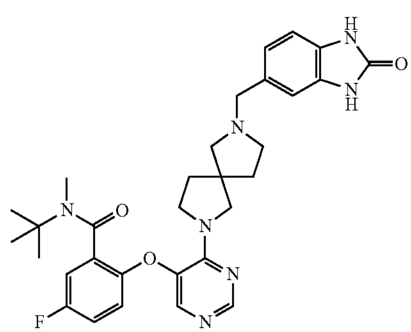 [SMILES: CN(C(=O)c1cc(F)ccc1Oc1cncnc1N1CCC2(CCN(Cc3ccc4[nH]c(=O)[nH]c4c3)C2)C1)C(C)(C)C] |

TABLE 6-continued
| No. | Structure |
|---|---|
| VI-176 | 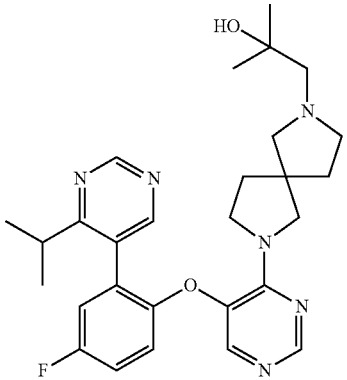 [SMILES: CC(C)c1ncncc1-c1cc(F)ccc1Oc1cncnc1N1CCC2(CCN(CC(C)(C)O)C2)C1] |
| VI-177 | 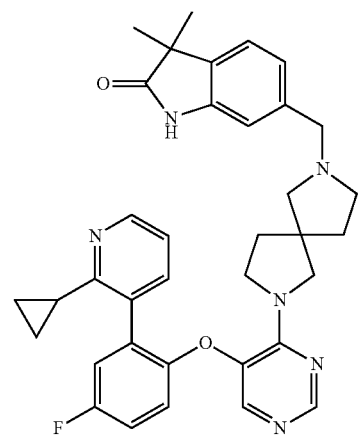 [SMILES: CC1(C)C(=O)Nc2cc(CN3CCC4(CCN(c5ncncc5Oc5ccc(F)cc5-c5cccnc5C5CC5)C4)C3)ccc21] |
| VI-178 | 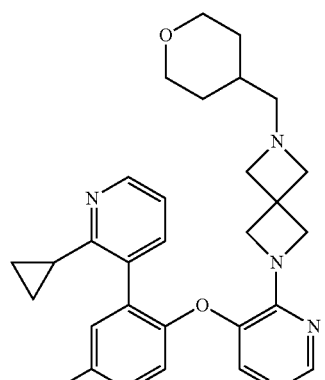 |
| VI-179 | 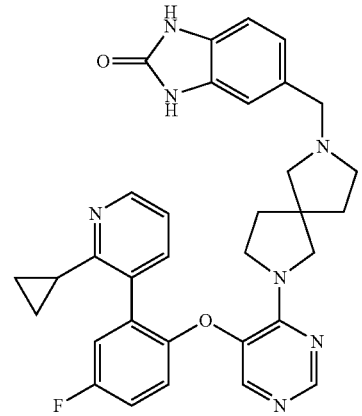 [SMILES: O=c1[nH]c2ccc(CN3CCC4(CCN(c5ncncc5Oc5ccc(F)cc5-c5cccnc5C5CC5)C4)C3)cc2[nH]1] |
| VI-180 | 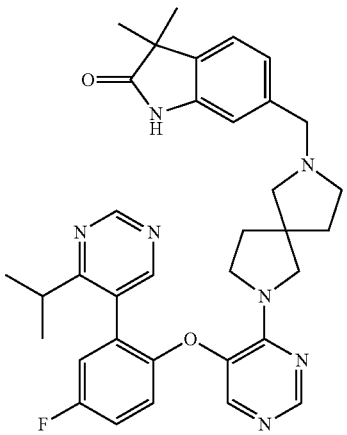 |
| VI-181 | 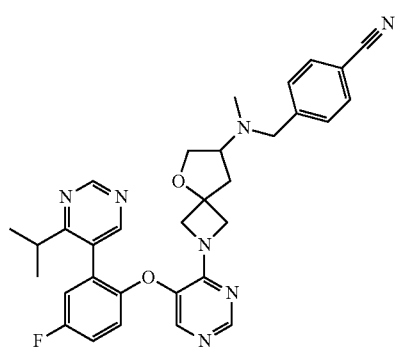 [SMILES: CC(C)c1ncncc1-c1cc(F)ccc1Oc1cncnc1N1CC2(CC(N(C)Cc3ccc(C#N)cc3)CO2)C1] |

TABLE 6-continued

| No. | Structure |
|---|---|
| VI-182 | 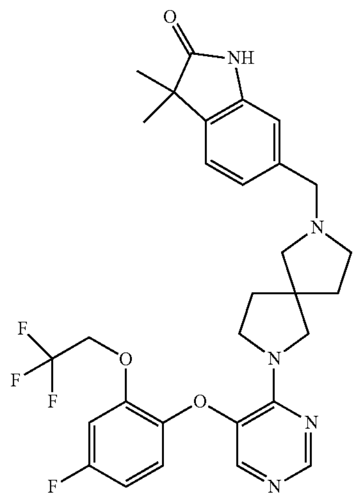 [SMILES: CC1(C)C(=O)Nc2cc(CN3CCC4(CCN(c5ncncc5Oc5ccc(F)cc5OCC(F)(F)F)C4)C3)ccc21] |
| VI-183 | 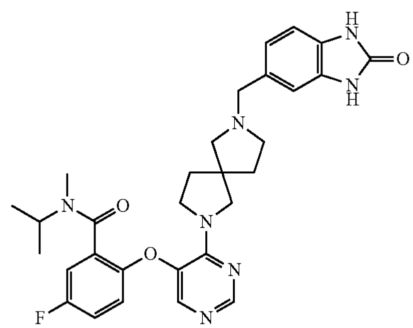 [SMILES: CC(C)N(C)C(=O)c1cc(F)ccc1Oc1cncnc1N1CCC2(CCN(Cc3ccc4[nH]c(=O)[nH]c4c3)C2)C1] |
| VI-184 | 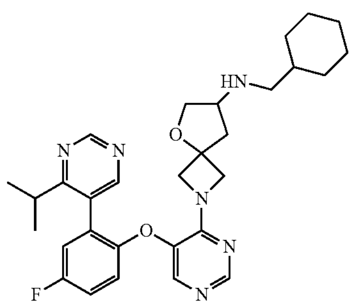 [SMILES: CC(C)c1ncncc1-c1cc(F)ccc1Oc1cncnc1N1CC2(CC(NCC3CCCCC3)CO2)C1] |
| VI-185 | 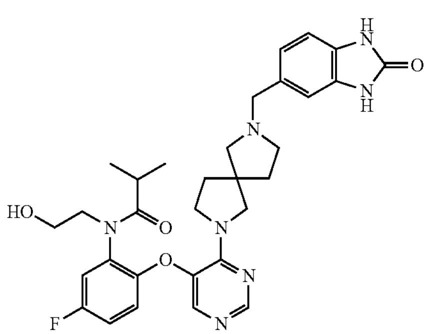 [SMILES: CC(C)C(=O)N(CCO)c1cc(F)ccc1Oc1cncnc1N1CCC2(CCN(Cc3ccc4[nH]c(=O)[nH]c4c3)C2)C1] |
| VI-186 | |
| VI-187 | |
| VI-188 | |
| VI-189 | |

TABLE 6-continued

| No. | Structure |
|---|---|
| VI-190 | 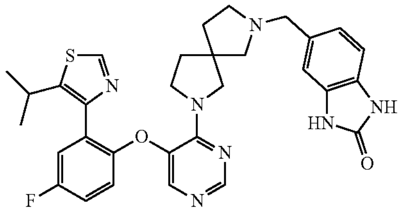 [SMILES: CC(C)c1scnc1-c1cc(F)ccc1Oc1cncnc1N1CCC2(CCN(Cc3ccc4[nH]c(=O)[nH]c4c3)C2)C1] |
| VI-191 | 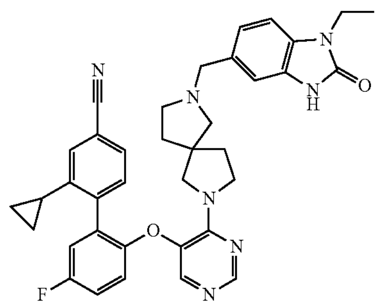 [SMILES: CCn1c(=O)[nH]c2cc(CN3CCC4(CCN(c5ncncc5Oc5ccc(F)cc5-c5ccc(C#N)cc5C5CC5)C4)C3)ccc21] |
| VI-192 | 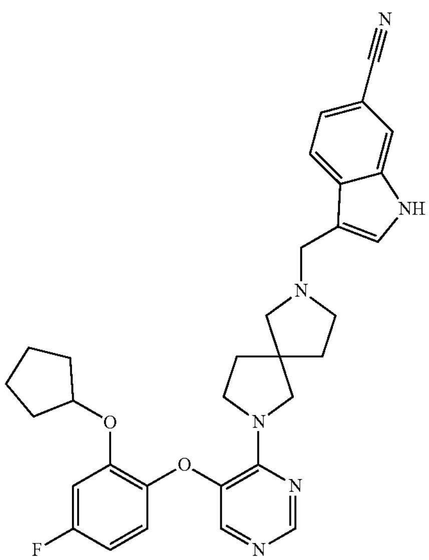 [SMILES: N#Cc1ccc2c(CN3CCC4(CCN(c5ncncc5Oc5ccc(F)cc5OC5CCCC5)C4)C3)c[nH]c2c1] |
| VI-193 | 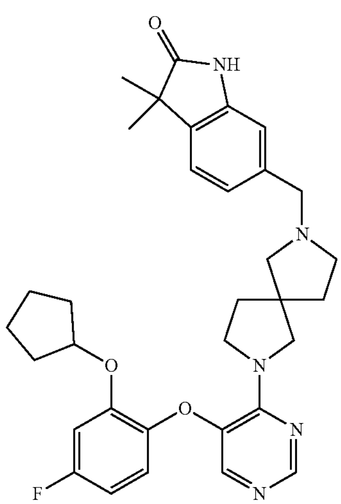 [SMILES: CC1(C)C(=O)Nc2cc(CN3CCC4(CCN(c5ncncc5Oc5ccc(F)cc5OC5CCCC5)C4)C3)ccc21] |
| VI-194 | |
| VI-195 | |
| VI-196 | |

TABLE 6-continued

| No. | Structure |
|---|---|
| VI-197 | 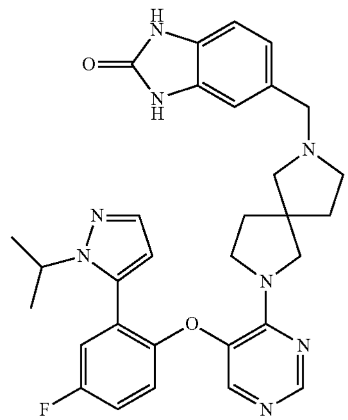 [SMILES: CC(C)n1nccc1-c1cc(F)ccc1Oc1cncnc1N1CCC2(CCN(Cc3ccc4[nH]c(=O)[nH]c4c3)C2)C1] |
| VI-198 | 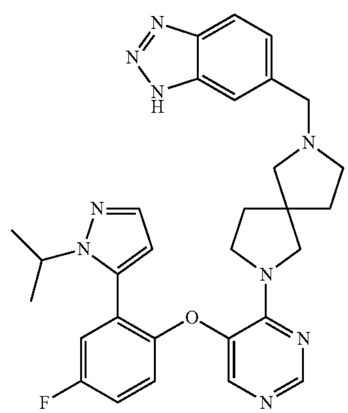 [SMILES: CC(C)n1nccc1-c1cc(F)ccc1Oc1cncnc1N1CCC2(CCN(Cc3ccc4nn[nH]c4c3)C2)C1] |
| VI-199 | 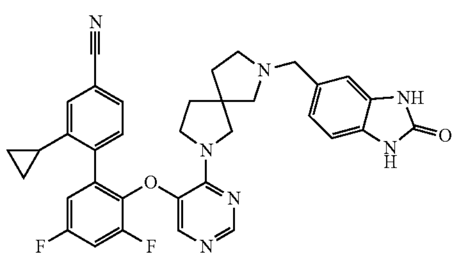 [SMILES: N#Cc1ccc(-c2cc(F)cc(F)c2Oc2cncnc2N2CCC3(CCN(Cc4ccc5[nH]c(=O)[nH]c5c4)C3)C2)c(C2CC2)c1] |
| VI-200 | 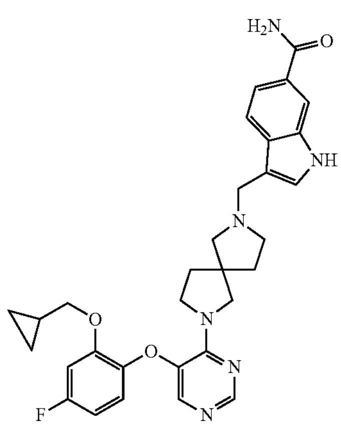 [SMILES: NC(=O)c1ccc2c(CN3CCC4(CCN(c5ncncc5Oc5ccc(F)cc5OCC5CC5)C4)C3)c[nH]c2c1] |
| VI-201 | |
| VI-202 | |
| VI-203 | |
| VI-204 | |

TABLE 6-continued
| No. | Structure |
|---|---|
| VI-205 | 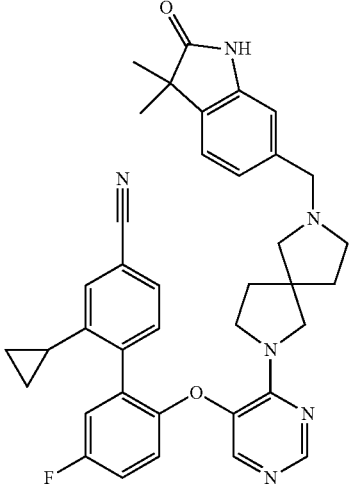 [SMILES: CC1(C)C(=O)Nc2cc(CN3CCC4(CCN(c5ncncc5Oc5ccc(F)cc5-c5ccc(C#N)cc5C5CC5)C4)C3)ccc21] |
| VI-206 | 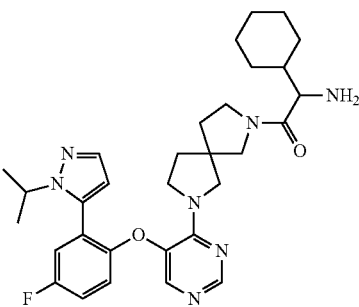 [SMILES: CC(C)n1nccc1-c1cc(F)ccc1Oc1cncnc1N1CCC2(CCN(C(=O)C(N)C3CCCCC3)C2)C1] |
| VI-207 | 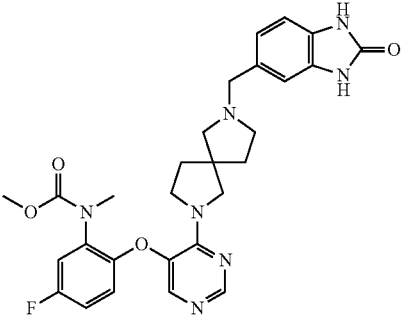 [SMILES: COC(=O)N(C)c1cc(F)ccc1Oc1cncnc1N1CCC2(CCN(Cc3ccc4[nH]c(=O)[nH]c4c3)C2)C1] |
| VI-208 | 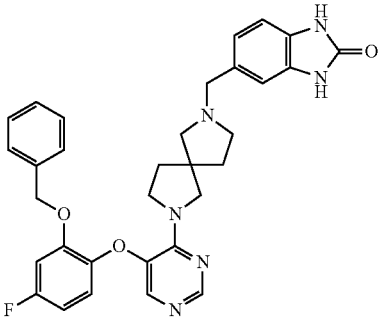 [SMILES: O=c1[nH]c2ccc(CN3CCC4(CCN(c5ncncc5Oc5ccc(F)cc5OCc5ccccc5)C4)C3)cc2[nH]1] |
| VI-209 | 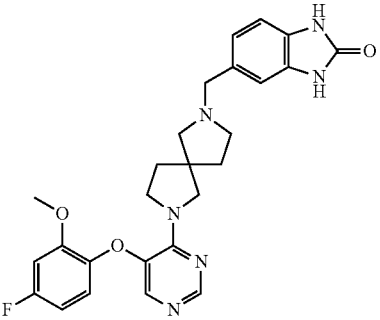 [SMILES: COc1cc(F)ccc1Oc1cncnc1N1CCC2(CCN(Cc3ccc4[nH]c(=O)[nH]c4c3)C2)C1] |
| VI-210 | 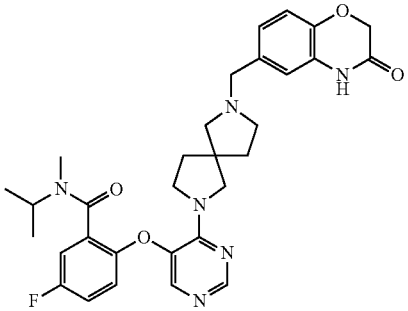 [SMILES: CC(C)N(C)C(=O)c1cc(F)ccc1Oc1cncnc1N1CCC2(CCN(Cc3ccc4c(c3)NC(=O)CO4)C2)C1] |
| VI-211 | 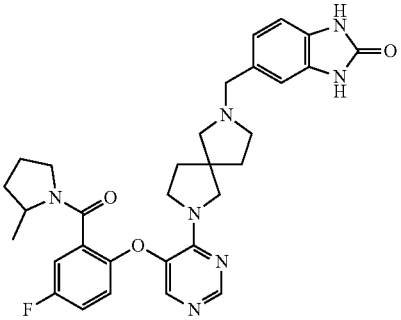 [SMILES: CC1CCCN1C(=O)c1cc(F)ccc1Oc1cncnc1N1CCC2(CCN(Cc3ccc4[nH]c(=O)[nH]c4c3)C2)C1] |
| VI-212 | 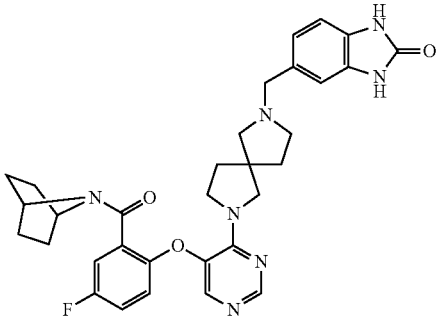 [SMILES: O=C(c1cc(F)ccc1Oc1cncnc1N1CCC2(CCN(Cc3ccc4[nH]c(=O)[nH]c4c3)C2)C1)N1C2CCC1CC2] |

TABLE 6-continued

| No. | Structure |
|---|---|
| VI-213 | 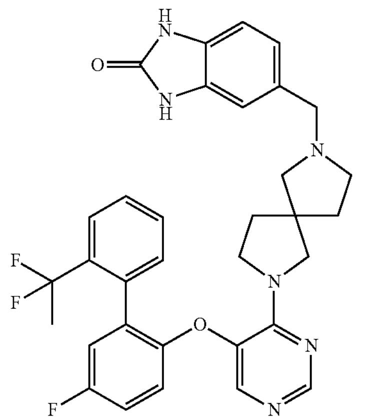 [SMILES: CC(F)(F)c1ccccc1-c1cc(F)ccc1Oc1cncnc1N1CCC2(CCN(Cc3ccc4[nH]c(=O)[nH]c4c3)C2)C1] |
| VI-214 | 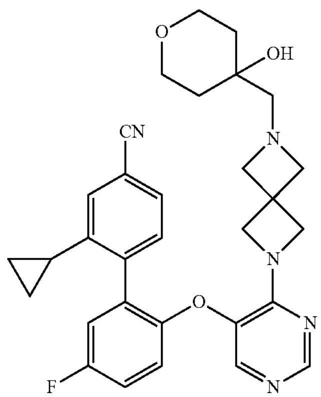 [SMILES: N#Cc1ccc(-c2cc(F)ccc2Oc2cncnc2N2CC3(CN(CC4(O)CCOCC4)C3)C2)c(C2CC2)c1] |
| VI-215 | 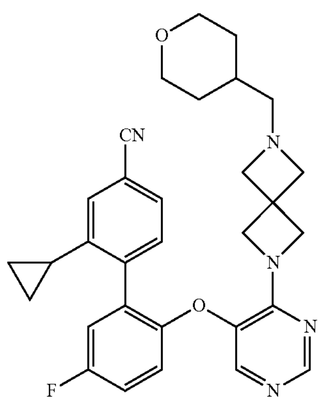 [SMILES: N#Cc1ccc(-c2cc(F)ccc2Oc2cncnc2N2CC3(CN(CC4CCOCC4)C3)C2)c(C2CC2)c1] |
| VI-216 | 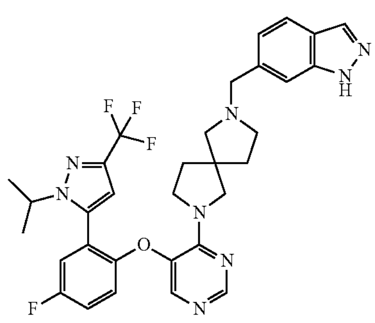 [SMILES: CC(C)n1nc(C(F)(F)F)cc1-c1cc(F)ccc1Oc1cncnc1N1CCC2(CCN(Cc3ccc4cn[nH]c4c3)C2)C1] |
| VI-217 | |
| VI-218 | |
| VI-219 | |
| VI-220 | |

TABLE 6-continued
| No. | Structure |
|---|---|
| VI-221 | 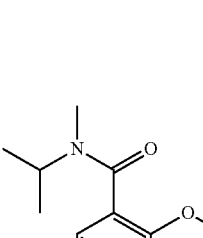 |
| VI-222 | 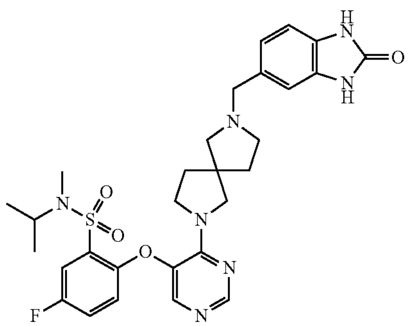 [SMILES: CC(C)N(C)S(=O)(=O)c1cc(F)ccc1Oc1cncnc1N1CCC2(CCN(Cc3ccc4[nH]c(=O)[nH]c4c3)C2)C1] |
| VI-223 | 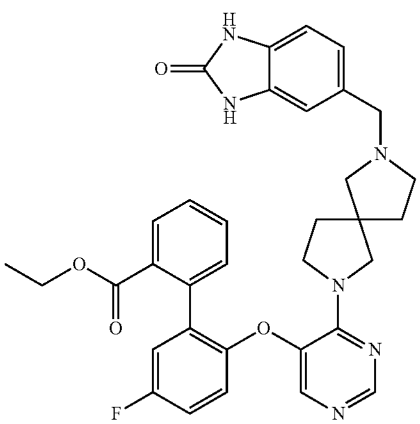 [SMILES: CCOC(=O)c1ccccc1-c1cc(F)ccc1Oc1cncnc1N1CCC2(CCN(Cc3ccc4[nH]c(=O)[nH]c4c3)C2)C1] |
| VI-224 | 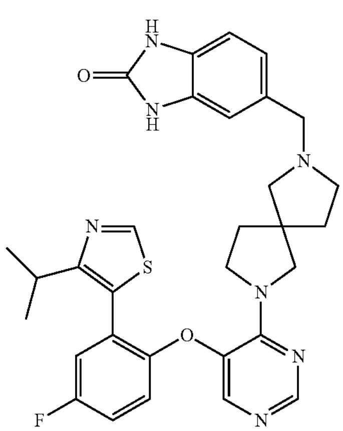 [SMILES: CC(C)c1ncsc1-c1cc(F)ccc1Oc1cncnc1N1CCC2(CCN(Cc3ccc4[nH]c(=O)[nH]c4c3)C2)C1] |
TABLE 6-continued
| No. | Structure |
|---|---|
| VI-225 | 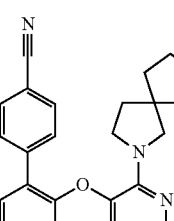 |
| VI-226 | 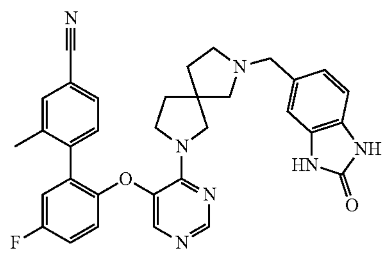 |
| VI-227 | 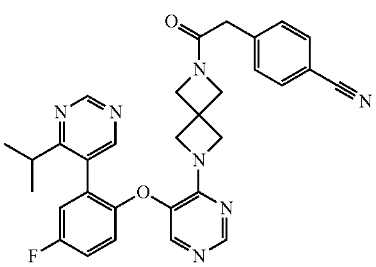 [SMILES: CC(C)c1ncncc1-c1cc(F)ccc1Oc1cncnc1N1CC2(CN(C(=O)Cc3ccc(C#N)cc3)C2)C1] |
| VI-228 | 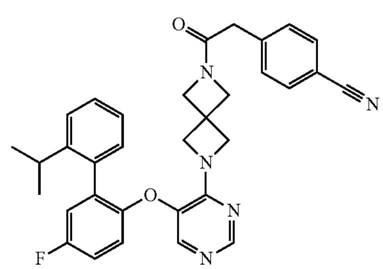 [SMILES: CC(C)c1ccccc1-c1cc(F)ccc1Oc1cncnc1N1CC2(CN(C(=O)Cc3ccc(C#N)cc3)C2)C1] |
| VI-229 | 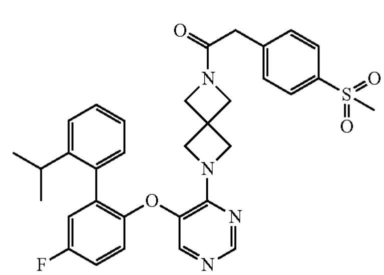 [SMILES: CC(C)c1ccccc1-c1cc(F)ccc1Oc1cncnc1N1CC2(CN(C(=O)Cc3ccc(S(C)(=O)=O)cc3)C2)C1] |

TABLE 6-continued
| No. | Structure |
|---|---|
| VI-230 | 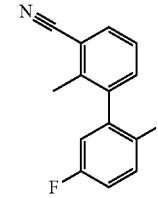 |
| VI-231 | 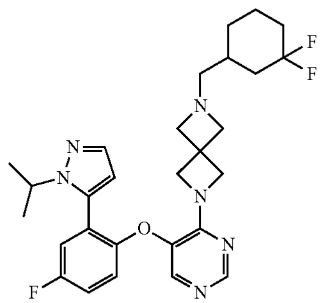 [SMILES: CC(C)n1nccc1-c1cc(F)ccc1Oc1cncnc1N1CC2(CN(CC3CCCC(F)(F)C3)C2)C1] |
| VI-232 | 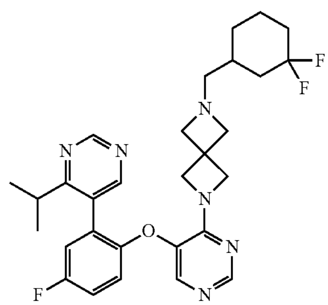 [SMILES: CC(C)c1ncncc1-c1cc(F)ccc1Oc1cncnc1N1CC2(CN(CC3CCCC(F)(F)C3)C2)C1] |
| VI-233 | 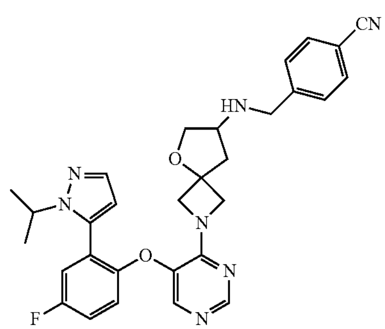 [SMILES: CC(C)n1nccc1-c1cc(F)ccc1Oc1cncnc1N1CC2(CC(NCc3ccc(C#N)cc3)CO2)C1] |
| VI-234 | 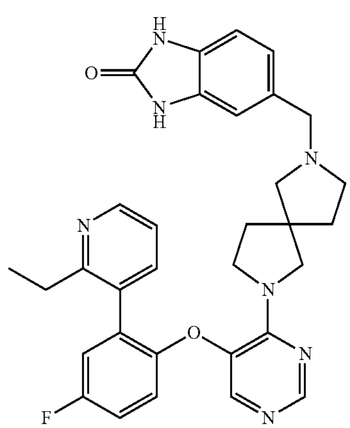 [SMILES: CCc1ncccc1-c1cc(F)ccc1Oc1cncnc1N1CCC2(CCN(Cc3ccc4[nH]c(=O)[nH]c4c3)C2)C1] |
TABLE 6-continued
| No. | Structure |
|---|---|
| VI-235 | 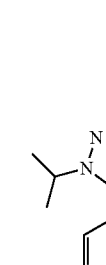 |
| VI-236 | 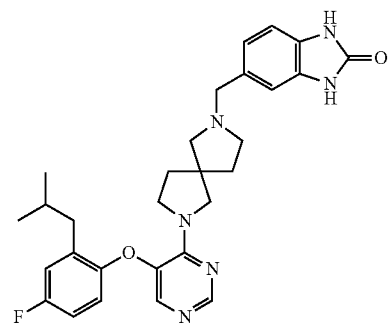 [SMILES: CC(C)Cc1cc(F)ccc1Oc1cncnc1N1CCC2(CCN(Cc3ccc4[nH]c(=O)[nH]c4c3)C2)C1] |
| VI-237 | 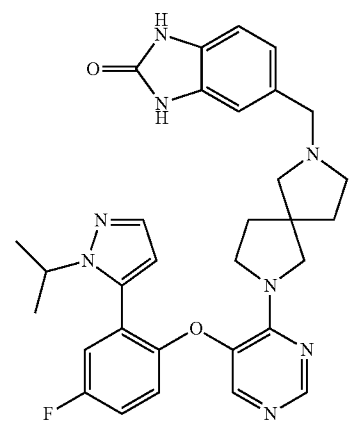 [SMILES: CC(C)n1nccc1-c1cc(F)ccc1Oc1cncnc1N1CCC2(CCN(Cc3ccc4[nH]c(=O)[nH]c4c3)C2)C1] |
| VI-238 | 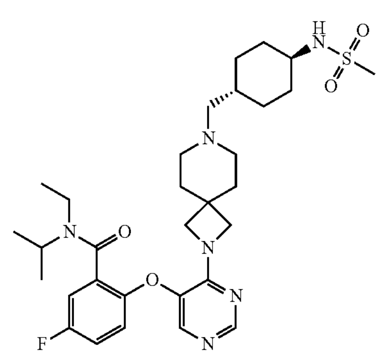 [SMILES: CCN(C(=O)c1cc(F)ccc1Oc1cncnc1N1CC2(CCN(C[C@H]3CC[C@H](NS(C)(=O)=O)CC3)CC2)C1)C(C)C] |

TABLE 6-continued

| No. | Structure |
|---|---|
| VI-239 | 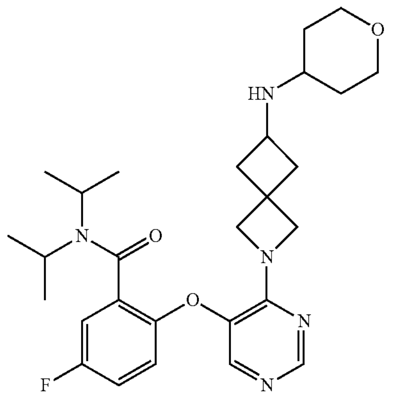 [SMILES: CC(C)N(C(=O)c1cc(F)ccc1Oc1cncnc1N1CC2(CC(NC3CCOCC3)C2)C1)C(C)C] |
| VI-240 | 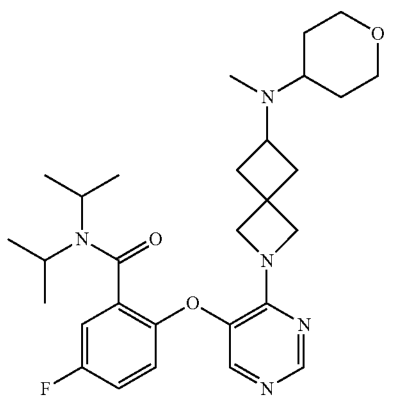 [SMILES: CC(C)N(C(=O)c1cc(F)ccc1Oc1cncnc1N1CC2(CC(N(C)C3CCOCC3)C2)C1)C(C)C] |
| VI-241 | 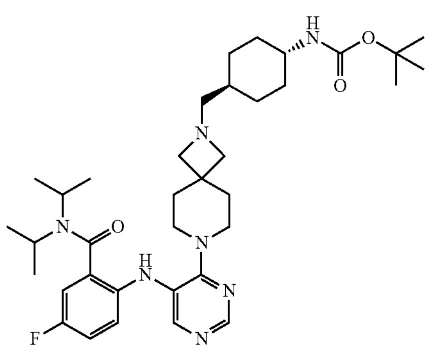 [SMILES: CC(C)N(C(=O)c1cc(F)ccc1Nc1cncnc1N1CCC2(CC1)CN(C[C@H]1CC[C@H](NC(=O)OC(C)(C)C)CC1)C2)C(C)C] |
| VI-242 | 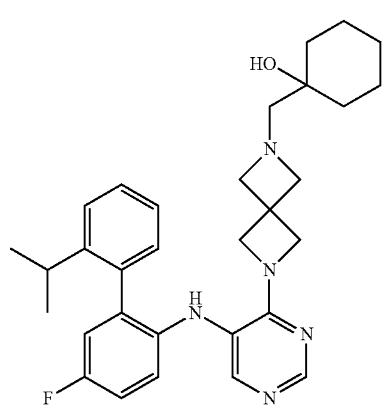 [SMILES: CC(C)c1ccccc1-c1cc(F)ccc1Nc1cncnc1N1CC2(CN(CC3(O)CCCCC3)C2)C1] |
| VI-243 | |
| VI-244 | |
| VI-245 | |
| VI-246 | |

TABLE 6-continued
| No. | Structure |
|---|---|
| VI-247 | 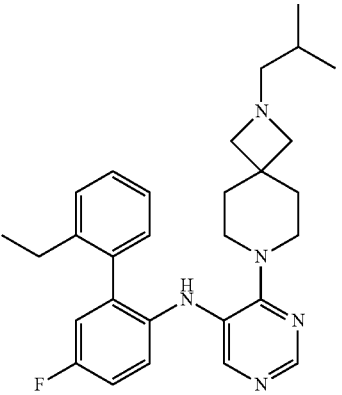 [SMILES: CCc1ccccc1-c1cc(F)ccc1Nc1cncnc1N1CCC2(CC1)CN(CC(C)C)C2] |
| VI-248 | 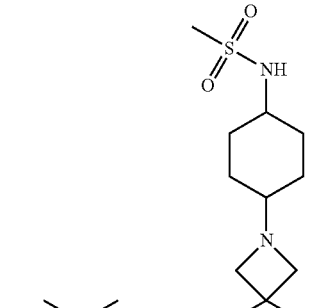 |
| VI-249 | 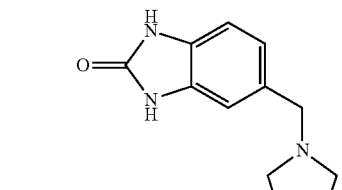 |
| VI-250 | 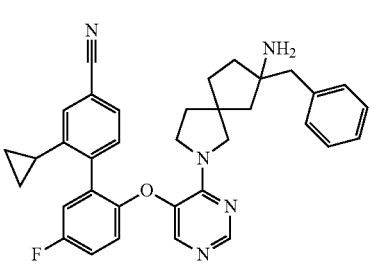 [SMILES: N#Cc1ccc(-c2cc(F)ccc2Oc2cncnc2N2CCC3(CCC(N)(Cc4ccccc4)C3)C2)c(C2CC2)c1] |
| VI-251 | 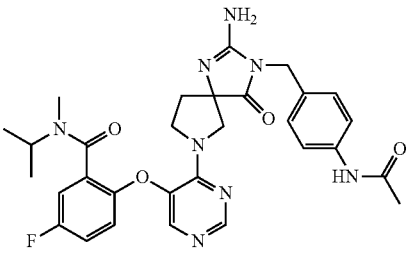 [SMILES: CC(=O)Nc1ccc(CN2C(=O)C3(CCN(c4ncncc4Oc4ccc(F)cc4C(=O)N(C)C(C)C)C3)N=C2N)cc1] |
| VI-252 | 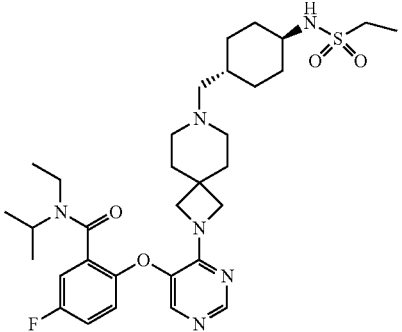 [SMILES: CCN(C(=O)c1cc(F)ccc1Oc1cncnc1N1CC2(CCN(C[C@H]3CC[C@H](NS(=O)(=O)CC)CC3)CC2)C1)C(C)C] |
| VI-253 | 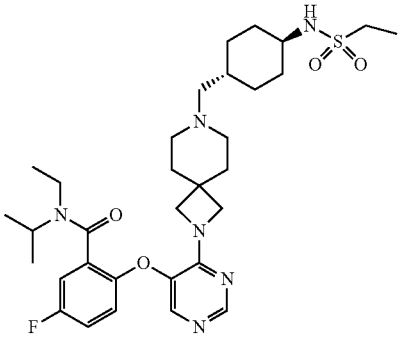 [SMILES: CCN(C(=O)c1cc(F)ccc1Oc1cncnc1N1CC2(CCN(C[C@H]3CC[C@H](NS(=O)(=O)CC)CC3)CC2)C1)C(C)C] |
TABLE 7
| No. | Structure |
|---|---|
| VII-1 | 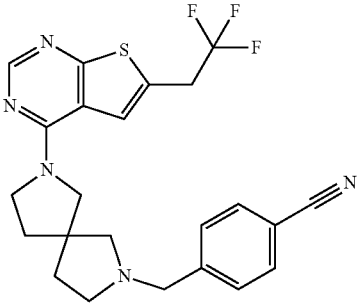 [SMILES: N#Cc1ccc(CN2CCC3(CCN(c4ncnc5sc(CC(F)(F)F)cc45)C3)C2)cc1] |

TABLE 7-continued

| No. | Structure |
|---|---|
| VII-2 | 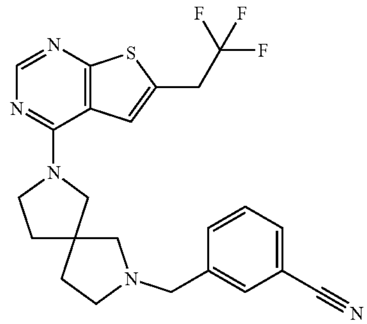 [SMILES: N#Cc1cccc(CN2CCC3(CCN(c4ncnc5sc(CC(F)(F)F)cc45)C3)C2)c1] |
| VII-3 | 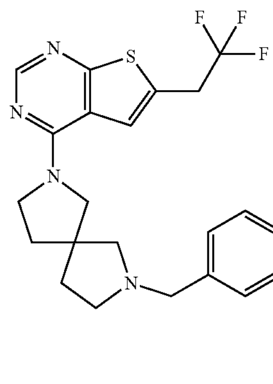 |
| VII-4 | 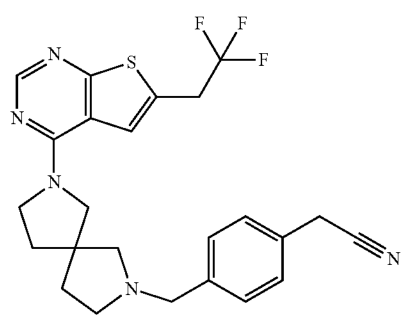 [SMILES: N#CCc1ccc(CN2CCC3(CCN(c4ncnc5sc(CC(F)(F)F)cc45)C3)C2)cc1] |
| VII-5 | 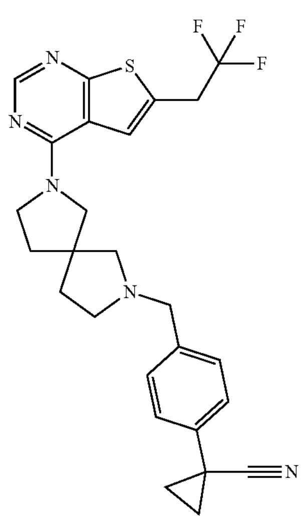 [SMILES: N#CC1(c2ccc(CN3CCC4(CCN(c5ncnc6sc(CC(F)(F)F)cc56)C4)C3)cc2)CC1] |
| VII-6 | |
| VII-7 | |
| VII-8 | |

TABLE 7-continued
| No. | Structure |
|---|---|
| VII-9 | 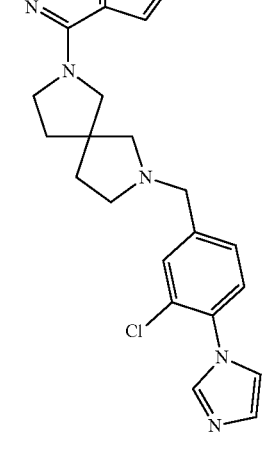 |
| VII-10 | |
| VII-11 | |
| VII-12 | 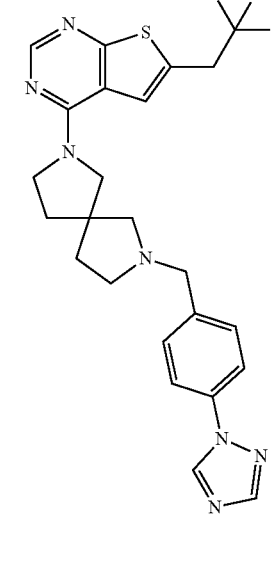 |
| VII-13 | 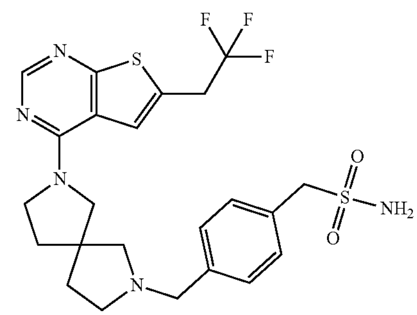 [SMILES: NS(=O)(=O)Cc1ccc(CN2CCC3(CCN(c4ncnc5sc(CC(F)(F)F)cc45)C3)C2)cc1] |
| VII-14 | 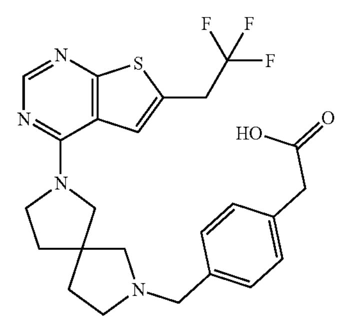 [SMILES: O=C(O)Cc1ccc(CN2CCC3(CCN(c4ncnc5sc(CC(F)(F)F)cc45)C3)C2)cc1] |
| VII-15 | 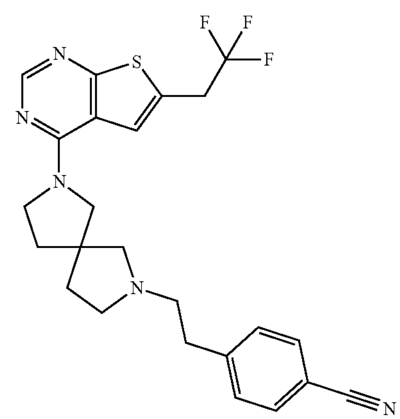 [SMILES: N#Cc1ccc(CCN2CCC3(CCN(c4ncnc5sc(CC(F)(F)F)cc45)C3)C2)cc1] |
| VII-16 | 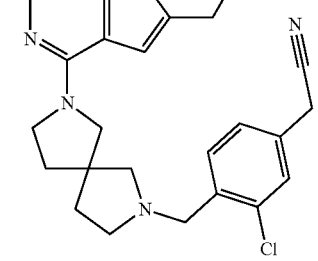 |

TABLE 7-continued

| No. | Structure |
|---|---|
| VII-17 | |
| VII-18 | |
| VII-19 | |
| VII-20 | |
| VII-21 | |
| VII-22 | 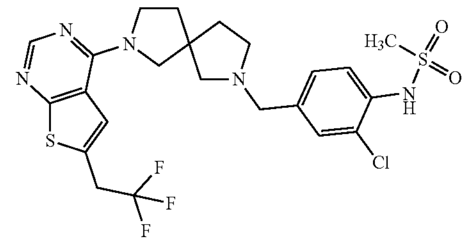 [SMILES: CS(=O)(=O)Nc1ccc(CN2CCC3(CCN(c4ncnc5sc(CC(F)(F)F)cc45)C3)C2)cc1Cl] |
| VII-23 | 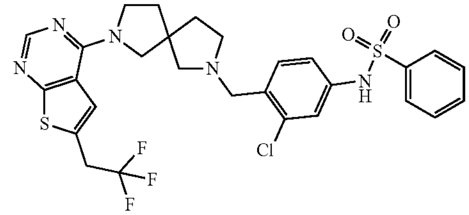 [SMILES: O=S(=O)(Nc1ccc(CN2CCC3(CCN(c4ncnc5sc(CC(F)(F)F)cc45)C3)C2)c(Cl)c1)c1ccccc1] |
| VII-24 | 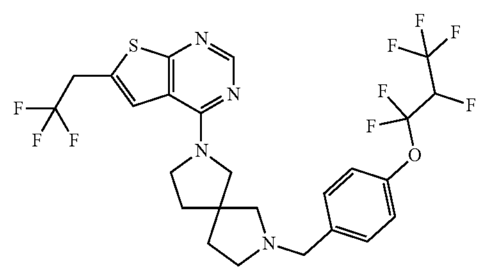 [SMILES: FC(C(F)(F)F)C(F)(F)Oc1ccc(CN2CCC3(CCN(c4ncnc5sc(CC(F)(F)F)cc45)C3)C2)cc1] |
| VII-25 | 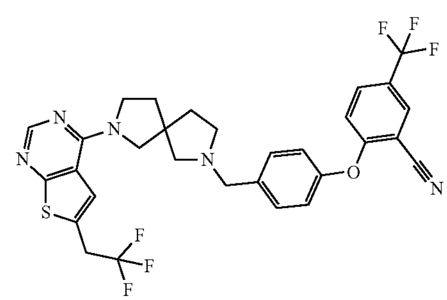 [SMILES: N#Cc1cc(C(F)(F)F)ccc1Oc1ccc(CN2CCC3(CCN(c4ncnc5sc(CC(F)(F)F)cc45)C3)C2)cc1] |
| VII-26 | 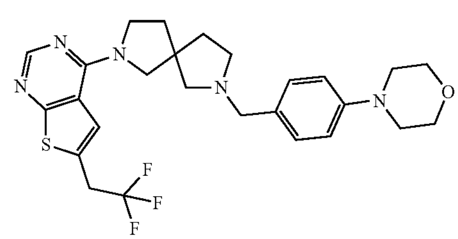 [SMILES: FC(F)(F)Cc1cc2c(N3CCC4(CCN(Cc5ccc(N6CCOCC6)cc5)C4)C3)ncnc2s1] |
| VII-27 | 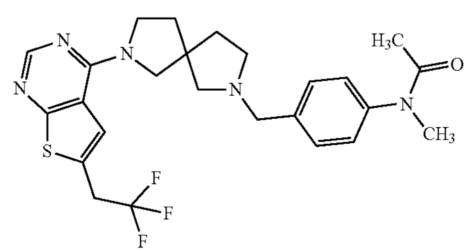 [SMILES: CC(=O)N(C)c1ccc(CN2CCC3(CCN(c4ncnc5sc(CC(F)(F)F)cc45)C3)C2)cc1] |

TABLE 7-continued

| No. | Structure |
|---|---|
| VII-28 | 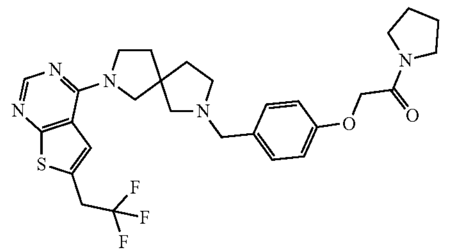 [SMILES: O=C(COc1ccc(CN2CCC3(CCN(c4ncnc5sc(CC(F)(F)F)cc45)C3)C2)cc1)N1CCCC1] |
| VII-29 | 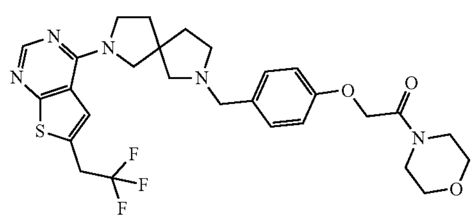 [SMILES: O=C(COc1ccc(CN2CCC3(CCN(c4ncnc5sc(CC(F)(F)F)cc45)C3)C2)cc1)N1CCOCC1] |
| VII-30 | 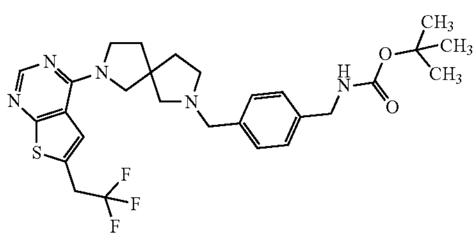 [SMILES: CC(C)(C)OC(=O)NCc1ccc(CN2CCC3(CCN(c4ncnc5sc(CC(F)(F)F)cc45)C3)C2)cc1] |
| VII-31 | 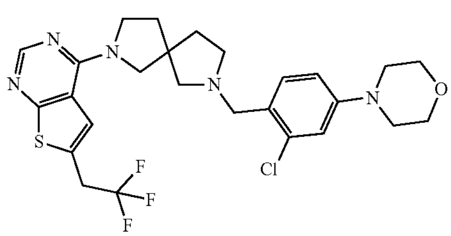 [SMILES: FC(F)(F)Cc1cc2c(N3CCC4(CCN(Cc5ccc(N6CCOCC6)cc5Cl)C4)C3)ncnc2s1] |
| VII-32 | 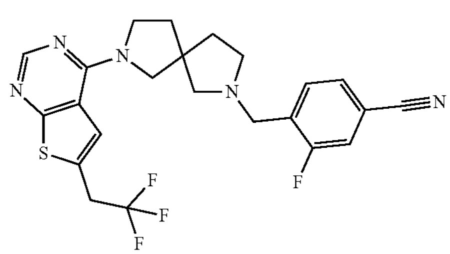 [SMILES: N#Cc1ccc(CN2CCC3(CCN(c4ncnc5sc(CC(F)(F)F)cc45)C3)C2)c(F)c1] |
| VII-33 | 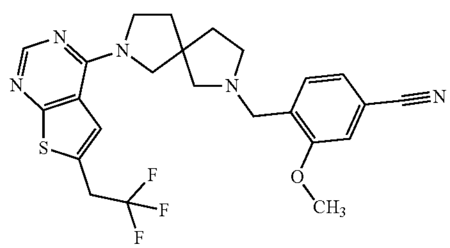 [SMILES: COc1cc(C#N)ccc1CN1CCC2(CCN(c3ncnc4sc(CC(F)(F)F)cc34)C2)C1] |
| VII-34 | |
| VII-35 | |
| VII-36 | |
| VII-37 | |
| VII-38 | |
| VII-39 | |

TABLE 7-continued

| No. | Structure |
|---|---|
| VII-40 | 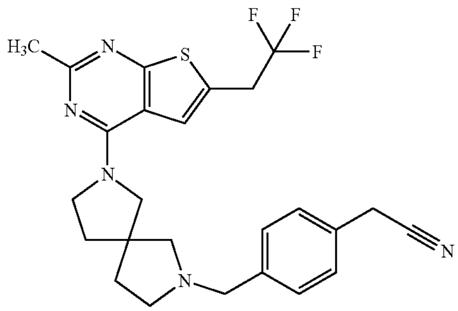 [SMILES: Cc1nc(N2CCC3(CCN(Cc4ccc(CC#N)cc4)C3)C2)c2cc(CC(F)(F)F)sc2n1] |
| VII-41 | 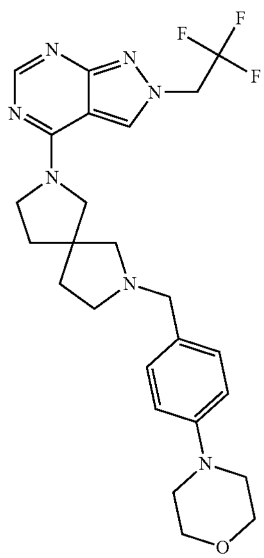 [SMILES: FC(F)(F)Cn1cc2c(N3CCC4(CCN(Cc5ccc(N6CCOCC6)cc5)C4)C3)ncnc2n1] |
| VII-42 | 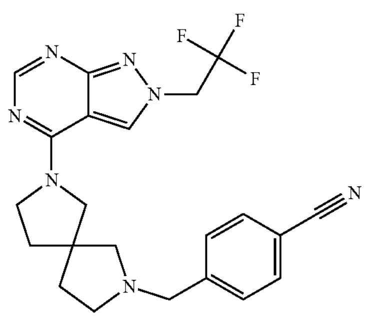 [SMILES: N#Cc1ccc(CN2CCC3(CCN(c4ncnc5nn(CC(F)(F)F)cc45)C3)C2)cc1] |
| VII-43 | 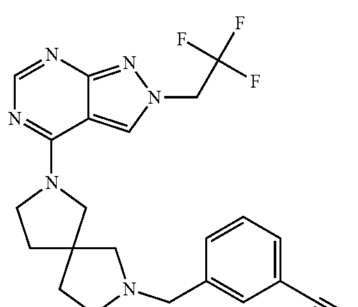 |
| VII-44 | |
| VII-45 | |
| VII-46 | |
| VII-47 | |

TABLE 7-continued
| No. | Structure |
|---|---|
| VII-48 | 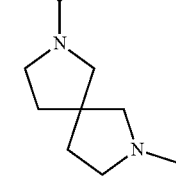 |
| VII-49 | 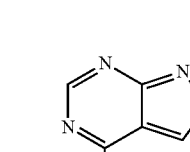 |
| VII-50 | 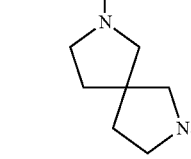 |
| VII-51 | 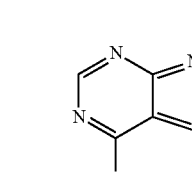 |
| VII-52 | 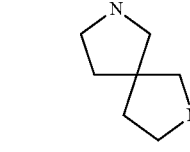 |
| VII-53 | 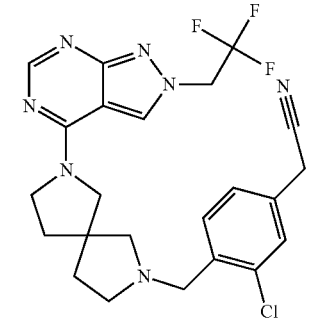 [SMILES: N#CCc1ccc(CN2CCC3(CCN(c4ncnc5nn(CC(F)(F)F)cc45)C3)C2)c(Cl)c1] |
| VII-54 | 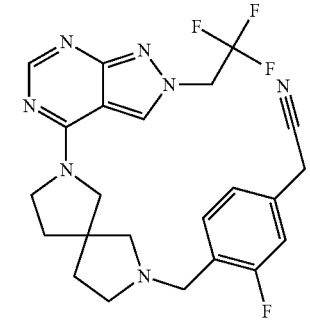 |
| VII-55 | 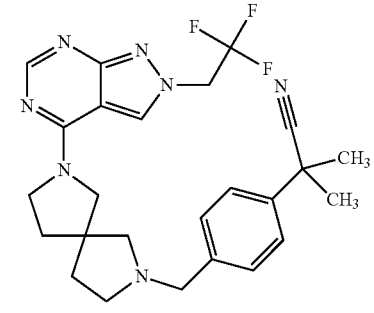 [SMILES: CC(C)(C#N)c1ccc(CN2CCC3(CCN(c4ncnc5nn(CC(F)(F)F)cc45)C3)C2)cc1] |
| VII-56 | 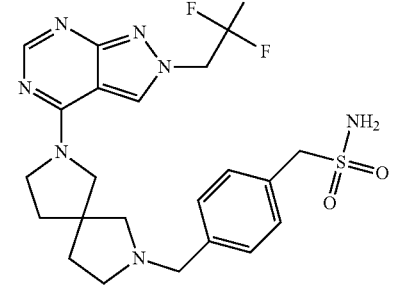 |

TABLE 7-continued

| No. | Structure |
|---|---|
| VII-57 | |
| VII-58 | |
| VII-59 | |
| VII-60 | |
| VII-61 | 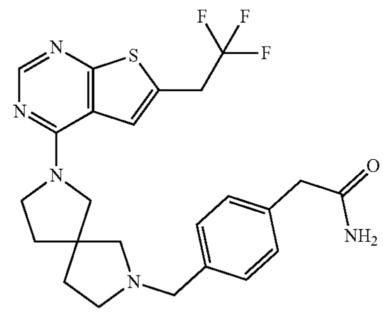 [SMILES: NC(=O)Cc1ccc(CN2CCC3(CCN(c4ncnc5sc(CC(F)(F)F)cc45)C3)C2)cc1] |
| VII-62 | 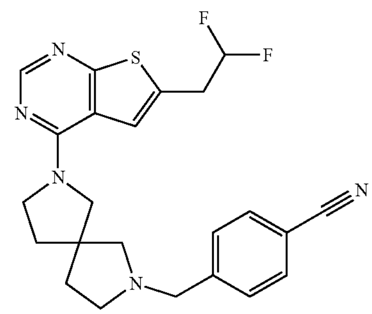 [SMILES: N#Cc1ccc(CN2CCC3(CCN(c4ncnc5sc(CC(F)F)cc45)C3)C2)cc1] |
| VII-63 | 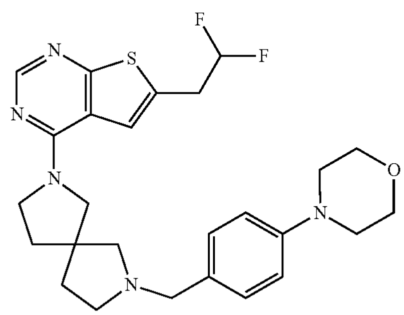 [SMILES: FC(F)Cc1cc2c(N3CCC4(CCN(Cc5ccc(N6CCOCC6)cc5)C4)C3)ncnc2s1] |
| VII-64 | 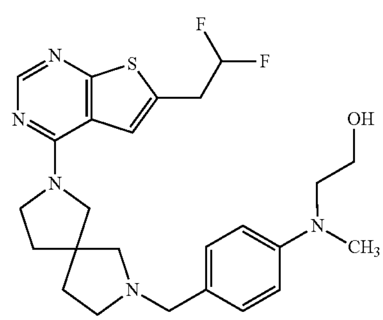 [SMILES: CN(CCO)c1ccc(CN2CCC3(CCN(c4ncnc5sc(CC(F)F)cc45)C3)C2)cc1] |
| VII-65 | 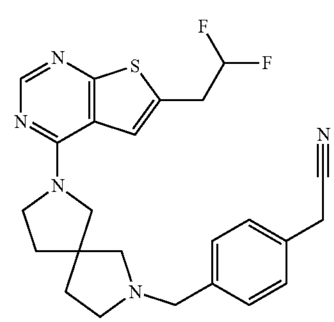 [SMILES: N#CCc1ccc(CN2CCC3(CCN(c4ncnc5sc(CC(F)F)cc45)C3)C2)cc1] |

TABLE 7-continued

| No. | Structure |
|---|---|
| VII-66 | 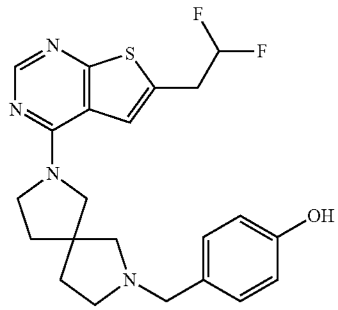 [SMILES: Oc1ccc(CN2CCC3(CCN(c4ncnc5sc(CC(F)F)cc45)C3)C2)cc1] |
| VII-67 | 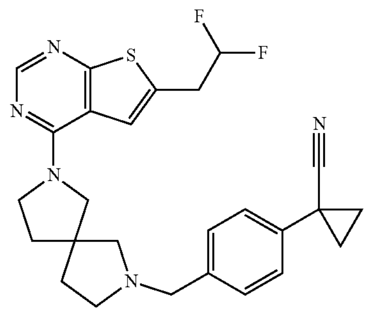 [SMILES: N#CC1(c2ccc(CN3CCC4(CCN(c5ncnc6sc(CC(F)F)cc56)C4)C3)cc2)CC1] |
| VII-68 | 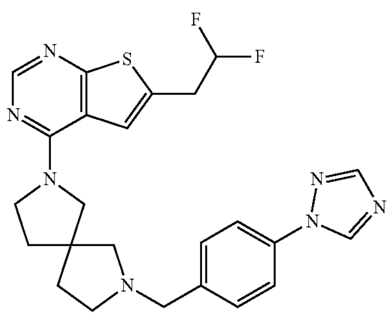 [SMILES: FC(F)Cc1cc2c(N3CCC4(CCN(Cc5ccc(-n6cncn6)cc5)C4)C3)ncnc2s1] |
| VII-69 | 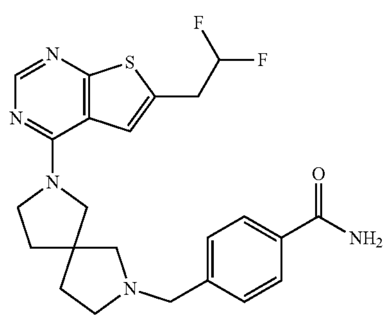 [SMILES: NC(=O)c1ccc(CN2CCC3(CCN(c4ncnc5sc(CC(F)F)cc45)C3)C2)cc1] |
| VII-70 | 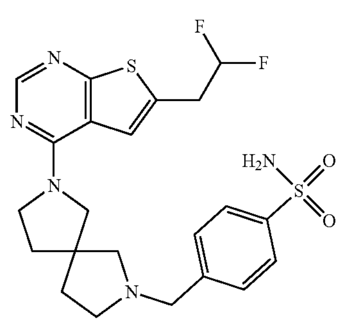 [SMILES: NS(=O)(=O)c1ccc(CN2CCC3(CCN(c4ncnc5sc(CC(F)F)cc45)C3)C2)cc1] |
| VII-71 | |
| VII-72 | |
| VII-73 | |
| VII-74 | |
| VII-75 | |

TABLE 7-continued
| No. | Structure |
|---|---|
| VII-76 | 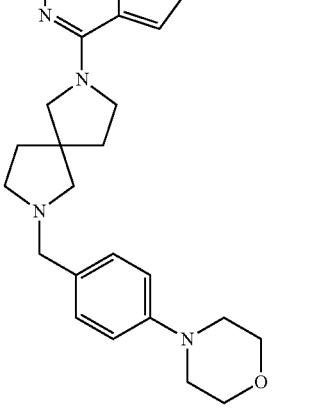 |
| VII-77 | 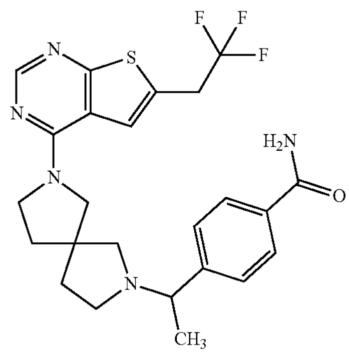 [SMILES: CC(c1ccc(C(N)=O)cc1)N1CCC2(CCN(c3ncnc4sc(CC(F)(F)F)cc34)C2)C1] |
| VII-78 | 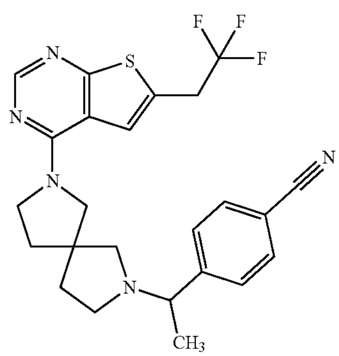 [SMILES: CC(c1ccc(C#N)cc1)N1CCC2(CCN(c3ncnc4sc(CC(F)(F)F)cc34)C2)C1] |
| VII-79 | 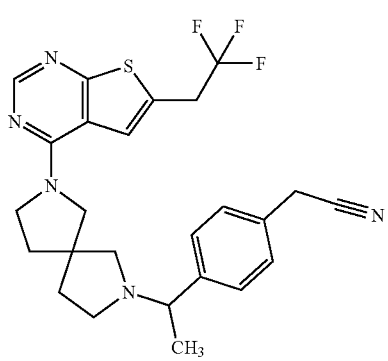 [SMILES: CC(c1ccc(CC#N)cc1)N1CCC2(CCN(c3ncnc4sc(CC(F)(F)F)cc34)C2)C1] |
| VII-80 | 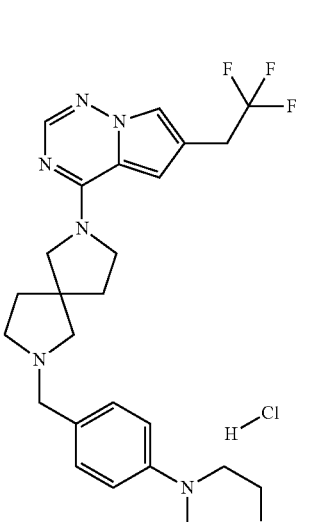 |
| VII-81 | |
| VII-82 | 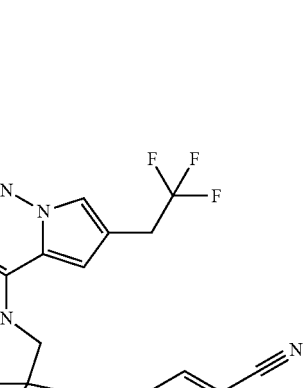 |

TABLE 7-continued

| No. | Structure |
|---|---|
| VII-83 | (structure) |
| VII-84 | (structure) |
| VII-85 | (structure) |
| VII-86 | (structure) |
| VII-87 | (structure) |
| VII-88 | (structure) |

TABLE 7-continued

| No. | Structure |
|---|---|
| VII-89 | |
| VII-90 | |
| VII-91 | |
| VII-92 | 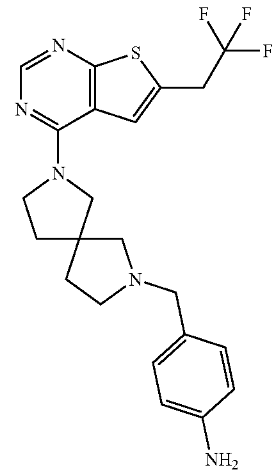 [SMILES: Nc1ccc(CN2CCC3(CCN(c4ncnc5sc(CC(F)(F)F)cc45)C3)C2)cc1] |
| VII-93 | 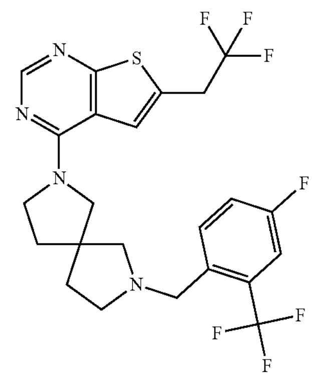 [SMILES: Fc1ccc(CN2CCC3(CCN(c4ncnc5sc(CC(F)(F)F)cc45)C3)C2)c(C(F)(F)F)c1] |
| VII-94 | 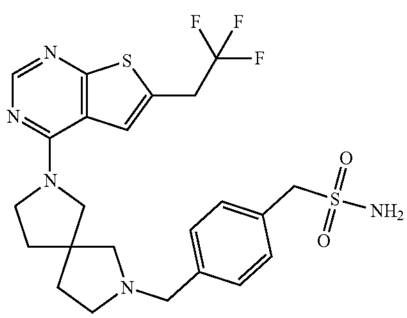 [SMILES: NS(=O)(=O)Cc1ccc(CN2CCC3(CCN(c4ncnc5sc(CC(F)(F)F)cc45)C3)C2)cc1] |
| VII-95 | 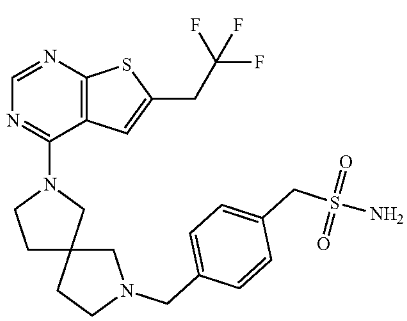 [SMILES: NS(=O)(=O)Cc1ccc(CN2CCC3(CCN(c4ncnc5sc(CC(F)(F)F)cc45)C3)C2)cc1] |

TABLE 7-continued

| No. | Structure |
|---|---|
| VII-96 | |
| VII-97 | |
| VII-98 | |
| VII-99 | |
| VII-100 | 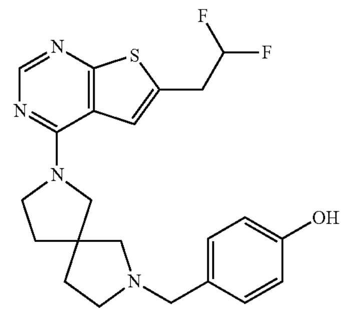 [SMILES: Oc1ccc(CN2CCC3(CCN(c4ncnc5sc(CC(F)F)cc45)C3)C2)cc1] |
| VII-101 | 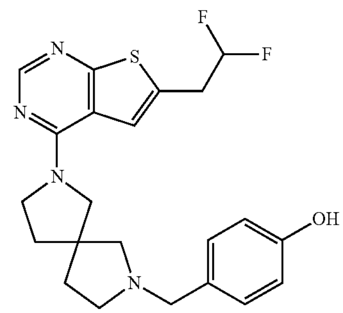 [SMILES: Oc1ccc(CN2CCC3(CCN(c4ncnc5sc(CC(F)F)cc45)C3)C2)cc1] |
| VII-102 | 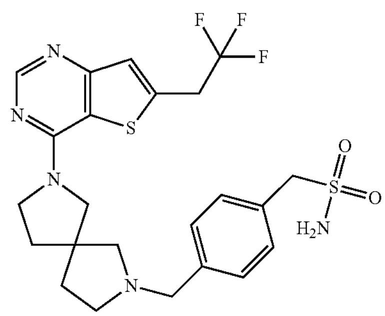 [SMILES: NS(=O)(=O)Cc1ccc(CN2CCC3(CCN(c4ncnc5cc(CC(F)(F)F)sc45)C3)C2)cc1] |
| VII-103 | 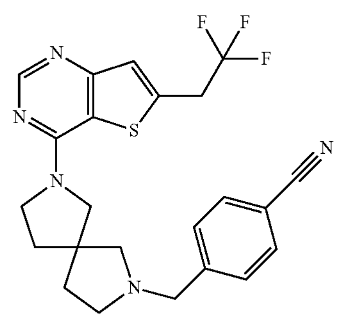 [SMILES: N#Cc1ccc(CN2CCC3(CCN(c4ncnc5cc(CC(F)(F)F)sc45)C3)C2)cc1] |
| VII-104 | 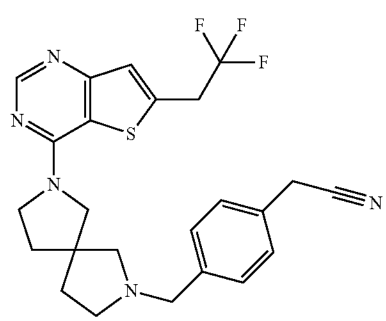 [SMILES: N#CCc1ccc(CN2CCC3(CCN(c4ncnc5cc(CC(F)(F)F)sc45)C3)C2)cc1] |

TABLE 7-continued

| No. | Structure |
|---|---|
| VII-105 | (structure) |
| VII-106 | (structure) |
| VII-107 | (structure) |
| VII-108 | (structure) |
| VII-109 | (structure) |
| VII-110 | (structure) |
| VII-111 | (structure) |
| VII-112 | (structure) |

TABLE 7-continued

| No. | Structure |
|---|---|
| VII-113 | 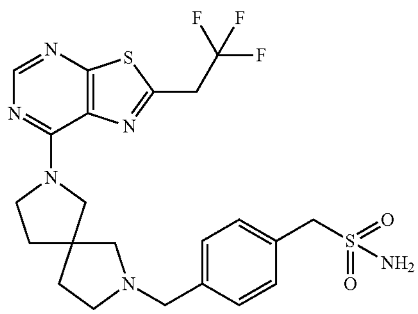 [SMILES: NS(=O)(=O)Cc1ccc(CN2CCC3(CCN(c4ncnc5sc(CC(F)(F)F)nc45)C3)C2)cc1] |
| VII-114 | 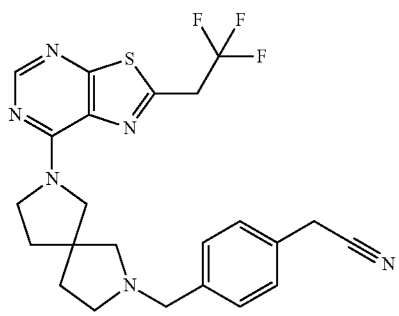 [SMILES: N#CCc1ccc(CN2CCC3(CCN(c4ncnc5sc(CC(F)(F)F)nc45)C3)C2)cc1] |
| VII-115 | 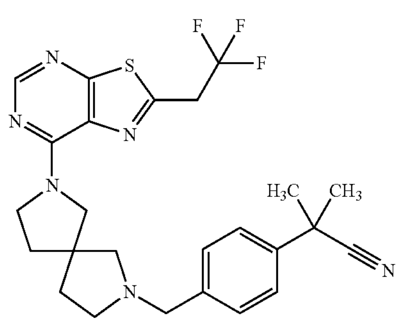 [SMILES: CC(C)(C#N)c1ccc(CN2CCC3(CCN(c4ncnc5sc(CC(F)(F)F)nc45)C3)C2)cc1] |
| VII-116 | 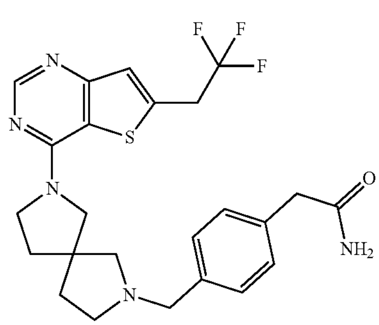 [SMILES: NC(=O)Cc1ccc(CN2CCC3(CCN(c4ncnc5cc(CC(F)(F)F)sc45)C3)C2)cc1] |
| VII-117 | |
| VII-118 | |
| VII-119 | |

TABLE 7-continued

| No. | Structure |
|---|---|
| VII-120 | (structure) |
| VII-121 | (structure) |
| VII-122 | (structure) |
| VII-123 | (structure) |
| VII-124 | (structure) |
| VII-125 | (structure) |

TABLE 7-continued

| No. | Structure |
|---|---|
| VII-126 | (structure) |
| VII-127 | (structure) |
| VII-128 | (structure) |
| VII-129 | (structure) |
| VII-130 | (structure) |
| VII-131 | (structure) |
| VII-132 | (structure) |

Pharmaceutical Compositions

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound or salt of Formula (I-A), Formula (I-B), Formula (II), Formula (III), Formula (IV), or Formula (VI) and a pharmaceutically acceptable carrier.

In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a composition of a compound or salt of Formula (I-A), Formula (I-B), Formula (II), Formula (III), Formula (IV), or Formula (VI) is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, a compound or salt of Formula (I-A), Formula (I-B), Formula (II), Formula (III), Formula (IV), or Formula (VI) is delivered in a targeted drug delivery system, for example, in a liposome coated with organ-specific antibody. In such embodiments, the liposomes are targeted to and taken up selectively by the organ. In yet other embodiments, the composition is provided in the form of a rapid release formulation, in the form of an extended release formulation, or in the form of an intermediate release formulation. In yet other embodiments, the composition is administered topically.

The compound of Formula (I-A), Formula (I-B), Formula (II), Formula (III), Formula (IV), or Formula (VI), or a pharmaceutically acceptable salt thereof, may be effective over a wide dosage range. For example, in the treatment of adult humans, dosages from 0.01 to 1000 mg per day, from 0.5 to 100 mg per day, from 1 to 50 mg per day, and from 5 to 40 mg per day are examples of dosages that may be used in some embodiments. The exact dosage will depend upon the route of administration, the form in which the compound is administered, the subject to be treated, the body weight of the subject to be treated, and the preference and experience of the attending physician.

In some embodiments, a compound or salt of Formula (I-A), Formula (I-B), Formula (II), Formula (III), Formula (IV), or Formula (VI) is administered in a single dose. Typically, such administration will be by injection, e.g., intravenous injection, in order to introduce the agent quickly. However, other routes are used as appropriate. In some embodiments, a single dose of a compound or salt of Formula (I-A), Formula (I-B), Formula (II), Formula (III), Formula (IV), or Formula (VI) is used for treatment of an acute condition.

In some embodiments, a compound or salt of Formula (I-A), Formula (I-B), Formula (II), Formula (III), Formula (IV), or Formula (VI) is administered in multiple doses. In some embodiments, dosing is about once, twice, three times, four times, five times, six times, or more than six times per day. In other embodiments, dosing is about once a month, once every two weeks, once a week, or once every other day. In another embodiment, a compound or salt of Formula (I-A), Formula (I-B), Formula (II), Formula (III), Formula (IV), or Formula (VI) and another agent are administered together about once per day to about 6 times per day. In another embodiment, the administration of a compound or salt of Formula (I-A), Formula (I-B), Formula (II), Formula (III), Formula (IV), or Formula (VI) and an agent continues for less than about 7 days. In yet another embodiment, the administration continues for more than about 6 days, more than about 10 days, more than about 14 days, more than about 28 days, more than about two months, more than about six months, or one year or more. In some cases, continuous dosing is achieved and maintained as long as necessary.

Administration of a compound or salt of Formula (I-A), Formula (I-B), Formula (II), Formula (III), Formula (IV), or Formula (VI) may continue as long as necessary. In some embodiments, a compound of the disclosure is administered for more than 1, more than 2, more than 3, more than 4, more than 5, more than 6, more than 7, more than 14, or more than 28 days. In some embodiments, a compound of the disclosure is administered 28 days or less, 14 days or less, 7 days or less, 6 days or less, 5 days or less, 4 days or less, 3 days or less, 2 days or less, or 1 day or a part thereof. In some embodiments, a compound or salt of Formula (I-A), Formula (I-B), Formula (II), Formula (III), Formula (IV), or Formula (VI) is administered chronically on an ongoing basis, e.g., for the treatment of chronic effects.

In some embodiments, a compound or salt of Formula (I-A), Formula (I-B), Formula (II), Formula (III), Formula (IV), or Formula (VI) is administered in dosages. It is known in the art that due to intersubject variability in compound pharmacokinetics, individualization of dosing regimen is necessary for optimal therapy. Dosing for a compound or salt of Formula (I-A), Formula (I-B), Formula (II), Formula (III), Formula (IV), or Formula (VI) may be found by routine experimentation in light of the instant disclosure.

In some embodiments, a compound or salt of Formula (I-A), Formula (I-B), Formula (II), Formula (III), Formula (IV), or Formula (VI) is formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N. Y., 1980; and Pharmaceutical Dosage Forms and Drug Delivery Systems, Seventh Ed. (Lippincott Williams & Wilkins 1999).

Provided herein are pharmaceutical compositions comprising a compound or salt of Formula (I-A), Formula (I-B), Formula (II), Formula (III), Formula (IV), or Formula (VI) and a pharmaceutically acceptable diluent(s), excipient(s), or carrier(s). In certain embodiments, the compounds or salts described are administered as pharmaceutical compositions in which a compound or salt of Formula (I-A), Formula (I-B), Formula (II), Formula (III), Formula (IV), or Formula (VI) is mixed with other active ingredients, as in combination therapy. Encompassed herein are all combinations of active ingredients set forth in the combination therapies section below and throughout this disclosure. In specific embodiments, the pharmaceutical compositions include one or more compounds of Formula (I-A), Formula (I-B), Formula (II), Formula (III), Formula (IV), or Formula (VI), or a pharmaceutically acceptable salt thereof.

A pharmaceutical composition, as used herein, refers to a mixture of a compound or salt of Formula (I-A), Formula (I-B), Formula (II), Formula (III), Formula (IV), or Formula (VI) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of a compound or salt of Formula (I-A), Formula (I-B), Formula (II), Formula (III), Formula (IV), or Formula (VI) are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. A compound or salt of Formula (I-A), Formula (I-B), Formula (II), Formula (III), Formula (IV), or Formula (VI) may be used singly or in combination with one or more therapeutic agents as components of mixtures.

In one embodiment, a compound or salt of Formula (I-A), Formula (I-B), Formula (II), Formula (III), Formula (IV), or Formula (VI) is formulated in an aqueous solution. In specific embodiments, the aqueous solution is selected from, by way of example only, a physiologically compatible buffer, such as Hank's solution, Ringer's solution, or physiological saline buffer. In other embodiments, a compound or salt of Formula (I-A), Formula (I-B), Formula (II), Formula (III), Formula (IV), or Formula (VI) is formulated for transmucosal administration. In specific embodiments, transmucosal formulations include penetrants that are appropriate to the barrier to be permeated. In still other embodiments wherein a compound or salt of Formula (I-A), Formula (I-B), Formula (II), Formula (III), Formula (IV), or Formula (VI) is formulated for other parenteral injections, appropriate formulations include aqueous or nonaqueous solutions. In specific embodiments, such solutions include physiologically compatible buffers and/or excipients.

In another embodiment, a compound or salt of Formula (I-A), Formula (I-B), Formula (II), Formula (III), Formula (IV), or Formula (VI) is formulated for oral administration. A compound or salt of Formula (I-A), Formula (I-B), Formula (II), Formula (III), Formula (IV), or Formula (VI) may be formulated by combining the active compounds with, e.g., pharmaceutically acceptable carriers or excipients. In various embodiments, a compound or salt of Formula (I-A), Formula (I-B), Formula (II), Formula (III), Formula (IV), or Formula (VI) is formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with a compound or salt of Formula (I-A), Formula (I-B), Formula (II), Formula (III), Formula (IV), or Formula (VI), optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, a therapeutically effective amount of a compound or salt of Formula (I-A), Formula (I-B), Formula (II), Formula (III), Formula (IV), or Formula (VI) is formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, a therapeutically effective amount of a compound or salt of Formula (I-A), Formula (I-B), Formula (II), Formula (III), Formula (IV), or Formula (VI) is formulated for buccal or sublingual administration. Formulations suitable for buccal or sublingual administration include, by way of example only, tablets, lozenges, or gels. In still other embodiments, a compound or salt of Formula (I-A), Formula (I-B), Formula (II), Formula (III), Formula (IV), or Formula (VI) is formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, a suspension of a compound or salt of Formula (I-A), Formula (I-B), Formula (II), Formula (III), Formula (IV), or Formula (VI) is prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. In certain embodiments, the active agent is in powder form for constitution with a suitable vehicle, e.g., sterile pyrogen-free water, before use.

In still other embodiments, a compound or salt of Formula (I-A), Formula (I-B), Formula (II), Formula (III), Formula (IV), or Formula (VI) is administered topically. A compound or salt of Formula (I-A), Formula (I-B), Formula (II), Formula (III), Formula (IV), or Formula (VI) may be formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, a compound or salt of Formula (I-A), Formula (I-B), Formula (II), Formula (III), Formula (IV), or Formula (VI) is formulated for transdermal administration. Transdermal formulations may employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound or salt of Formula (I-A), Formula (I-B), Formula (II), Formula (III), Formula (IV), or Formula (VI) is accomplished by means of iontophoretic patches and the like. In certain embodiments, transdermal patches provide controlled delivery of a compound or salt of Formula (I-A), Formula (I-B), Formula (II), Formula (III), Formula (IV), or Formula (VI). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing a compound or salt of Formula (I-A), Formula (I-B), Formula (II), Formula (III), Formula (IV), or Formula (VI), optionally with carriers, optionally a rate controlling barrier to deliver the compound to the skin of the host at a controlled and predetermined rate over a prolonged period of time, and means to secure the device to the skin.

In other embodiments, a compound or salt of Formula (I-A), Formula (I-B), Formula (II), Formula (III), Formula (IV), or Formula (VI) is formulated for administration by inhalation. Various forms suitable for administration by inhalation include, but are not limited to, aerosols, mists or powders. Pharmaceutical compositions of a compound or salt of Formula (I-A), Formula (I-B), Formula (II), Formula (III), Formula (IV), or Formula (VI) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of a compound or salt of Formula (I-A), Formula (I-B), Formula (II), Formula (III), Formula (IV), or Formula (VI) and a suitable powder base such as lactose or starch.

In still other embodiments, a compound or salt of Formula (I-A), Formula (I-B), Formula (II), Formula (III), Formula (IV), or Formula (VI) is formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients may be optionally used as suitable. Pharmaceutical compositions comprising a compound or salt of Formula (I-A), Formula (I-B), Formula (II), Formula (III), Formula (IV), or Formula (VI) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and a compound or salt of Formula (I-A), Formula (I-B), Formula (II), Formula (III), Formula (IV), or Formula (VI), sometimes referred to herein as an active agent or ingredient. The active ingredient may be in free-acid or free-base form, or in a pharmaceutically acceptable salt form. Additionally, a compound or salt of Formula (I-A), Formula (I-B), Formula (II), Formula (III), Formula (IV), or Formula (VI) may be in unsolvated or solvated forms with pharmaceutically acceptable solvents such as water and ethanol. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising a compound or salt of Formula (I-A), Formula (I-B), Formula (II), Formula (III), Formula (IV), or Formula (VI) include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound or salt of Formula (I-A), Formula (I-B), Formula (II), Formula (III), Formula (IV), or Formula (VI). Semi-solid compositions include, but are not limited to, gels, suspensions and creams. The form of the pharmaceutical compositions of a compound or salt of Formula (I-A), Formula (I-B), Formula (II), Formula (III), Formula (IV), or Formula (VI) include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, a pharmaceutical composition comprising a compound or salt of Formula (I-A), Formula (I-B), Formula (II), Formula (III), Formula (IV), or Formula (VI) takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of a compound described herein. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Pharmaceutical compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Pharmaceutical compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In certain embodiments, delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, a compound or salt of Formula (I-A), Formula (I-B), Formula (II), Formula (III), Formula (IV), or Formula (VI) is delivered using a sustained-release system, such as semipermeable matrices of solid hydrophobic polymers containing the therapeutic agent. Various sustained-release materials may be used herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (j) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of a compound or salt of Formula (I-A), Formula (I-B), Formula (II), Formula (III), Formula (IV), or Formula (VI) provided in a pharmaceutical compositions is less than about: 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of a compound or salt of Formula (I-A), Formula (I-B), Formula (II), Formula (III), Formula (IV), or Formula (VI) provided in a pharmaceutical composition is greater than about: 90%, 80%, 70%, 60%, 50%, 40%, 30%, 20%, 19.75%, 19.50%, 19.25%, 19%, 18.75%, 18.50%, 18.25%, 18%, 17.75%, 17.50%, 17.25%, 17%, 16.75%, 16.50%, 16.25%, 16%, 15.75%, 15.50%, 15.25%, 15%, 14.75%, 14.50%, 14.25%, 14%, 13.75%, 13.50%, 13.25%, 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of a compound or salt of Formula (I-A), Formula (I-B), Formula (II), Formula (III), Formula (IV), or Formula (VI) is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of a compound or salt of Formula (I-A), Formula (I-B), Formula (II), Formula (III), Formula (IV), or Formula (VI) is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of a compound or salt of Formula (I-A), Formula (I-B), Formula (II), Formula (III), Formula (IV), or Formula (VI) is equal to or less than about: 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of a compound or salt of Formula (I-A), Formula (I-B), Formula (II), Formula (III), Formula (IV), or Formula (VI) is more than about: 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes a compound or salt of Formula (I-A), Formula (I-B), Formula (II), Formula (III), Formula (IV), or Formula (VI), optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

The present disclosure provides a method of treating a hematological malignancy, such as acute myeloid leukemia, or Ewing's sarcoma. A subject method typically involves administering to a subject in need thereof a menin inhibitor. The menin inhibitor can inhibit the interaction of menin and one or more proteins (e.g., MLL1, MLL2, an MLL fusion protein). Inhibition of the interaction of menin and one or more proteins (e.g., MLL1, MLL2, an MLL fusion protein) can be assessed and demonstrated by a wide variety of ways known in the art. Non-limiting examples include a showing of (a) a decrease in menin binding to one or more proteins or protein fragments (e.g., MLL1, MLL2, an MLL fusion protein, or a peptide fragment thereof); (b) a decrease in cell proliferation and/or cell viability; (c) an increase in cell differentiation; (d) a decrease in the levels of downstream targets of MLL1, MLL2, and/or an MLL fusion protein (e.g., Hoxa9, DLX2, PBX3, and Meis1); and/or (e) decrease in tumor volume and/or tumor volume growth rate. Kits and commercially available assays can be utilized for determining one or more of the above.

The disclosure also provides methods of using the compounds or pharmaceutical compositions of the present disclosure to treat disease conditions, including but not limited to conditions implicated by menin, MLL, MLL1, MLL2, and/or MLL fusion proteins (e.g., acute myeloid leukemia and Ewing's sarcoma).

In some embodiments, a method for treatment of a hematological malignancy or Ewing's sarcoma is provided, the method comprising administering an effective amount of any of the foregoing pharmaceutical compositions comprising a compound or salt of Formula (I-A), Formula (I-B), Formula (II), Formula (III), Formula (IV), or Formula (VI) to a subject in need thereof.

The hematological condition may be any condition or disease which primarily affects the blood. Hematological malignancies include, but are not limited to, malignant lymphoma (such as lymphoma NOS, microglioma, non-Hodgkin lymphoma NOS, B cell lymphoma NOS, malignant lymphoma, (non-cleaved cell NOS and diffuse NOS), malignant lymphoma (lymphocytic intermediate differentiation nodular, small cell noncleaved diffuse, undifferentiated cell non-Burkitt, and undifferentiated cell type NOS), lymphosarcoma (NOS and diffuse), reticulum cell sarcoma (NOS and diffuse), reticulosarcoma (NOS and diffuse), composite Hodgkin and non-Hodgkin lymphoma); leukemia (such as acute myeloid leukemia (AML), acute lymphocytic leukemia (ALL), chronic myeloid leukemia (CIVIL)), mixed lineage leukemia (MLL), blast cell leukemia, undifferentiated leukemia, stem cell leukemia, acute leukemia of ambiguous lineage, acute mixed lineage leukemia, acutel bilineal leukemia, chronic lymphocytic leukemia (CLL), chronic myelomonocytic leukemia (CMML), lymphocytic leukemia, lymphatic leukemia); mature B cell neoplasms (such as B-cell chronic lyphocytic leukemia (BCLL)/small cell lymphoma, B-cell prolymphocytic leukemia, lymphoplasmacytic lymphoma, splenic marginal zone lymphoma, hairy cell leukemia (HCL), plasma cell myeloma, plasmacytoma, monoclonal immunoglobulin deposition diseases, heavy chain diseases, marginal zone B cell lymphoma, lymphoplasmacytic lymphoma, immunocytoma, malignant lymphoma plasmacytoid, plasmacytic lymphoma, nodal marginal zone B cell lymphoma, follicular lymphoma (grade 1, 2 or 3), primary cutaneous follicle center lymphoma, diffuse large B-cell lymphoma (DLBCL), diffuse large B-cell immunoblastic NOS lymphoma, Epstein-Barr virus-positive DLBCL of the elderly, lymphomatoid granulomatosis, mantle zone lymphoma, primary mediastinal large B-cell lymphoma, intravascular large B-cell lymphoma, plasmablastic lymphoma, primary effusion lymphoma, large B-cell lymphoma arising in HHV8-associated multicentric Castleman's disease, and Burkitt lymphoma/leukemia); mature T cell and natural killer (NK) cell neoplasms (such as T-cell prolymphocytic leukemia (T-PLL), T-cell large granular lymphocytic leukemia, aggressive NK cell leukemia, mature T-cell leukemia/lymphoma, extranodal NK/T-cell nasal type lymphoma, intestinal T-cell lymphoma, enteropathy-associated T-cell lymphoma, hepatosplenic T-cell lymphoma, hepatosplenic T-cell lymphoma, blastic NK cell lymphoma, mycosis fungoides or Sezary syndrome, primary cutaneous CD30-positive T cell lymphoproliferative disorders, anaplastic large cell lymphoma (T-cell and null cell types), peripheral non-specific T-cell lymphoma, angioimmunoblastic T-cell lymphoma, anaplastic large cell lymphoma, cutaneous T-cell lymphoma, and subcutaneous panniculitis-like T-cell lymphoma); precursor lymphoid neoplasms (such as non-specific precursor B-lymphoblastic leukemia/lymphoma, B-lymphoblastic leukemia/lymphoma with recurrent genetic abnormalities, precursor cell lymphoblastic lymphoma, and precursor T-lymphoblastic leukemia/ lymphoma); Hodgkin lymphoma (HL) (such as classical Hodgkin lymphoma, nodular sclerosis form HL, Hodgkin paragranuloma, Hodgkin granuloma, mixed cellularlity HL, nodular sclerosis cellular phase HL, lymphocyte-rich HL, nodular sclerosis grade 1 HL, nodular sclerosis grade 2 HL lymphocyte depleted HL, lyphocytic-histiocytic predominance HL, mixed cellularity NOS HL, lymphocyte depleted diffuse fibrosis HL, lymphocyte depleted reticular HL, lymphocyte predominance diffuse HL, and nodular lymphocyte-predominant HL); plasma cell tumors (such as plasmacytoma, multiple myeloma (MM), plasma cell leukemia, and plasmacytoma extramedullary); mast cell tumors (such as mastocytoma, mast cell sarcoma, malignant mastocytosis, and mast cell leukemia); neoplasms of histiocytes and accessory lymphoid cells (such as malignant histiocytosis, Langerhans cell histiocytosis (NOS, unifocal, multifocal, or disseminated), histiocytic sarcoma, Langerhans cell sarcoma, dendritic cell sarcoma, and follicular dendritic cell sarcoma); immunoproliferative diseases (such as Waldenstrom macroglobulinemia, heavy chain disease, immunoproliferative small intestinal disease, monoglonal gammopathy of undetermined significance, angiocentric immunoproliferative lesion, angioimmunoblastic lymphadenopathy, T-gamma lymphoproliferative disease, and immunoglobulin deposition disease); myeloid leukemias (such as erythroleukemia, acute myeloid leukemia (NOS, with abnormal marrow eosinophils, minimally differentiated, multilineage dysplasia without maturation, or with maturation), lymphosarcoma cell leukemia, myeloid leukemia NOS, chronic myeloid leukemia NOS, acute promyelocytic leukemia, FAB-M3, acute myelomonocytic leukemia, basophilic leukemia, chronic myelogenous leukemia (BCR/ABL positive, BCR/ABL negative or atypical), acute monoblastic and monocytic leukemia, chloroma or myeloid sarcoma, acute panmyelosis with myelofibrosis); and myelodysplastic syndromes (MDS) (such as polycythemia vera, essential thrombocythemia, myelofibrosis, refractory anemia, (with ringed sideroblasts or excess blasts), and refractory cytopenia with multilineage dysplasia).

In practicing any of the subject methods, the hematoligical malignancy may be selected from acute myeloid leukemia, acute lymphocytic leukemia, chronic myeloid leukemia, non-Hodgkin's lymphoma, multiple myeloma, mixed lineage leukemia and myelodysplastic syndromes. In some embodiments, the hematological malignancy is acute myeloid leukemia.

Determining whether a tumor or cancer comprises a nucleoporin 98 (NUP98) gene fusion, mutation in the nucleophosmin (NPM1) gene, mutation in the DNA (cytosine-5)-methyltransferase 3A (DNMT3A) gene, mutation in the FMS-like tyrosine kinase-3 (FLT3) gene, mutation in the isocitrate dehydrogenase 1 (IDH1) gene, mutation in the isocitrate dehydrogenase 2 (IDH2) gene, or mixed lineage leukemia (MLL) gene amplification can be undertaken by assessing the nucleotide sequence encoding the protein, by assessing the amino acid sequence of the protein, or by assessing the characteristics of a putative protein.

Determining whether a tumor or cancer comprises an MLL rearrangement or partial tandem duplication of MLL (MLL-PTD) can be undertaken by assessing the nucleotide sequence encoding the protein, by assessing the amino acid sequence of the protein, or by assessing the characteristics of a putative protein.

Determining whether a tumor or cancer comprises elevated MEIS1 expression levels can be assessed by any appropriate method. The expression level of a gene, such as MEIS1, may be assessed by detecting a level of mRNA transcribed from the gene, by detecting a level of cDNA produced from reverse transcription of mRNA transcribed from the gene, by detecting a level of polypeptide encoded by the gene, or by a nucleic acid amplification assay, a hybridization assay, sequencing, or a combination thereof. Regulation of a target gene or gene transcript can also be determined indirectly, such as by measuring the effect on a phenotypic indicator of the gene or gene transcript activity, such as by cellular assay. Methods of detecting gene expression products are known in the art. These methods can be performed on a sample by sample basis or modified for high throughput analysis, for example, using Affymetrix™ U133 microarray chips.

Methods for detecting a nucleotide sequence of a nucleoporin 98 (NUP98) gene fusion, mutation in the nucleophosmin (NPM1) gene, mutation in the DNA (cytosine-5)-methyltransferase 3A (DNMT3A) gene, mutation in the FMS-like tyrosine kinase-3 (FLT3) gene, mutation in the isocitrate dehydrogenase 1 (IDH1) gene, mutation in the isocitrate dehydrogenase 2 (IDH2) gene, or mixed lineage leukemia (MLL) gene amplification are known by those of skill in the art. Similarly, methods for detecting an MLL rearrangement, elevated MEIS1 expression levels, or partial tandem duplication of MLL (MLL-PTD) are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, the NUP98 fusion protein is identified using a direct sequencing method of specific regions in the NUP98 or fusion partner gene, for example. In some embodiments, the mutation in the nucleophosmin (NPM1) gene, mutation in the DNA (cytosine-5)-methyltransferase 3A (DNMT3A) gene, mutation in the FMS-like tyrosine kinase-3 (FLT3) gene, mutation in the isocitrate dehydrogenase 1 (IDH1) gene, mutation in the isocitrate dehydrogenase 2 (IDH2) gene, or mixed lineage leukemia (MLL) gene amplification is identified using a direct sequencing method of specific regions in the gene, for example. This technique can identify all possible mutations in the region sequenced.

Methods for detecting an NUP98 fusion protein, mutant nucleophosmin (NPM1) protein, mutant FMS-like tyrosine kinase-3 (FLT3) protein, mutant isocitrate dehydrogenase 1 (IDH1) protein, mutant isocitrate dehydrogenase 2 (IDH2) protein, or mutant DNA (cytosine-5)-methyltransferase 3A (DNMT3A) protein are known by those of skill in the art. These methods include, but are not limited to, detection of a mutant protein or fusion protein, such as an NUP98 fusion protein, using a binding agent (e.g., an antibody) specific for the mutant protein or fusion protein, protein electrophoresis and Western blotting, and direct peptide sequencing.

Methods for determining whether a tumor or cancer comprises a nucleoporin 98 (NUP98) gene fusion, mutation in the nucleophosmin (NPM1) gene, mutation in the DNA (cytosine-5)-methyltransferase 3A (DNMT3A) gene, mutation in the FMS-like tyrosine kinase-3 (FLT3) gene, mutation in the isocitrate dehydrogenase 1 (IDH1) gene, mutation in the isocitrate dehydrogenase 2 (IDH2) gene, or mixed lineage leukemia (MLL) gene amplification can use a variety of samples. Similarly, methods for determining whether a tumor or cancer comprises an MLL rearrangement, elevated MEIS1 expression levels, or partial tandem duplication of MLL (MLL-PTD) can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

Subjects that can be treated with a compound of the disclosure, or a pharmaceutically acceptable salt, ester, prodrug, solvate, tautomer, stereoisomer, isotopologue, hydrate or derivative of the compound, according to the methods of this disclosure include, for example, subjects that have been diagnosed as having a hematological malignancy or Ewing's sarcoma.

The present disclosure also provides methods for combination therapies in which an agent known to modulate other pathways, or other components of the same pathway, or even overlapping sets of target enzymes are used in combination with a compound or salt of Formula (I-A), Formula (I-B), Formula (II), Formula (III), Formula (IV), or Formula (VI). In one aspect, such therapy includes but is not limited to the combination of one or more compounds of the disclosure with chemotherapeutic agents, therapeutic antibodies, and radiation treatment, to provide a synergistic or additive therapeutic effect.

Where desired, a compound or pharmaceutical composition of the present disclosure can be used in combination with Notch inhibitors and/or c-Myb inhibitors. Where desired, a compound or pharmaceutical composition of the present disclosure can be used in combination with MLL-WDR5 inhibitors. Where desired, a compound or pharmaceutical composition of the present disclosure can be used in combination with FLT3 inhibitors and/or Dot1L inhibitors.

In some embodiments, a compound or pharmaceutical composition of the present disclosure is administered in combination with a second therapeutic that is effective in treating subjects that exhibit a FLT3 mutation, such as FLT3-ITD, or who otherwise exhibit oncogenic FLT3. In some embodiments, a compound or pharmaceutical composition of the present disclosure is administered in combination with a FLT3 inhibitor, such as quizartinib. Exemplary FLT3 inhibitors include quizartinib (AC220), crenolanib besylate (CP-868596-26), gilteritinib (ASP2215), lestaurtinib (CEP-701), midostaurin (Rydapt®, PKC412), pexidartinib (PLX3397), ponatinib (AP24534), SKLB1028, sorafenib (Nexavar®), sunitinib (Sutent®, SU11248), and XL999. In some embodiments, a compound or pharmaceutical composition of the present disclosure is administered in combination with as IDH2 inhibitor such as enasidenib.

Many chemotherapeutics are presently known in the art and can be used in combination with a compound of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including, for example, tamoxifen, (Nolvadex™), raloxifene, aromatase inhibiting 4 (5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17—N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, TriS(2-chloroethyl)amine, Troxacitabine, Uramustine, Vadimezan, Vinflunine, ZD6126 or Zosuquidar.

This disclosure further relates to a method for using a compound or salt of Formula (I-A), Formula (I-B), Formula (II), Formula (III), Formula (IV), or Formula (VI) or a pharmaceutical composition provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, 1-131, 1-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as 1-125, 1-131, Yb-169, Ir-192 as a solid source, 1-125 as a solid source, or other radionuclides that emit photons, beta particles, gamma radiation, or other therapeutic rays. The radioactive material can also be a fluid made from any solution of radionuclide(s), e.g., a solution of 1-125 or 1-131, or a radioactive fluid can be produced using a slurry of a suitable fluid containing small particles of solid radionuclides, such as Au-198, Y-90. Moreover, the radionuclide (s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. 5,861, 510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with a compound of the disclosure include, but are not limited to, anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present disclosure with sorafenib and/or avastin. For treating an endometrial disorder, one may combine a compound of the present disclosure with doxorubincin, taxotere (taxol), and/or cisplatin (carboplatin). For treating ovarian cancer, one may combine a compound of the present disclosure with cisplatin (carboplatin), taxotere, doxorubincin, topotecan, and/or tamoxifen. For treating breast cancer, one may combine a compound of the present disclosure with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present disclosure with taxotere (taxol), gemcitabine, cisplatin, pemetrexed, Tarceva, PD0325901, and/or avastin.

Further therapeutic agents that can be combined with a compound of the disclosure are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

The following examples are given for the purpose of illustrating various embodiments of the disclosure and are not meant to limit the present disclosure in any fashion. The present examples, along with the methods and compositions described herein, are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

EXAMPLES

Example 1

Synthesis of Compound I-59 in Table 1

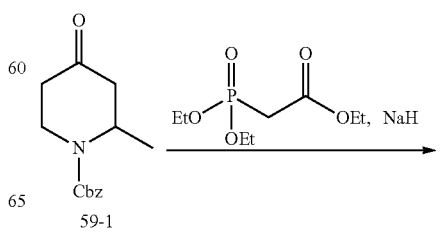

581
-continued

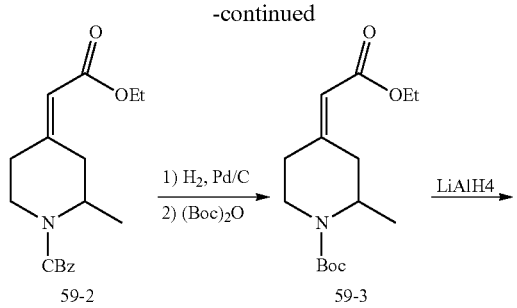
59-2 → 59-3

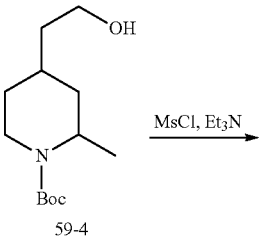
59-4

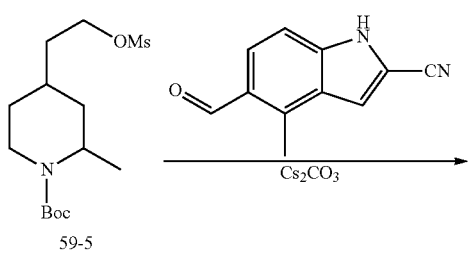
59-5

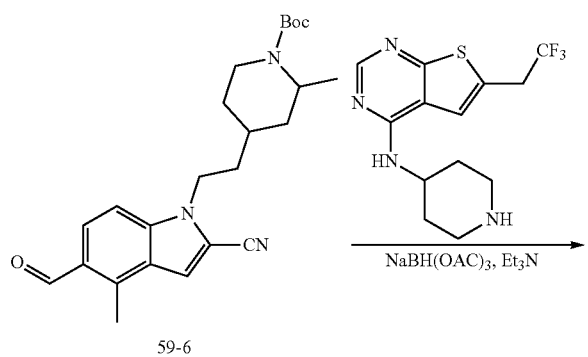
59-6

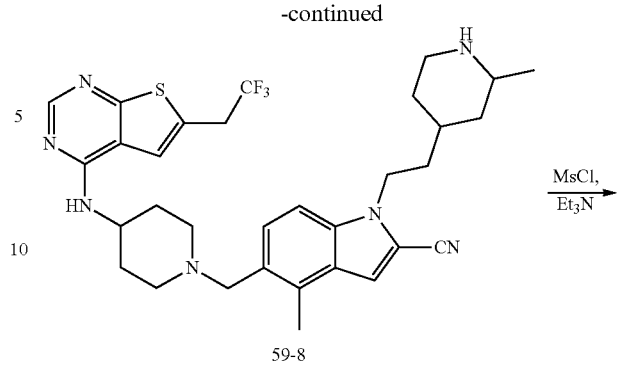
59-7

582
-continued

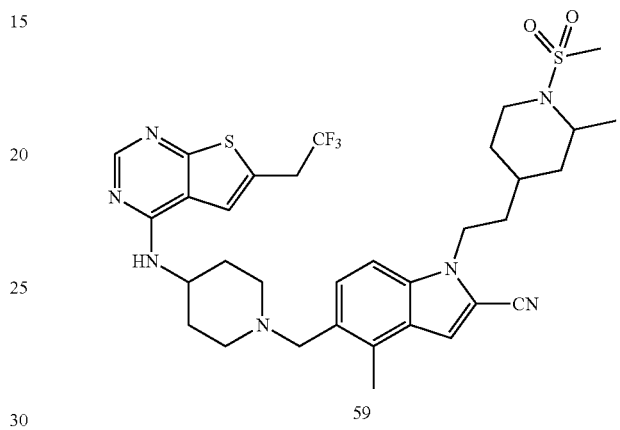
59-8

59

Step A: Preparation of Compound I-59-2: To a solution of ethyl-2-(diethoxylphosphoryl) acetate (1.91 g, 8.5 mmol) in THF (30 mL) was added NaH (421 mg, 10.5 mmol) at 0° C. The reaction was stirred at 0° C. for 0.5 hour before I-59-1 (2 g, 8 mmol) was added. The reaction mixture was stirred at room temperature for 5 h. Ice-water (50 mL) was added, and the product extracted with ethyl acetate (50 mL×2). The combined organic layer was washed with brine (50 mL), dried over sodium sulfate and concentrated in vacuo. The residue was purified by flash chromatography (eluted 20% EtOAc in pet. ether) to afford 2.15 g of I-59-2 as a white solid (yield: 85%).

Step B: Preparation of Compound I-59-3: To a solution of I-59-2 (905 mg, 2.85 mmol) in MeOH (20 mL) was added (Boc)$_2$O (1.24 g, 5.71 mmol) and Pd/C catalyst. The reaction mixture was stirred at room temperature for 8 hours under H$_2$. TLC showed the reaction was complete. The reaction was filtered and concentrated. The residue was purified by silica gel column chromatography (eluted 20% EtOAc in pet. ether) to give I-59-3 as a solid (740 mg, yield: 91%).

Step C: Preparation of Compound I-59-4: To a solution of I-59-3 (670 mg, 2.35 mmol) in THF (20 mL) was added LiAlH$_4$ (179 mg, 4.7 mmol) at 0° C. The reaction was stirred at 0° C. for 2 h, then 0.2 mL H$_2$O, 0.2 mL 15% NaOH, and 0.5 mL H$_2$O added. The mixture was stirred at room temperature for 1 h. The mixture was filtered and the organic solution was concentrated. The residue was purified by silica gel column chromatography (eluted 40% EtOAc in pet. ether) to give I-59-4 as a solid (525 mg, yield: 92%).

Step D: Preparation of Compound I-59-5: To a solution of I-59-4 (486 mg, 2 mmol) and Et$_3$N (404 mg, 4 mmol) in CH$_2$Cl$_2$ (20 mL) was added MSCl (344 mg, 3 mmol) at 0° C. The reaction was stirred at room temperature for 1 h. TLC showed the reaction was complete. The combined organic layer was washed with H$_2$O and brine, dried over sodium sulfate and concentrated in vacuo to afford 500 mg of I-59-5 as a white solid (yield: 78%).

Step E: Preparation of Compound I-59-6: A mixture of I-59-5 (500 mg, 1.56 mmol), Cs₂CO₃ (846 mg, 2.33 mmol), and 5-formyl-4-methyl-1H-indole-2-carbonitrile (143 mg, 0.78 mmol) was mixed in DMF (20 mL). The reaction mixture was heated at 85° C. for 3 h. EtOAc (200 mL) was added into the resulting mixture. The combined organic layer was washed with H₂O and brine, dried over sodium sulfate and concentrated. The residue was purified by flash column (eluted 30% EtOAc in pet. ether) to afford 278 mg of I-59-6 as a white solid (yield: 43%).

Step F: Preparation of Compound I-59-7: A mixture of I-59-6 (278 mg, 0.68 mmol), N-(piperidin-4-yl)-6-(2,2,2-trifluoroethyl)thieno[2,3-d]pyrimidin-4-amine (280 mg, 0.88 mmol) and Et₃N (412 mg, 4.08 mmol) in CH₂Cl₂ (20 mL) was stirred at room temperature for 1 hour. NaBH(OAc)₃ (865 mg, 4.08 mmol) was added to the reaction under ice bath and the reaction mixture stirred at room temperature overnight. The solvent was removed by vacuum and the residue was purified by silica gel column chromatography (eluted 2.5% MeOH in dichloromethane) to give I-59-7 as a white solid (400 mg, yield: 82%).

Step G: Preparation of Compound I-59-8: A solution of I-59-7 (200 mg, 0.28 mmol) in TFA (15 mL) was stirred at room temperature for 2 hours. Solvent was removed and a solution of NH₃ (7N) in MeOH (10 mL) was added. The resulting mixture was concentrated and the residue was purified by silica gel column chromatography (eluted 10% MeOH in dichloromethane) to give I-59-8 as an oil (164 mg, yield: 96%).

Step H: Preparation of Compound I-59: To a solution of I-59-8 (127 mg, 0.21 mmol) and Et₃N (43 mg, 0.42 mmol) in CH₂Cl₂ (20 mL) was added MSCl (29 mg, 0.25 mmol) at 0° C. The reaction was stirred at room temperature for 1 h. TLC showed the reaction was complete. The combined organic layer was washed with H₂O and brine, dried over sodium sulfate, and concentrated in vacuo to afford 45 mg of I-59 as a white solid (yield: 31%). $^1$HNMR (400 MHz, DMSO) δ: 8.33 (s, 1H), 7.87 (s, 1H), 7.67 (s, 1H) 7.45~7.56 (m, 3H), 4.35~4.32 (m, 2H), 4.08~4.02 (m, 4H), 3.57~3.54 (m, 3H), 3.17 (m, 1H, 2.88~2.83 (m, 6H), 2.54 (s, 3H), 2.20~1.47 (m, 12H), 1.25 (d, 3H). ESI-MS m/z: 688.84 (M+H).

Example 2

Synthesis of Compound I-48 in Table 1

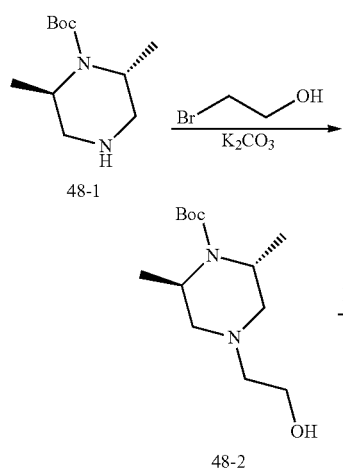

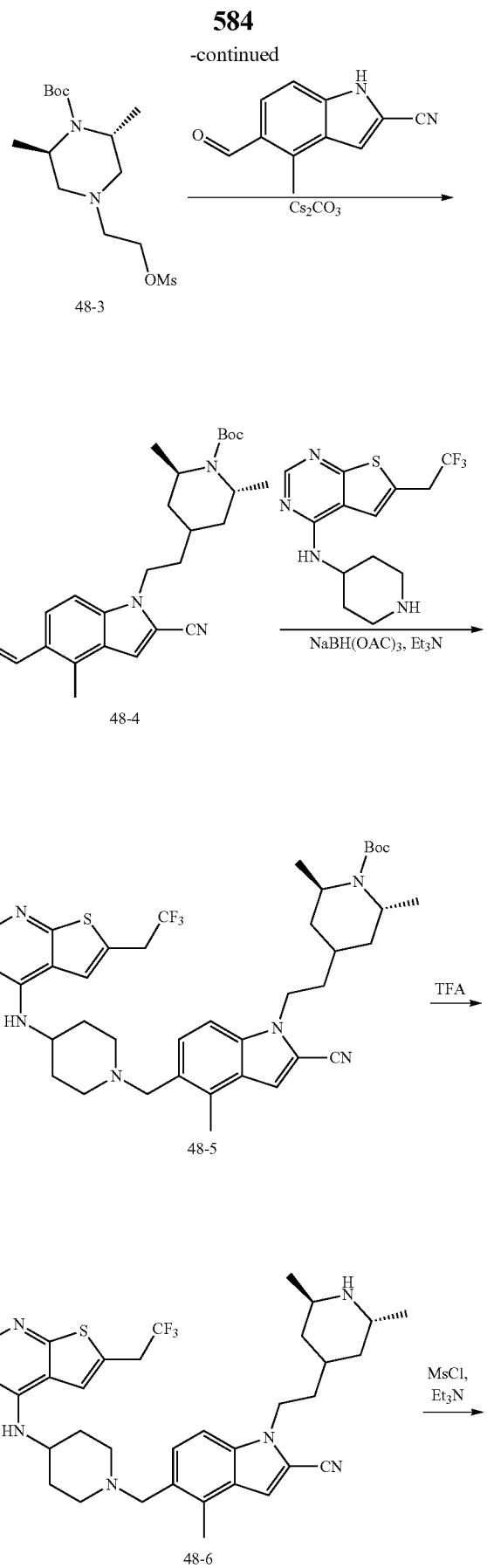

-continued

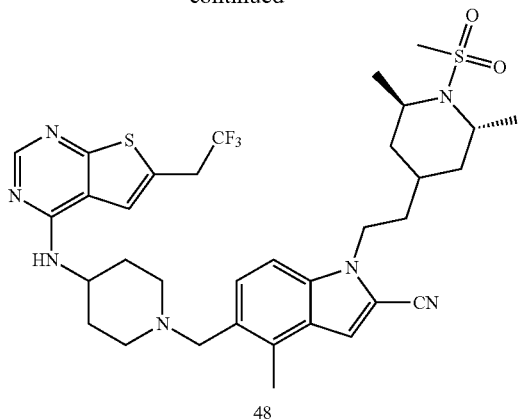

48

Step A: Preparation of Compound I-48-2: A mixture of I-48-1 (300 mg, 1.40 mmol), 2-bromoethanol (347 mg, 2.80 mmol) and K$_2$CO$_3$ (772 mg, 5.60 mmol) in CH$_3$CN (30 mL) was stirred at 90° C. under N2 overnight. TLC showed the reaction was complete. Solid was removed by filtration and solvent was removed under vacuum. The residue was purified by silica gel column chromatography (eluted 2.5% MeOH in dichloromethane) to give I-48-2 as a yellow oil (296 mg, yield: 82%).

Step B: Preparation of Compound I-48-3: To a mixture of I-48-2 (296 mg, 1.15 mmol) and Et$_3$N (232 mg, 2.30 mmol) in dichloromethane (20 mL) was added MSCI (197 mg, 1.73 mmol) at 0° C. The reaction mixture was stirred at room temperature for 1 h. TLC showed the reaction was complete. Saturated aqueous NaHCO$_3$ was added to the reaction mixture. The organic layer was separated, washed with brine, dried over anhydrous Na$_2$SO$_4$, and concentrated. The residue was purified by silica gel column chromatography (eluted petroleum) to give I-48-3 as an oil (270 mg, yield: 70%).

Step C: Preparation of Compound I-48-4: A mixture of I-48-3 (270 mg, 0.8 mmol), 5-formyl-4-methyl-1H-indole-2-carbonitrile (123 mg, 0.67 mmol) and Cs$_2$CO$_3$ (524 mg, 1.6 mmol) in DMF (10 mL) was stirred at 80° C. under N$_2$ overnight. Solid was removed by filtration before the reaction mixture was diluted with water and ethyl acetate. The organic layer was separated, washed with brine, dried over anhydrous Na$_2$SO$_4$, concentrated and purified by silica gel column chromatography (eluted 20% ethyl acetate in petroleum) to give I-48-4 as an oil (169 mg, yield: 50%). ESI-MS m/z: 424.54 (M+H).

Step D: Preparation of Compound I-48-5: A mixture of I-48-4 (169 mg, 0.4 mmol), N-(piperidin-4-yl)-6-(2,2,2-trifluoroethyl)thieno[2,3-d]pyrimidin-4-amine (190 mg, 0.6 mmol) and Et$_3$N (242 mg, 2.4 mmol) in CH$_2$Cl$_2$ (20 mL) was stirred at room temperature for 1 hour. NaBH(OAc)$_3$ (508 mg, 2.4 mmol) was added to the reaction under ice bath cooling and the mixture reaction was stirred at room temperature overnight. Solvent was removed by vacuum and the residue was purified by silica gel column chromatography (eluted 2.5% MeOH in dichloromethane) to give I-48-5 as an oil (174 mg, yield: 60%). ESI-MS m/z: 724.88 (M+H).

Step E: Preparation of Compound I-48-6: To a solution of I-48-5 (174 mg, 0.24 mmol) in CH$_2$Cl$_2$ (15 mL) was added TFA (5 mL). The reaction was stirred at room temperature for 2 hours before solvent was removed. A solution of NH$_3$/MeOH (7N, 10 mL) was added and the resulting mixture was concentrated. The residue and purified by silica gel column chromatography (eluted 10% MeOH in dichloromethane) to give I-48-6 as an oil (120 mg, yield: 80%). ESI-MS m/z: 624.30 (M+H).

Step F: Preparation of Compound I-48: To a mixture of I-48-6 (120 mg, 0.192 mmol) and Et$_3$N (39 mg, 0.384 mmol) in CH$_2$Cl$_2$ (10 mL) was added slowly methanesulfonyl chloride (33 mg, 0.288 mmol) in CH$_2$Cl$_2$ (5 mL) at −20° C. under N$_2$. The reaction mixture was stirred at room temperature for 2 hours. TLC showed the reaction was complete. Saturated aqueous NaHCO$_3$ was added to the reaction mixture. The organic layer was separated, washed with brine, dried over anhydrous Na$_2$SO$_4$, concentrated and purified by silica gel column chromatography (eluted 10% MeOH in dichloromethane) to give final product I-48 as a solid (54 mg, yield: 40%). $^1$H NMR (400 MHz, CDCl$_3$) δ: 8.48 (s, 1H), 7.38 (d, 1H), 7.21 (s, 1H), 7.15 (d, 1H), 7.08 (s, 1H), 5.10 (d, 1H), 4.34 (m, 2H), 4.24 (m, 1H), 3.87 (m, 2H), 3.65 (m, 4H), 2.93 (m, 5H), 2.71 (m, 2H), 2.63 (m, 2H), 2.57 (s, 3H), 2.29 (m, 2H), 2.21 (m, 2H), 2.10 (d, 2H), 1.61 (m, 2H), 1.31 (d, 6H); ESI-MS m/z: 702.27 (M+H).

Example 3

Synthesis of Compound I-2 in Table 1

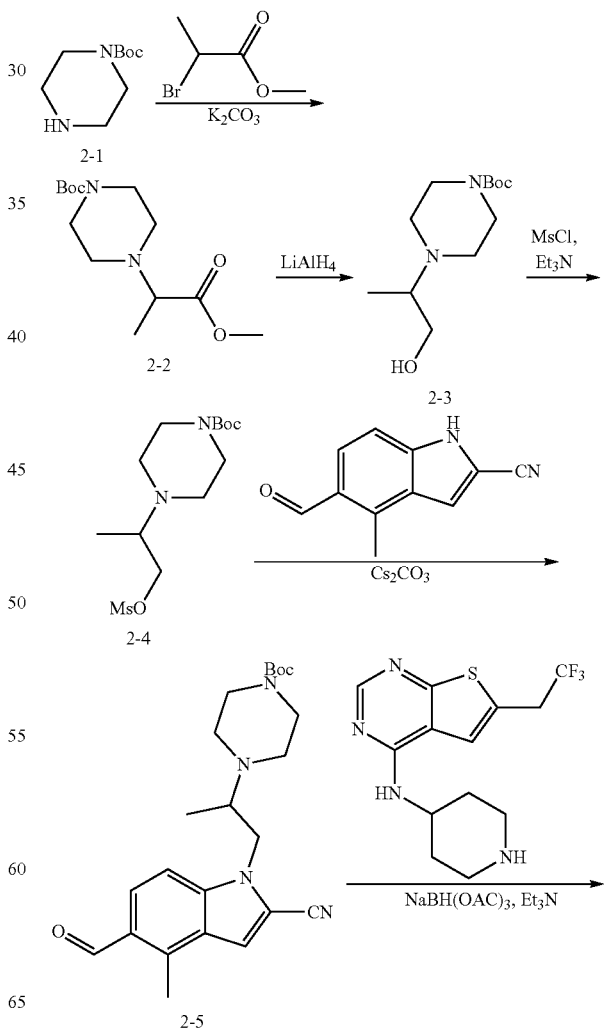

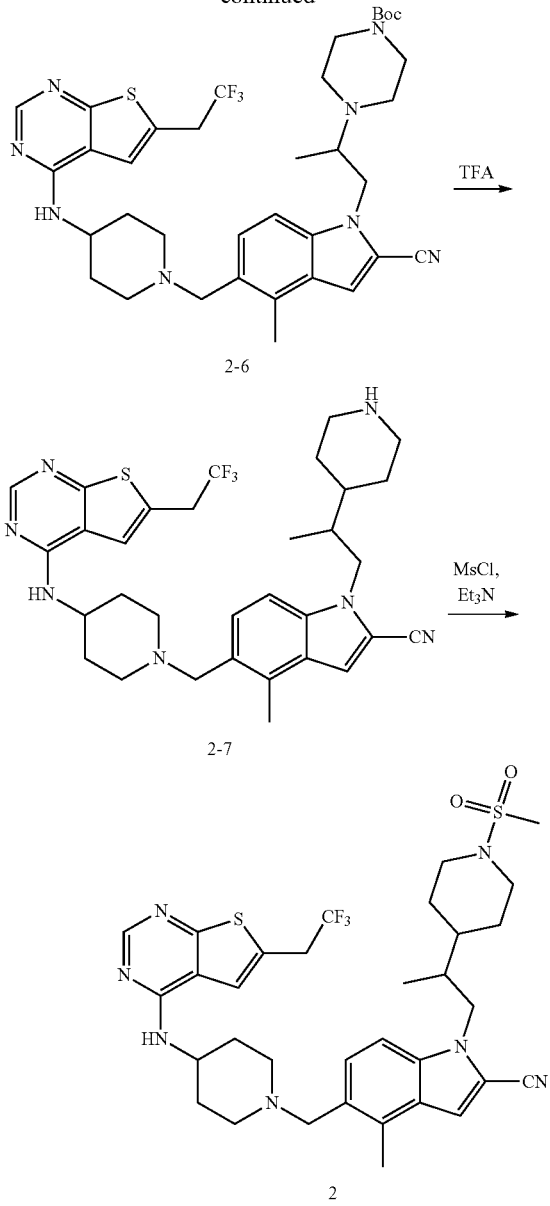

Step A: Preparation of Compound I-2-2: To a suspension of K$_2$CO$_3$ (3.6 g, 26.5 mmol) and tert-butyl piperazine-1-carboxylate (1.0 g, 5.3 mmol) in CH$_3$CN (15 mL) was added methyl 2-bromopropanoate (2.2 g, 13.4 mmol). The reaction was stirred at 80° C. for 10 hours. TLC showed that the reaction was complete. The reaction mixture was allowed to cool to room temperature, then the solid filtered off and solvent removed under vacuum. The residue was purified by silica gel column chromatography (CH$_2$Cl$_2$/MeOH=50:1) to give tert-butyl 4-(1-methoxy-1-oxopropan-2-yl)piperazine-1-carboxylate (I-2-2) as a brown oil (1.4 g, yield: 99%).

Step B: Preparation of Compound I-2-3: To a solution of tert-butyl 4-(1-methoxy-1-oxopropan-2-yl)piperazine-1-carboxylate (540 mg, 2 mmol) in THF (10 mL) was added LiAlH$_4$ (1.0 mL, 2.5 mol in THF) at 0° C. dropwise. The reaction mixture was stirred at the same temperature for 2 hours. TLC showed that the reaction was complete. The reaction was quenched with EtOAc. The reaction was partitioned between EtOAc and H$_2$O, and the organic layer was washed with brine and dried over Na$_2$SO$_4$. Solvent was removed under vacuum and the residue was purified by silica gel column chromatography (CH$_2$Cl$_2$/MeOH=20:1) to give tert-butyl 4-(1-hydroxypropan-2-yl)piperazine-1-carboxylate (I-2-3) as a brown oil (300 mg, yield: 65%).

Step C: Preparation of Compound I-2-5: To a solution of tert-butyl 4-(1-hydroxypropan-2-yl)piperazine-1-carboxylate (200 mg, 0.82 mmol) and Et$_3$N (171 mg, 1.64 mmol) in CH$_2$Cl$_2$ (10 mL) was added MSCl (112 mg, 0.98 mmol) at 0° C. The reaction was stirred at room temperature for 30 min. The reaction was quenched with NaHCO$_3$, washed with brine and dried over Na$_2$SO$_4$. Solvent was removed under vacuum to give tert-butyl 4-(1-((methylsulfonyl)oxy)propan-2-yl)piperazine-1-carboxylate (I-2-4), used in the next step without further purification.

To a mixture of Cs$_2$CO$_3$ (682 mg, 2.1 mmol) and 5-formyl-4-methyl-1H-indole-2-carbonitrile (77 mg, 0.42 mmol) in DMF was added tert-butyl 4-(1-((methylsulfonyl)oxy)propan-2-yl)piperazine-1-carboxylate in DMF. The reaction was stirred at 100° C. for 10 hours. The reaction mixture was partitioned between EtOAc and H$_2$O, and the organic layer was washed with brine and dried over Na$_2$SO$_4$. Solvent was removed under vacuum and the residue was purified by silica gel column chromatography (pet. ether/EtOAc=5:13:1) to give tert-butyl 4-(1-(2-cyano-5-formyl-4-methyl-1H-indol-1-yl)propan-2-yl)piperazine-1-carboxylate (I-2-5) as a yellow solid (90 mg, yield: 53%).

Step D: Preparation of Compound I-2-6: A mixture of tert-butyl 4-(1-(2-cyano-5-formyl-4-methyl-1H-indol-1-yl)propan-2-yl)piperazine-1-carboxylate (90 mg, 0.22 mmol), 6-(2,2,2-trifluoroethyl)—N-(piperidin-4-yl)thieno-[2,3-d]pyrimidin-4-amine (100 mg, 0.26 mmol) and Et$_3$N (130 mg, 1.32 mmol) in CH$_2$Cl$_2$ (10 mL) was stirred at room temperature for 1 hour before NaBH(OAc)$_3$ (280 mg, 1.32 mmol) was added. The reaction mixture was stirred at room temperature overnight, then partitioned between CH$_2$Cl$_2$ and NaHCO$_3$. The organic layer was washed with brine and dried over Na$_2$SO$_4$. Solvent was removed under vacuum and the residue was purified by silica gel column chromatography (CH$_2$Cl$_2$:MeOH=50:1-20:1) to give tert-butyl 4-(1-(2-cyano-4-methyl-5-((4-((6-(2,2,2-trifluoroethyl)thieno[2,3-d]pyrimidin-4-yl)amino)piperidin-1-yl)methyl)-1H-indol-1-yl)propan-2-yl)piperazine-1-carboxylate (I-2-6) as a yellow solid (130 mg, yield: 81%).

Step E: Preparation of Compound I-2-7: To a solution of tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)-1-hydroxyethyl)piperidine-1-carboxylate (130 mg, 0.21 mmol) in CH$_2$Cl$_2$ (3 mL) was added TFA (2 mL). The reaction was stirred for 4 hours before solvent was removed under vacuum. The residue was diluted with CH$_2$Cl$_2$ and washed with NaHCO$_3$. The organic layer was washed with brine and dried over Na$_2$SO$_4$. Solvent was removed under vacuum and the residue (I-2-7) was used without further purification as a yellow foam (100 mg, yield: 98%).

Step F: Preparation of Compound I-2: To a solution of 4-methyl-1-(2-(piperazin-1-yl)propyl)-5-((4-((6-(2,2,2-trifluoroethyl)thieno[2,3-d]pyrimidin-4-yl)amino)piperidin-1-yl)methyl)-1H-indole-2-carbonitrile (60 mg, 0.1 mmol) and Et$_3$N (36 mg, 0.4 mmol) in CH$_2$Cl$_2$ (10 mL) was added MSCl (21 mg, 0.2 mmol) at 0° C. The reaction was stirred at room temperature for 30 min. The reaction was quenched by NaHCO$_3$, washed with brine and dried over Na$_2$SO$_4$. Solvent was removed and the residue was purified by Prep-TLC (CH$_2$Cl$_2$:MeOH=15:1) to give 4-methyl-1-(2-(4-(methylsulfonyl)piperazin-1-yl)propyl)-5-((4-((6-(2,2,2-trifluoroethyl)thieno[2,3-d]pyrimidin-4-yl)amino)piperidin-1-yl)methyl)-1H-indole-2-carbonitrile (compound I-2) as a white solid (10 mg, yield: 20%). $^1$H NMR (400 MHz, CDCl$_3$) 8.48 (s, 1H), 7.36 (d, 1H), 7.20 (s, 1H), 7.00~7.15 (m, 2H), 5.16 (d, 1H), 4.20~4.40 (m, 2H), 4.00~4.10 (m, 1H), 3.60~3.70 (m, 4H), 3.10~3.30 (m, 5H), 2.80~2.90 (m, 4H), 2.77 (s, 3H), 2.57 (s, 3H), 1.56~2.53 (m, 8H), 1.08 (d, 3H). ESI-MS m/z: 689.25 (M+H).

Example 4

Synthesis of Compound I-61 in Table 1

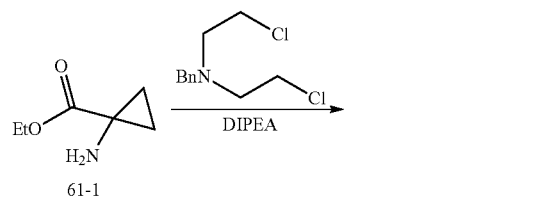

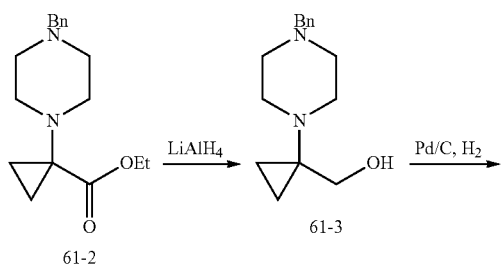

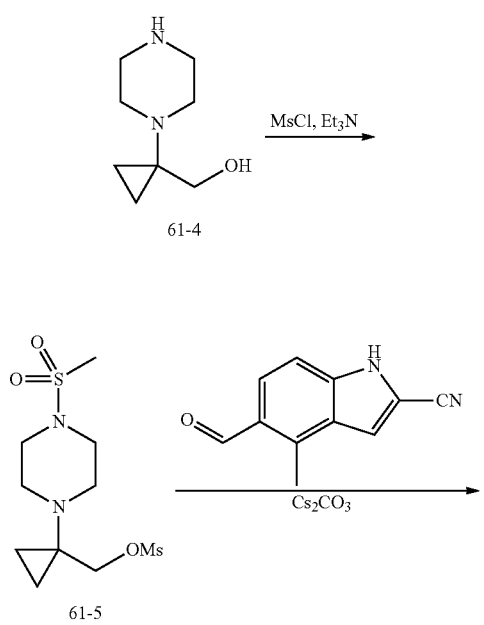

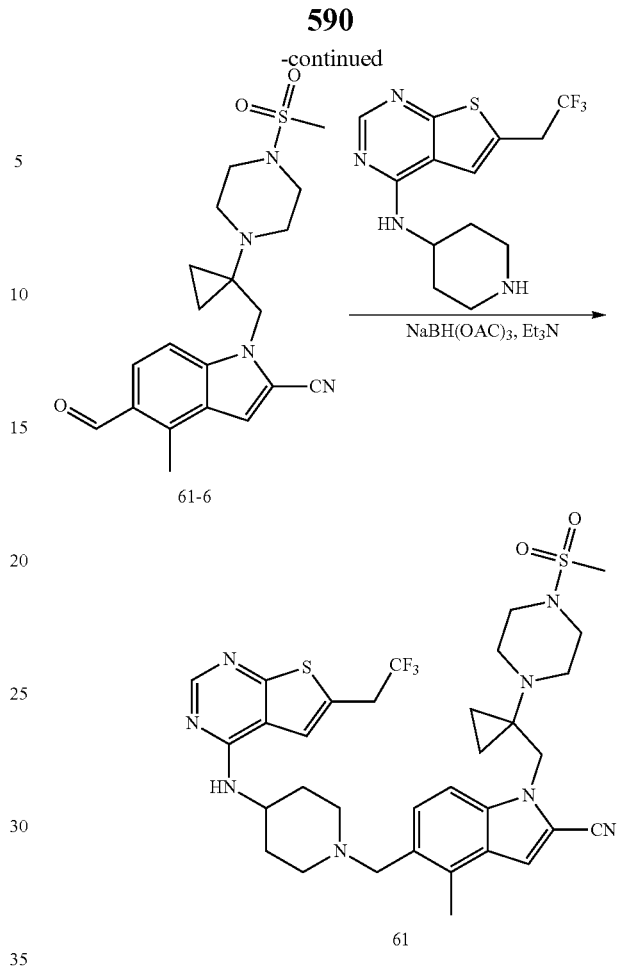

Step A: Preparation of Compound I-61-2: A mixture of ethyl 1-aminocyclopropanecarboxylate hydrochloride (2.4 g, 14.5 mmol), N-benzyl-2-chloro-N-(2-chloroethyl)ethanamine hydrochloride (4.26 g, 15.8 mmol), and N,N-Diisopropylethylamine (25 mL) in ethanol (32 mL) was stirred at reflux for 16 hours. The reaction mixture was concentrated to dryness. The residue was partitioned between dichloromethane and water. Two layers were separated, and the aqueous layer was extracted with dichloromethane. The combined organic layers were concentrated. The residue was purified by silica gel column (pet. ether/EtOAc=1:010:1) to give ethyl 1-(4-benzylpiperazin-1-yl)cyclopropanecarboxylate (I-61-2, 1.8 g, yield: 43%) as a yellow oil. $^1$H NMR (400 MHz, CDCl$_3$) δ: 7.37-7.27 (m, 5H), 4.19-4.13 (m, 2H), 3.54 (s, 2H), 3.00 (brs, 2H), 2.39 (brs, 2H), 1.31-1.26 (m, 5H), 7.52 (m 1H), 0.93-0.91 (m, 2H).

Step B: Preparation of Compound I-61-3: To a mixture of ethyl 1-(4-benzylpiperazin-1-yl)cyclopropanecarboxylate (880 mg, 3 mmol) in THF (12 mL) was added LiAlH$_4$ (290 mg, 6 mmol) slowly at 0° C. The resulting mixture was stirred at 0° C. for 1 h. Water (0.5 mL) was added, followed by ethyl acetate (20 mL). Solid was filtered off and solvent was removed. The residue was purified by silica gel column (pet. ether/EtOAc=3:1) to give (1-(4-benzylpiperazin-1-yl)cyclopropyl)methanol (I-61-3, 660 mg, yield: 88%) as a white solid.

Step C: Preparation of Compound I-61-4: A mixture of (1-(4-benzylpiperazin-1-yl)cyclopropyl)methanol (600 mg, 2.4 mmol) and Pd/C (10%, 50 mg) in ethanol (10 mL) was stirred at 50° C. overnight under H$_2$. The reaction mixture was filtered and the filtrate concentrated to give (1-(piperazin-1-yl)cyclopropyl)methanol (I-61-4) as an oil (400 mg, yield: 96%). The crude product was used in the next step without further purification.

Step D: Preparation of Compound I-61-5: To a mixture of (1-(piperazin-1-yl)cyclopropyl)methanol (400 mg, 2.5 mmol) in dichloromethane (10 mL) was added $Et_3N$ (1.1 mL, 7.5 mmol), followed by a mixture of methanesulfonyl chloride (925 mg, 7.5 mmol) in dichloromethane (5 mL). The resulting mixture was stirred at room temperature for 4 h. The reaction mixture was diluted with water and $CH_2Cl_2$. The organic layer was dried over $Na_2SO_4$, and concentrated to give a crude product (1-(4-(methylsulfonyl)piperazin-1-yl)cyclopropyl)methyl methanesulfonate (I-61-5) as a brown oil (500 mg).

Step E: Preparation of Compound I-61-6: A mixture of crude (1-(4-(methylsulfonyl)piperazin-1-yl)cyclopropyl)methyl methanesulfonate (500 mg), 5-formyl-4-methyl-1H-indole-2-carbonitrile (200 mg, 1.1 mmol), and $K_2CO_3$ (800 mg, 5.8 mmol) in acetonitrile was stirred at 80° C. overnight. The mixture was filtered and the filtrate was concentrated to dryness. The residue was purified by silica gel column (pet. ether/EtOAc=3:1) to give 5-formyl-4-methyl-1-((1-(4-(methylsulfonyl)piperazin-1-yl)cyclopropyl)methyl)-1H-indole-2-carbonitrile (I-61-6, 330 mg) as a brown solid. ESI-MS m/z: 401 (M+H).

Step F: Preparation of Compound I-61: A mixture of 5-formyl-4-methyl-1-((1-(4-(methylsulfonyl)piperazin-1-yl)cyclopropyl)methyl)-1H-indole-2-carbonitrile (330 mg, crude), N-(piperidin-4-yl)-6-(2,2,2-trifluoroethyl)thieno[2,3-d]pyrimidin-4-amine hydrochloride (391 mg, 1.1 mmol), and $Et_3N$ (0.5 mL) in dichloromethane (12 mL) was stirred at room temperature overnight. The reaction mixture was diluted with water and $CH_2Cl_2$. The organic layer was separated, dried over $Na_2SO_4$, and concentrated. The residue was purified by silica gel column (dichloromethane/methanol=50:1-30:1) to give a crude product. The crude product was purified by Prep-TLC with dichloromethane/methanol (7N $NH_3$/MeOH)=50:1 to give the product (compound I-61) as a colorless solid (12 mg). ESI-MS m/z: 701 (M+H). $^1H$ NMR (400 MHz, $CDCl_3$) δ: 8.46 (s, 1H), 7.20~7.28 (m, 3H), 4.30~4.36 (m, 3H), 3.84 (brs, 2H), 3.61~3.68 (m, 2H), 3.09~3.13 (m, 6H), 2.76 (s, 3H), 2.64~2.66 (m, 4H), 2.59 (s, 3H), 2.40~2.48 (m, 2H), 2.14~2.18 (m, 2H), 1.87~1.90 (m, 2H), 0.79~0.82 (t, 2H), 0.61~0.64 (t, 2H).

Example 5

Synthesis of Compound I-35 in Table 1

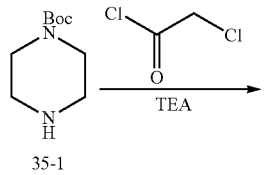

35-1

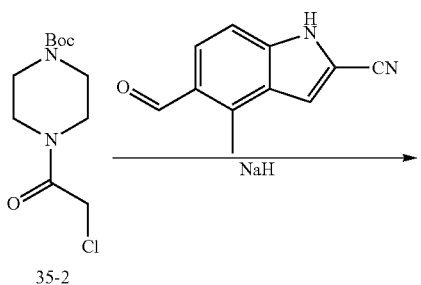

35-2

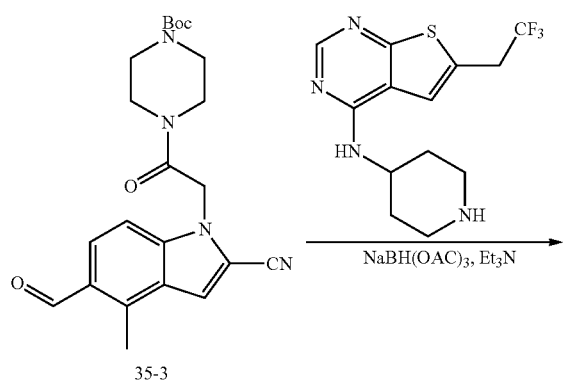

35-3

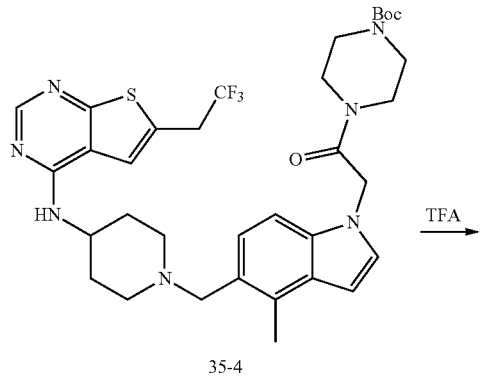

35-4

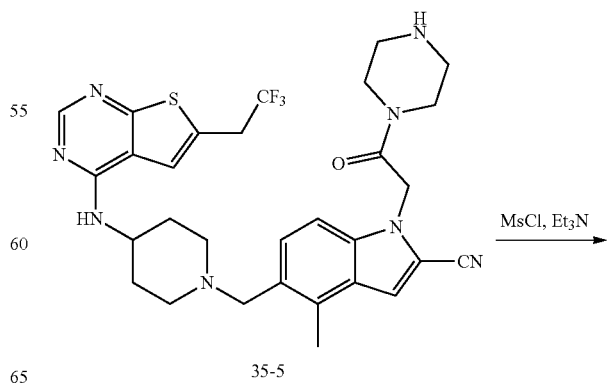

35-5

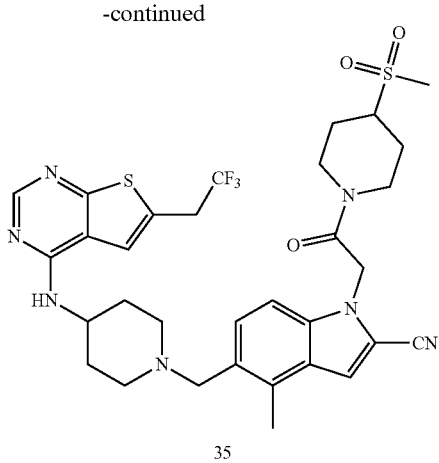

35

Step A: Preparation of Compound I-35-2: A mixture of tert-butyl piperazine-1-carboxylate (1.9 g, 10 mmol) and Et₃N (3 g, 30 mmol) in CH₂Cl₂ (40 mL) was stirred at 0° C. before 2-chloroacetyl chloride (2.2 g, 20 mmol) was added slowly. The reaction mixture was stirred at 0° C. under N₂ for 4 hr. TLC showed that the reaction was complete. The reaction mixture was partitioned between CH₂Cl₂ and H₂O, and the organic layer was washed with brine and dried over Na₂SO₄. Solvent was removed under vacuum and the residue (I-35-2) was used without further purifications as light yellow oil (2.5 g, yield: 95%).

Step B: Preparation of Compound I-35-3: To a mixture of N-(piperidin-4-yl)-6-(2,2,2-trifluoroethyl)thieno[2,3-d]pyrimidin-4-amine (1 g, 4 mmol), and 5-formyl-4-methyl-1H-indole-2-carbonitrile (540 mg, 3 mmol) in THF (10 mL) was added NaH (180 mg, 4.5 mmol) at 0° C. The reaction mixture was stirred at room temperature for 16 hours. The reaction mixture was then partitioned between EtOAc and H₂O, and the organic layer was washed with brine and dried over Na₂SO₄. Solvent was removed under vacuum and the residue purified by silica gel column chromatography (pet. ether:EtOAc=10:1-1:1) to give tert-butyl 4-(2-(2-cyano-5-formyl-4-methyl-1H-indol-1-yl)acetyl)piperazine-1-carboxylate (I-35-3) as a light yellow solid (60 mg, yield: 4%).

Step C: Preparation of Compound I-35-4: A mixture of methyl tert-butyl 4-(2-(2-cyano-5-formyl-4-methyl-1H-indol-1-yl)acetyl)piperazine-1-carboxylate (40 mg, 0.1 mmol), N-(piperidin-4-yl)-6-(2,2,2-trifluoroethyl)thieno[2,3-d]pyrimidin-4-amine hydrochloride (60 mg, 0.2 mmol) and Et₃N (60 mg, 0.6 mmol) in CH₂Cl₂ (5 mL) was stirred at room temperature for 2 hours. NaBH(OAc)₃ (120 mg, 0.6 mmol) was then added to the reaction with ice bath cooling. The reaction mixture was stirred at room temperature overnight. The reaction was partitioned between CH₂Cl₂ and NaHCO₃, and the organic layer was washed with brine and dried over Na₂SO₄. Solvent was removed under vacuum and the residue was purified by silica gel column chromatography (CH₂Cl₂:MeOH=100:1-20:1) to give tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)acetyl)piperazine-1-carboxylate (I-35-4) as a yellow solid (40 mg, yield: 55%).

Step D: Preparation of Compound I-35-5: A solution of tert-butyl 4-(2-(2-cyano-4-methyl-5-((4-((6-(2,2,2-trifluoroethyl)thieno[2,3-d]pyrimidin-4-yl)amino)piperidin-1-yl)methyl)-1H-indol-1-yl)acetyl)piperazine-1-carboxylate (40 mg, 0.06 mmol) in HCl·MeOH (10 mL) was stirred at room temperature for 16 h. TLC showed that the reaction was complete. Solvent was removed under vacuum and the residue (I-35-5) was used without further purification in next step as a yellow solid (35 mg, yield: 85%).

Step E: Preparation of Compound I-35: To a mixture of 4-methyl-1-(2-oxo-2-(piperazin-1-yl)ethyl)-5-((4-((6-(2,2,2-trifluoroethyl)thieno[2,3-d]pyrimidin-4-yl)amino)piperidin-1-yl)methyl)-1H-indole-2-carbonitrile(35 mg, 0.05 mmol) and Et₃N (15 mg, 0.15 mmol) in CH₂Cl₂ (10 mL) was slowly added MsCl (12 mg, 0.1 mmol) at 0° C. The reaction mixture was stirred at room temperature for 4 hours and then partitioned between CH₂Cl₂ and NaHCO₃. The organic layer was washed with brine and dried over Na₂SO₄. Solvent was removed under vacuum and the residue was purified by Prep-TLC (CH₂Cl₂:MeOH=20:1) to give 4-methyl-1-(2-(4-(methylsulfonyl)piperazin-1-yl)-2-oxoethyl)-5-((4-((6-(2,2,2-trifluoroethyl)thieno[2,3-d]pyrimidin-4-yl)amino)piperidin-1-yl)methyl)-1H-indole-2-carbonitrile (compound I-35) as a white solid (16 mg, yield: 56%). ¹HNMR (400 MHz, CDCl₃) 8.42 (s, 1H), 7.84~7.76 (m, 1H), 7.33~7.22 (m, 3H), 5.15 (s, 2H), 4.37~4.08 (m, 2H), 3.78 (s, 3H), 3.69~3.61 (m, 2H), 3.44~3.30 (m, 5H), 2.86 (s, 3H), 2.70~2.54 (m, 4H), 2.15~2.06 (m, 3H), 1.35~1.23 (m, 4H), 0.91~0.85 (m, 2H).

Example 6

Synthesis of Compounds II-13 and II-3 in Table 2

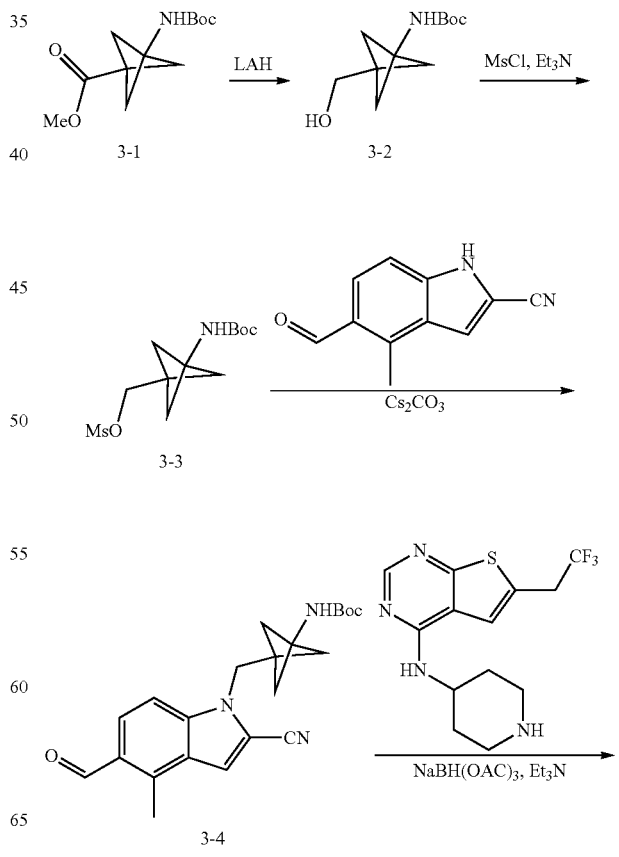

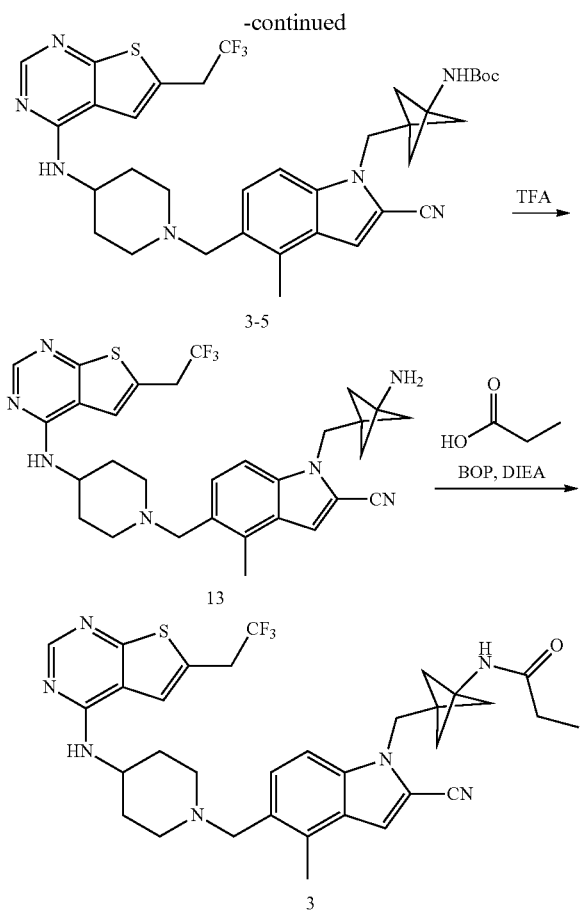

stirred at room temperature for 1 hour before NaBH(OAc)$_3$ (7.3 g, 34 mmol) was added to the reaction. The reaction mixture was stirred at room temperature overnight. The reaction mixture was then partitioned between CH$_2$Cl$_2$ and NaHCO$_3$. The organic layer was washed with brine and dried over Na$_2$SO$_4$. Solvent was removed under vacuum and the residue was purified by silica gel column chromatography (CH$_2$Cl$_2$:MeOH=50:120:1) to give II-3-5 as a yellow solid (3.9 g, yield: 98%).

Step D: Preparation of Compound II-13: To a solution II-3-5 (3.9 g, 5.7 mmol) in CH$_2$Cl$_2$ (30 mL) was added TFA (20 mL). The reaction mixture was stirred for 4 h at room temperature. Solvent was removed under vacuum to afford a residue, which was diluted with CH$_2$Cl$_2$ and washed with NaHCO$_3$. The organic layer was washed with brine and dried over Na$_2$SO$_4$. Solvent was removed under vacuum and the residue was purified by silica gel column chromatography (CH$_2$Cl$_2$:MeOH=10:1) to give compound II-13 as a white foam (2.6 g, yield: 79%).

Step E: Preparation of Compound II-3: To a solution of propionic acid (450 mg, 6.0 mmol), BOP (3.0 g, 6.9 mmol) and iPr$_2$NEt (3.0 g, 23 mmol) in CH$_2$Cl$_2$ (30 mL) was added compound II-13 (2.7 g, 4.6 mmol). The reaction mixture was stirred at room temperature for 30 min before it was quenched by NaHCO$_3$, washed with brine and dried over Na$_2$SO$_4$. Solvent was removed and the residue purified by silica gel column chromatography (CH$_2$Cl$_2$:MeOH=10:1) to afford compound II-3 (1.8 g, yield: 61%). $^1$H NMR (400 MHz, CDCl$_3$): 8.49 (s, 1H), 7.34 (d, 1H), 7.21 (s, 1H), 7.11 (d, 1H), 7.08 (s, 1H), 5.78 (s, 1H), 5.07 (d, 1H), 4.45 (s, 2H), 4.25 (m, 1H), 3.61~3.70 (m, 4H), 2.93 (m, 2H), 2.57 (s, 3H), 2.33~2.20 (m, 2H), 2.00~2.13 (m, 2H), 2.02 (s, 6H), 1.90 (s, 3H), 1.50~1.70 (m, 2H).

Step A: Preparation of Compound II-3-2: To a solution of II-3-1 (6 g, 25 mmol) in THF (100 mL) was added LiAlH$_4$ (1.5 g, 37 mol) in small portions at 0° C. The reaction was stirred until the TLC showed that the reaction was complete (about 2h). The reaction mixture was quenched by addition of EtOAc and partitioned between EtOAc and H$_2$O. The organic layer was washed with brine and dried over Na$_2$SO$_4$. Solvent was removed under vacuum to give II-3-2 as a yellow solid (5.2 g, yield: 97%).

Step B: Preparation of Compound II-3-4: To a solution of II-3-2 (800 mg, 3.7 mmol) and Et$_3$N (740 mg, 7.4 mmol) in CH$_2$Cl$_2$ (10 mL) was added MSCI (428 mg, 4.4 mmol) at 0° C. The reaction was stirred at room temperature for 30 min, then quenched by addition of NaHCO$_3$, washed with brine and dried over Na$_2$SO$_4$. Solvent was removed under vacuum to give II-3-3, which was used in the next step without further purification.

To a mixture of Cs$_2$CO$_3$ (3.0 g, 9.3 mmol) and 5-formyl-4-methyl-1H-indole-2-carbonitrile (800 mg, 4.4 mmol) in DMF (10 mL) was added II-3-3 in DMF. The reaction mixture was stirred at 100° C. for 10 h. The reaction mixture was then partitioned between EtOAc and H$_2$O. The organic layer was washed with brine and dried over Na$_2$SO$_4$. Solvent was removed under vacuum and the residue purified by silica gel column chromatography (pet. ether/EtOAc=5:13:1) to give II-3-4 as a yellow solid (600 mg, yield: 42% according to alcohol).

Step C: Preparation of Compound II-3-5: A mixture of II-3-4 (2.2 g, 5.8 mmol), 6-(2,2,2-trifluoroethyl)—N-(piperidin-4-yl)thieno-[2,3-d]pyrimidin-4-amine (2.3 g, 6.9 mmol) and Et$_3$N (3.5 g, 34 mmol) in CH$_2$Cl$_2$ (50 mL) was Example 7

Synthesis of Compound II-29 in Table 2

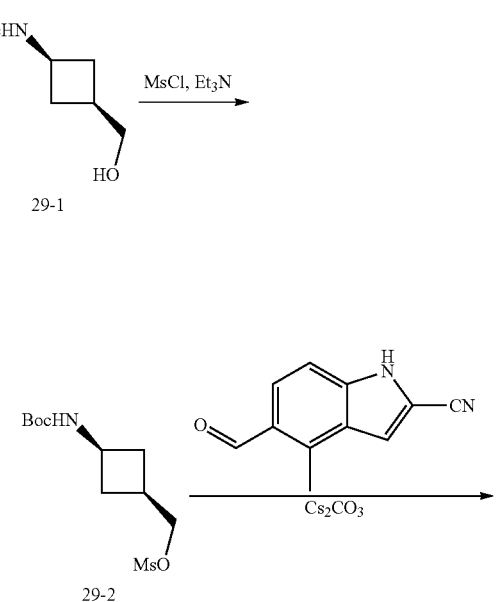

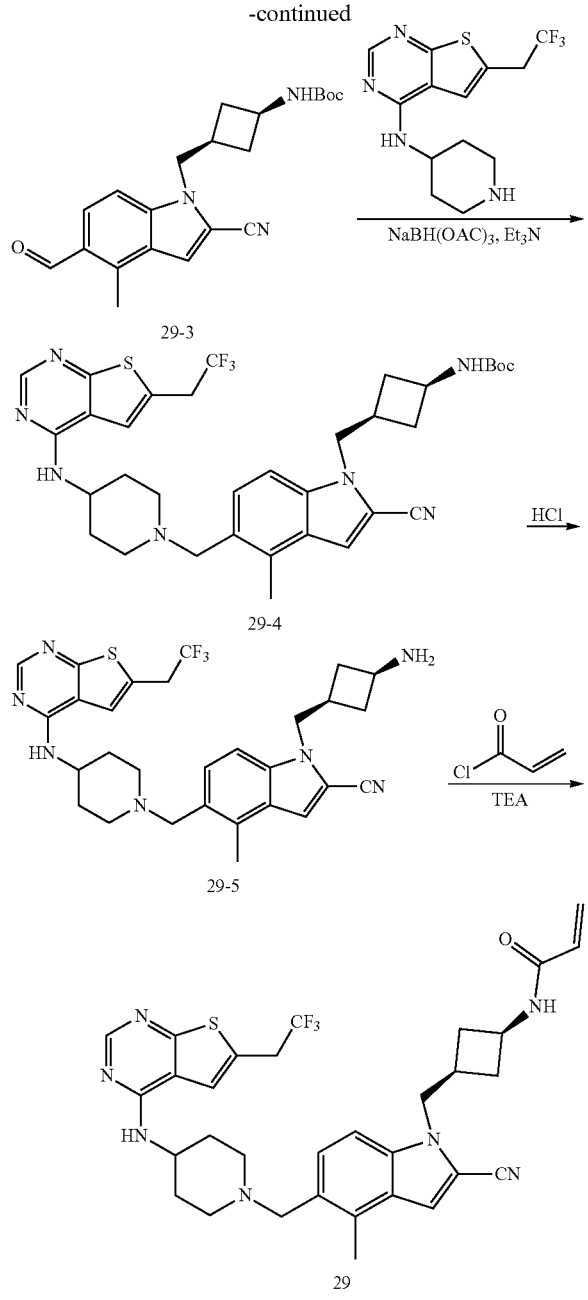

Step A: Preparation of Compound II-29-2: To a solution of II-29-1 (200 mg, 1.0 mmol) and Et₃N (202 mg, 2.0 mmol) in CH₂Cl₂ (10 mL) was added MSCI (172 mg, 1.5 mmol) at 0° C. The reaction mixture was stirred at room temperature overnight before water was added to the reaction. The solution mixture was extracted with CH₂Cl₂ 3 times. The organic layer was washed with brine and dried over Na₂SO₄. The solution was filtered and concentrated to give II-29-2 as a white solid (250 mg, yield: 90%).

Step B: Preparation of Compound II-29-3: A mixture of II-29-2 (250 mg, 0.9 mmol), 5-formyl-4-methyl-1H-indole-2-carbonitrile (82 mg, 0.45 mmol) and Cs₂CO₃ (438 mg, 1.35 mmol) in DMF (6 mL) was stirred at 60° C. for 6 hours before water (15 mL) was added. The reaction mixture was extracted with ethyl acetate (20 mL×3). The combined organic solution was washed with brine and dried over Na₂SO₄, filtered, and concentrated. The residue was purified by silica gel column chromatography (33% EtOAc in pet. ether to 50% EtOAc in pet. ether) to give II-29-3 as a yellow solid (110 mg, yield: 33%).

Step C: Preparation of Compound II-29-4: A mixture of I-29-3 (110 mg, 0.3 mmol), 6-(2,2,2-trifluoroethyl)—N-(piperidin-4-yl)thieno[2,3-d]pyrimidin-4-amine hydrochloride (116 mg, 0.3 mmol) and Et₃N (185 mg, 1.8 mmol) in CH₂Cl₂ (20 mL) was stirred at room temperature for 1 hour before NaBH(OAc)₃ (381 mg, 1.8 mmol) was added to the reaction under ice bath. The reaction mixture was stirred at room temperature overnight. Solvent was removed by vacuum and the residue was purified by silica gel column chromatography (2.5% MeOH in CH₂Cl₂) to give II-29-4 as a solid (180 mg, yield: 90%).

Step D: Preparation of Compound II-29-5: A solution of tert-butyl carbamate II-29-4 (180 mg, 0.27 mmol) in HCl/MeOH (10 mL) was stirred at room temperature for 2 hours. Solvent was removed and a solution of NH₃ (7N) in MeOH (10 mL) was added. The reaction mixture was stirred for 10 minutes before solvent was removed and the residue purified by silica gel column chromatography (10% MeOH in CH₂Cl₂) to give II-29-5 as an oil (100 mg, yield: 65%).

Step E: Preparation of Compound II-29: To a mixture of II-29-5 (100 mg, 0.17 mmol) and Et₃N (27 mg, 0.26 mmol) in CH₂Cl₂/THF (10 mL, 1:1) was add slowly acryloyl chloride (19 mg, 0.21 mmol) at −78° C. under N₂. The mixture was stirred at room temperature for 15 min, then NH₃·MeOH was added. Solvent was removed and the residue was purified by silica gel column chromatography (10% MeOH in CH₂Cl₂) to give final product II-29 as a solid (78 mg, yield: 71%). ¹H NMR (400 MHz, DMSO): δ: 8.32 (s, 1H), 7.81~7.80 (d, 1H), 7.64 (s, 1H), 7.55 (s, 1H), 7.39 (s, 1H), 7.34~7.32 (m, 2H), 6.16~6.01 (m, 2H), 5.57~6.54 (m, 1H), 4.33~4.31 (d, 2H), 4.09~4.00 (m, 4H), 3.68 (s, 3H), 2.86~2.85 (m, 2H), 2.45~2.41 (m, 1H), 2.26~2.24 (m, 2H), 2.10 (brs, 2H), 1.99 (s, 1H), 1.89 (brs, 2H), 1.75~1.67 (m, 2H), 1.57 (brs, 2H); ESI-MS m/z: 622.40 (M+H).

Example 8

Synthesis of Compound II-10 in Table 2

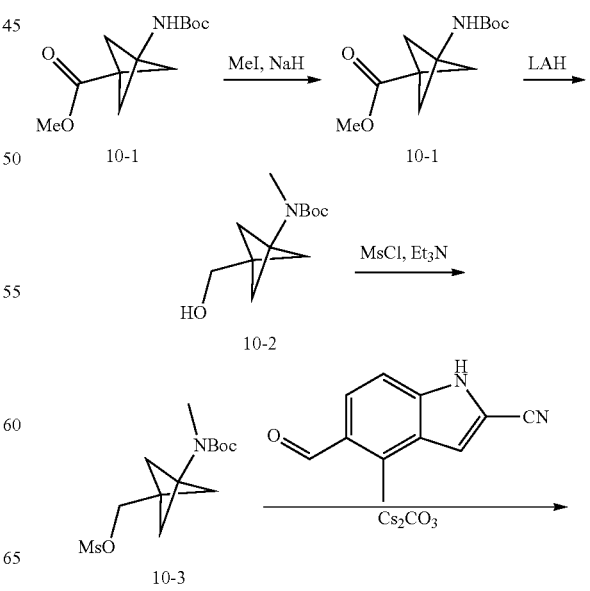

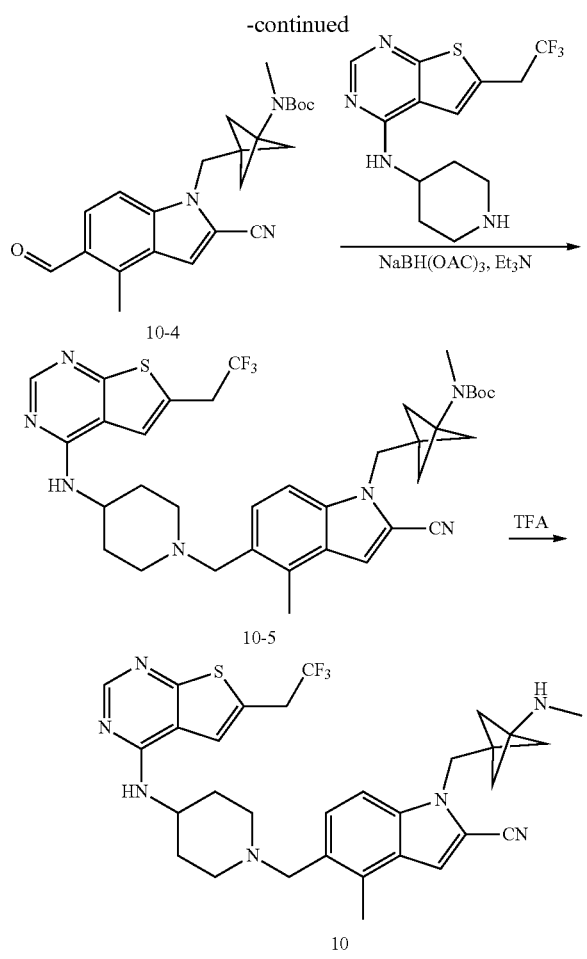

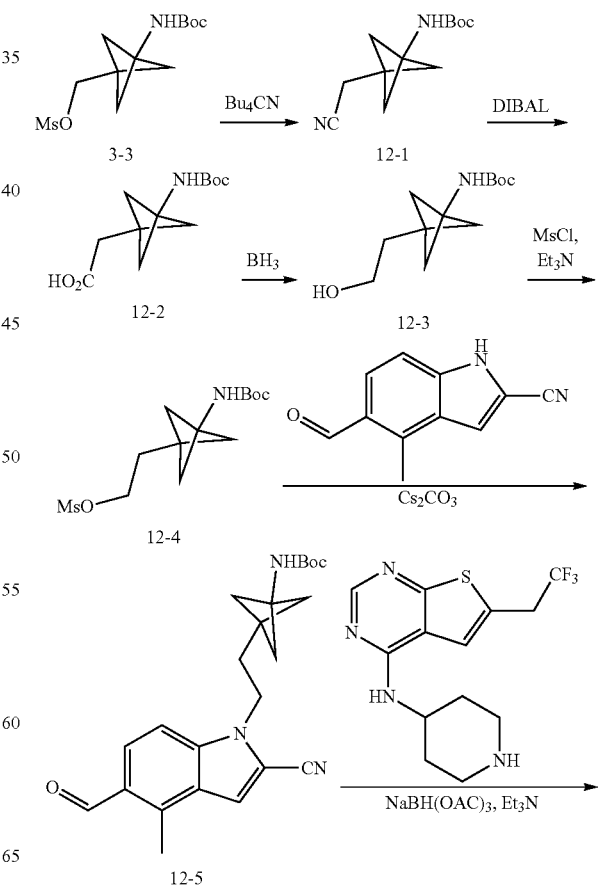

Step A: Preparation of Compound II-10-1: To a solution of II-3-1 (300 mg, 1.24 mmol) in DMF (15 mL) was added NaH (210 mg, 2.5 mmol) at 0° C. The reaction mixture was stirred at the same temperature for 20 min before iodomethane (50 mg, 2.5 mmol) was added. The resulting mixture was stirred at room temperature for 3h before water was added. The reaction mixture was extracted with ethyl acetate. The combined organic layer was concentrated to dryness. The residue was purified by silica gel column (pet. ether/EtOAc=5:1) to give II-10-1 (310 mg, yield: 97%) as a colorless oil.

Step B: Preparation of Compound II-10-2: To a mixture of methyl ester II-10-1 (310 mg, 1.21 mmol) in THF (10 mL) was slowly added LiAlH₄ at 0° C. The reaction mixture was stirred at room temperature for 1 h before water (0.2 mL) was added, followed by EtOAc. The reaction mixture was filtered and concentrated to dryness. The residue was purified by silica gel column (pet. ether/EtOAc=3:1) to give II-10-2 (237 mg, yield: 86%).

Step C: Preparation of Compound II-10-3: To a solution of II-10-2 (230 mg, 1.01 mmol) in CH₂Cl₂ was added Et₃N (0.42 mL, 3.03 mmol) at 0° C., followed by methanesulfonyl chloride (231 mg, 2.02 mmol). The resulting mixture was stirred at room temperature for 1 h. CH₂Cl₂ was added, the mixture was washed with NaHCO₃, and the organic layer was washed with brine and dried over Na₂SO₄. Solvent was removed to give II-10-3 (330 mg) as a brown oil.

Step D: Preparation of Compound II-10-4: A mixture of crude II-10-3 (330 mg), 5-formyl-4-methyl-1H-indole-2-carbonitrile (200 mg, 1.08 mmol), and Cs₂CO₃ (1 g, 3.24 mmol) in DMF (10 mL) was stirred at 100° C. overnight. Water was added and the reaction mixture was extracted with ethyl acetate. The organic layer was dried over Na₂SO₄ and concentrated to dryness. The residue was purified by silica gel column (pet. ether/EtOAc=4:1) to give II-10-4 (177 mg, yield: 41%). ESI-MS m/z: 394 (M+H).

Step E: Preparation of Compound II-10-5: A mixture of II-10-4 (177 mg, 0.45 mmol), N-(piperidin-4-yl)-6-(2,2,2-trifluoroethyl)thieno[2,3-d]pyrimidin-4-amine hydrochloride (238 mg, 0.68 mmol), Et₃N (0.2 mL, 1.3 mmol), and NaBH(OAc)₃ in CH₂Cl₂ was stirred at room temperature overnight. The reaction mixture was diluted with CH₂Cl₂, washed with brine, and concentrated. The residue was purified by silica gel column (CH₂Cl₂/MeOH=30:1) to give II-10-5 (210 mg, yield: 67%). ESI-MS m/z: 694 (M+H).

Step F: Preparation of Compound II-10: A solution of II-10-5 (100 mg, 0.14 mmol), TFA (1 mL) in CH₂Cl₂ (5 mL) was stirred at room temperature for 3 h. The mixture was concentrated and the residue dissolved in CH₂Cl₂, washed with NaHCO₃, dried over Na₂SO₄, and concentrated. The residue was purified by silica gel column (CH₂Cl₂/MeOH=30:1) to give II-10 (50 mg, yield: 58%). ESI-MS m/z: 594 (M+H). ¹H NMR (400 MHz, CDCl₃) δ: 8.48 (s, 1H), 7.38 (d, 1H), 7.22 (s, 1H), 71.5 (s, 1H), 7.13 (s, 1H), 5.23 (brs, 1H), 4.46 (s, 2H), 4.26~4.28 (m, 1H), 3.62~3.69 (m, 4H), 2.97 (d, 2H), 2.63 (s, 3H), 2.31~2.37 (m, 5H), 2.08~2.14 (m, 2H), 1.65~1.73 (m, 8H).

Example 9

Synthesis of Compounds II-11 and II-12 in Table 2

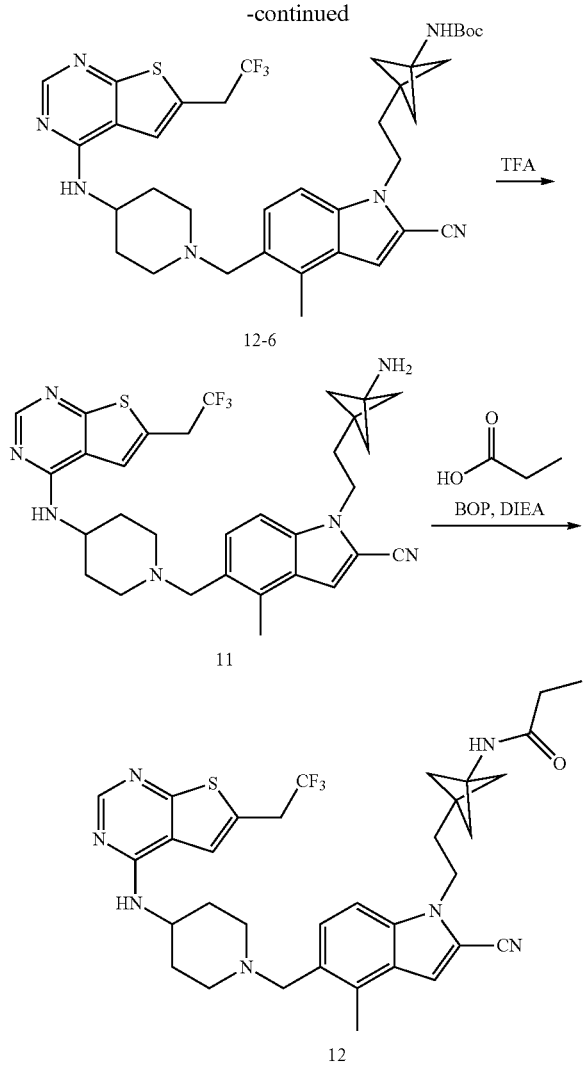

Step A: Preparation of Compound II-12-1: A mixture of II-3-3 and Bu₄CN (3.5 g, 13 mmol) in CH₃CN (30 mL) was stirred under reflux for 10 h until TLC showed that the reaction was complete. Solvent was removed and the residue was purified by silica gel column chromatography (pet. ether/EtOAc=3:1) to give II-12-1 as a white solid (1.0 g, yield: 86% according to alcohol).

Step B: Preparation of Compound II-12-2: To a solution of II-12-1 (460 mg, 2 mmol) in CH₂Cl₂ was added DIBAL-H (6 mmol) dropwise at −78° C. and the reaction mixture stirred at the same temperature for 2 h. The reaction was quenched with NH₄Cl and dried over Na₂SO₄. Solvent was removed under vacuum and the residue was purified by silica gel column chromatography (pet. ether/EtOAc=5:1-3:1) to give II-12-2 as a white solid (200 mg, yield: 44%).

Step C: Preparation of Compound II-12-3: To a solution of II-12-2 (200 mg, 1 mmol) in THF was added BH₃/THF (4 mmol) dropwise at −78° C. The reaction was stirred for 10 h before it was quenched by MeOH. Solvent was removed under vacuum to give II-12-3 as a white solid (200 mg, yield: 99%), used in the next step without further purifications.

Step D: Preparation of Compound II-12-5: To a solution of II-12-3 (120 mg, 0.54 mmol) and Et₃N (109 mg, 1.0 mmol) in CH₂Cl₂ (10 mL) was added MSCl (73 mg, 0.63 mmol) at 0° C. The reaction was stirred at room temperature for 30 min. The reaction was quenched by NaHCO₃, washed with brine and dried over Na₂SO₄. Solvent was removed under vacuum to give crude II-12-4, used in the next step without further purification.

To a mixture of Cs₂CO₃ (400 mg, 1.2 mmol) and 5-formyl-4-methyl-1H-indole-2-carbonitrile (70 mg, 0.3 mmol) in DMF (10 mL) was added II-12-4 in DMF. The reaction was stirred at 100° C. for 10 h. The reaction mixture was partitioned between EtOAc and H₂O. The organic layer was washed with brine and dried over Na₂SO₄. Solvent was removed under vacuum to get a residue, which was purified by silica gel column chromatography (pet. ether/EtOAc=5:1-3:1) to give II-12-5 as a white solid (100 mg, yield: 52% 2 steps).

Step E: Preparation of Compound II-12-6: A mixture of II-12-5 (30 mg, 0.1 mmol), 6-(2,2,2-trifluoroethyl)—N-(piperidin-4-yl)thieno-[2,3-d]pyrimidin-4-amine (50 mg, 0.12 mmol) and Et₃N (60 mg, 0.6 mmol) in CH₂Cl₂ (10 mL) was stirred at room temperature for 1 hour before NaBH(OAc)₃ (130 mg, 0.6 mmol) was added. The mixture reaction was stirred at room temperature overnight. The reaction was partitioned between CH₂Cl₂ and NaHCO₃, and the organic layer was washed with brine and dried over Na₂SO₄. Solvent was removed under vacuum to give a residue, which was purified by silica gel column chromatography (CH₂Cl₂:MeOH=50:1-20:1) to give II-12-6 as a yellow solid (40 mg, yield: 60%).

Step F: Preparation of Compound II-11: To a solution of II-12-6 (130 mg, 0.19 mmol) in CH₂Cl₂ (3 mL) was added TFA (2 mL). The reaction was stirred for 4 h at room temperature. Solvent was removed under vacuum to give a residue, which was diluted with CH₂Cl₂ and washed with NaHCO₃. The organic layer was washed with brine and dried over Na₂SO₄. Solvent was removed under vacuum to give compound II-11 as a yellow foam (100 mg, crude).

Step G: Preparation of Compound II-12: To a solution of propionic acid (6 mg, 0.07 mmol), BOP (40 g, 0.09 mmol), and iPr₂NEt (40 mg, 0.3 mmol) in CH₂Cl₂ (10 mL) was added compound II-11 (35 mg, 0.06 mmol), then the reaction was stirred at room temperature for 30 min. The reaction was quenched by addition of NaHCO₃, washed with brine and dried over Na₂SO₄. Solvent was removed give a residue, which was purified by Prep-TLC (CH₂Cl₂:MeOH=10:1) to give II-12 (10 mg, yield: 30%). ¹H NMR (400 MHz, CDCl₃) 8.46 (s, 1H), 7.51 (d, 1H), 7.17~7.22 (m, 3H), 5.85 (s, 1H), 5.79 (br, 1H), 4.23~4.32 (m, 3H), 3.86 (s, 2H), 3.66 (q, 2H), 3.12 (m, 2H), 2.58 (s, 3H), 2.53~2.40 (m, 2H), 2.20~2.14 (m, 6H), 1.99 (s, 6H), 1.86~1.90 (m, 2H), 1.12 (t, 3H). ESI-MS m/z: 650.25 (M+H).

Example 10

Synthesis of Compounds II-20 and II-18 in Table 2

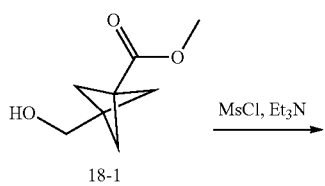

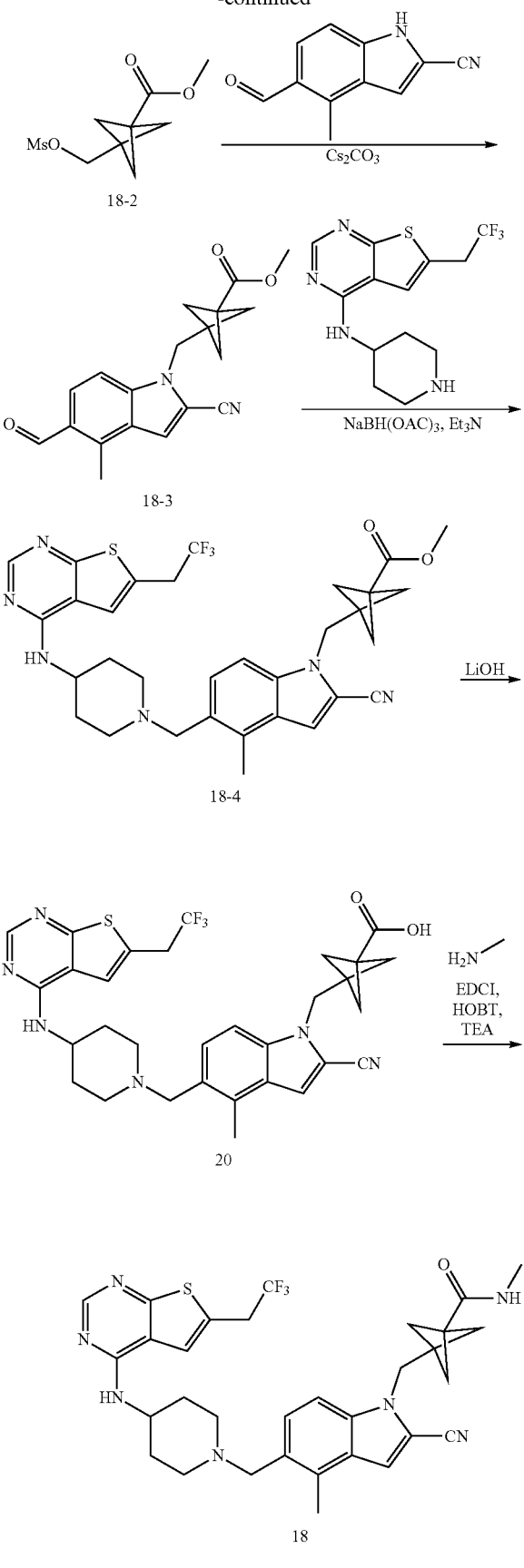

Step A: Preparation of Compound II-18-2: A mixture of II-18-1 and Et₃N (600 mg, 6 mmol) in CH₂Cl₂ was stirred at 0° C. before MSCl (460 mg, 4 mmol) was added slowly. The reaction mixture was stirred at 0° C. under N₂ for 2 hr. TLC showed that the reaction was complete. The reaction mixture was partitioned between CH₂Cl₂ and H₂O, and the organic layer was washed with brine and dried over Na₂SO₄. Solvent was removed under vacuum and the resulting compound (II-18-2) was used without further purification as a light yellow oil (460 mg, yield: 99%).

Step B: Preparation of Compound II-18-3: A mixture of crude II-18-2 (460 mg, 2 mmol), 5-formyl-4-methyl-1H-indole-2-carbonitrile (440 mg, 2.4 mmol) and Cs₂CO₃ (1.3 g, 4 mmol) in DMF (10 mL) was stirred at 60° C. for 4 hours. The reaction was cooled and the solid was removed by filtration. The reaction mixture was partitioned between EtOAc and H₂O, and the organic layer was washed by brine and dried over Na₂SO₄. Solvent was removed under vacuum to give a residue, which was purified by silica gel column chromatography (pet. ether:EtOAc=10:14:1) to give II-18-3 as a light yellow solid (280 mg, yield: 43%). ESI-MS m/z: 323 (M+H).

Step C: Preparation of Compound II-18-4: A mixture of II-18-3 (280 mg, 0.87 mmol), N-(piperidin-4-yl)-6-(2,2,2-trifluoroethyl)thieno[2,3-d]pyrimidin-4-amine hydrochloride (435 mg, 1.35 mmol) and Et₃N (400 mg, 4 mmol) in CH₂Cl₂ (30 mL) was stirred at room temperature for 2 hours before NaBH(OAc)₃ (570 mg, 2.7 mmol) was added with ice bath cooling. The reaction mixture was stirred at room temperature overnight. The reaction was partitioned between CH₂Cl₂ and NaHCO₃, and the organic layer was washed by brine and dried over Na₂SO₄. Solvent was removed under vacuum to give a residue, which was purified by silica gel column chromatography (pet. ether:EtOAc=10: 1~1:1) to give II-18-4 as a yellow solid (300 mg, yield: 56%). ESI-MS m/z: 623 (M+H).

Step D: Preparation of Compound II-20: To a solution of II-18-4 (180 mg, 0.3 mmol) in water (4 mL) and THF (10 mL) was added LiOH (24 mg, 0.6 mmol). The reaction was stirred at room temperature for 16 h. TLC showed that the reaction was complete. The pH of the mixture was adjusted to pH 4 with HCl (a.q., 1N). The reaction mixture was diluted with EtOAc and the organic layer was dried over Na₂SO₄. Solvent was removed under vacuum to give compound II-20, which was used without further purification as a yellow solid (130 mg, yield: 75%)

Step E: Preparation of Compound II-18: A mixture of crude compound II-20 (40 mg, 0.07 mmol), methylamine hydrochloride (30 mg, 0.44 mmol), EDCI (40 mg, 0.28 mmol), HOBT (15 mg, 0.11 mmol) and Et₃N (50 mg, 0.5 mmol) in CH₂Cl₂ (10 mL) was stirred at room temperature for 40 hours. The reaction mixture was partitioned between CH₂Cl₂ and NaHCO₃, and the organic layer was washed by brine and dried over Na₂SO₄. The solvent was removed under vacuum to give a residue, which was purified by prep-TLC (CH₂Cl₂:MeOH=10:1) to provide compound II-18 as a white solid (15 mg, yield: 35%). ¹HNMR (400 MHz, MeOD) 8.31 (s, 1H), 7.54 (s, 1H), 7.41~7.32 (m, 3H), 4.45 (s, 2H), 4.24~4.17 (m, 1H), 3.89~3.81 (m, 2H), 3.74 (s, 2H), 3.08~3.05 (m, 2H), 2.66 (s, 3H), 2.60 (s, 3H), 2.40~2.34 (m, 2H), 2.07~2.03 (m, 2H), 1.88 (s, 6H), 1.76~1.70 (m, 2H). ESI-MS m/z: 622 (M+H).

Example 11

Synthesis of Compounds II-17 and II-33 in Table 2

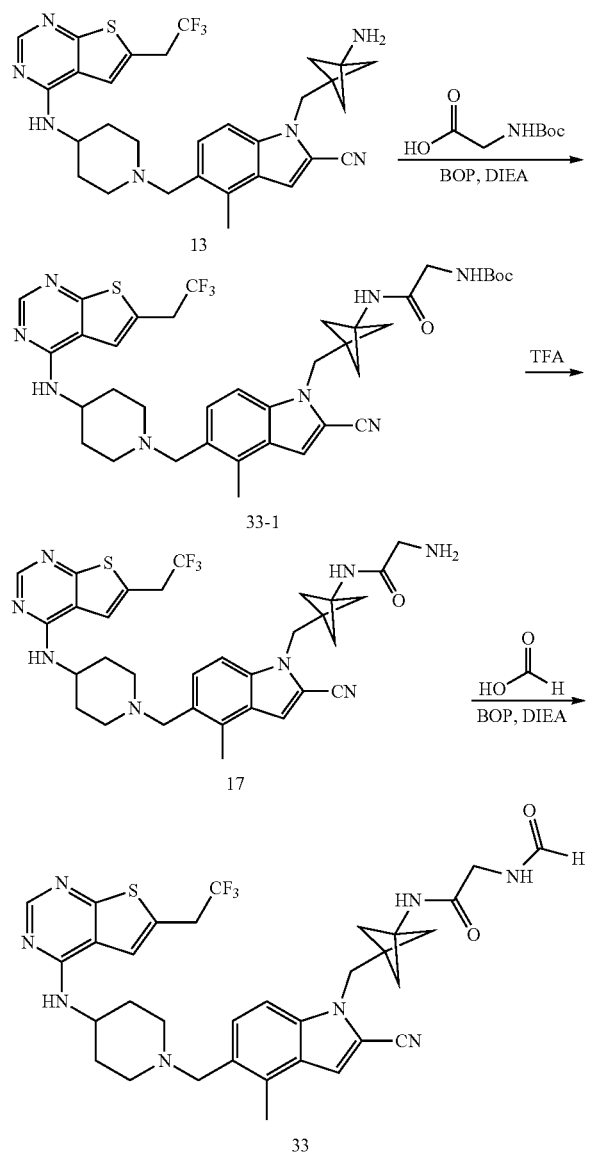 [SMILES: Cc1c(CN2CCC(Nc3ncnc4sc(CC(F)(F)F)cc34)CC2)ccc2c1cc(C#N)n2CC12CC(N)(C1)C2 ; CC(C)(C)OC(=O)NCC(=O)O ; Cc1c(CN2CCC(Nc3ncnc4sc(CC(F)(F)F)cc34)CC2)ccc2c1cc(C#N)n2CC12CC(NC(=O)CNC(=O)OC(C)(C)C)(C1)C2 ; Cc1c(CN2CCC(Nc3ncnc4sc(CC(F)(F)F)cc34)CC2)ccc2c1cc(C#N)n2CC12CC(NC(=O)CN)(C1)C2 ; O=CO ; Cc1c(CN2CCC(Nc3ncnc4sc(CC(F)(F)F)cc34)CC2)ccc2c1cc(C#N)n2CC12CC(NC(=O)CNC=O)(C1)C2]

Step A: Preparation of Compound II-33-1: A mixture of compound II-13 (190 mg, 0.33 mmol), 2-(tert-butoxycarbonyl)acetic acid (79 mg, 0.43 mmol), benzotriazol-1-yloxy-triS(dimethylamino)-phosphonium hexafluorophosphate (229 mg, 0.5 mmol), and iPr₂NEt (0.3 mL, 1.65 mmol) in CH₂Cl₂ (10 mL) was stirred at room temperature for 30 min. Water was added and the resulting mixture was extracted with CH₂Cl₂. The organic layer was concentrated and the residue was purified by silica gel column (CH₂Cl₂/MeOH=20:1) to give 33-1 (210 mg, yield: 87%) as a solid. ESI-MS m/z: 737 (M+H).

Step B: Preparation of Compound II-17: A mixture of II-33-1 (230 mg, 0.34 mmol) in CH₂Cl₂ (5 mL) and trifluoroacetic acid (5 mL) was stirred at room temperature for 2 h. The reaction mixture was concentrated to dryness and the residue was dissolved in NH₃/MeOH (7N). The mixture was concentrated to dryness. The residue was purified by silica gel column to give compound II-17 as a yellow solid (210 mg, yield: 83%). ESI-MS m/z: 637 (M+H).

Step C: Preparation of Compound II-33: A mixture of compound II-17 (50 mg, 0.08 mmol), formic acid (8 mg, 0.16 mmol), benzotriazol-1-yloxytris(dimethylamino)-phosphonium hexafluorophosphate (52 mg, 0.12 mmol), and iPr₂NEt (0.07 mL, 0.4 mmol) in CH₂Cl₂ (5 mL) was stirred at room temperature for 30 min. Water was added and the resulting reaction mixture was extracted with CH₂Cl₂. The organic layer was concentrated and the residue was purified by silica gel column (CH₂Cl₂/MeOH=15:1) to give compound II-33 as a solid (40 mg, yield: 77%). $^{1}$H NMR (400 MHz, CD₃OD) δ: 8.30 (s, 1H), 8.09 (s, 1H), 7.52 (s, 1H), 7.30~7.34 (m, 3H), 4.51 (s, 2H), 4.20 (m, 1H), 3.67~3.85 (m, 6H), 3.07~3.10 (m, 2H), 2.59 (s, 3H), 2.34~2.44 (m, 2H), 2.05~2.08 (m, 2H), 1.96 (s, 6H), 1.62~1.76 (m, 2H). ESI-MS m/z: 664 (M+H).

Example 12

Fluorescence Polarization Assay

This example illustrates an assay effective in monitoring the binding of MLL to menin. Fluorescence polarization (FP) competition experiments were performed to determine the effectiveness with which a compound inhibits the menin-MLL interaction, reported as an $IC_{50}$ value. A fluorescein-labeled peptide containing the high affinity menin binding motif found in MLL was produced according to Yokoyama et al. (Cell, 2005, 123 (2): 207-218), herein incorporated by reference in its entirety. Binding of the labeled peptide (1.7 kDa) to the much larger menin (~67 kDa) is accompanied by a significant change in the rotational correlation time of the fluorophore, resulting in a substantial increase in the fluorescence polarization and fluorescence anisotropy (excitation at 500 nm, emission at 525 nm). The effectiveness with which a compound inhibits the menin-MLL interaction was measured in an FP competition experiment, wherein a decrease in fluorescence anisotropy correlates with inhibition of the interaction and was used as a read-out for $IC_{50}$ determination.

Table 8 shows biological activities of selected compounds in a fluorescence polarization assay. Compound numbers correspond to the numbers and structures provided in Tables 1-7 and Examples 1-11.

TABLE 8

| | Less than 50 nM (++++) | 50 nM to less than 250 nM (+++) | 250 nM to 1000 nM (++) | Greater than 1000 nM (+) |
|---|---|---|---|---|
| Menin MLL 4-43 $IC_{50}$ (nM) | I-6, I-8, I-10, I-12, I-13, I-14, I-18, I-20, I-22, I-28, I-64, I-65, I-73, I-80, I-89, I-115, | I-2, I-4, I-5, I-7, I-11, I-17, I-19, I-21, I-25, I-29, I-30, I-43, I-46, I-48, I-49, I-54, | I-1, I-3, I-24, I-26, I-44, I-45, I-52, I-53, I-55, I-56, I-57, I-58, I-59, I-66, I-67, I-82, | I-9, I-15, I-16, I-23, I-35, I-47, I-60, I-62, I-170, I-200, II-12, II-20 |

TABLE 8-continued

| Less than 50 nM (++++) | 50 nM to less than 250 nM (+++) | 250 nM to 1000 nM (++) | Greater than 1000 nM (+) |
|---|---|---|---|
| I-119, I-123, I-131, I-132, I-134, I-135, I-136, I-138, I-139, I-141, I-147, I-148, I-151, I-154, I-158, I-163, I-165, I-166, I-172, I-175, I-176, I-177, I-178, I-181, I-182, I-183, I-184, I-186, I-187, I-189, I-191, I-192, I-193, I-194, I-196, I-197, I-202, I-203, I-204, I-205, I-206, I-207, I-209, I-210, I-212, I-213, I-214, I-215, I-216, I-217, I-218, I-219, I-220, I-221, I-243, I-244, I-247, I-248, I-249, II-7, II-15, II-17, II-35, II-37, II-39 | I-61, I-68, I-72, I-74, I-87, I-116, I-117, I-120, I-121, I-122, I-127, I-128, I-133, I-140, I-142, I-143, I-146, I-150, I-153, I-155, I-156, I-159, I-160, I-161, I-162, I-164, I-167, I-168, I-171, I-174, I-179, I-180, I-185, I-188, I-190, I-195, I-199, I-208, I-211, II-1, II-2, II-3, II-8, II-9, II-10, II-13, II-16, II-18, II-29, II-30, II-32, II-34, II-36, II-38, III-30a, III-38 | I-118, I-157, I-173, I-201, II-4, II-5, II-6, II-11, II-14, II-31, II-33, III-48 | |

Example 13

Homogenous Time-Resolve Fluorescence (HTRF) Assay

A homogeneous time-resolve fluorescence (HTRF) assay is utilized as a secondary assay to confirm the results of the FP assay. In some embodiments, the HTRF assay is the primary assay and the FP assay is used as a secondary assay to confirm results. HTRF is based on the non-radiative energy transfer of the long-lived emission from the Europium cryptate ($Eu^{3+}$-cryptate) donor to the allophycocyanin (XL665) acceptor, combined with time-resolved detection. An $Eu^{3+}$-cryptate donor is conjugated with mouse anti-6His monoclonal antibody (which binds His-tagged menin) and XL665-acceptor is conjugate to streptavidin (which binds biotinylated MLL peptide). When these two fluorophores are brought together by the interaction of menin with the MLL peptide, energy transfer to the acceptor results in an increase in fluorescence emission at 665 nm and increased HTRF ratio (emission intensity at 665 nm/emission intensity at 620 nm). Inhibition of the menin-MLL interaction separates the donor from the acceptor, resulting in a decrease in emission at 665 nm and decreased HTRF ratio.

Example 14

Menin Engagement Assay

Sample Preparation: 2.5 µL of 100 µM compound is added to 47.5 µL of 526 nM menin in PBS (5 µM compound 500 nM menin in 5% DMSO final concentration). The reaction is incubated at room temperature for variable lengths of time and quenched with 2.5 µL of 4% formic acid (FA, 0.2% final concentration). Method: A Thermo Finnigan Surveyor Autosampler, PDA Plus UV detector and MS Pump along with an LTQ linear ion trap mass spectrometer were used to collect sample data under XCalibur software control. A 5 µL sample in "no waste" mode was injected onto a Phenomenex Jupiter 5u 300A C5 (guard column) 2×4.00 mm at 45° C. Mobile phase composition: Buffer A (95:5 water:acetonitrile, 0.1% FA) and Buffer B (acetonitrile, 0.1% FA). Gradient elution was used with an initial mobile phase of 85:15 (Buffer A:B) and a flow rate of 250 µL/min. Upon injection, 85:15 A:B was held for 1.3 min, Buffer B was increased to 90% over 3.2 min, held for 1 min, and then returned to initial conditions in 0.1 min and held for 2.4 min. The total run time is 8 min. A post-column divert valve employed to direct void volume salts to waste was used for the first 2 min of the sample method. Blank injection of Buffer A is used in between each of the sample injections. A needle wash of 1:1 acetonitrile:water with 0.1% FA was used. The electrospray ionization (ESI) source used a 300° C. capillary temperature, 40 units sheath gas flow, 20 units aux gas flow, 3 units sweep gas flow, 3.5 kV spray voltage, 120 V tube lens. Data Collection: Data collection was performed in the positive ion full scan mode 550-1500 Da, 10 microscans, 200 ms max ion time. Data analysis: Protein mass spectra were acquired as XCalibur datafiles. The best scans were added together using XCalibur Qual Browser. The spectra were displayed using "View/Spectrum List with a Display option to display all peaks. The Edit/Copy cell menu was used to copy the mass spectrum into the PC clipboard. The spectrum in the PC clipboard was pasted into Excel. The first two columns (m/z and Intensity were kept and the third column (Relative) was deleted. The remaining two columns were then saved as a tab delimited file (m/z and intensity) as filename.txt from Excel. The Masslynx Databridge program was then used to convert the filename.txt tab delimited file to Masslynx format. In some cases, an external calibration using a (similarly converted) myoglobin spectrum was applied in Masslynx to correct the m/z values of the menin protein m/z data. MaxEntl software from the MassLynx software suite was used for deconvolution of the mass spectrum to yield the average MW of the protein(s). The percentage of covalent adduct formation was determined from the deconvoluted spectrum and used to calculate the reaction rate (k) of the covalent reaction.

Example 15

Cell Culture

Cells expressing a genetic fusion abnormality and/or genetic mutation can be cultured and maintained according to a variety of existing methods. Cell lines are typically maintained under standard conditions, for example using recommended protocols from ATCC, DSMZ, or Children's Oncology Group cell bank (cogcell.org).

For example, NP23 cell lines (e.g., 106A, 748T, 1057d, and 961C) are established from single-cell suspensions prepared from BM ($1\times10^6$ cells) and maintained in Iscove's Modified Dulbecco's Medium (IMDM) supplemented with 20% FBS, 100 mmol/L L-glutamine, and 100 µg/mL penicillin/streptomycin (Invitrogen).

The AML cell lines OCI-AML3, SET2, MOLM13, and HL60 can be cultured under standard conditions using RPMI supplemented with 10% fetal bovine serum (FBS) and 1% Penicillin/Streptomycin (PS). OCI-AML2 cells can be cultured under standard conditions using alpha-MEM supplemented with 10% fetal bovine serum (FBS) and 1% Penicillin/Streptomycin (PS).

The MLL-amplified myeloid cell line UoC-M1 can be cultured under standard conditions using 90% McCoy's 5a medium supplemented with +10% heat-inactivated FBS. The cells are seeded at approximately $0.5 \times 10^6$ cells/mL and split at a ratio 1:2 every 2-3 days to maintain cell densities of approximately $0.5\text{-}1.5 \times 10^6$ cells/ml. Adherent cells can be detached by tapping or using trypsin/EDTA.

Ewing's sarcoma cell line TC-71 can be grown in a base medium of Iscove's Modified Dulbecco's Medium supplemented with 20% Fetal Bovine Serum, 4 mM L-Glutamine, and 1× ITS (5 µg/mL insulin, 5 µg/mL transferrin, 5 ng/mL selenous acid) at 37.0° C. and in 5% $CO_2$ and 20% $O_2$.

Ewing's sarcoma cell line A-673 can be grown in Dulbecco's Modified Eagle's Medium supplemented with 10% fetal bovine serum.

Cell line authentication testing (ATCC) can be used to verify the identity and purity of human cell lines.

Murine leukemia cells are cultured in DMEM supplemented with 15% FBS, 1% PS, and cytokines (SCF 100 ng/µl, IL-3 20 ng/µl, and IL-6 20 ng/µl).

Example 16

Cell Proliferation Assay

The ability of a compound of the present disclosure to inhibit the growth of selected cells was tested using a cell viability assay, such as the Promega CellTiter-Glo® Luminescent Cell Viability Assay (Promega Technical Bulletin, 2015, "CellTiter-Glo® Luminescent Cell Viability Assay": 1-15, herein incorporated by reference in its entirety) or MTT cell proliferation assay (ATCC® 30-1010K) or cell counting. Compounds of the present disclosure can be tested in both acute myeloid leukemia cell lines or Ewing's sarcoma cell lines and control cell lines without the genetic abnormality or mutation being investigated (e.g., K562, REH, U937, KG-1, and/or HL-60). Selected cells can include, but are not limited to, cells such as human leukemia cell, acute myeloid leukemia cell, Ewing's sarcoma cell (e.g., SK-NEP-1, EW5, EW8, TC-71, TC-106, CHLA258, CHLA-9, CHLA-10, SK-ES-1, Hs 822.T, A-673, A-4573, Hs 863.T, RD-ES, CHLA-25, CHLA-32, CHLA-99, COG-E-352, TC-32, SK-N-MC), VCaP, LNCaP, 22RV1, DU145, LNCaP-AR, MV4;11, KOPN-8, ML-2, MOLM-13, RS4;11, SEM, bone marrow cells (BMCs), myeloblast cell, lymphoblast cell, NUP98 gene fusion cell (e.g., NUP98-PHF23 cell), NUP98-PHF23 (NP23) myeloblast cell (e.g., 961C), NUP98-PHF23 (NP23) lymphoblast cell (e.g., 748T, 106A), cell with an NPM1 mutation (e.g., OCI-AML3), cell without an NPM1 mutation, cell with a DNMT3A mutation (e.g., OCI-AML3, OCI-AML2, SET2), cell without a DNMT3A mutation, cell with a FLT3 mutation, cell without a FLT3 mutation, cell with an IDH1 mutation, cell without an IDH1 mutation, cell with an IDH2 mutation, cell without an IDH2 mutation, cell with a mixed lineage leukemia (MLL) gene amplification (e.g., UoC-M1, 2L1), cell without a mixed lineage leukemia (MLL) gene amplification, MLL-AF9, MLL-AF4, MLL-ENL, HM-2, E2A-HLF, REH, U937, HL-60, NB4, K562, KG-1, and OCI-AML2 cells. Cells were plated at relevant concentrations, for example about $1 \times 10^5\text{-}2 \times 10^5$ cells per well in a 96-well plate. A compound of the present disclosure was added at a concentration up to about 2 µM with seven or eight, 2-fold serial dilutions for each compound. Cells were incubated at 37° C. for a period of time, for example, 72 hours, then cells in the control wells were counted. Media was changed to restore viable cell numbers to the original concentration, and compounds were re-supplied. Proliferation was measured about 72 hours later or about 96 hours later using Promega CellTiter-Glo® reagents or MTT reagents, as per kit instructions. One or more compounds disclosed herein, e.g., a compound provided in Table 1, 2, 3, 4, 5, 6 or 7 having an $IC_{50}$ value of less than 1 preferably less than 100 nM or less than 50 nM (a measurement reflecting the ability of the compound to disrupt the menin-MLL interaction, measured in accordance with Example 12), are expected to inhibit the proliferation of acute myeloid leukemia cell lines or Ewing's sarcoma cell lines while having a much weaker inhibitory effect on the proliferation of the control cell lines (e.g., K562 and REH cells) at the same concentration. Certain compounds disclosed herein exhibited GI50 values in the range of 5 nM to 25 nM when tested in MV4;11 cells (MLL-AF4 AML), MOLM13 cells (MLL-AF9 AML), murine bone marrow cells (rMML-AF9 AML), KOPN8 (MLL-ENL AML) cells, RS4; 11 cells (MLL-AF4 ALL, MLL-rearranged, MEIS1$^{high}$), or SEM (MLL-AF4 ALL) cells. As used in the Examples, the GI50 value of a compound is the concentration of the compound for 50% of maximal inhibition of cell proliferation. It is expected that one or more menin inhibitors disclosed herein are able to inhibit growth of acute myeloid leukemia cells or Ewing's sarcoma cells by 50% at a concentration no more than 100 nM, preferably at a concentration no more than 50 nM, in some situations exhibiting $GI_{50}$ values in the range of 1 nM to 50 nM.

Table 9 shows biological activities of selected compounds in a cell proliferation assay. Compound numbers correspond to the numbers and structures provided in Tables 1-7 and Examples 1-11.

TABLE 9

|  | Less than 10 nM (++++) | 10 nM to less than 50 nM (+++) | 50 nM to less than 250 nM (++) | 250 nM to 1000 nM (+) |
|---|---|---|---|---|
| MLL-AF9 BMC $GI_{50}$ (nM) | I-132, I-135, I-151, I-163, I-165, I-172, I-177, I-183, I-199, I-203, I-205, I-207, I-214 | I-10, I-80, I-138, I-139, I-171, I-174, I-175, I-176, I-181, I-217 |  | I-9 |

Example 17

Colony-Forming Unit Assays

Colony-forming unit assays are performed by pre-treating test cells with a menin inhibitor disclosed herein or vehicle control for several days (e.g., about 6 days) and then plating equal numbers of viable cells in soft agar for approximately 2-4 weeks in the absence of compound. The cells being tested can include, but are not limited to, human leukemia cell, acute myeloid leukemia cell, Ewing's sarcoma cell (e.g., SK-NEP-1, EW5, EW8, TC-71, TC-106, CHLA258, CHLA-9, CHLA-10, SK-ES-1, Hs 822.T, A-673, A-4573, Hs 863.T, RD-ES, CHLA-25, CHLA-32, CHLA-99, COG-E-352, TC-32, SK-N-MC), VCaP, LNCaP, 22RV1, DU145, LNCaP-AR, MV4;11, KOPN-8, ML-2, MOLM-13, RS4;11, SEM, bone marrow cells (BMCs), myeloblast cell, lymphoblast cell, NUP98 gene fusion cell (e.g., NUP98-PHF23 cell), NUP98-PHF23 (NP23) myeloblast cell (e.g., 961C), NUP98-PHF23 (NP23) lymphoblast cell (e.g., 748T, 106A), cell with an NPM1 mutation (e.g., OCI-AML3), cell without an NPM1 mutation, cell with a DNMT3A mutation (e.g., OCI-AML3, OCI-AML2, SET2), cell without a DNMT3A mutation, cell with a FLT3 mutation, cell without a FLT3 mutation, cell with an IDH1 mutation, cell without an IDH1 mutation, cell with an IDH2 mutation, cell without an IDH2 mutation, cell with a mixed lineage leukemia (MLL) gene amplification (e.g., UoC-M1, 2L1), cell without a mixed lineage leukemia (MLL) gene amplification, MLL-AF9, MLL-AF4, MLL-ENL, HM-2, E2A-HLF, REH, U937, HL-60, NB4, K562, KG-1, and OCI-AML2 cells. It is expected that pre-treatment with the menin inhibitor leads to a significant reduction in colony formation in soft agar.

NP23 BM colony-forming unit (CFU) assays are performed using MethoCult GF M3434 (STEMCELL Technologies; www.stemcell.com), according to the manufacturer's instructions. One or more of the menin inhibitors disclosed herein are solubilized in dimethyl sulfoxide (DMSO; Sigma). Cells are seeded at $2\times10^5$/mL for drug treatment assays.

Example 18

RT-PCR Analysis Of Protein Downstream Targets

The effect of a compound of the present disclosure on expression of one or more downstream targets of menin, an MLL protein, NUP98 fusion protein, FMS-like tyrosine kinase-3 (FLT3), isocitrate dehydrogenase 1 (IDH1), isocitrate dehydrogenase 2 (IDH2), nucleophosmin (NPM1), or DNA (cytosine-5)-methyltransferase 3A (DNMT3A) is assessed by RT-PCR. Test cells are treated with an effective concentration of a compound disclosed herein for about 7 days or less, then total RNA is extracted from cells using any available kit such as an RNeasy mini kit (QIAGEN) according to the manufacturer's instructions. The cells being tested can include, but are not limited to, human leukemia cell, acute myeloid leukemia cell, Ewing's sarcoma cell (e.g., SK-NEP-1, EW5, EW8, TC-71, TC-106, CHLA258, CHLA-9, CHLA-10, SK-ES-1, Hs 822.T, A-673, A-4573, Hs 863.T, RD-ES, CHLA-25, CHLA-32, CHLA-99, COG-E-352, TC-32, SK-N-MC), VCaP, LNCaP, 22RV1, DU145, LNCaP-AR, MV4;11, KOPN-8, ML-2, MOLM-13, RS4;11, SEM, bone marrow cells (BMCs), myeloblast cell, lymphoblast cell, NUP98 gene fusion cell (e.g., NUP98-PHF23 cell), NUP98-PHF23 (NP23) myeloblast cell (e.g., 961C), NUP98-PHF23 (NP23) lymphoblast cell (e.g., 748T, 106A), cell with an NPM1 mutation (e.g., OCI-AML3), cell without an NPM1 mutation, cell with a FLT3 mutation, cell without a FLT3 mutation, cell with an IDH1 mutation, cell without an IDH1 mutation, cell with an IDH2 mutation, cell without an IDH2 mutation, cell with a DNMT3A mutation (e.g., OCI-AML3, OCI-AML2, SET2), cell without a DNMT3A mutation, cell with a mixed lineage leukemia (MLL) gene amplification (e.g., UoC-M1, 2L1), cell without a mixed lineage leukemia (MLL) gene amplification, MLL-AF9, MLL-AF4, MLL-ENL, HM-2, E2A-HLF, REH, U937, HL-60, NB4, K562, KG-1, and OCI-AML2 cells. Total RNA is reverse transcribed using a High Capacity cDNA Reverse Transcription Kit (Applied Biosystems), and relative quantification of relevant gene transcripts (e.g., Hoxa9, DLX2, PBX3, Meis1) is determined by real-time PCR. Effective inhibition of the menin-MLL interaction is expected to result in the downregulation of downstream targets of MLL, for example one or more of Hoxa9, DLX2, PBX3, and Meis1.

In NUP98 gene fusion cells, effective inhibition of the menin-MLL interaction is expected to result in the downregulation of one or more downstream targets, for example one or more of Hoxa5, Hoxa7, Hoxa9, Hoxa10, Hoxb5, Meis1, Mir196b, and/or Bahcc1.

In cells with an NPM1 mutation, effective inhibition of the menin-MLL interaction is expected to result in the downregulation of one or more downstream targets, for example one or more of Hoxa9, Hoxa10, Hoxb2, Hoxb3, Hoxb4, Meis1, and/or Flt3.

In cells with a DNMT3A mutation, effective inhibition of the menin-MLL interaction is expected to result in the downregulation of one or more downstream targets, for example one or more of Hoxa9, Hoxb3, Hoxb8, and/or Meis1.

In Ewing's sarcoma cells, effective inhibition of the menin-MLL interaction is expected to result in the downregulation of one or more downstream targets, for example one or more of Hoxd10, Hoxd11, and/or Hoxd13.

Example 19

Cellular Thermal Shift Assay (CETSA)

For the cell lysate CETSA experiments, cultured cells from cell lines expressing menin are harvested and washed with PBS. The cells are diluted in kinase buffer (KB) (25 mM TriS(hydroxymethyl)-aminomethane hydrochloride (Tris-HCl, pH 7.5), 5 mM beta-glycerophosphate, 2 mM dithiothreitol (DTT), 0.1 mM sodium vanadium oxide, 10 mM magnesium chloride) or in phosphate-buffered saline (PBS) (10 mM phosphate buffer (pH 7.4), 2.7 mM potassium chloride and 137 mM sodium chloride). All buffers are supplemented with complete protease inhibitor cocktail. The cell suspensions are freeze-thawed three times using liquid nitrogen. The soluble fraction (lysate) is separated from the cell debris by centrifugation at 20000×g for 20 minutes at 4° C. The cell lysates are diluted with appropriate buffer and divided into two aliquots, with one aliquot being treated with drug and the other aliquot with the diluent of the inhibitor (control). After 10-30 minute incubation at room temperature the respective lysates are divided into smaller (50 µL) aliquots and heated individually at different temperatures for 3 minutes followed by cooling for 3 minutes at room temperature. The appropriate temperatures are determined in preliminary CETSA experiments. The heated lysates are centrifuged at 20000×g for 20 minutes at 4° C. in order to separate the soluble fractions from precipitates. The supernatants are transferred to new microtubes and analyzed by sodium dodecyl sulfate polyacrylamide gel electrophoresis (SDS-PAGE) followed by western blot analysis.

For the intact cell experiments the drug-treated cells from the in vitro experiments above are heated as previously described followed by addition of KB (30 µL) and lysed using 2 cycles of freeze-thawing with liquid nitrogen. The soluble fractions are isolated and analyzed by western blot.

For the in vivo mice experiments, lysates of frozen tissues are used. The frozen organs (e.g., liver or kidney) are thawed on ice and briefly rinsed with PBS. The organs are homogenized in cold PBS using tissue grinders followed by 3 cycles of freeze-thawing using liquid nitrogen. Tissue lysates are separated from the cellular debris and lipids. The tissue lysates are diluted with PBS containing protease inhibitors, divided into 50 µL, aliquots and heated at different temperatures. Soluble fractions are isolated and analyzed by western blot.

It is expected that the aliquots treated with one or more of the menin inhibitors disclosed herein exhibit increased thermal stabilization of menin compared to the control aliquots.

Example 20

CETSA-Like Dot-Blot Experiments On Purified Proteins

Purified protein (0.5 µg) is added to the wells of a PCR plate and the volume adjusted to 50 µL by addition of buffer or cell lysates and ligands depending on the experimental setup. The samples are heated for the designated time and temperature in a thermocycler. After heating, the samples are immediately centrifuged for 15 min at 3000×g and filtered using a 0.65 µm Multiscreen HTS 96 well filter plate. 3 µL of each filtrate are blotted onto a nitrocellulose membrane. Primary antibody and secondary conjugate are used for immunoblotting. All membranes are blocked with blocking buffer; standard transfer and western blot protocols recommended by the manufacturers are used. All antibodies are diluted in blocking buffer. The dot-blot is developed. Chemiluminescence intensities are detected and imaged. Raw dot blot images are processed. The background is subtracted and intensities are quantified. Graphs are plotted and fitted using sigmoidal dose-response (variable slope).

Example 21

FACS Analysis of Cell Surface cd11b Expression

The ability of a compound of the present disclosure to induce the expression of the differentiation marker cd11b on selected cells was tested using a flow cytometry based assay. Cells were plated at relevant concentrations, for example about $2 \times 10^5$-$4 \times 10^5$ cells per mL in a tissue culture flask. A compound of the present disclosure was added at a concentration up to about 2 µM with 3 or 4, 10-fold serial dilutions for each compound. Cells were incubated at 37° C. for a period of time, for example, approximately 3 days, and cells in the control wells were counted. Media was changed to restore viable cell numbers to the original concentration, and compounds were re-supplied. Cell surface expression of cd11b was measured about 72-96 hours later using standard cell staining methods. Cells were washed with saline with 1% fetal bovine serum, incubated with fluorescently labeled antibody specific for cd11b, washed extensively to remove excess antibody, and assessed for staining by flow cytometry. One or more compounds disclosed herein, e.g., a compound provided in Table 1, 2, 3, 4, 5, 6 or 7 having an $IC_{50}$ value of less than 1 µM, preferably less than 100 nM (a measurement reflecting the ability of the compound to disrupt the menin-MLL interaction, measured in accordance with Example 12), are expected to induce expression of cd11b on the surface of acute myeloid leukemia cell lines or Ewing's sarcoma cells. As shown in FIG. 4, expression of differentiation marker cd11b was elevated in Compound A-treated OCI-AML3 cells relative to DMSO-treated cells.

Example 22

Cell Apoptosis Assay Using Flow Cytometry

Cells expressing a genetic abnormality and/or mutation disclosed herein are subjected to an apoptosis assay in the presence or absence of a menin inhibitor disclosed herein. A compound of the present disclosure is added at a concentration up to about 10 µM (e.g., at a concentration of about 50 nM, 100 nM, 200 nM, 500 nM, 1 µM, 2 µM, 5 µM, or 10 µM). Cells are analyzed at one or more time points after treatment (e.g., at approximately 6 hours, 12 hours, 24 hours, 2 days, 3 days, 5 days, or 7 days after treatment).

Changes in cell apoptosis in the presence of a menin inhibitor disclosed herein can be detected by flow cytometry by Annexin V staining. Annexin V is a protein that has a high affinity for the membrane phosphatidylserine (PS), which is translocated from the inner face of the plasma membrane to the cell surface after cells initiate apoptosis. Once on the cell surface, PS can be detected by staining with a fluorescent conjugate of Annexin V (e.g., Annexin V-FITC). Detection can be analyzed by flow cytometry or fluorescence microscopy. Apoptosis can be differentiated from necrosis when Annexin V staining is performed in combination with staining with a cell viability dye (e.g., propidium iodide (PI), SYTOX Blue (Invitrogen), or DAPI). Viable cells are counted by flow cytometry using a viability stain. Cells are split and replated with fresh media and drug every 3-4 days. Apoptosis assays can be conducted using Annexin V-FITC Apoptosis Detection Kit I following the manufacturer's recommended protocol. It is expected that treatment with one or more of the menin inhibitors disclosed herein can lead to increased apoptosis of acute myeloid leukemia or Ewing's sarcoma cells compared with vehicle-treated cells.

Example 23

Pharmacokinetic Studies in Mice

The pharmacokinetics of menin-MLL inhibitors are determined in female C57BL/6 mice following intravenous (iv) dosing at 15 mg/kg and oral dosing (po) at 30 mg/kg. Compounds are dissolved in the vehicle containing, e.g., 25% (v/v) DMSO, 25% (v/v) PEG-400 and 50% (v/v) PBS. Serial blood samples (~50 µL) are collected over 24 h, centrifuged at 15,000 rpm for 10 min and saved for analysis. Plasma concentrations of the compounds are determined by the LC-MS/MS method developed and validated for this study. The LC-MS/MS method consists of an Agilent 1200 HPLC system and chromatographic separation of tested compound is achieved using an Agilent Zorbax Extend-C18 column (5 cm×2.1 mm, 3.5 µm; Waters). An AB Sciex QTrap 3200 mass spectrometer equipped with an electrospray ionization source (ABI-Sciex, Toronto, Canada) in the positive-ion multiple reaction monitoring (MRM) mode is used for detection. All pharmacokinetic parameters are calculated by noncompartmental methods using WinNonlin® version 3.2 (Pharsight Corporation, Mountain View, CA, USA).

Example 24

Efficacy Study in Mouse Xenograft Tumor Model

One or more compounds disclosed herein, e.g., a compound provided in Table 1, 2, 3, 4, 5, 6 or 7 having an $IC_{50}$ value of less than 1 µM, preferably less than 50 nM (a measurement reflecting the ability of the compound to disrupt the menin-MLL interaction, measured in accordance with Example 12), are expected to provide suppression of acute myeloid leukemia or Ewing's sarcoma tumor growth in mouse xenograft models. Immunocompromised 8-10 week-old female nude (nu/nu) mice were used for in vivo efficacy studies in accordance with IACUC guidelines. The nude mice were implanted subcutaneously with approximately $5 \times 10^6$ selected cells/mouse. The selected cells can include, but are not limited to, human acute myeloid leukemia cells (e.g., NUP98 gene fusion cell (e.g., NUP98-PHF23 cell), NUP98-PHF23 (NP23) myeloblast cell (e.g., 961C), NUP98-PHF23 (NP23) lymphoblast cell (e.g., 748T, 106A), cell with an NPM1 mutation (e.g., OCI-AML3), cell with a FLT3 mutation, cell with an IDH1 mutation, cell with an IDH2 mutation, cell with a DNMT3A mutation (e.g., OCI-AML3, OCI-AML2, SET2), cell with a mixed lineage leukemia (MLL) gene amplification (e.g., UoC-M1, 2L1)) or Ewing's sarcoma cells (e.g., SK-NEP-1, EW5, EW8, TC-71, TC-106, CHLA258, CHLA-9, CHLA-10, SK-ES-1, Hs 822.T, A-673, A-4573, Hs 863.T, RD-ES, CHLA-25, CHLA-32, CHLA-99, COG-E-352, TC-32, SK-N-MC) such as those available from ATCC. When the tumor reached a size of approximately 150 to 250 mm³, the tumor-bearing mice were randomly assigned to a vehicle control or a compound treatment group (8 mice per group). Mice in each treatment group were administered a compound of the present disclosure by oral gavage or intraperitoneal injection in an appropriate amount and frequency at the dosage indicated (e.g., 50 mg/kg, bid; 50 gm/kg, qd; 100 mg/kg, bid; 100 mg/kg, qd; 200 mg/kg, qd.; or 200 mg/kg, bid). Subcutaneous tumor volume and mouse body weight were measured twice weekly. Tumor volumes were calculated by measuring two perpendicular diameters with calipers (V=(length×width)/2). Percentage tumor growth inhibition (% TGI=1−[change of tumor volume in treatment group/change of tumor volume in control group]*100) was used to evaluate anti-tumor efficacy. Statistical significance was evaluated using a one-tailed, two sample t test. P<0.05 is considered statistically significant. It is expected that the animal group being treated with one or more of the menin inhibitors disclosed herein exhibits reduction in tumor volume compared to the vehicle control group. A compound provided in Table 1, 2, 3, 4, 5, 6 or 7 having an $IC_{50}$ value of less than 50 nM (a measurement reflecting the ability of the compound to disrupt the menin-MLL interaction, measured in accordance with Example 12) is expected to inhibit tumor growth and induced tumor regression relative to the vehicle control group in a dose-dependent manner.

Figure 5:
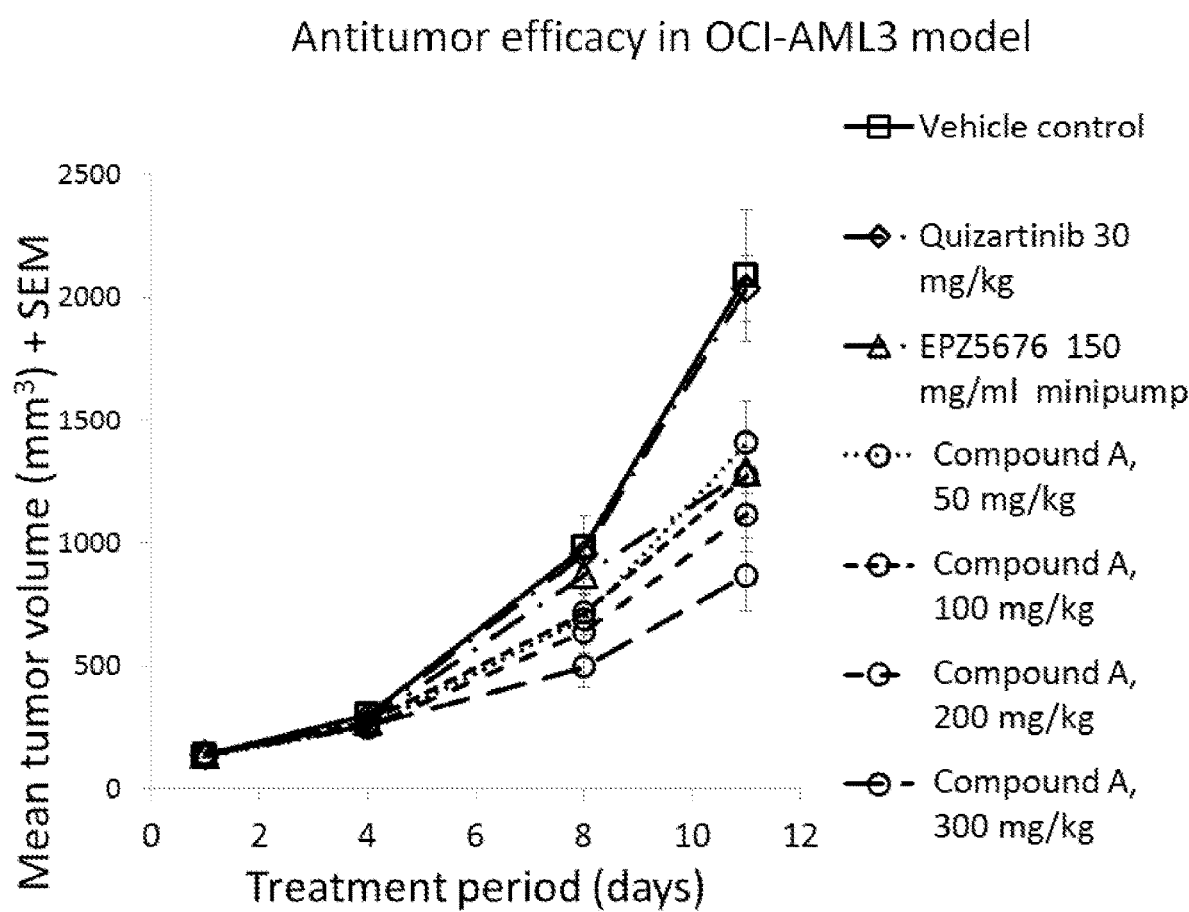
FIG. 5 depicts the change in volume of OCI-AML3 tumors in vehicle and compound treated mice.

As shown in FIG. 5, a compound provided in Table 8 having an $IC_{50}$ value of less than 50 nM (a measurement reflecting the ability of the compound to disrupt the menin-MLL interaction, measured in accordance with Example 12), labeled Compound A throughout the figures, inhibited OCI-AML3 tumor growth relative to the vehicle control group and relative to quizartinib (FLT3 inhibitor) treated and EPZ5676 (DOT1L inhibitor) treated mice in a dose-dependent manner.

Example 25

Efficacy Study in Xenotransplantation Mouse Model

One or more compounds disclosed herein, e.g., a compound provided in Table 1, 2, 3, 4, 5, 6 or 7 having an $IC_{50}$ value of less than 1 µM, preferably less than 50 nM (a measurement reflecting the ability of the compound to disrupt the menin-MLL interaction, measured in accordance with Example 12), are expected to provide suppression of acute myeloid leukemia or Ewing's sarcoma tumor growth in a xenotransplantation mouse model. Immunocompromised 8-10 week-old female NSG mice are used for in vivo efficacy studies in accordance with IACUC guidelines. Luciferase expressing test cells are engrafted intravenously via tail vein injection ($1 \times 10^7$ cells/animal). Test cells can include, but are not limited to, human acute myeloid leukemia cells (e.g., NUP98 gene fusion cell (e.g., NUP98-PHF23 cell), NUP98-PHF23 (NP23) myeloblast cell (e.g., 961C), NUP98-PHF23 (NP23) lymphoblast cell (e.g., 748T, 106A), cell with an NPM1 mutation (e.g., OCI-AML3), cell with a FLT3 mutation, cell with an IDH1 mutation, cell with an IDH2 mutation, cell with a DNMT3A mutation (e.g., OCI-AML3, OCI-AML2, SET2), cell with a mixed lineage leukemia (MLL) gene amplification (e.g., UoC-M1, 2L1)) and Ewing's sarcoma cells (e.g., SK-NEP-1, EW5, EW8, TC-71, TC-106, CHLA258, CHLA-9, CHLA-10, SK-ES-1, Hs 822.T, A-673, A-4573, Hs 863.T, RD-ES, CHLA-25, CHLA-32, CHLA-99, COG-E-352, TC-32, SK-N-MC). When the mean luminescence of the cells reaches approximately $1.5 \times 10^6$, the tumor-bearing mice are randomly assigned to a vehicle control or a compound treatment group (5 animals per group). Animals in each of the treatment groups are administered a different compound of the present disclosure by oral gavage (120 mg/kg b.i.d, 150 mg/kg b.i.d., 200 mg/kg b.i.d., or 200 mg/kg q.d.). Body weight is measured daily, while mean luminescence was measured several days (e.g., 6 days) after initiating the treatment with compound or vehicle. It is expected that treatment with one or more of the menin inhibitors disclosed herein inhibit tumor growth and induce tumor regression relative to the vehicle control group.

Animals are sacrificed several days after treatment (e.g., on Day 7) and bone marrow samples are collected and prepared for gene expression analysis. Expression levels of target genes including, but not limited to, HOXA9, DLX2, PBX3, and/or MEIS1 are measured by qRT-PCR and can be presented as fold changes normalized to GAPDH expression. Expression of differentiation marker CD11b is expected to be elevated in bone marrow samples from menin inhibitor treated animals, suggesting that these cells undergo differentiation. The expression levels of tested downstream target genes including MEIS1 and HOXA9 are expected to be substantially reduced upon treatment with one or more of the menin inhibitors disclosed herein, consistent with inhibition of leukemia progression induced by this compound.

Example 26

Survival Study in Xenotransplantation Mouse Model

For survival studies in the xenotransplantation xenograft model, 6 to 8-week old female NSG mice are intravenously injected with 1×10⁷ luciferase-expressing cells (e.g., Ewing's sarcoma cells or cells harboring a NUP98 gene fusion, NPM1 mutation, FLT3 mutation, IDH1 mutation, IDH2 mutation, DNMT3A mutation, or mixed lineage leukemia (MLL) gene amplification). Several days after the transplantation e.g., at day 12 after transplantation), treatment is initiated with one or more of the menin inhibitors disclosed herein, 120 mg/kg, p.o, or vehicle (20% 2-hydroxypropyl-b-cyclodextrin with 5% cremophore) and is continued for approximately 22 consecutive days. It is expected that treatment with one or more of the menin inhibitors disclosed herein extends median survival time relative to the vehicle control group.

Alternatively, 6 to 8-week old female NSG mice are intravenously injected with 0.5×10⁶ cells (e.g., Ewing's sarcoma cells or acute myeloid leukemia cells such as cells harboring a NUP98 gene fusion, NPM1 mutation (including the patient-derived xenograft (PDX) models AM7577 and LEXFAM 2734), FLT3 mutation (including the patient-derived xenograft (PDX) models AM7577 and LEXFAM 2734), IDH1 mutation, IDH2 mutation (including the patient-derived xenograft (PDX) model AM7577), DNMT3A mutation (including the patient-derived xenograft (PDX) model AM7577), or mixed lineage leukemia (MLL) gene amplification). Several days after transplantation (e.g., approximately 2, 3, 4, 5, 6 or 7 days or longer after transplantation), treatment is initiated with one or more of the menin inhibitors disclosed herein, ~75 mg b.i.d., p.o. or vehicle (20% 2-hydroxypropyl-b-cyclodextrin with 5% cremophore) and is continued for 16 consecutive days in the compound treated mice or until terminal leukemia or Ewing's sarcoma develops in the vehicle-treated mice. It is expected that treatment with one or more of the menin inhibitors disclosed herein extends median survival time relative to the vehicle control group.

Similarly, a ~120 mg/kg b.i.d. treatment regimen of one or more of the menin inhibitors disclosed herein is initiated several days (e.g., on day 6) after cell transplantation and continued for approximately 16 consecutive days in the compound treated mice or until terminal leukemia or Ewing's sarcoma develops in the vehicle-treated mice. It is expected that treatment with one or more of the menin inhibitors disclosed herein extends median survival time relative to the vehicle control group.

Example 27

Serial Bleed FACS Analysis and Survival Study in A1117577 Mouse Model

For survival studies in the xenotransplantation xenograft model, 3 to 4-week old female NOD/SCID mice were intravenously injected with approximately 1-2×10⁶ AM7577 cells (NPM1/DNMT3A$^{mut}$ disseminated ANIL PDX model with an additional mutation in IDH2). Several days after transplantation (e.g., approximately 2, 3, 4, 5, 6, or 7 days or longer after transplantation), treatment was initiated with Compound A, ~200 mg/kg, p.o., qd, in 5 mice or vehicle (20% 2-hydroxypropyl-b-cyclodextrin with 5% cremophore), p.o., qd, in 5 mice and was continued for 3-5 weeks in the compound treated mice or until terminal leukemia developed in the vehicle-treated mice.

Figure 6A:
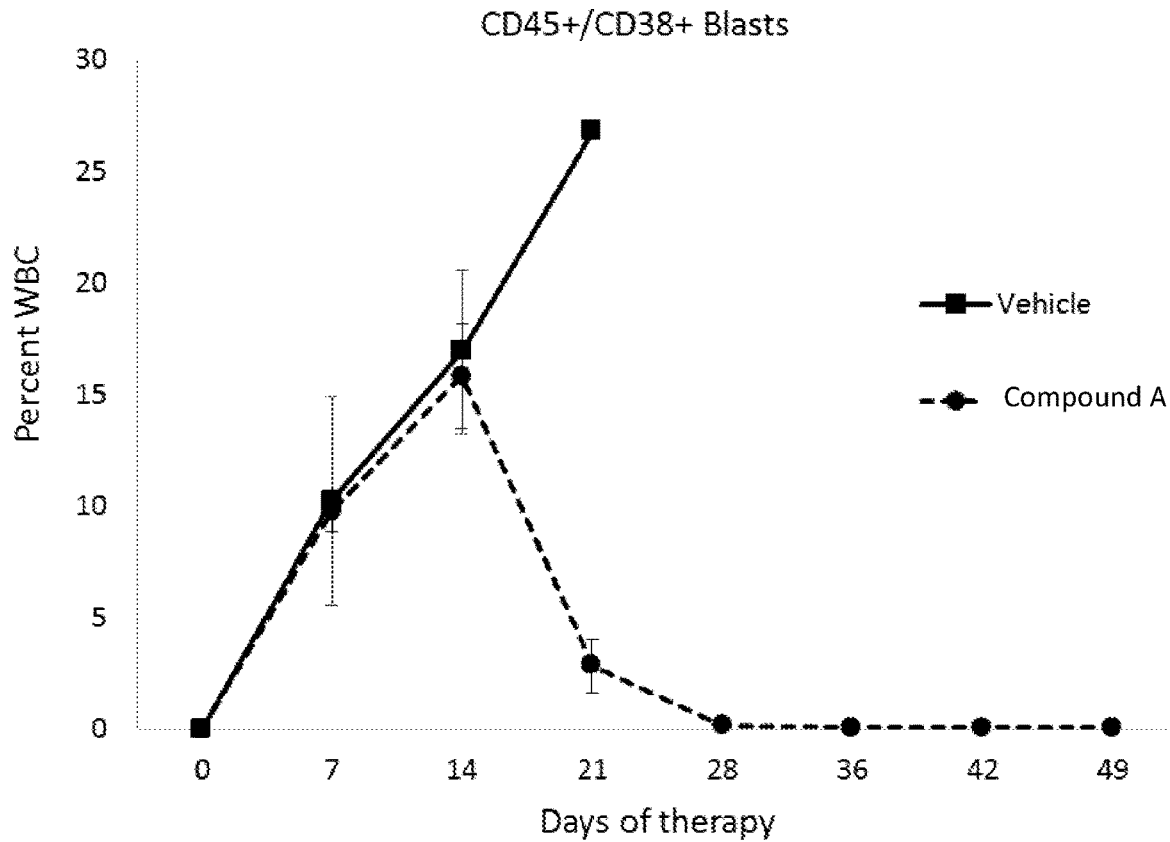
FIGS. 6A, 6B and 6C depict percentages of CD45+/CD38+ blasts, CD45+/CD11b+ monocytes, and CD45+/CD14+ monocytes in vehicle and compound treated AM7577 models.
Figure 6B:
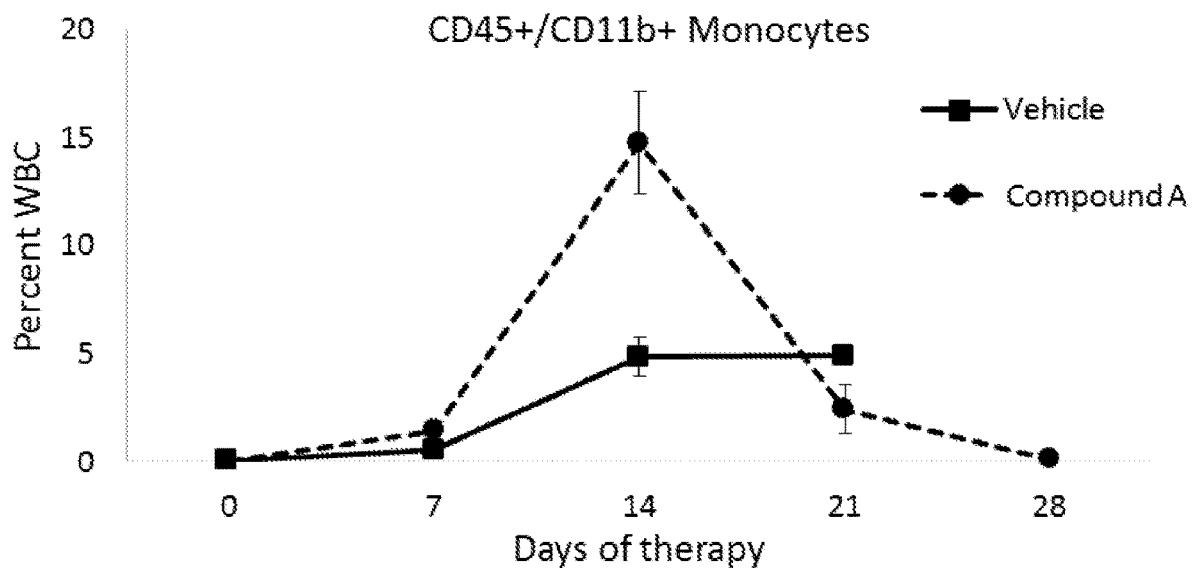
Figure 6C:
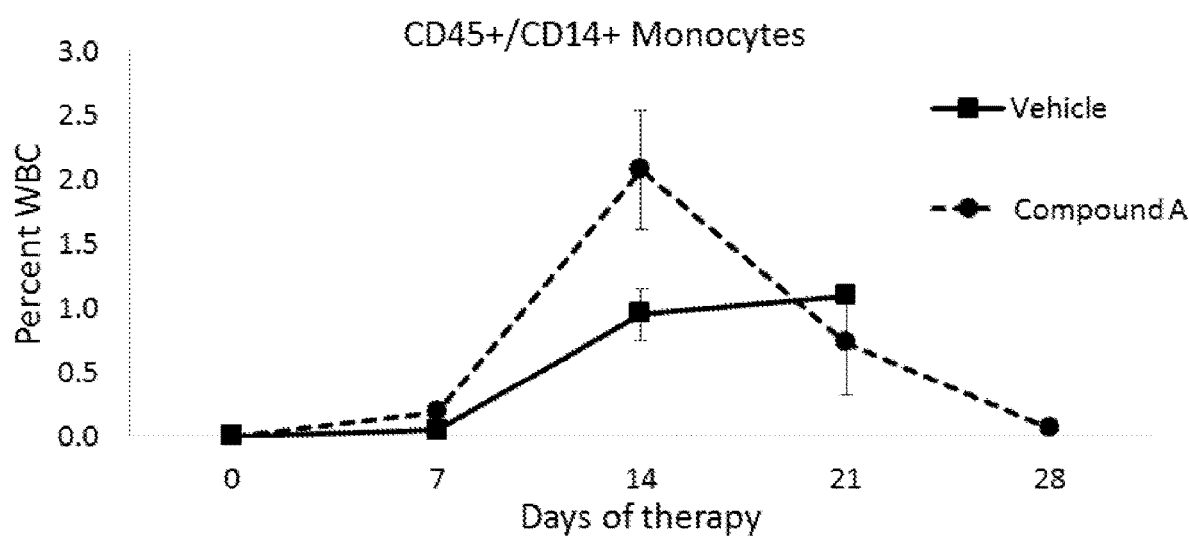

Human leukemia cells were detected by FACS weekly starting from week 4 post-cell inoculation. Eye bleed (~50 µL) was collected and anti-human CD45 antibody, anti-human CD11b antibody, anti-human CD14 antibody, and anti-human CD38 antibody were added. Samples were incubated on ice for 30 min in the dark. Red blood cell lysing buffer (1 mL) was added to each tube, samples were mixed thoroughly, and samples were incubated on ice for another 30 min in the dark. Cells were washed twice with ice cold PBS (2 mL), and the supernatant was discarded. Cells were re-suspended in FACS wash buffer (150 µL), and the samples were analyzed using FACS. FIG. 6A-6C depict percentages of CD45+/CD38+ blasts, CD45+/CD11b+ monocytes, and CD45+/CD14+ monocytes in vehicle and compound treated AM7577 models. Treatment with Compound A reversed leukemic progression and induced myeloid differentiation.

Figure 7A:
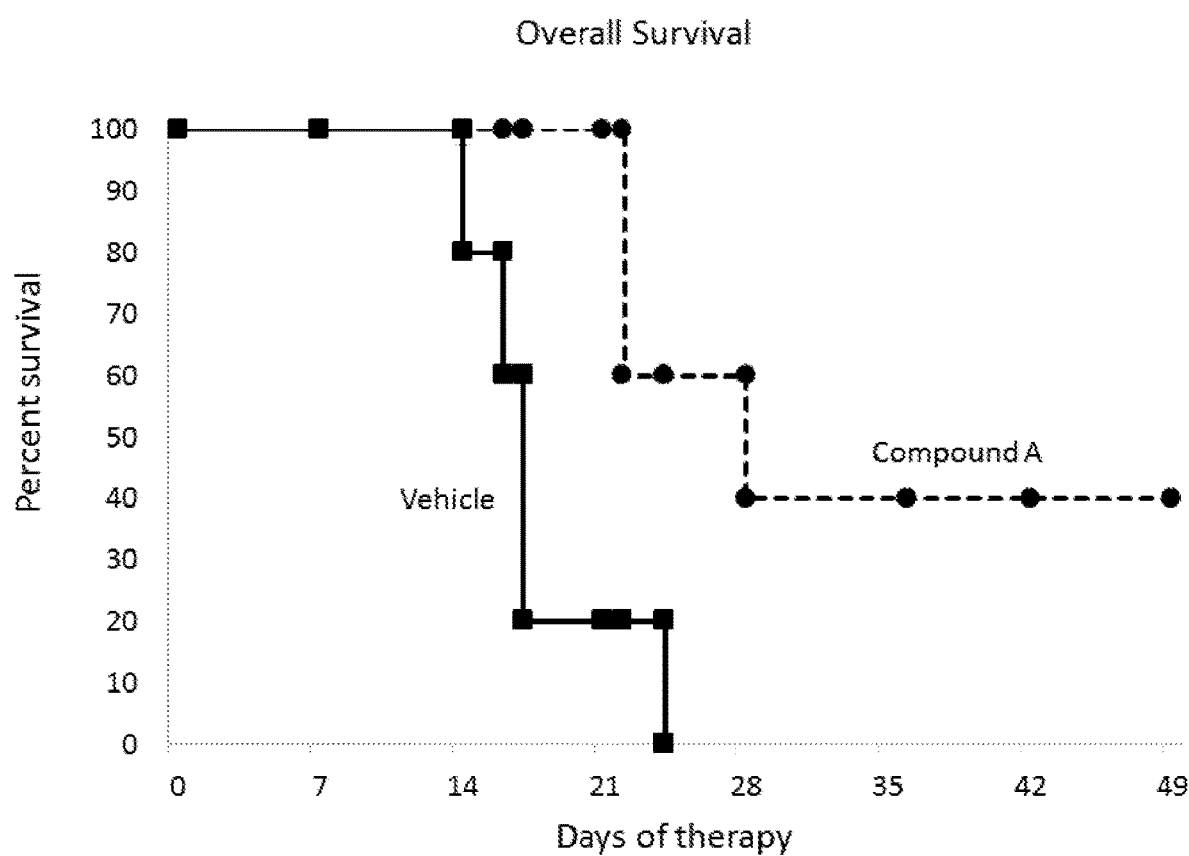
FIGS. 7A, 7B and 7C depict overall survival, bone marrow phenotype at sacrifice, and spleen weight at sacrifice in vehicle and compound treated AM7577 models.
Figure 7B:
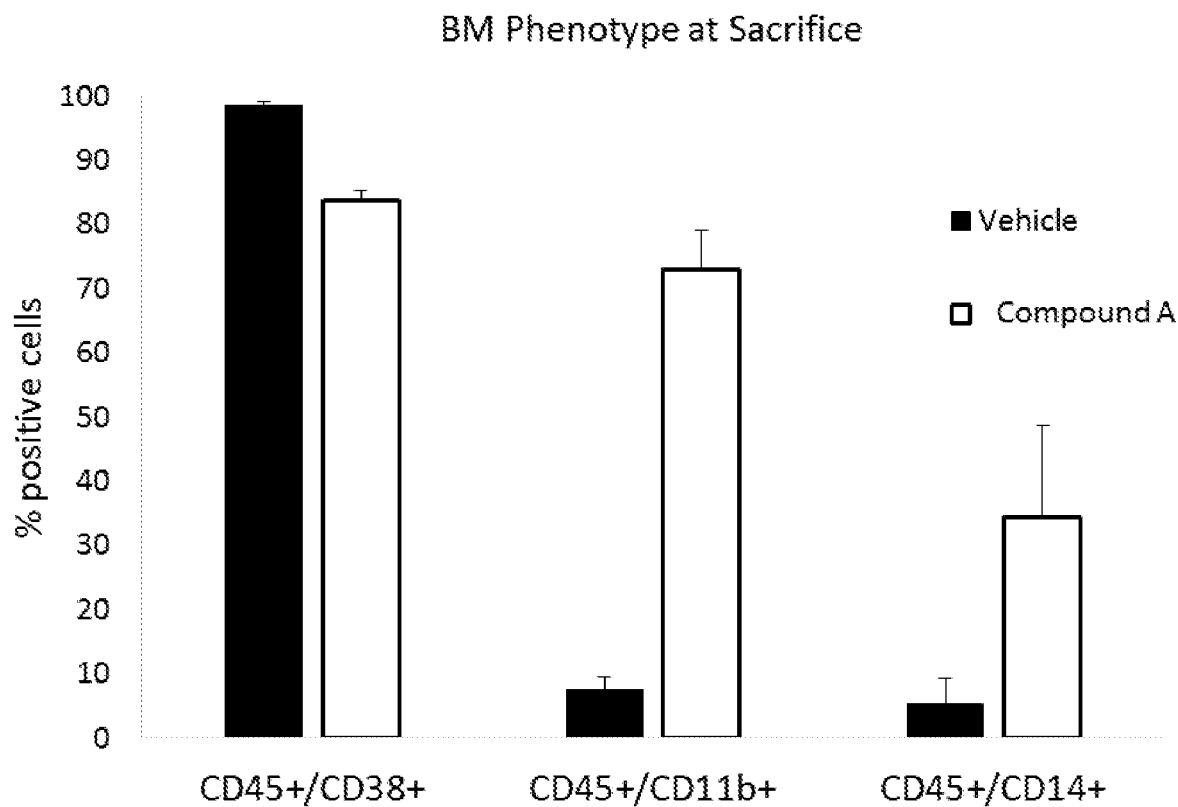
Figure 7C:
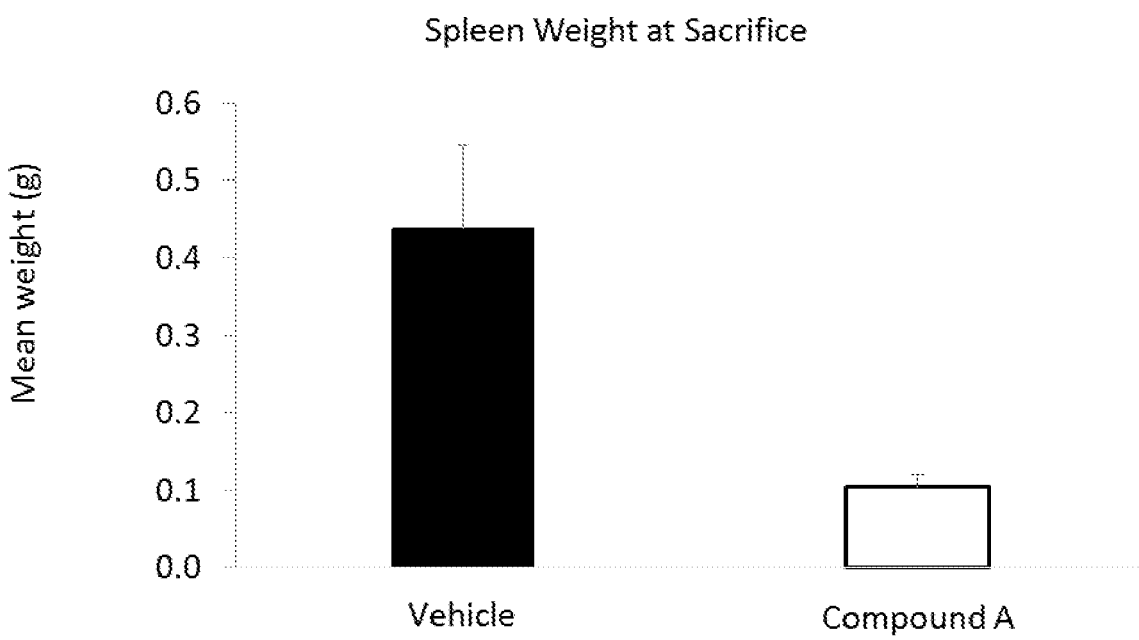

Spleen weight was measured for sacrificed animals. Blood and bone marrow cells of sacrificed animals were tested with anti-human CD45 antibody, anti-human CD11b antibody, anti-human CD14 antibody, and anti-human CD38 antibody. FIG. 7A depicts overall survival in vehicle and compound treated AM7577 models. Two out of five animals treated with Compound A demonstrated lasting complete remissions. Treatment with Compound A prolonged survival compared to treatment with vehicle. FIG. 7B depicts bone marrow phenotype at sacrifice in vehicle and compound treated AM7577 models. Compound A treated animals that succumbed to disease had differentiated human cells in the bone marrow. All vehicle treated animals had ~100% undifferentiated human blasts in bone marrow. Peripheral disease was completely cleared in all treated animals. FIG. 7C depicts spleen weight at sacrifice in vehicle and compound treated AM7577 models. Spleen weight was normal in compound treated animals at sacrifice but increased by an average of over four-fold over normal in vehicle-treated animals at sacrifice.

Example 28

Generation of Transgenic NP23 Mice

PCR primers are used to introduce Sfi I and Not I restriction sites and a C-terminal V5 epitope tag into the NP23 transgene construct, as described in Gough et al.; Cancer Discov. 2014 May; 4 (5):564-77. This PCR product is subcloned into the Sfi I and Not I sites of the HS21/45-vav vector (Ogilvy et al., Blood. 1999 Sep. 15;94 (6):1855-63.), placing the expression of the fusion gene under the control of hematopoietic-specific Vav regulatory elements. Founders are generated by injection of the purified Pme I-released fragment from p898/NP23-2 containing Vav 1—NP23-V5-vav 2 into C57BL/6 zygotes. Positive NP23 founder mice are bred with WT C57BL/6, and pups are genotyped for the NP23 transgene by PCR with the forward and reverse primers NUPPHF(C)F and PHF23R1. WT controls are age-matched littermate controls.

Example 29

Chromatin Immunoprecipitation (ChIP) and ChIP-Seq Assay

Chromatin immunoprecipitation (ChIP) is performed using the Zymo-Spin ChIP kit (Zymo Research Corp, Irvine, CA), according to the manufacturer's instructions, or using a ChIP-IT kit from Active Motif, following the manufacturer's recommended protocol with minor modifications (Gough et al.; Cancer Discov. 2014 May; 4 (5):564-77). Antibodies used can include anti-menin (Bethyl A300-105A), 4 µg; anti-MLL (Millipore 05-765), 10 µg; anti-H3K4me3 (Invitrogen 49-1005), 2 µg; anti-histone H3 (Cell Signaling Technology 2650), 15 µg; anti-H3K4me3 (17-614; Millipore), anti-H3K27me3 (07-449; Millipore), anti-V5 (R960-25; Life Technologies), anti-FLAG (M2; Sigma-Aldrich), and anti-RNA polymerase II (CTD4H8; Santa Cruz Biotechnology). Non-immune rabbit or mouse IgG can be used as negative controls.

It is expected that treatment with one or more of the menin inhibitors disclosed herein leads to a reduction in H3K4me3 enrichment at genes found to be downregulated in Example 18, suggesting epigenetic repression and decreased transcriptional activity. It can also be expected that treatment with one or more of the menin inhibitors disclosed herein leads to an increase in total H3 levels at the promoters for genes found to be downregulated in Example 18, suggesting chromatin compaction.

Example 30

Serial Bleed FACS Analysis and Survival Study in A1117577 Mouse Model

For survival studies in the xenotransplantation xenograft model, 6 to 8-week old female NOD/SCID mice were intravenously injected with approximately 1-2×10⁶ AM7577 cells (NPM1$^{mut}$/DNMT3A$^{mut}$/FLT3-ITD disseminated AML PDS model with an additional mutation in IDH2). Several weeks after transplantation (e.g., approximately 3 weeks after transplantation, when average tumor burden reaches 2-4% of hCD45+ cells), treatment was initiated with Compound A, ~100 mg/kg, p.o., qd in 5 mice, Compound A ~150 mg/kg, p.o., qd, in 5 mice, quizartinib ~3 mg/kg p.o., qd in 5 mice, a combination of Compound A (~100 mg/kg, p.o., qd) and quizartinib (~2 mg/kg, p.o., qd) in 5 mice, or vehicle (20% 2-hydroxypropyl-b-cyclodextrin with 5% cremophore), p.o., qd, in 5 mice and was continued for 3-5 weeks in the compound treated mice or until terminal leukemia developed in the vehicle-treated mice.

Figure 8A:
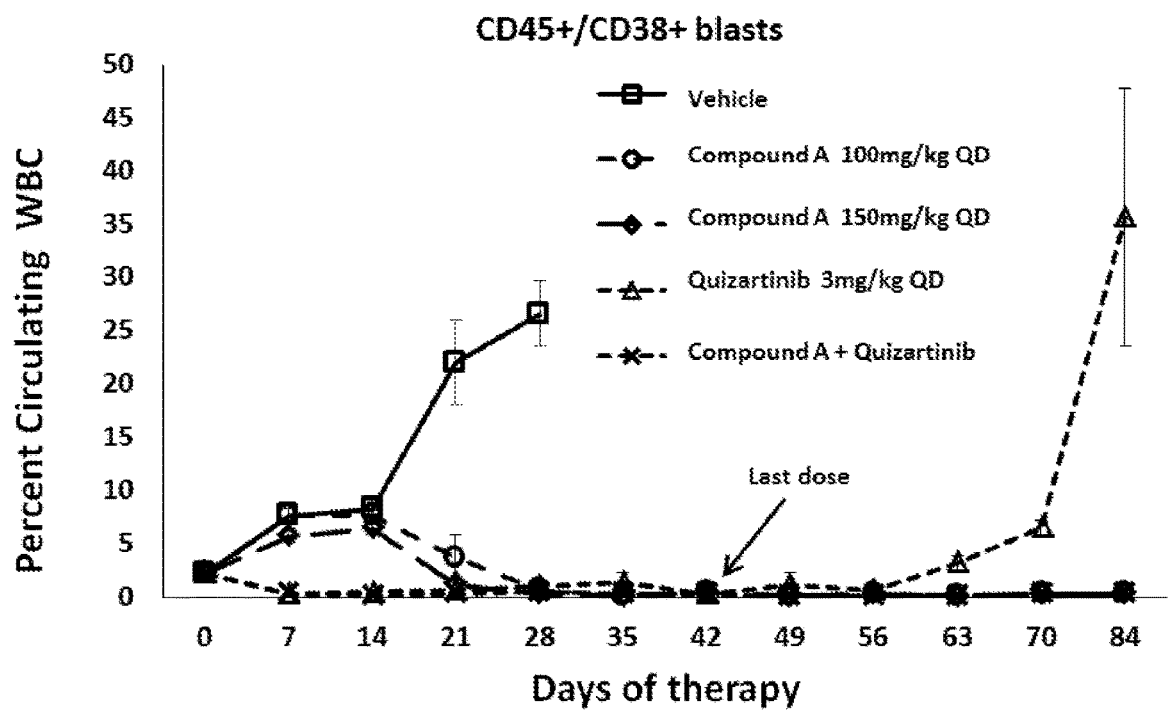
FIGS. 8A and 8B depict percentages of CD45+/CD38+ blasts and CD45+/CD11b+ monocytes in vehicle, compound and quizartinib treated AM7577 models.
Figure 8B:
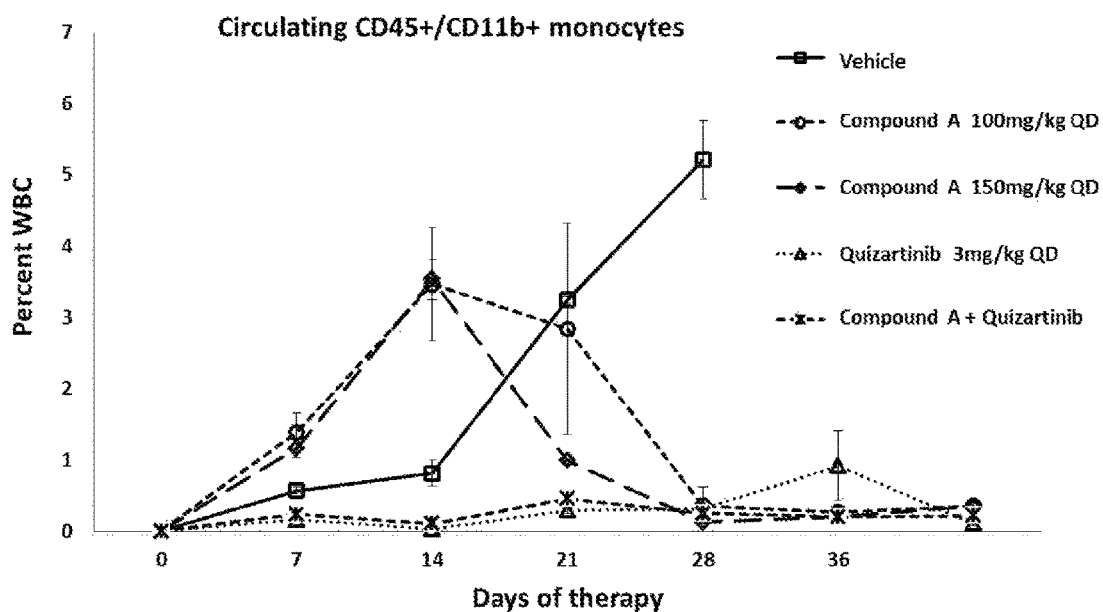

Human leukemia cells were detected by FACS weekly starting from week 3 post-cell inoculation. Eye bleed (~50 µL) was collected and anti-human CD45 antibody, anti-human CD11b antibody, anti-human CD14 antibody, and anti-human CD38 antibody were added. Samples were incubated on ice for 30 min in the dark. Red blood cell lysing buffer (1 mL) was added to each tube, samples were mixed thoroughly, and samples were incubated on ice for another 30 min in the dark. Cells were washed twice with ice cold PBS (2 mL), and the supernatant was discarded. Cells were re-suspended in FACS wash buffer (150 µL), and the samples were analyzed using FACS. FIGS. 8A and 8B depict percentages of CD45+/CD38+ blasts and circulating CD45+/CD11b+ monocytes. Treatment with Compound A and a combination of Compound A and quizartinib reversed leukemic progression and induced myeloid differentiation. Treatment with only quizartinib showed evidence of leukemia breakout after 63 days.

Figure 9A:
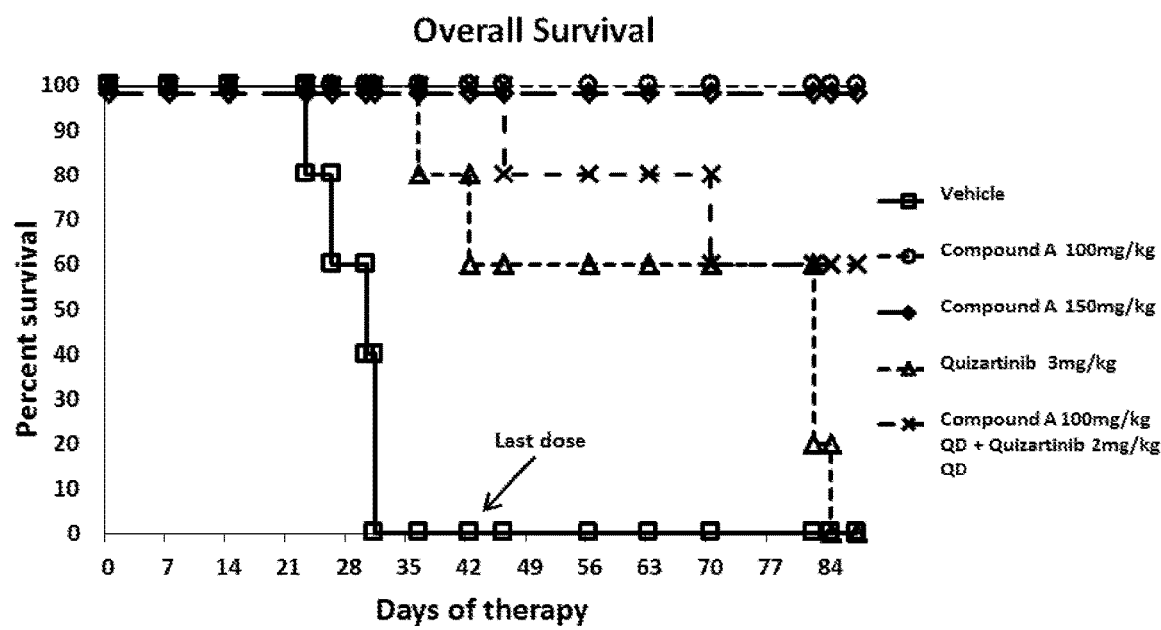
FIGS. 9A, 9B, 9C, 9D and 9E depict overall survival, bone marrow phenotype after seven and 21 days, bone marrow AML blasts at sacrifice, and spleen weight at sacrifice in vehicle, compound and quizartinib treated AM7577 models.
Figure 9B:
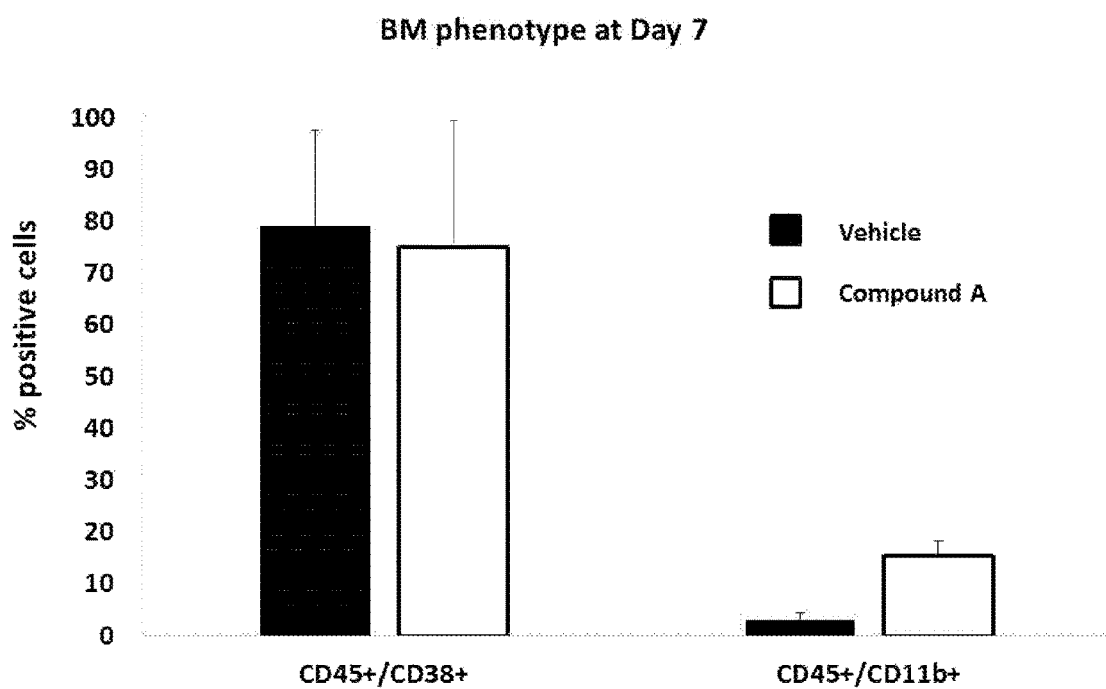
Figure 9C:
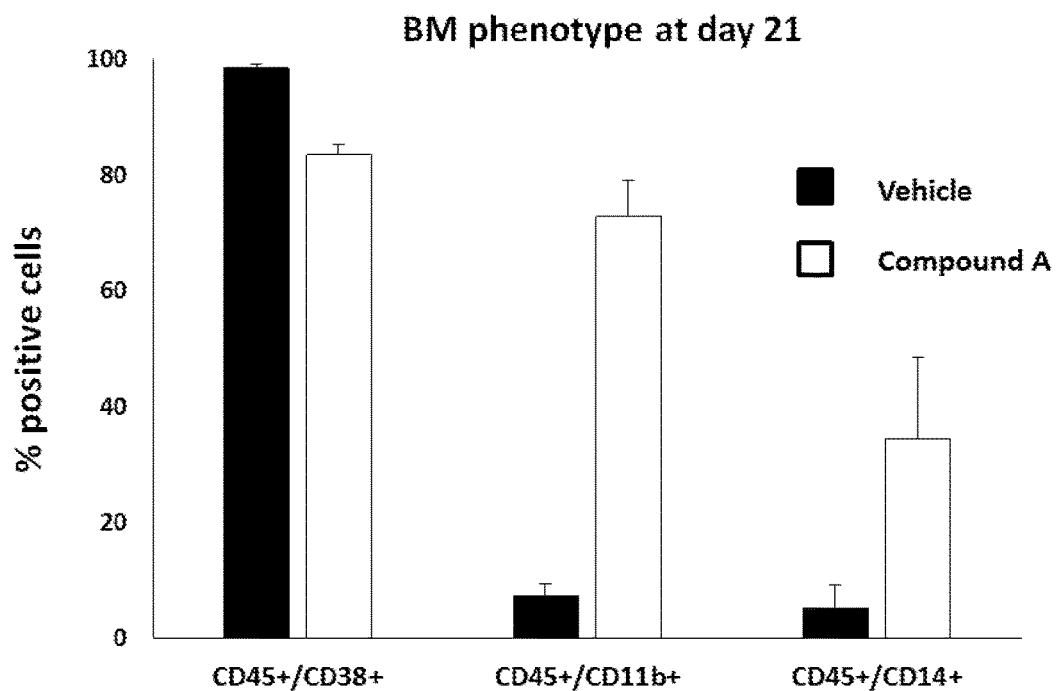
Figure 9D:
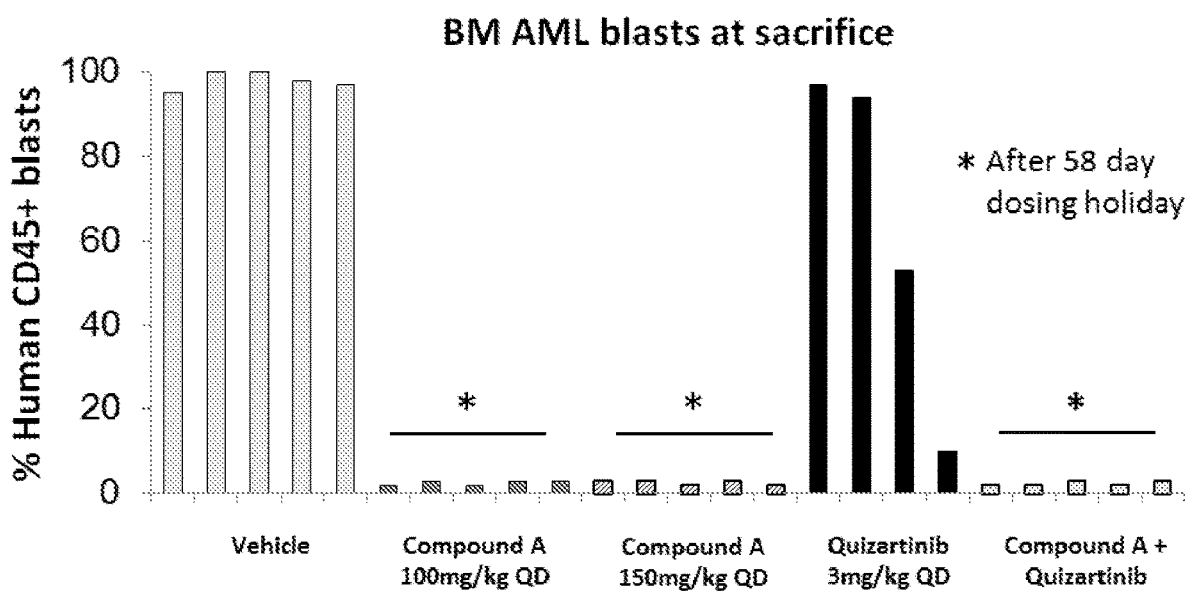
Figure 9E:
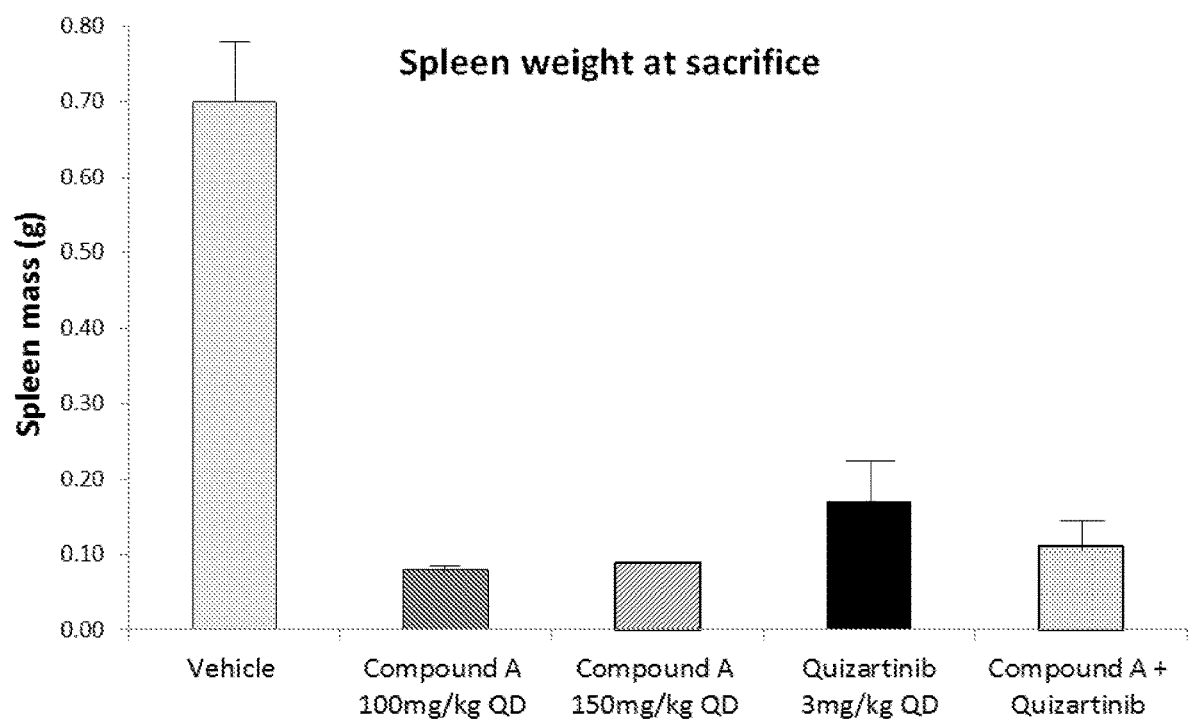

Spleen weight was measured for sacrificed animals. Blood and bone marrow cells of sacrificed animals were tested with anti-human CD45 antibody, anti-human CD11b antibody, anti-human CD14 antibody, and anti-human CD38 antibody. FIG. 9A depicts overall survival in vehicle, Compound A, quizartinib and Compound A+quizartinib treated AM7577 models. All animals treated with Compound A demonstrated lasting complete remissions, including those treated with a combination of Compound A and quizartinib. Treatment with quizartinib showed evidence of leukemia breakout and dose-dependency in rate of clearance of leukemia. Treatment with Compound A and quizartinib prolonged survival compared to treatment with vehicle, but quizartinib only treatment resulted in no surviving animals after 84 days. FIGS. 9B and 9C depict bone marrow phenotype after treatment for seven and 21 days, respectively, in vehicle and Compound A treated AM7577 models. FIG. 9D depicts bone marrow AML blasts at sacrifice in vehicle, Compound A, quizartinib, and Compound A+quizartinib treated animals. The data gathered for Compound A and Compound A+quizartinib treated animals were obtained after a 58 day dosing holiday. FIG. 9E depicts spleen weight at sacrifice in vehicle, Compound A, quizartinib, and Compound A+quizartinib treated animals. Compound A treated animals that succumbed to disease had differentiated human cells in the bone marrow. Vehicle treated animals had 80% undifferentiated human blasts in bone marrow.

Example 31

Serial Bleed FACS Analysis and Survival Study in LXFE 2734 Mouse Model

For survival studies in the xenotransplantation xenograft model, 4 to 6-week old female NOG mice were intravenously injected with approximately 3×10⁶ LXFE 2734 cells (NPM1$^{mut}$/DNMT3A-WT/FLT3$^{mut}$ disseminated AMI, PDX model). Several weeks after transplantation (e.g., approximately 2 or 3 weeks after transplantation), treatment was initiated with Compound A, ~150 mg/kg, p.o., qd in 5 mice, quizartinib ~3 mg/kg qd in 5 mice, or vehicle (20% 2-hydroxypropyl-b-cyclodextrin with 5% cremophore), p.o., qd, in 5 mice and was continued for 3-5 weeks in the compound treated mice or until terminal leukemia developed in the vehicle-treated mice.

Figure 10:
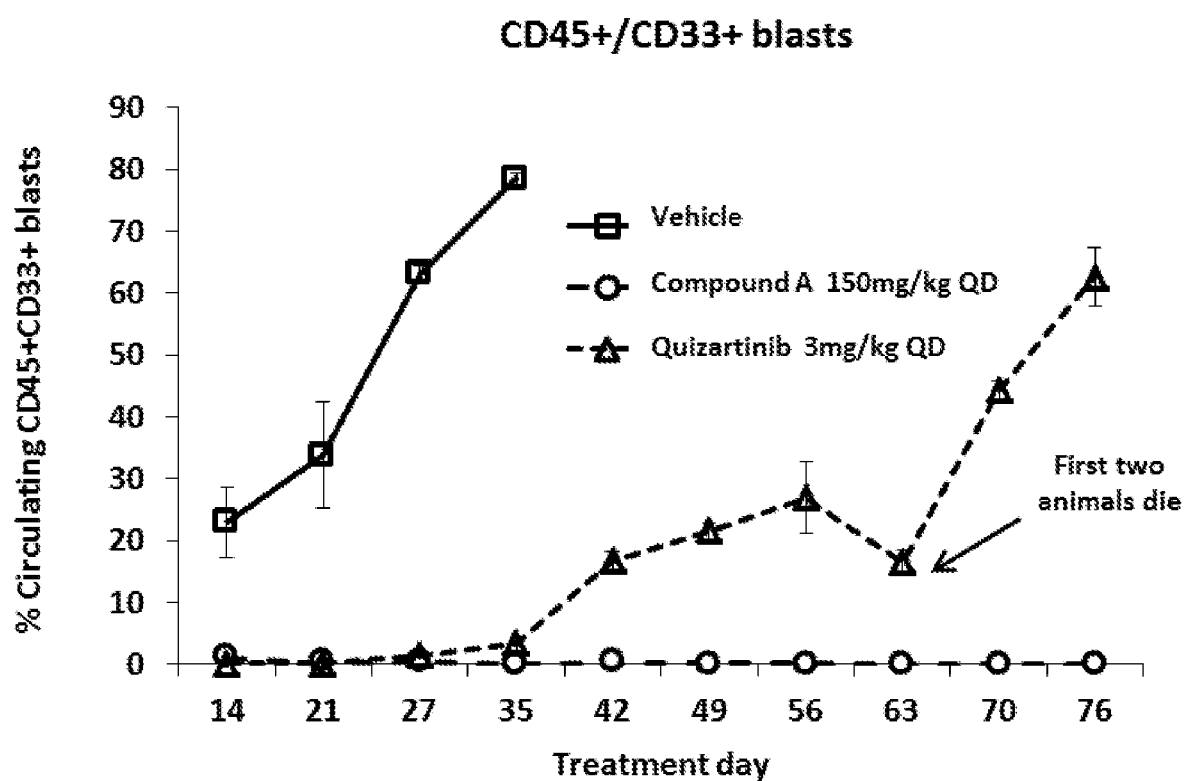
FIG. 10 depicts percentages of CD45+/CD33+ blasts in vehicle, compound and quizartinib treated LXFE 2734 models.

Human leukemia cells were detected by FACS biweekly starting from week 2 post-cell inoculation. Li-heparin whole blood was collected and anti-human CD45 antibody, anti-human CD11b antibody, anti-human CD14 antibody, and anti-human CD33 antibody were added. FIG. 10 depicts percentages of CD45+/CD33+ blasts. Treatment with Compound A reversed leukemic progression and showed no evidence of peripheral leukemia. Treatment with quizartinib showed evidence of leukemia relapse.

Figure 11:
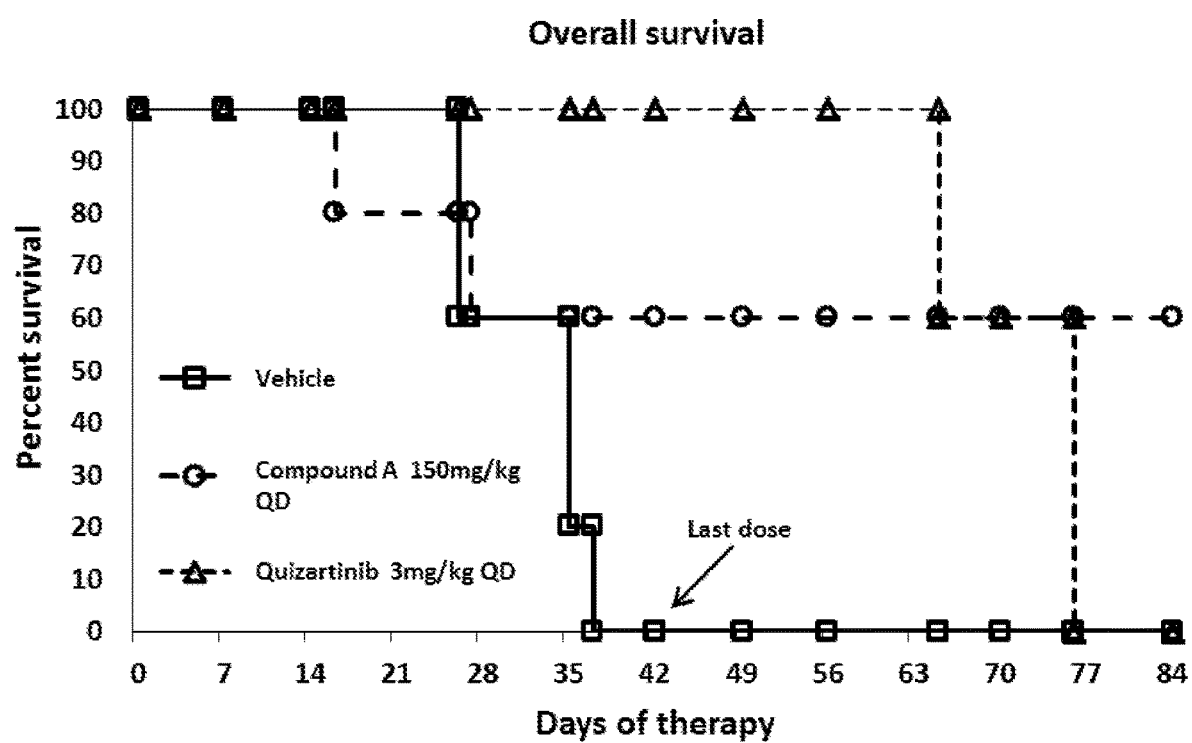
FIG. 11 depicts overall survival in vehicle, compound and quizartinib treated LXFE 2734 models.

Spleen weight was measured for sacrificed animals. Blood and bone marrow cells of sacrificed animals were tested with anti-human CD45 antibody, anti-human CD11b antibody, anti-human CD14 antibody, and anti-human CD33 antibody. FIG. 11 depicts overall survival in vehicle and Compound A and quizartinib treated LXFE 2734 models. Treatment with Compound A and quizartinib prolonged survival compared to treatment with vehicle, with no quizartinib treated animals surviving after 77 days.

Example 32

Cell Proliferation Assay

The ability of a compound of the present disclosure to inhibit the growth of selected cells was tested using a cell viability assay, such as the Promega CellTiter-Glo® Luminescent Cell Viability Assay (Promega Technical Bulletin, 2015, "CellTiter-Glo® Luminescent Cell Viability Assay": 1-15, herein incorporated by reference in its entirety), MTT cell proliferation assay (ATCC® 30-1010K) or cell counting. The efficacy of one or more compounds of the present disclosure was tested in KG1, MV4;11, THP-1, ML-2, NB4 (APL), U-937, EOL-1, MOLM-13 and OCI-AML3 acute myeloid leukemia cells and Reh, RS4; 11, MUTZ-5, MHH- CALL2 and NALM6 B-cell acute lymphoblastic leukemia cells. Cells were plated at relevant concentrations, for example about $1\times10^5$-$2\times10^5$ cells per well in a 96-well plate. A compound of the present disclosure was added at a concentration up to about 10 µM with seven or eight, 2-fold serial dilutions. Cells were incubated at 37° C. for a period of time, for example, 72 hours, then cells in the control wells were counted. Media was changed to restore viable cell numbers to the original concentration, and compounds were re-supplied. Proliferation was measured about 72 hours later or about 96 hours later using Promega CellTiter-Glo® reagents or MTT reagents, as per kit instructions. One or more compounds disclosed herein, e.g., a compound provided in Table 1, 2, 3, 4, 5, 6 or 7 having an $IC_{50}$ value of less than 1 µM, preferably less than 100 nM or less than 50 nM (a measurement reflecting the ability of the compound to disrupt the menin-MLL interaction, measured in accordance with Example 12), are expected to inhibit the proliferation of acute myeloid leukemia cell lines or B-cell acute lymphoblastic leukemia leukemia cell lines. Certain cell lines were responsive to treatment with one or more compounds disclosed herein, such as MV4; 11 cells (MLL-AF4 AML, MLL-rearranged, MEIS1$^{high}$), MOLM13 cells (MLL-AF9 AML, MLL-rearranged, MEIS1$^{high}$), OCI-AML3 cells (AML, NPM1$^{mut}$, DNMT3A$^{mut}$), EOL-1 cells (AML, MEL-PTD), and RS4; 11 cells (MLL-AF4 ALL, MEL-rearranged, MEIS1$^{high}$). Certain cell lines were less responsive to treatment with one or more compounds disclosed herein, such as THP-1 (AML, MEL-rearranged, MEIS1$^{low}$, RAS$^{mut}$), ME-2 (AML, MEL-rearranged, MEIS1$^{low}$, RAS$^{mut}$), Reh (B-ALL, MEL-WT), MUTZ-5 (B-ALL, MEL-WT), MHH-CALL2 (B-ALL, MEL-WT), and NALM6 (B-ALL, MEL-WT).

Figure 12:
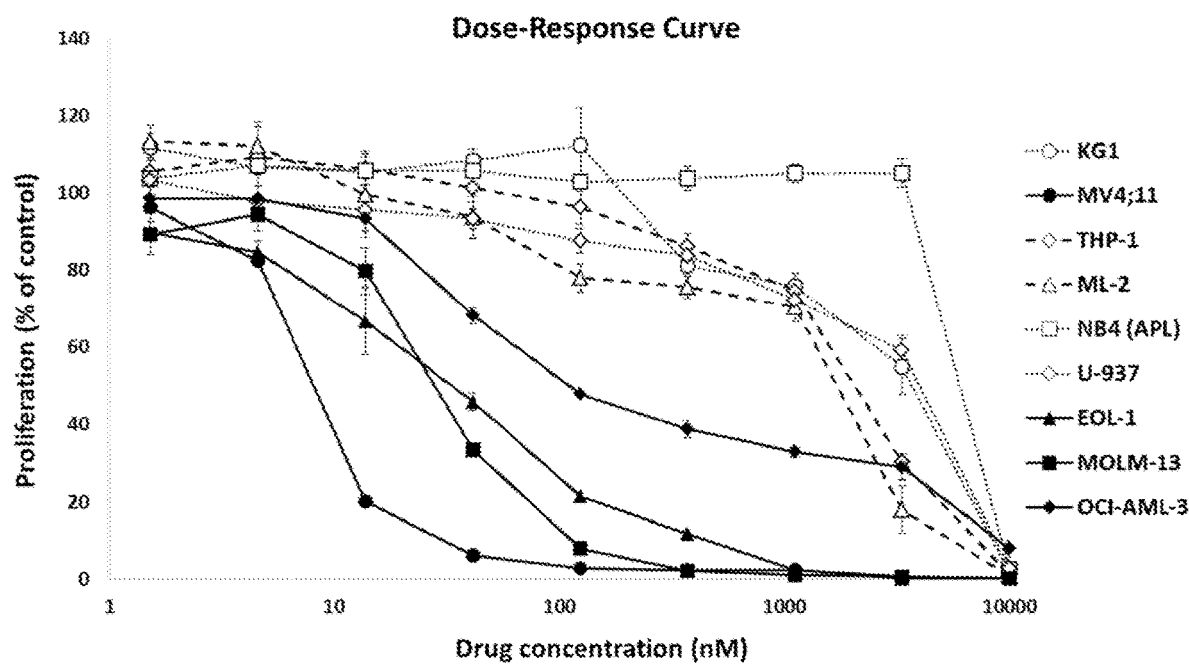
FIG. 12 depicts dose-response curves for acute myeloid leukemia cells treated with Compound A.
Figure 13:
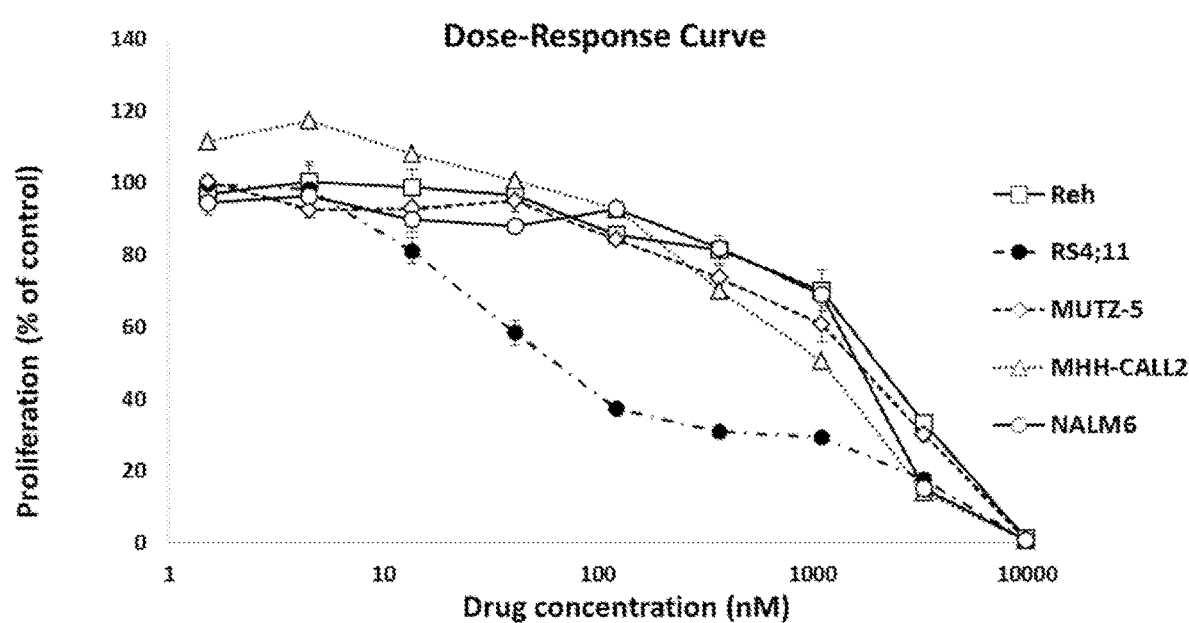
FIG. 13 depicts dose-response curves for B-cell acute lymphoblastic leukemia cells treated with Compound A.

It is expected that one or more menin inhibitors disclosed herein are able to inhibit growth of acute myeloid leukemia cells or acute lymphoblastic leukemia cells by 50% at a concentration no more than 1000 nM, preferably at a concentration no more than 100 nM, more preferably at a concentration no more than 50 nM, in some situations exhibiting $GI_{50}$ values in the range of 1 nM to 50 nM. FIG. 12 depicts dose-response curves for acute myeloid leukemia cells treated with Compound A. Dose-response curves for B-cell acute lymphoblastic leukemia cells treated with Compound A are presented in FIG. 13.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating acute myeloid leukemia or acute lymphoblastic leukemia in a subject, comprising administering a menin inhibitor to the subject, wherein the subject has elevated myeloid ecotropic viral integration site 1 (MEIS1) expression levels, and wherein the menin inhibitor is a compound of Formula (I-B-1):

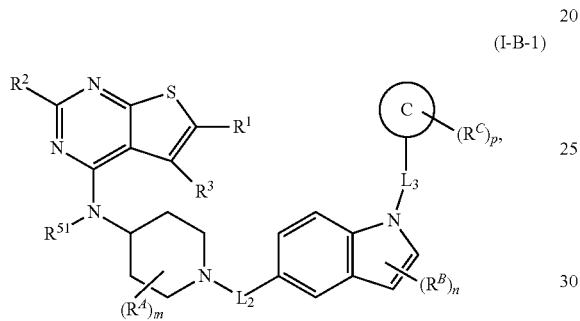

(I-B-1)

or a pharmaceutically acceptable salt thereof, wherein:
C is selected from $C_{3-12}$ carbocycle and 3- to 12-membered heterocycle;
$L_2$ is selected from bond, —C(O)—, —C(O)O—, —C(O)N($R^{51}$)—, —C(O)N($R^{51}$)C(O)—, —C(O)N($R^{51}$)C(O)N($R^{51}$)—, —C(N$R^{51}$)—, —C(N$R^{51}$)N($R^{51}$)—, —S(O)$_2$—, —S(O)O—, —S(O)—, S(O)$_2$O—, —S(O)$_2$N($R^{51}$)—, —S(O)N($R^{51}$)—, alkylene, alkenylene, alkynylene, heteroalkylene, heteroalkenylene, and heteroalkynylene, wherein each alkylene, alkenylene, alkynylene, heteroalkylene, heteroalkenylene, and heteroalkynylene is optionally substituted with one or more $R^{50}$;
$L_3$ is selected from alkylene, alkenylene, and alkynylene, each of which is substituted with one or more $R^{56}$ and optionally further substituted with one or more $R^{50}$;
$R^1$ and $R^3$ are each independently selected from hydrogen and $R^{50}$;
$R^2$ is $R^{50}$;
$R^A$, $R^B$, and $R^C$ are each independently selected at each occurrence from $R^{50}$, or two $R^A$ groups, two $R^B$ groups, or two $R^C$ groups attached to the same atom or different atoms can together optionally form a bridge or ring;
m and p are each independently an integer from 0 to 6;
n is an integer from 0 to 5;
$R^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, and —P(O)(R$^{52}$)$_2$, or two $R^{50}$ groups attached to the same carbon are taken together to form =O, =S, or =N(R$^{52}$);
$C_{1-10}$ alkyl, $C_{2-10}$ alkenyl, and $C_{2-10}$ alkynyl, each of which is optionally substituted at each occurrence with one or more substituents independently selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and
$C_{3-12}$ carbocycle and 3- to 12-membered heterocycle,
wherein each $C_{3-12}$ carbocycle and 3- to 12-membered heterocycle in $R^{50}$ is optionally substituted with one or more substituents independently selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;
$R^{51}$ is independently selected at each occurrence from: hydrogen, —C(O)R$^{52}$, —C(O)OR$^{52}$, —C(O)N(R$^{52}$)$_2$, and —C(O)NR$^{53}$R$^{54}$;
$C_{1-6}$ alkyl, $C_{2-6}$ alkenyl, and $C_{2-6}$ alkynyl, each of which is optionally substituted at each occurrence with one or more substituents independently selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle,
  wherein each $C_{3-12}$ carbocycle and 3- to 12-membered heterocycle in $R^{51}$ is optionally substituted with one or more substituents independently selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;
$R^{52}$ is independently selected at each occurrence from hydrogen; and $C_{1-20}$ alkyl, $C_{2-20}$ alkenyl, $C_{2-20}$ alkynyl, $C_{1-6}$ heteroalkyl, $C_{3-12}$ carbocycle, and 3- to 12-membered heterocycle, each of which is optionally substituted by halogen, $-CN$, $-NO_2$, $-NH_2$, $-NHCH_3$, $-NHCH_2CH_3$, $=O$, $-OH$, $-OCH_3$, $-OCH_2CH_3$, $C_{3-12}$ carbocycle, or 3- to 6-membered heterocycle;
$R^{53}$ and $R^{54}$ are taken together with the nitrogen atom to which they are attached to form a heterocycle;
$R^{56}$ is independently selected at each occurrence from:
  $-NO_2$, $-OR^{59}$, $-SR^{52}$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $C_{1-10}$ alkyl, $C_{2-10}$ alkenyl, $C_{2-10}$ alkynyl, $C_{3-12}$ carbocycle and 3- to 12-membered heterocycle, or two $R^{56}$ groups attached to the same carbon are taken together to form $=O$, $=S$, or $=N(R^{52})$,
  wherein each $C_{1-10}$ alkyl, $C_{2-10}$ alkenyl, and $C_{2-10}$ alkynyl in $R^{56}$ is optionally substituted at each occurrence with one or more substituents independently selected from halogen, $-NO_2$, $-CN$, $-OR^{59}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle, and 3- to 12-membered heterocycle;
  wherein each $C_{3-12}$ carbocycle and 3- to 12-membered heterocycle in $R^{56}$ is optionally substituted with one or more substituents independently selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl; and further wherein $R^{56}$ optionally forms a bond to ring C; and $R^{59}$ is independently selected at each occurrence from $C_{1-20}$ alkyl, $C_{2-20}$ alkenyl, $C_{2-20}$ alkynyl, $C_{1-6}$ heteroalkyl, $C_{3-12}$ carbocycle, and 3- to 12-membered heterocycle, each of which is optionally substituted by halogen, $-CN$, $-NO_2$, $-NH_2$, $-NHCH_3$, $-NHCH_2CH_3$, $=O$, $-OH$, $-OCH_3$, $-OCH_2CH_3$, $C_{3-12}$ carbocycle, or 3- to 6-membered heterocycle;
  wherein when $R^{56}$ is $-CH_3$, $L^3$ is not further substituted with $-OH$, $-NH_2$, or $-CN$.

2. The method of claim 1, wherein the administering reduces expression of a target gene.

3. The method of claim 2, wherein the target gene is Meis1.

4. The method of claim 1, wherein the subject has a nucleoporin 98 (NUP98) gene fusion, a mutation in the nucleophosmin (NPM1) gene, a mutation in the DNA (cytosine-5)-methyltransferase 3A (DNMT3A) gene, a mutation in the FMS-like tyrosine kinase-3 (FLT3) gene, a mutation in the isocitrate dehydrogenase 1 (IDH1) gene, a mutation in the isocitrate dehydrogenase 2 (IDH2) gene, or a mixed lineage leukemia (MLL) gene amplification.

5. The method of claim 1, wherein the subject has a mixed lineage leukemia (MLL) gene rearrangement or a partial tandem duplication of MLL.

6. The method of claim 1, wherein the subject has a mixed lineage luekemia (MLL) gene rearrangement.

7. The method of claim 1, wherein the subject has a partial tandem duplication of the mixed lineage leukemia (MLL) gene.

8. The method of claim 1, wherein the subject has a mutation in the nucleophosmin (NPM1) gene.

9. The method of claim 1, wherein the subject has a nucleoporin 98 (NUP98) gene fusion.

10. The method of claim 1, wherein the subject has a mutation in the isocitrate dehydrogenase 1 (IDH1) gene.

11. The method of claim 1, wherein the subject has a mutation in the isocitrate dehydrogenase 2 (IDH2) gene.

12. The method of claim 1, wherein the subject has a mutation in the DNA (cytosine-5)-methyltransferase 3A (DNMT3A) gene.

13. The method of claim 1, wherein the subject has a mutation in the FMS-like tyrosine kinase-3 (FLT3) gene.

14. The method of claim 1, wherein
  $R^2$ is selected from halogen, $-OR^{52}$, $N(R^{52})_2$, $-CN$, $C_{1-3}$ alkyl, $-CH_2OR^{52}$, $-CH_2N(R^{52})_2$, $C_{1-3}$ alkyl-N $(R^{52})_2$, $C_{1-3}$ haloalkyl, $C_{2-3}$ alkenyl, and $C_{2-3}$ alkynyl; and
  $R^3$ is selected from hydrogen, halogen, $-OH$, $-N(R^{52})_2$, $-CN$, $-C(O)OR^{52}$, $C_{1-3}$ alkyl, and $C_{1-3}$ haloalkyl.

15. The method of claim 1, wherein $R^1$ is $C_{1-3}$ haloalkyl.

16. The method of claim 1, wherein m is 0 and n is an integer from 1 to 3.

17. The method of claim 1, wherein $L_2$ is $C_{1-4}$ alkylene, optionally substituted with one or more $R^{50}$; and $L_3$ is $C_{1-4}$ alkylene, optionally substituted with one or more $R^{50}$.

18. The method of claim 1, wherein the compound of Formula (I-B-1) or a pharmaceutically acceptable salt thereof is a compound of Formula (I-B-6) or Formula (I-B-8):

(I-B-6)

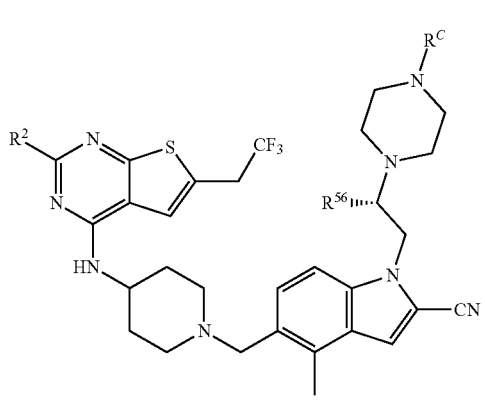

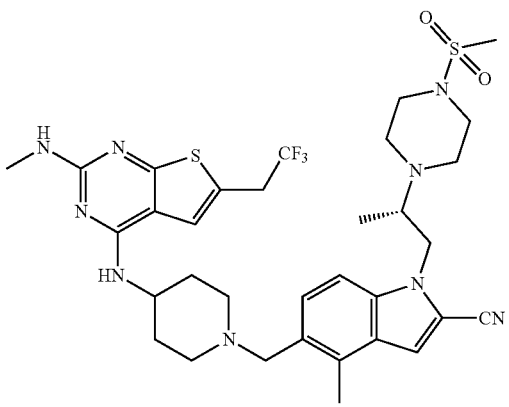

or a pharmaceutically acceptable salt thereof.

20. A method of treating acute myeloid leukemia or acute lymphoblastic leukemia in a subject comprising administering to the subject a compound that is:

(I-B-8)

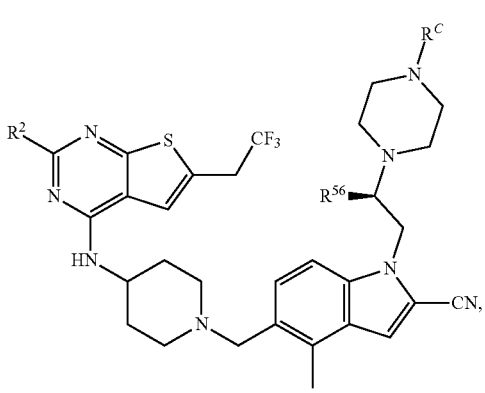

or a pharmaceutically acceptable salt thereof.

19. The method of claim 1, wherein the compound of Formula (I-B-1) is:

or a pharmaceutically acceptable salt thereof;
wherein the subject has elevated MEIS1 expression levels.

* * * * *